US011897922B2

(12) United States Patent
Reed et al.

(10) Patent No.: US 11,897,922 B2
(45) Date of Patent: Feb. 13, 2024

(54) **IMMUNOGENIC COMPOSITIONS COMPRISING *MYCOBACTERIUM TUBERCULOSIS* POLYPEPTIDES AND FUSIONS THEREOF**

(71) Applicant: ACCESS TO ADVANCED HEALTH INSTITUTE, Seattle, WA (US)

(72) Inventors: Steven G. Reed, Bellevue, WA (US); Rhea N. Coler, Seattle, WA (US); Gregory C. Ireton, Seattle, WA (US); Sylvie Bertholet, Gaithersburg, MD (US)

(73) Assignee: ACCESS TO ADVANCED HEALTH INSTITUTE, Seattle, WA (US)

( * ) Notice: Subject to any disclaimer, the term of this patent is extended or adjusted under 35 U.S.C. 154(b) by 27 days.

(21) Appl. No.: 17/367,812

(22) Filed: Jul. 6, 2021

(65) Prior Publication Data

US 2022/0017578 A1 Jan. 20, 2022

Related U.S. Application Data

(60) Division of application No. 15/815,512, filed on Nov. 16, 2017, now Pat. No. 11,091,521, which is a division of application No. 13/791,511, filed on Mar. 8, 2013, now Pat. No. 9,822,152, which is a continuation of application No. 12/594,806, filed as application No. PCT/US2008/059500 on Apr. 4, 2008, now Pat. No. 8,486,414.

(60) Provisional application No. 60/910,169, filed on Apr. 4, 2007.

(51) Int. Cl.

| | |
|---|---|
| ***C07K 14/35*** | (2006.01) |
| ***A61K 39/04*** | (2006.01) |
| ***C07K 14/285*** | (2006.01) |
| ***G01N 33/569*** | (2006.01) |
| ***G01N 33/68*** | (2006.01) |
| ***A61K 39/00*** | (2006.01) |

(52) U.S. Cl.
CPC .............. *C07K 14/35* (2013.01); *A61K 39/04* (2013.01); *C07K 14/285* (2013.01); *G01N 33/5695* (2013.01); *G01N 33/68* (2013.01); *A61K 2039/55561* (2013.01); *C07K 2319/00* (2013.01); *G01N 2469/20* (2013.01); *Y02A 50/30* (2018.01)

(58) Field of Classification Search
CPC .. C07K 14/35; C07K 14/285; C07K 2319/00; A61K 39/04; A61K 2039/55561; G01N 35/5965; G01N 33/68; G01N 2469/20; Y02A 50/30
See application file for complete search history.

(56) References Cited

PUBLICATIONS

Greenspan et al, Nature Biotechnology 17:936-937, 1999).*
Harlow et al, (Antibodies A Laboratory Manual, Cold Spring Harbor Laboratory Press Inc., 1988).*
Colman et al. (Research in Immunology 145: 33-36, 1994).*
Houghten et al. (New Approaches to Immunization, Vaccines 86, Cold Spring Harbor Laboratory, p. 21-25, 1986.*
Ellis (Vaccines, W.B. Saunders Company, Chapter 29, 1988, pp. 568-574).*
Boslego et al (Vaccines and Immunotherapy, 1991, Chapter 17).*
Skolnick et al. (Trends in Biotechnology 18: 34-39, 2000).*
Application No. 201618010553—Notice of Hearing, mailed Dec. 14, 2021, 2 pages. (partial English translation).
Application No. 201618010553—Written Submission, mailed Jan. 25, 2022, 31 pages.

* cited by examiner

*Primary Examiner* — Robert A Zeman
(74) *Attorney, Agent, or Firm* — Benjamin Keim; Newport IP, LLC

(57) ABSTRACT

The present invention relates to compositions and fusion proteins containing at least two *Mycobacterium* sp.) antigens, and polynucleotides encoding such compositions and fusion proteins. The invention also relates to methods for their use in the treatment, prevention and/or diagnosis of tuberculosis infections.

12 Claims, 9 Drawing Sheets

Specification includes a Sequence Listing.

Levels of IFN-γ released by antigen stimulated human PBMC

Immune responses to Rv1813, Rv2608, and Rv3620 with CpG in C57BL/6 mice and protection against aerosol challenge with Mtb Immune responses ID83 and ID93 fusion proteins with GLA-SE in C57BL/6 mice Immune responses ID83 with different adjuvant formulations in C57BL/6 mice Survival of Mtb-infected guinea pigs vaccinated with ID83 in different adjuvant formulations Ad5-ID83-dependent IFN-γ responses and protection against *M. tuberculosis* in C57BL/6 mice Survival of Mtb-infected SWR mice after antibiotics + immunotherapy with Rv1813, Rv2608, Rv3620 and GLA-SE Serological diagnostic of TB

SEQUENCE LISTING

```
<160> NUMBER OF SEQ ID NOS: 318

<210> SEQ ID NO 1
<211> LENGTH: 161
<212> TYPE: PRT
<213> ORGANISM: Mycobacterium tuberculosis

<400> SEQUENCE: 1

Met Thr Ala Ile Ser Cys Ser Pro Arg Pro Arg Tyr Ala Ser Arg Met
1               5                   10                  15

Pro Val Leu Ser Lys Thr Val Glu Val Thr Ala Asp Ala Ala Ser Ile
            20                  25                  30

Met Ala Ile Val Ala Asp Ile Glu Arg Tyr Pro Glu Trp Asn Glu Gly
        35                  40                  45

Val Lys Gly Ala Trp Val Leu Ala Arg Tyr Asp Asp Gly Arg Pro Ser
    50                  55                  60

Gln Val Arg Leu Asp Thr Ala Val Gln Gly Ile Glu Gly Thr Tyr Ile
65                  70                  75                  80

His Ala Val Tyr Tyr Pro Gly Glu Asn Gln Ile Gln Thr Val Met Gln
                85                  90                  95

Gln Gly Glu Leu Phe Ala Lys Gln Glu Gln Leu Phe Ser Val Val Ala
            100                 105                 110

Thr Gly Ala Ala Ser Leu Leu Thr Val Asp Met Asp Val Gln Val Thr
        115                 120                 125

Met Pro Val Pro Glu Pro Met Val Lys Met Leu Leu Asn Asn Val Leu
    130                 135                 140
```

Glu His Leu Ala Glu Asn Leu Lys Gln Arg Ala Glu Gln Leu Ala Ala
145 150 155 160

Ser

<210> SEQ ID NO 2
<211> LENGTH: 495
<212> TYPE: DNA
<213> ORGANISM: Mycobacterium tuberculosis

<400> SEQUENCE: 2
catatgacgg caatctcgtg ctcaccgcga cccaggtatg cttcccgaat gccagttttg 60
agcaagaccg tcgaggtcac cgccgacgcc gcatcgatca tggccatcgt tgccgatatc 120
gagcgctacc cagagtggaa tgaaggggtc aagggcgcat gggtgctcgc tcgctacgat 180
gacgggcgtc ccagccaggt gcggctcgac accgctgttc aaggcatcga gggcacctat 240
atccacgccg tgtactaccc aggcgaaaac cagattcaaa ccgtcatgca gcagggtgaa 300
ctgtttgcca agcaggagca gctgttcagt gtggtggcaa ccggcgccgc gagcttgctc 360
acggtggaca tggacgtcca ggtcaccatg ccggtgcccg agccgatggt gaagatgctg 420
ctcaacaacg tcctggagca tctcgccgaa aatctcaagc agcgcgccga gcagctggcg 480
gccagctaaa agctt 495

<210> SEQ ID NO 3
<211> LENGTH: 181
<212> TYPE: PRT
<213> ORGANISM: Mycobacterium tuberculosis

<400> SEQUENCE: 3

Met Gly Ser Ser His His His His His His Ser Ser Gly Leu Val Pro
1 5 10 15

Arg Gly Ser His Met Thr Ala Ile Ser Cys Ser Pro Arg Pro Arg Tyr
20 25 30

Ala Ser Arg Met Pro Val Leu Ser Lys Thr Val Glu Val Thr Ala Asp
35 40 45

Ala Ala Ser Ile Met Ala Ile Val Ala Asp Ile Glu Arg Tyr Pro Glu
50 55 60

Trp Asn Glu Gly Val Lys Gly Ala Trp Val Leu Ala Arg Tyr Asp Asp
65 70 75 80

Gly Arg Pro Ser Gln Val Arg Leu Asp Thr Ala Val Gln Gly Ile Glu
85 90 95

Gly Thr Tyr Ile His Ala Val Tyr Tyr Pro Gly Glu Asn Gln Ile Gln
100 105 110

Thr Val Met Gln Gln Gly Glu Leu Phe Ala Lys Gln Glu Gln Leu Phe
115 120 125

Ser Val Val Ala Thr Gly Ala Ala Ser Leu Leu Thr Val Asp Met Asp
130 135 140

Val Gln Val Thr Met Pro Val Pro Glu Pro Met Val Lys Met Leu Leu
145 150 155 160

Asn Asn Val Leu Glu His Leu Ala Glu Asn Leu Lys Gln Arg Ala Glu
165 170 175

Gln Leu Ala Ala Ser
180

<210> SEQ ID NO 4
<211> LENGTH: 33

<212> TYPE: DNA
<213> ORGANISM: Artificial Sequence
<220> FEATURE:
<223> OTHER INFORMATION: Cloning primer

<400> SEQUENCE: 4
taggatccca tatgacggca atctcgtgct cac 33

<210> SEQ ID NO 5
<211> LENGTH: 35
<212> TYPE: DNA
<213> ORGANISM: Artificial Sequence
<220> FEATURE:
<223> OTHER INFORMATION: Cloning primer

<400> SEQUENCE: 5
tagaattcaa gcttttagct ggccgccagc tgctc 35

<210> SEQ ID NO 6
<211> LENGTH: 328
<212> TYPE: PRT
<213> ORGANISM: Mycobacterium tuberculosis

<400> SEQUENCE: 6

```
Val Val Asp Ala His Arg Gly Gly His Pro Thr Pro Met Ser Ser Thr
1               5                   10                  15

Lys Ala Thr Leu Arg Leu Ala Glu Ala Thr Asp Ser Ser Gly Lys Ile
            20                  25                  30

Thr Lys Arg Gly Ala Asp Lys Leu Ile Ser Thr Ile Asp Glu Phe Ala
        35                  40                  45

Lys Ile Ala Ile Ser Ser Gly Cys Ala Glu Leu Met Ala Phe Ala Thr
    50                  55                  60

Ser Ala Val Arg Asp Ala Glu Asn Ser Glu Asp Val Leu Ser Arg Val
65                  70                  75                  80

Arg Lys Glu Thr Gly Val Glu Leu Gln Ala Leu Arg Gly Glu Asp Glu
                85                  90                  95

Ser Arg Leu Thr Phe Leu Ala Val Arg Arg Trp Tyr Gly Trp Ser Ala
            100                 105                 110

Gly Arg Ile Leu Asn Leu Asp Ile Gly Gly Gly Ser Leu Glu Val Ser
        115                 120                 125

Ser Gly Val Asp Glu Glu Pro Glu Ile Ala Leu Ser Leu Pro Leu Gly
    130                 135                 140

Ala Gly Arg Leu Thr Arg Glu Trp Leu Pro Asp Asp Pro Pro Gly Arg
145                 150                 155                 160

Arg Arg Val Ala Met Leu Arg Asp Trp Leu Asp Ala Glu Leu Ala Glu
                165                 170                 175

Pro Ser Val Thr Val Leu Glu Ala Gly Ser Pro Asp Leu Ala Val Ala
            180                 185                 190

Thr Ser Lys Thr Phe Arg Ser Leu Ala Arg Leu Thr Gly Ala Ala Pro
        195                 200                 205

Ser Met Ala Gly Pro Arg Val Lys Arg Thr Leu Thr Ala Asn Gly Leu
    210                 215                 220

Arg Gln Leu Ile Ala Phe Ile Ser Arg Met Thr Ala Val Asp Arg Ala
225                 230                 235                 240

Glu Leu Glu Gly Val Ser Ala Asp Arg Ala Pro Gln Ile Val Ala Gly
                245                 250                 255

Ala Leu Val Ala Glu Ala Ser Met Arg Ala Leu Ser Ile Glu Ala Val
            260                 265                 270
```

```
Glu Ile Cys Pro Trp Ala Leu Arg Glu Gly Leu Ile Leu Arg Lys Leu
        275                 280                 285

Asp Ser Glu Ala Asp Gly Thr Ala Leu Ile Glu Ser Ser Ser Val His
    290                 295                 300

Thr Ser Val Arg Ala Val Gly Gly Gln Pro Ala Asp Arg Asn Ala Ala
305                 310                 315                 320

Asn Arg Ser Arg Gly Ser Lys Pro
                325


<210> SEQ ID NO 7
<211> LENGTH: 996
<212> TYPE: DNA
<213> ORGANISM: Mycobacterium tuberculosis

<400> SEQUENCE: 7

catatggtcg atgcccaccg cggcggccac ccgaccccga tgagctcgac gaaggccacg     60

ctgcggctgg ccgaggccac cgacagctcg ggcaagatca ccaagcgcgg agccgacaag    120

ctgatttcca ccatcgacga attcgccaag attgccatca gctcgggctg tgccgagctg    180

atggccttcg ccacgtcggc ggtccgcgac gccgagaatt ccgaggacgt cctgtcccgg    240

gtgcgcaaag agaccggtgt cgagttgcag gcgctgcgtg gggaggacga gtcacggctg    300

accttcctgg ccgtgcgacg atggtacggg tggagcgctg ggcgcatcct caacctcgac    360

atcggcggcg gctcgctgga agtgtccagt ggcgtggacg aggagcccga gattgcgtta    420

tcgctgcccc tgggcgccgg acggttgacc cgagagtggc tgcccgacga tccgccgggc    480

cggcgccggg tggcgatgct gcgagactgg ctggatgccg agctggccga gcccagtgtg    540

accgtcctgg aagccggcag ccccgacctg gcggtcgcaa cgtcgaagac gtttcgctcg    600

ttggcgcgac taaccggtgc ggccccatcc atggccgggc cgcgggtgaa gaggacccta    660

acggcaaatg gtctgcggca actcatcgcg tttatctcta ggatgacggc ggttgaccgt    720

gcagaactgg aaggggtaag cgccgaccga gcgccgcaga ttgtggccgg cgccctggtg    780

gcagaggcga gcatgcgagc actgtcgata gaagcggtgg aaatctgccc gtgggcgctg    840

cgggaaggtc tcatcttgcg caaactcgac agcgaagccg acggaaccgc cctcatcgag    900

tcttcgtctg tgcacacttc ggtgcgtgcc gtcggaggtc agccagctga tcggaacgcg    960

gccaaccgat cgagaggcag caaaccatga aagctt                              996


<210> SEQ ID NO 8
<211> LENGTH: 348
<212> TYPE: PRT
<213> ORGANISM: Mycobacterium tuberculosis

<400> SEQUENCE: 8

Met Gly Ser Ser His His His His His His Ser Ser Gly Leu Val Pro
1               5                   10                  15

Arg Gly Ser His Met Val Asp Ala His Arg Gly Gly His Pro Thr Pro
            20                  25                  30

Met Ser Ser Thr Lys Ala Thr Leu Arg Leu Ala Glu Ala Thr Asp Ser
        35                  40                  45

Ser Gly Lys Ile Thr Lys Arg Gly Ala Asp Lys Leu Ile Ser Thr Ile
    50                  55                  60

Asp Glu Phe Ala Lys Ile Ala Ile Ser Ser Gly Cys Ala Glu Leu Met
65                  70                  75                  80

Ala Phe Ala Thr Ser Ala Val Arg Asp Ala Glu Asn Ser Glu Asp Val
```

```
                85                  90                  95

Leu Ser Arg Val Arg Lys Glu Thr Gly Val Glu Leu Gln Ala Leu Arg
            100                 105                 110

Gly Glu Asp Glu Ser Arg Leu Thr Phe Leu Ala Val Arg Arg Trp Tyr
        115                 120                 125

Gly Trp Ser Ala Gly Arg Ile Leu Asn Leu Asp Ile Gly Gly Gly Ser
    130                 135                 140

Leu Glu Val Ser Ser Gly Val Asp Glu Glu Pro Glu Ile Ala Leu Ser
145                 150                 155                 160

Leu Pro Leu Gly Ala Gly Arg Leu Thr Arg Glu Trp Leu Pro Asp Asp
                165                 170                 175

Pro Pro Gly Arg Arg Arg Val Ala Met Leu Arg Asp Trp Leu Asp Ala
            180                 185                 190

Glu Leu Ala Glu Pro Ser Val Thr Val Leu Glu Ala Gly Ser Pro Asp
        195                 200                 205

Leu Ala Val Ala Thr Ser Lys Thr Phe Arg Ser Leu Ala Arg Leu Thr
    210                 215                 220

Gly Ala Ala Pro Ser Met Ala Gly Pro Arg Val Lys Arg Thr Leu Thr
225                 230                 235                 240

Ala Asn Gly Leu Arg Gln Leu Ile Ala Phe Ile Ser Arg Met Thr Ala
                245                 250                 255

Val Asp Arg Ala Glu Leu Glu Gly Val Ser Ala Asp Arg Ala Pro Gln
            260                 265                 270

Ile Val Ala Gly Ala Leu Val Ala Glu Ala Ser Met Arg Ala Leu Ser
        275                 280                 285

Ile Glu Ala Val Glu Ile Cys Pro Trp Ala Leu Arg Glu Gly Leu Ile
    290                 295                 300

Leu Arg Lys Leu Asp Ser Glu Ala Asp Gly Thr Ala Leu Ile Glu Ser
305                 310                 315                 320

Ser Ser Val His Thr Ser Val Arg Ala Val Gly Gly Gln Pro Ala Asp
                325                 330                 335

Arg Asn Ala Ala Asn Arg Ser Arg Gly Ser Lys Pro
            340                 345
```

<210> SEQ ID NO 9
<211> LENGTH: 32
<212> TYPE: DNA
<213> ORGANISM: Artificial Sequence
<220> FEATURE:
<223> OTHER INFORMATION: Cloning primer

<400> SEQUENCE: 9
taggatccca tatggtcgat gcccaccgcg gc 32

<210> SEQ ID NO 10
<211> LENGTH: 35
<212> TYPE: DNA
<213> ORGANISM: Artificial Sequence
<220> FEATURE:
<223> OTHER INFORMATION: Cloning primer

<400> SEQUENCE: 10
tagaattcaa gctttcatgg tttgctgcct ctcga 35

<210> SEQ ID NO 11
<211> LENGTH: 94
<212> TYPE: PRT
<213> ORGANISM: Mycobacterium tuberculosis

<400> SEQUENCE: 11

```
Met Cys Gly Asp Gln Ser Asp His Val Leu Gln His Trp Thr Val Asp
1               5                   10                  15

Ile Ser Ile Asp Glu His Glu Gly Leu Thr Arg Ala Lys Ala Arg Leu
            20                  25                  30

Arg Trp Arg Glu Lys Glu Leu Val Gly Val Gly Leu Ala Arg Leu Asn
        35                  40                  45

Pro Ala Asp Arg Asn Val Pro Glu Ile Gly Asp Glu Leu Ser Val Ala
    50                  55                  60

Arg Ala Leu Ser Asp Leu Gly Lys Arg Met Leu Lys Val Ser Thr His
65                  70                  75                  80

Asp Ile Glu Ala Val Thr His Gln Pro Ala Arg Leu Leu Tyr
                85                  90
```

<210> SEQ ID NO 12
<211> LENGTH: 315
<212> TYPE: DNA
<213> ORGANISM: Mycobacterium tuberculosis

<400> SEQUENCE: 12

```
catatgcatc accatcacca tcacatgtgc ggcgaccagt cggatcacgt gctgcagcac      60

tggaccgtcg acatatcgat cgacgaacac gaaggattga ctcgggcgaa ggcacggctg     120

cgttggcggg aaaaggaatt ggtgggtgtt ggcctggcaa ggctcaatcc ggccgaccgc     180

aacgtccccg agatcggcga tgaactctcg gtcgcccgag ccttgtccga cttggggaag     240

cgaatgttga aggtgtcgac ccacgacatc gaagctgtta cccatcagcc ggcgcgattg     300

ttgtattgag aattc                                                      315
```

<210> SEQ ID NO 13
<211> LENGTH: 101
<212> TYPE: PRT
<213> ORGANISM: Mycobacterium tuberculosis

<400> SEQUENCE: 13

```
Met His His His His His His Met Cys Gly Asp Gln Ser Asp His Val
1               5                   10                  15

Leu Gln His Trp Thr Val Asp Ile Ser Ile Asp Glu His Glu Gly Leu
            20                  25                  30

Thr Arg Ala Lys Ala Arg Leu Arg Trp Arg Glu Lys Glu Leu Val Gly
        35                  40                  45

Val Gly Leu Ala Arg Leu Asn Pro Ala Asp Arg Asn Val Pro Glu Ile
    50                  55                  60

Gly Asp Glu Leu Ser Val Ala Arg Ala Leu Ser Asp Leu Gly Lys Arg
65                  70                  75                  80

Met Leu Lys Val Ser Thr His Asp Ile Glu Ala Val Thr His Gln Pro
                85                  90                  95

Ala Arg Leu Leu Tyr
            100
```

<210> SEQ ID NO 14
<211> LENGTH: 51
<212> TYPE: DNA
<213> ORGANISM: Artificial Sequence
<220> FEATURE:
<223> OTHER INFORMATION: Cloning primer

<400> SEQUENCE: 14
caattacata tgcatcacca tcaccatcac atgtgcggcg accagtcgga t 51

<210> SEQ ID NO 15
<211> LENGTH: 33
<212> TYPE: DNA
<213> ORGANISM: Artificial Sequence
<220> FEATURE:
<223> OTHER INFORMATION: Cloning primer

<400> SEQUENCE: 15
caattagaat tctcaataca acaatcgcgc cgg 33

<210> SEQ ID NO 16
<211> LENGTH: 143
<212> TYPE: PRT
<213> ORGANISM: Mycobacterium tuberculosis

<400> SEQUENCE: 16

Met Ile Thr Asn Leu Arg Arg Arg Thr Ala Met Ala Ala Ala Gly Leu
1 5 10 15

Gly Ala Ala Leu Gly Leu Gly Ile Leu Leu Val Pro Thr Val Asp Ala
20 25 30

His Leu Ala Asn Gly Ser Met Ser Glu Val Met Met Ser Glu Ile Ala
35 40 45

Gly Leu Pro Ile Pro Pro Ile Ile His Tyr Gly Ala Ile Ala Tyr Ala
50 55 60

Pro Ser Gly Ala Ser Gly Lys Ala Trp His Gln Arg Thr Pro Ala Arg
65 70 75 80

Ala Glu Gln Val Ala Leu Glu Lys Cys Gly Asp Lys Thr Cys Lys Val
85 90 95

Val Ser Arg Phe Thr Arg Cys Gly Ala Val Ala Tyr Asn Gly Ser Lys
100 105 110

Tyr Gln Gly Gly Thr Gly Leu Thr Arg Arg Ala Ala Glu Asp Asp Ala
115 120 125

Val Asn Arg Leu Glu Gly Gly Arg Ile Val Asn Trp Ala Cys Asn
130 135 140

<210> SEQ ID NO 17
<211> LENGTH: 363
<212> TYPE: DNA
<213> ORGANISM: Mycobacterium tuberculosis

<400> SEQUENCE: 17
catatgcatc accatcacca tcatctcgcc aacggttcga tgtcggaagt catgatgtcg 60
gaaattgccg ggttgcctat ccctccgatt atccattacg gggcgattgc ctatgccccc 120
agcggcgcgt cgggcaaagc gtggcaccag cgcacaccgg cgcgagcaga gcaagtcgca 180
ctagaaaagt gcggtgacaa gacttgcaaa gtggttagtc gcttcaccag gtgcggcgcg 240
gtcgcctaca acggctcgaa ataccaaggc ggaaccggac tcacgcgccg cgcggcagaa 300
gacgacgccg tgaaccgact cgaaggcggg cggatcgtca actgggcgtg caactaagaa 360
ttc 363

<210> SEQ ID NO 18
<211> LENGTH: 117
<212> TYPE: PRT
<213> ORGANISM: Mycobacterium tuberculosis

<400> SEQUENCE: 18

```
Met His His His His His His Leu Ala Asn Gly Ser Met Ser Glu Val
1               5                   10                  15

Met Met Ser Glu Ile Ala Gly Leu Pro Ile Pro Pro Ile Ile His Tyr
            20                  25                  30

Gly Ala Ile Ala Tyr Ala Pro Ser Gly Ala Ser Gly Lys Ala Trp His
        35                  40                  45

Gln Arg Thr Pro Ala Arg Ala Glu Gln Val Ala Leu Glu Lys Cys Gly
    50                  55                  60

Asp Lys Thr Cys Lys Val Val Ser Arg Phe Thr Arg Cys Gly Ala Val
65                  70                  75                  80

Ala Tyr Asn Gly Ser Lys Tyr Gln Gly Gly Thr Gly Leu Thr Arg Arg
                85                  90                  95

Ala Ala Glu Asp Asp Ala Val Asn Arg Leu Glu Gly Gly Arg Ile Val
            100                 105                 110

Asn Trp Ala Cys Asn
        115


<210> SEQ ID NO 19
<211> LENGTH: 51
<212> TYPE: DNA
<213> ORGANISM: Artificial Sequence
<220> FEATURE:
<223> OTHER INFORMATION: Cloning primer

<400> SEQUENCE: 19

caattacata tgcatcacca tcaccatcac catctcgcca acggttcgat g              51


<210> SEQ ID NO 20
<211> LENGTH: 33
<212> TYPE: DNA
<213> ORGANISM: Artificial Sequence
<220> FEATURE:
<223> OTHER INFORMATION: Cloning primer

<400> SEQUENCE: 20

caattagaat tcttagttgc acgcccagtt gac                                  33


<210> SEQ ID NO 21
<211> LENGTH: 154
<212> TYPE: PRT
<213> ORGANISM: Mycobacterium tuberculosis

<400> SEQUENCE: 21

Met Thr Pro Gly Leu Leu Thr Thr Ala Gly Ala Gly Arg Pro Arg Asp
1               5                   10                  15

Arg Cys Ala Arg Ile Val Cys Thr Val Phe Ile Glu Thr Ala Val Val
            20                  25                  30

Ala Thr Met Phe Val Ala Leu Leu Gly Leu Ser Thr Ile Ser Ser Lys
        35                  40                  45

Ala Asp Asp Ile Asp Trp Asp Ala Ile Ala Gln Cys Glu Ser Gly Gly
    50                  55                  60

Asn Trp Ala Ala Asn Thr Gly Asn Gly Leu Tyr Gly Gly Leu Gln Ile
65                  70                  75                  80

Ser Gln Ala Thr Trp Asp Ser Asn Gly Gly Val Gly Ser Pro Ala Ala
                85                  90                  95

Ala Ser Pro Gln Gln Gln Ile Glu Val Ala Asp Asn Ile Met Lys Thr
            100                 105                 110

Gln Gly Pro Gly Ala Trp Pro Lys Cys Ser Ser Cys Ser Gln Gly Asp
```

-continued

```
        115                 120                 125

Ala Pro Leu Gly Ser Leu Thr His Ile Leu Thr Phe Leu Ala Ala Glu
    130                 135                 140

Thr Gly Gly Cys Ser Gly Ser Arg Asp Asp
145                 150


<210> SEQ ID NO 22
<211> LENGTH: 347
<212> TYPE: DNA
<213> ORGANISM: Mycobacterium tuberculosis

<400> SEQUENCE: 22

catatgcatc accatcacca tcacgacgac atcgattggg acgccatcgc gcaatgcgaa      60

tccggcggca attgggcggc caacaccggt aacgggttat acggtggtct gcagatcagc     120

caggcgacgt gggattccaa cggtggtgtc gggtcgccgg cggccgcgag tccccagcaa     180

cagatcgagg tcgcagacaa cattatgaaa acccaaggcc cgggtgcgtg gccgaaatgt     240

agttcttgta gtcagggaga cgcaccgctg ggctgctcac ccacatcctg acgttcctcg     300

cggccgagac tggaggttgt tcggggagca gggacgattg agaattc                   347


<210> SEQ ID NO 23
<211> LENGTH: 112
<212> TYPE: PRT
<213> ORGANISM: Mycobacterium tuberculosis

<400> SEQUENCE: 23

Met His His His His His His Asp Asp Ile Asp Trp Asp Ala Ile Ala
1               5                   10                  15

Gln Cys Glu Ser Gly Gly Asn Trp Ala Ala Asn Thr Gly Asn Gly Leu
            20                  25                  30

Tyr Gly Gly Leu Gln Ile Ser Gln Ala Thr Trp Asp Ser Asn Gly Gly
        35                  40                  45

Val Gly Ser Pro Ala Ala Ala Ser Pro Gln Gln Gln Ile Glu Val Ala
    50                  55                  60

Asp Asn Ile Met Lys Thr Gln Gly Pro Gly Ala Trp Pro Lys Cys Ser
65                  70                  75                  80

Ser Cys Ser Gln Gly Asp Ala Pro Leu Gly Ser Leu Thr His Ile Leu
                85                  90                  95

Thr Phe Leu Ala Ala Glu Thr Gly Gly Cys Ser Gly Ser Arg Asp Asp
            100                 105                 110


<210> SEQ ID NO 24
<211> LENGTH: 51
<212> TYPE: DNA
<213> ORGANISM: Artificial Sequence
<220> FEATURE:
<223> OTHER INFORMATION: Cloning primer

<400> SEQUENCE: 24

caattacata tgcatcacca tcaccatcac gacgacatcg attgggacgc c               51


<210> SEQ ID NO 25
<211> LENGTH: 33
<212> TYPE: DNA
<213> ORGANISM: Artificial Sequence
<220> FEATURE:
<223> OTHER INFORMATION: Cloning primer

<400> SEQUENCE: 25
```

```
caattagaat tctcaatcgt ccctgctccc cga                                    33


<210> SEQ ID NO 26
<211> LENGTH: 580
<212> TYPE: PRT
<213> ORGANISM: Mycobacterium tuberculosis

<400> SEQUENCE: 26

Met Asn Phe Ala Val Leu Pro Pro Glu Val Asn Ser Ala Arg Ile Phe
1               5                   10                  15

Ala Gly Ala Gly Leu Gly Pro Met Leu Ala Ala Ala Ser Ala Trp Asp
            20                  25                  30

Gly Leu Ala Glu Glu Leu His Ala Ala Ala Gly Ser Phe Ala Ser Val
        35                  40                  45

Thr Thr Gly Leu Ala Gly Asp Ala Trp His Gly Pro Ala Ser Leu Ala
    50                  55                  60

Met Thr Arg Ala Ala Ser Pro Tyr Val Gly Trp Leu Asn Thr Ala Ala
65                  70                  75                  80

Gly Gln Ala Ala Gln Ala Ala Gly Gln Ala Arg Leu Ala Ala Ser Ala
                85                  90                  95

Phe Glu Ala Thr Leu Ala Ala Thr Val Ser Pro Ala Met Val Ala Ala
            100                 105                 110

Asn Arg Thr Arg Leu Ala Ser Leu Val Ala Ala Asn Leu Leu Gly Gln
        115                 120                 125

Asn Ala Pro Ala Ile Ala Ala Ala Glu Ala Glu Tyr Glu Gln Ile Trp
    130                 135                 140

Ala Gln Asp Val Ala Ala Met Phe Gly Tyr His Ser Ala Ala Ser Ala
145                 150                 155                 160

Val Ala Thr Gln Leu Ala Pro Ile Gln Glu Gly Leu Gln Gln Gln Leu
                165                 170                 175

Gln Asn Val Leu Ala Gln Leu Ala Ser Gly Asn Leu Gly Ser Gly Asn
            180                 185                 190

Val Gly Val Gly Asn Ile Gly Asn Asp Asn Ile Gly Asn Ala Asn Ile
        195                 200                 205

Gly Phe Gly Asn Arg Gly Asp Ala Asn Ile Gly Ile Gly Asn Ile Gly
    210                 215                 220

Asp Arg Asn Leu Gly Ile Gly Asn Thr Gly Asn Trp Asn Ile Gly Ile
225                 230                 235                 240

Gly Ile Thr Gly Asn Gly Gln Ile Gly Phe Gly Lys Pro Ala Asn Pro
                245                 250                 255

Asp Val Leu Val Val Gly Asn Gly Gly Pro Gly Val Thr Ala Leu Val
            260                 265                 270

Met Gly Gly Thr Asp Ser Leu Leu Pro Leu Pro Asn Ile Pro Leu Leu
        275                 280                 285

Glu Tyr Ala Ala Arg Phe Ile Thr Pro Val His Pro Gly Tyr Thr Ala
    290                 295                 300

Thr Phe Leu Glu Thr Pro Ser Gln Phe Phe Pro Phe Thr Gly Leu Asn
305                 310                 315                 320

Ser Leu Thr Tyr Asp Val Ser Val Ala Gln Gly Val Thr Asn Leu His
                325                 330                 335

Thr Ala Ile Met Ala Gln Leu Ala Ala Gly Asn Glu Val Val Val Phe
            340                 345                 350

Gly Thr Ser Gln Ser Ala Thr Ile Ala Thr Phe Glu Met Arg Tyr Leu
        355                 360                 365
```

```
Gln Ser Leu Pro Ala His Leu Arg Pro Gly Leu Asp Glu Leu Ser Phe
    370                 375                 380

Thr Leu Thr Gly Asn Pro Asn Arg Pro Asp Gly Gly Ile Leu Thr Arg
385                 390                 395                 400

Phe Gly Phe Ser Ile Pro Gln Leu Gly Phe Thr Leu Ser Gly Ala Thr
                405                 410                 415

Pro Ala Asp Ala Tyr Pro Thr Val Asp Tyr Ala Phe Gln Tyr Asp Gly
            420                 425                 430

Val Asn Asp Phe Pro Lys Tyr Pro Leu Asn Val Phe Ala Thr Ala Asn
        435                 440                 445

Ala Ile Ala Gly Ile Leu Phe Leu His Ser Gly Leu Ile Ala Leu Pro
    450                 455                 460

Pro Asp Leu Ala Ser Gly Val Val Gln Pro Val Ser Ser Pro Asp Val
465                 470                 475                 480

Leu Thr Thr Tyr Ile Leu Leu Pro Ser Gln Asp Leu Pro Leu Leu Val
                485                 490                 495

Pro Leu Arg Ala Ile Pro Leu Leu Gly Asn Pro Leu Ala Asp Leu Ile
            500                 505                 510

Gln Pro Asp Leu Arg Val Leu Val Glu Leu Gly Tyr Asp Arg Thr Ala
        515                 520                 525

His Gln Asp Val Pro Ser Pro Phe Gly Leu Phe Pro Asp Val Asp Trp
    530                 535                 540

Ala Glu Val Ala Ala Asp Leu Gln Gln Gly Ala Val Gln Gly Val Asn
545                 550                 555                 560

Asp Ala Leu Ser Gly Leu Gly Leu Pro Pro Pro Trp Gln Pro Ala Leu
                565                 570                 575

Pro Arg Leu Phe
            580
```

<210> SEQ ID NO 27
<211> LENGTH: 1752
<212> TYPE: DNA
<213> ORGANISM: Mycobacterium tuberculosis

<400> SEQUENCE: 27

```
catatgaatt tcgccgtttt gccgccggag gtgaattcgg cgcgcatatt cgccggtgcg      60

ggcctgggcc caatgctggc ggcggcgtcg gcctgggacg ggttggccga ggagttgcat     120

gccgcggcgg gctcgttcgc gtcggtgacc accgggttgg cgggcgacgc gtggcatggt     180

ccggcgtcgc tggcgatgac ccgcgcggcc agcccgtatg tggggtggtt gaacacggcg     240

gcgggtcagg ccgcgcaggc ggccggccag gcgcggctag cggcgagcgc gttcgaggcg     300

acgctggcgg ccaccgtgtc tccagcgatg gtcgcggcca accggacacg gctggcgtcg     360

ctggtggcag ccaacttgct gggccagaac gccccggcga tcgcggccgc ggaggctgaa     420

tacgagcaga tatgggccca ggacgtggcc gcgatgttcg gctatcactc cgccgcgtcg     480

gcggtggcca cgcagctggc gcctattcaa gagggtttgc agcagcagct gcaaaacgtg     540

ctggcccagt tggctagcgg gaacctgggc agcggaaatg tgggcgtcgg caacatcggc     600

aacgacaaca ttggcaacgc aaacatcggc ttcggaaatc gaggcgacgc caacatcggc     660

atcgggaata tcggcgacag aaacctcggc attgggaaca ccggcaattg gaatatcggc     720

atcggcatca ccggcaacgg acaaatcggc ttcggcaagc ctgccaaccc cgacgtcttg     780

gtggtgggca acggcggccc gggagtaacc gcgttggtca tgggcggcac cgacagccta     840

ctgccgctgc ccaacatccc cttactcgag tacgctgcgc ggttcatcac ccccgtgcat     900
```

```
cccggataca ccgctacgtt cctggaaacg ccatcgcagt ttttcccatt caccgggctg    960

aatagcctga cctatgacgt ctccgtggcc cagggcgtaa cgaatctgca caccgcgatc   1020

atggcgcaac tcgcggcggg aaacgaagtc gtcgtcttcg gcacctccca aagcgccacg   1080

atagccacct tcgaaatgcg ctatctgcaa tccctgccag cacacctgcg tccgggtctc   1140

gacgaattgt cctttacgtt gaccggcaat cccaaccggc ccgacggtgg cattcttacg   1200

cgttttggct tctccatacc gcagttgggt ttcacattgt ccggcgcgac gcccgccgac   1260

gcctacccca ccgtcgatta cgcgttccag tacgacggcg tcaacgactt ccccaaatac   1320

ccgctgaatg tcttcgcgac cgccaacgcg atcgcgggca tccttttcct gcactccggg   1380

ttgattgcgt tgccgcccga tcttgcctcg ggcgtggttc aaccggtgtc ctcaccggac   1440

gtcctgacca cctacatcct gctgcccagc caagatctgc cgctgctggt cccgctgcgt   1500

gctatccccc tgctgggaaa cccgcttgcc gacctcatcc agccggactt gcgggtgctc   1560

gtcgagttgg gttatgaccg caccgcccac caggacgtgc ccagcccgtt cggactgttt   1620

ccggacgtcg attgggccga ggtggccgcg gacctgcagc aaggcgccgt gcaaggcgtc   1680

aacgacgccc tgtccggact ggggctgccg ccgccgtggc agccggcgct accccgactt   1740

ttctaaaagc tt                                                       1752
```

<210> SEQ ID NO 28
<211> LENGTH: 600
<212> TYPE: PRT
<213> ORGANISM: Mycobacterium tuberculosis

<400> SEQUENCE: 28

```
Met Gly Ser Ser His His His His His His Ser Ser Gly Leu Val Pro
1               5                   10                  15

Arg Gly Ser His Met Asn Phe Ala Val Leu Pro Pro Glu Val Asn Ser
            20                  25                  30

Ala Arg Ile Phe Ala Gly Ala Gly Leu Gly Pro Met Leu Ala Ala Ala
        35                  40                  45

Ser Ala Trp Asp Gly Leu Ala Glu Glu Leu His Ala Ala Ala Gly Ser
    50                  55                  60

Phe Ala Ser Val Thr Thr Gly Leu Ala Gly Asp Ala Trp His Gly Pro
65                  70                  75                  80

Ala Ser Leu Ala Met Thr Arg Ala Ala Ser Pro Tyr Val Gly Trp Leu
                85                  90                  95

Asn Thr Ala Ala Gly Gln Ala Ala Gln Ala Ala Gly Gln Ala Arg Leu
            100                 105                 110

Ala Ala Ser Ala Phe Glu Ala Thr Leu Ala Ala Thr Val Ser Pro Ala
        115                 120                 125

Met Val Ala Ala Asn Arg Thr Arg Leu Ala Ser Leu Val Ala Ala Asn
    130                 135                 140

Leu Leu Gly Gln Asn Ala Pro Ala Ile Ala Ala Ala Glu Ala Glu Tyr
145                 150                 155                 160

Glu Gln Ile Trp Ala Gln Asp Val Ala Ala Met Phe Gly Tyr His Ser
                165                 170                 175

Ala Ala Ser Ala Val Ala Thr Gln Leu Ala Pro Ile Gln Glu Gly Leu
            180                 185                 190

Gln Gln Gln Leu Gln Asn Val Leu Ala Gln Leu Ala Ser Gly Asn Leu
        195                 200                 205

Gly Ser Gly Asn Val Gly Val Gly Asn Ile Gly Asn Asp Asn Ile Gly
```

```
    210                 215                 220

Asn Ala Asn Ile Gly Phe Gly Asn Arg Gly Asp Ala Asn Ile Gly Ile
225                 230                 235                 240

Gly Asn Ile Gly Asp Arg Asn Leu Gly Ile Gly Asn Thr Gly Asn Trp
                245                 250                 255

Asn Ile Gly Ile Gly Ile Thr Gly Asn Gly Gln Ile Gly Phe Gly Lys
            260                 265                 270

Pro Ala Asn Pro Asp Val Leu Val Val Gly Asn Gly Gly Pro Gly Val
        275                 280                 285

Thr Ala Leu Val Met Gly Gly Thr Asp Ser Leu Leu Pro Leu Pro Asn
    290                 295                 300

Ile Pro Leu Leu Glu Tyr Ala Ala Arg Phe Ile Thr Pro Val His Pro
305                 310                 315                 320

Gly Tyr Thr Ala Thr Phe Leu Glu Thr Pro Ser Gln Phe Phe Pro Phe
                325                 330                 335

Thr Gly Leu Asn Ser Leu Thr Tyr Asp Val Ser Val Ala Gln Gly Val
            340                 345                 350

Thr Asn Leu His Thr Ala Ile Met Ala Gln Leu Ala Ala Gly Asn Glu
        355                 360                 365

Val Val Val Phe Gly Thr Ser Gln Ser Ala Thr Ile Ala Thr Phe Glu
    370                 375                 380

Met Arg Tyr Leu Gln Ser Leu Pro Ala His Leu Arg Pro Gly Leu Asp
385                 390                 395                 400

Glu Leu Ser Phe Thr Leu Thr Gly Asn Pro Asn Arg Pro Asp Gly Gly
                405                 410                 415

Ile Leu Thr Arg Phe Gly Phe Ser Ile Pro Gln Leu Gly Phe Thr Leu
            420                 425                 430

Ser Gly Ala Thr Pro Ala Asp Ala Tyr Pro Thr Val Asp Tyr Ala Phe
        435                 440                 445

Gln Tyr Asp Gly Val Asn Asp Phe Pro Lys Tyr Pro Leu Asn Val Phe
    450                 455                 460

Ala Thr Ala Asn Ala Ile Ala Gly Ile Leu Phe Leu His Ser Gly Leu
465                 470                 475                 480

Ile Ala Leu Pro Pro Asp Leu Ala Ser Gly Val Val Gln Pro Val Ser
                485                 490                 495

Ser Pro Asp Val Leu Thr Thr Tyr Ile Leu Leu Pro Ser Gln Asp Leu
            500                 505                 510

Pro Leu Leu Val Pro Leu Arg Ala Ile Pro Leu Leu Gly Asn Pro Leu
        515                 520                 525

Ala Asp Leu Ile Gln Pro Asp Leu Arg Val Leu Val Glu Leu Gly Tyr
    530                 535                 540

Asp Arg Thr Ala His Gln Asp Val Pro Ser Pro Phe Gly Leu Phe Pro
545                 550                 555                 560

Asp Val Asp Trp Ala Glu Val Ala Ala Asp Leu Gln Gln Gly Ala Val
                565                 570                 575

Gln Gly Val Asn Asp Ala Leu Ser Gly Leu Gly Leu Pro Pro Pro Trp
            580                 585                 590

Gln Pro Ala Leu Pro Arg Leu Phe
        595                 600
```

<210> SEQ ID NO 29
<211> LENGTH: 32
<212> TYPE: DNA
<213> ORGANISM: Artificial Sequence
<220> FEATURE:
<223> OTHER INFORMATION: Cloning primer

<400> SEQUENCE: 29
taggatccca tatgaatttc gccgttttgc cg 32

<210> SEQ ID NO 30
<211> LENGTH: 36
<212> TYPE: DNA
<213> ORGANISM: Artificial Sequence
<220> FEATURE:
<223> OTHER INFORMATION: Cloning primer

<400> SEQUENCE: 30
tagaattcaa gcttttagaa aagtcggggt agcgcc 36

<210> SEQ ID NO 31
<211> LENGTH: 87
<212> TYPE: PRT
<213> ORGANISM: Mycobacterium tuberculosis

<400> SEQUENCE: 31

```
Met Pro Tyr Thr Val Arg Phe Thr Thr Thr Ala Arg Arg Asp Leu His
1               5                   10                  15

Lys Leu Pro Pro Arg Ile Leu Ala Ala Val Val Glu Phe Ala Phe Gly
            20                  25                  30

Asp Leu Ser Arg Glu Pro Leu Arg Val Gly Lys Pro Leu Arg Arg Glu
        35                  40                  45

Leu Ala Gly Thr Phe Ser Ala Arg Arg Gly Thr Tyr Arg Leu Leu Tyr
    50                  55                  60

Arg Ile Asp Asp Glu His Thr Thr Val Val Ile Leu Arg Val Asp His
65                  70                  75                  80

Arg Ala Asp Ile Tyr Arg Arg
                85
```

<210> SEQ ID NO 32
<211> LENGTH: 33
<212> TYPE: DNA
<213> ORGANISM: Artificial Sequence
<220> FEATURE:
<223> OTHER INFORMATION: Cloning primer

<400> SEQUENCE: 32
caattacata tgccttccac cgtgcccttc acc 33

<210> SEQ ID NO 33
<211> LENGTH: 36
<212> TYPE: DNA
<213> ORGANISM: Artificial Sequence
<220> FEATURE:
<223> OTHER INFORMATION: Cloning primer

<400> SEQUENCE: 33
caattaaagc ttctatcggc ggtagatgtc cgcgcg 36

<210> SEQ ID NO 34
<211> LENGTH: 330
<212> TYPE: DNA
<213> ORGANISM: Mycobacterium tuberculosis

<400> SEQUENCE: 34
atgggcagca gccatcatca tcatcatcac agcagcggcc tggtgccgcg cggcagccat 60

-continued

```
atgccttaca ccgtgcggtt caccacaacc gcgcgtcgag acctccacaa gctgccaccg    120

cgcatcctcg cggcagtggt cgaattcgcg ttcggcgatc tgtcgcgcga gcccctgcgg    180

gtgggcaagc cccttcggcg cgagttggcc ggcacgttca gcgcgcgtcg cggaacgtac    240

cgcctgctgt accggattga cgacgagcac acaacggtag tgatcctgcg cgtcgatcac    300

cgcgcggaca tctaccgccg atagaagctt                                      330
```

```
<210> SEQ ID NO 35
<211> LENGTH: 107
<212> TYPE: PRT
<213> ORGANISM: Mycobacterium tuberculosis
<220> FEATURE:
<221> NAME/KEY: VARIANT
<222> LOCATION: 21
<223> OTHER INFORMATION: Xaa = Any Amino Acid

<400> SEQUENCE: 35

Met Gly Ser Ser His His His His His His Ser Ser Gly Leu Val Pro
1               5                   10                  15

Arg Gly Ser His Xaa Pro Tyr Thr Val Arg Phe Thr Thr Thr Ala Arg
            20                  25                  30

Arg Asp Leu His Lys Leu Pro Pro Arg Ile Leu Ala Ala Val Val Glu
        35                  40                  45

Phe Ala Phe Gly Asp Leu Ser Arg Glu Pro Leu Arg Val Gly Lys Pro
    50                  55                  60

Leu Arg Arg Glu Leu Ala Gly Thr Phe Ser Ala Arg Arg Gly Thr Tyr
65                  70                  75                  80

Arg Leu Leu Tyr Arg Ile Asp Asp Glu His Thr Thr Val Val Ile Leu
                85                  90                  95

Arg Val Asp His Arg Ala Asp Ile Tyr Arg Arg
            100                 105


<210> SEQ ID NO 36
<211> LENGTH: 97
<212> TYPE: PRT
<213> ORGANISM: Mycobacterium tuberculosis

<400> SEQUENCE: 36

Met Ser Leu Leu Asp Ala His Ile Pro Gln Leu Ile Ala Ser His Thr
1               5                   10                  15

Ala Phe Ala Ala Lys Ala Gly Leu Met Arg His Thr Ile Gly Gln Ala
            20                  25                  30

Glu Gln Gln Ala Met Ser Ala Gln Ala Phe His Gln Gly Glu Ser Ala
        35                  40                  45

Ala Ala Phe Gln Gly Ala His Ala Arg Phe Val Ala Ala Ala Ala Lys
    50                  55                  60

Val Asn Thr Leu Leu Asp Ile Ala Gln Ala Asn Leu Gly Glu Ala Ala
65                  70                  75                  80

Gly Thr Tyr Val Ala Ala Asp Ala Ala Ala Ala Ser Ser Tyr Thr Gly
                85                  90                  95

Phe


<210> SEQ ID NO 37
<211> LENGTH: 303
<212> TYPE: DNA
<213> ORGANISM: Mycobacterium tuberculosis

<400> SEQUENCE: 37
```

catatgagtt tgttggatgc ccatattccg cagttgatcg cttcgcatac ggcgtttgcc 60
gctaaggcgg ggttgatgcg gcatacgatc ggtcaggccg agcagcaggc gatgtcggcg 120
caggcgtttc atcagggaga gtccgcggcg gcgtttcagg gtgcgcatgc ccggtttgtg 180
gccgcggccg ccaaggtcaa taccttgctg gatatcgcgc aagccaattt gggtgaggcc 240
gcgggcacgt atgtggccgc cgatgccgcc gccgcgtcca gctacaccgg gttttaaaag 300
ctt 303

<210> SEQ ID NO 38
<211> LENGTH: 117
<212> TYPE: PRT
<213> ORGANISM: Mycobacterium tuberculosis

<400> SEQUENCE: 38

Met Gly Ser Ser His His His His His His Ser Ser Gly Leu Val Pro
1 5 10 15

Arg Gly Ser His Met Ser Leu Leu Asp Ala His Ile Pro Gln Leu Ile
20 25 30

Ala Ser His Thr Ala Phe Ala Ala Lys Ala Gly Leu Met Arg His Thr
35 40 45

Ile Gly Gln Ala Glu Gln Gln Ala Met Ser Ala Gln Ala Phe His Gln
50 55 60

Gly Glu Ser Ala Ala Ala Phe Gln Gly Ala His Ala Arg Phe Val Ala
65 70 75 80

Ala Ala Ala Lys Val Asn Thr Leu Leu Asp Ile Ala Gln Ala Asn Leu
85 90 95

Gly Glu Ala Ala Gly Thr Tyr Val Ala Ala Asp Ala Ala Ala Ala Ser
100 105 110

Ser Tyr Thr Gly Phe
115

<210> SEQ ID NO 39
<211> LENGTH: 34
<212> TYPE: DNA
<213> ORGANISM: Artificial Sequence
<220> FEATURE:
<223> OTHER INFORMATION: Cloning primer

<400> SEQUENCE: 39
taggatccca tatgagtttg ttggatgccc atat 34

<210> SEQ ID NO 40
<211> LENGTH: 36
<212> TYPE: DNA
<213> ORGANISM: Artificial Sequence
<220> FEATURE:
<223> OTHER INFORMATION: Cloning primer

<400> SEQUENCE: 40
tagaattcaa gcttttaaaa cccggtgtag ctggac 36

<210> SEQ ID NO 41
<211> LENGTH: 393
<212> TYPE: PRT
<213> ORGANISM: Mycobacterium tuberculosis

<400> SEQUENCE: 41

Val Val Asp Phe Gly Ala Leu Pro Pro Glu Ile Asn Ser Ala Arg Met
1 5 10 15

```
Tyr Ala Gly Pro Gly Ser Ala Ser Leu Val Ala Ala Ala Lys Met Trp
            20                  25                  30

Asp Ser Val Ala Ser Asp Leu Phe Ser Ala Ala Ser Ala Phe Gln Ser
        35                  40                  45

Val Val Trp Gly Leu Thr Val Gly Ser Trp Ile Gly Ser Ser Ala Gly
    50                  55                  60

Leu Met Ala Ala Ala Ala Ser Pro Tyr Val Ala Trp Met Ser Val Thr
65                  70                  75                  80

Ala Gly Gln Ala Gln Leu Thr Ala Ala Gln Val Arg Val Ala Ala Ala
                85                  90                  95

Ala Tyr Glu Thr Ala Tyr Arg Leu Thr Val Pro Pro Pro Val Ile Ala
            100                 105                 110

Glu Asn Arg Thr Glu Leu Met Thr Leu Thr Ala Thr Asn Leu Leu Gly
        115                 120                 125

Gln Asn Thr Pro Ala Ile Glu Ala Asn Gln Ala Ala Tyr Ser Gln Met
    130                 135                 140

Trp Gly Gln Asp Ala Glu Ala Met Tyr Gly Tyr Ala Ala Thr Ala Ala
145                 150                 155                 160

Thr Ala Thr Glu Ala Leu Leu Pro Phe Glu Asp Ala Pro Leu Ile Thr
                165                 170                 175

Asn Pro Gly Gly Leu Leu Glu Gln Ala Val Ala Val Glu Glu Ala Ile
            180                 185                 190

Asp Thr Ala Ala Ala Asn Gln Leu Met Asn Asn Val Pro Gln Ala Leu
        195                 200                 205

Gln Gln Leu Ala Gln Pro Ala Gln Gly Val Val Pro Ser Ser Lys Leu
    210                 215                 220

Gly Gly Leu Trp Thr Ala Val Ser Pro His Leu Ser Pro Leu Ser Asn
225                 230                 235                 240

Val Ser Ser Ile Ala Asn Asn His Met Ser Met Met Gly Thr Gly Val
                245                 250                 255

Ser Met Thr Asn Thr Leu His Ser Met Leu Lys Gly Leu Ala Pro Ala
            260                 265                 270

Ala Ala Gln Ala Val Glu Thr Ala Ala Glu Asn Gly Val Trp Ala Met
        275                 280                 285

Ser Ser Leu Gly Ser Gln Leu Gly Ser Ser Leu Gly Ser Ser Gly Leu
    290                 295                 300

Gly Ala Gly Val Ala Ala Asn Leu Gly Arg Ala Ala Ser Val Gly Ser
305                 310                 315                 320

Leu Ser Val Pro Pro Ala Trp Ala Ala Ala Asn Gln Ala Val Thr Pro
                325                 330                 335

Ala Ala Arg Ala Leu Pro Leu Thr Ser Leu Thr Ser Ala Ala Gln Thr
            340                 345                 350

Ala Pro Gly His Met Leu Gly Gly Leu Pro Leu Gly His Ser Val Asn
        355                 360                 365

Ala Gly Ser Gly Ile Asn Asn Ala Leu Arg Val Pro Ala Arg Ala Tyr
    370                 375                 380

Ala Ile Pro Arg Thr Pro Ala Ala Gly
385                 390
```

<210> SEQ ID NO 42
<211> LENGTH: 1191
<212> TYPE: DNA
<213> ORGANISM: Mycobacterium tuberculosis

<400> SEQUENCE: 42

```
catatggtgg atttcggggc gttaccaccg gagatcaact ccgcgaggat gtacgccggc     60

ccgggttcgg cctcgctggt ggccgccgcg aagatgtggg acagcgtggc gagtgacctg    120

ttttcggccg cgtcggcgtt tcagtcggtg gtctggggtc tgacggtggg gtcgtggata    180

ggttcgtcgg cgggtctgat ggcggcggcg gcctcgccgt atgtggcgtg gatgagcgtc    240

accgcggggc aggcccagct gaccgccgcc caggtccggg ttgctgcggc ggcctacgag    300

acagcgtata ggctgacggt gcccccgccg gtgatcgccg agaaccgtac cgaactgatg    360

acgctgaccg cgaccaacct cttggggcaa aacacgccgg cgatcgaggc caatcaggcc    420

gcatacagcc agatgtgggg ccaagacgcg gaggcgatgt atggctacgc cgccacggcg    480

gcgacggcga ccgaggcgtt gctgccgttc gaggacgccc cactgatcac caaccccggc    540

gggctccttg agcaggccgt cgcggtcgag gaggccatcg acaccgccgc ggcgaaccag    600

ttgatgaaca atgtgcccca agcgctgcaa cagctggccc agccagcgca gggcgtcgta    660

ccttcttcca agctgggtgg gctgtggacg gcggtctcgc cgcatctgtc gccgctcagc    720

aacgtcagtt cgatagccaa caaccacatg tcgatgatgg gcacgggtgt gtcgatgacc    780

aacaccttgc actcgatgtt gaagggctta gctccggcgg cggctcaggc cgtggaaacc    840

gcggcggaaa acggggtctg ggcgatgagc tcgctgggca gccagctggg ttcgtcgctg    900

ggttcttcgg gtctgggcgc tggggtggcc gccaacttgg gtcgggcggc ctcggtcggt    960

tcgttgtcgg tgccgccagc atgggccgcg gccaaccagg cggtcacccc ggcggcgcgg   1020

gcgctgccgc tgaccagcct gaccagcgcc gcccaaaccg cccccggaca catgctgggc   1080

gggctaccgc tggggcactc ggtcaacgcc ggcagcggta tcaacaatgc gctgcgggtg   1140

ccggcacggg cctacgcgat accccgcaca ccggccgccg gatagaagct t            1191
```

<210> SEQ ID NO 43
<211> LENGTH: 413
<212> TYPE: PRT
<213> ORGANISM: Mycobacterium tuberculosis

<400> SEQUENCE: 43

```
Met Gly Ser Ser His His His His His His Ser Ser Gly Leu Val Pro
1               5                   10                  15

Arg Gly Ser His Met Val Asp Phe Gly Ala Leu Pro Pro Glu Ile Asn
            20                  25                  30

Ser Ala Arg Met Tyr Ala Gly Pro Gly Ser Ala Ser Leu Val Ala Ala
        35                  40                  45

Ala Lys Met Trp Asp Ser Val Ala Ser Asp Leu Phe Ser Ala Ala Ser
    50                  55                  60

Ala Phe Gln Ser Val Val Trp Gly Leu Thr Val Gly Ser Trp Ile Gly
65                  70                  75                  80

Ser Ser Ala Gly Leu Met Ala Ala Ala Ala Ser Pro Tyr Val Ala Trp
                85                  90                  95

Met Ser Val Thr Ala Gly Gln Ala Gln Leu Thr Ala Ala Gln Val Arg
            100                 105                 110

Val Ala Ala Ala Ala Tyr Glu Thr Ala Tyr Arg Leu Thr Val Pro Pro
        115                 120                 125

Pro Val Ile Ala Glu Asn Arg Thr Glu Leu Met Thr Leu Thr Ala Thr
    130                 135                 140

Asn Leu Leu Gly Gln Asn Thr Pro Ala Ile Glu Ala Asn Gln Ala Ala
145                 150                 155                 160
```

-continued

```
Tyr Ser Gln Met Trp Gly Gln Asp Ala Glu Ala Met Tyr Gly Tyr Ala
                165                 170                 175

Ala Thr Ala Ala Thr Ala Thr Glu Ala Leu Leu Pro Phe Glu Asp Ala
            180                 185                 190

Pro Leu Ile Thr Asn Pro Gly Gly Leu Leu Glu Gln Ala Val Ala Val
        195                 200                 205

Glu Glu Ala Ile Asp Thr Ala Ala Ala Asn Gln Leu Met Asn Asn Val
    210                 215                 220

Pro Gln Ala Leu Gln Gln Leu Ala Gln Pro Ala Gln Gly Val Val Pro
225                 230                 235                 240

Ser Ser Lys Leu Gly Gly Leu Trp Thr Ala Val Ser Pro His Leu Ser
                245                 250                 255

Pro Leu Ser Asn Val Ser Ser Ile Ala Asn Asn His Met Ser Met Met
            260                 265                 270

Gly Thr Gly Val Ser Met Thr Asn Thr Leu His Ser Met Leu Lys Gly
        275                 280                 285

Leu Ala Pro Ala Ala Ala Gln Ala Val Glu Thr Ala Ala Glu Asn Gly
    290                 295                 300

Val Trp Ala Met Ser Ser Leu Gly Ser Gln Leu Gly Ser Ser Leu Gly
305                 310                 315                 320

Ser Ser Gly Leu Gly Ala Gly Val Ala Ala Asn Leu Gly Arg Ala Ala
                325                 330                 335

Ser Val Gly Ser Leu Ser Val Pro Pro Ala Trp Ala Ala Ala Asn Gln
            340                 345                 350

Ala Val Thr Pro Ala Ala Arg Ala Leu Pro Leu Thr Ser Leu Thr Ser
        355                 360                 365

Ala Ala Gln Thr Ala Pro Gly His Met Leu Gly Gly Leu Pro Leu Gly
    370                 375                 380

His Ser Val Asn Ala Gly Ser Gly Ile Asn Asn Ala Leu Arg Val Pro
385                 390                 395                 400

Ala Arg Ala Tyr Ala Ile Pro Arg Thr Pro Ala Ala Gly
                405                 410
```

<210> SEQ ID NO 44
<211> LENGTH: 33
<212> TYPE: DNA
<213> ORGANISM: Artificial Sequence
<220> FEATURE:
<223> OTHER INFORMATION: Cloning primer

<400> SEQUENCE: 44
taggatccca tatggtggat ttcggggcgt tac 33

<210> SEQ ID NO 45
<211> LENGTH: 35
<212> TYPE: DNA
<213> ORGANISM: Artificial Sequence
<220> FEATURE:
<223> OTHER INFORMATION: Cloning primer

<400> SEQUENCE: 45
tagaattcaa gcttctatcc ggcggccggt gtgcg 35

<210> SEQ ID NO 46
<211> LENGTH: 94
<212> TYPE: PRT
<213> ORGANISM: Mycobacterium tuberculosis

<400> SEQUENCE: 46

```
Met Thr Ile Asn Tyr Gln Phe Gly Asp Val Asp Ala His Gly Ala Met
1               5                   10                  15

Ile Arg Ala Gln Ala Gly Ser Leu Glu Ala Glu His Gln Ala Ile Ile
            20                  25                  30

Ser Asp Val Leu Thr Ala Ser Asp Phe Trp Gly Gly Ala Gly Ser Ala
        35                  40                  45

Ala Cys Gln Gly Phe Ile Thr Gln Leu Gly Arg Asn Phe Gln Val Ile
    50                  55                  60

Tyr Glu Gln Ala Asn Ala His Gly Gln Lys Val Gln Ala Ala Gly Asn
65                  70                  75                  80

Asn Met Ala Gln Thr Asp Ser Ala Val Gly Ser Ser Trp Ala
                85                  90


<210> SEQ ID NO 47
<211> LENGTH: 294
<212> TYPE: DNA
<213> ORGANISM: Mycobacterium tuberculosis

<400> SEQUENCE: 47

catatgacca tcaactatca attcggggac gtcgacgctc acggcgccat gatccgcgct      60

caggccgggt cgctggaggc cgagcatcag gccatcattt ctgatgtgtt gaccgcgagt     120

gacttttggg gcggcgccgg ttcggcggcc tgccaggggt tcattaccca gctgggccgt     180

aacttccagg tgatctacga gcaggccaac gcccacgggc agaaggtgca ggctgccggc     240

aacaacatgg cacaaaccga cagcgccgtc ggctccagct gggcctaaaa gctt           294


<210> SEQ ID NO 48
<211> LENGTH: 114
<212> TYPE: PRT
<213> ORGANISM: Mycobacterium tuberculosis

<400> SEQUENCE: 48

Met Gly Ser Ser His His His His His His Ser Ser Gly Leu Val Pro
1               5                   10                  15

Arg Gly Ser His Met Thr Ile Asn Tyr Gln Phe Gly Asp Val Asp Ala
            20                  25                  30

His Gly Ala Met Ile Arg Ala Gln Ala Gly Ser Leu Glu Ala Glu His
        35                  40                  45

Gln Ala Ile Ile Ser Asp Val Leu Thr Ala Ser Asp Phe Trp Gly Gly
    50                  55                  60

Ala Gly Ser Ala Ala Cys Gln Gly Phe Ile Thr Gln Leu Gly Arg Asn
65                  70                  75                  80

Phe Gln Val Ile Tyr Glu Gln Ala Asn Ala His Gly Gln Lys Val Gln
                85                  90                  95

Ala Ala Gly Asn Asn Met Ala Gln Thr Asp Ser Ala Val Gly Ser Ser
            100                 105                 110

Trp Ala


<210> SEQ ID NO 49
<211> LENGTH: 33
<212> TYPE: DNA
<213> ORGANISM: Artificial Sequence
<220> FEATURE:
<223> OTHER INFORMATION: Cloning primer

<400> SEQUENCE: 49

taggatccca tatgaccatc aactatcaat tcg                                    33
```

<210> SEQ ID NO 50
<211> LENGTH: 35
<212> TYPE: DNA
<213> ORGANISM: Artificial Sequence
<220> FEATURE:
<223> OTHER INFORMATION: Cloning primer

<400> SEQUENCE: 50
tagaattcaa gcttttaggc ccagctggag ccgac 35

<210> SEQ ID NO 51
<211> LENGTH: 98
<212> TYPE: PRT
<213> ORGANISM: Mycobacterium tuberculosis

<400> SEQUENCE: 51

Met Thr Ser Arg Phe Met Thr Asp Pro His Ala Met Arg Asp Met Ala
1 5 10 15

Gly Arg Phe Glu Val His Ala Gln Thr Val Glu Asp Glu Ala Arg Arg
20 25 30

Met Trp Ala Ser Ala Gln Asn Ile Ser Gly Ala Gly Trp Ser Gly Met
35 40 45

Ala Glu Ala Thr Ser Leu Asp Thr Met Thr Gln Met Asn Gln Ala Phe
50 55 60

Arg Asn Ile Val Asn Met Leu His Gly Val Arg Asp Gly Leu Val Arg
65 70 75 80

Asp Ala Asn Asn Tyr Glu Gln Gln Glu Gln Ala Ser Gln Gln Ile Leu
85 90 95

Ser Ser

<210> SEQ ID NO 52
<211> LENGTH: 306
<212> TYPE: DNA
<213> ORGANISM: Mycobacterium tuberculosis

<400> SEQUENCE: 52
catatgacct cgcgttttat gacggatccg cacgcgatgc gggacatggc gggccgtttt 60
gaggtgcacg cccagacggt ggaggacgag gctcgccgga tgtgggcgtc cgcgcaaaac 120
atttccggcg cgggctggag tggcatggcc gaggcgacct cgctagacac catgacccag 180
atgaatcagg cgtttcgcaa catcgtgaac atgctgcacg gggtgcgtga cgggctggtt 240
cgcgacgcca acaactacga acagcaagag caggcctccc agcagatcct cagcagctga 300
aagctt 306

<210> SEQ ID NO 53
<211> LENGTH: 118
<212> TYPE: PRT
<213> ORGANISM: Mycobacterium tuberculosis

<400> SEQUENCE: 53

Met Gly Ser Ser His His His His His His Ser Ser Gly Leu Val Pro
1 5 10 15

Arg Gly Ser His Met Thr Ser Arg Phe Met Thr Asp Pro His Ala Met
20 25 30

Arg Asp Met Ala Gly Arg Phe Glu Val His Ala Gln Thr Val Glu Asp
35 40 45

Glu Ala Arg Arg Met Trp Ala Ser Ala Gln Asn Ile Ser Gly Ala Gly

```
    50                  55                  60

Trp Ser Gly Met Ala Glu Ala Thr Ser Leu Asp Thr Met Thr Gln Met
65                  70                  75                  80

Asn Gln Ala Phe Arg Asn Ile Val Asn Met Leu His Gly Val Arg Asp
                85                  90                  95

Gly Leu Val Arg Asp Ala Asn Asn Tyr Glu Gln Gln Glu Gln Ala Ser
            100                 105                 110

Gln Gln Ile Leu Ser Ser
        115


<210> SEQ ID NO 54
<211> LENGTH: 32
<212> TYPE: DNA
<213> ORGANISM: Artificial Sequence
<220> FEATURE:
<223> OTHER INFORMATION: Cloning primer

<400> SEQUENCE: 54

taggatccca tatgacctcg cgttttatga cg                                  32


<210> SEQ ID NO 55
<211> LENGTH: 35
<212> TYPE: DNA
<213> ORGANISM: Artificial Sequence
<220> FEATURE:
<223> OTHER INFORMATION: Cloning primer

<400> SEQUENCE: 55

tagaattcaa gctttcagct gctgaggatc tgctg                               35


<210> SEQ ID NO 56
<211> LENGTH: 284
<212> TYPE: PRT
<213> ORGANISM: Mycobacterium tuberculosis

<400> SEQUENCE: 56

Val Pro Asn Arg Arg Arg Arg Lys Leu Ser Thr Ala Met Ser Ala Val
1               5                   10                  15

Ala Ala Leu Ala Val Ala Ser Pro Cys Ala Tyr Phe Leu Val Tyr Glu
            20                  25                  30

Ser Thr Glu Thr Thr Glu Arg Pro Glu His His Glu Phe Lys Gln Ala
        35                  40                  45

Ala Val Leu Thr Asp Leu Pro Gly Glu Leu Met Ser Ala Leu Ser Gln
    50                  55                  60

Gly Leu Ser Gln Phe Gly Ile Asn Ile Pro Pro Val Pro Ser Leu Thr
65                  70                  75                  80

Gly Ser Gly Asp Ala Ser Thr Gly Leu Thr Gly Pro Gly Leu Thr Ser
                85                  90                  95

Pro Gly Leu Thr Ser Pro Gly Leu Thr Ser Pro Gly Leu Thr Asp Pro
            100                 105                 110

Ala Leu Thr Ser Pro Gly Leu Thr Pro Thr Leu Pro Gly Ser Leu Ala
        115                 120                 125

Ala Pro Gly Thr Thr Leu Ala Pro Thr Pro Gly Val Gly Ala Asn Pro
    130                 135                 140

Ala Leu Thr Asn Pro Ala Leu Thr Ser Pro Thr Gly Ala Thr Pro Gly
145                 150                 155                 160

Leu Thr Ser Pro Thr Gly Leu Asp Pro Ala Leu Gly Gly Ala Asn Glu
                165                 170                 175
```

-continued

```
Ile Pro Ile Thr Thr Pro Val Gly Leu Asp Pro Gly Ala Asp Gly Thr
            180                 185                 190

Tyr Pro Ile Leu Gly Asp Pro Thr Leu Gly Thr Ile Pro Ser Ser Pro
        195                 200                 205

Ala Thr Thr Ser Thr Gly Gly Gly Gly Leu Val Asn Asp Val Met Gln
    210                 215                 220

Val Ala Asn Glu Leu Gly Ala Ser Gln Ala Ile Asp Leu Leu Lys Gly
225                 230                 235                 240

Val Leu Met Pro Ser Ile Met Gln Ala Val Gln Asn Gly Gly Ala Ala
                245                 250                 255

Ala Pro Ala Ala Ser Pro Pro Val Pro Pro Ile Pro Ala Ala Ala Ala
            260                 265                 270

Val Pro Pro Thr Asp Pro Ile Thr Val Pro Val Ala
        275                 280
```

<210> SEQ ID NO 57
<211> LENGTH: 819
<212> TYPE: DNA
<213> ORGANISM: Mycobacterium tuberculosis

<400> SEQUENCE: 57

```
catatgcatc accatcacca tcacagtcct tgtgcatatt ttcttgtcta cgaatcaacc      60

gaaacgaccg agcggcccga gcaccatgaa ttcaagcagg cggcggtgtt gaccgacctg     120

cccggcgagc tgatgtccgc gctatcgcag ggtttgtccc agttcgggat caacataccg     180

ccggtgccca gcctgaccgg gagcggcgat gccagcacgg gtctaaccgg tcctggcctg     240

actagtccgg gattgaccag cccgggattg accagcccgg gcctcaccga ccctgccctt     300

accagtccgg gcctgacgcc aaccctgccc ggatcactcg ccgcgcccgg caccaccctg     360

gcgccaacgc ccggcgtggg ggccaatccg gcgctcacca accccgcgct gaccagcccg     420

accggggcga cgccgggatt gaccagcccg acgggtttgg atcccgcgct gggcggcgcc     480

aacgaaatcc cgattacgac gccggtcgga ttggatcccg gggctgacgg cacctatccg     540

atcctcggtg atccaacact ggggaccata ccgagcagcc ccgccaccac ctccaccggc     600

ggcggcggtc tcgtcaacga cgtgatgcag gtggccaacg agttgggcgc cagtcaggct     660

atcgacctgc taaaaggtgt gctaatgccg tcgatcatgc aggccgtcca gaatggcggc     720

gcggccgcgc cggcagccag cccgccggtc ccgcccatcc ccgcggccgc ggcggtgcca     780

ccgacggacc caatcaccgt gccggtcgcc taactcgag                            819
```

<210> SEQ ID NO 58
<211> LENGTH: 269
<212> TYPE: PRT
<213> ORGANISM: Mycobacterium tuberculosis

<400> SEQUENCE: 58

```
Met His His His His His His Ser Pro Cys Ala Tyr Phe Leu Val Tyr
1               5                   10                  15

Glu Ser Thr Glu Thr Thr Glu Arg Pro Glu His His Glu Phe Lys Gln
            20                  25                  30

Ala Ala Val Leu Thr Asp Leu Pro Gly Glu Leu Met Ser Ala Leu Ser
        35                  40                  45

Gln Gly Leu Ser Gln Phe Gly Ile Asn Ile Pro Pro Val Pro Ser Leu
    50                  55                  60

Thr Gly Ser Gly Asp Ala Ser Thr Gly Leu Thr Gly Pro Gly Leu Thr
65                  70                  75                  80
```

```
Ser Pro Gly Leu Thr Ser Pro Gly Leu Thr Ser Pro Gly Leu Thr Asp
                85                  90                  95

Pro Ala Leu Thr Ser Pro Gly Leu Thr Pro Thr Leu Pro Gly Ser Leu
            100                 105                 110

Ala Ala Pro Gly Thr Thr Leu Ala Pro Thr Pro Gly Val Gly Ala Asn
        115                 120                 125

Pro Ala Leu Thr Asn Pro Ala Leu Thr Ser Pro Thr Gly Ala Thr Pro
    130                 135                 140

Gly Leu Thr Ser Pro Thr Gly Leu Asp Pro Ala Leu Gly Gly Ala Asn
145                 150                 155                 160

Glu Ile Pro Ile Thr Thr Pro Val Gly Leu Asp Pro Gly Ala Asp Gly
                165                 170                 175

Thr Tyr Pro Ile Leu Gly Asp Pro Thr Leu Gly Thr Ile Pro Ser Ser
            180                 185                 190

Pro Ala Thr Thr Ser Thr Gly Gly Gly Gly Leu Val Asn Asp Val Met
        195                 200                 205

Gln Val Ala Asn Glu Leu Gly Ala Ser Gln Ala Ile Asp Leu Leu Lys
    210                 215                 220

Gly Val Leu Met Pro Ser Ile Met Gln Ala Val Gln Asn Gly Gly Ala
225                 230                 235                 240

Ala Ala Pro Ala Ala Ser Pro Pro Val Pro Pro Ile Pro Ala Ala Ala
                245                 250                 255

Ala Val Pro Pro Thr Asp Pro Ile Thr Val Pro Val Ala
            260                 265
```

<210> SEQ ID NO 59
<211> LENGTH: 54
<212> TYPE: DNA
<213> ORGANISM: Artificial Sequence
<220> FEATURE:
<223> OTHER INFORMATION: Cloning primer

<400> SEQUENCE: 59
caattacata tgcatcacca tcaccatcac agtccttgtg catattttct tgtc 54

<210> SEQ ID NO 60
<211> LENGTH: 36
<212> TYPE: DNA
<213> ORGANISM: Artificial Sequence
<220> FEATURE:
<223> OTHER INFORMATION: Cloning primer

<400> SEQUENCE: 60
caattactcg agttaggcga ccggcacggt gattgg 36

<210> SEQ ID NO 61
<211> LENGTH: 666
<212> TYPE: PRT
<213> ORGANISM: Mycobacterium tuberculosis

<400> SEQUENCE: 61

```
Met Ala Ala Asp Tyr Asp Lys Leu Phe Arg Pro His Glu Gly Met Glu
1               5                   10                  15

Ala Pro Asp Asp Met Ala Ala Gln Pro Phe Phe Asp Pro Ser Ala Ser
            20                  25                  30

Phe Pro Pro Ala Pro Ala Ser Ala Asn Leu Pro Lys Pro Asn Gly Gln
        35                  40                  45

Thr Pro Pro Pro Thr Ser Asp Asp Leu Ser Glu Arg Phe Val Ser Ala
```

-continued

```
    50                  55                  60

Pro Pro Pro Pro Pro Pro Pro Pro Pro Pro Pro Pro Pro Thr Pro Met
65                  70                  75                  80

Pro Ile Ala Ala Gly Glu Pro Pro Ser Pro Glu Pro Ala Ala Ser Lys
                85                  90                  95

Pro Pro Thr Pro Pro Met Pro Ile Ala Gly Pro Glu Pro Ala Pro Pro
            100                 105                 110

Lys Pro Pro Thr Pro Pro Met Pro Ile Ala Gly Pro Glu Pro Ala Pro
        115                 120                 125

Pro Lys Pro Pro Thr Pro Pro Met Pro Ile Ala Gly Pro Ala Pro Thr
    130                 135                 140

Pro Thr Glu Ser Gln Leu Ala Pro Pro Arg Pro Pro Thr Pro Gln Thr
145                 150                 155                 160

Pro Thr Gly Ala Pro Gln Gln Pro Glu Ser Pro Ala Pro His Val Pro
                165                 170                 175

Ser His Gly Pro His Gln Pro Arg Arg Thr Ala Pro Ala Pro Pro Trp
            180                 185                 190

Ala Lys Met Pro Ile Gly Glu Pro Pro Pro Ala Pro Ser Arg Pro Ser
        195                 200                 205

Ala Ser Pro Ala Glu Pro Pro Thr Arg Pro Ala Pro Gln His Ser Arg
    210                 215                 220

Arg Ala Arg Arg Gly His Arg Tyr Arg Thr Asp Thr Glu Arg Asn Val
225                 230                 235                 240

Gly Lys Val Ala Thr Gly Pro Ser Ile Gln Ala Arg Leu Arg Ala Glu
                245                 250                 255

Glu Ala Ser Gly Ala Gln Leu Ala Pro Gly Thr Glu Pro Ser Pro Ala
            260                 265                 270

Pro Leu Gly Gln Pro Arg Ser Tyr Leu Ala Pro Pro Thr Arg Pro Ala
        275                 280                 285

Pro Thr Glu Pro Pro Pro Ser Pro Ser Pro Gln Arg Asn Ser Gly Arg
    290                 295                 300

Arg Ala Glu Arg Arg Val His Pro Asp Leu Ala Ala Gln His Ala Ala
305                 310                 315                 320

Ala Gln Pro Asp Ser Ile Thr Ala Ala Thr Thr Gly Gly Arg Arg Arg
                325                 330                 335

Lys Arg Ala Ala Pro Asp Leu Asp Ala Thr Gln Lys Ser Leu Arg Pro
            340                 345                 350

Ala Ala Lys Gly Pro Lys Val Lys Lys Val Lys Pro Gln Lys Pro Lys
        355                 360                 365

Ala Thr Lys Pro Pro Lys Val Val Ser Gln Arg Gly Trp Arg His Trp
    370                 375                 380

Val His Ala Leu Thr Arg Ile Asn Leu Gly Leu Ser Pro Asp Glu Lys
385                 390                 395                 400

Tyr Glu Leu Asp Leu His Ala Arg Val Arg Arg Asn Pro Arg Gly Ser
                405                 410                 415

Tyr Gln Ile Ala Val Val Gly Leu Lys Gly Gly Ala Gly Lys Thr Thr
            420                 425                 430

Leu Thr Ala Ala Leu Gly Ser Thr Leu Ala Gln Val Arg Ala Asp Arg
        435                 440                 445

Ile Leu Ala Leu Asp Ala Asp Pro Gly Ala Gly Asn Leu Ala Asp Arg
    450                 455                 460

Val Gly Arg Gln Ser Gly Ala Thr Ile Ala Asp Val Leu Ala Glu Lys
465                 470                 475                 480
```

```
Glu Leu Ser His Tyr Asn Asp Ile Arg Ala His Thr Ser Val Asn Ala
                485                 490                 495

Val Asn Leu Glu Val Leu Pro Ala Pro Glu Tyr Ser Ser Ala Gln Arg
            500                 505                 510

Ala Leu Ser Asp Ala Asp Trp His Phe Ile Ala Asp Pro Ala Ser Arg
        515                 520                 525

Phe Tyr Asn Leu Val Leu Ala Asp Cys Gly Ala Gly Phe Phe Asp Pro
    530                 535                 540

Leu Thr Arg Gly Val Leu Ser Thr Val Ser Gly Val Val Val Val Ala
545                 550                 555                 560

Ser Val Ser Ile Asp Gly Ala Gln Gln Ala Ser Val Ala Leu Asp Trp
                565                 570                 575

Leu Arg Asn Asn Gly Tyr Gln Asp Leu Ala Ser Arg Ala Cys Val Val
            580                 585                 590

Ile Asn His Ile Met Pro Gly Glu Pro Asn Val Ala Val Lys Asp Leu
        595                 600                 605

Val Arg His Phe Glu Gln Gln Val Gln Pro Gly Arg Val Val Val Met
    610                 615                 620

Pro Trp Asp Arg His Ile Ala Ala Gly Thr Glu Ile Ser Leu Asp Leu
625                 630                 635                 640

Leu Asp Pro Ile Tyr Lys Arg Lys Val Leu Glu Leu Ala Ala Ala Leu
                645                 650                 655

Ser Asp Asp Phe Glu Arg Ala Gly Arg Arg
            660                 665
```

<210> SEQ ID NO 62
<211> LENGTH: 2010
<212> TYPE: DNA
<213> ORGANISM: Mycobacterium tuberculosis

<400> SEQUENCE: 62

```
catatggcgg ccgactacga caagctcttc cggccgcacg aaggtatgga agctccggac     60

gatatggcag cgcagccgtt cttcgacccc agtgcttcgt ttccgccggc gcccgcatcg    120

gcaaacctac cgaagcccaa cggccagact ccgcccccga cgtccgacga cctgtcggag    180

cggttcgtgt cggccccgcc gccgccaccc ccaccccccac ctccgcctcc gccaactccg    240

atgccgatcg ccgcaggaga gccgccctcg ccggaaccgg ccgcatctaa accacccaca    300

ccccccatgc ccatcgccgg acccgaaccg gccccaccca aaccacccac acccccccatg    360

cccatcgccg gacccgaacc ggccccaccc aaaccaccca cacctccgat gcccatcgcc    420

ggacctgcac ccaccccaac cgaatcccag ttggcgcccc ccagaccacc gacaccacaa    480

acgccaaccg gagcgccgca gcaaccggaa tcaccggcgc cccacgtacc ctcgcacggg    540

ccacatcaac cccggcgcac cgcaccagca ccgccctggg caaagatgcc aatcggcgaa    600

cccccgcccg ctccgtccag accgtctgcg tccccggccg aaccaccgac ccggcctgcc    660

ccccaacact cccgacgtgc gcgccggggt caccgctatc gcacagacac cgaacgaaac    720

gtcgggaagg tagcaactgg tccatccatc caggcgcggc tgcgggcaga ggaagcatcc    780

ggcgcgcagc tcgcccccgg aacggagccc tcgccagcgc cgttgggcca accgagatcg    840

tatctggctc cgcccacccg ccccgcgccg acagaacctc cccccagccc ctcgccgcag    900

cgcaactccg gtcggcgtgc cgagcgacgc gtccaccccg atttagccgc ccaacatgcc    960

gcggcgcaac ctgattcaat tacggccgca accactggcg gtcgtcgccg caagcgtgca   1020
```

gcgccggatc tcgacgcgac acagaaatcc ttaaggccgg cggccaaggg gccgaaggtg 1080
aagaaggtga agccccagaa accgaaggcc acgaagccgc ccaaagtggt gtcgcagcgc 1140
ggctggcgac attgggtgca tgcgttgacg cgaatcaacc tgggcctgtc acccgacgag 1200
aagtacgagc tggacctgca cgctcgagtc cgccgcaatc cccgcgggtc gtatcagatc 1260
gccgtcgtcg gtctcaaagg tggggctggc aaaaccacgc tgacagcagc gttggggtcg 1320
acgttggctc aggtgcgggc cgaccggatc ctggctctag acgcggatcc aggcgccgga 1380
aacctcgccg atcgggtagg gcgacaatcg ggcgcgacca tcgctgatgt gcttgcagaa 1440
aaagagctgt cgcactacaa cgacatccgc gcacacacta gcgtcaatgc ggtcaatctg 1500
gaagtgctgc cggcaccgga atacagctcg gcgcagcgcg cgctcagcga cgccgactgg 1560
catttcatcg ccgatcctgc gtcgaggttt tacaacctcg tcttggctga ttgtggggcc 1620
ggcttcttcg acccgctgac ccgcggcgtg ctgtccacgg tgtccggtgt cgtggtcgtg 1680
gcaagtgtct caatcgacgg cgcacaacag gcgtcggtcg cgttggactg gttgcgcaac 1740
aacggttacc aagatttggc gagccgcgca tgcgtggtca tcaatcacat catgccggga 1800
gaacccaatg tcgcagttaa agacctggtg cggcatttcg aacagcaagt tcaacccggc 1860
cgggtcgtgg tcatgccgtg ggacaggcac attgcggccg gaaccgagat ttcactcgac 1920
ttgctcgacc ctatctacaa gcgcaaggtc ctcgaattgg ccgcagcgct atccgacgat 1980
ttcgagaggg ctggacgtcg ttgaggattc 2010

<210> SEQ ID NO 63
<211> LENGTH: 452
<212> TYPE: PRT
<213> ORGANISM: Mycobacterium tuberculosis

<400> SEQUENCE: 63

His Met His His His His His His Ser Arg Arg Ala Arg Arg Gly His
1 5 10 15

Arg Tyr Arg Thr Asp Thr Glu Arg Asn Val Gly Lys Val Ala Thr Gly
20 25 30

Pro Ser Ile Gln Ala Arg Leu Arg Ala Glu Glu Ala Ser Gly Ala Gln
35 40 45

Leu Ala Pro Gly Thr Glu Pro Ser Pro Ala Pro Leu Gly Gln Pro Arg
50 55 60

Ser Tyr Leu Ala Pro Pro Thr Arg Pro Ala Pro Thr Glu Pro Pro Pro
65 70 75 80

Ser Pro Ser Pro Gln Arg Asn Ser Gly Arg Arg Ala Glu Arg Arg Val
85 90 95

His Pro Asp Leu Ala Ala Gln His Ala Ala Ala Gln Pro Asp Ser Ile
100 105 110

Thr Ala Ala Thr Thr Gly Gly Arg Arg Arg Lys Arg Ala Ala Pro Asp
115 120 125

Leu Asp Ala Thr Gln Lys Ser Leu Arg Pro Ala Ala Lys Gly Pro Lys
130 135 140

Val Lys Lys Val Lys Pro Gln Lys Pro Lys Ala Thr Lys Pro Pro Lys
145 150 155 160

Val Val Ser Gln Arg Gly Trp Arg His Trp Val His Ala Leu Thr Arg
165 170 175

Ile Asn Leu Gly Leu Ser Pro Asp Glu Lys Tyr Glu Leu Asp Leu His
180 185 190

Ala Arg Val Arg Arg Asn Pro Arg Gly Ser Tyr Gln Ile Ala Val Val

```
        195                 200                 205

Gly Leu Lys Gly Gly Ala Gly Lys Thr Thr Leu Thr Ala Ala Leu Gly
    210                 215                 220

Ser Thr Leu Ala Gln Val Arg Ala Asp Arg Ile Leu Ala Leu Asp Ala
225                 230                 235                 240

Asp Pro Gly Ala Gly Asn Leu Ala Asp Arg Val Gly Arg Gln Ser Gly
                245                 250                 255

Ala Thr Ile Ala Asp Val Leu Ala Glu Lys Glu Leu Ser His Tyr Asn
            260                 265                 270

Asp Ile Arg Ala His Thr Ser Val Asn Ala Val Asn Leu Glu Val Leu
        275                 280                 285

Pro Ala Pro Glu Tyr Ser Ser Ala Gln Arg Ala Leu Ser Asp Ala Asp
    290                 295                 300

Trp His Phe Ile Ala Asp Pro Ala Ser Arg Phe Tyr Asn Leu Val Leu
305                 310                 315                 320

Ala Asp Cys Gly Ala Gly Phe Phe Asp Pro Leu Thr Arg Gly Val Leu
                325                 330                 335

Ser Thr Val Ser Gly Val Val Val Val Ala Ser Val Ser Ile Asp Gly
            340                 345                 350

Ala Gln Gln Ala Ser Val Ala Leu Asp Trp Leu Arg Asn Asn Gly Tyr
        355                 360                 365

Gln Asp Leu Ala Ser Arg Ala Cys Val Val Ile Asn His Ile Met Pro
    370                 375                 380

Gly Glu Pro Asn Val Ala Val Lys Asp Leu Val Arg His Phe Glu Gln
385                 390                 395                 400

Gln Val Gln Pro Gly Arg Val Val Val Met Pro Trp Asp Arg His Ile
                405                 410                 415

Ala Ala Gly Thr Glu Ile Ser Leu Asp Leu Leu Asp Pro Ile Tyr Lys
            420                 425                 430

Arg Lys Val Leu Glu Leu Ala Ala Ala Leu Ser Asp Asp Phe Glu Arg
        435                 440                 445

Ala Gly Arg Arg
    450
```

<210> SEQ ID NO 64
<211> LENGTH: 32
<212> TYPE: DNA
<213> ORGANISM: Artificial Sequence
<220> FEATURE:
<223> OTHER INFORMATION: Cloning primer

<400> SEQUENCE: 64
gatcccatgg gcatatggcg gccgactacg ac 32

<210> SEQ ID NO 65
<211> LENGTH: 28
<212> TYPE: DNA
<213> ORGANISM: Artificial Sequence
<220> FEATURE:
<223> OTHER INFORMATION: Cloning primer

<400> SEQUENCE: 65
gtcagaattc tcaacgacgt ccagccct 28

<210> SEQ ID NO 66
<211> LENGTH: 1185
<212> TYPE: DNA
<213> ORGANISM: Artificial Sequence
<220> FEATURE:
<223> OTHER INFORMATION: Mycobaterium tuberculosi fusion sequence

<400> SEQUENCE: 66
atgggcagca gccatcatca tcatcatcac agcagcggcc tggtgccgcg cggcagccat 60
atggacgaca tcgattggga cgccatcgcg caatgcgaat ccggcggcaa ttgggcggcc 120
aacaccggta acgggttata cggtggtctg cagatcagcc aggcgacgtg ggattccaac 180
ggtggtgtcg ggtcgccggc ggccgcgagt ccccagcaac agatcgaggt cgcagacaac 240
attatgaaaa cccaaggccc gggtgcgtgg ccgaaatgta gttcttgtag tcagggagac 300
gcaccgctgg gctcgctcac ccacatcctg acgttcctcg cggccgagac tggaggttgt 360
tcggggagca gggacgatga gctcagtcct tgtgcatatt ttcttgtcta cgaatcaacc 420
gaaacgaccg agcggcccga gcaccatgaa ttcaagcagg cggcggtgtt gaccgacctg 480
cccggcgagc tgatgtccgc gctatcgcag gggttgtccc agttcgggat caacataccg 540
ccggtgccca gcctgaccgg gagcggcgat gccagcacgg gtctaaccgg tcctggcctg 600
actagtccgg gattgaccag cccgggattg accagcccgg gcctcaccga ccctgccctt 660
accagtccgg gcctgacgcc aaccctgccc ggatcactcg ccgcgcccgg caccaccctg 720
gcgccaacgc ccggcgtggg ggccaatccg gcgctcacca accccgcgct gaccagcccg 780
accggggcga cgccgggatt gaccagcccg acgggtttgg atcccgcgct gggcggcgcc 840
aacgaaatcc cgattacgac gccggtcgga ttggatcccg ggggctgacgg cacctatccg 900 atcctcggtg atccaacact ggggaccata ccgagcagcc ccgccaccac ctccaccggc 960
ggcggcggtc tcgtcaacga cgtgatgcag gtggccaacg agttgggcgc cagtcaggct 1020
atcgacctgc taaaaggtgt gctaatgccg tcgatcatgc aggccgtcca gaatggcggc 1080
gcggccgcgc cggcagccag cccgccggtc ccgcccatcc ccgcggccgc ggcggtgcca 1140
ccgacggacc caatcaccgt gccggtcgcc ggtacctaaa agctt 1185

<210> SEQ ID NO 67
<211> LENGTH: 392
<212> TYPE: PRT
<213> ORGANISM: Artificial Sequence
<220> FEATURE:
<223> OTHER INFORMATION: Mycobaterium tuberculosi fusion sequence

<400> SEQUENCE: 67

Met Gly Ser Ser His His His His His His Ser Ser Gly Leu Val Pro
1 5 10 15

Arg Gly Ser His Met Asp Asp Ile Asp Trp Asp Ala Ile Ala Gln Cys
20 25 30

Glu Ser Gly Gly Asn Trp Ala Ala Asn Thr Gly Asn Gly Leu Tyr Gly
35 40 45

Gly Leu Gln Ile Ser Gln Ala Thr Trp Asp Ser Asn Gly Gly Val Gly
50 55 60

Ser Pro Ala Ala Ala Ser Pro Gln Gln Gln Ile Glu Val Ala Asp Asn
65 70 75 80

Ile Met Lys Thr Gln Gly Pro Gly Ala Trp Pro Lys Cys Ser Ser Cys
85 90 95

Ser Gln Gly Asp Ala Pro Leu Gly Ser Leu Thr His Ile Leu Thr Phe
100 105 110

Leu Ala Ala Glu Thr Gly Gly Cys Ser Gly Ser Arg Asp Asp Glu Leu
115 120 125

```
Ser Pro Cys Ala Tyr Phe Leu Val Tyr Glu Ser Thr Glu Thr Thr Glu
    130                 135                 140

Arg Pro Glu His His Glu Phe Lys Gln Ala Ala Val Leu Thr Asp Leu
145                 150                 155                 160

Pro Gly Glu Leu Met Ser Ala Leu Ser Gln Gly Leu Ser Gln Phe Gly
                165                 170                 175

Ile Asn Ile Pro Pro Val Pro Ser Leu Thr Gly Ser Gly Asp Ala Ser
            180                 185                 190

Thr Gly Leu Thr Gly Pro Gly Leu Thr Ser Pro Gly Leu Thr Ser Pro
        195                 200                 205

Gly Leu Thr Ser Pro Gly Leu Thr Asp Pro Ala Leu Thr Ser Pro Gly
    210                 215                 220

Leu Thr Pro Thr Leu Pro Gly Ser Leu Ala Ala Pro Gly Thr Thr Leu
225                 230                 235                 240

Ala Pro Thr Pro Gly Val Gly Ala Asn Pro Ala Leu Thr Asn Pro Ala
                245                 250                 255

Leu Thr Ser Pro Thr Gly Ala Thr Pro Gly Leu Thr Ser Pro Thr Gly
            260                 265                 270

Leu Asp Pro Ala Leu Gly Gly Ala Asn Glu Ile Pro Ile Thr Thr Pro
        275                 280                 285

Val Gly Leu Asp Pro Gly Ala Asp Gly Thr Tyr Pro Ile Leu Gly Asp
    290                 295                 300

Pro Thr Leu Gly Thr Ile Pro Ser Ser Pro Ala Thr Thr Ser Thr Gly
305                 310                 315                 320

Gly Gly Gly Leu Val Asn Asp Val Met Gln Val Ala Asn Glu Leu Gly
                325                 330                 335

Ala Ser Gln Ala Ile Asp Leu Leu Lys Gly Val Leu Met Pro Ser Ile
            340                 345                 350

Met Gln Ala Val Gln Asn Gly Gly Ala Ala Ala Pro Ala Ala Ser Pro
        355                 360                 365

Pro Val Pro Pro Ile Pro Ala Ala Ala Ala Val Pro Pro Thr Asp Pro
    370                 375                 380

Ile Thr Val Pro Val Ala Gly Thr
385                 390
```

<210> SEQ ID NO 68
<211> LENGTH: 33
<212> TYPE: DNA
<213> ORGANISM: Artificial Sequence
<220> FEATURE:
<223> OTHER INFORMATION: Cloning primer

<400> SEQUENCE: 68
caattacata tggacgacat cgattgggac gcc 33

<210> SEQ ID NO 69
<211> LENGTH: 33
<212> TYPE: DNA
<213> ORGANISM: Artificial Sequence
<220> FEATURE:
<223> OTHER INFORMATION: Cloning primer

<400> SEQUENCE: 69
caattagagc tcatcgtccc tgctccccga aca 33

<210> SEQ ID NO 70
<211> LENGTH: 34
<212> TYPE: DNA

-continued

<213> ORGANISM: Artificial Sequence
<220> FEATURE:
<223> OTHER INFORMATION: Cloning primer

<400> SEQUENCE: 70
caattagagc tcagtccttg tgcatatttt cttg 34

<210> SEQ ID NO 71
<211> LENGTH: 42
<212> TYPE: DNA
<213> ORGANISM: Artificial Sequence
<220> FEATURE:
<223> OTHER INFORMATION: Cloning primer

<400> SEQUENCE: 71
caattaaagc ttttaggtac cggcgaccgg cacggtgatt gg 42

<210> SEQ ID NO 72
<211> LENGTH: 1707
<212> TYPE: DNA
<213> ORGANISM: Artificial Sequence
<220> FEATURE:
<223> OTHER INFORMATION: Mycobacterium tuberculosis fusion sequence

<400> SEQUENCE: 72
atgggcagca gccatcatca tcatcatcac agcagcggcc tggtgccgcg cggcagccat 60
atgggtaccc atctcgccaa cggttcgatg tcggaagtca tgatgtcgga aattgccggg 120
ttgcctatcc ctccgattat ccattacggg gcgattgcct atgcccccag cggcgcgtcg 180
ggcaaagcgt ggcaccagcg cacaccggcg cgagcagagc aagtcgcact agaaaagtgc 240
ggtgacaaga cttgcaaagt ggttagtcgc ttcaccaggt gcggcgcggt cgcctacaac 300
ggctcgaaat accaaggcgg aaccggactc acgcgccgcg cggcagaaga cgacgccgtg 360
aaccgactcg aaggcgggcg gatcgtcaac tgggcgtgca acgagctcat gacctcgcgt 420
tttatgacgg atccgcacgc gatgcgggac atggcgggcc gttttgaggt gcacgcccag 480
acggtggagg acgaggctcg ccggatgtgg gcgtccgcgc aaaacatctc gggcgcgggc 540
tggagtggca tggccgaggc gacctcgcta gacaccatga cccagatgaa tcaggcgttt 600
cgcaacatcg tgaacatgct gcacggggtg cgtgacgggc tggttcgcga cgccaacaac 660
tacgaacagc aagagcaggc ctcccagcag atcctcagca gcgtcgacgt ggtcgatgcc 720
caccgcggcg gccacccgac cccgatgagc tcgacgaagg ccacgctgcg gctggccgag 780
gccaccgaca gctcgggcaa gatcaccaag cgcggagccg acaagctgat ttccaccatc 840
gacgaattcg ccaagattgc catcagctcg ggctgtgccg agctgatggc cttcgccacg 900
tcggcggtcc gcgacgccga gaattccgag gacgtcctgt cccgggtgcg caaagagacc 960
ggtgtcgagt tgcaggcgct gcgtggggag gacgagtcac ggctgacctt cctggccgtg 1020
cgacgatggt acgggtggag cgctgggcgc atcctcaacc tcgacatcgg cggcggctcg 1080
ctggaagtgt ccagtggcgt ggacgaggag cccgagattg cgttatcgct gcccctgggc 1140
gccggacggt tgacccgaga gtggctgccc gacgatccgc cgggccggcg ccgggtggcg 1200
atgctgcgag actggctgga tgccgagctg gccgagccca gtgtgaccgt cctggaagcc 1260
ggcagccccg acctggcggt cgcaacgtcg aagacgtttc gctcgttggc gcgactaacc 1320
ggtgcggccc catccatggc cgggccgcgg gtgaagagga ccctaacggc aaatggtctg 1380
cggcaactca tcgcgtttat ctctaggatg acggcggttg accgtgcaga actggaaggg 1440
gtaagcgccg accgagcgcc gcagattgtg gccggcgccc tggtggcaga ggcgagcatg 1500
cgagcactgt cgatagaagc ggtggaaatc tgcccgtggg cgctgcggga aggtctcatc 1560
ttgcgcaaac tcgacagcga agccgacgga accgccctca tcgagtcttc gtctgtgcac 1620
acttcggtgc gtgccgtcgg aggtcagcca gctgatcgga acgcggccaa ccgatcgaga 1680
ggcagcaaac caagtactta aaagctt 1707

<210> SEQ ID NO 73
<211> LENGTH: 39
<212> TYPE: DNA
<213> ORGANISM: Artificial Sequence
<220> FEATURE:
<223> OTHER INFORMATION: Cloning primer

<400> SEQUENCE: 73
caattacata tgggtaccca tctcgccaac ggttcgatg 39

<210> SEQ ID NO 74
<211> LENGTH: 33
<212> TYPE: DNA
<213> ORGANISM: Artificial Sequence
<220> FEATURE:
<223> OTHER INFORMATION: Cloning primer

<400> SEQUENCE: 74
caattagagc tcgttgcacg cccagttgac gat 33

<210> SEQ ID NO 75
<211> LENGTH: 33
<212> TYPE: DNA
<213> ORGANISM: Artificial Sequence
<220> FEATURE:
<223> OTHER INFORMATION: Cloning primer

<400> SEQUENCE: 75
caattagagc tcatgacctc gcgttttatg acg 33

<210> SEQ ID NO 76
<211> LENGTH: 33
<212> TYPE: DNA
<213> ORGANISM: Artificial Sequence
<220> FEATURE:
<223> OTHER INFORMATION: Cloning primer

<400> SEQUENCE: 76
caattagtcg acgctgctga ggatctgctg gga 33

<210> SEQ ID NO 77
<211> LENGTH: 33
<212> TYPE: DNA
<213> ORGANISM: Artificial Sequence
<220> FEATURE:
<223> OTHER INFORMATION: Cloning primer

<400> SEQUENCE: 77
caattagtcg acatggtcga tgcccaccgc ggc 33

<210> SEQ ID NO 78
<211> LENGTH: 42
<212> TYPE: DNA
<213> ORGANISM: Artificial Sequence
<220> FEATURE:
<223> OTHER INFORMATION: Cloning primer

<400> SEQUENCE: 78

-continued caattaaagc ttttaagtac ttggtttgct gcctctcgat cg 42

<210> SEQ ID NO 79
<211> LENGTH: 566
<212> TYPE: PRT
<213> ORGANISM: Artificial Sequence
<220> FEATURE:
<223> OTHER INFORMATION: Mycobacterium tuberculosis fusion sequence

<400> SEQUENCE: 79

Met Gly Ser Ser His His His His His His Ser Ser Gly Leu Val Pro
1 5 10 15

Arg Gly Ser His Met Gly Thr His Leu Ala Asn Gly Ser Met Ser Glu
20 25 30

Val Met Met Ser Glu Ile Ala Gly Leu Pro Ile Pro Pro Ile Ile His
35 40 45

Tyr Gly Ala Ile Ala Tyr Ala Pro Ser Gly Ala Ser Gly Lys Ala Trp
50 55 60

His Gln Arg Thr Pro Ala Arg Ala Glu Gln Val Ala Leu Glu Lys Cys
65 70 75 80

Gly Asp Lys Thr Cys Lys Val Val Ser Arg Phe Thr Arg Cys Gly Ala
85 90 95

Val Ala Tyr Asn Gly Ser Lys Tyr Gln Gly Gly Thr Gly Leu Thr Arg
100 105 110

Arg Ala Ala Glu Asp Asp Ala Val Asn Arg Leu Glu Gly Gly Arg Ile
115 120 125

Val Asn Trp Ala Cys Asn Glu Leu Met Thr Ser Arg Phe Met Thr Asp
130 135 140

Pro His Ala Met Arg Asp Met Ala Gly Arg Phe Glu Val His Ala Gln
145 150 155 160

Thr Val Glu Asp Glu Ala Arg Arg Met Trp Ala Ser Ala Gln Asn Ile
165 170 175

Ser Gly Ala Gly Trp Ser Gly Met Ala Glu Ala Thr Ser Leu Asp Thr
180 185 190

Met Thr Gln Met Asn Gln Ala Phe Arg Asn Ile Val Asn Met Leu His
195 200 205

Gly Val Arg Asp Gly Leu Val Arg Asp Ala Asn Asn Tyr Glu Gln Gln
210 215 220

Glu Gln Ala Ser Gln Gln Ile Leu Ser Ser Val Asp Val Val Asp Ala
225 230 235 240

His Arg Gly Gly His Pro Thr Pro Met Ser Ser Thr Lys Ala Thr Leu
245 250 255

Arg Leu Ala Glu Ala Thr Asp Ser Ser Gly Lys Ile Thr Lys Arg Gly
260 265 270

Ala Asp Lys Leu Ile Ser Thr Ile Asp Glu Phe Ala Lys Ile Ala Ile
275 280 285

Ser Ser Gly Cys Ala Glu Leu Met Ala Phe Ala Thr Ser Ala Val Arg
290 295 300

Asp Ala Glu Asn Ser Glu Asp Val Leu Ser Arg Val Arg Lys Glu Thr
305 310 315 320

Gly Val Glu Leu Gln Ala Leu Arg Gly Glu Asp Glu Ser Arg Leu Thr
325 330 335

Phe Leu Ala Val Arg Arg Trp Tyr Gly Trp Ser Ala Gly Arg Ile Leu
340 345 350

Asn Leu Asp Ile Gly Gly Gly Ser Leu Glu Val Ser Ser Gly Val Asp

```
        355                 360                 365

Glu Glu Pro Glu Ile Ala Leu Ser Leu Pro Leu Gly Ala Gly Arg Leu
    370                 375                 380

Thr Arg Glu Trp Leu Pro Asp Asp Pro Pro Gly Arg Arg Arg Val Ala
385                 390                 395                 400

Met Leu Arg Asp Trp Leu Asp Ala Glu Leu Ala Glu Pro Ser Val Thr
                405                 410                 415

Val Leu Glu Ala Gly Ser Pro Asp Leu Ala Val Ala Thr Ser Lys Thr
            420                 425                 430

Phe Arg Ser Leu Ala Arg Leu Thr Gly Ala Ala Pro Ser Met Ala Gly
        435                 440                 445

Pro Arg Val Lys Arg Thr Leu Thr Ala Asn Gly Leu Arg Gln Leu Ile
    450                 455                 460

Ala Phe Ile Ser Arg Met Thr Ala Val Asp Arg Ala Glu Leu Glu Gly
465                 470                 475                 480

Val Ser Ala Asp Arg Ala Pro Gln Ile Val Ala Gly Ala Leu Val Ala
                485                 490                 495

Glu Ala Ser Met Arg Ala Leu Ser Ile Glu Ala Val Glu Ile Cys Pro
            500                 505                 510

Trp Ala Leu Arg Glu Gly Leu Ile Leu Arg Lys Leu Asp Ser Glu Ala
        515                 520                 525

Asp Gly Thr Ala Leu Ile Glu Ser Ser Ser Val His Thr Ser Val Arg
    530                 535                 540

Ala Val Gly Gly Gln Pro Ala Asp Arg Asn Ala Ala Asn Arg Ser Arg
545                 550                 555                 560

Gly Ser Lys Pro Ser Thr
                565
```

<210> SEQ ID NO 80
<211> LENGTH: 2022
<212> TYPE: DNA
<213> ORGANISM: Artificial Sequence
<220> FEATURE:
<223> OTHER INFORMATION: Mycobacterium tuberculosis fusion sequence

<400> SEQUENCE: 80

```
atgggcagca gccatcatca tcatcatcac agcagcggcc tggtgccgcg cggcagccat      60

atggacgaca tcgattggga cgccatcgcg caatgcgaat ccggcggcaa ttgggcggcc     120

aacaccggta acgggttata cggtggtctg cagatcagcc aggcgacgtg ggattccaac     180

ggtggtgtcg ggtcgccggc ggccgcgagt ccccagcaac agatcgaggt cgcagacaac     240

attatgaaaa cccaaggccc gggtgcgtgg ccgaaatgta gttcttgtag tcagggagac     300

gcaccgctgg gctcgctcac ccacatcctg acgttcctcg cggccgagac tggaggttgt     360

tcggggagca gggacgatgg tacccatctc gccaacggtt cgatgtcgga agtcatgatg     420

tcggaaattg ccgggttgcc tatccctccg attatccatt acggggcgat tgcctatgcc     480

cccagcggcg cgtcgggcaa agcgtggcac cagcgcacac cggcgcgagc agagcaagtc     540

gcactagaaa agtgcggtga caagacttgc aaagtggtta gtcgcttcac caggtgcggc     600

gcggtcgcct acaacggctc gaaataccaa ggcggaaccg gactcacgcg ccgcgcggca     660

gaagacgacg ccgtgaaccg actcgaaggc gggcggatcg tcaactgggc gtgcaacgag     720

ctcatgacct cgcgttttat gacggatccg cacgcgatgc gggacatggc gggccgtttt     780

gaggtgcacg cccagacggt ggaggacgag gctcgccgga tgtgggcgtc cgcgcaaaac     840
```

-continued

```
atctcgggcg cgggctggag tggcatggcc gaggcgacct cgctagacac catgacccag    900

atgaatcagg cgtttcgcaa catcgtgaac atgctgcacg gggtgcgtga cgggctggtt    960

cgcgacgcca acaactacga acagcaagag caggcctccc agcagatcct cagcagcgtc   1020

gacatggtcg atgcccaccg cggcggccac ccgaccccga tgagctcgac gaaggccacg   1080

ctgcggctgg ccgaggccac cgacagctcg ggcaagatca ccaagcgcgg agccgacaag   1140

ctgatttcca ccatcgacga attcgccaag attgccatca gctcgggctg tgccgagctg   1200

atggccttcg ccacgtcggc ggtccgcgac gccgagaatt ccgaggacgt cctgtcccgg   1260

gtgcgcaaag agaccggtgt cgagttgcag gcgctgcgtg gggaggacga gtcacggctg   1320

accttcctgg ccgtgcgacg atggtacggg tggagcgctg ggcgcatcct caacctcgac   1380

atcggcggcg gctcgctgga agtgtccagt ggcgtggacg aggagcccga gattgcgtta   1440

tcgctgcccc tgggcgccgg acggttgacc cgagagtggc tgcccgacga tccgccgggc   1500

cggcgccggg tggcgatgct gcgagactgg ctggatgccg agctggccga gcccagtgtg   1560

accgtcctgg aagccggcag ccccgacctg gcggtcgcaa cgtcgaagac gtttcgctcg   1620

ttggcgcgac taaccggtgc ggccccatcc atggccgggc cgcgggtgaa gaggacccta   1680

acggcaaatg gtctgcggca actcatcgcg tttatctcta ggatgacggc ggttgaccgt   1740

gcagaactgg aaggggtaag cgccgaccga gcgccgcaga ttgtggccgg cgccctggtg   1800

gcagaggcga gcatgcgagc actgtcgata gaagcggtgg aaatctgccc gtgggcgctg   1860

cgggaaggtc tcatcttgcg caaactcgac agcgaagccg acggaaccgc cctcatcgag   1920

tcttcgtctg tgcacacttc ggtgcgtgcc gtcggaggtc agccagctga tcggaacgcg   1980

gccaaccgat cgagaggcag caaaccaagt acttaaaagc tt                      2022
```

<210> SEQ ID NO 81
<211> LENGTH: 33
<212> TYPE: DNA
<213> ORGANISM: Artificial Sequence
<220> FEATURE:
<223> OTHER INFORMATION: Cloning primer

<400> SEQUENCE: 81

```
caattacata tggacgacat cgattgggac gcc                                 33
```

<210> SEQ ID NO 82
<211> LENGTH: 42
<212> TYPE: DNA
<213> ORGANISM: Artificial Sequence
<220> FEATURE:
<223> OTHER INFORMATION: Cloning primer

<400> SEQUENCE: 82

```
caattaaagc ttttaagtac ttggtttgct gcctctcgat cg                       42
```

<210> SEQ ID NO 83
<211> LENGTH: 671
<212> TYPE: PRT
<213> ORGANISM: Artificial Sequence
<220> FEATURE:
<223> OTHER INFORMATION: Mycobacterium tuberculosis fusion sequence

<400> SEQUENCE: 83

```
Met Gly Ser Ser His His His His His His Ser Ser Gly Leu Val Pro
1               5                   10                  15

Arg Gly Ser His Met Asp Asp Ile Asp Trp Asp Ala Ile Ala Gln Cys
            20                  25                  30
```

```
Glu Ser Gly Gly Asn Trp Ala Ala Asn Thr Gly Asn Gly Leu Tyr Gly
        35                  40                  45

Gly Leu Gln Ile Ser Gln Ala Thr Trp Asp Ser Asn Gly Gly Val Gly
    50                  55                  60

Ser Pro Ala Ala Ala Ser Pro Gln Gln Gln Ile Glu Val Ala Asp Asn
65                  70                  75                  80

Ile Met Lys Thr Gln Gly Pro Gly Ala Trp Pro Lys Cys Ser Ser Cys
                85                  90                  95

Ser Gln Gly Asp Ala Pro Leu Gly Ser Leu Thr His Ile Leu Thr Phe
            100                 105                 110

Leu Ala Ala Glu Thr Gly Gly Cys Ser Gly Ser Arg Asp Asp Gly Thr
        115                 120                 125

His Leu Ala Asn Gly Ser Met Ser Glu Val Met Met Ser Glu Ile Ala
    130                 135                 140

Gly Leu Pro Ile Pro Pro Ile Ile His Tyr Gly Ala Ile Ala Tyr Ala
145                 150                 155                 160

Pro Ser Gly Ala Ser Gly Lys Ala Trp His Gln Arg Thr Pro Ala Arg
                165                 170                 175

Ala Glu Gln Val Ala Leu Glu Lys Cys Gly Asp Lys Thr Cys Lys Val
            180                 185                 190

Val Ser Arg Phe Thr Arg Cys Gly Ala Val Ala Tyr Asn Gly Ser Lys
        195                 200                 205

Tyr Gln Gly Gly Thr Gly Leu Thr Arg Arg Ala Ala Glu Asp Asp Ala
    210                 215                 220

Val Asn Arg Leu Glu Gly Gly Arg Ile Val Asn Trp Ala Cys Asn Glu
225                 230                 235                 240

Leu Met Thr Ser Arg Phe Met Thr Asp Pro His Ala Met Arg Asp Met
                245                 250                 255

Ala Gly Arg Phe Glu Val His Ala Gln Thr Val Glu Asp Glu Ala Arg
            260                 265                 270

Arg Met Trp Ala Ser Ala Gln Asn Ile Ser Gly Ala Gly Trp Ser Gly
        275                 280                 285

Met Ala Glu Ala Thr Ser Leu Asp Thr Met Thr Gln Met Asn Gln Ala
    290                 295                 300

Phe Arg Asn Ile Val Asn Met Leu His Gly Val Arg Asp Gly Leu Val
305                 310                 315                 320

Arg Asp Ala Asn Asn Tyr Glu Gln Gln Glu Gln Ala Ser Gln Gln Ile
                325                 330                 335

Leu Ser Ser Val Asp Met Val Asp Ala His Arg Gly Gly His Pro Thr
            340                 345                 350

Pro Met Ser Ser Thr Lys Ala Thr Leu Arg Leu Ala Glu Ala Thr Asp
        355                 360                 365

Ser Ser Gly Lys Ile Thr Lys Arg Gly Ala Asp Lys Leu Ile Ser Thr
    370                 375                 380

Ile Asp Glu Phe Ala Lys Ile Ala Ile Ser Ser Gly Cys Ala Glu Leu
385                 390                 395                 400

Met Ala Phe Ala Thr Ser Ala Val Arg Asp Ala Glu Asn Ser Glu Asp
                405                 410                 415

Val Leu Ser Arg Val Arg Lys Glu Thr Gly Val Glu Leu Gln Ala Leu
            420                 425                 430

Arg Gly Glu Asp Glu Ser Arg Leu Thr Phe Leu Ala Val Arg Arg Trp
        435                 440                 445
```

-continued

```
Tyr Gly Trp Ser Ala Gly Arg Ile Leu Asn Leu Asp Ile Gly Gly Gly
    450                 455                 460

Ser Leu Glu Val Ser Ser Gly Val Asp Glu Glu Pro Glu Ile Ala Leu
465                 470                 475                 480

Ser Leu Pro Leu Gly Ala Gly Arg Leu Thr Arg Glu Trp Leu Pro Asp
                485                 490                 495

Asp Pro Pro Gly Arg Arg Arg Val Ala Met Leu Arg Asp Trp Leu Asp
            500                 505                 510

Ala Glu Leu Ala Glu Pro Ser Val Thr Val Leu Glu Ala Gly Ser Pro
        515                 520                 525

Asp Leu Ala Val Ala Thr Ser Lys Thr Phe Arg Ser Leu Ala Arg Leu
    530                 535                 540

Thr Gly Ala Ala Pro Ser Met Ala Gly Pro Arg Val Lys Arg Thr Leu
545                 550                 555                 560

Thr Ala Asn Gly Leu Arg Gln Leu Ile Ala Phe Ile Ser Arg Met Thr
                565                 570                 575

Ala Val Asp Arg Ala Glu Leu Glu Gly Val Ser Ala Asp Arg Ala Pro
            580                 585                 590

Gln Ile Val Ala Gly Ala Leu Val Ala Glu Ala Ser Met Arg Ala Leu
        595                 600                 605

Ser Ile Glu Ala Val Glu Ile Cys Pro Trp Ala Leu Arg Glu Gly Leu
    610                 615                 620

Ile Leu Arg Lys Leu Asp Ser Glu Ala Asp Gly Thr Ala Leu Ile Glu
625                 630                 635                 640

Ser Ser Ser Val His Thr Ser Val Arg Ala Val Gly Gly Gln Pro Ala
                645                 650                 655

Asp Arg Asn Ala Ala Asn Arg Ser Arg Gly Ser Lys Pro Ser Thr
            660                 665                 670


<210> SEQ ID NO 84
<211> LENGTH: 2463
<212> TYPE: DNA
<213> ORGANISM: Artificial Sequence
<220> FEATURE:
<223> OTHER INFORMATION: Mycobacterium tuberculosis fusion sequence

<400> SEQUENCE: 84

atgggcagca gccatcatca tcatcatcac agcagcggcc tggtgccgcg cggcagccat      60

atgggtaccc atctcgccaa cggttcgatg tcggaagtca tgatgtcgga aattgccggg     120

ttgcctatcc ctccgattat ccattacggg gcgattgcct atgcccccag cggcgcgtcg     180

ggcaaagcgt ggcaccagcg cacaccggcg cgagcagagc aagtcgcact agaaaagtgc     240

ggtgacaaga cttgcaaagt ggttagtcgc ttcaccaggt gcggcgcggt cgcctacaac     300

ggctcgaaat accaaggcgg aaccggactc acgcgccgcg cggcagaaga cgacgccgtg     360

aaccgactcg aaggcgggcg gatcgtcaac tgggcgtgca acgagctcat gacctcgcgt     420

tttatgacgg atccgcacgc gatgcgggac atggcgggcc gttttgaggt gcacgcccag     480

acggtggagg acgaggctcg ccggatgtgg gcgtccgcgc aaaacatctc gggcgcgggc     540

tggagtggca tggccgaggc gacctcgcta gacaccatga cccagatgaa tcaggcgttt     600

cgcaacatcg tgaacatgct gcacggggtg cgtgacgggc tggttcgcga cgccaacaac     660

tacgaacagc aagagcaggc ctcccagcag atcctcagca gcgtcgacat caatttcgcc     720

gttttgccgc cggaggtgaa ttcggcgcgc atattcgccg gtgcgggcct gggcccaatg     780

ctggcggcgg cgtcggcctg ggacgggttg gccgaggagt tgcatgccgc ggcgggctcg     840
```

ttcgcgtcgg tgaccaccgg gttggcgggc gacgcgtggc atggtccggc gtcgctggcg 900
atgacccgcg cggccagccc gtatgtgggg tggttgaaca cggcggcggg tcaggccgcg 960
caggcggccg gccaggcgcg gctagcggcg agcgcgttcg aggcgacgct ggcggccacc 1020
gtgtctccag cgatggtcgc ggccaaccgg acacggctgg cgtcgctggt ggcagccaac 1080
ttgctgggcc agaacgcccc ggcgatcgcg gccgcggagg ctgaatacga gcagatatgg 1140
gcccaggacg tggccgcgat gttcggctat cactccgccg cgtcggcggt ggccacgcag 1200
ctggcgccta ttcaagaggg tttgcagcag cagctgcaaa acgtgctggc ccagttggct 1260
agcgggaacc tgggcagcgg aaatgtgggc gtcggcaaca tcggcaacga caacattggc 1320
aacgcaaaca tcggcttcgg aaatcgaggc gacgccaaca tcggcatcgg gaatatcggc 1380
gacagaaacc tcggcattgg gaacaccggc aattggaata tcggcatcgg catcaccggc 1440
aacggacaaa tcggcttcgg caagcctgcc aaccccgacg tcttggtggt gggcaacggc 1500
ggcccgggag taaccgcgtt ggtcatgggc ggcaccgaca gcctactgcc gctgcccaac 1560
atccccttac tcgagtacgc tgcgcggttc atcacccccg tgcatcccgg atacaccgct 1620
acgttcctgg aaacgccatc gcagtttttc ccattcaccg ggctgaatag cctgacctat 1680
gacgtctccg tggcccaggg cgtaacgaat ctgcacaccg cgatcatggc gcaactcgcg 1740
gcgggaaacg aagtcgtcgt cttcggcacc tcccaaagcg ccacgatagc caccttcgaa 1800
atgcgctatc tgcaatccct gccagcacac ctgcgtccgg gtctcgacga attgtccttt 1860
acgttgaccg gcaatcccaa ccggcccgac ggtggcattc ttacgcgttt tggcttctcc 1920
ataccgcagt tgggtttcac attgtccggc gcgacgcccg ccgacgccta ccccaccgtc 1980
gattacgcgt tccagtacga cggcgtcaac gacttcccca aatacccgct gaatgtcttc 2040
gcgaccgcca acgcgatcgc gggcatcctt ttcctgcact ccgggttgat tgcgttgccg 2100
cccgatcttg cctcgggcgt ggttcaaccg gtgtcctcac cggacgtcct gaccacctac 2160
atcctgctgc ccagccaaga tctgccgctg ctggtcccgc tgcgtgctat ccccctgctg 2220
ggaaacccgc ttgccgacct catccagccg gacttgcggg tgctcgtcga gttgggttat 2280
gaccgcaccg cccaccagga cgtgcccagc ccgttcggac tgtttccgga cgtcgattgg 2340
gccgaggtgg ccgcggacct gcagcaaggc gccgtgcaag gcgtcaacga cgccctgtcc 2400
ggactggggc tgccgccgcc gtggcagccg gcgctacccc gacttttcag tacttaaaag 2460
ctt 2463

<210> SEQ ID NO 85
<211> LENGTH: 39
<212> TYPE: DNA
<213> ORGANISM: Artificial Sequence
<220> FEATURE:
<223> OTHER INFORMATION: Cloning primer

<400> SEQUENCE: 85
caattacata tgggtaccca tctcgccaac ggttcgatg 39

<210> SEQ ID NO 86
<211> LENGTH: 33
<212> TYPE: DNA
<213> ORGANISM: Artificial Sequence
<220> FEATURE:
<223> OTHER INFORMATION: Cloning primer

<400> SEQUENCE: 86

-continued caattagagc tcgttgcacg cccagttgac gat 33

<210> SEQ ID NO 87
<211> LENGTH: 33
<212> TYPE: DNA
<213> ORGANISM: Artificial Sequence
<220> FEATURE:
<223> OTHER INFORMATION: Cloning primer

<400> SEQUENCE: 87
caattagagc tcatgacctc gcgttttatg acg 33

<210> SEQ ID NO 88
<211> LENGTH: 33
<212> TYPE: DNA
<213> ORGANISM: Artificial Sequence
<220> FEATURE:
<223> OTHER INFORMATION: Cloning primer

<400> SEQUENCE: 88
caattagtcg acgctgctga ggatctgctg gga 33

<210> SEQ ID NO 89
<211> LENGTH: 33
<212> TYPE: DNA
<213> ORGANISM: Artificial Sequence
<220> FEATURE:
<223> OTHER INFORMATION: Cloning primer

<400> SEQUENCE: 89
caattagtcg acatgaattt cgccgttttg ccg 33

<210> SEQ ID NO 90
<211> LENGTH: 42
<212> TYPE: DNA
<213> ORGANISM: Artificial Sequence
<220> FEATURE:
<223> OTHER INFORMATION: Cloning primer

<400> SEQUENCE: 90
caattaaagc ttttaagtac tgaaaagtcg ggtagcgcc gg 42

<210> SEQ ID NO 91
<211> LENGTH: 818
<212> TYPE: PRT
<213> ORGANISM: Artificial Sequence
<220> FEATURE:
<223> OTHER INFORMATION: Mycobacterium tuberculosis fusion sequence

<400> SEQUENCE: 91

Met Gly Ser Ser His His His His His His Ser Ser Gly Leu Val Pro
1 5 10 15

Arg Gly Ser His Met Gly Thr His Leu Ala Asn Gly Ser Met Ser Glu
20 25 30

Val Met Met Ser Glu Ile Ala Gly Leu Pro Ile Pro Pro Ile Ile His
35 40 45

Tyr Gly Ala Ile Ala Tyr Ala Pro Ser Gly Ala Ser Gly Lys Ala Trp
50 55 60

His Gln Arg Thr Pro Ala Arg Ala Glu Gln Val Ala Leu Glu Lys Cys
65 70 75 80

Gly Asp Lys Thr Cys Lys Val Val Ser Arg Phe Thr Arg Cys Gly Ala
85 90 95

Val Ala Tyr Asn Gly Ser Lys Tyr Gln Gly Gly Thr Gly Leu Thr Arg

-continued

```
            100                 105                 110

Arg Ala Ala Glu Asp Asp Ala Val Asn Arg Leu Glu Gly Gly Arg Ile
        115                 120                 125

Val Asn Trp Ala Cys Asn Glu Leu Met Thr Ser Arg Phe Met Thr Asp
    130                 135                 140

Pro His Ala Met Arg Asp Met Ala Gly Arg Phe Glu Val His Ala Gln
145                 150                 155                 160

Thr Val Glu Asp Glu Ala Arg Arg Met Trp Ala Ser Ala Gln Asn Ile
                165                 170                 175

Ser Gly Ala Gly Trp Ser Gly Met Ala Glu Ala Thr Ser Leu Asp Thr
            180                 185                 190

Met Thr Gln Met Asn Gln Ala Phe Arg Asn Ile Val Asn Met Leu His
        195                 200                 205

Gly Val Arg Asp Gly Leu Val Arg Asp Ala Asn Asn Tyr Glu Gln Gln
    210                 215                 220

Glu Gln Ala Ser Gln Gln Ile Leu Ser Ser Val Asp Ile Asn Phe Ala
225                 230                 235                 240

Val Leu Pro Pro Glu Val Asn Ser Ala Arg Ile Phe Ala Gly Ala Gly
                245                 250                 255

Leu Gly Pro Met Leu Ala Ala Ala Ser Ala Trp Asp Gly Leu Ala Glu
            260                 265                 270

Glu Leu His Ala Ala Ala Gly Ser Phe Ala Ser Val Thr Thr Gly Leu
        275                 280                 285

Ala Gly Asp Ala Trp His Gly Pro Ala Ser Leu Ala Met Thr Arg Ala
    290                 295                 300

Ala Ser Pro Tyr Val Gly Trp Leu Asn Thr Ala Ala Gly Gln Ala Ala
305                 310                 315                 320

Gln Ala Ala Gly Gln Ala Arg Leu Ala Ala Ser Ala Phe Glu Ala Thr
                325                 330                 335

Leu Ala Ala Thr Val Ser Pro Ala Met Val Ala Ala Asn Arg Thr Arg
            340                 345                 350

Leu Ala Ser Leu Val Ala Ala Asn Leu Leu Gly Gln Asn Ala Pro Ala
        355                 360                 365

Ile Ala Ala Ala Glu Ala Glu Tyr Glu Gln Ile Trp Ala Gln Asp Val
    370                 375                 380

Ala Ala Met Phe Gly Tyr His Ser Ala Ala Ser Ala Val Ala Thr Gln
385                 390                 395                 400

Leu Ala Pro Ile Gln Glu Gly Leu Gln Gln Gln Leu Gln Asn Val Leu
                405                 410                 415

Ala Gln Leu Ala Ser Gly Asn Leu Gly Ser Gly Asn Val Gly Val Gly
            420                 425                 430

Asn Ile Gly Asn Asp Asn Ile Gly Asn Ala Asn Ile Gly Phe Gly Asn
        435                 440                 445

Arg Gly Asp Ala Asn Ile Gly Ile Gly Asn Ile Gly Asp Arg Asn Leu
    450                 455                 460

Gly Ile Gly Asn Thr Gly Asn Trp Asn Ile Gly Ile Gly Ile Thr Gly
465                 470                 475                 480

Asn Gly Gln Ile Gly Phe Gly Lys Pro Ala Asn Pro Asp Val Leu Val
                485                 490                 495

Val Gly Asn Gly Gly Pro Gly Val Thr Ala Leu Val Met Gly Gly Thr
            500                 505                 510

Asp Ser Leu Leu Pro Leu Pro Asn Ile Pro Leu Leu Glu Tyr Ala Ala
        515                 520                 525
```

```
Arg Phe Ile Thr Pro Val His Pro Gly Tyr Thr Ala Thr Phe Leu Glu
    530                 535                 540

Thr Pro Ser Gln Phe Phe Pro Phe Thr Gly Leu Asn Ser Leu Thr Tyr
545                 550                 555                 560

Asp Val Ser Val Ala Gln Gly Val Thr Asn Leu His Thr Ala Ile Met
                565                 570                 575

Ala Gln Leu Ala Ala Gly Asn Glu Val Val Val Phe Gly Thr Ser Gln
            580                 585                 590

Ser Ala Thr Ile Ala Thr Phe Glu Met Arg Tyr Leu Gln Ser Leu Pro
        595                 600                 605

Ala His Leu Arg Pro Gly Leu Asp Glu Leu Ser Phe Thr Leu Thr Gly
    610                 615                 620

Asn Pro Asn Arg Pro Asp Gly Gly Ile Leu Thr Arg Phe Gly Phe Ser
625                 630                 635                 640

Ile Pro Gln Leu Gly Phe Thr Leu Ser Gly Ala Thr Pro Ala Asp Ala
                645                 650                 655

Tyr Pro Thr Val Asp Tyr Ala Phe Gln Tyr Asp Gly Val Asn Asp Phe
            660                 665                 670

Pro Lys Tyr Pro Leu Asn Val Phe Ala Thr Ala Asn Ala Ile Ala Gly
        675                 680                 685

Ile Leu Phe Leu His Ser Gly Leu Ile Ala Leu Pro Pro Asp Leu Ala
    690                 695                 700

Ser Gly Val Val Gln Pro Val Ser Ser Pro Asp Val Leu Thr Thr Tyr
705                 710                 715                 720

Ile Leu Leu Pro Ser Gln Asp Leu Pro Leu Leu Val Pro Leu Arg Ala
                725                 730                 735

Ile Pro Leu Leu Gly Asn Pro Leu Ala Asp Leu Ile Gln Pro Asp Leu
            740                 745                 750

Arg Val Leu Val Glu Leu Gly Tyr Asp Arg Thr Ala His Gln Asp Val
        755                 760                 765

Pro Ser Pro Phe Gly Leu Phe Pro Asp Val Asp Trp Ala Glu Val Ala
    770                 775                 780

Ala Asp Leu Gln Gln Gly Ala Val Gln Gly Val Asn Asp Ala Leu Ser
785                 790                 795                 800

Gly Leu Gly Leu Pro Pro Pro Trp Gln Pro Ala Leu Pro Arg Leu Phe
                805                 810                 815

Ser Thr


<210> SEQ ID NO 92
<211> LENGTH: 2778
<212> TYPE: DNA
<213> ORGANISM: Artificial Sequence
<220> FEATURE:
<223> OTHER INFORMATION: Mycobacterium tuberculosis fusion sequence

<400> SEQUENCE: 92

atgggcagca gccatcatca tcatcatcac agcagcggcc tggtgccgcg cggcagccat      60

atggacgaca tcgattggga cgccatcgcg caatgcgaat ccggcggcaa ttgggcggcc     120

aacaccggta acgggttata cggtggtctg cagatcagcc aggcgacgtg ggattccaac     180

ggtggtgtcg ggtcgccggc ggccgcgagt ccccagcaac agatcgaggt cgcagacaac     240

attatgaaaa cccaaggccc gggtgcgtgg ccgaaatgta gttcttgtag tcagggagac     300

gcaccgctgg gctcgctcac ccacatcctg acgttcctcg cggccgagac tggaggttgt     360
```

-continued

```
tcggggagca gggacgatgg tacccatctc gccaacggtt cgatgtcgga agtcatgatg    420
tcggaaattg ccgggttgcc tatccctccg attatccatt acggggcgat tgcctatgcc    480
cccagcggcg cgtcgggcaa agcgtggcac cagcgcacac cggcgcgagc agagcaagtc    540
gcactagaaa agtgcggtga caagacttgc aaagtggtta gtcgcttcac caggtgcggc    600
gcggtcgcct acaacggctc gaaataccaa ggcggaaccg gactcacgcg ccgcgcggca    660
gaagacgacg ccgtgaaccg actcgaaggc gggcggatcg tcaactgggc gtgcaacgag    720
ctcatgacct cgcgttttat gacggatccg cacgcgatgc gggacatggc gggccgtttt    780
gaggtgcacg cccagacggt ggaggacgag gctcgccgga tgtgggcgtc cgcgcaaaac    840
atctcgggcg cgggctggag tggcatggcc gaggcgacct cgctagacac catgacccag    900
atgaatcagg cgtttcgcaa catcgtgaac atgctgcacg gggtgcgtga cgggctggtt    960
cgcgacgcca acaactacga acagcaagag caggcctccc agcagatcct cagcagcgtc   1020
gacatcaatt tcgccgtttt gccgccggag gtgaattcgg cgcgcatatt cgccggtgcg   1080
ggcctgggcc caatgctggc ggcggcgtcg gcctgggacg ggttggccga ggagttgcat   1140
gccgcggcgg gctcgttcgc gtcggtgacc accgggttgg cgggcgacgc gtggcatggt   1200
ccggcgtcgc tggcgatgac ccgcgcggcc agcccgtatg tggggtggtt gaacacggcg   1260
gcgggtcagg ccgcgcaggc ggccggccag gcgcggctag cggcgagcgc gttcgaggcg   1320
acgctggcgg ccaccgtgtc tccagcgatg gtcgcggcca accggacacg gctggcgtcg   1380
ctggtggcag ccaacttgct gggccagaac gccccggcga tcgcggccgc ggaggctgaa   1440
tacgagcaga tatgggccca ggacgtggcc gcgatgttcg gctatcactc cgccgcgtcg   1500
gcggtggcca cgcagctggc gcctattcaa gagggtttgc agcagcagct gcaaaacgtg   1560
ctggcccagt tggctagcgg gaacctgggc agcggaaatg tgggcgtcgg caacatcggc   1620
aacgacaaca ttggcaacgc aaacatcggc ttcggaaatc gaggcgacgc caacatcggc   1680
atcgggaata tcggcgacag aaacctcggc attgggaaca ccggcaattg gaatatcggc   1740
atcggcatca ccggcaacgg acaaatcggc ttcggcaagc ctgccaaccc cgacgtcttg   1800
gtggtgggca acggcggccc gggagtaacc gcgttggtca tgggcggcac cgacagccta   1860
ctgccgctgc ccaacatccc cttactcgag tacgctgcgc ggttcatcac cccgtgcat    1920
cccggataca ccgctacgtt cctggaaacg ccatcgcagt ttttcccatt caccgggctg   1980
aatagcctga cctatgacgt ctccgtggcc cagggcgtaa cgaatctgca caccgcgatc   2040
atggcgcaac tcgcggcggg aaacgaagtc gtcgtcttcg gcacctccca aagcgccacg   2100
atagccacct tcgaaatgcg ctatctgcaa tccctgccag cacacctgcg tccgggtctc   2160
gacgaattgt cctttacgtt gaccggcaat cccaaccggc ccgacggtgg cattcttacg   2220
cgttttggct tctccatacc gcagttgggt ttcacattgt ccggcgcgac gcccgccgac   2280
gcctacccca ccgtcgatta cgcgttccag tacgacggcg tcaacgactt ccccaaatac   2340
ccgctgaatg tcttcgcgac cgccaacgcg atcgcgggca tccttttcct gcactccggg   2400
ttgattgcgt tgccgcccga tcttgcctcg ggcgtggttc aaccggtgtc ctcaccggac   2460
gtcctgacca cctacatcct gctgcccagc caagatctgc cgctgctggt cccgctgcgt   2520
gctatccccc tgctgggaaa cccgcttgcc gacctcatcc agccggactt gcgggtgctc   2580
gtcgagttgg gttatgaccg caccgcccac caggacgtgc ccagcccgtt cggactgttt   2640
ccggacgtcg attgggccga ggtggccgcg gacctgcagc aaggcgccgt gcaaggcgtc   2700
aacgacgccc tgtccggact ggggctgccg ccgccgtggc agccggcgct accccgactt   2760
```

ttcagtactt aaaagctt 2778

<210> SEQ ID NO 93
<211> LENGTH: 33
<212> TYPE: DNA
<213> ORGANISM: Artificial Sequence
<220> FEATURE:
<223> OTHER INFORMATION: Cloning primer

<400> SEQUENCE: 93
caattacata tggacgacat cgattgggac gcc 33

<210> SEQ ID NO 94
<211> LENGTH: 42
<212> TYPE: DNA
<213> ORGANISM: Artificial Sequence
<220> FEATURE:
<223> OTHER INFORMATION: Cloning primer

<400> SEQUENCE: 94
caattaaagc ttttaagtac ttggtttgct gcctctcgat cg 42

<210> SEQ ID NO 95
<211> LENGTH: 923
<212> TYPE: PRT
<213> ORGANISM: Artificial Sequence
<220> FEATURE:
<223> OTHER INFORMATION: Mycobacterium tuberculosis fusion sequence

<400> SEQUENCE: 95

Met Gly Ser Ser His His His His His His Ser Ser Gly Leu Val Pro
1 5 10 15

Arg Gly Ser His Met Asp Asp Ile Asp Trp Asp Ala Ile Ala Gln Cys
20 25 30

Glu Ser Gly Gly Asn Trp Ala Ala Asn Thr Gly Asn Gly Leu Tyr Gly
35 40 45

Gly Leu Gln Ile Ser Gln Ala Thr Trp Asp Ser Asn Gly Gly Val Gly
50 55 60

Ser Pro Ala Ala Ala Ser Pro Gln Gln Gln Ile Glu Val Ala Asp Asn
65 70 75 80

Ile Met Lys Thr Gln Gly Pro Gly Ala Trp Pro Lys Cys Ser Ser Cys
85 90 95

Ser Gln Gly Asp Ala Pro Leu Gly Ser Leu Thr His Ile Leu Thr Phe
100 105 110

Leu Ala Ala Glu Thr Gly Gly Cys Ser Gly Ser Arg Asp Asp Gly Thr
115 120 125

His Leu Ala Asn Gly Ser Met Ser Glu Val Met Met Ser Glu Ile Ala
130 135 140

Gly Leu Pro Ile Pro Pro Ile Ile His Tyr Gly Ala Ile Ala Tyr Ala
145 150 155 160

Pro Ser Gly Ala Ser Gly Lys Ala Trp His Gln Arg Thr Pro Ala Arg
165 170 175

Ala Glu Gln Val Ala Leu Glu Lys Cys Gly Asp Lys Thr Cys Lys Val
180 185 190

Val Ser Arg Phe Thr Arg Cys Gly Ala Val Ala Tyr Asn Gly Ser Lys
195 200 205

Tyr Gln Gly Gly Thr Gly Leu Thr Arg Arg Ala Ala Glu Asp Asp Ala
210 215 220

-continued

```
Val Asn Arg Leu Glu Gly Gly Arg Ile Val Asn Trp Ala Cys Asn Glu
225                 230                 235                 240

Leu Met Thr Ser Arg Phe Met Thr Asp Pro His Ala Met Arg Asp Met
                245                 250                 255

Ala Gly Arg Phe Glu Val His Ala Gln Thr Val Glu Asp Glu Ala Arg
            260                 265                 270

Arg Met Trp Ala Ser Ala Gln Asn Ile Ser Gly Ala Gly Trp Ser Gly
        275                 280                 285

Met Ala Glu Ala Thr Ser Leu Asp Thr Met Thr Gln Met Asn Gln Ala
    290                 295                 300

Phe Arg Asn Ile Val Asn Met Leu His Gly Val Arg Asp Gly Leu Val
305                 310                 315                 320

Arg Asp Ala Asn Asn Tyr Glu Gln Gln Glu Gln Ala Ser Gln Gln Ile
                325                 330                 335

Leu Ser Ser Val Asp Ile Asn Phe Ala Val Leu Pro Pro Glu Val Asn
            340                 345                 350

Ser Ala Arg Ile Phe Ala Gly Ala Gly Leu Gly Pro Met Leu Ala Ala
        355                 360                 365

Ala Ser Ala Trp Asp Gly Leu Ala Glu Glu Leu His Ala Ala Ala Gly
    370                 375                 380

Ser Phe Ala Ser Val Thr Thr Gly Leu Ala Gly Asp Ala Trp His Gly
385                 390                 395                 400

Pro Ala Ser Leu Ala Met Thr Arg Ala Ala Ser Pro Tyr Val Gly Trp
                405                 410                 415

Leu Asn Thr Ala Ala Gly Gln Ala Ala Gln Ala Ala Gly Gln Ala Arg
            420                 425                 430

Leu Ala Ala Ser Ala Phe Glu Ala Thr Leu Ala Ala Thr Val Ser Pro
        435                 440                 445

Ala Met Val Ala Ala Asn Arg Thr Arg Leu Ala Ser Leu Val Ala Ala
    450                 455                 460

Asn Leu Leu Gly Gln Asn Ala Pro Ala Ile Ala Ala Ala Glu Ala Glu
465                 470                 475                 480

Tyr Glu Gln Ile Trp Ala Gln Asp Val Ala Ala Met Phe Gly Tyr His
                485                 490                 495

Ser Ala Ala Ser Ala Val Ala Thr Gln Leu Ala Pro Ile Gln Glu Gly
            500                 505                 510

Leu Gln Gln Gln Leu Gln Asn Val Leu Ala Gln Leu Ala Ser Gly Asn
        515                 520                 525

Leu Gly Ser Gly Asn Val Gly Val Gly Asn Ile Gly Asn Asp Asn Ile
    530                 535                 540

Gly Asn Ala Asn Ile Gly Phe Gly Asn Arg Gly Asp Ala Asn Ile Gly
545                 550                 555                 560

Ile Gly Asn Ile Gly Asp Arg Asn Leu Gly Ile Gly Asn Thr Gly Asn
                565                 570                 575

Trp Asn Ile Gly Ile Gly Ile Thr Gly Asn Gly Gln Ile Gly Phe Gly
            580                 585                 590

Lys Pro Ala Asn Pro Asp Val Leu Val Val Gly Asn Gly Gly Pro Gly
        595                 600                 605

Val Thr Ala Leu Val Met Gly Gly Thr Asp Ser Leu Leu Pro Leu Pro
    610                 615                 620

Asn Ile Pro Leu Leu Glu Tyr Ala Ala Arg Phe Ile Thr Pro Val His
625                 630                 635                 640

Pro Gly Tyr Thr Ala Thr Phe Leu Glu Thr Pro Ser Gln Phe Phe Pro
```

-continued

```
                645                 650                 655

Phe Thr Gly Leu Asn Ser Leu Thr Tyr Asp Val Ser Val Ala Gln Gly
            660                 665                 670

Val Thr Asn Leu His Thr Ala Ile Met Ala Gln Leu Ala Ala Gly Asn
        675                 680                 685

Glu Val Val Val Phe Gly Thr Ser Gln Ser Ala Thr Ile Ala Thr Phe
    690                 695                 700

Glu Met Arg Tyr Leu Gln Ser Leu Pro Ala His Leu Arg Pro Gly Leu
705                 710                 715                 720

Asp Glu Leu Ser Phe Thr Leu Thr Gly Asn Pro Asn Arg Pro Asp Gly
                725                 730                 735

Gly Ile Leu Thr Arg Phe Gly Phe Ser Ile Pro Gln Leu Gly Phe Thr
            740                 745                 750

Leu Ser Gly Ala Thr Pro Ala Asp Ala Tyr Pro Thr Val Asp Tyr Ala
        755                 760                 765

Phe Gln Tyr Asp Gly Val Asn Asp Phe Pro Lys Tyr Pro Leu Asn Val
    770                 775                 780

Phe Ala Thr Ala Asn Ala Ile Ala Gly Ile Leu Phe Leu His Ser Gly
785                 790                 795                 800

Leu Ile Ala Leu Pro Pro Asp Leu Ala Ser Gly Val Val Gln Pro Val
                805                 810                 815

Ser Ser Pro Asp Val Leu Thr Thr Tyr Ile Leu Leu Pro Ser Gln Asp
            820                 825                 830

Leu Pro Leu Leu Val Pro Leu Arg Ala Ile Pro Leu Leu Gly Asn Pro
        835                 840                 845

Leu Ala Asp Leu Ile Gln Pro Asp Leu Arg Val Leu Val Glu Leu Gly
    850                 855                 860

Tyr Asp Arg Thr Ala His Gln Asp Val Pro Ser Pro Phe Gly Leu Phe
865                 870                 875                 880

Pro Asp Val Asp Trp Ala Glu Val Ala Ala Asp Leu Gln Gln Gly Ala
                885                 890                 895

Val Gln Gly Val Asn Asp Ala Leu Ser Gly Leu Gly Leu Pro Pro Pro
            900                 905                 910

Trp Gln Pro Ala Leu Pro Arg Leu Phe Ser Thr
        915                 920
```

<210> SEQ ID NO 96
<211> LENGTH: 2814
<212> TYPE: DNA
<213> ORGANISM: Artificial Sequence
<220> FEATURE:
<223> OTHER INFORMATION: Mycobacterium tuberculosis fusion sequence

<400> SEQUENCE: 96

```
atgggcagca gccatcatca tcatcatcac agcagcggcc tggtgccgcg cggcagccat      60

atggacgaca tcgattggga cgccatcgcg caatgcgaat ccggcggcaa ttgggcggcc     120

aacaccggta acgggttata cggtggtctg cagatcagcc aggcgacgtg ggattccaac     180

ggtggtgtcg ggtcgccggc ggccgcgagt ccccagcaac agatcgaggt cgcagacaac     240

attatgaaaa cccaaggccc gggtgcgtgg ccgaaatgta gttcttgtag tcagggagac     300

gcaccgctgg gctcgctcac ccacatcctg acgttcctcg cggccgagac tggaggttgt     360

tcggggagca gggacgatga gctcagtcct tgtgcatatt ttcttgtcta cgaatcaacc     420

gaaacgaccg agcggcccga gcaccatgaa ttcaagcagg cggcggtgtt gaccgacctg     480
```

-continued

```
cccggcgagc tgatgtccgc gctatcgcag ggttgtccc agttcgggat caacataccg    540
ccggtgccca gcctgaccgg gagcggcgat gccagcacgg gtctaaccgg tcctggcctg    600
actagtccgg gattgaccag cccgggattg accagcccgg gcctcaccga ccctgccctt    660
accagtccgg gcctgacgcc aaccctgccc ggatcactcg ccgcgcccgg caccaccctg    720
gcgccaacgc ccggcgtggg ggccaatccg gcgctcacca accccgcgct gaccagcccg    780
accggggcga cgccgggatt gaccagcccg acgggtttgg atcccgcgct gggcggcgcc    840
aacgaaatcc cgattacgac gccggtcgga ttggatcccg gggctgacgg cacctatccg    900
atcctcggtg atccaacact ggggaccata ccgagcagcc ccgccaccac ctccaccggc    960
ggcggcggtc tcgtcaacga cgtgatgcag gtggccaacg agttgggcgc cagtcaggct   1020
atcgacctgc taaaaggtgt gctaatgccg tcgatcatgc aggccgtcca gaatggcggc   1080
gcggccgcgc cggcagccag cccgccggtc ccgcccatcc ccgcggccgc ggcggtgcca   1140
ccgacggacc caatcaccgt gccggtcgcc ggtacccatc tcgccaacgg ttcgatgtcg   1200
gaagtcatga tgtcggaaat tgccgggttg cctatccctc cgattatcca ttacggggcg   1260
attgcctatg cccccagcgg cgcgtcgggc aaagcgtggc accagcgcac accggcgcga   1320
gcagagcaag tcgcactaga aaagtgcggt gacaagactt gcaaagtggt tagtcgcttc   1380
accaggtgcg gcgcggtcgc ctacaacggc tcgaaatacc aaggcggaac cggactcacg   1440
cgccgcgcgg cagaagacga cgccgtgaac cgactcgaag gcgggcggat cgtcaactgg   1500
gcgtgcaacg agctcatgac ctcgcgtttt atgacggatc cgcacgcgat gcgggacatg   1560
gcgggccgtt ttgaggtgca cgcccagacg gtggaggacg aggctcgccg gatgtgggcg   1620
tccgcgcaaa acatctcggg cgcgggctgg agtggcatgg ccgaggcgac ctcgctagac   1680
accatgaccc agatgaatca ggcgtttcgc aacatcgtga acatgctgca cggggtgcgt   1740
gacgggctgg ttcgcgacgc caacaactac gaacagcaag agcaggcctc ccagcagatc   1800
ctcagcagcg tcgacatggt cgatgcccac cgcggcggcc acccgacccc gatgagctcg   1860
acgaaggcca cgctgcggct ggccgaggcc accgacagct cgggcaagat caccaagcgc   1920
ggagccgaca agctgatttc caccatcgac gaattcgcca agattgccat cagctcgggc   1980
tgtgccgagc tgatggcctt cgccacgtcg gcggtccgcg acgccgagaa ttccgaggac   2040
gtcctgtccc gggtgcgcaa agagaccggt gtcgagttgc aggcgctgcg tggggaggac   2100
gagtcacggc tgaccttcct ggccgtgcga cgatggtacg ggtggagcgc tgggcgcatc   2160
ctcaacctcg acatcggcgg cggctcgctg gaagtgtcca gtggcgtgga cgaggagccc   2220
gagattgcgt tatcgctgcc cctgggcgcc ggacggttga cccgagagtg gctgcccgac   2280
gatccgccgg gccggcgccg ggtggcgatg ctgcgagact ggctggatgc cgagctggcc   2340
gagcccagtg tgaccgtcct ggaagccggc agccccgacc tggcggtcgc aacgtcgaag   2400
acgtttcgct cgttggcgcg actaaccggt gcggccccat ccatggccgg gccgcgggtg   2460
aagaggaccc taacggcaaa tggtctgcgg caactcatcg cgtttatctc taggatgacg   2520
gcggttgacc gtgcagaact ggaaggggta agcgccgacc gagcgccgca gattgtggcc   2580
ggcgccctgg tggcagaggc gagcatgcga gcactgtcga tagaagcggt ggaaatctgc   2640
ccgtgggcgc tgcgggaagg tctcatcttg cgcaaactcg acagcgaagc cgacggaacc   2700
gccctcatcg agtcttcgtc tgtgcacact tcggtgcgtg ccgtcggagg tcagccagct   2760
gatcggaacg cggccaaccg atcgagaggc agcaaaccaa gtacttaaaa gctt         2814
```

<210> SEQ ID NO 97
<211> LENGTH: 935
<212> TYPE: PRT
<213> ORGANISM: Artificial Sequence
<220> FEATURE:
<223> OTHER INFORMATION: Mycobacterium tuberculosis fusion sequence

<400> SEQUENCE: 97

```
Met Gly Ser Ser His His His His His His Ser Ser Gly Leu Val Pro
1               5                   10                  15

Arg Gly Ser His Met Asp Asp Ile Asp Trp Asp Ala Ile Ala Gln Cys
            20                  25                  30

Glu Ser Gly Gly Asn Trp Ala Ala Asn Thr Gly Asn Gly Leu Tyr Gly
        35                  40                  45

Gly Leu Gln Ile Ser Gln Ala Thr Trp Asp Ser Asn Gly Gly Val Gly
    50                  55                  60

Ser Pro Ala Ala Ala Ser Pro Gln Gln Gln Ile Glu Val Ala Asp Asn
65                  70                  75                  80

Ile Met Lys Thr Gln Gly Pro Gly Ala Trp Pro Lys Cys Ser Ser Cys
                85                  90                  95

Ser Gln Gly Asp Ala Pro Leu Gly Ser Leu Thr His Ile Leu Thr Phe
            100                 105                 110

Leu Ala Ala Glu Thr Gly Gly Cys Ser Gly Ser Arg Asp Asp Glu Leu
        115                 120                 125

Ser Pro Cys Ala Tyr Phe Leu Val Tyr Glu Ser Thr Glu Thr Thr Glu
    130                 135                 140

Arg Pro Glu His His Glu Phe Lys Gln Ala Ala Val Leu Thr Asp Leu
145                 150                 155                 160

Pro Gly Glu Leu Met Ser Ala Leu Ser Gln Gly Leu Ser Gln Phe Gly
                165                 170                 175

Ile Asn Ile Pro Pro Val Pro Ser Leu Thr Gly Ser Gly Asp Ala Ser
            180                 185                 190

Thr Gly Leu Thr Gly Pro Gly Leu Thr Ser Pro Gly Leu Thr Ser Pro
        195                 200                 205

Gly Leu Thr Ser Pro Gly Leu Thr Asp Pro Ala Leu Thr Ser Pro Gly
    210                 215                 220

Leu Thr Pro Thr Leu Pro Gly Ser Leu Ala Ala Pro Gly Thr Thr Leu
225                 230                 235                 240

Ala Pro Thr Pro Gly Val Gly Ala Asn Pro Ala Leu Thr Asn Pro Ala
                245                 250                 255

Leu Thr Ser Pro Thr Gly Ala Thr Pro Gly Leu Thr Ser Pro Thr Gly
            260                 265                 270

Leu Asp Pro Ala Leu Gly Gly Ala Asn Glu Ile Pro Ile Thr Thr Pro
        275                 280                 285

Val Gly Leu Asp Pro Gly Ala Asp Gly Thr Tyr Pro Ile Leu Gly Asp
    290                 295                 300

Pro Thr Leu Gly Thr Ile Pro Ser Ser Pro Ala Thr Thr Ser Thr Gly
305                 310                 315                 320

Gly Gly Gly Leu Val Asn Asp Val Met Gln Val Ala Asn Glu Leu Gly
                325                 330                 335

Ala Ser Gln Ala Ile Asp Leu Leu Lys Gly Val Leu Met Pro Ser Ile
            340                 345                 350

Met Gln Ala Val Gln Asn Gly Gly Ala Ala Ala Pro Ala Ala Ser Pro
        355                 360                 365

Pro Val Pro Pro Ile Pro Ala Ala Ala Ala Val Pro Pro Thr Asp Pro
```

```
    370                 375                 380

Ile Thr Val Pro Val Ala Gly Thr His Leu Ala Asn Gly Ser Met Ser
385                 390                 395                 400

Glu Val Met Met Ser Glu Ile Ala Gly Leu Pro Ile Pro Pro Ile Ile
                405                 410                 415

His Tyr Gly Ala Ile Ala Tyr Ala Pro Ser Gly Ala Ser Gly Lys Ala
            420                 425                 430

Trp His Gln Arg Thr Pro Ala Arg Ala Glu Gln Val Ala Leu Glu Lys
        435                 440                 445

Cys Gly Asp Lys Thr Cys Lys Val Val Ser Arg Phe Thr Arg Cys Gly
    450                 455                 460

Ala Val Ala Tyr Asn Gly Ser Lys Tyr Gln Gly Gly Thr Gly Leu Thr
465                 470                 475                 480

Arg Arg Ala Ala Glu Asp Asp Ala Val Asn Arg Leu Glu Gly Gly Arg
                485                 490                 495

Ile Val Asn Trp Ala Cys Asn Glu Leu Met Thr Ser Arg Phe Met Thr
            500                 505                 510

Asp Pro His Ala Met Arg Asp Met Ala Gly Arg Phe Glu Val His Ala
        515                 520                 525

Gln Thr Val Glu Asp Glu Ala Arg Arg Met Trp Ala Ser Ala Gln Asn
    530                 535                 540

Ile Ser Gly Ala Gly Trp Ser Gly Met Ala Glu Ala Thr Ser Leu Asp
545                 550                 555                 560

Thr Met Thr Gln Met Asn Gln Ala Phe Arg Asn Ile Val Asn Met Leu
                565                 570                 575

His Gly Val Arg Asp Gly Leu Val Arg Asp Ala Asn Asn Tyr Glu Gln
            580                 585                 590

Gln Glu Gln Ala Ser Gln Gln Ile Leu Ser Ser Val Asp Met Val Asp
        595                 600                 605

Ala His Arg Gly Gly His Pro Thr Pro Met Ser Ser Thr Lys Ala Thr
    610                 615                 620

Leu Arg Leu Ala Glu Ala Thr Asp Ser Ser Gly Lys Ile Thr Lys Arg
625                 630                 635                 640

Gly Ala Asp Lys Leu Ile Ser Thr Ile Asp Glu Phe Ala Lys Ile Ala
                645                 650                 655

Ile Ser Ser Gly Cys Ala Glu Leu Met Ala Phe Ala Thr Ser Ala Val
            660                 665                 670

Arg Asp Ala Glu Asn Ser Glu Asp Val Leu Ser Arg Val Arg Lys Glu
        675                 680                 685

Thr Gly Val Glu Leu Gln Ala Leu Arg Gly Glu Asp Glu Ser Arg Leu
    690                 695                 700

Thr Phe Leu Ala Val Arg Arg Trp Tyr Gly Trp Ser Ala Gly Arg Ile
705                 710                 715                 720

Leu Asn Leu Asp Ile Gly Gly Gly Ser Leu Glu Val Ser Ser Gly Val
                725                 730                 735

Asp Glu Glu Pro Glu Ile Ala Leu Ser Leu Pro Leu Gly Ala Gly Arg
            740                 745                 750

Leu Thr Arg Glu Trp Leu Pro Asp Asp Pro Pro Gly Arg Arg Arg Val
        755                 760                 765

Ala Met Leu Arg Asp Trp Leu Asp Ala Glu Leu Ala Glu Pro Ser Val
    770                 775                 780

Thr Val Leu Glu Ala Gly Ser Pro Asp Leu Ala Val Ala Thr Ser Lys
785                 790                 795                 800
```

```
Thr Phe Arg Ser Leu Ala Arg Leu Thr Gly Ala Ala Pro Ser Met Ala
                805                 810                 815

Gly Pro Arg Val Lys Arg Thr Leu Thr Ala Asn Gly Leu Arg Gln Leu
            820                 825                 830

Ile Ala Phe Ile Ser Arg Met Thr Ala Val Asp Arg Ala Glu Leu Glu
        835                 840                 845

Gly Val Ser Ala Asp Arg Ala Pro Gln Ile Val Ala Gly Ala Leu Val
    850                 855                 860

Ala Glu Ala Ser Met Arg Ala Leu Ser Ile Glu Ala Val Glu Ile Cys
865                 870                 875                 880

Pro Trp Ala Leu Arg Glu Gly Leu Ile Leu Arg Lys Leu Asp Ser Glu
                885                 890                 895

Ala Asp Gly Thr Ala Leu Ile Glu Ser Ser Ser Val His Thr Ser Val
            900                 905                 910

Arg Ala Val Gly Gly Gln Pro Ala Asp Arg Asn Ala Ala Asn Arg Ser
        915                 920                 925

Arg Gly Ser Lys Pro Ser Thr
    930                 935


<210> SEQ ID NO 98
<211> LENGTH: 3570
<212> TYPE: DNA
<213> ORGANISM: Artificial Sequence
<220> FEATURE:
<223> OTHER INFORMATION: Mycobacterium tuberculosis fusion sequence

<400> SEQUENCE: 98

atgggcagca gccatcatca tcatcatcac agcagcggcc tggtgccgcg cggcagccat     60

atggacgaca tcgattggga cgccatcgcg caatgcgaat ccggcggcaa ttgggcggcc    120

aacaccggta acgggttata cggtggtctg cagatcagcc aggcgacgtg ggattccaac    180

ggtggtgtcg ggtcgccggc ggccgcgagt ccccagcaac agatcgaggt cgcagacaac    240

attatgaaaa cccaaggccc gggtgcgtgg ccgaaatgta gttcttgtag tcagggagac    300

gcaccgctgg gctcgctcac ccacatcctg acgttcctcg cggccgagac tggaggttgt    360

tcggggagca gggacgatga gctcagtcct tgtgcatatt ttcttgtcta cgaatcaacc    420

gaaacgaccg agcggcccga gcaccatgaa ttcaagcagg cggcggtgtt gaccgacctg    480

cccggcgagc tgatgtccgc gctatcgcag gggttgtccc agttcgggat caacataccg    540

ccggtgccca gcctgaccgg gagcggcgat gccagcacgg gtctaaccgg tcctggcctg    600

actagtccgg gattgaccag cccgggattg accagcccgg gcctcaccga ccctgccctt    660

accagtccgg gcctgacgcc aaccctgccc ggatcactcg ccgcgcccgg caccaccctg    720

gcgccaacgc ccggcgtggg ggccaatccg gcgctcacca accccgcgct gaccagcccg    780

accggggcga cgccgggatt gaccagcccg acgggtttgg atcccgcgct gggcggcgcc    840

aacgaaatcc cgattacgac gccggtcgga ttggatcccg gggctgacgg cacctatccg    900

atcctcggtg atccaacact ggggaccata ccgagcagcc ccgccaccac ctccaccggc    960

ggcggcggtc tcgtcaacga cgtgatgcag gtggccaacg agttgggcgc cagtcaggct   1020

atcgacctgc taaaaggtgt gctaatgccg tcgatcatgc aggccgtcca gaatggcggc   1080

gcggccgcgc cggcagccag cccgccggtc ccgcccatcc ccgcggccgc ggcggtgcca   1140

ccgacggacc caatcaccgt gccggtcgcc ggtacccatc tcgccaacgg ttcgatgtcg   1200

gaagtcatga tgtcggaaat tgccgggttg cctatccctc cgattatcca ttacggggcg   1260
```

```
attgcctatg cccccagcgg cgcgtcgggc aaagcgtggc accagcgcac accggcgcga   1320
gcagagcaag tcgcactaga aaagtgcggt gacaagactt gcaaagtggt tagtcgcttc   1380
accaggtgcg gcgcggtcgc ctacaacggc tcgaaatacc aaggcggaac cggactcacg   1440
cgccgcgcgg cagaagacga cgccgtgaac cgactcgaag gcgggcggat cgtcaactgg   1500
gcgtgcaacg agctcatgac ctcgcgtttt atgacggatc cgcacgcgat gcgggacatg   1560
gcgggccgtt ttgaggtgca cgcccagacg gtggaggacg aggctcgccg gatgtgggcg   1620
tccgcgcaaa acatctcggg cgcgggctgg agtggcatgg ccgaggcgac ctcgctagac   1680
accatgaccc agatgaatca ggcgtttcgc aacatcgtga acatgctgca cggggtgcgt   1740
gacgggctgg ttcgcgacgc caacaactac gaacagcaag agcaggcctc ccagcagatc   1800
ctcagcagcg tcgacatcaa tttcgccgtt ttgccgccgg aggtgaattc ggcgcgcata   1860
ttcgccggtg cgggcctggg cccaatgctg gcggcggcgt cggcctggga cgggttggcc   1920
gaggagttgc atgccgcggc gggctcgttc gcgtcggtga ccaccgggtt ggcgggcgac   1980
gcgtggcatg gtccggcgtc gctggcgatg acccgcgcgg ccagcccgta tgtggggtgg   2040
ttgaacacgg cggcgggtca ggccgcgcag gcggccggcc aggcgcggct agcggcgagc   2100
gcgttcgagg cgacgctggc ggccaccgtg tctccagcga tggtcgcggc caaccggaca   2160
cggctggcgt cgctggtggc agccaacttg ctgggccaga acgccccggc gatcgcggcc   2220
gcggaggctg aatacgagca gatatgggcc caggacgtgg ccgcgatgtt cggctatcac   2280
tccgccgcgt cggcggtggc cacgcagctg gcgcctattc aagagggttt gcagcagcag   2340
ctgcaaaacg tgctggccca gttggctagc gggaacctgg gcagcggaaa tgtgggcgtc   2400
ggcaacatcg gcaacgacaa cattggcaac gcaaacatcg gcttcggaaa tcgaggcgac   2460
gccaacatcg gcatcgggaa tatcggcgac agaaacctcg gcattgggaa caccggcaat   2520
tggaatatcg gcatcggcat caccggcaac ggacaaatcg gcttcggcaa gcctgccaac   2580
cccgacgtct tggtggtggg caacggcggc ccgggagtaa ccgcgttggt catgggcggc   2640
accgacagcc tactgccgct gcccaacatc cccttactcg agtacgctgc gcggttcatc   2700
acccccgtgc atcccggata caccgctacg ttcctggaaa cgccatcgca gtttttccca   2760
ttcaccgggc tgaatagcct gacctatgac gtctccgtgg cccagggcgt aacgaatctg   2820
cacaccgcga tcatggcgca actcgcggcg ggaaacgaag tcgtcgtctt cggcacctcc   2880
caaagcgcca cgatagccac cttcgaaatg cgctatctgc aatccctgcc agcacacctg   2940
cgtccgggtc tcgacgaatt gtcctttacg ttgaccggca atcccaaccg gcccgacggt   3000
ggcattctta cgcgttttgg cttctccata ccgcagttgg gtttcacatt gtccggcgcg   3060
acgcccgccg acgcctaccc caccgtcgat tacgcgttcc agtacgacgg cgtcaacgac   3120
ttccccaaat acccgctgaa tgtcttcgcg accgccaacg cgatcgcggg catccttttc   3180
ctgcactccg ggttgattgc gttgccgccc gatcttgcct cgggcgtggt tcaaccggtg   3240
tcctcaccgg acgtcctgac cacctacatc ctgctgccca gccaagatct gccgctgctg   3300
gtcccgctgc gtgctatccc cctgctggga aacccgcttg ccgacctcat ccagccggac   3360
ttgcgggtgc tcgtcgagtt gggttatgac cgcaccgccc accaggacgt gcccagcccg   3420
ttcggactgt ttccggacgt cgattgggcc gaggtggccg cggacctgca gcaaggcgcc   3480
gtgcaaggcg tcaacgacgc cctgtccgga ctggggctgc cgccgccgtg gcagccggcg   3540
ctaccccgac ttttcagtac ttaaaagctt                                    3570
```

```
<210> SEQ ID NO 99
<211> LENGTH: 1187
<212> TYPE: PRT
<213> ORGANISM: Artificial Sequence
<220> FEATURE:
<223> OTHER INFORMATION: Mycobacterium tuberculosis fusion sequence

<400> SEQUENCE: 99

Met Gly Ser Ser His His His His His His Ser Ser Gly Leu Val Pro
1               5                   10                  15

Arg Gly Ser His Met Asp Asp Ile Asp Trp Asp Ala Ile Ala Gln Cys
            20                  25                  30

Glu Ser Gly Gly Asn Trp Ala Ala Asn Thr Gly Asn Gly Leu Tyr Gly
        35                  40                  45

Gly Leu Gln Ile Ser Gln Ala Thr Trp Asp Ser Asn Gly Gly Val Gly
    50                  55                  60

Ser Pro Ala Ala Ala Ser Pro Gln Gln Gln Ile Glu Val Ala Asp Asn
65                  70                  75                  80

Ile Met Lys Thr Gln Gly Pro Gly Ala Trp Pro Lys Cys Ser Ser Cys
                85                  90                  95

Ser Gln Gly Asp Ala Pro Leu Gly Ser Leu Thr His Ile Leu Thr Phe
            100                 105                 110

Leu Ala Ala Glu Thr Gly Gly Cys Ser Gly Ser Arg Asp Asp Glu Leu
        115                 120                 125

Ser Pro Cys Ala Tyr Phe Leu Val Tyr Glu Ser Thr Glu Thr Thr Glu
    130                 135                 140

Arg Pro Glu His His Glu Phe Lys Gln Ala Ala Val Leu Thr Asp Leu
145                 150                 155                 160

Pro Gly Glu Leu Met Ser Ala Leu Ser Gln Gly Leu Ser Gln Phe Gly
                165                 170                 175

Ile Asn Ile Pro Pro Val Pro Ser Leu Thr Gly Ser Gly Asp Ala Ser
            180                 185                 190

Thr Gly Leu Thr Gly Pro Gly Leu Thr Ser Pro Gly Leu Thr Ser Pro
        195                 200                 205

Gly Leu Thr Ser Pro Gly Leu Thr Asp Pro Ala Leu Thr Ser Pro Gly
    210                 215                 220

Leu Thr Pro Thr Leu Pro Gly Ser Leu Ala Ala Pro Gly Thr Thr Leu
225                 230                 235                 240

Ala Pro Thr Pro Gly Val Gly Ala Asn Pro Ala Leu Thr Asn Pro Ala
                245                 250                 255

Leu Thr Ser Pro Thr Gly Ala Thr Pro Gly Leu Thr Ser Pro Thr Gly
            260                 265                 270

Leu Asp Pro Ala Leu Gly Gly Ala Asn Glu Ile Pro Ile Thr Thr Pro
        275                 280                 285

Val Gly Leu Asp Pro Gly Ala Asp Gly Thr Tyr Pro Ile Leu Gly Asp
    290                 295                 300

Pro Thr Leu Gly Thr Ile Pro Ser Ser Pro Ala Thr Thr Ser Thr Gly
305                 310                 315                 320

Gly Gly Gly Leu Val Asn Asp Val Met Gln Val Ala Asn Glu Leu Gly
                325                 330                 335

Ala Ser Gln Ala Ile Asp Leu Leu Lys Gly Val Leu Met Pro Ser Ile
            340                 345                 350

Met Gln Ala Val Gln Asn Gly Gly Ala Ala Ala Pro Ala Ala Ser Pro
        355                 360                 365
```

-continued

```
Pro Val Pro Pro Ile Pro Ala Ala Ala Ala Val Pro Pro Thr Asp Pro
    370                 375                 380

Ile Thr Val Pro Val Ala Gly Thr His Leu Ala Asn Gly Ser Met Ser
385                 390                 395                 400

Glu Val Met Met Ser Glu Ile Ala Gly Leu Pro Ile Pro Pro Ile Ile
                405                 410                 415

His Tyr Gly Ala Ile Ala Tyr Ala Pro Ser Gly Ala Ser Gly Lys Ala
            420                 425                 430

Trp His Gln Arg Thr Pro Ala Arg Ala Glu Gln Val Ala Leu Glu Lys
        435                 440                 445

Cys Gly Asp Lys Thr Cys Lys Val Val Ser Arg Phe Thr Arg Cys Gly
    450                 455                 460

Ala Val Ala Tyr Asn Gly Ser Lys Tyr Gln Gly Gly Thr Gly Leu Thr
465                 470                 475                 480

Arg Arg Ala Ala Glu Asp Asp Ala Val Asn Arg Leu Glu Gly Gly Arg
                485                 490                 495

Ile Val Asn Trp Ala Cys Asn Glu Leu Met Thr Ser Arg Phe Met Thr
            500                 505                 510

Asp Pro His Ala Met Arg Asp Met Ala Gly Arg Phe Glu Val His Ala
        515                 520                 525

Gln Thr Val Glu Asp Glu Ala Arg Arg Met Trp Ala Ser Ala Gln Asn
    530                 535                 540

Ile Ser Gly Ala Gly Trp Ser Gly Met Ala Glu Ala Thr Ser Leu Asp
545                 550                 555                 560

Thr Met Thr Gln Met Asn Gln Ala Phe Arg Asn Ile Val Asn Met Leu
                565                 570                 575

His Gly Val Arg Asp Gly Leu Val Arg Asp Ala Asn Asn Tyr Glu Gln
            580                 585                 590

Gln Glu Gln Ala Ser Gln Gln Ile Leu Ser Ser Val Asp Ile Asn Phe
        595                 600                 605

Ala Val Leu Pro Pro Glu Val Asn Ser Ala Arg Ile Phe Ala Gly Ala
    610                 615                 620

Gly Leu Gly Pro Met Leu Ala Ala Ala Ser Ala Trp Asp Gly Leu Ala
625                 630                 635                 640

Glu Glu Leu His Ala Ala Ala Gly Ser Phe Ala Ser Val Thr Thr Gly
                645                 650                 655

Leu Ala Gly Asp Ala Trp His Gly Pro Ala Ser Leu Ala Met Thr Arg
            660                 665                 670

Ala Ala Ser Pro Tyr Val Gly Trp Leu Asn Thr Ala Ala Gly Gln Ala
        675                 680                 685

Ala Gln Ala Ala Gly Gln Ala Arg Leu Ala Ala Ser Ala Phe Glu Ala
    690                 695                 700

Thr Leu Ala Ala Thr Val Ser Pro Ala Met Val Ala Ala Asn Arg Thr
705                 710                 715                 720

Arg Leu Ala Ser Leu Val Ala Ala Asn Leu Leu Gly Gln Asn Ala Pro
                725                 730                 735

Ala Ile Ala Ala Ala Glu Ala Glu Tyr Glu Gln Ile Trp Ala Gln Asp
            740                 745                 750

Val Ala Ala Met Phe Gly Tyr His Ser Ala Ala Ser Ala Val Ala Thr
        755                 760                 765

Gln Leu Ala Pro Ile Gln Glu Gly Leu Gln Gln Gln Leu Gln Asn Val
    770                 775                 780

Leu Ala Gln Leu Ala Ser Gly Asn Leu Gly Ser Gly Asn Val Gly Val
```

785 790 795 800

Gly Asn Ile Gly Asn Asp Asn Ile Gly Asn Ala Asn Ile Gly Phe Gly
805 810 815

Asn Arg Gly Asp Ala Asn Ile Gly Ile Gly Asn Ile Gly Asp Arg Asn
820 825 830

Leu Gly Ile Gly Asn Thr Gly Asn Trp Asn Ile Gly Ile Gly Ile Thr
835 840 845

Gly Asn Gly Gln Ile Gly Phe Gly Lys Pro Ala Asn Pro Asp Val Leu
850 855 860

Val Val Gly Asn Gly Gly Pro Gly Val Thr Ala Leu Val Met Gly Gly
865 870 875 880

Thr Asp Ser Leu Leu Pro Leu Pro Asn Ile Pro Leu Leu Glu Tyr Ala
885 890 895

Ala Arg Phe Ile Thr Pro Val His Pro Gly Tyr Thr Ala Thr Phe Leu
900 905 910

Glu Thr Pro Ser Gln Phe Phe Pro Phe Thr Gly Leu Asn Ser Leu Thr
915 920 925

Tyr Asp Val Ser Val Ala Gln Gly Val Thr Asn Leu His Thr Ala Ile
930 935 940

Met Ala Gln Leu Ala Ala Gly Asn Glu Val Val Val Phe Gly Thr Ser
945 950 955 960

Gln Ser Ala Thr Ile Ala Thr Phe Glu Met Arg Tyr Leu Gln Ser Leu
965 970 975

Pro Ala His Leu Arg Pro Gly Leu Asp Glu Leu Ser Phe Thr Leu Thr
980 985 990

Gly Asn Pro Asn Arg Pro Asp Gly Gly Ile Leu Thr Arg Phe Gly Phe
995 1000 1005

Ser Ile Pro Gln Leu Gly Phe Thr Leu Ser Gly Ala Thr Pro Ala Asp
1010 1015 1020

Ala Tyr Pro Thr Val Asp Tyr Ala Phe Gln Tyr Asp Gly Val Asn Asp
1025 1030 1035 1040

Phe Pro Lys Tyr Pro Leu Asn Val Phe Ala Thr Ala Asn Ala Ile Ala
1045 1050 1055

Gly Ile Leu Phe Leu His Ser Gly Leu Ile Ala Leu Pro Pro Asp Leu
1060 1065 1070

Ala Ser Gly Val Val Gln Pro Val Ser Ser Pro Asp Val Leu Thr Thr
1075 1080 1085

Tyr Ile Leu Leu Pro Ser Gln Asp Leu Pro Leu Leu Val Pro Leu Arg
1090 1095 1100

Ala Ile Pro Leu Leu Gly Asn Pro Leu Ala Asp Leu Ile Gln Pro Asp
1105 1110 1115 1120

Leu Arg Val Leu Val Glu Leu Gly Tyr Asp Arg Thr Ala His Gln Asp
1125 1130 1135

Val Pro Ser Pro Phe Gly Leu Phe Pro Asp Val Asp Trp Ala Glu Val
1140 1145 1150

Ala Ala Asp Leu Gln Gln Gly Ala Val Gln Gly Val Asn Asp Ala Leu
1155 1160 1165

Ser Gly Leu Gly Leu Pro Pro Pro Trp Gln Pro Ala Leu Pro Arg Leu
1170 1175 1180

Phe Ser Thr
1185

<210> SEQ ID NO 100

<211> LENGTH: 164
<212> TYPE: PRT
<213> ORGANISM: Mycobacterium tuberculosis

<400> SEQUENCE: 100

Val Ala Gly Asp Thr Thr Ile Thr Ile Val Gly Asn Leu Thr Ala Asp
1 5 10 15

Pro Glu Leu Arg Phe Thr Pro Ser Gly Ala Ala Val Ala Asn Phe Thr
20 25 30

Val Ala Ser Thr Pro Arg Ile Tyr Asp Arg Gln Thr Gly Glu Trp Lys
35 40 45

Asp Gly Glu Ala Leu Phe Leu Arg Cys Asn Ile Trp Arg Glu Ala Ala
50 55 60

Glu Asn Val Ala Glu Ser Leu Thr Arg Gly Ala Arg Val Ile Val Ser
65 70 75 80

Gly Arg Leu Lys Gln Arg Ser Phe Glu Thr Arg Glu Gly Glu Lys Arg
85 90 95

Thr Val Ile Glu Val Glu Val Asp Glu Ile Gly Pro Ser Leu Arg Tyr
100 105 110

Ala Thr Ala Lys Val Asn Lys Ala Ser Arg Ser Gly Gly Phe Gly Ser
115 120 125

Gly Ser Arg Pro Ala Pro Ala Gln Thr Ser Ser Ala Ser Gly Asp Asp
130 135 140

Pro Trp Gly Ser Ala Pro Ala Ser Gly Ser Phe Gly Gly Gly Asp Asp
145 150 155 160

Glu Pro Pro Phe

<210> SEQ ID NO 101
<211> LENGTH: 507
<212> TYPE: DNA
<213> ORGANISM: Mycobacterium tuberculosis

<400> SEQUENCE: 101
catatggtgg ctggtgacac caccatcacc atcgtcggaa atctgaccgc tgaccccgag 60
ctgcggttca ccccgtccgg tgcggccgtg gcgaatttca ccgtggcgtc aacgccccgg 120
atctatgacc gtcagaccgg cgaatggaaa gacggcgaag cgctgttcct ccggtgcaat 180
atctggcggg aggcggccga gaacgtggcc gagagcctca cccggggggc acgagtcatc 240
gttagcgggc ggcttaagca gcggtcgttt gaaacccgtg agggcgagaa gcgcaccgtc 300
atcgaggtcg aggtcgatga gattgggcct tcgcttcggt acgccaccgc caaggtcaac 360
aaggccagcc gcagcggcgg gtttggcagc ggatcccgtc cggcgccggc gcagaccagc 420
agcgcctcgg gagatgaccc gtggggcagc gcaccggcgt cgggttcgtt cggcggcggc 480
gatgacgaac cgccattctg aaagctt 507

<210> SEQ ID NO 102
<211> LENGTH: 185
<212> TYPE: PRT
<213> ORGANISM: Mycobacterium tuberculosis

<400> SEQUENCE: 102

Met Gly Ser Ser His His His His His His Ser Ser Gly Leu Val Pro
1 5 10 15

Arg Gly Ser His Met Val Ala Gly Asp Thr Thr Ile Thr Ile Val Gly
20 25 30

Asn Leu Thr Ala Asp Pro Glu Leu Arg Phe Thr Pro Ser Gly Ala Ala

```
        35                  40                  45

Val Ala Asn Phe Thr Val Ala Ser Thr Pro Arg Ile Tyr Asp Arg Gln
    50                  55                  60

Thr Gly Glu Trp Lys Asp Gly Glu Ala Leu Phe Leu Arg Cys Asn Ile
65                  70                  75                  80

Trp Arg Glu Ala Ala Glu Asn Val Ala Glu Ser Leu Thr Arg Gly Ala
                85                  90                  95

Arg Val Ile Val Ser Gly Arg Leu Lys Gln Arg Ser Phe Glu Thr Arg
            100                 105                 110

Glu Gly Glu Lys Arg Thr Val Ile Glu Val Glu Val Asp Glu Ile Gly
        115                 120                 125

Pro Ser Leu Arg Tyr Ala Thr Ala Lys Val Asn Lys Ala Ser Arg Ser
    130                 135                 140

Gly Gly Phe Gly Ser Gly Ser Arg Pro Ala Pro Ala Gln Thr Ser Ser
145                 150                 155                 160

Ala Ser Gly Asp Asp Pro Trp Gly Ser Ala Pro Ala Ser Gly Ser Phe
                165                 170                 175

Gly Gly Gly Asp Asp Glu Pro Pro Phe
            180                 185


<210> SEQ ID NO 103
<211> LENGTH: 161
<212> TYPE: PRT
<213> ORGANISM: Mycobacterium tuberculosis

<400> SEQUENCE: 103

Met Thr Ala Ile Ser Cys Ser Pro Arg Pro Arg Tyr Ala Ser Arg Met
1               5                   10                  15

Pro Val Leu Ser Lys Thr Val Glu Val Thr Ala Asp Ala Ala Ser Ile
            20                  25                  30

Met Ala Ile Val Ala Asp Ile Glu Arg Tyr Pro Glu Trp Asn Glu Gly
        35                  40                  45

Val Lys Gly Ala Trp Val Leu Ala Arg Tyr Asp Asp Gly Arg Pro Ser
    50                  55                  60

Gln Val Arg Leu Asp Thr Ala Val Gln Gly Ile Glu Gly Thr Tyr Ile
65                  70                  75                  80

His Ala Val Tyr Tyr Pro Gly Glu Asn Gln Ile Gln Thr Val Met Gln
                85                  90                  95

Gln Gly Glu Leu Phe Ala Lys Gln Glu Gln Leu Phe Ser Val Val Ala
            100                 105                 110

Thr Gly Ala Ala Ser Leu Leu Thr Val Asp Met Asp Val Gln Val Thr
        115                 120                 125

Met Pro Val Pro Glu Pro Met Val Lys Met Leu Leu Asn Asn Val Leu
    130                 135                 140

Glu His Leu Ala Glu Asn Leu Lys Gln Arg Ala Glu Gln Leu Ala Ala
145                 150                 155                 160

Ser


<210> SEQ ID NO 104
<211> LENGTH: 495
<212> TYPE: DNA
<213> ORGANISM: Mycobacterium tuberculosis

<400> SEQUENCE: 104

catatgacgg caatctcgtg ctcaccgcga cccaggtatg cttcccgaat gccagttttg     60
```

```
agcaagaccg tcgaggtcac cgccgacgcc gcatcgatca tggccatcgt tgccgatatc    120

gagcgctacc cagagtggaa tgaaggggtc aagggcgcat gggtgctcgc tcgctacgat    180

gacgggcgtc ccagccaggt gcggctcgac accgctgttc aaggcatcga gggcacctat    240

atccacgccg tgtactaccc aggcgaaaac cagattcaaa ccgtcatgca gcagggtgaa    300

ctgtttgcca agcaggagca gctgttcagt gtggtggcaa ccggcgccgc gagcttgctc    360

acggtggaca tggacgtcca ggtcaccatg ccggtgcccg agccgatggt gaagatgctg    420

ctcaacaacg tcctggagca tctcgccgaa aatctcaagc agcgcgccga gcagctggcg    480

gccagctaaa agctt                                                      495
```

<210> SEQ ID NO 105
<211> LENGTH: 181
<212> TYPE: PRT
<213> ORGANISM: Mycobacterium tuberculosis

<400> SEQUENCE: 105

```
Met Gly Ser Ser His His His His His His Ser Ser Gly Leu Val Pro
1               5                   10                  15

Arg Gly Ser His Met Thr Ala Ile Ser Cys Ser Pro Arg Pro Arg Tyr
            20                  25                  30

Ala Ser Arg Met Pro Val Leu Ser Lys Thr Val Glu Val Thr Ala Asp
        35                  40                  45

Ala Ala Ser Ile Met Ala Ile Val Ala Asp Ile Glu Arg Tyr Pro Glu
    50                  55                  60

Trp Asn Glu Gly Val Lys Gly Ala Trp Val Leu Ala Arg Tyr Asp Asp
65                  70                  75                  80

Gly Arg Pro Ser Gln Val Arg Leu Asp Thr Ala Val Gln Gly Ile Glu
                85                  90                  95

Gly Thr Tyr Ile His Ala Val Tyr Tyr Pro Gly Glu Asn Gln Ile Gln
            100                 105                 110

Thr Val Met Gln Gln Gly Glu Leu Phe Ala Lys Gln Glu Gln Leu Phe
        115                 120                 125

Ser Val Val Ala Thr Gly Ala Ala Ser Leu Leu Thr Val Asp Met Asp
    130                 135                 140

Val Gln Val Thr Met Pro Val Pro Glu Pro Met Val Lys Met Leu Leu
145                 150                 155                 160

Asn Asn Val Leu Glu His Leu Ala Glu Asn Leu Lys Gln Arg Ala Glu
                165                 170                 175

Gln Leu Ala Ala Ser
            180
```

<210> SEQ ID NO 106
<211> LENGTH: 750
<212> TYPE: PRT
<213> ORGANISM: Mycobacterium tuberculosis

<400> SEQUENCE: 106

```
Met Ala Lys Ala Ser Glu Thr Glu Arg Ser Gly Pro Gly Thr Gln Pro
1               5                   10                  15

Ala Asp Ala Gln Thr Ala Thr Ser Ala Thr Val Arg Pro Leu Ser Thr
            20                  25                  30

Gln Ala Val Phe Arg Pro Asp Phe Gly Asp Glu Asp Asn Phe Pro His
        35                  40                  45

Pro Thr Leu Gly Pro Asp Thr Glu Pro Gln Asp Arg Met Ala Thr Thr
    50                  55                  60
```

-continued

```
Ser Arg Val Arg Pro Pro Val Arg Arg Leu Gly Gly Gly Leu Val Glu
65                  70                  75                  80

Ile Pro Arg Ala Pro Asp Ile Asp Pro Leu Glu Ala Leu Met Thr Asn
                85                  90                  95

Pro Val Val Pro Glu Ser Lys Arg Phe Cys Trp Asn Cys Gly Arg Pro
            100                 105                 110

Val Gly Arg Ser Asp Ser Glu Thr Lys Gly Ala Ser Glu Gly Trp Cys
        115                 120                 125

Pro Tyr Cys Gly Ser Pro Tyr Ser Phe Leu Pro Gln Leu Asn Pro Gly
    130                 135                 140

Asp Ile Val Ala Gly Gln Tyr Glu Val Lys Gly Cys Ile Ala His Gly
145                 150                 155                 160

Gly Leu Gly Trp Ile Tyr Leu Ala Leu Asp Arg Asn Val Asn Gly Arg
                165                 170                 175

Pro Val Val Leu Lys Gly Leu Val His Ser Gly Asp Ala Glu Ala Gln
            180                 185                 190

Ala Met Ala Met Ala Glu Arg Gln Phe Leu Ala Glu Val Val His Pro
        195                 200                 205

Ser Ile Val Gln Ile Phe Asn Phe Val Glu His Thr Asp Arg His Gly
    210                 215                 220

Asp Pro Val Gly Tyr Ile Val Met Glu Tyr Val Gly Gly Gln Ser Leu
225                 230                 235                 240

Lys Arg Ser Lys Gly Gln Lys Leu Pro Val Ala Glu Ala Ile Ala Tyr
                245                 250                 255

Leu Leu Glu Ile Leu Pro Ala Leu Ser Tyr Leu His Ser Ile Gly Leu
            260                 265                 270

Val Tyr Asn Asp Leu Lys Pro Glu Asn Ile Met Leu Thr Glu Glu Gln
        275                 280                 285

Leu Lys Leu Ile Asp Leu Gly Ala Val Ser Arg Ile Asn Ser Phe Gly
    290                 295                 300

Tyr Leu Tyr Gly Thr Pro Gly Phe Gln Ala Pro Glu Ile Val Arg Thr
305                 310                 315                 320

Gly Pro Thr Val Ala Thr Asp Ile Tyr Thr Val Gly Arg Thr Leu Ala
                325                 330                 335

Ala Leu Thr Leu Asp Leu Pro Thr Arg Asn Gly Arg Tyr Val Asp Gly
            340                 345                 350

Leu Pro Glu Asp Asp Pro Val Leu Lys Thr Tyr Asp Ser Tyr Gly Arg
        355                 360                 365

Leu Leu Arg Arg Ala Ile Asp Pro Asp Pro Arg Gln Arg Phe Thr Thr
    370                 375                 380

Ala Glu Glu Met Ser Ala Gln Leu Thr Gly Val Leu Arg Glu Val Val
385                 390                 395                 400

Ala Gln Asp Thr Gly Val Pro Arg Pro Gly Leu Ser Thr Ile Phe Ser
                405                 410                 415

Pro Ser Arg Ser Thr Phe Gly Val Asp Leu Leu Val Ala His Thr Asp
            420                 425                 430

Val Tyr Leu Asp Gly Gln Val His Ala Glu Lys Leu Thr Ala Asn Glu
        435                 440                 445

Ile Val Thr Ala Leu Ser Val Pro Leu Val Asp Pro Thr Asp Val Ala
    450                 455                 460

Ala Ser Val Leu Gln Ala Thr Val Leu Ser Gln Pro Val Gln Thr Leu
465                 470                 475                 480
```

-continued

```
Asp Ser Leu Arg Ala Ala Arg His Gly Ala Leu Asp Ala Asp Gly Val
                485                 490                 495

Asp Phe Ser Glu Ser Val Glu Leu Pro Leu Met Glu Val Arg Ala Leu
            500                 505                 510

Leu Asp Leu Gly Asp Val Ala Lys Ala Thr Arg Lys Leu Asp Asp Leu
        515                 520                 525

Ala Glu Arg Val Gly Trp Arg Trp Arg Leu Val Trp Tyr Arg Ala Val
    530                 535                 540

Ala Glu Leu Leu Thr Gly Asp Tyr Asp Ser Ala Thr Lys His Phe Thr
545                 550                 555                 560

Glu Val Leu Asp Thr Phe Pro Gly Glu Leu Ala Pro Lys Leu Ala Leu
                565                 570                 575

Ala Ala Thr Ala Glu Leu Ala Gly Asn Thr Asp Glu His Lys Phe Tyr
            580                 585                 590

Gln Thr Val Trp Ser Thr Asn Asp Gly Val Ile Ser Ala Ala Phe Gly
        595                 600                 605

Leu Ala Arg Ala Arg Ser Ala Glu Gly Asp Arg Val Gly Ala Val Arg
    610                 615                 620

Thr Leu Asp Glu Val Pro Pro Thr Ser Arg His Phe Thr Thr Ala Arg
625                 630                 635                 640

Leu Thr Ser Ala Val Thr Leu Leu Ser Gly Arg Ser Thr Ser Glu Val
                645                 650                 655

Thr Glu Glu Gln Ile Arg Asp Ala Ala Arg Arg Val Glu Ala Leu Pro
            660                 665                 670

Pro Thr Glu Pro Arg Val Leu Gln Ile Arg Ala Leu Val Leu Gly Gly
        675                 680                 685

Ala Leu Asp Trp Leu Lys Asp Asn Lys Ala Ser Thr Asn His Ile Leu
    690                 695                 700

Gly Phe Pro Phe Thr Ser His Gly Leu Arg Leu Gly Val Glu Ala Ser
705                 710                 715                 720

Leu Arg Ser Leu Ala Arg Val Ala Pro Thr Gln Arg His Arg Tyr Thr
                725                 730                 735

Leu Val Asp Met Ala Asn Lys Val Arg Pro Thr Ser Thr Phe
            740                 745                 750
```

<210> SEQ ID NO 107
<211> LENGTH: 2289
<212> TYPE: DNA
<213> ORGANISM: Mycobacterium tuberculosis

<400> SEQUENCE: 107

```
catatgcata tgcatcacca tcaccatcac atggccaaag cgtcagagac cgaacgttcg      60

ggccccggca cccaaccggc ggacgcccag accgcgacgt ccgcgacggt tcgacccctg     120

agcacccagg cggtgttccg ccccgatttc ggcgatgagg acaacttccc ccatccgacg     180

ctcggcccgg acaccgagcc gcaagaccgg atggccacca ccagccgggt gcgcccgccg     240

gtcagacggc tgggcggcgg cctggtggaa atcccgcggg cgcccgatat cgatccgctt     300

gaggccctga tgaccaaccc ggtggtgccg gagtccaagc ggttctgctg gaactgtgga     360

cgtcccgtcg gccggtccga ctcggagacc aagggagctt cagagggctg gtgtccctat     420

tgcggcagcc cgtattcgtt cctgccgcag ctaaatcccg gggacatcgt cgccggccag     480

tacgaggtca aaggctgcat cgcgcacggc ggactgggct ggatctacct cgctctcgac     540

cgcaatgtca acggccgtcc ggtggtgctc aagggcctgg tgcattccgg tgatgccgaa     600
```

-continued

```
gcgcaggcaa tggcgatggc cgaacgccag ttcctggccg aggtggtgca cccgtcgatc    660

gtgcagatct tcaactttgt cgagcacacc gacaggcacg gggatccggt cggctacatc    720

gtgatggaat acgtcggcgg gcaatcgctc aaacgcagca agggtcagaa actgcccgtc    780

gcggaggcca tcgcctacct gctggagatc ctgccggcgc tgagctacct gcattccatc    840

ggcttggtct acaacgacct gaagccggaa aacatcatgc tgaccgagga acagctcaag    900

ctgatcgacc tgggcgcggt atcgcggatc aactcgttcg gctacctcta cgggacccca    960

ggcttccagg cgcccgagat cgtgcggacc ggtccgacgg tggccaccga catctacacc   1020

gtgggacgca cgctcgcggc gctcacgctg gacctgccca cccgcaatgg ccgttatgtg   1080

gatgggctac ccgaagacga cccggtgctg aaaacctacg actcttacgg ccggttgctg   1140

cgcagggcca tcgaccccga tccgcggcaa cggttcacca ccgccgaaga gatgtccgcg   1200

caattgacgg gcgtgttgcg ggaggtggtc gcccaggaca ccggggtgcc gcggccaggg   1260

ctatcaacga tcttcagtcc cagtcggtcg acatttggag tggacctgct ggtggcgcac   1320

accgacgtgt atctggacgg gcaggtgcac gcggagaagc tgaccgccaa cgagatcgtg   1380

accgcgctgt cggtgccgct ggtcgatccg accgacgtcg cagcttcggt cctgcaggcc   1440

acggtgctct cccagccggt gcagacccta gactcgctgc gcgcggcccg ccacggtgcg   1500

ctggacgccg acggcgtcga cttctccgag tcagtggagc tgccgctaat ggaagtccgc   1560

gcgctgctgg atctcggcga tgtggccaag gccacccgaa aactcgacga tctggccgaa   1620

cgcgttggct ggcgatggcg attggtctgg taccgggccg tcgccgagct gctcaccggc   1680

gactatgact cggccaccaa acatttcacc gaggtgctgg atacctttcc cggcgagctg   1740

gcgcccaagc tcgccctggc cgccaccgcc gaactagccg gcaacaccga cgaacacaag   1800

ttctatcaga cggtgtggag caccaacgac ggcgtgatct cggcggcttt cggactggcc   1860

agagcccggt cggccgaagg tgatcgggtc ggcgccgtgc gcacgctcga cgaggtaccg   1920

cccacttctc ggcatttcac cacggcacgg ctgaccagcg cggtgactct gttgtccggc   1980

cggtcaacga gtgaagtcac cgaggaacag atccgcgacg ccgcccgaag agtggaggcg   2040

ctgcccccga ccgaaccacg cgtgctgcag atccgcgccc tggtgctggg tggcgcgctg   2100

gactggctga aggacaacaa ggccagcacc aaccacatcc tcggtttccc gttcaccagt   2160

cacgggctgc ggctgggtgt cgaggcgtca ctgcgcagcc tggcccgggt agctcccact   2220

caacggcatc gctacacgct ggtggacatg gccaacaagg tccggcccac cagcacgttc   2280

taagaattc                                                           2289
```

```
<210> SEQ ID NO 108
<211> LENGTH: 758
<212> TYPE: PRT
<213> ORGANISM: Mycobacterium tuberculosis

<400> SEQUENCE: 108

His Met His His His His His His Met Ala Lys Ala Ser Glu Thr Glu
1               5                   10                  15

Arg Ser Gly Pro Gly Thr Gln Pro Ala Asp Ala Gln Thr Ala Thr Ser
            20                  25                  30

Ala Thr Val Arg Pro Leu Ser Thr Gln Ala Val Phe Arg Pro Asp Phe
        35                  40                  45

Gly Asp Glu Asp Asn Phe Pro His Pro Thr Leu Gly Pro Asp Thr Glu
    50                  55                  60

Pro Gln Asp Arg Met Ala Thr Thr Ser Arg Val Arg Pro Pro Val Arg
```

-continued

```
65                  70                  75                  80

Arg Leu Gly Gly Gly Leu Val Glu Ile Pro Arg Ala Pro Asp Ile Asp
                85                  90                  95

Pro Leu Glu Ala Leu Met Thr Asn Pro Val Val Pro Glu Ser Lys Arg
            100                 105                 110

Phe Cys Trp Asn Cys Gly Arg Pro Val Gly Arg Ser Asp Ser Glu Thr
        115                 120                 125

Lys Gly Ala Ser Glu Gly Trp Cys Pro Tyr Cys Gly Ser Pro Tyr Ser
    130                 135                 140

Phe Leu Pro Gln Leu Asn Pro Gly Asp Ile Val Ala Gly Gln Tyr Glu
145                 150                 155                 160

Val Lys Gly Cys Ile Ala His Gly Gly Leu Gly Trp Ile Tyr Leu Ala
                165                 170                 175

Leu Asp Arg Asn Val Asn Gly Arg Pro Val Val Leu Lys Gly Leu Val
            180                 185                 190

His Ser Gly Asp Ala Glu Ala Gln Ala Met Ala Met Ala Glu Arg Gln
        195                 200                 205

Phe Leu Ala Glu Val Val His Pro Ser Ile Val Gln Ile Phe Asn Phe
    210                 215                 220

Val Glu His Thr Asp Arg His Gly Asp Pro Val Gly Tyr Ile Val Met
225                 230                 235                 240

Glu Tyr Val Gly Gly Gln Ser Leu Lys Arg Ser Lys Gly Gln Lys Leu
                245                 250                 255

Pro Val Ala Glu Ala Ile Ala Tyr Leu Leu Glu Ile Leu Pro Ala Leu
            260                 265                 270

Ser Tyr Leu His Ser Ile Gly Leu Val Tyr Asn Asp Leu Lys Pro Glu
        275                 280                 285

Asn Ile Met Leu Thr Glu Glu Gln Leu Lys Leu Ile Asp Leu Gly Ala
    290                 295                 300

Val Ser Arg Ile Asn Ser Phe Gly Tyr Leu Tyr Gly Thr Pro Gly Phe
305                 310                 315                 320

Gln Ala Pro Glu Ile Val Arg Thr Gly Pro Thr Val Ala Thr Asp Ile
                325                 330                 335

Tyr Thr Val Gly Arg Thr Leu Ala Ala Leu Thr Leu Asp Leu Pro Thr
            340                 345                 350

Arg Asn Gly Arg Tyr Val Asp Gly Leu Pro Glu Asp Asp Pro Val Leu
        355                 360                 365

Lys Thr Tyr Asp Ser Tyr Gly Arg Leu Leu Arg Arg Ala Ile Asp Pro
    370                 375                 380

Asp Pro Arg Gln Arg Phe Thr Thr Ala Glu Glu Met Ser Ala Gln Leu
385                 390                 395                 400

Thr Gly Val Leu Arg Glu Val Val Ala Gln Asp Thr Gly Val Pro Arg
                405                 410                 415

Pro Gly Leu Ser Thr Ile Phe Ser Pro Ser Arg Ser Thr Phe Gly Val
            420                 425                 430

Asp Leu Leu Val Ala His Thr Asp Val Tyr Leu Asp Gly Gln Val His
        435                 440                 445

Ala Glu Lys Leu Thr Ala Asn Glu Ile Val Thr Ala Leu Ser Val Pro
    450                 455                 460

Leu Val Asp Pro Thr Asp Val Ala Ala Ser Val Leu Gln Ala Thr Val
465                 470                 475                 480

Leu Ser Gln Pro Val Gln Thr Leu Asp Ser Leu Arg Ala Ala Arg His
                485                 490                 495
```

```
Gly Ala Leu Asp Ala Asp Gly Val Asp Phe Ser Glu Ser Val Glu Leu
            500                 505                 510

Pro Leu Met Glu Val Arg Ala Leu Leu Asp Leu Gly Asp Val Ala Lys
        515                 520                 525

Ala Thr Arg Lys Leu Asp Asp Leu Ala Glu Arg Val Gly Trp Arg Trp
    530                 535                 540

Arg Leu Val Trp Tyr Arg Ala Val Ala Glu Leu Leu Thr Gly Asp Tyr
545                 550                 555                 560

Asp Ser Ala Thr Lys His Phe Thr Glu Val Leu Asp Thr Phe Pro Gly
                565                 570                 575

Glu Leu Ala Pro Lys Leu Ala Leu Ala Ala Thr Ala Glu Leu Ala Gly
            580                 585                 590

Asn Thr Asp Glu His Lys Phe Tyr Gln Thr Val Trp Ser Thr Asn Asp
        595                 600                 605

Gly Val Ile Ser Ala Ala Phe Gly Leu Ala Arg Ala Arg Ser Ala Glu
    610                 615                 620

Gly Asp Arg Val Gly Ala Val Arg Thr Leu Asp Glu Val Pro Pro Thr
625                 630                 635                 640

Ser Arg His Phe Thr Thr Ala Arg Leu Thr Ser Ala Val Thr Leu Leu
                645                 650                 655

Ser Gly Arg Ser Thr Ser Glu Val Thr Glu Glu Gln Ile Arg Asp Ala
            660                 665                 670

Ala Arg Arg Val Glu Ala Leu Pro Pro Thr Glu Pro Arg Val Leu Gln
        675                 680                 685

Ile Arg Ala Leu Val Leu Gly Gly Ala Leu Asp Trp Leu Lys Asp Asn
    690                 695                 700

Lys Ala Ser Thr Asn His Ile Leu Gly Phe Pro Phe Thr Ser His Gly
705                 710                 715                 720

Leu Arg Leu Gly Val Glu Ala Ser Leu Arg Ser Leu Ala Arg Val Ala
                725                 730                 735

Pro Thr Gln Arg His Arg Tyr Thr Leu Val Asp Met Ala Asn Lys Val
            740                 745                 750

Arg Pro Thr Ser Thr Phe
        755


<210> SEQ ID NO 109
<211> LENGTH: 328
<212> TYPE: PRT
<213> ORGANISM: Mycobacterium tuberculosis

<400> SEQUENCE: 109

Val Val Asp Ala His Arg Gly Gly His Pro Thr Pro Met Ser Ser Thr
1               5                   10                  15

Lys Ala Thr Leu Arg Leu Ala Glu Ala Thr Asp Ser Ser Gly Lys Ile
            20                  25                  30

Thr Lys Arg Gly Ala Asp Lys Leu Ile Ser Thr Ile Asp Glu Phe Ala
        35                  40                  45

Lys Ile Ala Ile Ser Ser Gly Cys Ala Glu Leu Met Ala Phe Ala Thr
    50                  55                  60

Ser Ala Val Arg Asp Ala Glu Asn Ser Glu Asp Val Leu Ser Arg Val
65                  70                  75                  80

Arg Lys Glu Thr Gly Val Glu Leu Gln Ala Leu Arg Gly Glu Asp Glu
                85                  90                  95

Ser Arg Leu Thr Phe Leu Ala Val Arg Arg Trp Tyr Gly Trp Ser Ala
```

-continued

```
            100                 105                 110

Gly Arg Ile Leu Asn Leu Asp Ile Gly Gly Gly Ser Leu Glu Val Ser
        115                 120                 125

Ser Gly Val Asp Glu Glu Pro Glu Ile Ala Leu Ser Leu Pro Leu Gly
    130                 135                 140

Ala Gly Arg Leu Thr Arg Glu Trp Leu Pro Asp Asp Pro Pro Gly Arg
145                 150                 155                 160

Arg Arg Val Ala Met Leu Arg Asp Trp Leu Asp Ala Glu Leu Ala Glu
                165                 170                 175

Pro Ser Val Thr Val Leu Glu Ala Gly Ser Pro Asp Leu Ala Val Ala
            180                 185                 190

Thr Ser Lys Thr Phe Arg Ser Leu Ala Arg Leu Thr Gly Ala Ala Pro
        195                 200                 205

Ser Met Ala Gly Pro Arg Val Lys Arg Thr Leu Thr Ala Asn Gly Leu
    210                 215                 220

Arg Gln Leu Ile Ala Phe Ile Ser Arg Met Thr Ala Val Asp Arg Ala
225                 230                 235                 240

Glu Leu Glu Gly Val Ser Ala Asp Arg Ala Pro Gln Ile Val Ala Gly
                245                 250                 255

Ala Leu Val Ala Glu Ala Ser Met Arg Ala Leu Ser Ile Glu Ala Val
            260                 265                 270

Glu Ile Cys Pro Trp Ala Leu Arg Glu Gly Leu Ile Leu Arg Lys Leu
        275                 280                 285

Asp Ser Glu Ala Asp Gly Thr Ala Leu Ile Glu Ser Ser Ser Val His
    290                 295                 300

Thr Ser Val Arg Ala Val Gly Gly Gln Pro Ala Asp Arg Asn Ala Ala
305                 310                 315                 320

Asn Arg Ser Arg Gly Ser Lys Pro
                325

<210> SEQ ID NO 110
<211> LENGTH: 996
<212> TYPE: DNA
<213> ORGANISM: Mycobacterium tuberculosis

<400> SEQUENCE: 110

catatggtcg atgcccaccg cggcggccac ccgaccccga tgagctcgac gaaggccacg      60

ctgcggctgg ccgaggccac cgacagctcg ggcaagatca ccaagcgcgg agccgacaag     120

ctgatttcca ccatcgacga attcgccaag attgccatca gctcgggctg tgccgagctg     180

atggccttcg ccacgtcggc ggtccgcgac gccgagaatt ccgaggacgt cctgtcccgg     240

gtgcgcaaag agaccggtgt cgagttgcag gcgctgcgtg gggaggacga gtcacggctg     300

accttcctgg ccgtgcgacg atggtacggg tggagcgctg ggcgcatcct caacctcgac     360

atcggcggcg gctcgctgga agtgtccagt ggcgtggacg aggagcccga gattgcgtta     420

tcgctgcccc tgggcgccgg acggttgacc cgagagtggc tgcccgacga tccgccgggc     480

cggcgccggg tggcgatgct gcgagactgg ctggatgccg agctggccga gcccagtgtg     540

accgtcctgg aagccggcag ccccgacctg gcggtcgcaa cgtcgaagac gtttcgctcg     600

ttggcgcgac taaccggtgc ggccccatcc atggccgggc cgcgggtgaa gaggacccta     660

acggcaaatg gtctgcggca actcatcgcg tttatctcta ggatgacggc ggttgaccgt     720

gcagaactgg aaggggtaag cgccgaccga gcgccgcaga ttgtggccgg cgccctggtg     780

gcagaggcga gcatgcgagc actgtcgata gaagcggtgg aaatctgccc gtgggcgctg     840
```

cgggaaggtc tcatcttgcg caaactcgac agcgaagccg acggaaccgc cctcatcgag 900
tcttcgtctg tgcacacttc ggtgcgtgcc gtcggaggtc agccagctga tcggaacgcg 960
gccaaccgat cgagaggcag caaaccatga aagctt 996

<210> SEQ ID NO 111
<211> LENGTH: 348
<212> TYPE: PRT
<213> ORGANISM: Mycobacterium tuberculosis

<400> SEQUENCE: 111

Met Gly Ser Ser His His His His His His Ser Ser Gly Leu Val Pro
1 5 10 15

Arg Gly Ser His Met Val Asp Ala His Arg Gly Gly His Pro Thr Pro
20 25 30

Met Ser Ser Thr Lys Ala Thr Leu Arg Leu Ala Glu Ala Thr Asp Ser
35 40 45

Ser Gly Lys Ile Thr Lys Arg Gly Ala Asp Lys Leu Ile Ser Thr Ile
50 55 60

Asp Glu Phe Ala Lys Ile Ala Ile Ser Ser Gly Cys Ala Glu Leu Met
65 70 75 80

Ala Phe Ala Thr Ser Ala Val Arg Asp Ala Glu Asn Ser Glu Asp Val
85 90 95

Leu Ser Arg Val Arg Lys Glu Thr Gly Val Glu Leu Gln Ala Leu Arg
100 105 110

Gly Glu Asp Glu Ser Arg Leu Thr Phe Leu Ala Val Arg Arg Trp Tyr
115 120 125

Gly Trp Ser Ala Gly Arg Ile Leu Asn Leu Asp Ile Gly Gly Gly Ser
130 135 140

Leu Glu Val Ser Ser Gly Val Asp Glu Glu Pro Glu Ile Ala Leu Ser
145 150 155 160

Leu Pro Leu Gly Ala Gly Arg Leu Thr Arg Glu Trp Leu Pro Asp Asp
165 170 175

Pro Pro Gly Arg Arg Arg Val Ala Met Leu Arg Asp Trp Leu Asp Ala
180 185 190

Glu Leu Ala Glu Pro Ser Val Thr Val Leu Glu Ala Gly Ser Pro Asp
195 200 205

Leu Ala Val Ala Thr Ser Lys Thr Phe Arg Ser Leu Ala Arg Leu Thr
210 215 220

Gly Ala Ala Pro Ser Met Ala Gly Pro Arg Val Lys Arg Thr Leu Thr
225 230 235 240

Ala Asn Gly Leu Arg Gln Leu Ile Ala Phe Ile Ser Arg Met Thr Ala
245 250 255

Val Asp Arg Ala Glu Leu Glu Gly Val Ser Ala Asp Arg Ala Pro Gln
260 265 270

Ile Val Ala Gly Ala Leu Val Ala Glu Ala Ser Met Arg Ala Leu Ser
275 280 285

Ile Glu Ala Val Glu Ile Cys Pro Trp Ala Leu Arg Glu Gly Leu Ile
290 295 300

Leu Arg Lys Leu Asp Ser Glu Ala Asp Gly Thr Ala Leu Ile Glu Ser
305 310 315 320

Ser Ser Val His Thr Ser Val Arg Ala Val Gly Gly Gln Pro Ala Asp
325 330 335

Arg Asn Ala Ala Asn Arg Ser Arg Gly Ser Lys Pro

```
340 345

<210> SEQ ID NO 112
<211> LENGTH: 359
<212> TYPE: PRT
<213> ORGANISM: Mycobacterium tuberculosis

<400> SEQUENCE: 112

Val Arg Tyr Ser Asp Ser Tyr His Thr Thr Gly Arg Trp Gln Pro Arg
1               5                   10                  15

Ala Ser Thr Glu Gly Phe Pro Met Gly Val Ser Ile Glu Val Asn Gly
            20                  25                  30

Leu Thr Lys Ser Phe Gly Ser Ser Arg Ile Trp Glu Asp Val Thr Leu
        35                  40                  45

Thr Ile Pro Ala Gly Glu Val Ser Val Leu Leu Gly Pro Ser Gly Thr
    50                  55                  60

Gly Lys Ser Val Phe Leu Lys Ser Leu Ile Gly Leu Leu Arg Pro Glu
65                  70                  75                  80

Arg Gly Ser Ile Ile Ile Asp Gly Thr Asp Ile Ile Glu Cys Ser Ala
                85                  90                  95

Lys Glu Leu Tyr Glu Ile Arg Thr Leu Phe Gly Val Leu Phe Gln Asp
            100                 105                 110

Gly Ala Leu Phe Gly Ser Met Asn Leu Tyr Asp Asn Thr Ala Phe Pro
        115                 120                 125

Leu Arg Glu His Thr Lys Lys Lys Glu Ser Glu Ile Arg Asp Ile Val
    130                 135                 140

Met Glu Lys Leu Ala Leu Val Gly Leu Gly Gly Asp Glu Lys Lys Phe
145                 150                 155                 160

Pro Gly Glu Ile Ser Gly Gly Met Arg Lys Arg Ala Gly Leu Ala Arg
                165                 170                 175

Ala Leu Val Leu Asp Pro Gln Ile Ile Leu Cys Asp Glu Pro Asp Ser
            180                 185                 190

Gly Leu Asp Pro Val Arg Thr Ala Tyr Leu Ser Gln Leu Ile Met Asp
        195                 200                 205

Ile Asn Ala Gln Ile Asp Ala Thr Ile Leu Ile Val Thr His Asn Ile
    210                 215                 220

Asn Ile Ala Arg Thr Val Pro Asp Asn Met Gly Met Leu Phe Arg Lys
225                 230                 235                 240

His Leu Val Met Phe Gly Pro Arg Glu Val Leu Leu Thr Ser Asp Glu
                245                 250                 255

Pro Val Val Arg Gln Phe Leu Asn Gly Arg Arg Ile Gly Pro Ile Gly
            260                 265                 270

Met Ser Glu Glu Lys Asp Glu Ala Thr Met Ala Glu Glu Gln Ala Leu
        275                 280                 285

Leu Asp Ala Gly His His Ala Gly Gly Val Glu Glu Ile Glu Gly Val
    290                 295                 300

Pro Pro Gln Ile Ser Ala Thr Pro Gly Met Pro Glu Arg Lys Ala Val
305                 310                 315                 320

Ala Arg Arg Gln Ala Arg Val Arg Glu Met Leu His Thr Leu Pro Lys
                325                 330                 335

Lys Ala Gln Ala Ala Ile Leu Asp Asp Leu Glu Gly Thr His Lys Tyr
            340                 345                 350

Ala Val His Glu Ile Gly Gln
        355
```

<210> SEQ ID NO 113
<211> LENGTH: 1088
<212> TYPE: DNA
<213> ORGANISM: Mycobacterium tuberculosis

<400> SEQUENCE: 113

```
catatgcgat acagtgactc ataccacaca acgggccggt ggcagccacg agcgtcgaca     60

gagggtttcc catgggcgtc agcatcgagg tcaacggact aacgaagtcc ttcgggtcct    120

cgaggatctg ggaagatgtc acgctaacga tccccgccgg ggaggtcagc gtgctgctgg    180

gcccatcggg taccggcaaa tcggtgtttc tgaaatctct gatcggcctc ctgcggccgg    240

agcgcggctc gatcatcatc gacggcaccg acatcatcga atgctcggcc aaggagcttt    300

acgagatccg cacattgttc ggcgtgctgt ttcaggacgg tgccctgttc gggtcgatga    360

acctctacga caacaccgcg ttccccctgc gtgagcacac caagaaaaag gaaagcgaga    420

tccgtgacat cgtcatggag aagctggccc tagtcggcct gggtggggac gagaagaagt    480

tccccggcga gatctccggc gggatgcgta agcgtgccgg cctagcgcgt gccctggtcc    540

ttgacccgca gatcattctc tgcgacgagc ccgactcggg tctggacccg gttcgtaccg    600

cctacctgag ccagctgatc atggacatca acgcccagat cgacgccacc atcctgatcg    660

tgacgcacaa catcaacatc gcccgcaccg tgccggacaa catgggcatg ttgttccgca    720

agcatttggt gatgttcggg ccgcgggagg tgctactcac cagcgacgag ccggtggtgc    780

ggcagttcct caacggccgg cgcatcggcc cgatcggcat gtccgaggag aaggacgagg    840

ccaccatggc cgaagagcag gccctgctcg atgccggcca ccacgcgggc ggtgtcgagg    900

aaatcgaggg cgtgccgccg cagatcagcg cgacaccggg catgccggag cgcaaagcgg    960

tcgcccggcg tcaggctcgg gttcgcgaga tgttgcacac gctgcccaaa aaggcccagg   1020

cggcgatcct cgacgatctc gagggcacgc acaagtacgc ggtgcacgaa atcggccagt   1080

aaaagctt                                                            1088
```

<210> SEQ ID NO 114
<211> LENGTH: 379
<212> TYPE: PRT
<213> ORGANISM: Mycobacterium tuberculosis

<400> SEQUENCE: 114

```
Met Gly Ser Ser His His His His His His Ser Ser Gly Leu Val Pro
1               5                   10                  15

Arg Gly Ser His Met Arg Tyr Ser Asp Ser Tyr His Thr Thr Gly Arg
            20                  25                  30

Trp Gln Pro Arg Ala Ser Thr Glu Gly Phe Pro Met Gly Val Ser Ile
        35                  40                  45

Glu Val Asn Gly Leu Thr Lys Ser Phe Gly Ser Ser Arg Ile Trp Glu
    50                  55                  60

Asp Val Thr Leu Thr Ile Pro Ala Gly Glu Val Ser Val Leu Leu Gly
65                  70                  75                  80

Pro Ser Gly Thr Gly Lys Ser Val Phe Leu Lys Ser Leu Ile Gly Leu
                85                  90                  95

Leu Arg Pro Glu Arg Gly Ser Ile Ile Ile Asp Gly Thr Asp Ile Ile
            100                 105                 110

Glu Cys Ser Ala Lys Glu Leu Tyr Glu Ile Arg Thr Leu Phe Gly Val
        115                 120                 125

Leu Phe Gln Asp Gly Ala Leu Phe Gly Ser Met Asn Leu Tyr Asp Asn
```

```
    130                 135                 140

Thr Ala Phe Pro Leu Arg Glu His Thr Lys Lys Lys Glu Ser Glu Ile
145                 150                 155                 160

Arg Asp Ile Val Met Glu Lys Leu Ala Leu Val Gly Leu Gly Gly Asp
                165                 170                 175

Glu Lys Lys Phe Pro Gly Glu Ile Ser Gly Gly Met Arg Lys Arg Ala
            180                 185                 190

Gly Leu Ala Arg Ala Leu Val Leu Asp Pro Gln Ile Ile Leu Cys Asp
        195                 200                 205

Glu Pro Asp Ser Gly Leu Asp Pro Val Arg Thr Ala Tyr Leu Ser Gln
    210                 215                 220

Leu Ile Met Asp Ile Asn Ala Gln Ile Asp Ala Thr Ile Leu Ile Val
225                 230                 235                 240

Thr His Asn Ile Asn Ile Ala Arg Thr Val Pro Asp Asn Met Gly Met
                245                 250                 255

Leu Phe Arg Lys His Leu Val Met Phe Gly Pro Arg Glu Val Leu Leu
            260                 265                 270

Thr Ser Asp Glu Pro Val Val Arg Gln Phe Leu Asn Gly Arg Arg Ile
        275                 280                 285

Gly Pro Ile Gly Met Ser Glu Glu Lys Asp Glu Ala Thr Met Ala Glu
    290                 295                 300

Glu Gln Ala Leu Leu Asp Ala Gly His His Ala Gly Gly Val Glu Glu
305                 310                 315                 320

Ile Glu Gly Val Pro Pro Gln Ile Ser Ala Thr Pro Gly Met Pro Glu
                325                 330                 335

Arg Lys Ala Val Ala Arg Arg Gln Ala Arg Val Arg Glu Met Leu His
            340                 345                 350

Thr Leu Pro Lys Lys Ala Gln Ala Ala Ile Leu Asp Asp Leu Glu Gly
        355                 360                 365

Thr His Lys Tyr Ala Val His Glu Ile Gly Gln
    370                 375


<210> SEQ ID NO 115
<211> LENGTH: 270
<212> TYPE: PRT
<213> ORGANISM: Mycobacterium tuberculosis

<400> SEQUENCE: 115

Met Leu Pro Glu Thr Asn Gln Asp Glu Val Gln Pro Asn Ala Pro Val
1               5                   10                  15

Ala Leu Val Thr Val Glu Ile Arg His Pro Thr Thr Asp Ser Leu Thr
            20                  25                  30

Glu Ser Ala Asn Arg Glu Leu Lys His Leu Leu Ile Asn Asp Leu Pro
        35                  40                  45

Ile Glu Arg Gln Ala Gln Asp Val Ser Trp Gly Met Thr Ala Pro Gly
    50                  55                  60

Gly Ala Pro Thr Pro Val Ala Asp Arg Phe Val Arg Tyr Val Asn Arg
65                  70                  75                  80

Asp Asn Thr Thr Ala Ala Ser Leu Lys Asn Gln Ala Ile Val Val Glu
                85                  90                  95

Thr Thr Ala Tyr Arg Ser Phe Glu Ala Phe Thr Asp Val Val Met Arg
            100                 105                 110

Val Val Asp Ala Arg Ala Gln Val Ser Ser Ile Val Gly Leu Glu Arg
        115                 120                 125
```

```
Ile Leu Arg Phe Val Leu Glu Ile Arg Val Pro Ala Gly Val Asp Gly
    130                 135                 140

Arg Ile Thr Trp Ser Asn Trp Ile Asp Glu Gln Leu Leu Gly Pro Gln
145                 150                 155                 160

Arg Phe Thr Pro Gly Gly Leu Val Leu Thr Glu Trp Gln Gly Ala Ala
                165                 170                 175

Val Tyr Arg Glu Leu Gln Pro Gly Lys Ser Leu Ile Val Arg Tyr Gly
            180                 185                 190

Pro Gly Met Gly Gln Ala Leu Asp Pro Asn Tyr His Leu Arg Arg Ile
        195                 200                 205

Thr Pro Ala Gln Thr Gly Pro Phe Phe Leu Leu Asp Ile Asp Ser Phe
    210                 215                 220

Trp Thr Pro Ser Gly Gly Ser Ile Pro Glu Tyr Asn Arg Asp Ala Leu
225                 230                 235                 240

Val Ser Thr Phe Gln Asp Leu Tyr Gly Pro Ala Gln Val Val Phe Gln
                245                 250                 255

Glu Met Ile Thr Ser Arg Leu Lys Asp Glu Leu Leu Arg Gln
            260                 265                 270
```

<210> SEQ ID NO 116
<211> LENGTH: 825
<212> TYPE: DNA
<213> ORGANISM: Mycobacterium tuberculosis

<400> SEQUENCE: 116

```
catatgctcc ccgagacaaa tcaggatgag gtccagccca acgcacccgt tgccctggtg     60

acggtggaaa tccgtcaccc gacaacggat tcgctcaccg aatcagcgaa ccgggagctc    120

aaacacctgc ttatcaatga tctaccgatc gaacgccagg cgcaggacgt cagctggggg    180

atgacggcgc ccggtggagc ccccaccccg gtcgcggatc gtttcgttcg ttatgtcaat    240

cgcgataaca ccaccgccgc ttcactgaag aaccaggcga tagtcgtgga gaccaccgcc    300

taccgcagct ttgaggcctt taccgacgtt gtgatgcggg tcgtggatgc tcgcgcgcag    360

gtctcgtcaa tcgttgggtt ggagcgtatc ggtcttcgct ttgttctgga gatccgcgtc    420

cccgcgggtg tcgacggccg gatcacgtgg agcaactgga tcgacgagca gctgctcggg    480

ccgcagcgtt tcactcccgg cggcctggtc ctgaccgagt ggcagggtgc cgcagtctac    540

cgtgagctac aaccaggcaa atcgctcatc gtgcgctacg gcccgggtat gggccaagcg    600

cttgatccca attaccatct gcgccgaata acacccgccc aaaccggacc attcttcctg    660

ctggacatcg atagcttttg gactcccagt ggcggctcca ttcccgagta caacagggac    720

gccttagtgt cgacattcca ggacctgtac ggtccggccc aggtcgtgtt tcaggagatg    780

atcaccagtc gcctgaaaga tgagctgctt cgccagtaaa agctt                    825
```

<210> SEQ ID NO 117
<211> LENGTH: 291
<212> TYPE: PRT
<213> ORGANISM: Mycobacterium tuberculosis

<400> SEQUENCE: 117

```
Met Gly Ser Ser His His His His His His Ser Ser Gly Leu Val Pro
1               5                   10                  15

Arg Gly Ser His Met Met Leu Pro Glu Thr Asn Gln Asp Glu Val Gln
            20                  25                  30

Pro Asn Ala Pro Val Ala Leu Val Thr Val Glu Ile Arg His Pro Thr
        35                  40                  45
```

Thr Asp Ser Leu Thr Glu Ser Ala Asn Arg Glu Leu Lys His Leu Leu
    50                  55                  60

Ile Asn Asp Leu Pro Ile Glu Arg Gln Ala Gln Asp Val Ser Trp Gly
65                  70                  75                  80

Met Thr Ala Pro Gly Gly Ala Pro Thr Pro Val Ala Asp Arg Phe Val
                85                  90                  95

Arg Tyr Val Asn Arg Asp Asn Thr Thr Ala Ala Ser Leu Lys Asn Gln
            100                 105                 110

Ala Ile Val Val Glu Thr Thr Ala Tyr Arg Ser Phe Glu Ala Phe Thr
        115                 120                 125

Asp Val Val Met Arg Val Val Asp Ala Arg Ala Gln Val Ser Ser Ile
    130                 135                 140

Val Gly Leu Glu Arg Ile Leu Arg Phe Val Leu Glu Ile Arg Val Pro
145                 150                 155                 160

Ala Gly Val Asp Gly Arg Ile Thr Trp Ser Asn Trp Ile Asp Glu Gln
                165                 170                 175

Leu Leu Gly Pro Gln Arg Phe Thr Pro Gly Gly Leu Val Leu Thr Glu
            180                 185                 190

Trp Gln Gly Ala Ala Val Tyr Arg Glu Leu Gln Pro Gly Lys Ser Leu
        195                 200                 205

Ile Val Arg Tyr Gly Pro Gly Met Gly Gln Ala Leu Asp Pro Asn Tyr
    210                 215                 220

His Leu Arg Arg Ile Thr Pro Ala Gln Thr Gly Pro Phe Phe Leu Leu
225                 230                 235                 240

Asp Ile Asp Ser Phe Trp Thr Pro Ser Gly Gly Ser Ile Pro Glu Tyr
                245                 250                 255

Asn Arg Asp Ala Leu Val Ser Thr Phe Gln Asp Leu Tyr Gly Pro Ala
            260                 265                 270

Gln Val Val Phe Gln Glu Met Ile Thr Ser Arg Leu Lys Asp Glu Leu
        275                 280                 285

Leu Arg Gln
    290

<210> SEQ ID NO 118
<211> LENGTH: 362
<212> TYPE: PRT
<213> ORGANISM: Mycobacterium tuberculosis

<400> SEQUENCE: 118

Met Leu Arg Leu Val Val Gly Ala Leu Leu Leu Val Leu Ala Phe Ala
1               5                   10                  15

Gly Gly Tyr Ala Val Ala Ala Cys Lys Thr Val Thr Leu Thr Val Asp
            20                  25                  30

Gly Thr Ala Met Arg Val Thr Thr Met Lys Ser Arg Val Ile Asp Ile
        35                  40                  45

Val Glu Glu Asn Gly Phe Ser Val Asp Asp Arg Asp Asp Leu Tyr Pro
    50                  55                  60

Ala Ala Gly Val Gln Val His Asp Ala Asp Thr Ile Val Leu Arg Arg
65                  70                  75                  80

Ser Arg Pro Leu Gln Ile Ser Leu Asp Gly His Asp Ala Lys Gln Val
                85                  90                  95

Trp Thr Thr Ala Ser Thr Val Asp Glu Ala Leu Ala Gln Leu Ala Met
            100                 105                 110

Thr Asp Thr Ala Pro Ala Ala Ala Ser Arg Ala Ser Arg Val Pro Leu

-continued

```
        115                 120                 125

Ser Gly Met Ala Leu Pro Val Val Ser Ala Lys Thr Val Gln Leu Asn
    130                 135                 140

Asp Gly Gly Leu Val Arg Thr Val His Leu Pro Ala Pro Asn Val Ala
145                 150                 155                 160

Gly Leu Leu Ser Ala Ala Gly Val Pro Leu Leu Gln Ser Asp His Val
                165                 170                 175

Val Pro Ala Ala Thr Ala Pro Ile Val Glu Gly Met Gln Ile Gln Val
            180                 185                 190

Thr Arg Asn Arg Ile Lys Lys Val Thr Glu Arg Leu Pro Leu Pro Pro
        195                 200                 205

Asn Ala Arg Arg Val Glu Asp Pro Glu Met Asn Met Ser Arg Glu Val
    210                 215                 220

Val Glu Asp Pro Gly Val Pro Gly Thr Gln Asp Val Thr Phe Ala Val
225                 230                 235                 240

Ala Glu Val Asn Gly Val Glu Thr Gly Arg Leu Pro Val Ala Asn Val
                245                 250                 255

Val Val Thr Pro Ala His Glu Ala Val Val Arg Val Gly Thr Lys Pro
            260                 265                 270

Gly Thr Glu Val Pro Pro Val Ile Asp Gly Ser Ile Trp Asp Ala Ile
        275                 280                 285

Ala Gly Cys Glu Ala Gly Gly Asn Trp Ala Ile Asn Thr Gly Asn Gly
    290                 295                 300

Tyr Tyr Gly Gly Val Gln Phe Asp Gln Gly Thr Trp Glu Ala Asn Gly
305                 310                 315                 320

Gly Leu Arg Tyr Ala Pro Arg Ala Asp Leu Ala Thr Arg Glu Glu Gln
                325                 330                 335

Ile Ala Val Ala Glu Val Thr Arg Leu Arg Gln Gly Trp Gly Ala Trp
            340                 345                 350

Pro Val Cys Ala Ala Arg Ala Gly Ala Arg
        355                 360
```

<210> SEQ ID NO 119
<211> LENGTH: 1053
<212> TYPE: DNA
<213> ORGANISM: Mycobacterium tuberculosis

<400> SEQUENCE: 119

```
catatgcatc accatcacca tcacgcatgc aaaacggtga cgttgaccgt cgacggaacc     60

gcgatgcggg tgaccacgat gaaatcgcgg gtgatcgaca tcgtcgaaga gaacgggttc    120

tcagtcgacg accgcgacga cctgtatccc gcggccggcg tgcaggtcca tgacgccgac    180

accatcgtgc tgcggcgtag ccgtccgctg cagatctcgc tggatggtca cgacgctaag    240

caggtgtgga cgaccgcgtc gacggtggac gaggcgctgg cccaactcgc gatgaccgac    300

acggcgccgg ccgcggcttc tcgcgccagc cgcgtcccgc tgtccgggat ggcgctaccg    360

gtcgtcagcg ccaagacggt gcagctcaac gacggcgggt tggtgcgcac ggtgcacttg    420

ccggccccca atgtcgcggg gctgctgagt gcggccggcg tgccgctgtt gcaaagcgac    480

cacgtggtgc ccgccgcgac ggccccgatc gtcgaaggca tgcagatcca ggtgacccgc    540

aatcggatca agaaggtcac cgagcggctg ccgctgccgc cgaacgcgcg tcgtgtcgag    600

gacccggaga tgaacatgag ccgggaggtc gtcgaagacc cgggggttcc ggggacccag    660

gatgtgacgt tcgcggtagc tgaggtcaac ggcgtcgaga ccggccgttt gcccgtcgcc    720
```

-continued

```
aacgtcgtgg tgaccccggc ccacgaagcc gtggtgcggg tgggcaccaa gcccggtacc    780

gaggtgcccc cggtgatcga cggaagcatc tgggacgcga tcgccggctg tgaggccggt    840

ggcaactggg cgatcaacac cggcaacggg tattacggtg gtgtgcagtt tgaccagggc    900

acctgggagg ccaacggcgg gctgcggtat gcaccccgcg ctgacctcgc cacccgcgaa    960

gagcagatcg ccgttgccga ggtgacccga ctgcgtcaag gttggggcgc ctggccggta   1020

tgtgctgcac gagcgggtgc gcgctgagaa ttc                                1053


<210> SEQ ID NO 120
<211> LENGTH: 348
<212> TYPE: PRT
<213> ORGANISM: Mycobacterium tuberculosis

<400> SEQUENCE: 120

His Met His His His His His His Ala Cys Lys Thr Val Thr Leu Thr
1               5                   10                  15

Val Asp Gly Thr Ala Met Arg Val Thr Thr Met Lys Ser Arg Val Ile
            20                  25                  30

Asp Ile Val Glu Glu Asn Gly Phe Ser Val Asp Asp Arg Asp Asp Leu
        35                  40                  45

Tyr Pro Ala Ala Gly Val Gln Val His Asp Ala Asp Thr Ile Val Leu
    50                  55                  60

Arg Arg Ser Arg Pro Leu Gln Ile Ser Leu Asp Gly His Asp Ala Lys
65                  70                  75                  80

Gln Val Trp Thr Thr Ala Ser Thr Val Asp Glu Ala Leu Ala Gln Leu
                85                  90                  95

Ala Met Thr Asp Thr Ala Pro Ala Ala Ala Ser Arg Ala Ser Arg Val
            100                 105                 110

Pro Leu Ser Gly Met Ala Leu Pro Val Val Ser Ala Lys Thr Val Gln
        115                 120                 125

Leu Asn Asp Gly Gly Leu Val Arg Thr Val His Leu Pro Ala Pro Asn
    130                 135                 140

Val Ala Gly Leu Leu Ser Ala Ala Gly Val Pro Leu Leu Gln Ser Asp
145                 150                 155                 160

His Val Val Pro Ala Ala Thr Ala Pro Ile Val Glu Gly Met Gln Ile
                165                 170                 175

Gln Val Thr Arg Asn Arg Ile Lys Lys Val Thr Glu Arg Leu Pro Leu
            180                 185                 190

Pro Pro Asn Ala Arg Arg Val Glu Asp Pro Glu Met Asn Met Ser Arg
        195                 200                 205

Glu Val Val Glu Asp Pro Gly Val Pro Gly Thr Gln Asp Val Thr Phe
    210                 215                 220

Ala Val Ala Glu Val Asn Gly Val Glu Thr Gly Arg Leu Pro Val Ala
225                 230                 235                 240

Asn Val Val Val Thr Pro Ala His Glu Ala Val Val Arg Val Gly Thr
                245                 250                 255

Lys Pro Gly Thr Glu Val Pro Pro Val Ile Asp Gly Ser Ile Trp Asp
            260                 265                 270

Ala Ile Ala Gly Cys Glu Ala Gly Gly Asn Trp Ala Ile Asn Thr Gly
        275                 280                 285

Asn Gly Tyr Tyr Gly Gly Val Gln Phe Asp Gln Gly Thr Trp Glu Ala
    290                 295                 300

Asn Gly Gly Leu Arg Tyr Ala Pro Arg Ala Asp Leu Ala Thr Arg Glu
305                 310                 315                 320
```

Glu Gln Ile Ala Val Ala Glu Val Thr Arg Leu Arg Gln Gly Trp Gly
325 330 335

Ala Trp Pro Val Cys Ala Ala Arg Ala Gly Ala Arg
340 345

<210> SEQ ID NO 121
<211> LENGTH: 328
<212> TYPE: PRT
<213> ORGANISM: Mycobacterium tuberculosis

<400> SEQUENCE: 121

Met Glu Leu Val Arg Val Thr Glu Ala Gly Ala Met Ala Ala Gly Arg
1 5 10 15

Trp Val Gly Arg Gly Asp Lys Glu Gly Gly Asp Gly Ala Ala Val Asp
20 25 30

Ala Met Arg Glu Leu Val Asn Ser Val Ser Met Arg Gly Val Val Val
35 40 45

Ile Gly Glu Gly Glu Lys Asp His Ala Pro Met Leu Tyr Asn Gly Glu
50 55 60

Glu Val Gly Asn Gly Asp Gly Pro Glu Cys Asp Phe Ala Val Asp Pro
65 70 75 80

Ile Asp Gly Thr Thr Leu Met Ser Lys Gly Met Thr Asn Ala Ile Ser
85 90 95

Val Leu Ala Val Ala Asp Arg Gly Thr Met Phe Asp Pro Ser Ala Val
100 105 110

Phe Tyr Met Asn Lys Ile Ala Val Gly Pro Asp Ala Ala His Val Leu
115 120 125

Asp Ile Thr Ala Pro Ile Ser Glu Asn Ile Arg Ala Val Ala Lys Val
130 135 140

Lys Asp Leu Ser Val Arg Asp Met Thr Val Cys Ile Leu Asp Arg Pro
145 150 155 160

Arg His Ala Gln Leu Ile His Asp Val Arg Ala Thr Gly Ala Arg Ile
165 170 175

Arg Leu Ile Thr Asp Gly Asp Val Ala Gly Ala Ile Ser Ala Cys Arg
180 185 190

Pro His Ser Gly Thr Asp Leu Leu Ala Gly Ile Gly Gly Thr Pro Glu
195 200 205

Gly Ile Ile Ala Ala Ala Ala Ile Arg Cys Met Gly Gly Ala Ile Gln
210 215 220

Ala Gln Leu Ala Pro Arg Asp Asp Ala Glu Arg Arg Lys Ala Leu Glu
225 230 235 240

Ala Gly Tyr Asp Leu Asn Gln Val Leu Thr Thr Glu Asp Leu Val Ser
245 250 255

Gly Glu Asn Val Phe Phe Cys Ala Thr Gly Val Thr Asp Gly Asp Leu
260 265 270

Leu Lys Gly Val Arg Tyr Tyr Pro Gly Gly Cys Thr Thr His Ser Ile
275 280 285

Val Met Arg Ser Lys Ser Gly Thr Val Arg Met Ile Glu Ala Tyr His
290 295 300

Arg Leu Ser Lys Leu Asn Glu Tyr Ser Ala Ile Asp Phe Thr Gly Asp
305 310 315 320

Ser Ser Ala Val Tyr Pro Leu Pro
325

<210> SEQ ID NO 122
<211> LENGTH: 999
<212> TYPE: DNA
<213> ORGANISM: Mycobacterium tuberculosis

<400> SEQUENCE: 122
catatgatgg agctggtccg ggtgaccgag gccggagcca tggccgcggg ccgctgggta 60
ggccgcggcg acaaggaggg cggcgacggc gcggcggtcg acgcgatgcg cgaactggtc 120
aactcggttt ccatgcgcgg ggtggtggtc atcggcgaag gcgaaaagga ccacgcacca 180
atgctctaca acggcgaaga agtgggcaac ggcgacggac cggaatgcga ctttgccgtc 240
gaccccattg acggcaccac gctgatgagc aagggcatga ccaacgccat ctcggtgctg 300
gcggtagccg atcgcggcac catgttcgac ccgtcggcgg tgttctacat gaacaaaatc 360
gccgtcggcc ccgatgccgc acacgtgctg gatatcaccg cgccgatctc ggaaaacatc 420
cgagcggtcg ccaaggtcaa ggacctgtcg gtgcgagaca tgacggtgtg catcctggac 480
aggccgcggc acgcgcaact catccacgac gtccgcgcca ccggggcccg gatccggctg 540
atcaccgatg gcgacgtcgc cggcgcgatc tcggcgtgcc gaccgcactc cggcaccgac 600
ctgctagctg ggatcggcgg caccccggag ggaatcatcg ccgccgcggc gatccgctgc 660
atgggcgggg cgatccaggc gcagctcgcc ccgcgcgacg acgcggaacg ccgcaaggcc 720
ctagaagccg gttacgacct gaaccaggtc ttgaccaccg aagatctggt gtccggggaa 780
aacgtcttct tctgcgccac tggggtcacc gacggcgacc tgctcaaggg agtgcgttac 840
taccccggcg gctgcaccac ccattcgatc gtgatgcgct cgaagtccgg caccgtccgg 900
atgatcgagg cctaccaccg gctttcaaag ctcaacgaat actccgcgat cgacttcacc 960
ggcgacagca gcgccgtgta cccattgccc taaaagctt 999

<210> SEQ ID NO 123
<211> LENGTH: 348
<212> TYPE: PRT
<213> ORGANISM: Mycobacterium tuberculosis

<400> SEQUENCE: 123

Met Gly Ser Ser His His His His His His Ser Ser Gly Leu Val Pro
1 5 10 15

Arg Gly Ser His Met Glu Leu Val Arg Val Thr Glu Ala Gly Ala Met
20 25 30

Ala Ala Gly Arg Trp Val Gly Arg Gly Asp Lys Glu Gly Gly Asp Gly
35 40 45

Ala Ala Val Asp Ala Met Arg Glu Leu Val Asn Ser Val Ser Met Arg
50 55 60

Gly Val Val Val Ile Gly Glu Gly Glu Lys Asp His Ala Pro Met Leu
65 70 75 80

Tyr Asn Gly Glu Glu Val Gly Asn Gly Asp Gly Pro Glu Cys Asp Phe
85 90 95

Ala Val Asp Pro Ile Asp Gly Thr Thr Leu Met Ser Lys Gly Met Thr
100 105 110

Asn Ala Ile Ser Val Leu Ala Val Ala Asp Arg Gly Thr Met Phe Asp
115 120 125

Pro Ser Ala Val Phe Tyr Met Asn Lys Ile Ala Val Gly Pro Asp Ala
130 135 140

Ala His Val Leu Asp Ile Thr Ala Pro Ile Ser Glu Asn Ile Arg Ala
145 150 155 160

```
Val Ala Lys Val Lys Asp Leu Ser Val Arg Asp Met Thr Val Cys Ile
                165                 170                 175

Leu Asp Arg Pro Arg His Ala Gln Leu Ile His Asp Val Arg Ala Thr
            180                 185                 190

Gly Ala Arg Ile Arg Leu Ile Thr Asp Gly Asp Val Ala Gly Ala Ile
        195                 200                 205

Ser Ala Cys Arg Pro His Ser Gly Thr Asp Leu Leu Ala Gly Ile Gly
    210                 215                 220

Gly Thr Pro Glu Gly Ile Ile Ala Ala Ala Ala Ile Arg Cys Met Gly
225                 230                 235                 240

Gly Ala Ile Gln Ala Gln Leu Ala Pro Arg Asp Asp Ala Glu Arg Arg
                245                 250                 255

Lys Ala Leu Glu Ala Gly Tyr Asp Leu Asn Gln Val Leu Thr Thr Glu
            260                 265                 270

Asp Leu Val Ser Gly Glu Asn Val Phe Phe Cys Ala Thr Gly Val Thr
        275                 280                 285

Asp Gly Asp Leu Leu Lys Gly Val Arg Tyr Tyr Pro Gly Gly Cys Thr
    290                 295                 300

Thr His Ser Ile Val Met Arg Ser Lys Ser Gly Thr Val Arg Met Ile
305                 310                 315                 320

Glu Ala Tyr His Arg Leu Ser Lys Leu Asn Glu Tyr Ser Ala Ile Asp
                325                 330                 335

Phe Thr Gly Asp Ser Ser Ala Val Tyr Pro Leu Pro
            340                 345


<210> SEQ ID NO 124
<211> LENGTH: 329
<212> TYPE: PRT
<213> ORGANISM: Mycobacterium tuberculosis

<400> SEQUENCE: 124

Val Ser Ala Ser Pro Leu Lys Val Ala Val Thr Gly Ala Ala Gly Gln
1               5                   10                  15

Ile Gly Tyr Ser Leu Leu Phe Arg Leu Ala Ser Gly Ser Leu Leu Gly
            20                  25                  30

Pro Asp Arg Pro Ile Glu Leu Arg Leu Leu Glu Ile Glu Pro Ala Leu
        35                  40                  45

Gln Ala Leu Glu Gly Val Val Met Glu Leu Asp Asp Cys Ala Phe Pro
    50                  55                  60

Leu Leu Ser Gly Val Glu Ile Gly Ser Asp Pro Gln Lys Ile Phe Asp
65                  70                  75                  80

Gly Val Ser Leu Ala Leu Leu Val Gly Ala Arg Pro Arg Gly Ala Gly
                85                  90                  95

Met Glu Arg Ser Asp Leu Leu Glu Ala Asn Gly Ala Ile Phe Thr Ala
            100                 105                 110

Gln Gly Lys Ala Leu Asn Ala Val Ala Ala Asp Asp Val Arg Val Gly
        115                 120                 125

Val Thr Gly Asn Pro Ala Asn Thr Asn Ala Leu Ile Ala Met Thr Asn
    130                 135                 140

Ala Pro Asp Ile Pro Arg Glu Arg Phe Ser Ala Leu Thr Arg Leu Asp
145                 150                 155                 160

His Asn Arg Ala Ile Ser Gln Leu Ala Ala Lys Thr Gly Ala Ala Val
                165                 170                 175

Thr Asp Ile Lys Lys Met Thr Ile Trp Gly Asn His Ser Ala Thr Gln
            180                 185                 190
```

```
Tyr Pro Asp Leu Phe His Ala Glu Val Ala Gly Lys Asn Ala Ala Glu
        195                 200                 205

Val Val Asn Asp Gln Ala Trp Ile Glu Asp Glu Phe Ile Pro Thr Val
    210                 215                 220

Ala Lys Arg Gly Ala Ala Ile Ile Asp Ala Arg Gly Ala Ser Ser Ala
225                 230                 235                 240

Ala Ser Ala Ala Ser Ala Thr Ile Asp Ala Ala Arg Asp Trp Leu Leu
                245                 250                 255

Gly Thr Pro Ala Asp Asp Trp Val Ser Met Ala Val Val Ser Asp Gly
            260                 265                 270

Ser Tyr Gly Val Pro Glu Gly Leu Ile Ser Ser Phe Pro Val Thr Thr
        275                 280                 285

Lys Gly Gly Asn Trp Thr Ile Val Ser Gly Leu Glu Ile Asp Glu Phe
    290                 295                 300

Ser Arg Gly Arg Ile Asp Lys Ser Thr Ala Glu Leu Ala Asp Glu Arg
305                 310                 315                 320

Ser Ala Val Thr Glu Leu Gly Leu Ile
                325
```

<210> SEQ ID NO 125
<211> LENGTH: 999
<212> TYPE: DNA
<213> ORGANISM: Mycobacterium tuberculosis

<400> SEQUENCE: 125

```
catatgagcg ctagtcctct caaggtcgcc gttaccggcg ccgccggcca aatcggctac     60

agcctgttgt tccgcctggc cagcggctct ttgctgggcc ctgaccgtcc gatcgagctg    120

cggctgctcg agatcgagcc ggcactgcag gcgctcgagg gtgtggtgat ggaactcgac    180

gactgcgctt tcccgctgtt gtccggggtg gagatcggtt cagatcccca gaagatcttc    240

gatggcgtga gcctggccct gctggtcgga gcccgccccc ggggcgcggg catggagcga    300

agtgacctgc tggaggccaa cggcgcgatc ttcaccgctc agggcaaagc cctcaacgct    360

gtcgccgcgg atgacgttcg cgtcggggtg accggcaacc ccgccaacac caacgcgctg    420

atcgcgatga ccaatgcgcc cgacattccc cgcgagcggt tctcggcgct cacccggctg    480

gaccacaatc gggcgatctc gcagctggcc gccaagaccg gcgcggcggt caccgacatc    540

aagaagatga cgatctgggg caatcactcg gccacccagt accccgacct gttccacgcg    600

gaggtcgccg gaaagaacgc ggccgaagtg gtcaacgacc aggcctggat cgaggatgaa    660

ttcatcccga cggtcgccaa gcgcggtgcg gcgatcatcg atgcgcgcgg cgcgtcgtcg    720

gccgcctcgg ccgcgtcggc aaccatcgac gctgcccggg actggttgct ggggacgccg    780

gcggacgatt gggtctcgat ggccgtcgtc tccgacgggt cctacggggt gccggagggc    840

ttgatctcct cgtttccggt caccaccaag ggcggcaact ggacgatcgt gagcggcttg    900

gagatcgacg agttctcccg cggccggatc gacaagtcaa ccgccgagtt ggctgacgag    960

cgcagcgcgg tcaccgagct cggcctgatc tgaaagctt                           999
```

<210> SEQ ID NO 126
<211> LENGTH: 349
<212> TYPE: PRT
<213> ORGANISM: Mycobacterium tuberculosis

<400> SEQUENCE: 126

```
Met Gly Ser Ser His His His His His His Ser Ser Gly Leu Val Pro
```

1 5 10 15

Arg Gly Ser His Met Ser Ala Ser Pro Leu Lys Val Ala Val Thr Gly
20 25 30

Ala Ala Gly Gln Ile Gly Tyr Ser Leu Leu Phe Arg Leu Ala Ser Gly
35 40 45

Ser Leu Leu Gly Pro Asp Arg Pro Ile Glu Leu Arg Leu Leu Glu Ile
50 55 60

Glu Pro Ala Leu Gln Ala Leu Glu Gly Val Val Met Glu Leu Asp Asp
65 70 75 80

Cys Ala Phe Pro Leu Leu Ser Gly Val Glu Ile Gly Ser Asp Pro Gln
85 90 95

Lys Ile Phe Asp Gly Val Ser Leu Ala Leu Leu Val Gly Ala Arg Pro
100 105 110

Arg Gly Ala Gly Met Glu Arg Ser Asp Leu Leu Glu Ala Asn Gly Ala
115 120 125

Ile Phe Thr Ala Gln Gly Lys Ala Leu Asn Ala Val Ala Ala Asp Asp
130 135 140

Val Arg Val Gly Val Thr Gly Asn Pro Ala Asn Thr Asn Ala Leu Ile
145 150 155 160

Ala Met Thr Asn Ala Pro Asp Ile Pro Arg Glu Arg Phe Ser Ala Leu
165 170 175

Thr Arg Leu Asp His Asn Arg Ala Ile Ser Gln Leu Ala Ala Lys Thr
180 185 190

Gly Ala Ala Val Thr Asp Ile Lys Lys Met Thr Ile Trp Gly Asn His
195 200 205

Ser Ala Thr Gln Tyr Pro Asp Leu Phe His Ala Glu Val Ala Gly Lys
210 215 220

Asn Ala Ala Glu Val Val Asn Asp Gln Ala Trp Ile Glu Asp Glu Phe
225 230 235 240

Ile Pro Thr Val Ala Lys Arg Gly Ala Ala Ile Ile Asp Ala Arg Gly
245 250 255

Ala Ser Ser Ala Ala Ser Ala Ala Ser Ala Thr Ile Asp Ala Ala Arg
260 265 270

Asp Trp Leu Leu Gly Thr Pro Ala Asp Asp Trp Val Ser Met Ala Val
275 280 285

Val Ser Asp Gly Ser Tyr Gly Val Pro Glu Gly Leu Ile Ser Ser Phe
290 295 300

Pro Val Thr Thr Lys Gly Gly Asn Trp Thr Ile Val Ser Gly Leu Glu
305 310 315 320

Ile Asp Glu Phe Ser Arg Gly Arg Ile Asp Lys Ser Thr Ala Glu Leu
325 330 335

Ala Asp Glu Arg Ser Ala Val Thr Glu Leu Gly Leu Ile
340 345

<210> SEQ ID NO 127
<211> LENGTH: 456
<212> TYPE: PRT
<213> ORGANISM: Mycobacterium tuberculosis

<400> SEQUENCE: 127

Met Val Ser Thr His Ala Val Val Ala Gly Glu Thr Leu Ser Ala Leu
1 5 10 15

Ala Leu Arg Phe Tyr Gly Asp Ala Glu Leu Tyr Arg Leu Ile Ala Ala
20 25 30

```
Ala Ser Gly Ile Ala Asp Pro Asp Val Val Asn Val Gly Gln Arg Leu
        35                  40                  45

Ile Met Pro Asp Phe Thr Arg Tyr Thr Val Val Ala Gly Asp Thr Leu
    50                  55                  60

Ser Ala Leu Ala Leu Arg Phe Tyr Gly Asp Ala Glu Leu Asn Trp Leu
65                  70                  75                  80

Ile Ala Ala Ala Ser Gly Ile Ala Asp Pro Asp Val Val Asn Val Gly
                85                  90                  95

Gln Arg Leu Ile Met Pro Asp Phe Thr Arg Tyr Thr Val Val Ala Gly
            100                 105                 110

Asp Thr Leu Ser Ala Leu Ala Ala Arg Phe Tyr Gly Asp Ala Ser Leu
        115                 120                 125

Tyr Pro Leu Ile Ala Ala Val Asn Gly Ile Ala Asp Pro Gly Val Ile
    130                 135                 140

Asp Val Gly Gln Val Leu Val Ile Phe Ile Gly Arg Ser Asp Gly Phe
145                 150                 155                 160

Gly Leu Arg Ile Val Asp Arg Asn Glu Asn Asp Pro Arg Leu Trp Tyr
                165                 170                 175

Tyr Arg Phe Gln Thr Ser Ala Ile Gly Trp Asn Pro Gly Val Asn Val
            180                 185                 190

Leu Leu Pro Asp Asp Tyr Arg Thr Ser Gly Arg Thr Tyr Pro Val Leu
        195                 200                 205

Tyr Leu Phe His Gly Gly Gly Thr Asp Gln Asp Phe Arg Thr Phe Asp
    210                 215                 220

Phe Leu Gly Ile Arg Asp Leu Thr Ala Gly Lys Pro Ile Ile Ile Val
225                 230                 235                 240

Met Pro Asp Gly Gly His Ala Gly Trp Tyr Ser Asn Pro Val Ser Ser
                245                 250                 255

Phe Val Gly Pro Arg Asn Trp Glu Thr Phe His Ile Ala Gln Leu Leu
            260                 265                 270

Pro Trp Ile Glu Ala Asn Phe Arg Thr Tyr Ala Glu Tyr Asp Gly Arg
        275                 280                 285

Ala Val Ala Gly Phe Ser Met Gly Gly Phe Gly Ala Leu Lys Tyr Ala
    290                 295                 300

Ala Lys Tyr Tyr Gly His Phe Ala Ser Ala Ser Ser His Ser Gly Pro
305                 310                 315                 320

Ala Ser Leu Arg Arg Asp Phe Gly Leu Val Val His Trp Ala Asn Leu
                325                 330                 335

Ser Ser Ala Val Leu Asp Leu Gly Gly Gly Thr Val Tyr Gly Ala Pro
            340                 345                 350

Leu Trp Asp Gln Ala Arg Val Ser Ala Asp Asn Pro Val Glu Arg Ile
        355                 360                 365

Asp Ser Tyr Arg Asn Lys Arg Ile Phe Leu Val Ala Gly Thr Ser Pro
    370                 375                 380

Asp Pro Ala Asn Trp Phe Asp Ser Val Asn Glu Thr Gln Val Leu Ala
385                 390                 395                 400

Gly Gln Arg Glu Phe Arg Glu Arg Leu Ser Asn Ala Gly Ile Pro His
                405                 410                 415

Glu Ser His Glu Val Pro Gly Gly His Val Phe Arg Pro Asp Met Phe
            420                 425                 430

Arg Leu Asp Leu Asp Gly Ile Val Ala Arg Leu Arg Pro Ala Ser Ile
        435                 440                 445

Gly Ala Ala Ala Glu Arg Ala Asp
```

450 455

<210> SEQ ID NO 128
<211> LENGTH: 1380
<212> TYPE: DNA
<213> ORGANISM: Mycobacterium tuberculosis

<400> SEQUENCE: 128
catatggtca gcacacatgc ggttgtcgcg ggggagacgc tgtcggcgtt ggcgttgcgc 60
ttctatggcg acgcggaact gtatcggctg atcgccgccg ccagcgggat cgccgatccc 120
gacgtcgtca atgtggggca gcggctgatt atgcctgact tcacgcgata caccgttgtt 180
gccggggaca cgctgtcggc gttggcgttg cgcttctatg gcgacgcgga attgaattgg 240
ctgatcgccg ccgccagcgg gatcgccgat cccgacgtcg tcaatgtggg gcagcggctg 300
attatgcctg acttcacgcg atacaccgtt gttgccgggg acacgctgtc ggcattggct 360
gcgcgcttct atggcgacgc ctccctatat ccgcttatcg ccgccgtcaa tggcatcgcc 420
gatcctggcg tcatcgacgt cgggcaggta ctggtcatat tcatcgggcg tagcgacggg 480
ttcggcctaa ggatcgtgga ccgcaacgag aacgatcccc gcctgtggta ctaccggttc 540
cagacctccg cgatcggctg gaaccccgga gtcaacgtcc tgcttcccga tgactaccgc 600
accagcggac gcacctatcc cgtcctctac ctgttccacg gcggcggcac cgaccaggat 660
ttccgcacgt tcgactttct gggcatccgc gacctgaccg ccggaaagcc gatcatcatc 720
gtgatgcccg acggcgggca cgcgggctgg tattccaacc cggtcagctc gttcgtcggc 780
ccacggaact gggagacatt ccacatcgcc cagctgctcc cctggatcga ggcgaacttc 840
cgaacctacg ccgaatacga cggccgcgcg gtcgccgggt tttcgatggg tggcttcggc 900
gcgctgaagt acgcagcaaa gtactacggc cacttcgcgt cggcgagcag ccactccgga 960
ccggcaagtc tgcgccgcga cttcggcctg gtagtgcatt gggcaaacct gtcctcggcg 1020
gtgctggatc taggcggcgg cacggtttac ggcgcgccgc tctgggacca agctagggtc 1080
agcgccgaca acccggtcga gcgtatcgac agctaccgca acaagcggat cttcctggtc 1140
gccggcacca gtccggaccc ggccaactgg ttcgacagcg tgaacgagac ccaggtgcta 1200
gccgggcaga gggagttccg cgaacgcctc agcaacgccg gcatcccgca tgaatcgcac 1260
gaggtgcctg gcggtcacgt cttccggccc gacatgttcc gtctcgacct cgacggcatc 1320
gtcgcccggc tgcgccccgc gagcatcggg gcggccgcag aacgcgccga ttagaagctt 1380

<210> SEQ ID NO 129
<211> LENGTH: 476
<212> TYPE: PRT
<213> ORGANISM: Mycobacterium tuberculosis

<400> SEQUENCE: 129

Met Gly Ser Ser His His His His His His Ser Ser Gly Leu Val Pro
1 5 10 15

Arg Gly Ser His Met Val Ser Thr His Ala Val Val Ala Gly Glu Thr
20 25 30

Leu Ser Ala Leu Ala Leu Arg Phe Tyr Gly Asp Ala Glu Leu Tyr Arg
35 40 45

Leu Ile Ala Ala Ala Ser Gly Ile Ala Asp Pro Asp Val Val Asn Val
50 55 60

Gly Gln Arg Leu Ile Met Pro Asp Phe Thr Arg Tyr Thr Val Val Ala
65 70 75 80

-continued

```
Gly Asp Thr Leu Ser Ala Leu Ala Leu Arg Phe Tyr Gly Asp Ala Glu
                85                  90                  95

Leu Asn Trp Leu Ile Ala Ala Ala Ser Gly Ile Ala Asp Pro Asp Val
            100                 105                 110

Val Asn Val Gly Gln Arg Leu Ile Met Pro Asp Phe Thr Arg Tyr Thr
        115                 120                 125

Val Val Ala Gly Asp Thr Leu Ser Ala Leu Ala Ala Arg Phe Tyr Gly
    130                 135                 140

Asp Ala Ser Leu Tyr Pro Leu Ile Ala Ala Val Asn Gly Ile Ala Asp
145                 150                 155                 160

Pro Gly Val Ile Asp Val Gly Gln Val Leu Val Ile Phe Ile Gly Arg
                165                 170                 175

Ser Asp Gly Phe Gly Leu Arg Ile Val Asp Arg Asn Glu Asn Asp Pro
            180                 185                 190

Arg Leu Trp Tyr Tyr Arg Phe Gln Thr Ser Ala Ile Gly Trp Asn Pro
        195                 200                 205

Gly Val Asn Val Leu Leu Pro Asp Asp Tyr Arg Thr Ser Gly Arg Thr
    210                 215                 220

Tyr Pro Val Leu Tyr Leu Phe His Gly Gly Gly Thr Asp Gln Asp Phe
225                 230                 235                 240

Arg Thr Phe Asp Phe Leu Gly Ile Arg Asp Leu Thr Ala Gly Lys Pro
                245                 250                 255

Ile Ile Ile Val Met Pro Asp Gly Gly His Ala Gly Trp Tyr Ser Asn
            260                 265                 270

Pro Val Ser Ser Phe Val Gly Pro Arg Asn Trp Glu Thr Phe His Ile
        275                 280                 285

Ala Gln Leu Leu Pro Trp Ile Glu Ala Asn Phe Arg Thr Tyr Ala Glu
    290                 295                 300

Tyr Asp Gly Arg Ala Val Ala Gly Phe Ser Met Gly Gly Phe Gly Ala
305                 310                 315                 320

Leu Lys Tyr Ala Ala Lys Tyr Tyr Gly His Phe Ala Ser Ala Ser Ser
                325                 330                 335

His Ser Gly Pro Ala Ser Leu Arg Arg Asp Phe Gly Leu Val Val His
            340                 345                 350

Trp Ala Asn Leu Ser Ser Ala Val Leu Asp Leu Gly Gly Gly Thr Val
        355                 360                 365

Tyr Gly Ala Pro Leu Trp Asp Gln Ala Arg Val Ser Ala Asp Asn Pro
    370                 375                 380

Val Glu Arg Ile Asp Ser Tyr Arg Asn Lys Arg Ile Phe Leu Val Ala
385                 390                 395                 400

Gly Thr Ser Pro Asp Pro Ala Asn Trp Phe Asp Ser Val Asn Glu Thr
                405                 410                 415

Gln Val Leu Ala Gly Gln Arg Glu Phe Arg Glu Arg Leu Ser Asn Ala
            420                 425                 430

Gly Ile Pro His Glu Ser His Glu Val Pro Gly Gly His Val Phe Arg
        435                 440                 445

Pro Asp Met Phe Arg Leu Asp Leu Asp Gly Ile Val Ala Arg Leu Arg
    450                 455                 460

Pro Ala Ser Ile Gly Ala Ala Ala Glu Arg Ala Asp
465                 470                 475
```

<210> SEQ ID NO 130
<211> LENGTH: 518
<212> TYPE: PRT

<213> ORGANISM: Mycobacterium tuberculosis

<400> SEQUENCE: 130

Met Arg Ala Gly Arg Arg Val Ala Ile Ser Ala Gly Ser Leu Ala Val
1               5                   10                  15

Leu Leu Gly Ala Leu Asp Thr Tyr Val Val Val Thr Ile Met Arg Asp
            20                  25                  30

Ile Met Asn Ser Val Gly Ile Pro Ile Asn Gln Leu His Arg Ile Thr
        35                  40                  45

Trp Ile Val Thr Met Tyr Leu Leu Gly Tyr Ile Ala Ala Met Pro Leu
    50                  55                  60

Leu Gly Arg Ala Ser Asp Arg Phe Gly Arg Lys Leu Met Leu Gln Val
65                  70                  75                  80

Ser Leu Ala Gly Phe Ile Ile Gly Ser Val Val Thr Ala Leu Ala Gly
                85                  90                  95

His Phe Gly Asp Phe His Met Leu Ile Ala Gly Arg Thr Ile Gln Gly
            100                 105                 110

Val Ala Ser Gly Ala Leu Leu Pro Ile Thr Leu Ala Leu Gly Ala Asp
        115                 120                 125

Leu Trp Ser Gln Arg Asn Arg Ala Gly Val Leu Gly Gly Ile Gly Ala
    130                 135                 140

Ala Gln Glu Leu Gly Ser Val Leu Gly Pro Leu Tyr Gly Ile Phe Ile
145                 150                 155                 160

Val Trp Leu Leu His Asp Trp Arg Asp Val Phe Trp Ile Asn Val Pro
                165                 170                 175

Leu Thr Ala Ile Ala Met Val Met Ile His Phe Ser Leu Pro Ser His
            180                 185                 190

Asp Arg Ser Thr Glu Pro Glu Arg Val Asp Leu Val Gly Gly Leu Leu
        195                 200                 205

Leu Ala Leu Ala Leu Gly Leu Ala Val Ile Gly Leu Tyr Asn Pro Asn
    210                 215                 220

Pro Asp Gly Lys His Val Leu Pro Asp Tyr Gly Ala Pro Leu Leu Val
225                 230                 235                 240

Gly Ala Leu Val Ala Ala Val Ala Phe Phe Gly Trp Glu Arg Phe Ala
                245                 250                 255

Arg Thr Arg Leu Ile Asp Pro Ala Gly Val His Phe Arg Pro Phe Leu
            260                 265                 270

Ser Ala Leu Gly Ala Ser Val Ala Ala Gly Ala Ala Leu Met Val Thr
        275                 280                 285

Leu Val Asp Val Glu Leu Phe Gly Gln Gly Val Leu Gln Met Asp Gln
    290                 295                 300

Ala Gln Ala Ala Gly Met Leu Leu Trp Phe Leu Ile Ala Leu Pro Ile
305                 310                 315                 320

Gly Ala Val Thr Gly Gly Trp Ile Ala Thr Arg Ala Gly Asp Arg Ala
                325                 330                 335

Val Ala Phe Ala Gly Leu Leu Ile Ala Ala Tyr Gly Tyr Trp Leu Ile
            340                 345                 350

Ser His Trp Pro Val Asp Leu Leu Ala Asp Arg His Asn Ile Leu Gly
        355                 360                 365

Leu Phe Thr Val Pro Ala Met His Thr Asp Leu Val Val Ala Gly Leu
    370                 375                 380

Gly Leu Gly Leu Val Ile Gly Pro Leu Ser Ser Ala Thr Leu Arg Val
385                 390                 395                 400

```
Val Pro Ser Ala Gln His Gly Ile Ala Ser Ala Ala Val Val Val Ala
                405                 410                 415

Arg Met Thr Gly Met Leu Ile Gly Val Ala Ala Leu Ser Ala Trp Gly
            420                 425                 430

Leu Tyr Arg Phe Asn Gln Ile Leu Ala Gly Leu Ser Ala Ala Ile Pro
        435                 440                 445

Pro Asn Ala Ser Leu Leu Glu Arg Ala Ala Ala Ile Gly Ala Arg Tyr
    450                 455                 460

Gln Gln Ala Phe Ala Leu Met Tyr Gly Glu Ile Phe Thr Ile Thr Ala
465                 470                 475                 480

Ile Val Cys Val Phe Gly Ala Val Leu Gly Leu Leu Ile Ser Gly Arg
                485                 490                 495

Lys Glu His Ala Asp Glu Pro Glu Val Gln Glu Gln Pro Thr Leu Ala
            500                 505                 510

Pro Gln Val Glu Pro Leu
        515


<210> SEQ ID NO 131
<211> LENGTH: 996
<212> TYPE: DNA
<213> ORGANISM: Mycobacterium tuberculosis

<400> SEQUENCE: 131

catatggagc tggtccgggt gaccgaggcc ggagccatgg ccgcgggccg ctgggtaggc      60

cgcggcgaca aggagggcgg cgacggcgcg gcggtcgacg cgatgcgcga actggtcaac     120

tcggtttcca tgcgcggggt ggtggtcatc ggcgaaggca aaaaggacca cgcaccaatg     180

ctctacaacg gcgaagaagt gggcaacggc gacggaccgg aatgcgactt tgccgtcgac     240

cccattgacg gcaccacgct gatgagcaag ggcatgacca acgccatctc ggtgctggcg     300

gtagccgatc gcggcaccat gttcgacccg tcggcggtgt tctacatgaa caaaatcgcc     360

gtcggccccg atgccgcaca cgtgctggat atcaccgcgc cgatctcgga aaacatccga     420

gcggtcgcca aggtcaagga cctgtcggtg cgagacatga cggtgtgcat cctggacagg     480

ccgcggcacg cgcaactcat ccacgacgtc cgcgccaccg ggcccggat ccggctgatc      540

accgatggcg acgtcgccgg cgcgatctcg gcgtgccgac cgcactccgg caccgacctg     600

ctagctggga tcggcggcac ccccggaggga atcatcgccg ccgcggcgat ccgctgcatg    660

ggcggggcga tccaggcgca gctcgccccg cgcgacgacg cggaacgccg caaggcccta     720

gaagccggtt acgacctgaa ccaggtcttg accaccgaag atctggtgtc cggggaaaac     780

gtcttcttct gcgccactgg ggtcaccgac ggcgacctgc tcaagggagt gcgttactac     840

cccggcggct gcaccaccca ttcgatcgtg atgcgctcga agtccggcac cgtccggatg     900

atcgaggcct accaccggct ttcaaagctc aacgaatact ccgcgatcga cttcaccggc     960

gacagcagcg ccgtgtaccc attgccctaa aagctt                               996


<210> SEQ ID NO 132
<211> LENGTH: 349
<212> TYPE: PRT
<213> ORGANISM: Mycobacterium tuberculosis

<400> SEQUENCE: 132

Met Gly Ser Ser His His His His His His Ser Ser Gly Leu Val Pro
1               5                   10                  15

Arg Gly Ser His His Met Glu Leu Val Arg Val Thr Glu Ala Gly Ala
            20                  25                  30
```

```
Met Ala Ala Gly Arg Trp Val Gly Arg Gly Asp Lys Glu Gly Gly Asp
        35                  40                  45

Gly Ala Ala Val Asp Ala Met Arg Glu Leu Val Asn Ser Val Ser Met
    50                  55                  60

Arg Gly Val Val Val Ile Gly Glu Gly Glu Lys Asp His Ala Pro Met
65                  70                  75                  80

Leu Tyr Asn Gly Glu Glu Val Gly Asn Gly Asp Gly Pro Glu Cys Asp
                85                  90                  95

Phe Ala Val Asp Pro Ile Asp Gly Thr Thr Leu Met Ser Lys Gly Met
            100                 105                 110

Thr Asn Ala Ile Ser Val Leu Ala Val Ala Asp Arg Gly Thr Met Phe
        115                 120                 125

Asp Pro Ser Ala Val Phe Tyr Met Asn Lys Ile Ala Val Gly Pro Asp
    130                 135                 140

Ala Ala His Val Leu Asp Ile Thr Ala Pro Ile Ser Glu Asn Ile Arg
145                 150                 155                 160

Ala Val Ala Lys Val Lys Asp Leu Ser Val Arg Asp Met Thr Val Cys
                165                 170                 175

Ile Leu Asp Arg Pro Arg His Ala Gln Leu Ile His Asp Val Arg Ala
            180                 185                 190

Thr Gly Ala Arg Ile Arg Leu Ile Thr Asp Gly Asp Val Ala Gly Ala
        195                 200                 205

Ile Ser Ala Cys Arg Pro His Ser Gly Thr Asp Leu Leu Ala Gly Ile
    210                 215                 220

Gly Gly Thr Pro Glu Gly Ile Ile Ala Ala Ala Ala Ile Arg Cys Met
225                 230                 235                 240

Gly Gly Ala Ile Gln Ala Gln Leu Ala Pro Arg Asp Asp Ala Glu Arg
                245                 250                 255

Arg Lys Ala Leu Glu Ala Gly Tyr Asp Leu Asn Gln Val Leu Thr Thr
            260                 265                 270

Glu Asp Leu Val Ser Gly Glu Asn Val Phe Phe Cys Ala Thr Gly Val
        275                 280                 285

Thr Asp Gly Asp Leu Leu Lys Gly Val Arg Tyr Tyr Pro Gly Gly Cys
    290                 295                 300

Thr Thr His Ser Ile Val Met Arg Ser Lys Ser Gly Thr Val Arg Met
305                 310                 315                 320

Ile Glu Ala Tyr His Arg Leu Ser Lys Leu Asn Glu Tyr Ser Ala Ile
                325                 330                 335

Asp Phe Thr Gly Asp Ser Ser Ala Val Tyr Pro Leu Pro
            340                 345
```

<210> SEQ ID NO 133
<211> LENGTH: 386
<212> TYPE: PRT
<213> ORGANISM: Mycobacterium tuberculosis

<400> SEQUENCE: 133

```
Met Lys Ala Ala Thr Gln Ala Arg Ile Asp Asp Ser Pro Leu Ala Trp
1               5                   10                  15

Leu Asp Ala Val Gln Arg Gln Arg His Glu Ala Gly Leu Arg Arg Cys
            20                  25                  30

Leu Arg Pro Arg Pro Ala Val Ala Thr Glu Leu Asp Leu Ala Ser Asn
        35                  40                  45

Asp Tyr Leu Gly Leu Ser Arg His Pro Ala Val Ile Asp Gly Gly Val
```

-continued

```
    50                  55                  60

Gln Ala Leu Arg Ile Trp Gly Ala Gly Ala Thr Gly Ser Arg Leu Val
65                  70                  75                  80

Thr Gly Asp Thr Lys Leu His Gln Gln Phe Glu Ala Glu Leu Ala Glu
                85                  90                  95

Phe Val Gly Ala Ala Ala Gly Leu Leu Phe Ser Ser Gly Tyr Thr Ala
            100                 105                 110

Asn Leu Gly Ala Val Val Gly Leu Ser Gly Pro Gly Ser Leu Leu Val
        115                 120                 125

Ser Asp Ala Arg Ser His Ala Ser Leu Val Asp Ala Cys Arg Leu Ser
    130                 135                 140

Arg Ala Arg Val Val Val Thr Pro His Arg Asp Val Asp Ala Val Asp
145                 150                 155                 160

Ala Ala Leu Arg Ser Arg Asp Glu Gln Arg Ala Val Val Val Thr Asp
                165                 170                 175

Ser Val Phe Ser Ala Asp Gly Ser Leu Ala Pro Val Arg Glu Leu Leu
            180                 185                 190

Glu Val Cys Arg Arg His Gly Ala Leu Leu Leu Val Asp Glu Ala His
        195                 200                 205

Gly Leu Gly Val Arg Gly Gly Gly Arg Gly Leu Leu Tyr Glu Leu Gly
    210                 215                 220

Leu Ala Gly Ala Pro Asp Val Val Met Thr Thr Thr Leu Ser Lys Ala
225                 230                 235                 240

Leu Gly Ser Gln Gly Gly Val Val Leu Gly Pro Thr Pro Val Arg Ala
                245                 250                 255

His Leu Ile Asp Ala Ala Arg Pro Phe Ile Phe Asp Thr Gly Leu Ala
            260                 265                 270

Pro Ala Ala Val Gly Ala Ala Arg Ala Ala Leu Arg Val Leu Gln Ala
        275                 280                 285

Glu Pro Trp Arg Pro Gln Ala Val Leu Asn His Ala Gly Glu Leu Ala
    290                 295                 300

Arg Met Cys Gly Val Ala Ala Val Pro Asp Ser Ala Met Val Ser Val
305                 310                 315                 320

Ile Leu Gly Glu Pro Glu Ser Ala Val Ala Ala Ala Ala Ala Cys Leu
                325                 330                 335

Asp Ala Gly Val Lys Val Gly Cys Phe Arg Pro Pro Thr Val Pro Ala
            340                 345                 350

Gly Thr Ser Arg Leu Arg Leu Thr Ala Arg Ala Ser Leu Asn Ala Gly
        355                 360                 365

Glu Leu Glu Leu Ala Arg Arg Val Leu Thr Asp Val Leu Ala Val Ala
    370                 375                 380

Arg Arg
385


<210> SEQ ID NO 134
<211> LENGTH: 1170
<212> TYPE: DNA
<213> ORGANISM: Mycobacterium tuberculosis

<400> SEQUENCE: 134

catatgaaag ccgccacgca ggcacggatc gacgattcac cgttggcctg gttggacgcg      60

gtgcagcggc agcgccacga ggccggactg cggcgctgcc tgcggccgcg tcccgcggtc     120

gccaccgagc tggacttggc ctccaacgac tatctcggtc tgtcccgaca tcccgccgtc     180
```

-continued

```
atcgacggcg gcgtccaggc gctgcggatc tggggcgccg gcgccaccgg gtcgcgcctg    240

gttaccggcg acaccaagct gcaccagcaa ttcgaggccg agctcgccga gttygtcggc    300

gctgccgcgg gattgctgtt ctcctctggc tacacggcca acctgggcgc cgtggtcggc    360

ctgtccggcc cgggttccct gctggtgtcc gacgcccgtt cgcatgcgtc gttggtggat    420

gcctgtcggc tgtcgcgggc gcgggttgtg gtgacgccgc accgcgacgt cgacgccgtg    480

gacgccgcgc tgcgatcgcg cgacgagcag cgcgccgtcg tcgtcaccga ctcggtgttc    540

agcgccgacg gctcgctggc gccggttcgg gagttgcttg aggtctgccg gcgtcatggt    600

gcgctgcttc tggtggacga ggcgcacggc ctgggtgtgc gtggcggcgg acgcgggctg    660

ctctacgagt taggtctagc gggtgcgccc gacgtggtga tgaccaccac gctgtccaag    720

gcgctgggca gccagggtgg tgtggtgctc gggccgacgc cggtgcgggc ccatctgatc    780

gatgctgccc ggccgttcat cttcgacacc ggtctggcgc cggcggcggt gggtgccgca    840

cgggccgcgc tgcgcgtctt gcaggccgag ccgtggcgac cgcaggcggt gctcaaccac    900

gctggtgaac ttgcgcggat gtgcggtgtg gctgcggtgc cggactcggc gatggtgtcg    960

gtgatcctgg gcgagccgga gtcggcagtg gccgccgcgg cggcctgcct ggacgccggg   1020

gtcaaggtgg gctgcttccg gccgccgacg gtgcccgcgg gtacgtcgcg gctgcggctg   1080

accgcgcgcg catcgctgaa cgccggcgag ctcgagctgg cccggcgggt gctgacggat   1140

gttctcgccg tggcgcgccg ttgaaagctt                                     1170
```

```
<210> SEQ ID NO 135
<211> LENGTH: 406
<212> TYPE: PRT
<213> ORGANISM: Mycobacterium tuberculosis

<400> SEQUENCE: 135

Met Gly Ser Ser His His His His His His Ser Ser Gly Leu Val Pro
1               5                   10                  15

Arg Gly Ser His Met Lys Ala Ala Thr Gln Ala Arg Ile Asp Asp Ser
            20                  25                  30

Pro Leu Ala Trp Leu Asp Ala Val Gln Arg Gln Arg His Glu Ala Gly
        35                  40                  45

Leu Arg Arg Cys Leu Arg Pro Arg Pro Ala Val Ala Thr Glu Leu Asp
    50                  55                  60

Leu Ala Ser Asn Asp Tyr Leu Gly Leu Ser Arg His Pro Ala Val Ile
65                  70                  75                  80

Asp Gly Gly Val Gln Ala Leu Arg Ile Trp Gly Ala Gly Ala Thr Gly
                85                  90                  95

Ser Arg Leu Val Thr Gly Asp Thr Lys Leu His Gln Gln Phe Glu Ala
            100                 105                 110

Glu Leu Ala Glu Phe Val Gly Ala Ala Ala Gly Leu Leu Phe Ser Ser
        115                 120                 125

Gly Tyr Thr Ala Asn Leu Gly Ala Val Val Gly Leu Ser Gly Pro Gly
    130                 135                 140

Ser Leu Leu Val Ser Asp Ala Arg Ser His Ala Ser Leu Val Asp Ala
145                 150                 155                 160

Cys Arg Leu Ser Arg Ala Arg Val Val Val Thr Pro His Arg Asp Val
                165                 170                 175

Asp Ala Val Asp Ala Ala Leu Arg Ser Arg Asp Glu Gln Arg Ala Val
            180                 185                 190

Val Val Thr Asp Ser Val Phe Ser Ala Asp Gly Ser Leu Ala Pro Val
```

195 200 205

Arg Glu Leu Leu Glu Val Cys Arg Arg His Gly Ala Leu Leu Leu Val
210 215 220

Asp Glu Ala His Gly Leu Gly Val Arg Gly Gly Gly Arg Gly Leu Leu
225 230 235 240

Tyr Glu Leu Gly Leu Ala Gly Ala Pro Asp Val Val Met Thr Thr Thr
245 250 255

Leu Ser Lys Ala Leu Gly Ser Gln Gly Gly Val Val Leu Gly Pro Thr
260 265 270

Pro Val Arg Ala His Leu Ile Asp Ala Ala Arg Pro Phe Ile Phe Asp
275 280 285

Thr Gly Leu Ala Pro Ala Ala Val Gly Ala Ala Arg Ala Ala Leu Arg
290 295 300

Val Leu Gln Ala Glu Pro Trp Arg Pro Gln Ala Val Leu Asn His Ala
305 310 315 320

Gly Glu Leu Ala Arg Met Cys Gly Val Ala Ala Val Pro Asp Ser Ala
325 330 335

Met Val Ser Val Ile Leu Gly Glu Pro Glu Ser Ala Val Ala Ala Ala
340 345 350

Ala Ala Cys Leu Asp Ala Gly Val Lys Val Gly Cys Phe Arg Pro Pro
355 360 365

Thr Val Pro Ala Gly Thr Ser Arg Leu Arg Leu Thr Ala Arg Ala Ser
370 375 380

Leu Asn Ala Gly Glu Leu Glu Leu Ala Arg Arg Val Leu Thr Asp Val
385 390 395 400

Leu Ala Val Ala Arg Arg
405

<210> SEQ ID NO 136
<211> LENGTH: 393
<212> TYPE: PRT
<213> ORGANISM: Mycobacterium tuberculosis

<400> SEQUENCE: 136

Met Asp Phe Gly Ala Leu Pro Pro Glu Val Asn Ser Val Arg Met Tyr
1 5 10 15

Ala Gly Pro Gly Ser Ala Pro Met Val Ala Ala Ala Ser Ala Trp Asn
20 25 30

Gly Leu Ala Ala Glu Leu Ser Ser Ala Ala Thr Gly Tyr Glu Thr Val
35 40 45

Ile Thr Gln Leu Ser Ser Glu Gly Trp Leu Gly Pro Ala Ser Ala Ala
50 55 60

Met Ala Glu Ala Val Ala Pro Tyr Val Ala Trp Met Ser Ala Ala Ala
65 70 75 80

Ala Gln Ala Glu Gln Ala Ala Thr Gln Ala Arg Ala Ala Ala Ala Ala
85 90 95

Phe Glu Ala Ala Phe Ala Ala Thr Val Pro Pro Pro Leu Ile Ala Ala
100 105 110

Asn Arg Ala Ser Leu Met Gln Leu Ile Ser Thr Asn Val Phe Gly Gln
115 120 125

Asn Thr Ser Ala Ile Ala Ala Ala Glu Ala Gln Tyr Gly Glu Met Trp
130 135 140

Ala Gln Asp Ser Ala Ala Met Tyr Ala Tyr Ala Gly Ser Ser Ala Ser
145 150 155 160

-continued

```
Ala Ser Ala Val Thr Pro Phe Ser Thr Pro Pro Gln Ile Ala Asn Pro
                165                 170                 175

Thr Ala Gln Gly Thr Gln Ala Ala Ala Val Ala Thr Ala Ala Gly Thr
            180                 185                 190

Ala Gln Ser Thr Leu Thr Glu Met Ile Thr Gly Leu Pro Asn Ala Leu
        195                 200                 205

Gln Ser Leu Thr Ser Pro Leu Leu Gln Ser Ser Asn Gly Pro Leu Ser
    210                 215                 220

Trp Leu Trp Gln Ile Leu Phe Gly Thr Pro Asn Phe Pro Thr Ser Ile
225                 230                 235                 240

Ser Ala Leu Leu Thr Asp Leu Gln Pro Tyr Ala Ser Phe Phe Tyr Asn
                245                 250                 255

Thr Glu Gly Leu Pro Tyr Phe Ser Ile Gly Met Gly Asn Asn Phe Ile
            260                 265                 270

Gln Ser Ala Lys Thr Leu Gly Leu Ile Gly Ser Ala Ala Pro Ala Ala
        275                 280                 285

Val Ala Ala Ala Gly Asp Ala Ala Lys Gly Leu Pro Gly Leu Gly Gly
    290                 295                 300

Met Leu Gly Gly Gly Pro Val Ala Ala Gly Leu Gly Asn Ala Ala Ser
305                 310                 315                 320

Val Gly Lys Leu Ser Val Pro Pro Val Trp Ser Gly Pro Leu Pro Gly
                325                 330                 335

Ser Val Thr Pro Gly Ala Ala Pro Leu Pro Val Ser Thr Val Ser Ala
            340                 345                 350

Ala Pro Glu Ala Ala Pro Gly Ser Leu Leu Gly Gly Leu Pro Leu Ala
        355                 360                 365

Gly Ala Gly Gly Ala Gly Ala Gly Pro Arg Tyr Gly Phe Arg Pro Thr
    370                 375                 380

Val Met Ala Arg Pro Pro Phe Ala Gly
385                 390
```

<210> SEQ ID NO 137
<211> LENGTH: 1191
<212> TYPE: DNA
<213> ORGANISM: Mycobacterium tuberculosis

<400> SEQUENCE: 137

```
catatggatt ttggggcgtt gccgccggag gtcaattcgg tgcggatgta tgccggtcct      60

ggctcggcac caatggtcgc tgcggcgtcg gcctggaacg ggttggccgc ggagctgagt     120

tcggcggcca ccggttatga gacggtgatc actcagctca gcagtgaggg gtggctaggt     180

ccggcgtcag cggcgatggc cgaggcagtt gcgccgtatg tggcgtggat gagtgccgct     240

gcggcgcaag ccgagcaggc ggccacacag gccagggccg ccgcggccgc ttttgaggcg     300

gcgtttgccg cgacggtgcc tccgccgttg atcgcggcca accgggcttc gttgatgcag     360

ctgatctcga cgaatgtctt tggtcagaac acctcggcga tcgcggccgc cgaagctcag     420

tacggcgaga tgtgggccca agactccgcg gcgatgtatg cctacgcggg cagttcggcg     480

agcgcctcgg cggtcacgcc gtttagcacg ccgccgcaga ttgccaaccc gaccgctcag     540

ggtacgcagg ccgcggccgt ggccaccgcc gccggtaccg cccagtcgac gctgacggag     600

atgatcaccg ggctacccaa cgcgctgcaa agcctcacct cacctctgtt gcagtcgtct     660

aacggtccgc tgtcgtggct gtggcagatc ttgttcggca cgcccaattt ccccacctca     720

atttcggcac tgctgaccga cctgcagccc tacgcgagct tcttctataa caccgagggc     780
```

-continued

```
ctgccgtact tcagcatcgg catgggcaac aacttcattc agtcggccaa gaccctggga    840

ttgatcggct cggcggcacc ggctgcggtc gcggctgctg gggatgccgc caagggcttg    900

cctggactgg gcgggatgct cggtggcggg ccggtggcgg cgggtctggg caatgcggct    960

tcggttggca agctgtcggt gccgccggtg tggagtggac cgttgcccgg gtcggtgact   1020

ccgggggctg ctccgctacc ggtgagtacg gtcagtgccg ccccggaggc ggcgcccgga   1080

agcctgttgg gcggcctgcc gctagctggt gcgggcgggg ccggcgcggg tccacgctac   1140

ggattccgtc ccaccgtcat ggctcgccca cccttcgccg gatagaagct t            1191


<210> SEQ ID NO 138
<211> LENGTH: 413
<212> TYPE: PRT
<213> ORGANISM: Mycobacterium tuberculosis

<400> SEQUENCE: 138

Met Gly Ser Ser His His His His His His Ser Ser Gly Leu Val Pro
1               5                   10                  15

Arg Gly Ser His Met Asp Phe Gly Ala Leu Pro Pro Glu Val Asn Ser
            20                  25                  30

Val Arg Met Tyr Ala Gly Pro Gly Ser Ala Pro Met Val Ala Ala Ala
        35                  40                  45

Ser Ala Trp Asn Gly Leu Ala Ala Glu Leu Ser Ser Ala Ala Thr Gly
    50                  55                  60

Tyr Glu Thr Val Ile Thr Gln Leu Ser Ser Glu Gly Trp Leu Gly Pro
65                  70                  75                  80

Ala Ser Ala Ala Met Ala Glu Ala Val Ala Pro Tyr Val Ala Trp Met
                85                  90                  95

Ser Ala Ala Ala Ala Gln Ala Glu Gln Ala Ala Thr Gln Ala Arg Ala
            100                 105                 110

Ala Ala Ala Ala Phe Glu Ala Ala Phe Ala Ala Thr Val Pro Pro Pro
        115                 120                 125

Leu Ile Ala Ala Asn Arg Ala Ser Leu Met Gln Leu Ile Ser Thr Asn
    130                 135                 140

Val Phe Gly Gln Asn Thr Ser Ala Ile Ala Ala Ala Glu Ala Gln Tyr
145                 150                 155                 160

Gly Glu Met Trp Ala Gln Asp Ser Ala Ala Met Tyr Ala Tyr Ala Gly
                165                 170                 175

Ser Ser Ala Ser Ala Ser Ala Val Thr Pro Phe Ser Thr Pro Pro Gln
            180                 185                 190

Ile Ala Asn Pro Thr Ala Gln Gly Thr Gln Ala Ala Ala Val Ala Thr
        195                 200                 205

Ala Ala Gly Thr Ala Gln Ser Thr Leu Thr Glu Met Ile Thr Gly Leu
    210                 215                 220

Pro Asn Ala Leu Gln Ser Leu Thr Ser Pro Leu Leu Gln Ser Ser Asn
225                 230                 235                 240

Gly Pro Leu Ser Trp Leu Trp Gln Ile Leu Phe Gly Thr Pro Asn Phe
                245                 250                 255

Pro Thr Ser Ile Ser Ala Leu Leu Thr Asp Leu Gln Pro Tyr Ala Ser
            260                 265                 270

Phe Phe Tyr Asn Thr Glu Gly Leu Pro Tyr Phe Ser Ile Gly Met Gly
        275                 280                 285

Asn Asn Phe Ile Gln Ser Ala Lys Thr Leu Gly Leu Ile Gly Ser Ala
    290                 295                 300
```

-continued

```
Ala Pro Ala Ala Val Ala Ala Ala Gly Asp Ala Ala Lys Gly Leu Pro
305                 310                 315                 320

Gly Leu Gly Gly Met Leu Gly Gly Gly Pro Val Ala Ala Gly Leu Gly
                325                 330                 335

Asn Ala Ala Ser Val Gly Lys Leu Ser Val Pro Pro Val Trp Ser Gly
            340                 345                 350

Pro Leu Pro Gly Ser Val Thr Pro Gly Ala Ala Pro Leu Pro Val Ser
        355                 360                 365

Thr Val Ser Ala Ala Pro Glu Ala Ala Pro Gly Ser Leu Leu Gly Gly
    370                 375                 380

Leu Pro Leu Ala Gly Ala Gly Gly Ala Gly Ala Gly Pro Arg Tyr Gly
385                 390                 395                 400

Phe Arg Pro Thr Val Met Ala Arg Pro Pro Phe Ala Gly
                405                 410


<210> SEQ ID NO 139
<211> LENGTH: 498
<212> TYPE: PRT
<213> ORGANISM: Mycobacterium tuberculosis

<400> SEQUENCE: 139

Met Ser Phe Val Val Thr Ile Pro Glu Ala Leu Ala Ala Val Ala Thr
1               5                   10                  15

Asp Leu Ala Gly Ile Gly Ser Thr Ile Gly Thr Ala Asn Ala Ala Ala
            20                  25                  30

Ala Val Pro Thr Thr Thr Val Leu Ala Ala Ala Ala Asp Glu Val Ser
        35                  40                  45

Ala Ala Met Ala Ala Leu Phe Ser Gly His Ala Gln Ala Tyr Gln Ala
    50                  55                  60

Leu Ser Ala Gln Ala Ala Leu Phe His Glu Gln Phe Val Arg Ala Leu
65                  70                  75                  80

Thr Ala Gly Ala Gly Ser Tyr Ala Ala Ala Glu Ala Ala Ser Ala Ala
                85                  90                  95

Pro Leu Glu Gly Val Leu Asp Val Ile Asn Ala Pro Ala Leu Ala Leu
            100                 105                 110

Leu Gly Arg Pro Leu Ile Gly Asn Gly Ala Asn Gly Ala Pro Gly Thr
        115                 120                 125

Gly Ala Asn Gly Gly Asp Gly Gly Ile Leu Ile Gly Asn Gly Gly Ala
    130                 135                 140

Gly Gly Ser Gly Ala Ala Gly Met Pro Gly Gly Asn Gly Gly Ala Ala
145                 150                 155                 160

Gly Leu Phe Gly Asn Gly Gly Ala Gly Gly Ala Gly Gly Asn Val Ala
                165                 170                 175

Ser Gly Thr Ala Gly Phe Gly Gly Ala Gly Gly Ala Gly Gly Leu Leu
            180                 185                 190

Tyr Gly Ala Gly Gly Ala Gly Gly Ala Gly Gly Arg Ala Gly Gly Gly
        195                 200                 205

Val Gly Gly Ile Gly Gly Ala Gly Gly Ala Gly Gly Asn Gly Gly Leu
    210                 215                 220

Leu Phe Gly Ala Gly Gly Ala Gly Gly Val Gly Gly Leu Ala Ala Asp
225                 230                 235                 240

Ala Gly Asp Gly Gly Ala Gly Gly Asp Gly Gly Leu Phe Phe Gly Val
                245                 250                 255

Gly Gly Ala Gly Gly Ala Gly Gly Thr Gly Thr Asn Val Thr Gly Gly
            260                 265                 270
```

Ala Gly Gly Ala Gly Gly Asn Gly Gly Leu Leu Phe Gly Ala Gly Gly
275 280 285

Val Gly Gly Val Gly Gly Asp Gly Val Ala Phe Leu Gly Thr Ala Pro
290 295 300

Gly Gly Pro Gly Gly Ala Gly Gly Ala Gly Gly Leu Phe Gly Val Gly
305 310 315 320

Gly Ala Gly Gly Ala Gly Gly Ile Gly Leu Val Gly Asn Gly Gly Ala
325 330 335

Gly Gly Ser Gly Gly Ser Ala Leu Leu Trp Gly Asp Gly Gly Ala Gly
340 345 350

Gly Ala Gly Gly Val Gly Ser Thr Thr Gly Gly Ala Gly Gly Ala Gly
355 360 365

Gly Asn Ala Gly Leu Leu Val Gly Ala Gly Gly Ala Gly Gly Ala Gly
370 375 380

Ala Leu Gly Gly Gly Ala Thr Gly Val Gly Gly Ala Gly Gly Asn Gly
385 390 395 400

Gly Thr Ala Gly Leu Leu Phe Gly Ala Gly Gly Ala Gly Gly Phe Gly
405 410 415

Phe Gly Gly Ala Gly Gly Ala Gly Gly Leu Gly Gly Lys Ala Gly Leu
420 425 430

Ile Gly Asp Gly Gly Asp Gly Gly Ala Gly Gly Asn Gly Thr Gly Ala
435 440 445

Lys Gly Gly Asp Gly Gly Ala Gly Gly Gly Ala Ile Leu Val Gly Asn
450 455 460

Gly Gly Asn Gly Gly Asn Ala Gly Ser Gly Thr Pro Asn Gly Ser Ala
465 470 475 480

Gly Thr Gly Gly Ala Gly Gly Leu Leu Gly Lys Asn Gly Met Asn Gly
485 490 495

Leu Pro

<210> SEQ ID NO 140
<211> LENGTH: 1506
<212> TYPE: DNA
<213> ORGANISM: Mycobacterium tuberculosis

<400> SEQUENCE: 140
catatgtcat ttgtggtcac gatcccggag gcgctagcgg cggtggcgac cgatttggcg 60
ggtatcgggt cgacgatcgg caccgccaac gcggccgccg cggtcccgac cacgacggtg 120
ttggccgccg ccgccgatga ggtgtcggcg gcgatggcgg cattgttctc cggacacgcc 180
caggcctatc aggcgctgag cgcccaggcg gcgctgtttc acgagcagtt cgtgcgggcg 240
ctcaccgccg gggcgggctc gtatgcggcc gccgaggccg ccagcgcggc cccgctagag 300
ggtgtgctcg acgtgatcaa cgccccccgcc ctggcgctgt tggggcgccc actgatcggt 360
aacggagcca acggggcccc ggggaccggg gcaaacggcg gcgacggcgg aatcttgatc 420
ggcaacggcg gggccggcgg ctccggcgcg gccggcatgc ccgggggcaa cggcggagcc 480
gctggcctgt tcggcaacgg cggggccggc ggcgccgggg ggaacgtagc gtccggcacc 540
gcagggttcg gcggggccgg cggggccggc gggctgctct acggcgccgg cggggccggc 600
ggcgccggcg gacgcgccgg tggtggggtg ggcggtattg gtggggccgg cggggccggc 660
ggcaatggcg ggctgctgtt cggcgccggc ggggccggcg gcgtcggcgg actcgcggct 720
gacgccggtg acggcggggc cggcggagac ggcgggttgt tcttcggcgt gggcggtgcc 780

```
ggcggggccg gcggcaccgg cactaatgtc accggcggtg ccggcggggc cggcggcaat    840

ggcgggctcc tgttcggcgc cggcggggtg ggcggtgttg gcggtgacgg tgtggcattc    900

ctgggcaccg cccccggcgg gcccggtggt gccggcgggg ccggtgggct gttcggcgtc    960

ggtggggccg gcggcgccgg cggaatcgga ttggtcggga acggcggtgc cggggggtcc   1020

ggcgggtccg ccctgctctg gggcgacggc ggtgccggcg gcgcgggtgg ggtcgggtcc   1080

actaccggcg gtgccggcgg ggcgggcggc aacgccggcc tgctggtagg cgccggcggg   1140

gccggcggcg ccggcgcact cggcggtggc gctaccgggg tgggcggcgc cggcggaaac   1200

ggcggcactg cgggcctgct gtttggtgcc ggcggcgccg gcggattcgg cttcggcggt   1260

gccgggggcg ccggtgggct cggcggcaaa gccgggctga tcggcgacgg cggtgacggc   1320

ggcgccggag gaaacggcac cggtgccaag ggcggtgacg gcggcgctgg cggcggtgcc   1380

atcctggtcg gcaacggcgg caacggcggc aacgccggga gtggcacacc taacggcagc   1440

gcgggcaccg gcggtgccgg cgggctgttg ggtaagaacg ggatgaacgg gttaccgtag   1500

aagctt                                                              1506
```

```
<210> SEQ ID NO 141
<211> LENGTH: 518
<212> TYPE: PRT
<213> ORGANISM: Mycobacterium tuberculosis

<400> SEQUENCE: 141

Met Gly Ser Ser His His His His His His Ser Ser Gly Leu Val Pro
1               5                   10                  15

Arg Gly Ser His Met Ser Phe Val Val Thr Ile Pro Glu Ala Leu Ala
            20                  25                  30

Ala Val Ala Thr Asp Leu Ala Gly Ile Gly Ser Thr Ile Gly Thr Ala
        35                  40                  45

Asn Ala Ala Ala Ala Val Pro Thr Thr Thr Val Leu Ala Ala Ala Ala
    50                  55                  60

Asp Glu Val Ser Ala Ala Met Ala Ala Leu Phe Ser Gly His Ala Gln
65                  70                  75                  80

Ala Tyr Gln Ala Leu Ser Ala Gln Ala Ala Leu Phe His Glu Gln Phe
                85                  90                  95

Val Arg Ala Leu Thr Ala Gly Ala Gly Ser Tyr Ala Ala Ala Glu Ala
            100                 105                 110

Ala Ser Ala Ala Pro Leu Glu Gly Val Leu Asp Val Ile Asn Ala Pro
        115                 120                 125

Ala Leu Ala Leu Leu Gly Arg Pro Leu Ile Gly Asn Gly Ala Asn Gly
    130                 135                 140

Ala Pro Gly Thr Gly Ala Asn Gly Gly Asp Gly Gly Ile Leu Ile Gly
145                 150                 155                 160

Asn Gly Gly Ala Gly Gly Ser Gly Ala Ala Gly Met Pro Gly Gly Asn
                165                 170                 175

Gly Gly Ala Ala Gly Leu Phe Gly Asn Gly Gly Ala Gly Gly Ala Gly
            180                 185                 190

Gly Asn Val Ala Ser Gly Thr Ala Gly Phe Gly Gly Ala Gly Gly Ala
        195                 200                 205

Gly Gly Leu Leu Tyr Gly Ala Gly Gly Ala Gly Gly Ala Gly Gly Arg
    210                 215                 220

Ala Gly Gly Gly Val Gly Gly Ile Gly Gly Ala Gly Gly Ala Gly Gly
225                 230                 235                 240
```

-continued

```
Asn Gly Gly Leu Leu Phe Gly Ala Gly Gly Ala Gly Gly Val Gly Gly
                245                 250                 255

Leu Ala Ala Asp Ala Gly Asp Gly Gly Ala Gly Gly Asp Gly Gly Leu
            260                 265                 270

Phe Phe Gly Val Gly Gly Ala Gly Gly Ala Gly Gly Thr Gly Thr Asn
        275                 280                 285

Val Thr Gly Gly Ala Gly Gly Ala Gly Gly Asn Gly Gly Leu Leu Phe
    290                 295                 300

Gly Ala Gly Gly Val Gly Gly Val Gly Gly Asp Gly Val Ala Phe Leu
305                 310                 315                 320

Gly Thr Ala Pro Gly Gly Pro Gly Gly Ala Gly Gly Ala Gly Gly Leu
                325                 330                 335

Phe Gly Val Gly Gly Ala Gly Gly Ala Gly Gly Ile Gly Leu Val Gly
            340                 345                 350

Asn Gly Gly Ala Gly Gly Ser Gly Gly Ser Ala Leu Leu Trp Gly Asp
        355                 360                 365

Gly Gly Ala Gly Gly Ala Gly Gly Val Gly Ser Thr Thr Gly Gly Ala
    370                 375                 380

Gly Gly Ala Gly Gly Asn Ala Gly Leu Leu Val Gly Ala Gly Gly Ala
385                 390                 395                 400

Gly Gly Ala Gly Ala Leu Gly Gly Gly Ala Thr Gly Val Gly Gly Ala
                405                 410                 415

Gly Gly Asn Gly Gly Thr Ala Gly Leu Leu Phe Gly Ala Gly Gly Ala
            420                 425                 430

Gly Gly Phe Gly Phe Gly Gly Ala Gly Gly Ala Gly Gly Leu Gly Gly
        435                 440                 445

Lys Ala Gly Leu Ile Gly Asp Gly Gly Asp Gly Gly Ala Gly Gly Asn
    450                 455                 460

Gly Thr Gly Ala Lys Gly Gly Asp Gly Gly Ala Gly Gly Gly Ala Ile
465                 470                 475                 480

Leu Val Gly Asn Gly Gly Asn Gly Gly Asn Ala Gly Ser Gly Thr Pro
                485                 490                 495

Asn Gly Ser Ala Gly Thr Gly Gly Ala Gly Gly Leu Leu Gly Lys Asn
            500                 505                 510

Gly Met Asn Gly Leu Pro
        515
```

<210> SEQ ID NO 142
<211> LENGTH: 325
<212> TYPE: PRT
<213> ORGANISM: Mycobacterium tuberculosis

<400> SEQUENCE: 142

```
Met His Gln Val Asp Pro Asn Leu Thr Arg Arg Lys Gly Arg Leu Ala
1               5                   10                  15

Ala Leu Ala Ile Ala Ala Met Ala Ser Ala Ser Leu Val Thr Val Ala
            20                  25                  30

Val Pro Ala Thr Ala Asn Ala Asp Pro Glu Pro Ala Pro Pro Val Pro
        35                  40                  45

Thr Thr Ala Ala Ser Pro Pro Ser Thr Ala Ala Ala Pro Pro Ala Pro
    50                  55                  60

Ala Thr Pro Val Ala Pro Pro Pro Pro Ala Ala Ala Asn Thr Pro Asn
65                  70                  75                  80

Ala Gln Pro Gly Asp Pro Asn Ala Ala Pro Pro Pro Ala Asp Pro Asn
                85                  90                  95
```

```
Ala Pro Pro Pro Pro Val Ile Ala Pro Asn Ala Pro Gln Pro Val Arg
            100                 105                 110

Ile Asp Asn Pro Val Gly Gly Phe Ser Phe Ala Leu Pro Ala Gly Trp
        115                 120                 125

Val Glu Ser Asp Ala Ala His Phe Asp Tyr Gly Ser Ala Leu Leu Ser
    130                 135                 140

Lys Thr Thr Gly Asp Pro Pro Phe Pro Gly Gln Pro Pro Pro Val Ala
145                 150                 155                 160

Asn Asp Thr Arg Ile Val Leu Gly Arg Leu Asp Gln Lys Leu Tyr Ala
                165                 170                 175

Ser Ala Glu Ala Thr Asp Ser Lys Ala Ala Ala Arg Leu Gly Ser Asp
            180                 185                 190

Met Gly Glu Phe Tyr Met Pro Tyr Pro Gly Thr Arg Ile Asn Gln Glu
        195                 200                 205

Thr Val Ser Leu Asp Ala Asn Gly Val Ser Gly Ser Ala Ser Tyr Tyr
    210                 215                 220

Glu Val Lys Phe Ser Asp Pro Ser Lys Pro Asn Gly Gln Ile Trp Thr
225                 230                 235                 240

Gly Val Ile Gly Ser Pro Ala Ala Asn Ala Pro Asp Ala Gly Pro Pro
                245                 250                 255

Gln Arg Trp Phe Val Val Trp Leu Gly Thr Ala Asn Asn Pro Val Asp
            260                 265                 270

Lys Gly Ala Ala Lys Ala Leu Ala Glu Ser Ile Arg Pro Leu Val Ala
        275                 280                 285

Pro Pro Pro Ala Pro Ala Pro Ala Pro Ala Glu Pro Ala Pro Ala Pro
    290                 295                 300

Ala Pro Ala Gly Glu Val Ala Pro Thr Pro Thr Thr Pro Thr Pro Gln
305                 310                 315                 320

Arg Thr Leu Pro Ala
                325


<210> SEQ ID NO 143
<211> LENGTH: 873
<212> TYPE: DNA
<213> ORGANISM: Mycobacterium tuberculosis

<400> SEQUENCE: 143

catatggatc cggagccagc gcccccggta cccacaacgg ccgcctcgcc gccgtcgacc     60

gctgcagcgc cacccgcacc ggcgacacct gttgcccccc caccaccggc cgccgccaac    120

acgccgaatg cccagccggg cgatcccaac gcagcacctc cgccggccga cccgaacgca    180

ccgccgccac ctgtcattgc cccaaacgca ccccaacctg tccggatcga caacccggtt    240

ggaggattca gcttcgcgct gcctgctggc tgggtggagt ctgacgccgc ccacttcgac    300

tacggttcag cactcctcag caaaaccacc ggggacccgc catttcccgg acagccgccg    360

ccggtggcca atgacacccg tatcgtgctc ggccggctag accaaaagct ttacgccagc    420

gccgaagcca ccgactccaa ggccgcggcc cggttgggct cggacatggg tgagttctat    480

atgccctacc cgggcacccg gatcaaccag gaaaccgtct cgctcgacgc caacggggtg    540

tctggaagcg cgtcgtatta cgaagtcaag ttcagcgatc cgagtaagcc gaacggccag    600

atctggacgg gcgtaatcgg ctcgcccgcg gcgaacgcac cggacgccgg gccccctcag    660

cgctggtttg tggtatggct cgggaccgcc aacaacccgg tggacaaggg cgcggccaag    720

gcgctggccg aatcgatccg gcctttggtc gccccgccgc cggcgccggc accggctcct    780
```

gcagagcccg ctccggcgcc ggcgccggcc ggggaagtcg ctcctacccc gacgacaccg 840
acaccgcagc ggaccttacc ggcctgagaa ttc 873

<210> SEQ ID NO 144
<211> LENGTH: 307
<212> TYPE: PRT
<213> ORGANISM: Mycobacterium tuberculosis

<400> SEQUENCE: 144

Met Gly Ser Ser His His His His His His Ser Ser Gly Leu Val Pro
1 5 10 15

Arg Gly Ser His Met Asp Pro Glu Pro Ala Pro Pro Val Pro Thr Thr
20 25 30

Ala Ala Ser Pro Pro Ser Thr Ala Ala Ala Pro Pro Ala Pro Ala Thr
35 40 45

Pro Val Ala Pro Pro Pro Pro Ala Ala Ala Asn Thr Pro Asn Ala Gln
50 55 60

Pro Gly Asp Pro Asn Ala Ala Pro Pro Pro Ala Asp Pro Asn Ala Pro
65 70 75 80

Pro Pro Pro Val Ile Ala Pro Asn Ala Pro Gln Pro Val Arg Ile Asp
85 90 95

Asn Pro Val Gly Gly Phe Ser Phe Ala Leu Pro Ala Gly Trp Val Glu
100 105 110

Ser Asp Ala Ala His Phe Asp Tyr Gly Ser Ala Leu Leu Ser Lys Thr
115 120 125

Thr Gly Asp Pro Pro Phe Pro Gly Gln Pro Pro Pro Val Ala Asn Asp
130 135 140

Thr Arg Ile Val Leu Gly Arg Leu Asp Gln Lys Leu Tyr Ala Ser Ala
145 150 155 160

Glu Ala Thr Asp Ser Lys Ala Ala Ala Arg Leu Gly Ser Asp Met Gly
165 170 175

Glu Phe Tyr Met Pro Tyr Pro Gly Thr Arg Ile Asn Gln Glu Thr Val
180 185 190

Ser Leu Asp Ala Asn Gly Val Ser Gly Ser Ala Ser Tyr Tyr Glu Val
195 200 205

Lys Phe Ser Asp Pro Ser Lys Pro Asn Gly Gln Ile Trp Thr Gly Val
210 215 220

Ile Gly Ser Pro Ala Ala Asn Ala Pro Asp Ala Gly Pro Pro Gln Arg
225 230 235 240

Trp Phe Val Val Trp Leu Gly Thr Ala Asn Asn Pro Val Asp Lys Gly
245 250 255

Ala Ala Lys Ala Leu Ala Glu Ser Ile Arg Pro Leu Val Ala Pro Pro
260 265 270

Pro Ala Pro Ala Pro Ala Pro Ala Glu Pro Ala Pro Ala Pro Ala Pro
275 280 285

Ala Gly Glu Val Ala Pro Thr Pro Thr Thr Pro Thr Pro Gln Arg Thr
290 295 300

Leu Pro Ala
305

<210> SEQ ID NO 145
<211> LENGTH: 325
<212> TYPE: PRT
<213> ORGANISM: Mycobacterium tuberculosis

<400> SEQUENCE: 145

```
Met Thr Asp Val Ser Arg Lys Ile Arg Ala Trp Gly Arg Arg Leu Met
1               5                   10                  15

Ile Gly Thr Ala Ala Ala Val Val Leu Pro Gly Leu Val Gly Leu Ala
            20                  25                  30

Gly Gly Ala Ala Thr Ala Gly Ala Phe Ser Arg Pro Gly Leu Pro Val
        35                  40                  45

Glu Tyr Leu Gln Val Pro Ser Pro Ser Met Gly Arg Asp Ile Lys Val
    50                  55                  60

Gln Phe Gln Ser Gly Gly Asn Asn Ser Pro Ala Val Tyr Leu Leu Asp
65                  70                  75                  80

Gly Leu Arg Ala Gln Asp Asp Tyr Asn Gly Trp Asp Ile Asn Thr Pro
                85                  90                  95

Ala Phe Glu Trp Tyr Tyr Gln Ser Gly Leu Ser Ile Val Met Pro Val
            100                 105                 110

Gly Gly Gln Ser Ser Phe Tyr Ser Asp Trp Tyr Ser Pro Ala Cys Gly
        115                 120                 125

Lys Ala Gly Cys Gln Thr Tyr Lys Trp Glu Thr Phe Leu Thr Ser Glu
    130                 135                 140

Leu Pro Gln Trp Leu Ser Ala Asn Arg Ala Val Lys Pro Thr Gly Ser
145                 150                 155                 160

Ala Ala Ile Gly Leu Ser Met Ala Gly Ser Ser Ala Met Ile Leu Ala
                165                 170                 175

Ala Tyr His Pro Gln Gln Phe Ile Tyr Ala Gly Ser Leu Ser Ala Leu
            180                 185                 190

Leu Asp Pro Ser Gln Gly Met Gly Pro Ser Leu Ile Gly Leu Ala Met
        195                 200                 205

Gly Asp Ala Gly Gly Tyr Lys Ala Ala Asp Met Trp Gly Pro Ser Ser
    210                 215                 220

Asp Pro Ala Trp Glu Arg Asn Asp Pro Thr Gln Gln Ile Pro Lys Leu
225                 230                 235                 240

Val Ala Asn Asn Thr Arg Leu Trp Val Tyr Cys Gly Asn Gly Thr Pro
                245                 250                 255

Asn Glu Leu Gly Gly Ala Asn Ile Pro Ala Glu Phe Leu Glu Asn Phe
            260                 265                 270

Val Arg Ser Ser Asn Leu Lys Phe Gln Asp Ala Tyr Asn Ala Ala Gly
        275                 280                 285

Gly His Asn Ala Val Phe Asn Phe Pro Pro Asn Gly Thr His Ser Trp
    290                 295                 300

Glu Tyr Trp Gly Ala Gln Leu Asn Ala Met Lys Gly Asp Leu Gln Ser
305                 310                 315                 320

Ser Leu Gly Ala Gly
                325
```

<210> SEQ ID NO 146
<211> LENGTH: 904
<212> TYPE: DNA
<213> ORGANISM: Mycobacterium tuberculosis

<400> SEQUENCE: 146

```
catatgcatc accatcacca tcacttctcc cggccggggc tgccggtcga gtacctgcag      60

gtgccgtcgc cgtcgatggg ccgcgacatc aaggttcagt tccagagcgg tgggaacaac     120

tcacctgcgg tttatctgct cgacggcctg cgcgcccaag acgactacaa cggctgggat     180
```

atcaacaccc cggcgttcga gtggtactac cagtcgggac tgtcgatagt catgccggtc 240
ggcgggcagt ccagcttcta cagcgactgg tacagcccgg cctgcggtaa ggctggctgc 300
cagacttaca agtgggaaac cttcctgacc agcgagctgc cgcaatggtt gtccgccaac 360
agggccgtga agcccaccgg cagcgctgca atcggcttgt cgatggccgg ctcgtcggca 420
atgatcttgg ccgcctacca cccccagcag ttcatctacg ccggctcgct gtcggccctg 480
ctggacccct ctcaggggat ggggcctagc ctgatcggcc tcgcgatggg tgacgccggc 540
ggttacaagg ccgcagacat gtggggtccc tcgagtgacc cggcatggga gcgcaacgac 600
cctacgcagc agatccccaa gctggtcgca aacaacaccc ggctatgggt ttattgcggg 660
aacggcaccc cgaacgagtt gggcggtgcc aacataccgg ccgagttctt ggagaacttc 720
gttcgtagca gcaacctgaa gttccaggat gcgtacaacg ccgcgggcgg gcacaacgcc 780
gtgttcaact tcccgcccaa cggcacgcac agctgggagt actggggcgc tcagctcaac 840
gccatgaagg gtgacctgca gagttcgtta ggcgccggct gacgggatca accgaaggga 900
attc 904

<210> SEQ ID NO 147
<211> LENGTH: 293
<212> TYPE: PRT
<213> ORGANISM: Mycobacterium tuberculosis

<400> SEQUENCE: 147

His Met His His His His His His Phe Ser Arg Pro Gly Leu Pro Val
1               5                   10                  15

Glu Tyr Leu Gln Val Pro Ser Pro Ser Met Gly Arg Asp Ile Lys Val
            20                  25                  30

Gln Phe Gln Ser Gly Gly Asn Asn Ser Pro Ala Val Tyr Leu Leu Asp
        35                  40                  45

Gly Leu Arg Ala Gln Asp Asp Tyr Asn Gly Trp Asp Ile Asn Thr Pro
    50                  55                  60

Ala Phe Glu Trp Tyr Tyr Gln Ser Gly Leu Ser Ile Val Met Pro Val
65                  70                  75                  80

Gly Gly Gln Ser Ser Phe Tyr Ser Asp Trp Tyr Ser Pro Ala Cys Gly
                85                  90                  95

Lys Ala Gly Cys Gln Thr Tyr Lys Trp Glu Thr Phe Leu Thr Ser Glu
            100                 105                 110

Leu Pro Gln Trp Leu Ser Ala Asn Arg Ala Val Lys Pro Thr Gly Ser
        115                 120                 125

Ala Ala Ile Gly Leu Ser Met Ala Gly Ser Ser Ala Met Ile Leu Ala
    130                 135                 140

Ala Tyr His Pro Gln Gln Phe Ile Tyr Ala Gly Ser Leu Ser Ala Leu
145                 150                 155                 160

Leu Asp Pro Ser Gln Gly Met Gly Pro Ser Leu Ile Gly Leu Ala Met
                165                 170                 175

Gly Asp Ala Gly Gly Tyr Lys Ala Ala Asp Met Trp Gly Pro Ser Ser
            180                 185                 190

Asp Pro Ala Trp Glu Arg Asn Asp Pro Thr Gln Gln Ile Pro Lys Leu
        195                 200                 205

Val Ala Asn Asn Thr Arg Leu Trp Val Tyr Cys Gly Asn Gly Thr Pro
    210                 215                 220

Asn Glu Leu Gly Gly Ala Asn Ile Pro Ala Glu Phe Leu Glu Asn Phe
225                 230                 235                 240

-continued

Val Arg Ser Ser Asn Leu Lys Phe Gln Asp Ala Tyr Asn Ala Ala Gly
245 250 255

Gly His Asn Ala Val Phe Asn Phe Pro Pro Asn Gly Thr His Ser Trp
260 265 270

Glu Tyr Trp Gly Ala Gln Leu Asn Ala Met Lys Gly Asp Leu Gln Ser
275 280 285

Ser Leu Gly Ala Gly
290

<210> SEQ ID NO 148
<211> LENGTH: 740
<212> TYPE: PRT
<213> ORGANISM: Mycobacterium tuberculosis

<400> SEQUENCE: 148

Val Pro Glu Gln His Pro Pro Ile Thr Glu Thr Thr Thr Gly Ala Ala
1 5 10 15

Ser Asn Gly Cys Pro Val Val Gly His Met Lys Tyr Pro Val Glu Gly
20 25 30

Gly Gly Asn Gln Asp Trp Trp Pro Asn Arg Leu Asn Leu Lys Val Leu
35 40 45

His Gln Asn Pro Ala Val Ala Asp Pro Met Gly Ala Ala Phe Asp Tyr
50 55 60

Ala Ala Glu Val Ala Thr Ile Asp Val Asp Ala Leu Thr Arg Asp Ile
65 70 75 80

Glu Glu Val Met Thr Thr Ser Gln Pro Trp Trp Pro Ala Asp Tyr Gly
85 90 95

His Tyr Gly Pro Leu Phe Ile Arg Met Ala Trp His Ala Ala Gly Thr
100 105 110

Tyr Arg Ile His Asp Gly Arg Gly Gly Ala Gly Gly Gly Met Gln Arg
115 120 125

Phe Ala Pro Leu Asn Ser Trp Pro Asp Asn Ala Ser Leu Asp Lys Ala
130 135 140

Arg Arg Leu Leu Trp Pro Val Lys Lys Lys Tyr Gly Lys Lys Leu Ser
145 150 155 160

Trp Ala Asp Leu Ile Val Phe Ala Gly Asn Cys Ala Leu Glu Ser Met
165 170 175

Gly Phe Lys Thr Phe Gly Phe Gly Phe Gly Arg Val Asp Gln Trp Glu
180 185 190

Pro Asp Glu Val Tyr Trp Gly Lys Glu Ala Thr Trp Leu Gly Asp Glu
195 200 205

Arg Tyr Ser Gly Lys Arg Asp Leu Glu Asn Pro Leu Ala Ala Val Gln
210 215 220

Met Gly Leu Ile Tyr Val Asn Pro Glu Gly Pro Asn Gly Asn Pro Asp
225 230 235 240

Pro Met Ala Ala Ala Val Asp Ile Arg Glu Thr Phe Arg Arg Met Ala
245 250 255

Met Asn Asp Val Glu Thr Ala Ala Leu Ile Val Gly Gly His Thr Phe
260 265 270

Gly Lys Thr His Gly Ala Gly Pro Ala Asp Leu Val Gly Pro Glu Pro
275 280 285

Glu Ala Ala Pro Leu Glu Gln Met Gly Leu Gly Trp Lys Ser Ser Tyr
290 295 300

Gly Thr Gly Thr Gly Lys Asp Ala Ile Thr Ser Gly Ile Glu Val Val
305 310 315 320

```
Trp Thr Asn Thr Pro Thr Lys Trp Asp Asn Ser Phe Leu Glu Ile Leu
                325                 330                 335

Tyr Gly Tyr Glu Trp Glu Leu Thr Lys Ser Pro Ala Gly Ala Trp Gln
            340                 345                 350

Tyr Thr Ala Lys Asp Gly Ala Gly Ala Gly Thr Ile Pro Asp Pro Phe
        355                 360                 365

Gly Gly Pro Gly Arg Ser Pro Thr Met Leu Ala Thr Asp Leu Ser Leu
    370                 375                 380

Arg Val Asp Pro Ile Tyr Glu Arg Ile Thr Arg Arg Trp Leu Glu His
385                 390                 395                 400

Pro Glu Glu Leu Ala Asp Glu Phe Ala Lys Ala Trp Tyr Lys Leu Ile
                405                 410                 415

His Arg Asp Met Gly Pro Val Ala Arg Tyr Leu Gly Pro Leu Val Pro
            420                 425                 430

Lys Gln Thr Leu Leu Trp Gln Asp Pro Val Pro Ala Val Ser His Asp
        435                 440                 445

Leu Val Gly Glu Ala Glu Ile Ala Ser Leu Lys Ser Gln Ile Arg Ala
    450                 455                 460

Ser Gly Leu Thr Val Ser Gln Leu Val Ser Thr Ala Trp Ala Ala Ala
465                 470                 475                 480

Ser Ser Phe Arg Gly Ser Asp Lys Arg Gly Gly Ala Asn Gly Gly Arg
                485                 490                 495

Ile Arg Leu Gln Pro Gln Val Gly Trp Glu Val Asn Asp Pro Asp Gly
            500                 505                 510

Asp Leu Arg Lys Val Ile Arg Thr Leu Glu Glu Ile Gln Glu Ser Phe
        515                 520                 525

Asn Ser Ala Ala Pro Gly Asn Ile Lys Val Ser Phe Ala Asp Leu Val
    530                 535                 540

Val Leu Gly Gly Cys Ala Ala Ile Glu Lys Ala Ala Lys Ala Ala Gly
545                 550                 555                 560

His Asn Ile Thr Val Pro Phe Thr Pro Gly Arg Thr Asp Ala Ser Gln
                565                 570                 575

Glu Gln Thr Asp Val Glu Ser Phe Ala Val Leu Glu Pro Lys Ala Asp
            580                 585                 590

Gly Phe Arg Asn Tyr Leu Gly Lys Gly Asn Pro Leu Pro Ala Glu Tyr
        595                 600                 605

Met Leu Leu Asp Lys Ala Asn Leu Leu Thr Leu Ser Ala Pro Glu Met
    610                 615                 620

Thr Val Leu Val Gly Gly Leu Arg Val Leu Gly Ala Asn Tyr Lys Arg
625                 630                 635                 640

Leu Pro Leu Gly Val Phe Thr Glu Ala Ser Glu Ser Leu Thr Asn Asp
                645                 650                 655

Phe Phe Val Asn Leu Leu Asp Met Gly Ile Thr Trp Glu Pro Ser Pro
            660                 665                 670

Ala Asp Asp Gly Thr Tyr Gln Gly Lys Asp Gly Ser Gly Lys Val Lys
        675                 680                 685

Trp Thr Gly Ser Arg Val Asp Leu Val Phe Gly Ser Asn Ser Glu Leu
    690                 695                 700

Arg Ala Leu Val Glu Val Tyr Gly Ala Asp Asp Ala Gln Pro Lys Phe
705                 710                 715                 720

Val Gln Asp Phe Val Ala Ala Trp Asp Lys Val Met Asn Leu Asp Arg
                725                 730                 735
```

Phe Asp Val Arg
740

<210> SEQ ID NO 149
<211> LENGTH: 2157
<212> TYPE: DNA
<213> ORGANISM: Mycobacterium tuberculosis

<400> SEQUENCE: 149
catatgaaat accccgtcga gggcggcgga aaccaggact ggtggcccaa ccggctcaat 60
ctgaaggtac tgcaccaaaa cccggccgtc gctgacccga tgggtgcggc gttcgactat 120
gccgcggagg tcgcgaccat cgacgttgac gccctgacgc gggacatcga ggaagtgatg 180
accacctcgc agccgtggtg gcccgccgac tacggccact acgggccgct gtttatccgg 240
atggcgtggc acgctgccgg cacctaccgc atccacgacg gccgcggcgg cgccgggggc 300
ggcatgcagc ggttcgcgcc gcttaacagc tggcccgaca acgccagctt ggacaaggcg 360
cgccggctgc tgtggccggt caagaagaag tacggcaaga agctctcatg ggcggacctg 420
attgttttcg ccggcaactg cgcgctggaa tcgatgggct tcaagacgtt cgggttcggc 480
ttcggccggg tcgaccagtg ggagcccgat gaggtctatt ggggcaagga agccacctgg 540
ctcggcgatg agcgttacag cggtaagcgg gatctggaga acccgctggc cgcggtgcag 600
atggggctga tctacgtgaa cccggagggg ccgaacggca acccggaccc catggccgcg 660
gcggtcgaca ttcgcgagac gtttcggcgc atggccatga acgacgtcga aacagcggcg 720
ctgatcgtcg gcggtcacac tttcggtaag acccatggcg ccggcccggc cgatctggtc 780
ggccccgaac ccgaggctgc tccgctggag cagatgggct tgggctggaa gagctcgtat 840
ggcaccggaa ccggtaagga cgcgatcacc agcggcatcg aggtcgtatg gacgaacacc 900
ccgacgaaat gggacaacag tttcctcgag atcctgtacg gctacgagtg ggagctgacg 960
aagagccctg ctggcgcttg gcaatacacc gccaaggacg gcgccggtgc cggcaccatc 1020
ccggacccgt tcggcgggcc agggcgctcc ccgacgatgc tggccactga cctctcgctg 1080
cgggtggatc cgatctatga gcggatcacg cgtcgctggc tggaacaccc cgaggaattg 1140
gccgacgagt tcgccaaggc ctggtacaag ctgatccacc gagacatggg tcccgttgcg 1200
agataccttg ggccgctggt ccccaagcag accctgctgt ggcaggatcc ggtccctgcg 1260
gtcagccacg acctcgtcgg cgaagccgag attgccagcc ttaagagcca gatccgggca 1320
tcgggattga ctgtctcaca gctagtttcg accgcatggg cggcggcgtc gtcgttccgt 1380
ggtagcgaca agcgcggcgg cgccaacggt ggtcgcatcc gcctgcagcc acaagtcggg 1440
tgggaggtca acgaccccga cggggatctg cgcaaggtca ttcgcaccct ggaagagatc 1500
caggagtcat tcaactccgc ggcgccgggg aacatcaaag tgtccttcgc cgacctcgtc 1560
gtgctcggtg gctgtgccgc catagagaaa gcagcaaagg cggctggcca caacatcacg 1620
gtgcccttca ccccgggccg cacggatgcg tcgcaggaac aaaccgacgt ggaatccttt 1680
gccgtgctgg agcccaaggc agatggcttc cgaaactacc tcggaaaggg caacccgttg 1740
ccggccgagt acatgctgct cgacaaggcg aacctgctta cgctcagtgc ccctgagatg 1800
acggtgctgg taggtggcct gcgcgtcctc ggcgcaaact acaagcgctt accgctgggc 1860
gtgttcaccg aggcctccga gtcactgacc aacgacttct tcgtgaacct gctcgacatg 1920
ggtatcacct gggagccctc gccagcagat gacgggacct accagggcaa ggatggcagt 1980
ggcaaggtga agtggaccgg cagccgcgtg gacctggtct tcgggtccaa ctcggagttg 2040

```
cgggcgcttg tcgaggtcta tggcgccgat gacgcgcagc cgaagttcgt gcaggacttc   2100

gtcgctgcct gggacaaggt gatgaacctc gacaggttcg acgtgcgctg aaagctt      2157


<210> SEQ ID NO 150
<211> LENGTH: 735
<212> TYPE: PRT
<213> ORGANISM: Mycobacterium tuberculosis

<400> SEQUENCE: 150

Met Gly Ser Ser His His His His His His Ser Ser Gly Leu Val Pro
1               5                   10                  15

Arg Gly Ser His Met Lys Tyr Pro Val Glu Gly Gly Gly Asn Gln Asp
            20                  25                  30

Trp Trp Pro Asn Arg Leu Asn Leu Lys Val Leu His Gln Asn Pro Ala
        35                  40                  45

Val Ala Asp Pro Met Gly Ala Ala Phe Asp Tyr Ala Ala Glu Val Ala
    50                  55                  60

Thr Ile Asp Val Asp Ala Leu Thr Arg Asp Ile Glu Glu Val Met Thr
65                  70                  75                  80

Thr Ser Gln Pro Trp Trp Pro Ala Asp Tyr Gly His Tyr Gly Pro Leu
                85                  90                  95

Phe Ile Arg Met Ala Trp His Ala Ala Gly Thr Tyr Arg Ile His Asp
            100                 105                 110

Gly Arg Gly Gly Ala Gly Gly Gly Met Gln Arg Phe Ala Pro Leu Asn
        115                 120                 125

Ser Trp Pro Asp Asn Ala Ser Leu Asp Lys Ala Arg Arg Leu Leu Trp
    130                 135                 140

Pro Val Lys Lys Lys Tyr Gly Lys Lys Leu Ser Trp Ala Asp Leu Ile
145                 150                 155                 160

Val Phe Ala Gly Asn Cys Ala Leu Glu Ser Met Gly Phe Lys Thr Phe
                165                 170                 175

Gly Phe Gly Phe Gly Arg Val Asp Gln Trp Glu Pro Asp Glu Val Tyr
            180                 185                 190

Trp Gly Lys Glu Ala Thr Trp Leu Gly Asp Glu Arg Tyr Ser Gly Lys
        195                 200                 205

Arg Asp Leu Glu Asn Pro Leu Ala Ala Val Gln Met Gly Leu Ile Tyr
    210                 215                 220

Val Asn Pro Glu Gly Pro Asn Gly Asn Pro Asp Pro Met Ala Ala Ala
225                 230                 235                 240

Val Asp Ile Arg Glu Thr Phe Arg Arg Met Ala Met Asn Asp Val Glu
                245                 250                 255

Thr Ala Ala Leu Ile Val Gly Gly His Thr Phe Gly Lys Thr His Gly
            260                 265                 270

Ala Gly Pro Ala Asp Leu Val Gly Pro Glu Pro Glu Ala Ala Pro Leu
        275                 280                 285

Glu Gln Met Gly Leu Gly Trp Lys Ser Ser Tyr Gly Thr Gly Thr Gly
    290                 295                 300

Lys Asp Ala Ile Thr Ser Gly Ile Glu Val Val Trp Thr Asn Thr Pro
305                 310                 315                 320

Thr Lys Trp Asp Asn Ser Phe Leu Glu Ile Leu Tyr Gly Tyr Glu Trp
                325                 330                 335

Glu Leu Thr Lys Ser Pro Ala Gly Ala Trp Gln Tyr Thr Ala Lys Asp
            340                 345                 350

Gly Ala Gly Ala Gly Thr Ile Pro Asp Pro Phe Gly Gly Pro Gly Arg
```

```
        355                 360                 365

Ser Pro Thr Met Leu Ala Thr Asp Leu Ser Leu Arg Val Asp Pro Ile
    370                 375                 380

Tyr Glu Arg Ile Thr Arg Arg Trp Leu Glu His Pro Glu Glu Leu Ala
385                 390                 395                 400

Asp Glu Phe Ala Lys Ala Trp Tyr Lys Leu Ile His Arg Asp Met Gly
                405                 410                 415

Pro Val Ala Arg Tyr Leu Gly Pro Leu Val Pro Lys Gln Thr Leu Leu
            420                 425                 430

Trp Gln Asp Pro Val Pro Ala Val Ser His Asp Leu Val Gly Glu Ala
        435                 440                 445

Glu Ile Ala Ser Leu Lys Ser Gln Ile Arg Ala Ser Gly Leu Thr Val
    450                 455                 460

Ser Gln Leu Val Ser Thr Ala Trp Ala Ala Ala Ser Ser Phe Arg Gly
465                 470                 475                 480

Ser Asp Lys Arg Gly Gly Ala Asn Gly Gly Arg Ile Arg Leu Gln Pro
                485                 490                 495

Gln Val Gly Trp Glu Val Asn Asp Pro Asp Gly Asp Leu Arg Lys Val
            500                 505                 510

Ile Arg Thr Leu Glu Glu Ile Gln Glu Ser Phe Asn Ser Ala Ala Pro
        515                 520                 525

Gly Asn Ile Lys Val Ser Phe Ala Asp Leu Val Val Leu Gly Gly Cys
    530                 535                 540

Ala Ala Ile Glu Lys Ala Ala Lys Ala Ala Gly His Asn Ile Thr Val
545                 550                 555                 560

Pro Phe Thr Pro Gly Arg Thr Asp Ala Ser Gln Glu Gln Thr Asp Val
                565                 570                 575

Glu Ser Phe Ala Val Leu Glu Pro Lys Ala Asp Gly Phe Arg Asn Tyr
            580                 585                 590

Leu Gly Lys Gly Asn Pro Leu Pro Ala Glu Tyr Met Leu Leu Asp Lys
        595                 600                 605

Ala Asn Leu Leu Thr Leu Ser Ala Pro Glu Met Thr Val Leu Val Gly
    610                 615                 620

Gly Leu Arg Val Leu Gly Ala Asn Tyr Lys Arg Leu Pro Leu Gly Val
625                 630                 635                 640

Phe Thr Glu Ala Ser Glu Ser Leu Thr Asn Asp Phe Phe Val Asn Leu
                645                 650                 655

Leu Asp Met Gly Ile Thr Trp Glu Pro Ser Pro Ala Asp Asp Gly Thr
            660                 665                 670

Tyr Gln Gly Lys Asp Gly Ser Gly Lys Val Lys Trp Thr Gly Ser Arg
        675                 680                 685

Val Asp Leu Val Phe Gly Ser Asn Ser Glu Leu Arg Ala Leu Val Glu
    690                 695                 700

Val Tyr Gly Ala Asp Asp Ala Gln Pro Lys Phe Val Gln Asp Phe Val
705                 710                 715                 720

Ala Ala Trp Asp Lys Val Met Asn Leu Asp Arg Phe Asp Val Arg
                725                 730                 735
```

<210> SEQ ID NO 151
<211> LENGTH: 331
<212> TYPE: PRT
<213> ORGANISM: Mycobacterium tuberculosis

<400> SEQUENCE: 151

-continued

```
Met Pro Asp Thr Met Val Thr Thr Asp Val Ile Lys Ser Ala Val Gln
1               5                   10                  15

Leu Ala Cys Arg Ala Pro Ser Leu His Asn Ser Gln Pro Trp Arg Trp
            20                  25                  30

Ile Ala Glu Asp His Thr Val Ala Leu Phe Leu Asp Lys Asp Arg Val
        35                  40                  45

Leu Tyr Ala Thr Asp His Ser Gly Arg Glu Ala Leu Leu Gly Cys Gly
    50                  55                  60

Ala Val Leu Asp His Phe Arg Val Ala Met Ala Ala Ala Gly Thr Thr
65                  70                  75                  80

Ala Asn Val Glu Arg Phe Pro Asn Pro Asn Asp Pro Leu His Leu Ala
                85                  90                  95

Ser Ile Asp Phe Ser Pro Ala Asp Phe Val Thr Glu Gly His Arg Leu
            100                 105                 110

Arg Ala Asp Ala Ile Leu Leu Arg Arg Thr Asp Arg Leu Pro Phe Ala
        115                 120                 125

Glu Pro Pro Asp Trp Asp Leu Val Glu Ser Gln Leu Arg Thr Thr Val
    130                 135                 140

Thr Ala Asp Thr Val Arg Ile Asp Val Ile Ala Asp Asp Met Arg Pro
145                 150                 155                 160

Glu Leu Ala Ala Ala Ser Lys Leu Thr Glu Ser Leu Arg Leu Tyr Asp
                165                 170                 175

Ser Ser Tyr His Ala Glu Leu Phe Trp Trp Thr Gly Ala Phe Glu Thr
            180                 185                 190

Ser Glu Gly Ile Pro His Ser Ser Leu Val Ser Ala Ala Glu Ser Asp
        195                 200                 205

Arg Val Thr Phe Gly Arg Asp Phe Pro Val Val Ala Asn Thr Asp Arg
    210                 215                 220

Arg Pro Glu Phe Gly His Asp Arg Ser Lys Val Leu Val Leu Ser Thr
225                 230                 235                 240

Tyr Asp Asn Glu Arg Ala Ser Leu Leu Arg Cys Gly Glu Met Leu Ser
                245                 250                 255

Ala Val Leu Leu Asp Ala Thr Met Ala Gly Leu Ala Thr Cys Thr Leu
            260                 265                 270

Thr His Ile Thr Glu Leu His Ala Ser Arg Asp Leu Val Ala Ala Leu
        275                 280                 285

Ile Gly Gln Pro Ala Thr Pro Gln Ala Leu Val Arg Val Gly Leu Ala
    290                 295                 300

Pro Glu Met Glu Glu Pro Pro Pro Ala Thr Pro Arg Arg Pro Ile Asp
305                 310                 315                 320

Glu Val Phe His Val Arg Ala Lys Asp His Arg
                325                 330
```

<210> SEQ ID NO 152
<211> LENGTH: 1026
<212> TYPE: DNA
<213> ORGANISM: Mycobacterium tuberculosis

<400> SEQUENCE: 152

```
catatgcatc accatcacca tcacatgccg gacaccatgg tgaccaccga tgtcatcaag      60

agcgcggtgc agttggcctg ccgcgcaccg tcgctccaca acagccagcc ctggcgctgg     120

atagccgagg accacacggt tgcgctgttc ctcgacaagg atcgggtgct ttacgcgacc     180

gaccactccg gccgggaagc gctgctgggg tgcggcgccg tactcgacca ctttcgggtg     240
```

```
gcgatggcgg ccgcgggtac caccgccaat gtggaacggt ttcccaaccc caacgatcct    300

ttgcatctgg cgtcaattga cttcagcccg gccgatttcg tcaccgaggg ccaccgtcta    360

agggcggatg cgatcctact gcgccgtacc gaccggctgc ctttcgccga gccgccggat    420

tgggacttgg tggagtcgca gttgcgcacg accgtcaccg ccgacacggt gcgcatcgac    480

gtcatcgccg acgatatgcg tcccgaactg gcggcggcgt ccaaactcac cgaatcgctg    540

cggctctacg attcgtcgta tcatgccgaa ctcttttggt ggacaggggc ttttgagact    600

tctgagggca taccgcacag ttcattggta tcggcggccg aaagtgaccg ggtcaccttc    660

ggacgcgact tcccggtcgt cgccaacacc gataggcgcc cggagtttgg ccacgaccgc    720

tctaaggtcc tggtgctctc cacctacgac aacgaacgcg ccagcctact gcgctgcggc    780

gagatgcttt ccgccgtatt gcttgacgcc accatggctg ggcttgccac ctgcacgctg    840

acccacatca ccgaactgca cgccagccga gacctggtcg cagcgctgat tgggcagccc    900

gcaactccgc aagccttggt tcgcgtcggt ctggccccgg agatggaaga gccgccaccg    960

gcaacgcctc ggcgaccaat cgatgaagtg tttcacgttc gggctaagga tcaccggtag   1020

gaattc                                                               1026
```

<210> SEQ ID NO 153
<211> LENGTH: 338
<212> TYPE: PRT
<213> ORGANISM: Mycobacterium tuberculosis

<400> SEQUENCE: 153

```
Met His His His His His His Met Pro Asp Thr Met Val Thr Thr Asp
1               5                   10                  15

Val Ile Lys Ser Ala Val Gln Leu Ala Cys Arg Ala Pro Ser Leu His
            20                  25                  30

Asn Ser Gln Pro Trp Arg Trp Ile Ala Glu Asp His Thr Val Ala Leu
        35                  40                  45

Phe Leu Asp Lys Asp Arg Val Leu Tyr Ala Thr Asp His Ser Gly Arg
    50                  55                  60

Glu Ala Leu Leu Gly Cys Gly Ala Val Leu Asp His Phe Arg Val Ala
65                  70                  75                  80

Met Ala Ala Ala Gly Thr Thr Ala Asn Val Glu Arg Phe Pro Asn Pro
                85                  90                  95

Asn Asp Pro Leu His Leu Ala Ser Ile Asp Phe Ser Pro Ala Asp Phe
            100                 105                 110

Val Thr Glu Gly His Arg Leu Arg Ala Asp Ala Ile Leu Leu Arg Arg
        115                 120                 125

Thr Asp Arg Leu Pro Phe Ala Glu Pro Pro Asp Trp Asp Leu Val Glu
    130                 135                 140

Ser Gln Leu Arg Thr Thr Val Thr Ala Asp Thr Val Arg Ile Asp Val
145                 150                 155                 160

Ile Ala Asp Asp Met Arg Pro Glu Leu Ala Ala Ala Ser Lys Leu Thr
                165                 170                 175

Glu Ser Leu Arg Leu Tyr Asp Ser Ser Tyr His Ala Glu Leu Phe Trp
            180                 185                 190

Trp Thr Gly Ala Phe Glu Thr Ser Glu Gly Ile Pro His Ser Ser Leu
        195                 200                 205

Val Ser Ala Ala Glu Ser Asp Arg Val Thr Phe Gly Arg Asp Phe Pro
    210                 215                 220

Val Val Ala Asn Thr Asp Arg Arg Pro Glu Phe Gly His Asp Arg Ser
```

```
225                 230                 235                 240

Lys Val Leu Val Leu Ser Thr Tyr Asp Asn Glu Arg Ala Ser Leu Leu
                245                 250                 255

Arg Cys Gly Glu Met Leu Ser Ala Val Leu Leu Asp Ala Thr Met Ala
            260                 265                 270

Gly Leu Ala Thr Cys Thr Leu Thr His Ile Thr Glu Leu His Ala Ser
        275                 280                 285

Arg Asp Leu Val Ala Ala Leu Ile Gly Gln Pro Ala Thr Pro Gln Ala
    290                 295                 300

Leu Val Arg Val Gly Leu Ala Pro Glu Met Glu Glu Pro Pro Pro Ala
305                 310                 315                 320

Thr Pro Arg Arg Pro Ile Asp Glu Val Phe His Val Arg Ala Lys Asp
                325                 330                 335

His Arg


<210> SEQ ID NO 154
<211> LENGTH: 478
<212> TYPE: PRT
<213> ORGANISM: Mycobacterium tuberculosis

<400> SEQUENCE: 154

Val Thr Glu Lys Thr Pro Asp Asp Val Phe Lys Leu Ala Lys Asp Glu
1               5                   10                  15

Lys Val Glu Tyr Val Asp Val Arg Phe Cys Asp Leu Pro Gly Ile Met
            20                  25                  30

Gln His Phe Thr Ile Pro Ala Ser Ala Phe Asp Lys Ser Val Phe Asp
        35                  40                  45

Asp Gly Leu Ala Phe Asp Gly Ser Ser Ile Arg Gly Phe Gln Ser Ile
    50                  55                  60

His Glu Ser Asp Met Leu Leu Leu Pro Asp Pro Glu Thr Ala Arg Ile
65                  70                  75                  80

Asp Pro Phe Arg Ala Ala Lys Thr Leu Asn Ile Asn Phe Phe Val His
                85                  90                  95

Asp Pro Phe Thr Leu Glu Pro Tyr Ser Arg Asp Pro Arg Asn Ile Ala
            100                 105                 110

Arg Lys Ala Glu Asn Tyr Leu Ile Ser Thr Gly Ile Ala Asp Thr Ala
        115                 120                 125

Tyr Phe Gly Ala Glu Ala Glu Phe Tyr Ile Phe Asp Ser Val Ser Phe
    130                 135                 140

Asp Ser Arg Ala Asn Gly Ser Phe Tyr Glu Val Asp Ala Ile Ser Gly
145                 150                 155                 160

Trp Trp Asn Thr Gly Ala Ala Thr Glu Ala Asp Gly Ser Pro Asn Arg
                165                 170                 175

Gly Tyr Lys Val Arg His Lys Gly Gly Tyr Phe Pro Val Ala Pro Asn
            180                 185                 190

Asp Gln Tyr Val Asp Leu Arg Asp Lys Met Leu Thr Asn Leu Ile Asn
        195                 200                 205

Ser Gly Phe Ile Leu Glu Lys Gly His His Glu Val Gly Ser Gly Gly
    210                 215                 220

Gln Ala Glu Ile Asn Tyr Gln Phe Asn Ser Leu Leu His Ala Ala Asp
225                 230                 235                 240

Asp Met Gln Leu Tyr Lys Tyr Ile Ile Lys Asn Thr Ala Trp Gln Asn
                245                 250                 255

Gly Lys Thr Val Thr Phe Met Pro Lys Pro Leu Phe Gly Asp Asn Gly
```

-continued

```
            260                 265                 270

Ser Gly Met His Cys His Gln Ser Leu Trp Lys Asp Gly Ala Pro Leu
        275                 280                 285

Met Tyr Asp Glu Thr Gly Tyr Ala Gly Leu Ser Asp Thr Ala Arg His
    290                 295                 300

Tyr Ile Gly Gly Leu Leu His His Ala Pro Ser Leu Leu Ala Phe Thr
305                 310                 315                 320

Asn Pro Thr Val Asn Ser Tyr Lys Arg Leu Val Pro Gly Tyr Glu Ala
                325                 330                 335

Pro Ile Asn Leu Val Tyr Ser Gln Arg Asn Arg Ser Ala Cys Val Arg
            340                 345                 350

Ile Pro Ile Thr Gly Ser Asn Pro Lys Ala Lys Arg Leu Glu Phe Arg
        355                 360                 365

Ser Pro Asp Ser Ser Gly Asn Pro Tyr Leu Ala Phe Ser Ala Met Leu
    370                 375                 380

Met Ala Gly Leu Asp Gly Ile Lys Asn Lys Ile Glu Pro Gln Ala Pro
385                 390                 395                 400

Val Asp Lys Asp Leu Tyr Glu Leu Pro Pro Glu Glu Ala Ala Ser Ile
                405                 410                 415

Pro Gln Thr Pro Thr Gln Leu Ser Asp Val Ile Asp Arg Leu Glu Ala
            420                 425                 430

Asp His Glu Tyr Leu Thr Glu Gly Gly Val Phe Thr Asn Asp Leu Ile
        435                 440                 445

Glu Thr Trp Ile Ser Phe Lys Arg Glu Asn Glu Ile Glu Pro Val Asn
    450                 455                 460

Ile Arg Pro His Pro Tyr Glu Phe Ala Leu Tyr Tyr Asp Val
465                 470                 475
```

<210> SEQ ID NO 155
<211> LENGTH: 1445
<212> TYPE: DNA
<213> ORGANISM: Mycobacterium tuberculosis

<400> SEQUENCE: 155

```
catatgacgg aaaagacgcc cgacgacgtc ttcaaacttg ccaaggacga gaaggtcgaa      60

tatgcgacgt ccggttctgt gacctgcctg gcatcatgca gcacttcacg attccggctt     120

cggcctttga caagagcgtg tttgacgacg gcttggcctt tgacggctcg tcgattcgcg     180

ggttccagtc gatccacgaa tccgacatgt tgcttcttcc cgatcccgag acggcgcgca     240

tcgacccgtt ccgcgcggcc aagacgctga atatcaactt ctttgtgcac gacccgttca     300

ccctggagcc gtactcccgc gacccgcgca acatcgcccg caaggccgag aactacctga     360

tcagcactgg catcgccgac accgcatact tcggcgccga ggccgagttc tacattttcg     420

attcggtgag cttcgactcg cgcgccaacg gctccttcta cgaggtggac gccatctcgg     480

ggtggtggaa caccggcgcg gcgaccgagg ccgacggcag tcccaaccgg ggctacaagg     540

tccgccacaa gggcgggtat ttcccagtgg cccccaacga ccaatacgtc gacctgcgcg     600

acaagatgct gaccaacctg atcaactccg gcttcatcct ggagaagggc caccacgagg     660

tgggcagcgg cggacaggcc gagatcaact accagttcaa ttcgctgctg cacgccgccg     720

acgacatgca gttgtacaag tacatcatca agaacaccgc ctggcagaac ggcaaaacgg     780

tcacgttcat gcccaagccg ctgttcggcg acaacgggtc cggcatgcac tgtcatcagt     840

cgctgtggaa ggacggggcc ccgctgatgt acgacgagac gggttatgcc ggtctgtcgg     900
```

acacggcccg tcattacatc ggcggcctgt tacaccacgc gccgtcgctg ctggccttca 960
ccaacccgac ggtgaactcc tacaagcggc tggttcccgg ttacgaggcc ccgatcaacc 1020
tggtctatag ccagcgcaac cggtcggcat gcgtgcgcat cccgatcacc ggcagcaacc 1080
cgaaggccaa gcggctggag ttccgaagcc ccgactcgtc gggcaacccg tatctggcgt 1140
tctcggccat gctgatggca ggcctggacg gtatcaagaa caagatcgag ccgcaggcgc 1200
ccgtcgacaa ggatctctac gagctgccgc cggaagaggc cgcgagtatc ccgcagactc 1260
cgacccagct gtcagatgtg atcgaccgtc tcgaggccga ccacgaatac ctcaccgaag 1320
gaggggtgtt cacaaacgac ctgatcgaga cgtggatcag tttcaagcgc gaaaacgaga 1380
tcgagccggt caacatccgg ccgcatccct acgaattcgc gctgtactac gacgtttaaa 1440
agctt 1445

<210> SEQ ID NO 156
<211> LENGTH: 498
<212> TYPE: PRT
<213> ORGANISM: Mycobacterium tuberculosis

<400> SEQUENCE: 156

Met Gly Ser Ser His His His His His His Ser Ser Gly Leu Val Pro
1               5                   10                  15

Arg Gly Ser His Met Thr Glu Lys Thr Pro Asp Asp Val Phe Lys Leu
            20                  25                  30

Ala Lys Asp Glu Lys Val Glu Tyr Val Asp Val Arg Phe Cys Asp Leu
        35                  40                  45

Pro Gly Ile Met Gln His Phe Thr Ile Pro Ala Ser Ala Phe Asp Lys
    50                  55                  60

Ser Val Phe Asp Asp Gly Leu Ala Phe Asp Gly Ser Ser Ile Arg Gly
65                  70                  75                  80

Phe Gln Ser Ile His Glu Ser Asp Met Leu Leu Leu Pro Asp Pro Glu
                85                  90                  95

Thr Ala Arg Ile Asp Pro Phe Arg Ala Ala Lys Thr Leu Asn Ile Asn
            100                 105                 110

Phe Phe Val His Asp Pro Phe Thr Leu Glu Pro Tyr Ser Arg Asp Pro
        115                 120                 125

Arg Asn Ile Ala Arg Lys Ala Glu Asn Tyr Leu Ile Ser Thr Gly Ile
    130                 135                 140

Ala Asp Thr Ala Tyr Phe Gly Ala Glu Ala Glu Phe Tyr Ile Phe Asp
145                 150                 155                 160

Ser Val Ser Phe Asp Ser Arg Ala Asn Gly Ser Phe Tyr Glu Val Asp
                165                 170                 175

Ala Ile Ser Gly Trp Trp Asn Thr Gly Ala Ala Thr Glu Ala Asp Gly
            180                 185                 190

Ser Pro Asn Arg Gly Tyr Lys Val Arg His Lys Gly Gly Tyr Phe Pro
        195                 200                 205

Val Ala Pro Asn Asp Gln Tyr Val Asp Leu Arg Asp Lys Met Leu Thr
    210                 215                 220

Asn Leu Ile Asn Ser Gly Phe Ile Leu Glu Lys Gly His His Glu Val
225                 230                 235                 240

Gly Ser Gly Gly Gln Ala Glu Ile Asn Tyr Gln Phe Asn Ser Leu Leu
                245                 250                 255

His Ala Ala Asp Asp Met Gln Leu Tyr Lys Tyr Ile Ile Lys Asn Thr
            260                 265                 270

```
Ala Trp Gln Asn Gly Lys Thr Val Thr Phe Met Pro Lys Pro Leu Phe
        275                 280                 285

Gly Asp Asn Gly Ser Gly Met His Cys His Gln Ser Leu Trp Lys Asp
    290                 295                 300

Gly Ala Pro Leu Met Tyr Asp Glu Thr Gly Tyr Ala Gly Leu Ser Asp
305                 310                 315                 320

Thr Ala Arg His Tyr Ile Gly Gly Leu Leu His His Ala Pro Ser Leu
                325                 330                 335

Leu Ala Phe Thr Asn Pro Thr Val Asn Ser Tyr Lys Arg Leu Val Pro
            340                 345                 350

Gly Tyr Glu Ala Pro Ile Asn Leu Val Tyr Ser Gln Arg Asn Arg Ser
        355                 360                 365

Ala Cys Val Arg Ile Pro Ile Thr Gly Ser Asn Pro Lys Ala Lys Arg
    370                 375                 380

Leu Glu Phe Arg Ser Pro Asp Ser Ser Gly Asn Pro Tyr Leu Ala Phe
385                 390                 395                 400

Ser Ala Met Leu Met Ala Gly Leu Asp Gly Ile Lys Asn Lys Ile Glu
                405                 410                 415

Pro Gln Ala Pro Val Asp Lys Asp Leu Tyr Glu Leu Pro Pro Glu Glu
            420                 425                 430

Ala Ala Ser Ile Pro Gln Thr Pro Thr Gln Leu Ser Asp Val Ile Asp
        435                 440                 445

Arg Leu Glu Ala Asp His Glu Tyr Leu Thr Glu Gly Gly Val Phe Thr
    450                 455                 460

Asn Asp Leu Ile Glu Thr Trp Ile Ser Phe Lys Arg Glu Asn Glu Ile
465                 470                 475                 480

Glu Pro Val Asn Ile Arg Pro His Pro Tyr Glu Phe Ala Leu Tyr Tyr
                485                 490                 495

Asp Val


<210> SEQ ID NO 157
<211> LENGTH: 580
<212> TYPE: PRT
<213> ORGANISM: Mycobacterium tuberculosis

<400> SEQUENCE: 157

Met Asn Phe Ala Val Leu Pro Pro Glu Val Asn Ser Ala Arg Ile Phe
1               5                   10                  15

Ala Gly Ala Gly Leu Gly Pro Met Leu Ala Ala Ala Ser Ala Trp Asp
            20                  25                  30

Gly Leu Ala Glu Glu Leu His Ala Ala Ala Gly Ser Phe Ala Ser Val
        35                  40                  45

Thr Thr Gly Leu Ala Gly Asp Ala Trp His Gly Pro Ala Ser Leu Ala
    50                  55                  60

Met Thr Arg Ala Ala Ser Pro Tyr Val Gly Trp Leu Asn Thr Ala Ala
65                  70                  75                  80

Gly Gln Ala Ala Gln Ala Ala Gly Gln Ala Arg Leu Ala Ala Ser Ala
                85                  90                  95

Phe Glu Ala Thr Leu Ala Ala Thr Val Ser Pro Ala Met Val Ala Ala
            100                 105                 110

Asn Arg Thr Arg Leu Ala Ser Leu Val Ala Ala Asn Leu Leu Gly Gln
        115                 120                 125

Asn Ala Pro Ala Ile Ala Ala Ala Glu Ala Glu Tyr Glu Gln Ile Trp
    130                 135                 140
```

-continued

```
Ala Gln Asp Val Ala Ala Met Phe Gly Tyr His Ser Ala Ala Ser Ala
145                 150                 155                 160

Val Ala Thr Gln Leu Ala Pro Ile Gln Glu Gly Leu Gln Gln Gln Leu
                165                 170                 175

Gln Asn Val Leu Ala Gln Leu Ala Ser Gly Asn Leu Gly Ser Gly Asn
            180                 185                 190

Val Gly Val Gly Asn Ile Gly Asn Asp Asn Ile Gly Asn Ala Asn Ile
        195                 200                 205

Gly Phe Gly Asn Arg Gly Asp Ala Asn Ile Gly Ile Gly Asn Ile Gly
    210                 215                 220

Asp Arg Asn Leu Gly Ile Gly Asn Thr Gly Asn Trp Asn Ile Gly Ile
225                 230                 235                 240

Gly Ile Thr Gly Asn Gly Gln Ile Gly Phe Gly Lys Pro Ala Asn Pro
                245                 250                 255

Asp Val Leu Val Val Gly Asn Gly Gly Pro Gly Val Thr Ala Leu Val
            260                 265                 270

Met Gly Gly Thr Asp Ser Leu Leu Pro Leu Pro Asn Ile Pro Leu Leu
        275                 280                 285

Glu Tyr Ala Ala Arg Phe Ile Thr Pro Val His Pro Gly Tyr Thr Ala
    290                 295                 300

Thr Phe Leu Glu Thr Pro Ser Gln Phe Phe Pro Phe Thr Gly Leu Asn
305                 310                 315                 320

Ser Leu Thr Tyr Asp Val Ser Val Ala Gln Gly Val Thr Asn Leu His
                325                 330                 335

Thr Ala Ile Met Ala Gln Leu Ala Ala Gly Asn Glu Val Val Val Phe
            340                 345                 350

Gly Thr Ser Gln Ser Ala Thr Ile Ala Thr Phe Glu Met Arg Tyr Leu
        355                 360                 365

Gln Ser Leu Pro Ala His Leu Arg Pro Gly Leu Asp Glu Leu Ser Phe
    370                 375                 380

Thr Leu Thr Gly Asn Pro Asn Arg Pro Asp Gly Gly Ile Leu Thr Arg
385                 390                 395                 400

Phe Gly Phe Ser Ile Pro Gln Leu Gly Phe Thr Leu Ser Gly Ala Thr
                405                 410                 415

Pro Ala Asp Ala Tyr Pro Thr Val Asp Tyr Ala Phe Gln Tyr Asp Gly
            420                 425                 430

Val Asn Asp Phe Pro Lys Tyr Pro Leu Asn Val Phe Ala Thr Ala Asn
        435                 440                 445

Ala Ile Ala Gly Ile Leu Phe Leu His Ser Gly Leu Ile Ala Leu Pro
    450                 455                 460

Pro Asp Leu Ala Ser Gly Val Val Gln Pro Val Ser Ser Pro Asp Val
465                 470                 475                 480

Leu Thr Thr Tyr Ile Leu Leu Pro Ser Gln Asp Leu Pro Leu Leu Val
                485                 490                 495

Pro Leu Arg Ala Ile Pro Leu Leu Gly Asn Pro Leu Ala Asp Leu Ile
            500                 505                 510

Gln Pro Asp Leu Arg Val Leu Val Glu Leu Gly Tyr Asp Arg Thr Ala
        515                 520                 525

His Gln Asp Val Pro Ser Pro Phe Gly Leu Phe Pro Asp Val Asp Trp
    530                 535                 540

Ala Glu Val Ala Ala Asp Leu Gln Gln Gly Ala Val Gln Gly Val Asn
545                 550                 555                 560

Asp Ala Leu Ser Gly Leu Gly Leu Pro Pro Pro Trp Gln Pro Ala Leu
```

565 570 575

Pro Arg Leu Phe
580

<210> SEQ ID NO 158
<211> LENGTH: 1752
<212> TYPE: DNA
<213> ORGANISM: Mycobacterium tuberculosis

<400> SEQUENCE: 158
catatgaatt tcgccgtttt gccgccggag gtgaattcgg cgcgcatatt cgccggtgcg 60
ggcctgggcc caatgctggc ggcggcgtcg gcctgggacg ggttggccga ggagttgcat 120
gccgcggcgg gctcgttcgc gtcggtgacc accgggttgg cgggcgacgc gtggcatggt 180
ccggcgtcgc tggcgatgac ccgcgcggcc agcccgtatg tggggtggtt gaacacggcg 240
gcgggtcagg ccgcgcaggc ggccggccag gcgcggctag cggcgagcgc gttcgaggcg 300
acgctggcgg ccaccgtgtc tccagcgatg gtcgcggcca accggacacg gctggcgtcg 360
ctggtggcag ccaacttgct gggccagaac gccccggcga tcgcggccgc ggaggctgaa 420
tacgagcaga tatgggccca ggacgtggcc gcgatgttcg gctatcactc cgccgcgtcg 480
gcggtggcca cgcagctggc gcctattcaa gagggtttgc agcagcagct gcaaaacgtg 540
ctggcccagt tggctagcgg gaacctgggc agcggaaatg tgggcgtcgg caacatcggc 600
aacgacaaca ttggcaacgc aaacatcggc ttcggaaatc gaggcgacgc caacatcggc 660
atcgggaata tcggcgacag aaacctcggc attgggaaca ccggcaattg gaatatcggc 720
atcggcatca ccggcaacgg acaaatcggc ttcggcaagc ctgccaaccc cgacgtcttg 780
gtggtgggca acggcggccc gggagtaacc gcgttggtca tgggcggcac cgacagccta 840
ctgccgctgc ccaacatccc cttactcgag tacgctgcgc ggttcatcac ccccgtgcat 900
cccggataca ccgctacgtt cctggaaacg ccatcgcagt tttcccatt caccgggctg 960 aatagcctga cctatgacgt ctccgtggcc cagggcgtaa cgaatctgca caccgcgatc 1020
atggcgcaac tcgcggcggg aaacgaagtc gtcgtcttcg gcacctccca aagcgccacg 1080
atagccacct tcgaaatgcg ctatctgcaa tccctgccag cacacctgcg tccgggtctc 1140
gacgaattgt cctttacgtt gaccggcaat cccaaccggc ccgacggtgg cattcttacg 1200
cgttttggct tctccatacc gcagttgggt ttcacattgt ccggcgcgac gcccgccgac 1260
gcctacccca ccgtcgatta cgcgttccag tacgacggcg tcaacgactt ccccaaatac 1320
ccgctgaatg tcttcgcgac cgccaacgcg atcgcgggca tcctttttcct gcactccggg 1380 ttgattgcgt tgccgcccga tcttgcctcg ggcgtggttc aaccggtgtc ctcaccggac 1440
gtcctgacca cctacatcct gctgcccagc caagatctgc cgctgctggt cccgctgcgt 1500
gctatccccc tgctgggaaa cccgcttgcc gacctcatcc agccggactt gcgggtgctc 1560
gtcgagttgg gttatgaccg caccgcccac caggacgtgc ccagcccgtt cggactgttt 1620
ccggacgtcg attgggccga ggtggccgcg gacctgcagc aaggcgccgt gcaaggcgtc 1680
aacgacgccc tgtccggact ggggctgccg ccgccgtggc agccggcgct accccgactt 1740
ttctaaaagc tt 1752

<210> SEQ ID NO 159
<211> LENGTH: 600
<212> TYPE: PRT
<213> ORGANISM: Mycobacterium tuberculosis

<400> SEQUENCE: 159

```
Met Gly Ser Ser His His His His His His Ser Ser Gly Leu Val Pro
1               5                   10                  15

Arg Gly Ser His Met Asn Phe Ala Val Leu Pro Pro Glu Val Asn Ser
            20                  25                  30

Ala Arg Ile Phe Ala Gly Ala Gly Leu Gly Pro Met Leu Ala Ala Ala
        35                  40                  45

Ser Ala Trp Asp Gly Leu Ala Glu Glu Leu His Ala Ala Ala Gly Ser
    50                  55                  60

Phe Ala Ser Val Thr Thr Gly Leu Ala Gly Asp Ala Trp His Gly Pro
65                  70                  75                  80

Ala Ser Leu Ala Met Thr Arg Ala Ala Ser Pro Tyr Val Gly Trp Leu
                85                  90                  95

Asn Thr Ala Ala Gly Gln Ala Ala Gln Ala Ala Gly Gln Ala Arg Leu
            100                 105                 110

Ala Ala Ser Ala Phe Glu Ala Thr Leu Ala Ala Thr Val Ser Pro Ala
        115                 120                 125

Met Val Ala Ala Asn Arg Thr Arg Leu Ala Ser Leu Val Ala Ala Asn
    130                 135                 140

Leu Leu Gly Gln Asn Ala Pro Ala Ile Ala Ala Ala Glu Ala Glu Tyr
145                 150                 155                 160

Glu Gln Ile Trp Ala Gln Asp Val Ala Ala Met Phe Gly Tyr His Ser
                165                 170                 175

Ala Ala Ser Ala Val Ala Thr Gln Leu Ala Pro Ile Gln Glu Gly Leu
            180                 185                 190

Gln Gln Gln Leu Gln Asn Val Leu Ala Gln Leu Ala Ser Gly Asn Leu
        195                 200                 205

Gly Ser Gly Asn Val Gly Val Gly Asn Ile Gly Asn Asp Asn Ile Gly
    210                 215                 220

Asn Ala Asn Ile Gly Phe Gly Asn Arg Gly Asp Ala Asn Ile Gly Ile
225                 230                 235                 240

Gly Asn Ile Gly Asp Arg Asn Leu Gly Ile Gly Asn Thr Gly Asn Trp
                245                 250                 255

Asn Ile Gly Ile Gly Ile Thr Gly Asn Gly Gln Ile Gly Phe Gly Lys
            260                 265                 270

Pro Ala Asn Pro Asp Val Leu Val Val Gly Asn Gly Gly Pro Gly Val
        275                 280                 285

Thr Ala Leu Val Met Gly Gly Thr Asp Ser Leu Leu Pro Leu Pro Asn
    290                 295                 300

Ile Pro Leu Leu Glu Tyr Ala Ala Arg Phe Ile Thr Pro Val His Pro
305                 310                 315                 320

Gly Tyr Thr Ala Thr Phe Leu Glu Thr Pro Ser Gln Phe Phe Pro Phe
                325                 330                 335

Thr Gly Leu Asn Ser Leu Thr Tyr Asp Val Ser Val Ala Gln Gly Val
            340                 345                 350

Thr Asn Leu His Thr Ala Ile Met Ala Gln Leu Ala Ala Gly Asn Glu
        355                 360                 365

Val Val Val Phe Gly Thr Ser Gln Ser Ala Thr Ile Ala Thr Phe Glu
    370                 375                 380

Met Arg Tyr Leu Gln Ser Leu Pro Ala His Leu Arg Pro Gly Leu Asp
385                 390                 395                 400

Glu Leu Ser Phe Thr Leu Thr Gly Asn Pro Asn Arg Pro Asp Gly Gly
                405                 410                 415
```

Ile Leu Thr Arg Phe Gly Phe Ser Ile Pro Gln Leu Gly Phe Thr Leu
420 425 430

Ser Gly Ala Thr Pro Ala Asp Ala Tyr Pro Thr Val Asp Tyr Ala Phe
435 440 445

Gln Tyr Asp Gly Val Asn Asp Phe Pro Lys Tyr Pro Leu Asn Val Phe
450 455 460

Ala Thr Ala Asn Ala Ile Ala Gly Ile Leu Phe Leu His Ser Gly Leu
465 470 475 480

Ile Ala Leu Pro Pro Asp Leu Ala Ser Gly Val Val Gln Pro Val Ser
485 490 495

Ser Pro Asp Val Leu Thr Thr Tyr Ile Leu Leu Pro Ser Gln Asp Leu
500 505 510

Pro Leu Leu Val Pro Leu Arg Ala Ile Pro Leu Leu Gly Asn Pro Leu
515 520 525

Ala Asp Leu Ile Gln Pro Asp Leu Arg Val Leu Val Glu Leu Gly Tyr
530 535 540

Asp Arg Thr Ala His Gln Asp Val Pro Ser Pro Phe Gly Leu Phe Pro
545 550 555 560

Asp Val Asp Trp Ala Glu Val Ala Ala Asp Leu Gln Gln Gly Ala Val
565 570 575

Gln Gly Val Asn Asp Ala Leu Ser Gly Leu Gly Leu Pro Pro Pro Trp
580 585 590

Gln Pro Ala Leu Pro Arg Leu Phe
595 600

<210> SEQ ID NO 160
<211> LENGTH: 297
<212> TYPE: PRT
<213> ORGANISM: Mycobacterium tuberculosis

<400> SEQUENCE: 160

Met Ser Ser Gly Asn Ser Ser Leu Gly Ile Ile Val Gly Ile Asp Asp
1 5 10 15

Ser Pro Ala Ala Gln Val Ala Val Arg Trp Ala Ala Arg Asp Ala Glu
20 25 30

Leu Arg Lys Ile Pro Leu Thr Leu Val His Ala Val Ser Pro Glu Val
35 40 45

Ala Thr Trp Leu Glu Val Pro Leu Pro Pro Gly Val Leu Arg Trp Gln
50 55 60

Gln Asp His Gly Arg His Leu Ile Asp Asp Ala Leu Lys Val Val Glu
65 70 75 80

Gln Ala Ser Leu Arg Ala Gly Pro Pro Thr Val His Ser Glu Ile Val
85 90 95

Pro Ala Ala Ala Val Pro Thr Leu Val Asp Met Ser Lys Asp Ala Val
100 105 110

Leu Met Val Val Gly Cys Leu Gly Ser Gly Arg Trp Pro Gly Arg Leu
115 120 125

Leu Gly Ser Val Ser Ser Gly Leu Leu Arg His Ala His Cys Pro Val
130 135 140

Val Ile Ile His Asp Glu Asp Ser Val Met Pro His Pro Gln Gln Ala
145 150 155 160

Pro Val Leu Val Gly Val Asp Gly Ser Ser Ala Ser Glu Leu Ala Thr
165 170 175

Ala Ile Ala Phe Asp Glu Ala Ser Arg Arg Asn Val Asp Leu Val Ala

```
            180                 185                 190

Leu His Ala Trp Ser Asp Val Asp Val Ser Glu Trp Pro Gly Ile Asp
        195                 200                 205

Trp Pro Ala Thr Gln Ser Met Ala Glu Gln Val Leu Ala Glu Arg Leu
    210                 215                 220

Ala Gly Trp Gln Glu Arg Tyr Pro Asn Val Ala Ile Thr Arg Val Val
225                 230                 235                 240

Val Arg Asp Gln Pro Ala Arg Gln Leu Val Gln Arg Ser Glu Glu Ala
                245                 250                 255

Gln Leu Val Val Val Gly Ser Arg Gly Arg Gly Gly Tyr Ala Gly Met
            260                 265                 270

Leu Val Gly Ser Val Gly Glu Thr Val Ala Gln Leu Ala Arg Thr Pro
        275                 280                 285

Val Ile Val Ala Arg Glu Ser Leu Thr
    290                 295


<210> SEQ ID NO 161
<211> LENGTH: 903
<212> TYPE: DNA
<213> ORGANISM: Mycobacterium tuberculosis

<400> SEQUENCE: 161

catatgtcat cgggcaattc atctctggga attatcgtcg ggatcgacga ttcaccggcc      60

gcacaggttg cggtgcggtg ggcagctcgg gatgcggagt tgcgaaaaat ccctctgacg     120

ctcgtgcacg cggtgtcgcc ggaagtagcc acctggctgg aggtgccact gccgccgggc     180

gtgctgcgat ggcagcagga tcacgggcgc cacctgatcg acgacgcact caaggtggtt     240

gaacaggctt cgctgcgcgc tggtcccccc acggtccaca gtgaaatcgt tccggcggca     300

gccgttccca cattggtcga catgtccaaa gacgcagtgc tgatggtcgt gggttgtctc     360

ggaagtgggc ggtggccggg ccggctgctc ggttcggtca gttccggcct gctccgccac     420

gcgcactgtc cggtcgtgat catccacgac gaagattcgg tgatgccgca tccccagcaa     480

gcgccggtgc tagttggcgt tgacggctcg tcggcctccg agctggcgac cgcaatcgca     540

ttcgacgaag cgtcgcggcg aaacgtggac ctggtggcgc tgcacgcatg gagcgacgtc     600

gatgtgtcgg agtggcccgg aatcgattgg ccggcaactc agtcgatggc cgagcaggtg     660

ctggccgagc ggttggcggg ttggcaggag cggtatccca acgtagccat aacccgcgtg     720

gtggtgcgcg atcagccggc ccgccagctc gtccaacgct ccgaggaagc ccagctggtc     780

gtggtcggca gccggggccg cggcggctac gccggaatgc tggtggggtc ggtaggcgaa     840

accgttgctc agctggcgcg gacgccggtc atcgtggcac gcgagtcgct gacttagaag     900

ctt                                                                   903


<210> SEQ ID NO 162
<211> LENGTH: 317
<212> TYPE: PRT
<213> ORGANISM: Mycobacterium tuberculosis

<400> SEQUENCE: 162

Met Gly Ser Ser His His His His His His Ser Ser Gly Leu Val Pro
1               5                   10                  15

Arg Gly Ser His Met Ser Ser Gly Asn Ser Ser Leu Gly Ile Ile Val
            20                  25                  30

Gly Ile Asp Asp Ser Pro Ala Ala Gln Val Ala Val Arg Trp Ala Ala
        35                  40                  45
```

```
Arg Asp Ala Glu Leu Arg Lys Ile Pro Leu Thr Leu Val His Ala Val
    50                  55                  60

Ser Pro Glu Val Ala Thr Trp Leu Glu Val Pro Leu Pro Pro Gly Val
65                  70                  75                  80

Leu Arg Trp Gln Gln Asp His Gly Arg His Leu Ile Asp Asp Ala Leu
                85                  90                  95

Lys Val Val Glu Gln Ala Ser Leu Arg Ala Gly Pro Pro Thr Val His
            100                 105                 110

Ser Glu Ile Val Pro Ala Ala Ala Val Pro Thr Leu Val Asp Met Ser
        115                 120                 125

Lys Asp Ala Val Leu Met Val Val Gly Cys Leu Gly Ser Gly Arg Trp
    130                 135                 140

Pro Gly Arg Leu Leu Gly Ser Val Ser Ser Gly Leu Leu Arg His Ala
145                 150                 155                 160

His Cys Pro Val Val Ile Ile His Asp Glu Asp Ser Val Met Pro His
                165                 170                 175

Pro Gln Gln Ala Pro Val Leu Val Gly Val Asp Gly Ser Ser Ala Ser
            180                 185                 190

Glu Leu Ala Thr Ala Ile Ala Phe Asp Glu Ala Ser Arg Arg Asn Val
        195                 200                 205

Asp Leu Val Ala Leu His Ala Trp Ser Asp Val Asp Val Ser Glu Trp
    210                 215                 220

Pro Gly Ile Asp Trp Pro Ala Thr Gln Ser Met Ala Glu Gln Val Leu
225                 230                 235                 240

Ala Glu Arg Leu Ala Gly Trp Gln Glu Arg Tyr Pro Asn Val Ala Ile
                245                 250                 255

Thr Arg Val Val Val Arg Asp Gln Pro Ala Arg Gln Leu Val Gln Arg
            260                 265                 270

Ser Glu Glu Ala Gln Leu Val Val Val Gly Ser Arg Gly Arg Gly Gly
        275                 280                 285

Tyr Ala Gly Met Leu Val Gly Ser Val Gly Glu Thr Val Ala Gln Leu
    290                 295                 300

Ala Arg Thr Pro Val Ile Val Ala Arg Glu Ser Leu Thr
305                 310                 315


<210> SEQ ID NO 163
<211> LENGTH: 193
<212> TYPE: PRT
<213> ORGANISM: Mycobacterium tuberculosis

<400> SEQUENCE: 163

Met Lys Val Lys Asn Thr Ile Ala Ala Thr Ser Phe Ala Ala Ala Gly
1               5                   10                  15

Leu Ala Ala Leu Ala Val Ala Val Ser Pro Pro Ala Ala Ala Gly Asp
            20                  25                  30

Leu Val Gly Pro Gly Cys Ala Glu Tyr Ala Ala Ala Asn Pro Thr Gly
        35                  40                  45

Pro Ala Ser Val Gln Gly Met Ser Gln Asp Pro Val Ala Val Ala Ala
    50                  55                  60

Ser Asn Asn Pro Glu Leu Thr Thr Leu Thr Ala Ala Leu Ser Gly Gln
65                  70                  75                  80

Leu Asn Pro Gln Val Asn Leu Val Asp Thr Leu Asn Ser Gly Gln Tyr
                85                  90                  95

Thr Val Phe Ala Pro Thr Asn Ala Ala Phe Ser Lys Leu Pro Ala Ser
```

```
            100                 105                 110

Thr Ile Asp Glu Leu Lys Thr Asn Ser Ser Leu Leu Thr Ser Ile Leu
        115                 120                 125

Thr Tyr His Val Val Ala Gly Gln Thr Ser Pro Ala Asn Val Val Gly
    130                 135                 140

Thr Arg Gln Thr Leu Gln Gly Ala Ser Val Thr Val Thr Gly Gln Gly
145                 150                 155                 160

Asn Ser Leu Lys Val Gly Asn Ala Asp Val Val Cys Gly Gly Val Ser
                165                 170                 175

Thr Ala Asn Ala Thr Val Tyr Met Ile Asp Ser Val Leu Met Pro Pro
            180                 185                 190

Ala


<210> SEQ ID NO 164
<211> LENGTH: 503
<212> TYPE: DNA
<213> ORGANISM: Mycobacterium tuberculosis

<400> SEQUENCE: 164

catatgggcg atctggtgag cccgggctgc gcggaatacg cggcagccaa tcccactggg      60

ccggcctcgg tgcagggaat gtcgcaggac ccggtcgcgg tggcggcctc gaacaatccg     120

gagttgacaa cgctgacggc tgcactgtcg ggccagctca atccgcaagt aaacctggtg     180

gacaccctca acagcggtca gtacacggtg ttcgcaccga ccaacgcggc atttagcaag     240

ctgccggcat ccacgatcga cgagctcaag accaattcgt cactgctgac cagcatcctg     300

acctaccacg tagtggccgg ccaaaccagc ccggccaacg tcgtcggcac ccgtcagacc     360

ctccagggcg ccagcgtgac ggtgaccggt cagggtaaca gcctcaaggt cggtaacgcc     420

gacgtcgtct gtggtggggt gtctaccgcc aacgcgacgg tgtacatgat tgacagcgtg     480

ctaatgcctc cggcgtaaaa gct                                             503


<210> SEQ ID NO 165
<211> LENGTH: 185
<212> TYPE: PRT
<213> ORGANISM: Mycobacterium tuberculosis

<400> SEQUENCE: 165

Met Gly Ser Ser His His His His His His Ser Ser Gly Leu Val Pro
1               5                   10                  15

Arg Gly Ser His Met Met Gly Asp Leu Val Ser Pro Gly Cys Ala Glu
            20                  25                  30

Tyr Ala Ala Ala Asn Pro Thr Gly Pro Ala Ser Val Gln Gly Met Ser
        35                  40                  45

Gln Asp Pro Val Ala Val Ala Ala Ser Asn Asn Pro Glu Leu Thr Thr
    50                  55                  60

Leu Thr Ala Ala Leu Ser Gly Gln Leu Asn Pro Gln Val Asn Leu Val
65                  70                  75                  80

Asp Thr Leu Asn Ser Gly Gln Tyr Thr Val Phe Ala Pro Thr Asn Ala
                85                  90                  95

Ala Phe Ser Lys Leu Pro Ala Ser Thr Ile Asp Glu Leu Lys Thr Asn
            100                 105                 110

Ser Ser Leu Leu Thr Ser Ile Leu Thr Tyr His Val Val Ala Gly Gln
        115                 120                 125

Thr Ser Pro Ala Asn Val Val Gly Thr Arg Gln Thr Leu Gln Gly Ala
    130                 135                 140
```

Ser Val Thr Val Thr Gly Gln Gly Asn Ser Leu Lys Val Gly Asn Ala
145 150 155 160

Asp Val Val Cys Gly Gly Val Ser Thr Ala Asn Ala Thr Val Tyr Met
165 170 175

Ile Asp Ser Val Leu Met Pro Pro Ala
180 185

<210> SEQ ID NO 166
<211> LENGTH: 359
<212> TYPE: PRT
<213> ORGANISM: Mycobacterium tuberculosis

<400> SEQUENCE: 166

Met Arg Ser Thr Val Ala Val Ala Val Ala Ala Ala Val Ile Ala Ala
1 5 10 15

Ser Ser Gly Cys Gly Ser Asp Gln Pro Ala His Lys Ala Ser Gln Ser
20 25 30

Met Ile Thr Pro Thr Thr Gln Ile Ala Gly Ala Gly Val Leu Gly Asn
35 40 45

Asp Arg Lys Pro Asp Glu Ser Cys Ala Arg Ala Ala Ala Ala Ala Asp
50 55 60

Pro Gly Pro Pro Thr Arg Pro Ala His Asn Ala Ala Gly Val Ser Pro
65 70 75 80

Glu Met Val Gln Val Pro Ala Glu Ala Gln Arg Ile Val Val Leu Ser
85 90 95

Gly Asp Gln Leu Asp Ala Leu Cys Ala Leu Gly Leu Gln Ser Arg Ile
100 105 110

Val Ala Ala Ala Leu Pro Asn Ser Ser Ser Ser Gln Pro Ser Tyr Leu
115 120 125

Gly Thr Thr Val His Asp Leu Pro Gly Val Gly Thr Arg Ser Ala Pro
130 135 140

Asp Leu Arg Ala Ile Ala Ala Ala His Pro Asp Leu Ile Leu Gly Ser
145 150 155 160

Gln Gly Leu Thr Pro Gln Leu Tyr Pro Gln Leu Ala Ala Ile Ala Pro
165 170 175

Thr Val Phe Thr Ala Ala Pro Gly Ala Asp Trp Glu Asn Asn Leu Arg
180 185 190

Gly Val Gly Ala Ala Thr Ala Arg Ile Ala Ala Val Asp Ala Leu Ile
195 200 205

Thr Gly Phe Ala Glu His Ala Thr Gln Val Gly Thr Lys His Asp Ala
210 215 220

Thr His Phe Gln Ala Ser Ile Val Gln Leu Thr Ala Asn Thr Met Arg
225 230 235 240

Val Tyr Gly Ala Asn Asn Phe Pro Ala Ser Val Leu Ser Ala Val Gly
245 250 255

Val Asp Arg Pro Pro Ser Gln Arg Phe Thr Asp Lys Ala Tyr Ile Glu
260 265 270

Ile Gly Thr Thr Ala Ala Asp Leu Ala Lys Ser Pro Asp Phe Ser Ala
275 280 285

Ala Asp Ala Asp Ile Val Tyr Leu Ser Cys Ala Ser Glu Ala Ala Ala
290 295 300

Glu Arg Ala Ala Val Ile Leu Asp Ser Asp Pro Trp Arg Lys Leu Ser
305 310 315 320

Ala Asn Arg Asp Asn Arg Val Phe Val Val Asn Asp Gln Val Trp Gln

```
                325                 330                 335

Thr Gly Glu Gly Met Val Ala Ala Arg Gly Ile Val Asp Asp Leu Arg
            340                 345                 350

Trp Val Asp Ala Pro Ile Asn
        355
```

<210> SEQ ID NO 167
<211> LENGTH: 1071
<212> TYPE: DNA
<213> ORGANISM: Mycobacterium tuberculosis

<400> SEQUENCE: 167

```
atgggcagca gccatcatca tcatcatcac agcagcggcc tggtgccgcg cggcagccat      60

atgcataagg cgtcacaatc gatgatcacg cccaccaccc agatcgccgg cgccggggtg     120

ctgggaaacg acagaaagcc ggatgagtcg tgcgcgcgtg cggcggccgc ggccgatccg     180

gggccaccga cccgaccagc gcacaatgcg gcgggagtca gcccggagat ggtgcaggtg     240

ccggcggagg cgcagcgcat cgtggtgctc tccggtgacc agctcgacgc gctgtgcgcg     300

ctgggcctgc aatcgcggat cgtcgccgcc gcgttgccga acagctcctc aagtcaacct     360

tcctatctgg gcacgaccgt gcatgatctg cccggtgtcg gtactcgcag cgcccccgac     420

ctgcgcgcca ttgcggcggc tcacccggat ctgatcctgg gttcgcaggg tttgacgccg     480

cagttgtatc cgcagctggc ggcgatcgcc ccgacggtgt ttaccgcggc accgggcgcg     540

gactgggaaa ataacctgcg tggtgtcggt gccgccacgg cccgtatcgc cgcggtggac     600

gcgctgatca ccgggttcgc cgaacacgcc acccaggtcg ggaccaagca tgacgcgacc     660

cacttccaag cgtcgatcgt gcagctgacc gccaacacca tgcgggtata cggcgccaac     720

aacttcccgg ccagcgtgct gagcgcggtc ggcgtcgacc gaccgccgtc tcaacggttc     780

accgacaagg cctacatcga gatcggcacc acggccgccg acctggcgaa atcaccggac     840

ttctcggcgg ccgacgccga tatcgtctac ctgtcgtgcg cgtcggaagc agccgcggaa     900

cgcgcggccg tcatcctgga tagcgaccca tggcgcaagc tgtccgccaa ccgtgacaac     960

cgggtcttcg tcgtcaacga ccaggtatgg cagaccggcg agggtatggt cgctgcccgc    1020

ggcattgtcg atgatctgcg ctgggtcgac gcgccgatca actagaagct t             1071
```

<210> SEQ ID NO 168
<211> LENGTH: 354
<212> TYPE: PRT
<213> ORGANISM: Mycobacterium tuberculosis

<400> SEQUENCE: 168

```
Met Gly Ser Ser His His His His His His Ser Ser Gly Leu Val Pro
1               5                   10                  15

Arg Gly Ser His Met His Lys Ala Ser Gln Ser Met Ile Thr Pro Thr
            20                  25                  30

Thr Gln Ile Ala Gly Ala Gly Val Leu Gly Asn Asp Arg Lys Pro Asp
        35                  40                  45

Glu Ser Cys Ala Arg Ala Ala Ala Ala Ala Asp Pro Gly Pro Pro Thr
    50                  55                  60

Arg Pro Ala His Asn Ala Ala Gly Val Ser Pro Glu Met Val Gln Val
65                  70                  75                  80

Pro Ala Glu Ala Gln Arg Ile Val Val Leu Ser Gly Asp Gln Leu Asp
                85                  90                  95

Ala Leu Cys Ala Leu Gly Leu Gln Ser Arg Ile Val Ala Ala Ala Leu
```

```
            100                 105                 110

Pro Asn Ser Ser Ser Ser Gln Pro Ser Tyr Leu Gly Thr Thr Val His
        115                 120                 125

Asp Leu Pro Gly Val Gly Thr Arg Ser Ala Pro Asp Leu Arg Ala Ile
    130                 135                 140

Ala Ala Ala His Pro Asp Leu Ile Leu Gly Ser Gln Gly Leu Thr Pro
145                 150                 155                 160

Gln Leu Tyr Pro Gln Leu Ala Ala Ile Ala Pro Thr Val Phe Thr Ala
                165                 170                 175

Ala Pro Gly Ala Asp Trp Glu Asn Asn Leu Arg Gly Val Gly Ala Ala
            180                 185                 190

Thr Ala Arg Ile Ala Ala Val Asp Ala Leu Ile Thr Gly Phe Ala Glu
        195                 200                 205

His Ala Thr Gln Val Gly Thr Lys His Asp Ala Thr His Phe Gln Ala
    210                 215                 220

Ser Ile Val Gln Leu Thr Ala Asn Thr Met Arg Val Tyr Gly Ala Asn
225                 230                 235                 240

Asn Phe Pro Ala Ser Val Leu Ser Ala Val Gly Val Asp Arg Pro Pro
                245                 250                 255

Ser Gln Arg Phe Thr Asp Lys Ala Tyr Ile Glu Ile Gly Thr Thr Ala
            260                 265                 270

Ala Asp Leu Ala Lys Ser Pro Asp Phe Ser Ala Ala Asp Ala Asp Ile
        275                 280                 285

Val Tyr Leu Ser Cys Ala Ser Glu Ala Ala Ala Glu Arg Ala Ala Val
    290                 295                 300

Ile Leu Asp Ser Asp Pro Trp Arg Lys Leu Ser Ala Asn Arg Asp Asn
305                 310                 315                 320

Arg Val Phe Val Val Asn Asp Gln Val Trp Gln Thr Gly Glu Gly Met
                325                 330                 335

Val Ala Ala Arg Gly Ile Val Asp Asp Leu Arg Trp Val Asp Ala Pro
            340                 345                 350

Ile Asn


<210> SEQ ID NO 169
<211> LENGTH: 299
<212> TYPE: PRT
<213> ORGANISM: Mycobacterium tuberculosis

<400> SEQUENCE: 169

Met Leu Arg Gly Ile Gln Ala Leu Ser Arg Pro Leu Thr Arg Val Tyr
1               5                   10                  15

Arg Ala Leu Ala Val Ile Gly Val Leu Ala Ala Ser Leu Leu Ala Ser
            20                  25                  30

Trp Val Gly Ala Val Pro Gln Val Gly Leu Ala Ala Ser Ala Leu Pro
        35                  40                  45

Thr Phe Ala His Val Val Ile Val Val Glu Glu Asn Arg Ser Gln Ala
    50                  55                  60

Ala Ile Ile Gly Asn Lys Ser Ala Pro Phe Ile Asn Ser Leu Ala Ala
65                  70                  75                  80

Asn Gly Ala Met Met Ala Gln Ala Phe Ala Glu Thr His Pro Ser Glu
                85                  90                  95

Pro Asn Tyr Leu Ala Leu Phe Ala Gly Asn Thr Phe Gly Leu Thr Lys
            100                 105                 110

Asn Thr Cys Pro Val Asn Gly Gly Ala Leu Pro Asn Leu Gly Ser Glu
```

```
        115                 120                 125

Leu Leu Ser Ala Gly Tyr Thr Phe Met Gly Phe Ala Glu Asp Leu Pro
    130                 135                 140

Ala Val Gly Ser Thr Val Cys Ser Ala Gly Lys Tyr Ala Arg Lys His
145                 150                 155                 160

Val Pro Trp Val Asn Phe Ser Asn Val Pro Thr Thr Leu Ser Val Pro
                165                 170                 175

Phe Ser Ala Phe Pro Lys Pro Gln Asn Tyr Pro Gly Leu Pro Thr Val
            180                 185                 190

Ser Phe Val Ile Pro Asn Ala Asp Asn Asp Met His Asp Gly Ser Ile
        195                 200                 205

Ala Gln Gly Asp Ala Trp Leu Asn Arg His Leu Ser Ala Tyr Ala Asn
    210                 215                 220

Trp Ala Lys Thr Asn Asn Ser Leu Leu Val Val Thr Trp Asp Glu Asp
225                 230                 235                 240

Asp Gly Ser Ser Arg Asn Gln Ile Pro Thr Val Phe Tyr Gly Ala His
                245                 250                 255

Val Arg Pro Gly Thr Tyr Asn Glu Thr Ile Ser His Tyr Asn Val Leu
            260                 265                 270

Ser Thr Leu Glu Gln Ile Tyr Gly Leu Pro Lys Thr Gly Tyr Ala Thr
        275                 280                 285

Asn Ala Pro Pro Ile Thr Asp Ile Trp Gly Asp
    290                 295
```

<210> SEQ ID NO 170
<211> LENGTH: 789
<212> TYPE: DNA
<213> ORGANISM: Mycobacterium tuberculosis

<400> SEQUENCE: 170

```
catatggcta gcatgagtgc cctgccgacc ttcgcgcacg tggtcatcgt ggtggaggag      60

aaccgctcgc aggccgccat catcggtaac aagtcggctc ccttcatcaa ttcgctggcc     120

gccaacggcg cgatgatggc ccaggcgttc gccgaaacac acccgagcga accgaactac     180

ctggcactgt tcgctggcaa cacattcggg ttgacgaaga acacctgccc cgtcaacggc     240

ggcgcgctgc ccaacctggg ttctgagttg ctcagcgccg gttacacatt catggggttc     300

gccgaagact tgcctgcggt cggctccacg gtgtgcagtg cgggcaaata cgcacgcaaa     360

cacgtgccgt gggtcaactt cagtaacgtg ccgacgacac tgtcggtgcc gttttcggca     420

tttccgaagc cgcagaatta ccccggcctg ccgacggtgt cgtttgtcat ccctaacgcc     480

gacaacgaca tgcacgacgg ctcgatcgcc caaggcgacg cctggctgaa ccgccacctg     540

tcggcatatg ccaactgggc caagacaaac aacagcctgc tcgttgtgac ctgggacgaa     600

gacgacggca gcagccgcaa tcagatcccg acggtgttct acggcgcgca cgtgcggccc     660

ggaacttaca acgagaccat cagccactac aacgtgctgt ccacattgga gcagatctac     720

ggactgccca agacgggtta tgcgaccaat gctccgccaa taaccgatat ttggggcgac     780

tagaagctt                                                             789
```

<210> SEQ ID NO 171
<211> LENGTH: 279
<212> TYPE: PRT
<213> ORGANISM: Mycobacterium tuberculosis

<400> SEQUENCE: 171

-continued

Met Gly Ser Ser His His His His His His Ser Ser Gly Leu Val Pro
1 5 10 15

Arg Gly Ser His Met Ala Ser Met Ser Ala Leu Pro Thr Phe Ala His
20 25 30

Val Val Ile Val Val Glu Glu Asn Arg Ser Gln Ala Ala Ile Ile Gly
35 40 45

Asn Lys Ser Ala Pro Phe Ile Asn Ser Leu Ala Ala Asn Gly Ala Met
50 55 60

Met Ala Gln Ala Phe Ala Glu Thr His Pro Ser Glu Pro Asn Tyr Leu
65 70 75 80

Ala Leu Phe Ala Gly Asn Thr Phe Gly Leu Thr Lys Asn Thr Cys Pro
85 90 95

Val Asn Gly Gly Ala Leu Pro Asn Leu Gly Ser Glu Leu Leu Ser Ala
100 105 110

Gly Tyr Thr Phe Met Gly Phe Ala Glu Asp Leu Pro Ala Val Gly Ser
115 120 125

Thr Val Cys Ser Ala Gly Lys Tyr Ala Arg Lys His Val Pro Trp Val
130 135 140

Asn Phe Ser Asn Val Pro Thr Thr Leu Ser Val Pro Phe Ser Ala Phe
145 150 155 160

Pro Lys Pro Gln Asn Tyr Pro Gly Leu Pro Thr Val Ser Phe Val Ile
165 170 175

Pro Asn Ala Asp Asn Asp Met His Asp Gly Ser Ile Ala Gln Gly Asp
180 185 190

Ala Trp Leu Asn Arg His Leu Ser Ala Tyr Ala Asn Trp Ala Lys Thr
195 200 205

Asn Asn Ser Leu Leu Val Val Thr Trp Asp Glu Asp Asp Gly Ser Ser
210 215 220

Arg Asn Gln Ile Pro Thr Val Phe Tyr Gly Ala His Val Arg Pro Gly
225 230 235 240

Thr Tyr Asn Glu Thr Ile Ser His Tyr Asn Val Leu Ser Thr Leu Glu
245 250 255

Gln Ile Tyr Gly Leu Pro Lys Thr Gly Tyr Ala Thr Asn Ala Pro Pro
260 265 270

Ile Thr Asp Ile Trp Gly Asp
275

<210> SEQ ID NO 172
<211> LENGTH: 94
<212> TYPE: PRT
<213> ORGANISM: Mycobacterium tuberculosis

<400> SEQUENCE: 172

Met Thr Ile Asn Tyr Gln Phe Gly Asp Val Asp Ala His Gly Ala Met
1 5 10 15

Ile Arg Ala Gln Ala Gly Ser Leu Glu Ala Glu His Gln Ala Ile Ile
20 25 30

Ser Asp Val Leu Thr Ala Ser Asp Phe Trp Gly Gly Ala Gly Ser Ala
35 40 45

Ala Cys Gln Gly Phe Ile Thr Gln Leu Gly Arg Asn Phe Gln Val Ile
50 55 60

Tyr Glu Gln Ala Asn Ala His Gly Gln Lys Val Gln Ala Ala Gly Asn
65 70 75 80

Asn Met Ala Gln Thr Asp Ser Ala Val Gly Ser Ser Trp Ala
85 90

<210> SEQ ID NO 173
<211> LENGTH: 294
<212> TYPE: DNA
<213> ORGANISM: Mycobacterium tuberculosis

<400> SEQUENCE: 173
catatgacca tcaactatca attcggggac gtcgacgctc acggcgccat gatccgcgct 60
caggccgggt cgctggaggc cgagcatcag gccatcattt ctgatgtgtt gaccgcgagt 120
gacttttggg gcggcgccgg ttcggcggcc tgccaggggt tcattaccca gctgggccgt 180
aacttccagg tgatctacga gcaggccaac gcccacgggc agaaggtgca ggctgccggc 240
aacaacatgg cacaaaccga cagcgccgtc ggctccagct gggcctaaaa gctt 294

<210> SEQ ID NO 174
<211> LENGTH: 114
<212> TYPE: PRT
<213> ORGANISM: Mycobacterium tuberculosis

<400> SEQUENCE: 174

Met Gly Ser Ser His His His His His His Ser Ser Gly Leu Val Pro
1 5 10 15

Arg Gly Ser His Met Thr Ile Asn Tyr Gln Phe Gly Asp Val Asp Ala
20 25 30

His Gly Ala Met Ile Arg Ala Gln Ala Gly Ser Leu Glu Ala Glu His
35 40 45

Gln Ala Ile Ile Ser Asp Val Leu Thr Ala Ser Asp Phe Trp Gly Gly
50 55 60

Ala Gly Ser Ala Ala Cys Gln Gly Phe Ile Thr Gln Leu Gly Arg Asn
65 70 75 80

Phe Gln Val Ile Tyr Glu Gln Ala Asn Ala His Gly Gln Lys Val Gln
85 90 95

Ala Ala Gly Asn Asn Met Ala Gln Thr Asp Ser Ala Val Gly Ser Ser
100 105 110

Trp Ala

<210> SEQ ID NO 175
<211> LENGTH: 284
<212> TYPE: PRT
<213> ORGANISM: Mycobacterium tuberculosis

<400> SEQUENCE: 175

Val Pro Asn Arg Arg Arg Arg Lys Leu Ser Thr Ala Met Ser Ala Val
1 5 10 15

Ala Ala Leu Ala Val Ala Ser Pro Cys Ala Tyr Phe Leu Val Tyr Glu
20 25 30

Ser Thr Glu Thr Thr Glu Arg Pro Glu His His Glu Phe Lys Gln Ala
35 40 45

Ala Val Leu Thr Asp Leu Pro Gly Glu Leu Met Ser Ala Leu Ser Gln
50 55 60

Gly Leu Ser Gln Phe Gly Ile Asn Ile Pro Pro Val Pro Ser Leu Thr
65 70 75 80

Gly Ser Gly Asp Ala Ser Thr Gly Leu Thr Gly Pro Gly Leu Thr Ser
85 90 95

Pro Gly Leu Thr Ser Pro Gly Leu Thr Ser Pro Gly Leu Thr Asp Pro
100 105 110

-continued

```
Ala Leu Thr Ser Pro Gly Leu Thr Pro Thr Leu Pro Gly Ser Leu Ala
        115                 120                 125

Ala Pro Gly Thr Thr Leu Ala Pro Thr Pro Gly Val Gly Ala Asn Pro
    130                 135                 140

Ala Leu Thr Asn Pro Ala Leu Thr Ser Pro Thr Gly Ala Thr Pro Gly
145                 150                 155                 160

Leu Thr Ser Pro Thr Gly Leu Asp Pro Ala Leu Gly Gly Ala Asn Glu
                165                 170                 175

Ile Pro Ile Thr Thr Pro Val Gly Leu Asp Pro Gly Ala Asp Gly Thr
            180                 185                 190

Tyr Pro Ile Leu Gly Asp Pro Thr Leu Gly Thr Ile Pro Ser Ser Pro
        195                 200                 205

Ala Thr Thr Ser Thr Gly Gly Gly Gly Leu Val Asn Asp Val Met Gln
    210                 215                 220

Val Ala Asn Glu Leu Gly Ala Ser Gln Ala Ile Asp Leu Leu Lys Gly
225                 230                 235                 240

Val Leu Met Pro Ser Ile Met Gln Ala Val Gln Asn Gly Gly Ala Ala
                245                 250                 255

Ala Pro Ala Ala Ser Pro Pro Val Pro Pro Ile Pro Ala Ala Ala Ala
            260                 265                 270

Val Pro Pro Thr Asp Pro Ile Thr Val Pro Val Ala
        275                 280
```

<210> SEQ ID NO 176
<211> LENGTH: 858
<212> TYPE: DNA
<213> ORGANISM: Mycobacterium tuberculosis

<400> SEQUENCE: 176

```
atgggcagca gccatcatca tcatcatcac agcagcggcc tggtgccgcg cggcagccat      60

atgagtcctt gtgcatattt tcttgtctac gaatcaaccg aaacgaccga gcggcccgag     120

caccatgaat tcaagcaggc ggcggtgttg accgacctgc ccggcgagct gatgtccgcg     180

ctatcgcagg ggttgtccca gttcgggatc aacataccgc cggtgcccag cctgaccggg     240

agcggcgatg ccagcacggg tctaaccggt cctggcctga ctagtccggg attgaccagc     300

ccgggattga ccagcccggg cctcaccgac cctgccctta ccagtccggg cctgacgcca     360

accctgcccg gatcactcgc cgcgcccggc accaccctgg cgccaacgcc cggcgtgggg     420

gccaatccgg cgctcaccaa ccccgcgctg accagcccga ccggggcgac gccgggattg     480

accagcccga cgggtttgga tcccgcgctg ggcggcgcca acgaaatccc gattacgacg     540

ccggtcggat tggatcccgg ggctgacggc acctatccga tcctcggtga tccaacactg     600

gggaccatac cgagcagccc cgccaccacc tccaccggcg gcggcggtct cgtcaacgac     660

gtgatgcagg tggccaacga gttgggcgcc agtcaggcta tcgacctgct aaaaggtgtg     720

ctaatgccgt cgatcatgca ggccgtccag aatggcggcg cggccgcgcc ggcagccagc     780

ccgccggtcc cgcccatccc cgcggccgcg gcggtgccac cgacggaccc aatcaccgtg     840

ccggtcgcct aaaagctt                                                   858
```

<210> SEQ ID NO 177
<211> LENGTH: 283
<212> TYPE: PRT
<213> ORGANISM: Mycobacterium tuberculosis

<400> SEQUENCE: 177

```
Met Gly Ser Ser His His His His His His Ser Ser Gly Leu Val Pro
1               5                   10                  15

Arg Gly Ser His Met Ser Pro Cys Ala Tyr Phe Leu Val Tyr Glu Ser
            20                  25                  30

Thr Glu Thr Thr Glu Arg Pro Glu His His Glu Phe Lys Gln Ala Ala
        35                  40                  45

Val Leu Thr Asp Leu Pro Gly Glu Leu Met Ser Ala Leu Ser Gln Gly
    50                  55                  60

Leu Ser Gln Phe Gly Ile Asn Ile Pro Pro Val Pro Ser Leu Thr Gly
65                  70                  75                  80

Ser Gly Asp Ala Ser Thr Gly Leu Thr Gly Pro Gly Leu Thr Ser Pro
                85                  90                  95

Gly Leu Thr Ser Pro Gly Leu Thr Ser Pro Gly Leu Thr Asp Pro Ala
            100                 105                 110

Leu Thr Ser Pro Gly Leu Thr Pro Thr Leu Pro Gly Ser Leu Ala Ala
        115                 120                 125

Pro Gly Thr Thr Leu Ala Pro Thr Pro Gly Val Gly Ala Asn Pro Ala
    130                 135                 140

Leu Thr Asn Pro Ala Leu Thr Ser Pro Thr Gly Ala Thr Pro Gly Leu
145                 150                 155                 160

Thr Ser Pro Thr Gly Leu Asp Pro Ala Leu Gly Gly Ala Asn Glu Ile
                165                 170                 175

Pro Ile Thr Thr Pro Val Gly Leu Asp Pro Gly Ala Asp Gly Thr Tyr
            180                 185                 190

Pro Ile Leu Gly Asp Pro Thr Leu Gly Thr Ile Pro Ser Ser Pro Ala
        195                 200                 205

Thr Thr Ser Thr Gly Gly Gly Gly Leu Val Asn Asp Val Met Gln Val
    210                 215                 220

Ala Asn Glu Leu Gly Ala Ser Gln Ala Ile Asp Leu Leu Lys Gly Val
225                 230                 235                 240

Leu Met Pro Ser Ile Met Gln Ala Val Gln Asn Gly Gly Ala Ala Ala
                245                 250                 255

Pro Ala Ala Ser Pro Pro Val Pro Pro Ile Pro Ala Ala Ala Ala Val
            260                 265                 270

Pro Pro Thr Asp Pro Ile Thr Val Pro Val Ala
        275                 280
```

<210> SEQ ID NO 178
<211> LENGTH: 460
<212> TYPE: PRT
<213> ORGANISM: Mycobacterium tuberculosis

<400> SEQUENCE: 178

```
Met Thr Gln Ser Gln Thr Val Thr Val Asp Gln Gln Glu Ile Leu Asn
1               5                   10                  15

Arg Ala Asn Glu Val Glu Ala Pro Met Ala Asp Pro Pro Thr Asp Val
            20                  25                  30

Pro Ile Thr Pro Cys Glu Leu Thr Ala Ala Lys Asn Ala Ala Gln Gln
        35                  40                  45

Leu Val Leu Ser Ala Asp Asn Met Arg Glu Tyr Leu Ala Ala Gly Ala
    50                  55                  60

Lys Glu Arg Gln Arg Leu Ala Thr Ser Leu Arg Asn Ala Ala Lys Ala
65                  70                  75                  80

Tyr Gly Glu Val Asp Glu Glu Ala Ala Thr Ala Leu Asp Asn Asp Gly
                85                  90                  95
```

```
Glu Gly Thr Val Gln Ala Glu Ser Ala Gly Ala Val Gly Gly Asp Ser
            100                 105                 110

Ser Ala Glu Leu Thr Asp Thr Pro Arg Val Ala Thr Ala Gly Glu Pro
        115                 120                 125

Asn Phe Met Asp Leu Lys Glu Ala Ala Arg Lys Leu Glu Thr Gly Asp
    130                 135                 140

Gln Gly Ala Ser Leu Ala His Phe Ala Asp Gly Trp Asn Thr Phe Asn
145                 150                 155                 160

Leu Thr Leu Gln Gly Asp Val Lys Arg Phe Arg Gly Phe Asp Asn Trp
                165                 170                 175

Glu Gly Asp Ala Ala Thr Ala Cys Glu Ala Ser Leu Asp Gln Gln Arg
            180                 185                 190

Gln Trp Ile Leu His Met Ala Lys Leu Ser Ala Ala Met Ala Lys Gln
        195                 200                 205

Ala Gln Tyr Val Ala Gln Leu His Val Trp Ala Arg Arg Glu His Pro
    210                 215                 220

Thr Tyr Glu Asp Ile Val Gly Leu Glu Arg Leu Tyr Ala Glu Asn Pro
225                 230                 235                 240

Ser Ala Arg Asp Gln Ile Leu Pro Val Tyr Ala Glu Tyr Gln Gln Arg
                245                 250                 255

Ser Glu Lys Val Leu Thr Glu Tyr Asn Asn Lys Ala Ala Leu Glu Pro
            260                 265                 270

Val Asn Pro Pro Lys Pro Pro Pro Ala Ile Lys Ile Asp Pro Pro Pro
        275                 280                 285

Pro Pro Gln Glu Gln Gly Leu Ile Pro Gly Phe Leu Met Pro Pro Ser
    290                 295                 300

Asp Gly Ser Gly Val Thr Pro Gly Thr Gly Met Pro Ala Ala Pro Met
305                 310                 315                 320

Val Pro Pro Thr Gly Ser Pro Gly Gly Gly Leu Pro Ala Asp Thr Ala
                325                 330                 335

Ala Gln Leu Thr Ser Ala Gly Arg Glu Ala Ala Ala Leu Ser Gly Asp
            340                 345                 350

Val Ala Val Lys Ala Ala Ser Leu Gly Gly Gly Gly Gly Gly Gly Val
        355                 360                 365

Pro Ser Ala Pro Leu Gly Ser Ala Ile Gly Gly Ala Glu Ser Val Arg
    370                 375                 380

Pro Ala Gly Ala Gly Asp Ile Ala Gly Leu Gly Gln Gly Arg Ala Gly
385                 390                 395                 400

Gly Gly Ala Ala Leu Gly Gly Gly Gly Met Gly Met Pro Met Gly Ala
                405                 410                 415

Ala His Gln Gly Gln Gly Gly Ala Lys Ser Lys Gly Ser Gln Gln Glu
            420                 425                 430

Asp Glu Ala Leu Tyr Thr Glu Asp Arg Ala Trp Thr Glu Ala Val Ile
        435                 440                 445

Gly Asn Arg Arg Arg Gln Asp Ser Lys Glu Ser Lys
    450                 455                 460
```

<210> SEQ ID NO 179
<211> LENGTH: 1449
<212> TYPE: DNA
<213> ORGANISM: Mycobacterium tuberculosis

<400> SEQUENCE: 179
atgggcagca gccatcatca tcatcatcac agcagcggcc tggtgccgcg cggcagccat     60

```
atgacgcagt cgcagaccgt gacggtggat cagcaagaga ttttgaacag ggccaacgag    120

gtggaggccc cgatggcgga cccaccgact gatgtcccca tcacaccgtg cgaactcacg    180

gcggctaaaa acgccgccca acagctggta ttgtccgccg acaacatgcg ggaatacctg    240

gcggccggtg ccaaagagcg gcagcgtctg gcgacctcgc tgcgcaacgc ggccaaggcg    300

tatggcgagg ttgatgagga ggctgcgacc gcgctggaca acgacggcga aggaactgtg    360

caggcagaat cggccggggc cgtcggaggg gacagttcgg ccgaactaac cgatacgccg    420

agggtggcca cggccggtga acccaacttc atggatctca aagaagcggc aaggaagctc    480

gaaacgggcg accaaggcgc atcgctcgcg cactttgcgg atgggtggaa cactttcaac    540

ctgacgctgc aaggcgacgt caagcggttc cgggggtttg acaactggga aggcgatgcg    600

gctaccgctt gcgaggcttc gctcgatcaa caacggcaat ggatactcca catggccaaa    660

ttgagcgctg cgatggccaa gcaggctcaa tatgtcgcgc agctgcacgt gtgggctagg    720

cgggaacatc cgacttatga agacatagtc gggctcgaac ggctttacgc ggaaaaccct    780

tcggcccgcg accaaattct cccggtgtac gcggagtatc agcagaggtc ggagaaggtg    840

ctgaccgaat acaacaacaa ggcagccctg gaaccggtaa acccgccgaa gcctcccccc    900

gccatcaaga tcgacccgcc cccgcctccg caagagcagg gattgatccc tggcttcctg    960

atgccgccgt ctgacggctc cggtgtgact cccggtaccg ggatgccagc cgcaccgatg   1020

gttccgccta ccggatcgcc gggtggtggc ctcccggctg acacggcggc acagctgacg   1080

tcggctgggc gggaagccgc agcgctgtcg ggcgacgtgg cggtcaaagc ggcatcgctc   1140

ggtggcggtg gaggcggcgg ggtgccgtcg gcgccgttgg gatccgcgat cgggggcgcc   1200

gaatcggtgc ggcccgctgg cgctggtgac attgccggct taggccaggg aagggccggc   1260

ggcggcgccg cgctgggcgg cggtggcatg ggaatgccga tgggtgccgc gcatcaggga   1320

caagggggcg ccaagtccaa gggttctcag caggaagacg aggcgctcta caccgaggat   1380

cgggcatgga ccgaggccgt cattggtaac cgtcggcgcc aggacagtaa ggagtcgaag   1440

tgaaagctt                                                           1449
```

<210> SEQ ID NO 180
<211> LENGTH: 480
<212> TYPE: PRT
<213> ORGANISM: Mycobacterium tuberculosis

<400> SEQUENCE: 180

```
Met Gly Ser Ser His His His His His His Ser Ser Gly Leu Val Pro
1               5                   10                  15

Arg Gly Ser His Met Thr Gln Ser Gln Thr Val Thr Val Asp Gln Gln
            20                  25                  30

Glu Ile Leu Asn Arg Ala Asn Glu Val Glu Ala Pro Met Ala Asp Pro
        35                  40                  45

Pro Thr Asp Val Pro Ile Thr Pro Cys Glu Leu Thr Ala Ala Lys Asn
    50                  55                  60

Ala Ala Gln Gln Leu Val Leu Ser Ala Asp Asn Met Arg Glu Tyr Leu
65                  70                  75                  80

Ala Ala Gly Ala Lys Glu Arg Gln Arg Leu Ala Thr Ser Leu Arg Asn
                85                  90                  95

Ala Ala Lys Ala Tyr Gly Glu Val Asp Glu Glu Ala Ala Thr Ala Leu
            100                 105                 110

Asp Asn Asp Gly Glu Gly Thr Val Gln Ala Glu Ser Ala Gly Ala Val
```

```
        115                 120                 125

Gly Gly Asp Ser Ser Ala Glu Leu Thr Asp Thr Pro Arg Val Ala Thr
    130                 135                 140

Ala Gly Glu Pro Asn Phe Met Asp Leu Lys Glu Ala Ala Arg Lys Leu
145                 150                 155                 160

Glu Thr Gly Asp Gln Gly Ala Ser Leu Ala His Phe Ala Asp Gly Trp
                165                 170                 175

Asn Thr Phe Asn Leu Thr Leu Gln Gly Asp Val Lys Arg Phe Arg Gly
            180                 185                 190

Phe Asp Asn Trp Glu Gly Asp Ala Ala Thr Ala Cys Glu Ala Ser Leu
        195                 200                 205

Asp Gln Gln Arg Gln Trp Ile Leu His Met Ala Lys Leu Ser Ala Ala
    210                 215                 220

Met Ala Lys Gln Ala Gln Tyr Val Ala Gln Leu His Val Trp Ala Arg
225                 230                 235                 240

Arg Glu His Pro Thr Tyr Glu Asp Ile Val Gly Leu Glu Arg Leu Tyr
                245                 250                 255

Ala Glu Asn Pro Ser Ala Arg Asp Gln Ile Leu Pro Val Tyr Ala Glu
            260                 265                 270

Tyr Gln Gln Arg Ser Glu Lys Val Leu Thr Glu Tyr Asn Asn Lys Ala
        275                 280                 285

Ala Leu Glu Pro Val Asn Pro Pro Lys Pro Pro Pro Ala Ile Lys Ile
    290                 295                 300

Asp Pro Pro Pro Pro Pro Gln Glu Gln Gly Leu Ile Pro Gly Phe Leu
305                 310                 315                 320

Met Pro Pro Ser Asp Gly Ser Gly Val Thr Pro Gly Thr Gly Met Pro
                325                 330                 335

Ala Ala Pro Met Val Pro Pro Thr Gly Ser Pro Gly Gly Gly Leu Pro
            340                 345                 350

Ala Asp Thr Ala Ala Gln Leu Thr Ser Ala Gly Arg Glu Ala Ala Ala
        355                 360                 365

Leu Ser Gly Asp Val Ala Val Lys Ala Ala Ser Leu Gly Gly Gly Gly
    370                 375                 380

Gly Gly Gly Val Pro Ser Ala Pro Leu Gly Ser Ala Ile Gly Gly Ala
385                 390                 395                 400

Glu Ser Val Arg Pro Ala Gly Ala Gly Asp Ile Ala Gly Leu Gly Gln
                405                 410                 415

Gly Arg Ala Gly Gly Gly Ala Ala Leu Gly Gly Gly Gly Met Gly Met
            420                 425                 430

Pro Met Gly Ala Ala His Gln Gly Gln Gly Gly Ala Lys Ser Lys Gly
        435                 440                 445

Ser Gln Gln Glu Asp Glu Ala Leu Tyr Thr Glu Asp Arg Ala Trp Thr
    450                 455                 460

Glu Ala Val Ile Gly Asn Arg Arg Arg Gln Asp Ser Lys Glu Ser Lys
465                 470                 475                 480


<210> SEQ ID NO 181
<211> LENGTH: 148
<212> TYPE: PRT
<213> ORGANISM: Mycobacterium tuberculosis

<400> SEQUENCE: 181

Met Ser Arg Leu Ser Ser Ile Leu Arg Ala Gly Ala Ala Phe Leu Val
1               5                   10                  15
```

```
Leu Gly Ile Ala Ala Ala Thr Phe Pro Gln Ser Ala Ala Ala Asp Ser
            20                  25                  30

Thr Glu Asp Phe Pro Ile Pro Arg Arg Met Ile Ala Thr Thr Cys Asp
        35                  40                  45

Ala Glu Gln Tyr Leu Ala Ala Val Arg Asp Thr Ser Pro Val Tyr Tyr
    50                  55                  60

Gln Arg Tyr Met Ile Asp Phe Asn Asn His Ala Asn Leu Gln Gln Ala
65                  70                  75                  80

Thr Ile Asn Lys Ala His Trp Phe Phe Ser Leu Ser Pro Ala Glu Arg
                85                  90                  95

Arg Asp Tyr Ser Glu His Phe Tyr Asn Gly Asp Pro Leu Thr Phe Ala
            100                 105                 110

Trp Val Asn His Met Lys Ile Phe Phe Asn Asn Lys Gly Val Val Ala
        115                 120                 125

Lys Gly Thr Glu Val Cys Asn Gly Tyr Pro Ala Gly Asp Met Ser Val
    130                 135                 140

Trp Asn Trp Ala
145


<210> SEQ ID NO 182
<211> LENGTH: 372
<212> TYPE: DNA
<213> ORGANISM: Mycobacterium tuberculosis

<400> SEQUENCE: 182

catatggccg actccacgga agactttcca atacctcgcc ggatgatcgc aaccacctgc      60

gacgccgaac aatatctggc ggcggtgcgg gataccagtc cggtgtacta ccagcggtac     120

atgatcgact tcaacaacca tgcaaacctt cagcaagcga cgatcaacaa ggcgcactgg     180

ttcttctcgc tgtcaccggc ggagcgccga gactactccg aacactttta caatggcgat     240

ccgctgacgt ttgcctgggt caatcacatg aaaatcttct tcaacaacaa gggcgtcgtc     300

gctaaaggga ccgaggtgtg caatggatac ccagccggcg acatgtcggt gtggaactgg     360

gcctaaaagc tt                                                         372


<210> SEQ ID NO 183
<211> LENGTH: 140
<212> TYPE: PRT
<213> ORGANISM: Mycobacterium tuberculosis

<400> SEQUENCE: 183

Met Gly Ser Ser His His His His His His Ser Ser Gly Leu Val Pro
1               5                   10                  15

Arg Gly Ser His Met Ala Asp Ser Thr Glu Asp Phe Pro Ile Pro Arg
            20                  25                  30

Arg Met Ile Ala Thr Thr Cys Asp Ala Glu Gln Tyr Leu Ala Ala Val
        35                  40                  45

Arg Asp Thr Ser Pro Val Tyr Tyr Gln Arg Tyr Met Ile Asp Phe Asn
    50                  55                  60

Asn His Ala Asn Leu Gln Gln Ala Thr Ile Asn Lys Ala His Trp Phe
65                  70                  75                  80

Phe Ser Leu Ser Pro Ala Glu Arg Arg Asp Tyr Ser Glu His Phe Tyr
                85                  90                  95

Asn Gly Asp Pro Leu Thr Phe Ala Trp Val Asn His Met Lys Ile Phe
            100                 105                 110

Phe Asn Asn Lys Gly Val Val Ala Lys Gly Thr Glu Val Cys Asn Gly
```

```
        115                 120                 125

Tyr Pro Ala Gly Asp Met Ser Val Trp Asn Trp Ala
    130                 135                 140


<210> SEQ ID NO 184
<211> LENGTH: 261
<212> TYPE: PRT
<213> ORGANISM: Mycobacterium tuberculosis

<400> SEQUENCE: 184

Met Pro Lys Arg Ser Glu Tyr Arg Gln Gly Thr Pro Asn Trp Val Asp
1               5                   10                  15

Leu Gln Thr Thr Asp Gln Ser Ala Ala Lys Lys Phe Tyr Thr Ser Leu
            20                  25                  30

Phe Gly Trp Gly Tyr Asp Asp Asn Pro Val Pro Gly Gly Gly Gly Val
        35                  40                  45

Tyr Ser Met Ala Thr Leu Asn Gly Glu Ala Val Ala Ala Ile Ala Pro
    50                  55                  60

Met Pro Pro Gly Ala Pro Glu Gly Met Pro Pro Ile Trp Asn Thr Tyr
65                  70                  75                  80

Ile Ala Val Asp Asp Val Asp Ala Val Val Asp Lys Val Val Pro Gly
                85                  90                  95

Gly Gly Gln Val Met Met Pro Ala Phe Asp Ile Gly Asp Ala Gly Arg
            100                 105                 110

Met Ser Phe Ile Thr Asp Pro Thr Gly Ala Ala Val Gly Leu Trp Gln
        115                 120                 125

Ala Asn Arg His Ile Gly Ala Thr Leu Val Asn Glu Thr Gly Thr Leu
    130                 135                 140

Ile Trp Asn Glu Leu Leu Thr Asp Lys Pro Asp Leu Ala Leu Ala Phe
145                 150                 155                 160

Tyr Glu Ala Val Val Gly Leu Thr His Ser Ser Met Glu Ile Ala Ala
                165                 170                 175

Gly Gln Asn Tyr Arg Val Leu Lys Ala Gly Asp Ala Glu Val Gly Gly
            180                 185                 190

Cys Met Glu Pro Pro Met Pro Gly Val Pro Asn His Trp His Val Tyr
        195                 200                 205

Phe Ala Val Asp Asp Ala Asp Ala Thr Ala Ala Lys Ala Ala Ala Ala
    210                 215                 220

Gly Gly Gln Val Ile Ala Glu Pro Ala Asp Ile Pro Ser Val Gly Arg
225                 230                 235                 240

Phe Ala Val Leu Ser Asp Pro Gln Gly Ala Ile Phe Ser Val Leu Lys
                245                 250                 255

Pro Ala Pro Gln Gln
            260


<210> SEQ ID NO 185
<211> LENGTH: 853
<212> TYPE: DNA
<213> ORGANISM: Mycobacterium tuberculosis

<400> SEQUENCE: 185

atgggcagca gccatcatca tcatcatcac agcagcggcc tggtgccgcg cggcagccat      60

atgcccaaga gaagcgaata caggcaaggc acgccgaact gggtcgacct tcagaccacc     120

gatcagtccg ccgccaaaaa gttctacaca tcgttgttcg gctggggtta cgacgacaac     180

ccggtccccg gaggcggtgg ggtctattcc atggccacgc tgaacggcga agccgtggcc     240
```

```
gccatcgcac cgatgccccc gggtgcaccg gaggggatgc cgccgatctg gaacacctat    300

atcgcggtgg acgacgtcga tgcggtggtg gacaaggtgg tgcccggggg cgggcaggtg    360

atgatgccgg ccttcgacat cggcgatgcc ggccggatgt cgttcatcac cgatccgacc    420

ggcgctgccg tgggcctatg gcaggccaat cggcacatcg gagcgacgtt ggtcaacgag    480

acgggcacgc tcatctggaa cgaactgctc acggacaagc cggatttggc gctagcgttc    540

tacgaggctg tggttggcct cacccactcg agcatggaga tagctgcggg ccagaactat    600

cgggtgctca aggccggcga cgcggaagtc ggcggctgta tggaaccgcc gatgcccggc    660

gtgccgaatc attggcacgt ctactttgcg gtggatgacg ccgacgccac ggcggccaaa    720

gccgccgcag cgggcggcca ggtcattgcg gaaccggctg acattccgtc ggtgggccgg    780

ttcgccgtgt tgtccgatcc gcagggcgcg atcttcagtg tgttgaagcc cgcaccgcag    840

caataggaag ctt                                                       853
```

```
<210> SEQ ID NO 186
<211> LENGTH: 281
<212> TYPE: PRT
<213> ORGANISM: Mycobacterium tuberculosis

<400> SEQUENCE: 186

Met Gly Ser Ser His His His His His His Ser Ser Gly Leu Val Pro
1               5                   10                  15

Arg Gly Ser His Met Pro Lys Arg Ser Glu Tyr Arg Gln Gly Thr Pro
            20                  25                  30

Asn Trp Val Asp Leu Gln Thr Thr Asp Gln Ser Ala Ala Lys Lys Phe
        35                  40                  45

Tyr Thr Ser Leu Phe Gly Trp Gly Tyr Asp Asp Asn Pro Val Pro Gly
    50                  55                  60

Gly Gly Gly Val Tyr Ser Met Ala Thr Leu Asn Gly Glu Ala Val Ala
65                  70                  75                  80

Ala Ile Ala Pro Met Pro Pro Gly Ala Pro Glu Gly Met Pro Pro Ile
                85                  90                  95

Trp Asn Thr Tyr Ile Ala Val Asp Asp Val Asp Ala Val Val Asp Lys
            100                 105                 110

Val Val Pro Gly Gly Gly Gln Val Met Met Pro Ala Phe Asp Ile Gly
        115                 120                 125

Asp Ala Gly Arg Met Ser Phe Ile Thr Asp Pro Thr Gly Ala Ala Val
    130                 135                 140

Gly Leu Trp Gln Ala Asn Arg His Ile Gly Ala Thr Leu Val Asn Glu
145                 150                 155                 160

Thr Gly Thr Leu Ile Trp Asn Glu Leu Leu Thr Asp Lys Pro Asp Leu
                165                 170                 175

Ala Leu Ala Phe Tyr Glu Ala Val Val Gly Leu Thr His Ser Ser Met
            180                 185                 190

Glu Ile Ala Ala Gly Gln Asn Tyr Arg Val Leu Lys Ala Gly Asp Ala
        195                 200                 205

Glu Val Gly Gly Cys Met Glu Pro Pro Met Pro Gly Val Pro Asn His
    210                 215                 220

Trp His Val Tyr Phe Ala Val Asp Asp Ala Asp Ala Thr Ala Ala Lys
225                 230                 235                 240

Ala Ala Ala Ala Gly Gly Gln Val Ile Ala Glu Pro Ala Asp Ile Pro
                245                 250                 255
```

```
Ser Val Gly Arg Phe Ala Val Leu Ser Asp Pro Gln Gly Ala Ile Phe
            260                 265                 270

Ser Val Leu Lys Pro Ala Pro Gln Gln
        275                 280


<210> SEQ ID NO 187
<211> LENGTH: 205
<212> TYPE: PRT
<213> ORGANISM: Mycobacterium tuberculosis

<400> SEQUENCE: 187

Met Thr Gly Pro Thr Thr Asp Ala Asp Ala Ala Val Pro Arg Arg Val
1               5                   10                  15

Leu Ile Ala Glu Asp Glu Ala Leu Ile Arg Met Asp Leu Ala Glu Met
            20                  25                  30

Leu Arg Glu Glu Gly Tyr Glu Ile Val Gly Glu Ala Gly Asp Gly Gln
        35                  40                  45

Glu Ala Val Glu Leu Ala Glu Leu His Lys Pro Asp Leu Val Ile Met
    50                  55                  60

Asp Val Lys Met Pro Arg Arg Asp Gly Ile Asp Ala Ala Ser Glu Ile
65                  70                  75                  80

Ala Ser Lys Arg Ile Ala Pro Ile Val Val Leu Thr Ala Phe Ser Gln
                85                  90                  95

Arg Asp Leu Val Glu Arg Ala Arg Asp Ala Gly Ala Met Ala Tyr Leu
            100                 105                 110

Val Lys Pro Phe Ser Ile Ser Asp Leu Ile Pro Ala Ile Glu Leu Ala
        115                 120                 125

Val Ser Arg Phe Arg Glu Ile Thr Ala Leu Glu Gly Glu Val Ala Thr
    130                 135                 140

Leu Ser Glu Arg Leu Glu Thr Arg Lys Leu Val Glu Arg Ala Lys Gly
145                 150                 155                 160

Leu Leu Gln Thr Lys His Gly Met Thr Glu Pro Asp Ala Phe Lys Trp
                165                 170                 175

Ile Gln Arg Ala Ala Met Asp Arg Arg Thr Thr Met Lys Arg Val Ala
            180                 185                 190

Glu Val Val Leu Glu Thr Leu Gly Thr Pro Lys Asp Thr
        195                 200                 205


<210> SEQ ID NO 188
<211> LENGTH: 684
<212> TYPE: DNA
<213> ORGANISM: Mycobacterium tuberculosis

<400> SEQUENCE: 188

atgggcagca gccatcatca tcatcatcac agcagcggcc tggtgccgcg cggcagccat      60

atgaccggcc ccaccaccga cgccgatgcc gctgtcccac gtcgggtctt gatcgcggaa     120

gatgaagcgc tcatccgcat ggacctggcc gagatgttgc gagaggaggg atatgaaatt     180

gtcggcgagg ccggcgacgg ccaggaagcc gtcgagctgg ccgagctgca caagcccgac     240

ctggtgatca tggacgtgaa gatgccgcgc cgggacggga tcgacgccgc atccgaaatc     300

gccagcaaac gtattgcccc gatcgtggtg ctgaccgcgt tcagccagcg tgatctggtc     360

gaacgtgcgc gtgatgccgg ggcgatggca tacctggtaa agcctttcag catcagcgac     420

ctgattccag cgattgaatt ggcggtcagc cggttcaggg agatcaccgc gttggaaggc     480

gaggtggcga cgctatctga acggttggaa acccgcaagc tggtggaacg agcaaaaggc     540
```

-continued

```
ctgctgcaga ccaaacatgg gatgaccgag ccggacgctt tcaagtggat tcaacgtgcc    600

gccatggatc ggcgcaccac catgaagcgg gtggccgaag tcgtgctgga aaccctcgga    660

acacccaaag acacctgaaa gctt                                           684
```

<210> SEQ ID NO 189
<211> LENGTH: 225
<212> TYPE: PRT
<213> ORGANISM: Mycobacterium tuberculosis

<400> SEQUENCE: 189

```
Met Gly Ser Ser His His His His His His Ser Ser Gly Leu Val Pro
1               5                   10                  15

Arg Gly Ser His Met Thr Gly Pro Thr Thr Asp Ala Asp Ala Ala Val
            20                  25                  30

Pro Arg Arg Val Leu Ile Ala Glu Asp Glu Ala Leu Ile Arg Met Asp
        35                  40                  45

Leu Ala Glu Met Leu Arg Glu Glu Gly Tyr Glu Ile Val Gly Glu Ala
    50                  55                  60

Gly Asp Gly Gln Glu Ala Val Glu Leu Ala Glu Leu His Lys Pro Asp
65                  70                  75                  80

Leu Val Ile Met Asp Val Lys Met Pro Arg Arg Asp Gly Ile Asp Ala
                85                  90                  95

Ala Ser Glu Ile Ala Ser Lys Arg Ile Ala Pro Ile Val Val Leu Thr
            100                 105                 110

Ala Phe Ser Gln Arg Asp Leu Val Glu Arg Ala Arg Asp Ala Gly Ala
        115                 120                 125

Met Ala Tyr Leu Val Lys Pro Phe Ser Ile Ser Asp Leu Ile Pro Ala
    130                 135                 140

Ile Glu Leu Ala Val Ser Arg Phe Arg Glu Ile Thr Ala Leu Glu Gly
145                 150                 155                 160

Glu Val Ala Thr Leu Ser Glu Arg Leu Glu Thr Arg Lys Leu Val Glu
                165                 170                 175

Arg Ala Lys Gly Leu Leu Gln Thr Lys His Gly Met Thr Glu Pro Asp
            180                 185                 190

Ala Phe Lys Trp Ile Gln Arg Ala Ala Met Asp Arg Arg Thr Thr Met
        195                 200                 205

Lys Arg Val Ala Glu Val Val Leu Glu Thr Leu Gly Thr Pro Lys Asp
    210                 215                 220

Thr
225
```

<210> SEQ ID NO 190
<211> LENGTH: 181
<212> TYPE: PRT
<213> ORGANISM: Mycobacterium tuberculosis

<400> SEQUENCE: 190

```
Met Arg Val Leu Leu Leu Gly Pro Pro Gly Ala Gly Lys Gly Thr Gln
1               5                   10                  15

Ala Val Lys Leu Ala Glu Lys Leu Gly Ile Pro Gln Ile Ser Thr Gly
            20                  25                  30

Glu Leu Phe Arg Arg Asn Ile Glu Glu Gly Thr Lys Leu Gly Val Glu
        35                  40                  45

Ala Lys Arg Tyr Leu Asp Ala Gly Asp Leu Val Pro Ser Asp Leu Thr
    50                  55                  60
```

-continued

```
Asn Glu Leu Val Asp Asp Arg Leu Asn Asn Pro Asp Ala Ala Asn Gly
65                  70                  75                  80

Phe Ile Leu Asp Gly Tyr Pro Arg Ser Val Glu Gln Ala Lys Ala Leu
                85                  90                  95

His Glu Met Leu Glu Arg Arg Gly Thr Asp Ile Asp Ala Val Leu Glu
            100                 105                 110

Phe Arg Val Ser Glu Glu Val Leu Leu Glu Arg Leu Lys Gly Arg Gly
        115                 120                 125

Arg Ala Asp Asp Thr Asp Asp Val Ile Leu Asn Arg Met Lys Val Tyr
    130                 135                 140

Arg Asp Glu Thr Ala Pro Leu Leu Glu Tyr Tyr Arg Asp Gln Leu Lys
145                 150                 155                 160

Thr Val Asp Ala Val Gly Thr Met Asp Glu Val Phe Ala Arg Ala Leu
                165                 170                 175

Arg Ala Leu Gly Lys
            180
```

<210> SEQ ID NO 191
<211> LENGTH: 613
<212> TYPE: DNA
<213> ORGANISM: Mycobacterium tuberculosis

<400> SEQUENCE: 191

```
atgggcagca gccatcatca tcatcatcac agcagcggcc tggtgccgcg cggcagccat      60

atgagagttt tgttgctggg accgcccggg gcgggcaagg ggacgcaggc ggtgaagctg     120

gccgagaagc tcgggatccc gcagatctcc accggcgaac tcttccggcg caacatcgaa     180

gagggcacca agctcggcgt ggaagccaaa cgctacttgg atgccggtga cttggtgccg     240

tccgacttga ccaatgaact cgtcgacgac cggctgaaca atccggacgc ggccaacgga     300

ttcatcttgg atggctatcc acgctcggtc gagcaggcca aggcgcttca cgagatgctc     360

gaacgccggg ggaccgacat cgacgcggtg ctggagtttc gtgtgtccga ggaggtgttg     420

ttggagcgac tcaaggggcg tggccgcgcc gacgacaccg acgacgtcat cctcaaccgg     480

atgaaggtct accgcgacga gaccgcgccg ctgctggagt actaccgcga ccaattgaag     540

accgtcgacg ccgtcggcac catggacgag gtgttcgccc gtgcgttgcg ggctctggga     600

aagttagaag ctt                                                        613
```

<210> SEQ ID NO 192
<211> LENGTH: 201
<212> TYPE: PRT
<213> ORGANISM: Mycobacterium tuberculosis

<400> SEQUENCE: 192

```
Met Gly Ser Ser His His His His His His Ser Ser Gly Leu Val Pro
1               5                   10                  15

Arg Gly Ser His Met Arg Val Leu Leu Leu Gly Pro Pro Gly Ala Gly
            20                  25                  30

Lys Gly Thr Gln Ala Val Lys Leu Ala Glu Lys Leu Gly Ile Pro Gln
        35                  40                  45

Ile Ser Thr Gly Glu Leu Phe Arg Arg Asn Ile Glu Glu Gly Thr Lys
    50                  55                  60

Leu Gly Val Glu Ala Lys Arg Tyr Leu Asp Ala Gly Asp Leu Val Pro
65                  70                  75                  80

Ser Asp Leu Thr Asn Glu Leu Val Asp Asp Arg Leu Asn Asn Pro Asp
                85                  90                  95
```

```
Ala Ala Asn Gly Phe Ile Leu Asp Gly Tyr Pro Arg Ser Val Glu Gln
            100                 105                 110

Ala Lys Ala Leu His Glu Met Leu Glu Arg Arg Gly Thr Asp Ile Asp
        115                 120                 125

Ala Val Leu Glu Phe Arg Val Ser Glu Glu Val Leu Leu Glu Arg Leu
    130                 135                 140

Lys Gly Arg Gly Arg Ala Asp Asp Thr Asp Asp Val Ile Leu Asn Arg
145                 150                 155                 160

Met Lys Val Tyr Arg Asp Glu Thr Ala Pro Leu Leu Glu Tyr Tyr Arg
                165                 170                 175

Asp Gln Leu Lys Thr Val Asp Ala Val Gly Thr Met Asp Glu Val Phe
            180                 185                 190

Ala Arg Ala Leu Arg Ala Leu Gly Lys
        195                 200


<210> SEQ ID NO 193
<211> LENGTH: 75
<212> TYPE: PRT
<213> ORGANISM: Mycobacterium tuberculosis

<400> SEQUENCE: 193

Met Val Asp Arg Asp Pro Asn Thr Ile Lys Gln Glu Ile Asp Gln Thr
1               5                   10                  15

Arg Asp Gln Leu Ala Ala Thr Ile Asp Ser Leu Ala Glu Arg Ala Asn
            20                  25                  30

Pro Arg Arg Leu Ala Asp Asp Ala Lys Thr Arg Val Ile Ala Phe Leu
        35                  40                  45

Arg Lys Pro Ile Val Thr Val Ser Leu Val Gly Ile Gly Ser Val Val
    50                  55                  60

Val Val Val Val Ile His Lys Ile Arg Asn Arg
65                  70                  75


<210> SEQ ID NO 194
<211> LENGTH: 258
<212> TYPE: DNA
<213> ORGANISM: Mycobacterium tuberculosis

<400> SEQUENCE: 194

catatgcatc accatcacca tcacgtggtg gaccgcgatc ccaataccat caagcaggag      60

atcgaccaaa cccgcgacca actggcggcg accatcgatt ccctcgccga gcgcgccaac     120

ccccgccgcc tcgccgacga cgcaaaaact cgggtgatcg ccttcctcag gaagcccatc     180

gtgaccgtgt cactggtcgg gatcgggtct gtggtcgtcg tcgtggtcat ccacaagatc     240

aggaatcgct gagaattc                                                   258


<210> SEQ ID NO 195
<211> LENGTH: 82
<212> TYPE: PRT
<213> ORGANISM: Mycobacterium tuberculosis

<400> SEQUENCE: 195

Met His His His His His His Val Val Asp Arg Asp Pro Asn Thr Ile
1               5                   10                  15

Lys Gln Glu Ile Asp Gln Thr Arg Asp Gln Leu Ala Ala Thr Ile Asp
            20                  25                  30

Ser Leu Ala Glu Arg Ala Asn Pro Arg Arg Leu Ala Asp Asp Ala Lys
        35                  40                  45
```

Thr Arg Val Ile Ala Phe Leu Arg Lys Pro Ile Val Thr Val Ser Leu
    50              55              60

Val Gly Ile Gly Ser Val Val Val Val Val Val Ile His Lys Ile Arg
65              70              75              80

Asn Arg

<210> SEQ ID NO 196
<211> LENGTH: 563
<212> TYPE: PRT
<213> ORGANISM: Mycobacterium tuberculosis

<400> SEQUENCE: 196

Met Ala Phe Pro Glu Tyr Ser Pro Ala Ala Ser Ala Ala Thr Phe Ala
1               5               10              15

Asp Leu Gln Ile His Pro Arg Val Leu Arg Ala Ile Gly Asp Val Gly
            20              25              30

Tyr Glu Ser Pro Thr Ala Ile Gln Ala Ala Thr Ile Pro Ala Leu Met
        35              40              45

Ala Gly Ser Asp Val Val Gly Leu Ala Gln Thr Gly Thr Gly Lys Thr
    50              55              60

Ala Ala Phe Ala Ile Pro Met Leu Ser Lys Ile Asp Ile Thr Ser Lys
65              70              75              80

Val Pro Gln Ala Leu Val Leu Val Pro Thr Arg Glu Leu Ala Leu Gln
                85              90              95

Val Ala Glu Ala Phe Gly Arg Tyr Gly Ala Tyr Leu Ser Gln Leu Asn
            100             105             110

Val Leu Pro Ile Tyr Gly Gly Ser Ser Tyr Ala Val Gln Leu Ala Gly
        115             120             125

Leu Arg Arg Gly Ala Gln Val Val Val Gly Thr Pro Gly Arg Met Ile
    130             135             140

Asp His Leu Glu Arg Ala Thr Leu Asp Leu Ser Arg Val Asp Phe Leu
145             150             155             160

Val Leu Asp Glu Ala Asp Glu Met Leu Thr Met Gly Phe Ala Asp Asp
                165             170             175

Val Glu Arg Ile Leu Ser Glu Thr Pro Glu Tyr Lys Gln Val Ala Leu
            180             185             190

Phe Ser Ala Thr Met Pro Pro Ala Ile Arg Lys Leu Ser Ala Lys Tyr
        195             200             205

Leu His Asp Pro Phe Glu Val Thr Cys Lys Ala Lys Thr Ala Val Ala
    210             215             220

Glu Asn Ile Ser Gln Ser Tyr Ile Gln Val Ala Arg Lys Met Asp Ala
225             230             235             240

Leu Thr Arg Val Leu Glu Val Glu Pro Phe Glu Ala Met Ile Val Phe
                245             250             255

Val Arg Thr Lys Gln Ala Thr Glu Glu Ile Ala Glu Lys Leu Arg Ala
            260             265             270

Arg Gly Phe Ser Ala Ala Ala Ile Ser Gly Asp Val Pro Gln Ala Gln
        275             280             285

Arg Glu Arg Thr Ile Thr Ala Leu Arg Asp Gly Asp Ile Asp Ile Leu
    290             295             300

Val Ala Thr Asp Val Ala Ala Arg Gly Leu Asp Val Glu Arg Ile Ser
305             310             315             320

His Val Leu Asn Tyr Asp Ile Pro His Asp Thr Glu Ser Tyr Val His
                325             330             335

```
Arg Ile Gly Arg Thr Gly Arg Ala Gly Arg Ser Gly Ala Ala Leu Ile
            340                 345                 350

Phe Val Ser Pro Arg Glu Leu His Leu Leu Lys Ala Ile Glu Lys Ala
        355                 360                 365

Thr Arg Gln Thr Leu Thr Glu Ala Gln Leu Pro Thr Val Glu Asp Val
    370                 375                 380

Asn Thr Gln Arg Val Ala Lys Phe Ala Asp Ser Ile Thr Asn Ala Leu
385                 390                 395                 400

Gly Gly Pro Gly Ile Glu Leu Phe Arg Arg Leu Val Glu Glu Tyr Glu
                405                 410                 415

Arg Glu His Asp Val Pro Met Ala Asp Ile Ala Ala Ala Leu Ala Val
            420                 425                 430

Gln Cys Arg Gly Gly Glu Ala Phe Leu Met Ala Pro Asp Pro Pro Leu
        435                 440                 445

Ser Arg Arg Asn Arg Asp Gln Arg Arg Asp Arg Pro Gln Arg Pro Lys
    450                 455                 460

Arg Arg Pro Asp Leu Thr Thr Tyr Arg Val Ala Val Gly Lys Arg His
465                 470                 475                 480

Lys Ile Gly Pro Gly Ala Ile Val Gly Ala Ile Ala Asn Glu Gly Gly
                485                 490                 495

Leu His Arg Ser Asp Phe Gly Gln Ile Arg Ile Gly Pro Asp Phe Ser
            500                 505                 510

Leu Val Glu Leu Pro Ala Lys Leu Pro Arg Ala Thr Leu Lys Lys Leu
        515                 520                 525

Ala Gln Thr Arg Ile Ser Gly Val Leu Ile Asp Leu Arg Pro Tyr Arg
    530                 535                 540

Pro Pro Asp Ala Ala Arg Arg His Asn Gly Gly Lys Pro Arg Arg Lys
545                 550                 555                 560

His Val Gly
```

<210> SEQ ID NO 197
<211> LENGTH: 1758
<212> TYPE: DNA
<213> ORGANISM: Mycobacterium tuberculosis

<400> SEQUENCE: 197

```
atgggcagca gccatcatca tcatcatcac agcagcggcc tggtgccgcg cggcagccat     60

atggccttcc cggaatattc gcctgcggcg tccgctgcga cgtttgctga cctgcagatt    120

catccccgcg tcttgcgggc gatcggcgac gtcggttacg agtcaccgac ggctatccag    180

gcggctacga tcccggcgtt gatggcaggc tccgacgtgg tggggctggc gcagaccggc    240

accggcaaga cggcggcatt tgcgattccg atgctgtcca agatcgacat caccagcaag    300

gtgccccagg cgctggtgct ggtgcccacc cgggagctgg ctctgcaggt ggccgaggcg    360

ttcggccgct acggtgccta tctgtcgcaa ctcaacgtgc tgccgatcta cggcggatcg    420

tcgtatgccg tgcaactggc cggattgaga cgcggcgcgc aggtggtggt tggcaccccc    480

ggtcgtatga tagaccatct cgaacgggcg accttggacc tgtcgcgggt ggactttcta    540

gtgctcgatg aggccgatga gatgctgacc atgggtttcg ccgacgacgt tgagcgcatt    600

ctgtccgaga cccccgaata caagcaggtc gccctgtttt ccgcgaccat gccgccggcg    660

atccgcaaac tcagcgccaa gtatctgcac gatccgttcg aagtcacttg taaggcgaaa    720

accgctgtgg ccgagaatat ttcgcagagc tacattcagg tagcacggaa gatggacgcg    780
```

```
ctcaccagag tgctcgaagt cgagccgttc gaggcgatga tcgtctttgt ccgcaccaag    840

caggcgaccg aggagattgc cgaaaagctg cgtgcccgag ggttttccgc ggctgccatc    900

agcggtgacg tcccgcaggc gcagcgggag cggaccatca cggcgctgcg ggacggcgac    960

atcgatatcc tggtcgccac cgatgtggcg gcgcgcggac tcgacgtgga gcggatatca   1020

cacgtgctta actacgacat cccgcacgac accgagtcct acgtacaccg gatcgggcgc   1080

accggcaggg ccgggcgttc gggagccgcg ctgatattcg tctcgccacg ggagcttcac   1140

ctgctcaagg cgatcgaaaa ggctacgcgg caaacgctta ccgaggcgca attgcccacc   1200

gtcgaggatg tcaacaccca gcgggtggcc aagttcgccg attccatcac caatgcgctg   1260

ggcggtccgg gaatcgagct gttccgccga ctggtcgagg agtatgaacg cgagcatgat   1320

gtcccgatgg ctgacatcgc cgcggcactg gccgtgcagt gccgcggcgg tgaggcattc   1380

ctgatggcac ccgacccgcc gctttcgcgg cgcaaccgcg accagcgtcg ggaccgtccg   1440

caaaggccca agcgtagacc ggacttgacc acctaccgcg tcgccgtcgg caagcggcac   1500

aagatcggtc caggcgccat cgtcggcgcc atcgccaatg agggtgggct gcaccgcagc   1560

gacttcggtc agatccgtat cgggccagac ttctcgctag tagaattgcc ggcgaagctg   1620

ccccgcgcga cgctcaaaaa gcttgcacag acccgtatct cgggtgtgct gatcgacctt   1680

cggccatacc ggccgcccga cgcggcgcgc cggcataatg gcggcaaacc acggcggaaa   1740

cacgtcggat gagaattc                                                 1758


<210> SEQ ID NO 198
<211> LENGTH: 583
<212> TYPE: PRT
<213> ORGANISM: Mycobacterium tuberculosis

<400> SEQUENCE: 198

Met Gly Ser Ser His His His His His His Ser Ser Gly Leu Val Pro
1               5                   10                  15

Arg Gly Ser His Met Ala Phe Pro Glu Tyr Ser Pro Ala Ala Ser Ala
            20                  25                  30

Ala Thr Phe Ala Asp Leu Gln Ile His Pro Arg Val Leu Arg Ala Ile
        35                  40                  45

Gly Asp Val Gly Tyr Glu Ser Pro Thr Ala Ile Gln Ala Ala Thr Ile
    50                  55                  60

Pro Ala Leu Met Ala Gly Ser Asp Val Val Gly Leu Ala Gln Thr Gly
65                  70                  75                  80

Thr Gly Lys Thr Ala Ala Phe Ala Ile Pro Met Leu Ser Lys Ile Asp
                85                  90                  95

Ile Thr Ser Lys Val Pro Gln Ala Leu Val Leu Val Pro Thr Arg Glu
            100                 105                 110

Leu Ala Leu Gln Val Ala Glu Ala Phe Gly Arg Tyr Gly Ala Tyr Leu
        115                 120                 125

Ser Gln Leu Asn Val Leu Pro Ile Tyr Gly Gly Ser Ser Tyr Ala Val
    130                 135                 140

Gln Leu Ala Gly Leu Arg Arg Gly Ala Gln Val Val Val Gly Thr Pro
145                 150                 155                 160

Gly Arg Met Ile Asp His Leu Glu Arg Ala Thr Leu Asp Leu Ser Arg
                165                 170                 175

Val Asp Phe Leu Val Leu Asp Glu Ala Asp Glu Met Leu Thr Met Gly
            180                 185                 190

Phe Ala Asp Asp Val Glu Arg Ile Leu Ser Glu Thr Pro Glu Tyr Lys
```

-continued

```
        195                 200                 205

Gln Val Ala Leu Phe Ser Ala Thr Met Pro Pro Ala Ile Arg Lys Leu
    210                 215                 220

Ser Ala Lys Tyr Leu His Asp Pro Phe Glu Val Thr Cys Lys Ala Lys
225                 230                 235                 240

Thr Ala Val Ala Glu Asn Ile Ser Gln Ser Tyr Ile Gln Val Ala Arg
                245                 250                 255

Lys Met Asp Ala Leu Thr Arg Val Leu Glu Val Glu Pro Phe Glu Ala
            260                 265                 270

Met Ile Val Phe Val Arg Thr Lys Gln Ala Thr Glu Glu Ile Ala Glu
        275                 280                 285

Lys Leu Arg Ala Arg Gly Phe Ser Ala Ala Ala Ile Ser Gly Asp Val
    290                 295                 300

Pro Gln Ala Gln Arg Glu Arg Thr Ile Thr Ala Leu Arg Asp Gly Asp
305                 310                 315                 320

Ile Asp Ile Leu Val Ala Thr Asp Val Ala Ala Arg Gly Leu Asp Val
                325                 330                 335

Glu Arg Ile Ser His Val Leu Asn Tyr Asp Ile Pro His Asp Thr Glu
            340                 345                 350

Ser Tyr Val His Arg Ile Gly Arg Thr Gly Arg Ala Gly Arg Ser Gly
        355                 360                 365

Ala Ala Leu Ile Phe Val Ser Pro Arg Glu Leu His Leu Leu Lys Ala
    370                 375                 380

Ile Glu Lys Ala Thr Arg Gln Thr Leu Thr Glu Ala Gln Leu Pro Thr
385                 390                 395                 400

Val Glu Asp Val Asn Thr Gln Arg Val Ala Lys Phe Ala Asp Ser Ile
                405                 410                 415

Thr Asn Ala Leu Gly Gly Pro Gly Ile Glu Leu Phe Arg Arg Leu Val
            420                 425                 430

Glu Glu Tyr Glu Arg Glu His Asp Val Pro Met Ala Asp Ile Ala Ala
        435                 440                 445

Ala Leu Ala Val Gln Cys Arg Gly Gly Glu Ala Phe Leu Met Ala Pro
    450                 455                 460

Asp Pro Pro Leu Ser Arg Arg Asn Arg Asp Gln Arg Arg Asp Arg Pro
465                 470                 475                 480

Gln Arg Pro Lys Arg Arg Pro Asp Leu Thr Thr Tyr Arg Val Ala Val
                485                 490                 495

Gly Lys Arg His Lys Ile Gly Pro Gly Ala Ile Val Gly Ala Ile Ala
            500                 505                 510

Asn Glu Gly Gly Leu His Arg Ser Asp Phe Gly Gln Ile Arg Ile Gly
        515                 520                 525

Pro Asp Phe Ser Leu Val Glu Leu Pro Ala Lys Leu Pro Arg Ala Thr
    530                 535                 540

Leu Lys Lys Leu Ala Gln Thr Arg Ile Ser Gly Val Leu Ile Asp Leu
545                 550                 555                 560

Arg Pro Tyr Arg Pro Pro Asp Ala Ala Arg Arg His Asn Gly Gly Lys
                565                 570                 575

Pro Arg Arg Lys His Val Gly
            580
```

<210> SEQ ID NO 199
<211> LENGTH: 228
<212> TYPE: PRT
<213> ORGANISM: Mycobacterium tuberculosis

<400> SEQUENCE: 199

Met Arg Ile Lys Ile Phe Met Leu Val Thr Ala Val Val Leu Leu Cys
1 5 10 15

Cys Ser Gly Val Ala Thr Ala Ala Pro Lys Thr Tyr Cys Glu Glu Leu
20 25 30

Lys Gly Thr Asp Thr Gly Gln Ala Cys Gln Ile Gln Met Ser Asp Pro
35 40 45

Ala Tyr Asn Ile Asn Ile Ser Leu Pro Ser Tyr Tyr Pro Asp Gln Lys
50 55 60

Ser Leu Glu Asn Tyr Ile Ala Gln Thr Arg Asp Lys Phe Leu Ser Ala
65 70 75 80

Ala Thr Ser Ser Thr Pro Arg Glu Ala Pro Tyr Glu Leu Asn Ile Thr
85 90 95

Ser Ala Thr Tyr Gln Ser Ala Ile Pro Pro Arg Gly Thr Gln Ala Val
100 105 110

Val Leu Lys Val Tyr Gln Asn Ala Gly Gly Thr His Pro Thr Thr Thr
115 120 125

Tyr Lys Ala Phe Asp Trp Asp Gln Ala Tyr Arg Lys Pro Ile Thr Tyr
130 135 140

Asp Thr Leu Trp Gln Ala Asp Thr Asp Pro Leu Pro Val Val Phe Pro
145 150 155 160

Ile Val Gln Gly Glu Leu Ser Lys Gln Thr Gly Gln Gln Val Ser Ile
165 170 175

Ala Pro Asn Ala Gly Leu Asp Pro Val Asn Tyr Gln Asn Phe Ala Val
180 185 190

Thr Asn Asp Gly Val Ile Phe Phe Phe Asn Pro Gly Glu Leu Leu Pro
195 200 205

Glu Ala Ala Gly Pro Thr Gln Val Leu Val Pro Arg Ser Ala Ile Asp
210 215 220

Ser Met Leu Ala
225

<210> SEQ ID NO 200
<211> LENGTH: 687
<212> TYPE: DNA
<213> ORGANISM: Mycobacterium tuberculosis

<400> SEQUENCE: 200
atgggcagca gccatcatca tcatcatcac agcagcggcc tggtgccgcg cggcagccat 60
atggcgccca agacctactg cgaggagttg aaaggcaccg ataccggcca ggcgtgccag 120
attcaaatgt ccgacccggc ctacaacatc aacatcagcc tgcccagtta ctaccccgac 180
cagaagtcgc tggaaaatta catcgcccag acgcgcgaca agttcctcag cgcggccaca 240
tcgtccactc cacgcgaagc cccctacgaa ttgaatatca cctcggccac ataccagtcc 300
gcgataccgc cgcgtggtac gcaggccgtg gtgctcaagg tctaccagaa cgccggcggc 360
acgcacccaa cgaccacgta caaggccttc gattgggacc aggcctatcg caagccaatc 420
acctatgaca cgctgtggca ggctgacacc gatccgctgc cagtcgtctt ccccattgtg 480
caaggtgaac tgagcaagca gaccggacaa caggtatcga tagcgccgaa tgccggcttg 540
gacccggtga attatcagaa cttcgcagtc acgaacgacg gggtgatttt cttcttcaac 600
ccgggggagt tgctgcccga agcagccggc ccaacccagg tattggtccc acgttccgcg 660
atcgactcga tgctggccta gaagctt 687

<210> SEQ ID NO 201
<211> LENGTH: 226
<212> TYPE: PRT
<213> ORGANISM: Mycobacterium tuberculosis

<400> SEQUENCE: 201

```
Met Gly Ser Ser His His His His His His Ser Ser Gly Leu Val Pro
1               5                   10                  15

Arg Gly Ser His Met Ala Pro Lys Thr Tyr Cys Glu Glu Leu Lys Gly
            20                  25                  30

Thr Asp Thr Gly Gln Ala Cys Gln Ile Gln Met Ser Asp Pro Ala Tyr
        35                  40                  45

Asn Ile Asn Ile Ser Leu Pro Ser Tyr Tyr Pro Asp Gln Lys Ser Leu
    50                  55                  60

Glu Asn Tyr Ile Ala Gln Thr Arg Asp Lys Phe Leu Ser Ala Ala Thr
65                  70                  75                  80

Ser Ser Thr Pro Arg Glu Ala Pro Tyr Glu Leu Asn Ile Thr Ser Ala
                85                  90                  95

Thr Tyr Gln Ser Ala Ile Pro Pro Arg Gly Thr Gln Ala Val Val Leu
            100                 105                 110

Lys Val Tyr Gln Asn Ala Gly Gly Thr His Pro Thr Thr Thr Tyr Lys
        115                 120                 125

Ala Phe Asp Trp Asp Gln Ala Tyr Arg Lys Pro Ile Thr Tyr Asp Thr
    130                 135                 140

Leu Trp Gln Ala Asp Thr Asp Pro Leu Pro Val Val Phe Pro Ile Val
145                 150                 155                 160

Gln Gly Glu Leu Ser Lys Gln Thr Gly Gln Gln Val Ser Ile Ala Pro
                165                 170                 175

Asn Ala Gly Leu Asp Pro Val Asn Tyr Gln Asn Phe Ala Val Thr Asn
            180                 185                 190

Asp Gly Val Ile Phe Phe Phe Asn Pro Gly Glu Leu Leu Pro Glu Ala
        195                 200                 205

Ala Gly Pro Thr Gln Val Leu Val Pro Arg Ser Ala Ile Asp Ser Met
    210                 215                 220

Leu Ala
225
```

<210> SEQ ID NO 202
<211> LENGTH: 162
<212> TYPE: PRT
<213> ORGANISM: Mycobacterium tuberculosis

<400> SEQUENCE: 202

```
Met Gln Phe Asp Val Thr Ile Glu Ile Pro Lys Gly Gln Arg Asn Lys
1               5                   10                  15

Tyr Glu Val Asp His Glu Thr Gly Arg Val Arg Leu Asp Arg Tyr Leu
            20                  25                  30

Tyr Thr Pro Met Ala Tyr Pro Thr Asp Tyr Gly Phe Ile Glu Asp Thr
        35                  40                  45

Leu Gly Asp Asp Gly Asp Pro Leu Asp Ala Leu Val Leu Leu Pro Gln
    50                  55                  60

Pro Val Phe Pro Gly Val Leu Val Ala Ala Arg Pro Val Gly Met Phe
65                  70                  75                  80

Arg Met Val Asp Glu His Gly Gly Asp Asp Lys Val Leu Cys Val Pro
                85                  90                  95
```

```
Ala Gly Asp Pro Arg Trp Asp His Val Gln Asp Ile Gly Asp Val Pro
            100                 105                 110

Ala Phe Glu Leu Asp Ala Ile Lys His Phe Phe Val His Tyr Lys Asp
        115                 120                 125

Leu Glu Pro Gly Lys Phe Val Lys Ala Ala Asp Trp Val Asp Arg Ala
    130                 135                 140

Glu Ala Glu Ala Glu Val Gln Arg Ser Val Glu Arg Phe Lys Ala Gly
145                 150                 155                 160

Thr His


<210> SEQ ID NO 203
<211> LENGTH: 519
<212> TYPE: DNA
<213> ORGANISM: Mycobacterium tuberculosis

<400> SEQUENCE: 203

catatgcatc accatcacca tcacatgcaa ttcgacgtga ccatcgaaat tcccaagggc      60

cagcgcaaca aatacgaggt cgaccatgag acggggcggg ttcgtctgga ccggtacctg     120

tacaccccga tggcctaccc gaccgactac ggcttcatcg aggacaccct aggtgacgat     180

ggcgacccgc tggacgcgct ggtgctgcta ccgcagccgg tcttccccgg ggtgctggtg     240

gcggcgcggc cggtggggat gttccggatg gtcgacgagc acggcggcga cgacaaagtg     300

ctgtgcgtcc cagccggtga cccccggtgg gaccacgtcc aagacatcgg ggacgttccg     360

gctttcgagc tggatgcgat caagcatttc tttgtgcact acaaggacct ggaaccaggt     420

aagttcgtca aggcggccga ctgggtcgac cgcgccgaag ccgaggcaga ggtgcagcgt     480

tcagtggagc gcttcaaggc cggtacacac tgagaattc                            519


<210> SEQ ID NO 204
<211> LENGTH: 169
<212> TYPE: PRT
<213> ORGANISM: Mycobacterium tuberculosis

<400> SEQUENCE: 204

Met His His His His His His Met Gln Phe Asp Val Thr Ile Glu Ile
1               5                   10                  15

Pro Lys Gly Gln Arg Asn Lys Tyr Glu Val Asp His Glu Thr Gly Arg
            20                  25                  30

Val Arg Leu Asp Arg Tyr Leu Tyr Thr Pro Met Ala Tyr Pro Thr Asp
        35                  40                  45

Tyr Gly Phe Ile Glu Asp Thr Leu Gly Asp Asp Gly Asp Pro Leu Asp
    50                  55                  60

Ala Leu Val Leu Leu Pro Gln Pro Val Phe Pro Gly Val Leu Val Ala
65                  70                  75                  80

Ala Arg Pro Val Gly Met Phe Arg Met Val Asp Glu His Gly Gly Asp
                85                  90                  95

Asp Lys Val Leu Cys Val Pro Ala Gly Asp Pro Arg Trp Asp His Val
            100                 105                 110

Gln Asp Ile Gly Asp Val Pro Ala Phe Glu Leu Asp Ala Ile Lys His
        115                 120                 125

Phe Phe Val His Tyr Lys Asp Leu Glu Pro Gly Lys Phe Val Lys Ala
    130                 135                 140

Ala Asp Trp Val Asp Arg Ala Glu Ala Glu Ala Glu Val Gln Arg Ser
145                 150                 155                 160
```

Val Glu Arg Phe Lys Ala Gly Thr His
165

<210> SEQ ID NO 205
<211> LENGTH: 176
<212> TYPE: PRT
<213> ORGANISM: Mycobacterium tuberculosis

<400> SEQUENCE: 205

Met His Pro Leu Pro Ala Asp His Gly Arg Ser Arg Cys Asn Arg His
1 5 10 15

Pro Ile Ser Pro Leu Ser Leu Ile Gly Asn Ala Ser Ala Thr Ser Gly
20 25 30

Asp Met Ser Ser Met Thr Arg Ile Ala Lys Pro Leu Ile Lys Ser Ala
35 40 45

Met Ala Ala Gly Leu Val Thr Ala Ser Met Ser Leu Ser Thr Ala Val
50 55 60

Ala His Ala Gly Pro Ser Pro Asn Trp Asp Ala Val Ala Gln Cys Glu
65 70 75 80

Ser Gly Gly Asn Trp Ala Ala Asn Thr Gly Asn Gly Lys Tyr Gly Gly
85 90 95

Leu Gln Phe Lys Pro Ala Thr Trp Ala Ala Phe Gly Gly Val Gly Asn
100 105 110

Pro Ala Ala Ala Ser Arg Glu Gln Gln Ile Ala Val Ala Asn Arg Val
115 120 125

Leu Ala Glu Gln Gly Leu Asp Ala Trp Pro Thr Cys Gly Ala Ala Ser
130 135 140

Gly Leu Pro Ile Ala Leu Trp Ser Lys Pro Ala Gln Gly Ile Lys Gln
145 150 155 160

Ile Ile Asn Glu Ile Ile Trp Ala Gly Ile Gln Ala Ser Ile Pro Arg
165 170 175

<210> SEQ ID NO 206
<211> LENGTH: 474
<212> TYPE: DNA
<213> ORGANISM: Mycobacterium tuberculosis

<400> SEQUENCE: 206
catatgcatc accatcacca tcacacttcc ggcgatatgt cgagcatgac aagaatcgcc 60
aagccgctca tcaagtccgc catggccgca ggactcgtca cggcatccat gtcgctctcc 120
accgccgttg cccacgccgg tcccagcccg aactgggacg ccgtcgcgca gtgcgaatcc 180
gggggcaact gggcggccaa caccggaaac ggcaaatacg gcggactgca gttcaagccg 240
gccacctggg ccgcattcgg cggtgtcggc aacccagcag ctgcctctcg ggaacaacaa 300
atcgcagttg ccaatcgggt tctcgccgaa cagggattgg acgcgtggcc gacgtgcggc 360
gccgcctctg gccttccgat cgcactgtgg tcgaaacccg cgcagggcat caagcaaatc 420
atcaacgaga tcatttgggc aggcattcag gcaagtattc cgcgctgaga attc 474

<210> SEQ ID NO 207
<211> LENGTH: 154
<212> TYPE: PRT
<213> ORGANISM: Mycobacterium tuberculosis

<400> SEQUENCE: 207

Met His His His His His His Thr Ser Gly Asp Met Ser Ser Met Thr
1 5 10 15

```
Arg Ile Ala Lys Pro Leu Ile Lys Ser Ala Met Ala Ala Gly Leu Val
            20                  25                  30

Thr Ala Ser Met Ser Leu Ser Thr Ala Val Ala His Ala Gly Pro Ser
        35                  40                  45

Pro Asn Trp Asp Ala Val Ala Gln Cys Glu Ser Gly Gly Asn Trp Ala
    50                  55                  60

Ala Asn Thr Gly Asn Gly Lys Tyr Gly Gly Leu Gln Phe Lys Pro Ala
65                  70                  75                  80

Thr Trp Ala Ala Phe Gly Gly Val Gly Asn Pro Ala Ala Ala Ser Arg
                85                  90                  95

Glu Gln Gln Ile Ala Val Ala Asn Arg Val Leu Ala Glu Gln Gly Leu
            100                 105                 110

Asp Ala Trp Pro Thr Cys Gly Ala Ala Ser Gly Leu Pro Ile Ala Leu
        115                 120                 125

Trp Ser Lys Pro Ala Gln Gly Ile Lys Gln Ile Ile Asn Glu Ile Ile
    130                 135                 140

Trp Ala Gly Ile Gln Ala Ser Ile Pro Arg
145                 150


<210> SEQ ID NO 208
<211> LENGTH: 99
<212> TYPE: PRT
<213> ORGANISM: Mycobacterium tuberculosis

<400> SEQUENCE: 208

Met Glu Lys Met Ser His Asp Pro Ile Ala Ala Asp Ile Gly Thr Gln
1               5                   10                  15

Val Ser Asp Asn Ala Leu His Gly Val Thr Ala Gly Ser Thr Ala Leu
            20                  25                  30

Thr Ser Val Thr Gly Leu Val Pro Ala Gly Ala Asp Glu Val Ser Ala
        35                  40                  45

Gln Ala Ala Thr Ala Phe Thr Ser Glu Gly Ile Gln Leu Leu Ala Ser
    50                  55                  60

Asn Ala Ser Ala Gln Asp Gln Leu His Arg Ala Gly Glu Ala Val Gln
65                  70                  75                  80

Asp Val Ala Arg Thr Tyr Ser Gln Ile Asp Asp Gly Ala Ala Gly Val
                85                  90                  95

Phe Ala Glu


<210> SEQ ID NO 209
<211> LENGTH: 366
<212> TYPE: DNA
<213> ORGANISM: Mycobacterium tuberculosis

<400> SEQUENCE: 209

atgggcagca gccatcatca tcatcatcac agcagcggcc tggtgccgcg cggcagccat      60

atggaaaaaa tgtcacatga tccgatcgct gccgacattg gcacgcaagt gagcgacaac     120

gctctgcacg gcgtgacggc cggctcgacg gcgctgacgt cggtgaccgg gctggttccc     180

gcgggggccg atgaggtctc cgcccaagcg gcgacggcgt tcacatcgga gggcatccaa     240

ttgctggctt ccaatgcatc ggcccaagac cagctccacc gtgcgggcga agcggtccag     300

gacgtcgccc gcacctattc gcaaatcgac gacggcgccg ccggcgtctt cgccgaatag     360

aagctt                                                                366


<210> SEQ ID NO 210
```

<211> LENGTH: 119
<212> TYPE: PRT
<213> ORGANISM: Mycobacterium tuberculosis

<400> SEQUENCE: 210

Met Gly Ser Ser His His His His His His Ser Ser Gly Leu Val Pro
1 5 10 15

Arg Gly Ser His Met Glu Lys Met Ser His Asp Pro Ile Ala Ala Asp
20 25 30

Ile Gly Thr Gln Val Ser Asp Asn Ala Leu His Gly Val Thr Ala Gly
35 40 45

Ser Thr Ala Leu Thr Ser Val Thr Gly Leu Val Pro Ala Gly Ala Asp
50 55 60

Glu Val Ser Ala Gln Ala Ala Thr Ala Phe Thr Ser Glu Gly Ile Gln
65 70 75 80

Leu Leu Ala Ser Asn Ala Ser Ala Gln Asp Gln Leu His Arg Ala Gly
85 90 95

Glu Ala Val Gln Asp Val Ala Arg Thr Tyr Ser Gln Ile Asp Asp Gly
100 105 110

Ala Ala Gly Val Phe Ala Glu
115

<210> SEQ ID NO 211
<211> LENGTH: 367
<212> TYPE: PRT
<213> ORGANISM: Mycobacterium tuberculosis

<400> SEQUENCE: 211

Met Leu Trp His Ala Met Pro Pro Glu Leu Asn Thr Ala Arg Leu Met
1 5 10 15

Ala Gly Ala Gly Pro Ala Pro Met Leu Ala Ala Ala Ala Gly Trp Gln
20 25 30

Thr Leu Ser Ala Ala Leu Asp Ala Gln Ala Val Glu Leu Thr Ala Arg
35 40 45

Leu Asn Ser Leu Gly Glu Ala Trp Thr Gly Gly Gly Ser Asp Lys Ala
50 55 60

Leu Ala Ala Ala Thr Pro Met Val Val Trp Leu Gln Thr Ala Ser Thr
65 70 75 80

Gln Ala Lys Thr Arg Ala Met Gln Ala Thr Ala Gln Ala Ala Ala Tyr
85 90 95

Thr Gln Ala Met Ala Thr Thr Pro Ser Leu Pro Glu Ile Ala Ala Asn
100 105 110

His Ile Thr Gln Ala Val Leu Thr Ala Thr Asn Phe Phe Gly Ile Asn
115 120 125

Thr Ile Pro Ile Ala Leu Thr Glu Met Asp Tyr Phe Ile Arg Met Trp
130 135 140

Asn Gln Ala Ala Leu Ala Met Glu Val Tyr Gln Ala Glu Thr Ala Val
145 150 155 160

Asn Thr Leu Phe Glu Lys Leu Glu Pro Met Ala Ser Ile Leu Asp Pro
165 170 175

Gly Ala Ser Gln Ser Thr Thr Asn Pro Ile Phe Gly Met Pro Ser Pro
180 185 190

Gly Ser Ser Thr Pro Val Gly Gln Leu Pro Pro Ala Ala Thr Gln Thr
195 200 205

Leu Gly Gln Leu Gly Glu Met Ser Gly Pro Met Gln Gln Leu Thr Gln
210 215 220

```
Pro Leu Gln Gln Val Thr Ser Leu Phe Ser Gln Val Gly Gly Thr Gly
225                 230                 235                 240

Gly Gly Asn Pro Ala Asp Glu Glu Ala Ala Gln Met Gly Leu Leu Gly
                245                 250                 255

Thr Ser Pro Leu Ser Asn His Pro Leu Ala Gly Gly Ser Gly Pro Ser
            260                 265                 270

Ala Gly Ala Gly Leu Arg Ala Glu Ser Leu Pro Gly Ala Gly Gly Ser
        275                 280                 285

Leu Thr Arg Thr Pro Leu Met Ser Gln Leu Ile Glu Lys Pro Val Ala
    290                 295                 300

Pro Ser Val Met Pro Ala Ala Ala Ala Gly Ser Ser Ala Thr Gly Gly
305                 310                 315                 320

Ala Ala Pro Val Gly Ala Gly Ala Met Gly Gln Gly Ala Gln Ser Gly
                325                 330                 335

Gly Ser Thr Arg Pro Gly Leu Val Ala Pro Ala Pro Leu Ala Gln Glu
            340                 345                 350

Arg Glu Glu Asp Asp Glu Asp Asp Trp Asp Glu Glu Asp Asp Trp
        355                 360                 365
```

<210> SEQ ID NO 212
<211> LENGTH: 1173
<212> TYPE: DNA
<213> ORGANISM: Mycobacterium tuberculosis

<400> SEQUENCE: 212

```
atgggcagca gccatcatca tcatcatcac agcagcggcc tggtgccgcg cggcagccat      60

atgctgtggc acgcaatgcc accggagcta aataccgcac ggctgatggc cggcgcgggt     120

ccggctccaa tgcttgcggc ggccgcggga tggcagacgc tttcggcggc tctggacgct     180

caggccgtcg agttgaccgc gcgcctgaac tctctgggag aagcctggac tggaggtggc     240

agcgacaagg cgcttgcggc tgcaacgccg atggtggtct ggctacaaac cgcgtcaaca     300

caggccaaga cccgtgcgat gcaggcgacg gcgcaagccg cggcatacac ccaggccatg     360

gccacgacgc cgtcgctgcc ggagatcgcc gccaaccaca tcacccaggc cgtccttacg     420

gccaccaact tcttcggtat caacacgatc ccgatcgcgt tgaccgagat ggattatttc     480

atccgtatgt ggaaccaggc agccctggca atggaggtct accaggccga gaccgcggtt     540

aacacgcttt tcgagaagct cgagccgatg gcgtcgatcc ttgatcccgg cgcgagccag     600

agcacgacga acccgatctt cggaatgccc tcccctggca gctcaacacc ggttggccag     660

ttgccgccgg cggctaccca gaccctcggc caactgggtg agatgagcgg cccgatgcag     720

cagctgaccc agccgctgca gcaggtgacg tcgttgttca gccaggtggg cggcaccggc     780

ggcggcaacc cagccgacga ggaagccgcg cagatgggcc tgctcggcac cagtccgctg     840

tcgaaccatc cgctggctgg tggatcaggc cccagcgcgg gcgcgggcct gctgcgcgcg     900

gagtcgctac ctggcgcagg tgggtcgttg acccgcacgc cgctgatgtc tcagctgatc     960

gaaaagccgg ttgccccctc ggtgatgccg gcggctgctg ccggatcgtc ggcgacgggt    1020

ggcgccgctc cggtgggtgc gggagcgatg ggccagggtg cgcaatccgg cggctccacc    1080

aggccgggtc tggtcgcgcc ggcaccgctc gcgcaggagc gtgaagaaga cgacgaggac    1140

gactgggacg aagaggacga ctggtgaaag ctt                                  1173
```

<210> SEQ ID NO 213
<211> LENGTH: 388

<212> TYPE: PRT
<213> ORGANISM: Mycobacterium tuberculosis

<400> SEQUENCE: 213

```
Met Gly Ser Ser His His His His His His Ser Ser Gly Leu Val Pro
1               5                   10                  15

Arg Gly Ser His Met Leu Trp His Ala Met Pro Pro Glu Leu Asn Thr
            20                  25                  30

Ala Arg Leu Met Ala Gly Ala Gly Pro Ala Pro Met Leu Ala Ala Ala
        35                  40                  45

Ala Gly Trp Gln Thr Leu Ser Ala Ala Leu Asp Ala Gln Ala Val Glu
    50                  55                  60

Leu Thr Ala Arg Leu Asn Ser Leu Gly Glu Ala Trp Thr Gly Gly Gly
65                  70                  75                  80

Ser Asp Lys Ala Leu Ala Ala Ala Thr Pro Met Val Val Trp Leu Gln
                85                  90                  95

Thr Ala Ser Thr Gln Ala Lys Thr Arg Ala Met Gln Ala Thr Ala Gln
            100                 105                 110

Ala Ala Ala Tyr Thr Gln Ala Met Ala Thr Thr Pro Ser Leu Pro Glu
        115                 120                 125

Ile Ala Ala Asn His Ile Thr Gln Ala Val Leu Thr Ala Thr Asn Phe
    130                 135                 140

Phe Gly Ile Asn Thr Ile Pro Ile Ala Leu Thr Glu Met Asp Tyr Phe
145                 150                 155                 160

Ile Arg Met Trp Asn Gln Ala Ala Leu Ala Met Glu Val Tyr Gln Ala
                165                 170                 175

Glu Thr Ala Val Asn Thr Leu Phe Glu Lys Leu Glu Pro Met Ala Ser
            180                 185                 190

Ile Leu Asp Pro Gly Ala Ser Gln Ser Thr Thr Asn Pro Ile Phe Gly
        195                 200                 205

Met Pro Ser Pro Gly Ser Ser Thr Pro Val Gly Gln Leu Pro Pro Ala
    210                 215                 220

Ala Thr Gln Thr Leu Gly Gln Leu Gly Glu Met Ser Gly Pro Met Gln
225                 230                 235                 240

Gln Leu Thr Gln Pro Leu Gln Gln Val Thr Ser Leu Phe Ser Gln Val
                245                 250                 255

Gly Gly Thr Gly Gly Gly Asn Pro Ala Asp Glu Glu Ala Ala Gln Met
            260                 265                 270

Gly Leu Leu Gly Thr Ser Pro Leu Ser Asn His Pro Leu Ala Gly Gly
        275                 280                 285

Ser Gly Pro Ser Ala Gly Ala Gly Leu Leu Arg Ala Glu Ser Leu Pro
    290                 295                 300

Gly Ala Gly Gly Ser Leu Thr Arg Thr Pro Leu Met Ser Gln Leu Ile
305                 310                 315                 320

Glu Lys Pro Val Ala Pro Ser Val Met Pro Ala Ala Ala Ala Gly Ser
                325                 330                 335

Ser Ala Thr Gly Gly Ala Ala Pro Val Gly Ala Gly Ala Met Gly Gln
            340                 345                 350

Gly Ala Gln Ser Gly Gly Ser Thr Arg Pro Gly Leu Val Ala Pro Ala
        355                 360                 365

Pro Leu Ala Gln Glu Arg Glu Glu Asp Asp Glu Asp Asp Trp Asp Glu
    370                 375                 380

Glu Asp Asp Trp
385
```

<210> SEQ ID NO 214
<211> LENGTH: 340
<212> TYPE: PRT
<213> ORGANISM: Mycobacterium tuberculosis

<400> SEQUENCE: 214

```
Met Lys Arg Ala Leu Ile Thr Gly Ile Thr Gly Gln Asp Gly Ser Tyr
1               5                   10                  15

Leu Ala Glu Leu Leu Leu Ala Lys Gly Tyr Glu Val His Gly Leu Ile
            20                  25                  30

Arg Arg Ala Ser Thr Phe Asn Thr Ser Arg Ile Asp His Leu Tyr Val
        35                  40                  45

Asp Pro His Gln Pro Gly Ala Arg Leu Phe Leu His Tyr Gly Asp Leu
    50                  55                  60

Ile Asp Gly Thr Arg Leu Val Thr Leu Leu Ser Thr Ile Glu Pro Asp
65                  70                  75                  80

Glu Val Tyr Asn Leu Ala Ala Gln Ser His Val Arg Val Ser Phe Asp
                85                  90                  95

Glu Pro Val His Thr Gly Asp Thr Thr Gly Met Gly Ser Met Arg Leu
            100                 105                 110

Leu Glu Ala Val Arg Leu Ser Arg Val His Cys Arg Phe Tyr Gln Ala
        115                 120                 125

Ser Ser Ser Glu Met Phe Gly Ala Ser Pro Pro Pro Gln Asn Glu Leu
    130                 135                 140

Thr Pro Phe Tyr Pro Arg Ser Pro Tyr Gly Ala Ala Lys Val Tyr Ser
145                 150                 155                 160

Tyr Trp Ala Thr Arg Asn Tyr Arg Glu Ala Tyr Gly Leu Phe Ala Val
                165                 170                 175

Asn Gly Ile Leu Phe Asn His Glu Ser Pro Arg Arg Gly Glu Thr Phe
            180                 185                 190

Val Thr Arg Lys Ile Thr Arg Ala Val Ala Arg Ile Lys Ala Gly Ile
        195                 200                 205

Gln Ser Glu Val Tyr Met Gly Asn Leu Asp Ala Val Arg Asp Trp Gly
    210                 215                 220

Tyr Ala Pro Glu Tyr Val Glu Gly Met Trp Arg Met Leu Gln Thr Asp
225                 230                 235                 240

Glu Pro Asp Asp Phe Val Leu Ala Thr Gly Arg Gly Phe Thr Val Arg
                245                 250                 255

Glu Phe Ala Arg Ala Ala Phe Glu His Ala Gly Leu Asp Trp Gln Gln
            260                 265                 270

Tyr Val Lys Phe Asp Gln Arg Tyr Leu Arg Pro Thr Glu Val Asp Ser
        275                 280                 285

Leu Ile Gly Asp Ala Thr Lys Ala Ala Glu Leu Leu Gly Trp Arg Ala
    290                 295                 300

Ser Val His Thr Asp Glu Leu Ala Arg Ile Met Val Asp Ala Asp Met
305                 310                 315                 320

Ala Ala Leu Glu Cys Glu Gly Lys Pro Trp Ile Asp Lys Pro Met Ile
                325                 330                 335

Ala Gly Arg Thr
            340
```

<210> SEQ ID NO 215
<211> LENGTH: 1053
<212> TYPE: DNA

<213> ORGANISM: Mycobacterium tuberculosis

<400> SEQUENCE: 215

```
catatgcatc accatcacca tcacgtgaag cgagcgctca tcaccggaat caccggccag     60
gacggctcgt atctcgccga actgctgctg gccaaggggt atgaggttca cgggctcatc    120
cggcgcgctt cgacgttcaa cacctcgcgg atcgatcacc tctacgtcga cccgcaccaa    180
ccgggcgcgc ggctgtttct gcactatggt gacctgatcg acggaacccg gttggtgacc    240
ctgctgagca ccatcgaacc cgacgaggtg tacaacctgg cggcgcagtc acacgtgcgg    300
gtgagcttcg acgaacccgt gcacaccggt gacaccaccg gcatgggatc catgcgactg    360
ctggaagccg ttcggctctc tcgggtgcac tgccgcttct atcaggcgtc ctcgtcggag    420
atgttcggcg cctcgccgcc accgcagaac gagctgacgc cgttctaccc gcggtcaccg    480
tatggcgccg ccaaggtcta ttcgtactgg gcgacccgca attatcgcga agcgtacgga    540
ttgttcgccg ttaacggcat cttgttcaat cacgaatcac cgcggcgcgg tgagacgttc    600
gtgacccgaa agatcaccag ggccgtggca cgcatcaagg ccggtatcca gtccgaggtc    660
tatatgggca atctggatgc ggtccgcgac tgggggtacg cgcccgaata cgtcgaaggc    720
atgtggcgga tgctgcagac cgacgagccc gacgacttcg ttttggcgac cgggcgcggt    780
ttcaccgtgc gtgagttcgc gcgggccgcg ttcgagcatg ccggtttgga ctggcagcag    840
tacgtgaaat tcgaccaacg ctatctgcgg cccaccgagg tggattcgct gatcggcgac    900
gcgaccaagg ctgccgaatt gctgggctgg agggcttcgg tgcacactga cgagttggct    960
cggatcatgg tcgacgcgga catggcggcg ctggagtgcg aaggcaagcc gtggatcgac   1020
aagccgatga tcgccggccg gacatgagaa ttc                               1053
```

<210> SEQ ID NO 216
<211> LENGTH: 347
<212> TYPE: PRT
<213> ORGANISM: Mycobacterium tuberculosis

<400> SEQUENCE: 216

```
Met His His His His His His Val Lys Arg Ala Leu Ile Thr Gly Ile
1               5                   10                  15

Thr Gly Gln Asp Gly Ser Tyr Leu Ala Glu Leu Leu Leu Ala Lys Gly
            20                  25                  30

Tyr Glu Val His Gly Leu Ile Arg Arg Ala Ser Thr Phe Asn Thr Ser
        35                  40                  45

Arg Ile Asp His Leu Tyr Val Asp Pro His Gln Pro Gly Ala Arg Leu
    50                  55                  60

Phe Leu His Tyr Gly Asp Leu Ile Asp Gly Thr Arg Leu Val Thr Leu
65                  70                  75                  80

Leu Ser Thr Ile Glu Pro Asp Glu Val Tyr Asn Leu Ala Ala Gln Ser
                85                  90                  95

His Val Arg Val Ser Phe Asp Glu Pro Val His Thr Gly Asp Thr Thr
            100                 105                 110

Gly Met Gly Ser Met Arg Leu Leu Glu Ala Val Arg Leu Ser Arg Val
        115                 120                 125

His Cys Arg Phe Tyr Gln Ala Ser Ser Ser Glu Met Phe Gly Ala Ser
    130                 135                 140

Pro Pro Pro Gln Asn Glu Leu Thr Pro Phe Tyr Pro Arg Ser Pro Tyr
145                 150                 155                 160

Gly Ala Ala Lys Val Tyr Ser Tyr Trp Ala Thr Arg Asn Tyr Arg Glu
```

```
                165                 170                 175

Ala Tyr Gly Leu Phe Ala Val Asn Gly Ile Leu Phe Asn His Glu Ser
            180                 185                 190

Pro Arg Arg Gly Glu Thr Phe Val Thr Arg Lys Ile Thr Arg Ala Val
        195                 200                 205

Ala Arg Ile Lys Ala Gly Ile Gln Ser Glu Val Tyr Met Gly Asn Leu
    210                 215                 220

Asp Ala Val Arg Asp Trp Gly Tyr Ala Pro Glu Tyr Val Glu Gly Met
225                 230                 235                 240

Trp Arg Met Leu Gln Thr Asp Glu Pro Asp Asp Phe Val Leu Ala Thr
                245                 250                 255

Gly Arg Gly Phe Thr Val Arg Glu Phe Ala Arg Ala Ala Phe Glu His
            260                 265                 270

Ala Gly Leu Asp Trp Gln Gln Tyr Val Lys Phe Asp Gln Arg Tyr Leu
        275                 280                 285

Arg Pro Thr Glu Val Asp Ser Leu Ile Gly Asp Ala Thr Lys Ala Ala
    290                 295                 300

Glu Leu Leu Gly Trp Arg Ala Ser Val His Thr Asp Glu Leu Ala Arg
305                 310                 315                 320

Ile Met Val Asp Ala Asp Met Ala Ala Leu Glu Cys Glu Gly Lys Pro
                325                 330                 335

Trp Ile Asp Lys Pro Met Ile Ala Gly Arg Thr
            340                 345


<210> SEQ ID NO 217
<211> LENGTH: 2742
<212> TYPE: DNA
<213> ORGANISM: Mycobacterium tuberculosis

<400> SEQUENCE: 217

atgggcagca gccatcatca tcatcatcac agcagcggcc tggtgccgcg cggcagccat      60

atgaccatca actatcaatt cggggacgtc gacgctcacg gcgccatgat ccgcgctcag     120

gccgggtcgc tggaggccga gcatcaggcc atcatttctg atgtgttgac cgcgagtgac     180

ttttggggcg gcgccggttc ggcggcctgc caggggttca ttacccagct gggccgtaac     240

ttccaggtga tctacgagca ggccaacgcc cacgggcaga aggtgcaggc tgccggcaac     300

aacatggcac aaaccgacag cgccgtcggc tccagctggg ccggtaccca tctcgccaac     360

ggttcgatgt cggaagtcat gatgtcggaa attgccgggt tgcctatccc tccgattatc     420

cattacgggg cgattgccta tgcccccagc ggcgcgtcgg gcaaagcgtg gcaccagcgc     480

acaccggcgc gagcagagca agtcgcacta gaaaagtgcg gtgacaagac ttgcaaagtg     540

gttagtcgct tcaccaggtg cggcgcggtc gcctacaacg gctcgaaata ccaaggcgga     600

accggactca cgcgccgcgc ggcagaagac gacgccgtga accgactcga aggcgggcgg     660

atcgtcaact gggcgtgcaa cgagctcatg acctcgcgtt ttatgacgga tccgcacgcg     720

atgcgggaca tggcgggccg ttttgaggtg cacgcccaga cggtggagga cgaggctcgc     780

cggatgtggg cgtccgcgca aaacatctcg ggcgcgggct ggagtggcat ggccgaggcg     840

acctcgctag acaccatgac ccagatgaat caggcgtttc gcaacatcgt gaacatgctg     900

cacggggtgc gtgacgggct ggttcgcgac gccaacaact acgaacagca agagcaggcc     960

tcccagcaga tcctcagcag cgtcgacatc aatttcgccg ttttgccgcc ggaggtgaat    1020

tcggcgcgca tattcgccgg tgcgggcctg ggcccaatgc tggcggcggc gtcggcctgg    1080
```

-continued

```
gacgggttgg ccgaggagtt gcatgccgcg gcgggctcgt tcgcgtcggt gaccaccggg   1140

ttggcgggcg acgcgtggca tggtccggcg tcgctggcga tgacccgcgc ggccagcccg   1200

tatgtggggt ggttgaacac ggcggcgggt caggccgcgc aggcggccgg ccaggcgcgg   1260

ctagcggcga gcgcgttcga ggcgacgctg gcggccaccg tgtctccagc gatggtcgcg   1320

gccaaccgga cacggctggc gtcgctggtg gcagccaact tgctgggcca gaacgccccg   1380

gcgatcgcgg ccgcggaggc tgaatacgag cagatatggg cccaggacgt ggccgcgatg   1440

ttcggctatc actccgccgc gtcggcggtg gccacgcagc tggcgcctat tcaagagggt   1500

ttgcagcagc agctgcaaaa cgtgctggcc cagttggcta gcgggaacct gggcagcgga   1560

aatgtgggcg tcggcaacat cggcaacgac aacattggca acgcaaacat cggcttcgga   1620

aatcgaggcg acgccaacat cggcatcggg aatatcggcg acagaaacct cggcattggg   1680

aacaccggca attggaatat cggcatcggc atcaccggca acggacaaat cggcttcggc   1740

aagcctgcca accccgacgt cttggtggtg ggcaacggcg gcccgggagt aaccgcgttg   1800

gtcatgggcg gcaccgacag cctactgccg ctgcccaaca tccccttact cgagtacgct   1860

gcgcggttca tcacccccgt gcatcccgga tacaccgcta cgttcctgga aacgccatcg   1920

cagtttttcc cattcaccgg gctgaatagc ctgacctatg acgtctccgt ggcccagggc   1980

gtaacgaatc tgcacaccgc gatcatggcg caactcgcgg cgggaaacga agtcgtcgtc   2040

ttcggcacct cccaaagcgc cacgatagcc accttcgaaa tgcgctatct gcaatccctg   2100

ccagcacacc tgcgtccggg tctcgacgaa ttgtccttta cgttgaccgg caatcccaac   2160

cggcccgacg gtggcattct tacgcgtttt ggcttctcca taccgcagtt gggtttcaca   2220

ttgtccggcg cgacgcccgc cgacgcctac ccaccgtcg attacgcgtt ccagtacgac   2280

ggcgtcaacg acttccccaa atacccgctg aatgtcttcg cgaccgccaa cgcgatcgcg   2340

ggcatccttt tcctgcactc cgggttgatt gcgttgccgc ccgatcttgc ctcgggcgtg   2400

gttcaaccgg tgtcctcacc ggacgtcctg accacctaca tcctgctgcc cagccaagat   2460

ctgccgctgc tggtcccgct gcgtgctatc cccctgctgg gaaacccgct tgccgacctc   2520

atccagccgg acttgcgggt gctcgtcgag ttgggttatg accgcaccgc ccaccaggac   2580

gtgcccagcc cgttcggact gtttccggac gtcgattggg ccgaggtggc cgcggacctg   2640

cagcaaggcg ccgtgcaagg cgtcaacgac gccctgtccg gactggggct gccgccgccg   2700

tggcagccgg cgctaccccg acttttcagt acttaaaagc tt                      2742
```

```
<210> SEQ ID NO 218
<211> LENGTH: 39
<212> TYPE: DNA
<213> ORGANISM: Artificial Sequence
<220> FEATURE:
<223> OTHER INFORMATION: Primer

<400> SEQUENCE: 218

caattacata tgggtaccca tctcgccaac ggttcgatg                             39


<210> SEQ ID NO 219
<211> LENGTH: 33
<212> TYPE: DNA
<213> ORGANISM: Artificial Sequence
<220> FEATURE:
<223> OTHER INFORMATION: Primer

<400> SEQUENCE: 219

caattagagc tcgttgcacg cccagttgac gat                                   33
```

<210> SEQ ID NO 220
<211> LENGTH: 33
<212> TYPE: DNA
<213> ORGANISM: Artificial Sequence
<220> FEATURE:
<223> OTHER INFORMATION: Primer

<400> SEQUENCE: 220
caattagagc tcatgacctc gcgttttatg acg 33

<210> SEQ ID NO 221
<211> LENGTH: 33
<212> TYPE: DNA
<213> ORGANISM: Artificial Sequence
<220> FEATURE:
<223> OTHER INFORMATION: Primer

<400> SEQUENCE: 221
caattagtcg acgctgctga ggatctgctg gga 33

<210> SEQ ID NO 222
<211> LENGTH: 33
<212> TYPE: DNA
<213> ORGANISM: Artificial Sequence
<220> FEATURE:
<223> OTHER INFORMATION: Primer

<400> SEQUENCE: 222
caattagtcg acatgaattt cgccgttttg ccg 33

<210> SEQ ID NO 223
<211> LENGTH: 42
<212> TYPE: DNA
<213> ORGANISM: Artificial Sequence
<220> FEATURE:
<223> OTHER INFORMATION: Primer

<400> SEQUENCE: 223
caattaaagc ttttaagtac tgaaaagtcg gggtagcgcc gg 42

<210> SEQ ID NO 224
<211> LENGTH: 30
<212> TYPE: DNA
<213> ORGANISM: Artificial Sequence
<220> FEATURE:
<223> OTHER INFORMATION: Primer

<400> SEQUENCE: 224
caattacata tgaccatcaa ctatcaattc 30

<210> SEQ ID NO 225
<211> LENGTH: 33
<212> TYPE: DNA
<213> ORGANISM: Artificial Sequence
<220> FEATURE:
<223> OTHER INFORMATION: Primer

<400> SEQUENCE: 225
caattaggta ccggcccagc tggagccgac ggc 33

<210> SEQ ID NO 226
<211> LENGTH: 911
<212> TYPE: PRT
<213> ORGANISM: Mycobacterium tuberculosis

<400> SEQUENCE: 226

```
Met Gly Ser Ser His His His His His His Ser Ser Gly Leu Val Pro
1               5                   10                  15

Arg Gly Ser His Met Thr Ile Asn Tyr Gln Phe Gly Asp Val Asp Ala
            20                  25                  30

His Gly Ala Met Ile Arg Ala Gln Ala Gly Ser Leu Glu Ala Glu His
        35                  40                  45

Gln Ala Ile Ile Ser Asp Val Leu Thr Ala Ser Asp Phe Trp Gly Gly
    50                  55                  60

Ala Gly Ser Ala Ala Cys Gln Gly Phe Ile Thr Gln Leu Gly Arg Asn
65                  70                  75                  80

Phe Gln Val Ile Tyr Glu Gln Ala Asn Ala His Gly Gln Lys Val Gln
                85                  90                  95

Ala Ala Gly Asn Asn Met Ala Gln Thr Asp Ser Ala Val Gly Ser Ser
            100                 105                 110

Trp Ala Gly Thr His Leu Ala Asn Gly Ser Met Ser Glu Val Met Met
        115                 120                 125

Ser Glu Ile Ala Gly Leu Pro Ile Pro Pro Ile Ile His Tyr Gly Ala
    130                 135                 140

Ile Ala Tyr Ala Pro Ser Gly Ala Ser Gly Lys Ala Trp His Gln Arg
145                 150                 155                 160

Thr Pro Ala Arg Ala Glu Gln Val Ala Leu Glu Lys Cys Gly Asp Lys
                165                 170                 175

Thr Cys Lys Val Val Ser Arg Phe Thr Arg Cys Gly Ala Val Ala Tyr
            180                 185                 190

Asn Gly Ser Lys Tyr Gln Gly Gly Thr Gly Leu Thr Arg Arg Ala Ala
        195                 200                 205

Glu Asp Asp Ala Val Asn Arg Leu Glu Gly Gly Arg Ile Val Asn Trp
    210                 215                 220

Ala Cys Asn Glu Leu Met Thr Ser Arg Phe Met Thr Asp Pro His Ala
225                 230                 235                 240

Met Arg Asp Met Ala Gly Arg Phe Glu Val His Ala Gln Thr Val Glu
                245                 250                 255

Asp Glu Ala Arg Arg Met Trp Ala Ser Ala Gln Asn Ile Ser Gly Ala
            260                 265                 270

Gly Trp Ser Gly Met Ala Glu Ala Thr Ser Leu Asp Thr Met Thr Gln
        275                 280                 285

Met Asn Gln Ala Phe Arg Asn Ile Val Asn Met Leu His Gly Val Arg
    290                 295                 300

Asp Gly Leu Val Arg Asp Ala Asn Asn Tyr Glu Gln Gln Glu Gln Ala
305                 310                 315                 320

Ser Gln Gln Ile Leu Ser Ser Val Asp Ile Asn Phe Ala Val Leu Pro
                325                 330                 335

Pro Glu Val Asn Ser Ala Arg Ile Phe Ala Gly Ala Gly Leu Gly Pro
            340                 345                 350

Met Leu Ala Ala Ala Ser Ala Trp Asp Gly Leu Ala Glu Glu Leu His
        355                 360                 365

Ala Ala Ala Gly Ser Phe Ala Ser Val Thr Thr Gly Leu Ala Gly Asp
    370                 375                 380

Ala Trp His Gly Pro Ala Ser Leu Ala Met Thr Arg Ala Ala Ser Pro
385                 390                 395                 400

Tyr Val Gly Trp Leu Asn Thr Ala Ala Gly Gln Ala Ala Gln Ala Ala
                405                 410                 415
```

```
Gly Gln Ala Arg Leu Ala Ala Ser Ala Phe Glu Ala Thr Leu Ala Ala
            420                 425                 430

Thr Val Ser Pro Ala Met Val Ala Ala Asn Arg Thr Arg Leu Ala Ser
        435                 440                 445

Leu Val Ala Ala Asn Leu Leu Gly Gln Asn Ala Pro Ala Ile Ala Ala
    450                 455                 460

Ala Glu Ala Glu Tyr Glu Gln Ile Trp Ala Gln Asp Val Ala Ala Met
465                 470                 475                 480

Phe Gly Tyr His Ser Ala Ala Ser Ala Val Ala Thr Gln Leu Ala Pro
                485                 490                 495

Ile Gln Glu Gly Leu Gln Gln Gln Leu Gln Asn Val Leu Ala Gln Leu
            500                 505                 510

Ala Ser Gly Asn Leu Gly Ser Gly Asn Val Gly Val Gly Asn Ile Gly
        515                 520                 525

Asn Asp Asn Ile Gly Asn Ala Asn Ile Gly Phe Gly Asn Arg Gly Asp
    530                 535                 540

Ala Asn Ile Gly Ile Gly Asn Ile Gly Asp Arg Asn Leu Gly Ile Gly
545                 550                 555                 560

Asn Thr Gly Asn Trp Asn Ile Gly Ile Gly Ile Thr Gly Asn Gly Gln
                565                 570                 575

Ile Gly Phe Gly Lys Pro Ala Asn Pro Asp Val Leu Val Val Gly Asn
            580                 585                 590

Gly Gly Pro Gly Val Thr Ala Leu Val Met Gly Gly Thr Asp Ser Leu
        595                 600                 605

Leu Pro Leu Pro Asn Ile Pro Leu Leu Glu Tyr Ala Ala Arg Phe Ile
    610                 615                 620

Thr Pro Val His Pro Gly Tyr Thr Ala Thr Phe Leu Glu Thr Pro Ser
625                 630                 635                 640

Gln Phe Phe Pro Phe Thr Gly Leu Asn Ser Leu Thr Tyr Asp Val Ser
                645                 650                 655

Val Ala Gln Gly Val Thr Asn Leu His Thr Ala Ile Met Ala Gln Leu
            660                 665                 670

Ala Ala Gly Asn Glu Val Val Val Phe Gly Thr Ser Gln Ser Ala Thr
        675                 680                 685

Ile Ala Thr Phe Glu Met Arg Tyr Leu Gln Ser Leu Pro Ala His Leu
    690                 695                 700

Arg Pro Gly Leu Asp Glu Leu Ser Phe Thr Leu Thr Gly Asn Pro Asn
705                 710                 715                 720

Arg Pro Asp Gly Gly Ile Leu Thr Arg Phe Gly Phe Ser Ile Pro Gln
                725                 730                 735

Leu Gly Phe Thr Leu Ser Gly Ala Thr Pro Ala Asp Ala Tyr Pro Thr
            740                 745                 750

Val Asp Tyr Ala Phe Gln Tyr Asp Gly Val Asn Asp Phe Pro Lys Tyr
        755                 760                 765

Pro Leu Asn Val Phe Ala Thr Ala Asn Ala Ile Ala Gly Ile Leu Phe
    770                 775                 780

Leu His Ser Gly Leu Ile Ala Leu Pro Pro Asp Leu Ala Ser Gly Val
785                 790                 795                 800

Val Gln Pro Val Ser Ser Pro Asp Val Leu Thr Thr Tyr Ile Leu Leu
                805                 810                 815

Pro Ser Gln Asp Leu Pro Leu Leu Val Pro Leu Arg Ala Ile Pro Leu
            820                 825                 830
```

-continued

```
Leu Gly Asn Pro Leu Ala Asp Leu Ile Gln Pro Asp Leu Arg Val Leu
        835                 840                 845

Val Glu Leu Gly Tyr Asp Arg Thr Ala His Gln Asp Val Pro Ser Pro
    850                 855                 860

Phe Gly Leu Phe Pro Asp Val Asp Trp Ala Glu Val Ala Ala Asp Leu
865                 870                 875                 880

Gln Gln Gly Ala Val Gln Gly Val Asn Asp Ala Leu Ser Gly Leu Gly
                885                 890                 895

Leu Pro Pro Pro Trp Gln Pro Ala Leu Pro Arg Leu Phe Ser Thr
            900                 905                 910


<210> SEQ ID NO 227
<211> LENGTH: 2664
<212> TYPE: DNA
<213> ORGANISM: Mycobacterium tuberculosis

<400> SEQUENCE: 227

catatgatga ccatcaacta tcaattcggg gacgtcgacg ctcacggcgc catgatccgc     60

gctcaggccg ggtcgctgga ggccgagcat caggccatca tttctgatgt gttgaccgcg    120

agtgactttt ggggcggcgc cggttcggcg gcctgccagg ggttcattac ccagctgggc    180

cgtaacttcc aggtgatcta cgagcaggcc aacgcccacg ggcagaaggt gcaggctgcc    240

ggcaacaaca tggcacaaac cgacagcgcc gtcggctcca gctgggccgg taccgacgac    300

atcgattggg acgccatcgc gcaatgcgaa tccggcggca attgggcggc caacaccggt    360

aacgggttat acggtggtct gcagatcagc caggcgacgt gggattccaa cggtggtgtc    420

gggtcgccgg cggccgcgag tccccagcaa cagatcgagg tcgcagacaa cattatgaaa    480

acccaaggcc cgggtgcgtg gccgaaatgt agttcttgta gtcagggaga cgcaccgctg    540

ggctcgctca cccacatcct gacgttcctc gcggccgaga ctggaggttg ttcggggagc    600

agggacgatg gatccgtggt ggatttcggg gcgttaccac cggagatcaa ctccgcgagg    660

atgtacgccg gcccgggttc ggcctcgctg gtggccgccg cgaagatgtg ggacagcgtg    720

gcgagtgacc tgttttcggc cgcgtcggcg tttcagtcgg tggtctgggg tctgacggtg    780

gggtcgtgga taggttcgtc ggcgggtctg atggcggcgg cggcctcgcc gtatgtggcg    840

tggatgagcg tcaccgcggg gcaggcccag ctgaccgccg cccaggtccg ggttgctgcg    900

gcggcctacg agacagcgta taggctgacg gtgcccccgc cggtgatcgc cgagaaccgt    960

accgaactga tgacgctgac cgcgaccaac ctcttggggc aaaacacgcc ggcgatcgag   1020

gccaatcagg ccgcatacag ccagatgtgg ggccaagacg cggaggcgat gtatggctac   1080

gccgccacgg cggcgacggc gaccgaggcg ttgctgccgt tcgaggacgc cccactgatc   1140

accaaccccg gcgggctcct tgagcaggcc gtcgcggtcg aggaggccat cgacaccgcc   1200

gcggcgaacc agttgatgaa caatgtgccc caagcgctgc aacagctggc ccagccagcg   1260

cagggcgtcg taccttcttc caagctgggt gggctgtgga cggcggtctc gccgcatctg   1320

tcgccgctca gcaacgtcag ttcgatagcc aacaaccaca tgtcgatgat gggcacgggt   1380

gtgtcgatga ccaacacctt gcactcgatg ttgaagggct tagctccggc ggcggctcag   1440

gccgtggaaa ccgcggcgga aaacggggtc tgggcgatga gctcgctggg cagccagctg   1500

ggttcgtcgc tgggttcttc gggtctgggc gctggggtgg ccgccaactt gggtcgggcg   1560

gcctcggtcg gttcgttgtc ggtgccgcca gcatgggccg cggccaacca ggcggtcacc   1620

ccggcggcgc gggcgctgcc gctgaccagc ctgaccagcg ccgcccaaac cgcccccgga   1680
```

cacatgctgg gcgggctacc gctggggcac tcggtcaacg ccggcagcgg tatcaacaat 1740
gcgctgcggg tgccggcacg ggcctacgcg ataccccgca caccggccgc cggagaattc 1800
ttctcccggc cggggctgcc ggtcgagtac ctgcaggtgc cgtcgccgtc gatgggccgc 1860
gacatcaagg ttcagttcca gagcggtggg aacaactcac ctgcggttta tctgctcgac 1920
ggcctgcgcg cccaagacga ctacaacggc tgggatatca acaccccggc gttcgagtgg 1980
tactaccagt cgggactgtc gatagtcatg ccggtcggcg ggcagtccag cttctacagc 2040
gactggtaca gcccggcctg cggtaaggct ggctgccaga cttacaagtg ggaaaccttc 2100
ctgaccagcg agctgccgca atggttgtcc gccaacaggg ccgtgaagcc caccggcagc 2160
gctgcaatcg gcttgtcgat ggccggctcg tcggcaatga tcttggccgc ctaccacccc 2220
cagcagttca tctacgccgg ctcgctgtcg gccctgctgg acccctctca ggggatgggg 2280
cctagcctga tcggcctcgc gatgggtgac gccggcggtt acaaggccgc agacatgtgg 2340
ggtccctcga gtgacccggc atgggagcgc aacgacccta cgcagcagat ccccaagctg 2400
gtcgcaaaca acacccggct atgggtttat tgcgggaacg gcaccccgaa cgagttgggc 2460
ggtgccaaca tacccgccga gttcttggag aacttcgttc gtagcagcaa cctgaagttc 2520
caggatgcgt acaacgccgc gggcgggcac aacgccgtgt tcaacttccc gcccaacggc 2580
acgcacagct gggagtactg ggcgctcag ctcaacgcca tgaagggtga cctgcagagt 2640
tcgttaggcg ccggctgaaa gctt 2664

<210> SEQ ID NO 228
<211> LENGTH: 30
<212> TYPE: DNA
<213> ORGANISM: Artificial Sequence
<220> FEATURE:
<223> OTHER INFORMATION: Primer

<400> SEQUENCE: 228
caattacata tgaccatcaa ctatcaattc 30

<210> SEQ ID NO 229
<211> LENGTH: 32
<212> TYPE: DNA
<213> ORGANISM: Artificial Sequence
<220> FEATURE:
<223> OTHER INFORMATION: Primer

<400> SEQUENCE: 229
caattaggta ccggcccagc tggagccgac gg 32

<210> SEQ ID NO 230
<211> LENGTH: 33
<212> TYPE: DNA
<213> ORGANISM: Artificial Sequence
<220> FEATURE:
<223> OTHER INFORMATION: Primer

<400> SEQUENCE: 230
tgggccggta ccgacgacat cgattgggac gcc 33

<210> SEQ ID NO 231
<211> LENGTH: 36
<212> TYPE: DNA
<213> ORGANISM: Artificial Sequence
<220> FEATURE:
<223> OTHER INFORMATION: Primer

<400> SEQUENCE: 231
aatccaccac ggatccatcg tccctgctcc ccgaac 36

<210> SEQ ID NO 232
<211> LENGTH: 38
<212> TYPE: DNA
<213> ORGANISM: Artificial Sequence
<220> FEATURE:
<223> OTHER INFORMATION: Primer

<400> SEQUENCE: 232
cagggacgat ggatccgtgg tggatttcgg ggcgttac 38

<210> SEQ ID NO 233
<211> LENGTH: 35
<212> TYPE: DNA
<213> ORGANISM: Artificial Sequence
<220> FEATURE:
<223> OTHER INFORMATION: Primer

<400> SEQUENCE: 233
ccgggagaag aattctccgg cggccggtgt gcggg 35

<210> SEQ ID NO 234
<211> LENGTH: 35
<212> TYPE: DNA
<213> ORGANISM: Artificial Sequence
<220> FEATURE:
<223> OTHER INFORMATION: Primer

<400> SEQUENCE: 234
gccgccggag aattcttctc ccggccgggg ctgcc 35

<210> SEQ ID NO 235
<211> LENGTH: 32
<212> TYPE: DNA
<213> ORGANISM: Artificial Sequence
<220> FEATURE:
<223> OTHER INFORMATION: Primer

<400> SEQUENCE: 235
gatatcaagc tttcagccgg cgcctaacga ac 32

<210> SEQ ID NO 236
<211> LENGTH: 905
<212> TYPE: PRT
<213> ORGANISM: Mycobacterium tuberculosis

<400> SEQUENCE: 236

Met Gly Ser Ser His His His His His His Ser Ser Gly Leu Val Pro
1 5 10 15

Arg Gly Ser His His Met Met Thr Ile Asn Tyr Gln Phe Gly Asp Val
20 25 30

Asp Ala His Gly Ala Met Ile Arg Ala Gln Ala Gly Ser Leu Glu Ala
35 40 45

Glu His Gln Ala Ile Ile Ser Asp Val Leu Thr Ala Ser Asp Phe Trp
50 55 60

Gly Gly Ala Gly Ser Ala Ala Cys Gln Gly Phe Ile Thr Gln Leu Gly
65 70 75 80

Arg Asn Phe Gln Val Ile Tyr Glu Gln Ala Asn Ala His Gly Gln Lys
85 90 95

Val Gln Ala Ala Gly Asn Asn Met Ala Gln Thr Asp Ser Ala Val Gly
100 105 110

```
Ser Ser Trp Ala Gly Thr Asp Asp Ile Asp Trp Asp Ala Ile Ala Gln
        115                 120                 125

Cys Glu Ser Gly Gly Asn Trp Ala Ala Asn Thr Gly Asn Gly Leu Tyr
    130                 135                 140

Gly Gly Leu Gln Ile Ser Gln Ala Thr Trp Asp Ser Asn Gly Gly Val
145                 150                 155                 160

Gly Ser Pro Ala Ala Ala Ser Pro Gln Gln Gln Ile Glu Val Ala Asp
                165                 170                 175

Asn Ile Met Lys Thr Gln Gly Pro Gly Ala Trp Pro Lys Cys Ser Ser
            180                 185                 190

Cys Ser Gln Gly Asp Ala Pro Leu Gly Ser Leu Thr His Ile Leu Thr
        195                 200                 205

Phe Leu Ala Ala Glu Thr Gly Gly Cys Ser Gly Ser Arg Asp Asp Gly
    210                 215                 220

Ser Val Val Asp Phe Gly Ala Leu Pro Pro Glu Ile Asn Ser Ala Arg
225                 230                 235                 240

Met Tyr Ala Gly Pro Gly Ser Ala Ser Leu Val Ala Ala Ala Lys Met
                245                 250                 255

Trp Asp Ser Val Ala Ser Asp Leu Phe Ser Ala Ala Ser Ala Phe Gln
            260                 265                 270

Ser Val Val Trp Gly Leu Thr Val Gly Ser Trp Ile Gly Ser Ser Ala
        275                 280                 285

Gly Leu Met Ala Ala Ala Ala Ser Pro Tyr Val Ala Trp Met Ser Val
    290                 295                 300

Thr Ala Gly Gln Ala Gln Leu Thr Ala Ala Gln Val Arg Val Ala Ala
305                 310                 315                 320

Ala Ala Tyr Glu Thr Ala Tyr Arg Leu Thr Val Pro Pro Pro Val Ile
                325                 330                 335

Ala Glu Asn Arg Thr Glu Leu Met Thr Leu Thr Ala Thr Asn Leu Leu
            340                 345                 350

Gly Gln Asn Thr Pro Ala Ile Glu Ala Asn Gln Ala Ala Tyr Ser Gln
        355                 360                 365

Met Trp Gly Gln Asp Ala Glu Ala Met Tyr Gly Tyr Ala Ala Thr Ala
    370                 375                 380

Ala Thr Ala Thr Glu Ala Leu Leu Pro Phe Glu Asp Ala Pro Leu Ile
385                 390                 395                 400

Thr Asn Pro Gly Gly Leu Leu Glu Gln Ala Val Ala Val Glu Glu Ala
                405                 410                 415

Ile Asp Thr Ala Ala Ala Asn Gln Leu Met Asn Asn Val Pro Gln Ala
            420                 425                 430

Leu Gln Gln Leu Ala Gln Pro Ala Gln Gly Val Val Pro Ser Ser Lys
        435                 440                 445

Leu Gly Gly Leu Trp Thr Ala Val Ser Pro His Leu Ser Pro Leu Ser
    450                 455                 460

Asn Val Ser Ser Ile Ala Asn Asn His Met Ser Met Met Gly Thr Gly
465                 470                 475                 480

Val Ser Met Thr Asn Thr Leu His Ser Met Leu Lys Gly Leu Ala Pro
                485                 490                 495

Ala Ala Ala Gln Ala Val Glu Thr Ala Ala Glu Asn Gly Val Trp Ala
            500                 505                 510

Met Ser Ser Leu Gly Ser Gln Leu Gly Ser Ser Leu Gly Ser Ser Gly
        515                 520                 525
```

-continued

```
Leu Gly Ala Gly Val Ala Ala Asn Leu Gly Arg Ala Ala Ser Val Gly
    530                 535                 540

Ser Leu Ser Val Pro Pro Ala Trp Ala Ala Ala Asn Gln Ala Val Thr
545                 550                 555                 560

Pro Ala Ala Arg Ala Leu Pro Leu Thr Ser Leu Thr Ser Ala Ala Gln
                565                 570                 575

Thr Ala Pro Gly His Met Leu Gly Gly Leu Pro Leu Gly His Ser Val
            580                 585                 590

Asn Ala Gly Ser Gly Ile Asn Asn Ala Leu Arg Val Pro Ala Arg Ala
        595                 600                 605

Tyr Ala Ile Pro Arg Thr Pro Ala Ala Gly Glu Phe Phe Ser Arg Pro
    610                 615                 620

Gly Leu Pro Val Glu Tyr Leu Gln Val Pro Ser Pro Ser Met Gly Arg
625                 630                 635                 640

Asp Ile Lys Val Gln Phe Gln Ser Gly Gly Asn Asn Ser Pro Ala Val
                645                 650                 655

Tyr Leu Leu Asp Gly Leu Arg Ala Gln Asp Asp Tyr Asn Gly Trp Asp
            660                 665                 670

Ile Asn Thr Pro Ala Phe Glu Trp Tyr Tyr Gln Ser Gly Leu Ser Ile
        675                 680                 685

Val Met Pro Val Gly Gly Gln Ser Ser Phe Tyr Ser Asp Trp Tyr Ser
    690                 695                 700

Pro Ala Cys Gly Lys Ala Gly Cys Gln Thr Tyr Lys Trp Glu Thr Phe
705                 710                 715                 720

Leu Thr Ser Glu Leu Pro Gln Trp Leu Ser Ala Asn Arg Ala Val Lys
                725                 730                 735

Pro Thr Gly Ser Ala Ala Ile Gly Leu Ser Met Ala Gly Ser Ser Ala
            740                 745                 750

Met Ile Leu Ala Ala Tyr His Pro Gln Gln Phe Ile Tyr Ala Gly Ser
        755                 760                 765

Leu Ser Ala Leu Leu Asp Pro Ser Gln Gly Met Gly Pro Ser Leu Ile
    770                 775                 780

Gly Leu Ala Met Gly Asp Ala Gly Gly Tyr Lys Ala Ala Asp Met Trp
785                 790                 795                 800

Gly Pro Ser Ser Asp Pro Ala Trp Glu Arg Asn Asp Pro Thr Gln Gln
                805                 810                 815

Ile Pro Lys Leu Val Ala Asn Asn Thr Arg Leu Trp Val Tyr Cys Gly
            820                 825                 830

Asn Gly Thr Pro Asn Glu Leu Gly Gly Ala Asn Ile Pro Ala Glu Phe
        835                 840                 845

Leu Glu Asn Phe Val Arg Ser Ser Asn Leu Lys Phe Gln Asp Ala Tyr
    850                 855                 860

Asn Ala Ala Gly Gly His Asn Ala Val Phe Asn Phe Pro Pro Asn Gly
865                 870                 875                 880

Thr His Ser Trp Glu Tyr Trp Gly Ala Gln Leu Asn Ala Met Lys Gly
                885                 890                 895

Asp Leu Gln Ser Ser Leu Gly Ala Gly
            900                 905
```

<210> SEQ ID NO 237
<211> LENGTH: 2025
<212> TYPE: DNA
<213> ORGANISM: Mycobacterium tuberculosis

<400> SEQUENCE: 237
catatgatga ccatcaacta tcaattcggg gacgtcgacg ctcacggcgc catgatccgc 60
gctcaggccg ggtcgctgga ggccgagcat caggccatca tttctgatgt gttgaccgcg 120
agtgactttt ggggcggcgc cggttcggcg gcctgccagg ggttcattac ccagctgggc 180
cgtaacttcc aggtgatcta cgagcaggcc aacgcccacg ggcagaaggt gcaggctgcc 240
ggcaacaaca tggcacaaac cgacagcgcc gtcggctcca gctgggccgg taccgacgac 300
atcgattggg acgccatcgc gcaatgcgaa tccggcggca attgggcggc caacaccggt 360
aacgggttat acggtggtct gcagatcagc caggcgacgt gggattccaa cggtggtgtc 420
gggtcgccgg cggccgcgag tccccagcaa cagatcgagg tcgcagacaa cattatgaaa 480
acccaaggcc cgggtgcgtg gccgaaatgt agttcttgta gtcagggaga cgcaccgctg 540
ggctcgctca cccacatcct gacgttcctc gcggccgaga ctggaggttg ttcggggagc 600
agggacgatg gatccgtggt ggatttcggg gcgttaccac cggagatcaa ctccgcgagg 660
atgtacgccg gcccgggttc ggcctcgctg gtggccgccg cgaagatgtg ggacagcgtg 720
gcgagtgacc tgttttcggc cgcgtcggcg tttcagtcgg tggtctgggg tctgacggtg 780
gggtcgtgga taggttcgtc ggcgggtctg atggcggcgg cggcctcgcc gtatgtggcg 840
tggatgagcg tcaccgcggg gcaggcccag ctgaccgccg cccaggtccg ggttgctgcg 900
gcggcctacg agacagcgta taggctgacg gtgcccccgc cggtgatcgc cgagaaccgt 960
accgaactga tgacgctgac cgcgaccaac ctcttggggc aaaacacgcc ggcgatcgag 1020
gccaatcagg ccgcatacag ccagatgtgg ggccaagacg cggaggcgat gtatggctac 1080
gccgccacgg cggcgacggc gaccgaggcg ttgctgccgt tcgaggacgc cccactgatc 1140
accaaccccg gcggggaatt cttctcccgg ccggggctgc cggtcgagta cctgcaggtg 1200
ccgtcgccgt cgatgggccg cgacatcaag gttcagttcc agagcggtgg gaacaactca 1260
cctgcggttt atctgctcga cggcctgcgc gcccaagacg actacaacgg ctgggatatc 1320
aacaccccgg cgttcgagtg gtactaccag tcgggactgt cgatagtcat gccggtcggc 1380
gggcagtcca gcttctacag cgactggtac agcccggcct gcggtaaggc tggctgccag 1440
acttacaagt gggaaacctt cctgaccagc gagctgccgc aatggttgtc cgccaacagg 1500
gccgtgaagc ccaccggcag cgctgcaatc ggcttgtcga tggccggctc gtcggcaatg 1560
atcttggccg cctaccaccc ccagcagttc atctacgccg gctcgctgtc ggccctgctg 1620
gacccctctc aggggatggg gcctagcctg atcggcctcg cgatgggtga cgccggcggt 1680
tacaaggccg cagacatgtg ggtccctcg agtgacccgg catgggagcg caacgaccct 1740
acgcagcaga tccccaagct ggtcgcaaac aacacccggc tatgggttta ttgcgggaac 1800
ggcaccccga acgagttggg cggtgccaac atacccgccg agttcttgga gaacttcgtt 1860
cgtagcagca acctgaagtt ccaggatgcg tacaacgccg cgggcgggca caacgccgtg 1920
ttcaacttcc cgcccaacgg cacgcacagc tgggagtact ggggcgctca gctcaacgcc 1980
atgaagggtg acctgcagag ttcgttaggc gccggctgaa agctt 2025

<210> SEQ ID NO 238
<211> LENGTH: 30
<212> TYPE: DNA
<213> ORGANISM: Artificial Sequence
<220> FEATURE:
<223> OTHER INFORMATION: Primer

<400> SEQUENCE: 238

-continued caattacata tgaccatcaa ctatcaattc 30

<210> SEQ ID NO 239
<211> LENGTH: 32
<212> TYPE: DNA
<213> ORGANISM: Artificial Sequence
<220> FEATURE:
<223> OTHER INFORMATION: Primer

<400> SEQUENCE: 239
caattaggta ccggcccagc tggagccgac gg 32

<210> SEQ ID NO 240
<211> LENGTH: 33
<212> TYPE: DNA
<213> ORGANISM: Artificial Sequence
<220> FEATURE:
<223> OTHER INFORMATION: Primer

<400> SEQUENCE: 240
tgggccggta ccgacgacat cgattgggac gcc 33

<210> SEQ ID NO 241
<211> LENGTH: 36
<212> TYPE: DNA
<213> ORGANISM: Artificial Sequence
<220> FEATURE:
<223> OTHER INFORMATION: Primer

<400> SEQUENCE: 241
aatccaccac ggatccatcg tccctgctcc ccgaac 36

<210> SEQ ID NO 242
<211> LENGTH: 39
<212> TYPE: DNA
<213> ORGANISM: Artificial Sequence
<220> FEATURE:
<223> OTHER INFORMATION: Primer

<400> SEQUENCE: 242
cggccgggag aagaattccc cgccggggtt ggtgatcag 39

<210> SEQ ID NO 243
<211> LENGTH: 35
<212> TYPE: DNA
<213> ORGANISM: Artificial Sequence
<220> FEATURE:
<223> OTHER INFORMATION: Primer

<400> SEQUENCE: 243
gccgccggag aattcttctc ccggccgggg ctgcc 35

<210> SEQ ID NO 244
<211> LENGTH: 32
<212> TYPE: DNA
<213> ORGANISM: Artificial Sequence
<220> FEATURE:
<223> OTHER INFORMATION: Primer

<400> SEQUENCE: 244
gatatcaagc tttcagccgg cgcctaacga ac 32

<210> SEQ ID NO 245
<211> LENGTH: 672
<212> TYPE: PRT
<213> ORGANISM: Mycobacterium tuberculosis

<400> SEQUENCE: 245

His Met Met Thr Ile Asn Tyr Gln Phe Gly Asp Val Asp Ala His Gly
1               5                   10                  15

Ala Met Ile Arg Ala Gln Ala Gly Ser Leu Glu Ala Glu His Gln Ala
            20                  25                  30

Ile Ile Ser Asp Val Leu Thr Ala Ser Asp Phe Trp Gly Gly Ala Gly
        35                  40                  45

Ser Ala Ala Cys Gln Gly Phe Ile Thr Gln Leu Gly Arg Asn Phe Gln
    50                  55                  60

Val Ile Tyr Glu Gln Ala Asn Ala His Gly Gln Lys Val Gln Ala Ala
65                  70                  75                  80

Gly Asn Asn Met Ala Gln Thr Asp Ser Ala Val Gly Ser Ser Trp Ala
                85                  90                  95

Gly Thr Asp Asp Ile Asp Trp Asp Ala Ile Ala Gln Cys Glu Ser Gly
            100                 105                 110

Gly Asn Trp Ala Ala Asn Thr Gly Asn Gly Leu Tyr Gly Gly Leu Gln
        115                 120                 125

Ile Ser Gln Ala Thr Trp Asp Ser Asn Gly Gly Val Gly Ser Pro Ala
    130                 135                 140

Ala Ala Ser Pro Gln Gln Gln Ile Glu Val Ala Asp Asn Ile Met Lys
145                 150                 155                 160

Thr Gln Gly Pro Gly Ala Trp Pro Lys Cys Ser Ser Cys Ser Gln Gly
                165                 170                 175

Asp Ala Pro Leu Gly Ser Leu Thr His Ile Leu Thr Phe Leu Ala Ala
            180                 185                 190

Glu Thr Gly Gly Cys Ser Gly Ser Arg Asp Asp Gly Ser Val Val Asp
        195                 200                 205

Phe Gly Ala Leu Pro Pro Glu Ile Asn Ser Ala Arg Met Tyr Ala Gly
    210                 215                 220

Pro Gly Ser Ala Ser Leu Val Ala Ala Ala Lys Met Trp Asp Ser Val
225                 230                 235                 240

Ala Ser Asp Leu Phe Ser Ala Ala Ser Ala Phe Gln Ser Val Val Trp
                245                 250                 255

Gly Leu Thr Val Gly Ser Trp Ile Gly Ser Ser Ala Gly Leu Met Ala
            260                 265                 270

Ala Ala Ala Ser Pro Tyr Val Ala Trp Met Ser Val Thr Ala Gly Gln
        275                 280                 285

Ala Gln Leu Thr Ala Ala Gln Val Arg Val Ala Ala Ala Ala Tyr Glu
    290                 295                 300

Thr Ala Tyr Arg Leu Thr Val Pro Pro Pro Val Ile Ala Glu Asn Arg
305                 310                 315                 320

Thr Glu Leu Met Thr Leu Thr Ala Thr Asn Leu Leu Gly Gln Asn Thr
                325                 330                 335

Pro Ala Ile Glu Ala Asn Gln Ala Ala Tyr Ser Gln Met Trp Gly Gln
            340                 345                 350

Asp Ala Glu Ala Met Tyr Gly Tyr Ala Ala Thr Ala Ala Thr Ala Thr
        355                 360                 365

Glu Ala Leu Leu Pro Phe Glu Asp Ala Pro Leu Ile Thr Asn Pro Gly
    370                 375                 380

Gly Glu Phe Phe Ser Arg Pro Gly Leu Pro Val Glu Tyr Leu Gln Val
385                 390                 395                 400

Pro Ser Pro Ser Met Gly Arg Asp Ile Lys Val Gln Phe Gln Ser Gly

```
                405                 410                 415

Gly Asn Asn Ser Pro Ala Val Tyr Leu Leu Asp Gly Leu Arg Ala Gln
            420                 425                 430

Asp Asp Tyr Asn Gly Trp Asp Ile Asn Thr Pro Ala Phe Glu Trp Tyr
        435                 440                 445

Tyr Gln Ser Gly Leu Ser Ile Val Met Pro Val Gly Gly Gln Ser Ser
    450                 455                 460

Phe Tyr Ser Asp Trp Tyr Ser Pro Ala Cys Gly Lys Ala Gly Cys Gln
465                 470                 475                 480

Thr Tyr Lys Trp Glu Thr Phe Leu Thr Ser Glu Leu Pro Gln Trp Leu
                485                 490                 495

Ser Ala Asn Arg Ala Val Lys Pro Thr Gly Ser Ala Ala Ile Gly Leu
            500                 505                 510

Ser Met Ala Gly Ser Ser Ala Met Ile Leu Ala Ala Tyr His Pro Gln
        515                 520                 525

Gln Phe Ile Tyr Ala Gly Ser Leu Ser Ala Leu Leu Asp Pro Ser Gln
    530                 535                 540

Gly Met Gly Pro Ser Leu Ile Gly Leu Ala Met Gly Asp Ala Gly Gly
545                 550                 555                 560

Tyr Lys Ala Ala Asp Met Trp Gly Pro Ser Ser Asp Pro Ala Trp Glu
                565                 570                 575

Arg Asn Asp Pro Thr Gln Gln Ile Pro Lys Leu Val Ala Asn Asn Thr
            580                 585                 590

Arg Leu Trp Val Tyr Cys Gly Asn Gly Thr Pro Asn Glu Leu Gly Gly
        595                 600                 605

Ala Asn Ile Pro Ala Glu Phe Leu Glu Asn Phe Val Arg Ser Ser Asn
    610                 615                 620

Leu Lys Phe Gln Asp Ala Tyr Asn Ala Ala Gly Gly His Asn Ala Val
625                 630                 635                 640

Phe Asn Phe Pro Pro Asn Gly Thr His Ser Trp Glu Tyr Trp Gly Ala
                645                 650                 655

Gln Leu Asn Ala Met Lys Gly Asp Leu Gln Ser Ser Leu Gly Ala Gly
            660                 665                 670
```

<210> SEQ ID NO 246
<211> LENGTH: 3318
<212> TYPE: DNA
<213> ORGANISM: Mycobacterium tuberculosis

<400> SEQUENCE: 246

```
atgggcagca gccatcatca tcatcatcac agcagcggcc tggtgccgcg cggcagccat     60

atgggtaccc atctcgccaa cggttcgatg tcggaagtca tgatgtcgga aattgccggg    120

ttgcctatcc ctccgattat ccattacggg gcgattgcct atgcccccag cggcgcgtcg    180

ggcaaagcgt ggcaccagcg cacaccggcg cgagcagagc aagtcgcact agaaaagtgc    240

ggtgacaaga cttgcaaagt ggttagtcgc ttcaccaggt gcggcgcggt cgcctacaac    300

ggctcgaaat accaaggcgg aaccggactc acgcgccgcg cggcagaaga cgacgccgtg    360

aaccgactcg aaggcgggcg gatcgtcaac tgggcgtgca acgagctcat gacctcgcgt    420

tttatgacgg atccgcacgc gatgcgggac atggcgggcc gttttgaggt gcacgcccag    480

acggtggagg acgaggctcg ccggatgtgg gcgtccgcgc aaaacatctc gggcgcgggc    540

tggagtggca tggccgaggc gacctcgcta gacaccatga cccagatgaa tcaggcgttt    600

cgcaacatcg tgaacatgct gcacggggtg cgtgacgggc tggttcgcga cgccaacaac    660
```

-continued

```
tacgaacagc aagagcaggc ctcccagcag atcctcagca gcgtcgacat caatttcgcc    720
gttttgccgc cggaggtgaa ttcggcgcgc atattcgccg gtgcgggcct gggcccaatg    780
ctggcggcgg cgtcggcctg ggacgggttg gccgaggagt tgcatgccgc ggcgggctcg    840
ttcgcgtcgg tgaccaccgg gttggcgggc gacgcgtggc atggtccggc gtcgctggcg    900
atgacccgcg cggccagccc gtatgtgggg tggttgaaca cggcggcggg tcaggccgcg    960
caggcggccg gccaggcgcg gctagcggcg agcgcgttcg aggcgacgct ggcggccacc   1020
gtgtctccag cgatggtcgc ggccaaccgg acacggctgg cgtcgctggt ggcagccaac   1080
ttgctgggcc agaacgcccc ggcgatcgcg gccgcggagg ctgaatacga gcagatatgg   1140
gcccaggacg tggccgcgat gttcggctat cactccgccg cgtcggcggt ggccacgcag   1200
ctggcgccta ttcaagaggg tttgcagcag cagctgcaaa acgtgctggc ccagttggct   1260
agcgggaacc tgggcagcgg aaatgtgggc gtcggcaaca tcggcaacga caacattggc   1320
aacgcaaaca tcggcttcgg aaatcgaggc gacgccaaca tcggcatcgg gaatatcggc   1380
gacagaaacc tcggcattgg gaacaccggc aattggaata tcggcatcgg catcaccggc   1440
aacggacaaa tcggcttcgg caagcctgcc aaccccgacg tcttggtggt gggcaacggc   1500
ggcccgggag taaccgcgtt ggtcatgggc ggcaccgaca gcctactgcc gctgcccaac   1560
atccccttac tcgagtacgc tgcgcggttc atcacccccg tgcatcccgg atacaccgct   1620
acgttcctgg aaacgccatc gcagtttttc ccattcaccg ggctgaatag cctgacctat   1680
gacgtctccg tggcccaggg cgtaacgaat ctgcacaccg cgatcatggc gcaactcgcg   1740
gcgggaaacg aagtcgtcgt cttcggcacc tcccaaagcg ccacgatagc caccttcgaa   1800
atgcgctatc tgcaatccct gccagcacac ctgcgtccgg gtctcgacga attgtccttt   1860
acgttgaccg gcaatcccaa ccggcccgac ggtggcattc ttacgcgttt tggcttctcc   1920
ataccgcagt tgggtttcac attgtccggc gcgacgcccg ccgacgccta ccccaccgtc   1980
gattacgcgt tccagtacga cggcgtcaac gacttcccca aatacccgct gaatgtcttc   2040
gcgaccgcca acgcgatcgc gggcatcctt ttcctgcact ccgggttgat tgcgttgccg   2100
cccgatcttg cctcgggcgt ggttcaaccg gtgtcctcac cggacgtcct gaccacctac   2160
atcctgctgc ccagccaaga tctgccgctg ctggtcccgc tgcgtgctat ccccctgctg   2220
ggaaacccgc ttgccgacct catccagccg gacttgcggg tgctcgtcga gttgggttat   2280
gaccgcaccg cccaccagga cgtgcccagc ccgttcggac tgtttccgga cgtcgattgg   2340
gccgaggtgg ccgcggacct gcagcaaggc gccgtgcaag gcgtcaacga cgccctgtcc   2400
ggactggggc tgccgccgcc gtggcagccg gcgctacccc gacttttcag tactttctcc   2460
cggccggggc tgccggtcga gtacctgcag gtgccgtcgc cgtcgatggg ccgcgacatc   2520
aaggttcagt tccagagcgg tgggaacaac tcacctgcgg tttatctgct cgacggcctg   2580
cgcgcccaag acgactacaa cggctgggat atcaacaccc cggcgttcga gtggtactac   2640
cagtcgggac tgtcgatagt catgccggtc ggcgggcagt ccagcttcta cagcgactgg   2700
tacagcccgg cctgcggtaa ggctggctgc cagacttaca agtgggaaac cttcctgacc   2760
agcgagctgc cgcaatggtt gtccgccaac agggccgtga agcccaccgg cagcgctgca   2820
atcggcttgt cgatggccgg ctcgtcggca atgatcttgg ccgcctacca cccccagcag   2880
ttcatctacg ccggctcgct gtcggccctg ctggacccct ctcaggggat ggggcctagc   2940
ctgatcggcc tcgcgatggg tgacgccggc ggttacaagg ccgcagacat gtggggtccc   3000
```

tcgagtgacc cggcatggga gcgcaacgac cctacgcagc agatccccaa gctggtcgca 3060
aacaacaccc ggctatgggt ttattgcggg aacggcaccc cgaacgagtt gggcggtgcc 3120 aacataccg ccgagttctt ggagaacttc gttcgtagca gcaacctgaa gttccaggat 3180
gcgtacaacg ccgcgggcgg gcacaacgcc gtgttcaact tcccgcccaa cggcacgcac 3240
agctgggagt actggggcgc tcagctcaac gccatgaagg gtgacctgca gagttcgtta 3300
ggcgccggct gaaagctt 3318

<210> SEQ ID NO 247
<211> LENGTH: 33
<212> TYPE: DNA
<213> ORGANISM: Artificial Sequence
<220> FEATURE:
<223> OTHER INFORMATION: Primer

<400> SEQUENCE: 247
caattagtcg acatgaattt cgccgttttg ccg 33

<210> SEQ ID NO 248
<211> LENGTH: 42
<212> TYPE: DNA
<213> ORGANISM: Artificial Sequence
<220> FEATURE:
<223> OTHER INFORMATION: Primer

<400> SEQUENCE: 248
caattaaagc ttttaagtac tgaaaagtcg ggtagcgcc gg 42

<210> SEQ ID NO 249
<211> LENGTH: 47
<212> TYPE: DNA
<213> ORGANISM: Artificial Sequence
<220> FEATURE:
<223> OTHER INFORMATION: Primer

<400> SEQUENCE: 249
cggcgctacc ccgacttttc agtactttct cccggccggg gctgccg 47

<210> SEQ ID NO 250
<211> LENGTH: 32
<212> TYPE: DNA
<213> ORGANISM: Artificial Sequence
<220> FEATURE:
<223> OTHER INFORMATION: Primer

<400> SEQUENCE: 250
gatatcaagc tttcagccgg cgcctaacga ac 32

<210> SEQ ID NO 251
<211> LENGTH: 1103
<212> TYPE: PRT
<213> ORGANISM: Mycobacterium tuberculosis

<400> SEQUENCE: 251

Met Gly Ser Ser His His His His His His Ser Ser Gly Leu Val Pro
1 5 10 15

Arg Gly Ser His Met Gly Thr His Leu Ala Asn Gly Ser Met Ser Glu
20 25 30

Val Met Met Ser Glu Ile Ala Gly Leu Pro Ile Pro Pro Ile Ile His
35 40 45

Tyr Gly Ala Ile Ala Tyr Ala Pro Ser Gly Ala Ser Gly Lys Ala Trp
50 55 60

-continued

```
His Gln Arg Thr Pro Ala Arg Ala Glu Gln Val Ala Leu Glu Lys Cys
65                  70                  75                  80

Gly Asp Lys Thr Cys Lys Val Val Ser Arg Phe Thr Arg Cys Gly Ala
                85                  90                  95

Val Ala Tyr Asn Gly Ser Lys Tyr Gln Gly Gly Thr Gly Leu Thr Arg
            100                 105                 110

Arg Ala Ala Glu Asp Asp Ala Val Asn Arg Leu Glu Gly Gly Arg Ile
        115                 120                 125

Val Asn Trp Ala Cys Asn Glu Leu Met Thr Ser Arg Phe Met Thr Asp
    130                 135                 140

Pro His Ala Met Arg Asp Met Ala Gly Arg Phe Glu Val His Ala Gln
145                 150                 155                 160

Thr Val Glu Asp Glu Ala Arg Arg Met Trp Ala Ser Ala Gln Asn Ile
                165                 170                 175

Ser Gly Ala Gly Trp Ser Gly Met Ala Glu Ala Thr Ser Leu Asp Thr
            180                 185                 190

Met Thr Gln Met Asn Gln Ala Phe Arg Asn Ile Val Asn Met Leu His
        195                 200                 205

Gly Val Arg Asp Gly Leu Val Arg Asp Ala Asn Asn Tyr Glu Gln Gln
    210                 215                 220

Glu Gln Ala Ser Gln Gln Ile Leu Ser Ser Val Asp Met Asn Phe Ala
225                 230                 235                 240

Val Leu Pro Pro Glu Val Asn Ser Ala Arg Ile Phe Ala Gly Ala Gly
                245                 250                 255

Leu Gly Pro Met Leu Ala Ala Ala Ser Ala Trp Asp Gly Leu Ala Glu
            260                 265                 270

Glu Leu His Ala Ala Ala Gly Ser Phe Ala Ser Val Thr Thr Gly Leu
        275                 280                 285

Ala Gly Asp Ala Trp His Gly Pro Ala Ser Leu Ala Met Thr Arg Ala
    290                 295                 300

Ala Ser Pro Tyr Val Gly Trp Leu Asn Thr Ala Ala Gly Gln Ala Ala
305                 310                 315                 320

Gln Ala Ala Gly Gln Ala Arg Leu Ala Ala Ser Ala Phe Glu Ala Thr
                325                 330                 335

Leu Ala Ala Thr Val Ser Pro Ala Met Val Ala Ala Asn Arg Thr Arg
            340                 345                 350

Leu Ala Ser Leu Val Ala Ala Asn Leu Leu Gly Gln Asn Ala Pro Ala
        355                 360                 365

Ile Ala Ala Ala Glu Ala Glu Tyr Glu Gln Ile Trp Ala Gln Asp Val
    370                 375                 380

Ala Ala Met Phe Gly Tyr His Ser Ala Ala Ser Ala Val Ala Thr Gln
385                 390                 395                 400

Leu Ala Pro Ile Gln Glu Gly Leu Gln Gln Gln Leu Gln Asn Val Leu
                405                 410                 415

Ala Gln Leu Ala Ser Gly Asn Leu Gly Ser Gly Asn Val Gly Val Gly
            420                 425                 430

Asn Ile Gly Asn Asp Asn Ile Gly Asn Ala Asn Ile Gly Phe Gly Asn
        435                 440                 445

Arg Gly Asp Ala Asn Ile Gly Ile Gly Asn Ile Gly Asp Arg Asn Leu
    450                 455                 460

Gly Ile Gly Asn Thr Gly Asn Trp Asn Ile Gly Ile Gly Ile Thr Gly
465                 470                 475                 480
```

```
Asn Gly Gln Ile Gly Phe Gly Lys Pro Ala Asn Pro Asp Val Leu Val
                485                 490                 495

Val Gly Asn Gly Gly Pro Gly Val Thr Ala Leu Val Met Gly Gly Thr
            500                 505                 510

Asp Ser Leu Leu Pro Leu Pro Asn Ile Pro Leu Leu Glu Tyr Ala Ala
        515                 520                 525

Arg Phe Ile Thr Pro Val His Pro Gly Tyr Thr Ala Thr Phe Leu Glu
    530                 535                 540

Thr Pro Ser Gln Phe Phe Pro Phe Thr Gly Leu Asn Ser Leu Thr Tyr
545                 550                 555                 560

Asp Val Ser Val Ala Gln Gly Val Thr Asn Leu His Thr Ala Ile Met
                565                 570                 575

Ala Gln Leu Ala Ala Gly Asn Glu Val Val Val Phe Gly Thr Ser Gln
            580                 585                 590

Ser Ala Thr Ile Ala Thr Phe Glu Met Arg Tyr Leu Gln Ser Leu Pro
        595                 600                 605

Ala His Leu Arg Pro Gly Leu Asp Glu Leu Ser Phe Thr Leu Thr Gly
    610                 615                 620

Asn Pro Asn Arg Pro Asp Gly Gly Ile Leu Thr Arg Phe Gly Phe Ser
625                 630                 635                 640

Ile Pro Gln Leu Gly Phe Thr Leu Ser Gly Ala Thr Pro Ala Asp Ala
                645                 650                 655

Tyr Pro Thr Val Asp Tyr Ala Phe Gln Tyr Asp Gly Val Asn Asp Phe
            660                 665                 670

Pro Lys Tyr Pro Leu Asn Val Phe Ala Thr Ala Asn Ala Ile Ala Gly
        675                 680                 685

Ile Leu Phe Leu His Ser Gly Leu Ile Ala Leu Pro Pro Asp Leu Ala
    690                 695                 700

Ser Gly Val Val Gln Pro Val Ser Ser Pro Asp Val Leu Thr Thr Tyr
705                 710                 715                 720

Ile Leu Leu Pro Ser Gln Asp Leu Pro Leu Leu Val Pro Leu Arg Ala
                725                 730                 735

Ile Pro Leu Leu Gly Asn Pro Leu Ala Asp Leu Ile Gln Pro Asp Leu
            740                 745                 750

Arg Val Leu Val Glu Leu Gly Tyr Asp Arg Thr Ala His Gln Asp Val
        755                 760                 765

Pro Ser Pro Phe Gly Leu Phe Pro Asp Val Asp Trp Ala Glu Val Ala
    770                 775                 780

Ala Asp Leu Gln Gln Gly Ala Val Gln Gly Val Asn Asp Ala Leu Ser
785                 790                 795                 800

Gly Leu Gly Leu Pro Pro Pro Trp Gln Pro Ala Leu Pro Arg Leu Phe
                805                 810                 815

Ser Thr Phe Ser Arg Pro Gly Leu Pro Val Glu Tyr Leu Gln Val Pro
            820                 825                 830

Ser Pro Ser Met Gly Arg Asp Ile Lys Val Gln Phe Gln Ser Gly Gly
        835                 840                 845

Asn Asn Ser Pro Ala Val Tyr Leu Leu Asp Gly Leu Arg Ala Gln Asp
    850                 855                 860

Asp Tyr Asn Gly Trp Asp Ile Asn Thr Pro Ala Phe Glu Trp Tyr Tyr
865                 870                 875                 880

Gln Ser Gly Leu Ser Ile Val Met Pro Val Gly Gly Gln Ser Ser Phe
                885                 890                 895

Tyr Ser Asp Trp Tyr Ser Pro Ala Cys Gly Lys Ala Gly Cys Gln Thr
```

-continued

```
            900                 905                 910

Tyr Lys Trp Glu Thr Phe Leu Thr Ser Glu Leu Pro Gln Trp Leu Ser
        915                 920                 925

Ala Asn Arg Ala Val Lys Pro Thr Gly Ser Ala Ala Ile Gly Leu Ser
    930                 935                 940

Met Ala Gly Ser Ser Ala Met Ile Leu Ala Ala Tyr His Pro Gln Gln
945                 950                 955                 960

Phe Ile Tyr Ala Gly Ser Leu Ser Ala Leu Leu Asp Pro Ser Gln Gly
                965                 970                 975

Met Gly Pro Ser Leu Ile Gly Leu Ala Met Gly Asp Ala Gly Gly Tyr
            980                 985                 990

Lys Ala Ala Asp Met Trp Gly Pro Ser Ser Asp Pro Ala Trp Glu Arg
        995                 1000                1005

Asn Asp Pro Thr Gln Gln Ile Pro Lys Leu Val Ala Asn Asn Thr Arg
    1010                1015                1020

Leu Trp Val Tyr Cys Gly Asn Gly Thr Pro Asn Glu Leu Gly Gly Ala
1025                1030                1035                1040

Asn Ile Pro Ala Glu Phe Leu Glu Asn Phe Val Arg Ser Ser Asn Leu
                1045                1050                1055

Lys Phe Gln Asp Ala Tyr Asn Ala Ala Gly Gly His Asn Ala Val Phe
            1060                1065                1070

Asn Phe Pro Pro Asn Gly Thr His Ser Trp Glu Tyr Trp Gly Ala Gln
        1075                1080                1085

Leu Asn Ala Met Lys Gly Asp Leu Gln Ser Ser Leu Gly Ala Gly
    1090                1095                1100


<210> SEQ ID NO 252
<211> LENGTH: 3597
<212> TYPE: DNA
<213> ORGANISM: Mycobacterium tuberculosis

<400> SEQUENCE: 252

atgggcagca gccatcatca tcatcatcac agcagcggcc tggtgccgcg cggcagccat      60

atgaccatca actatcaatt cggggacgtc gacgctcacg gcgccatgat ccgcgctcag     120

gccgggtcgc tggaggccga gcatcaggcc atcatttctg atgtgttgac cgcgagtgac     180

ttttggggcg gcgccggttc ggcggcctgc caggggttca ttacccagct gggccgtaac     240

ttccaggtga tctacgagca ggccaacgcc cacgggcaga aggtgcaggc tgccggcaac     300

aacatggcac aaaccgacag cgccgtcggc tccagctggg ccggtaccca tctcgccaac     360

ggttcgatgt cggaagtcat gatgtcggaa attgccgggt tgcctatccc tccgattatc     420

cattacgggg cgattgccta tgcccccagc ggcgcgtcgg gcaaagcgtg gcaccagcgc     480

acaccggcgc gagcagagca agtcgcacta gaaaagtgcg gtgacaagac ttgcaaagtg     540

gttagtcgct tcaccaggtg cggcgcggtc gcctacaacg gctcgaaata ccaaggcgga     600

accggactca cgcgccgcgc ggcagaagac gacgccgtga accgactcga aggcgggcgg     660

atcgtcaact gggcgtgcaa cgagctcatg acctcgcgtt ttatgacgga tccgcacgcg     720

atgcgggaca tggcgggccg ttttgaggtg cacgcccaga cggtggagga cgaggctcgc     780

cggatgtggg cgtccgcgca aaacatctcg ggcgcgggct ggagtggcat ggccgaggcg     840

acctcgctag acaccatgac ccagatgaat caggcgtttc gcaacatcgt gaacatgctg     900

cacggggtgc gtgacgggct ggttcgcgac gccaacaact acgaacagca agagcaggcc     960

tcccagcaga tcctcagcag cgtcgacatc aatttcgccg ttttgccgcc ggaggtgaat    1020
```

tcggcgcgca tattcgccgg tgcgggcctg ggcccaatgc tggcggcggc gtcggcctgg 1080
gacgggttgg ccgaggagtt gcatgccgcg gcgggctcgt tcgcgtcggt gaccaccggg 1140
ttggcgggcg acgcgtggca tggtccggcg tcgctggcga tgacccgcgc ggccagcccg 1200
tatgtggggt ggttgaacac ggcggcgggt caggccgcgc aggcggccgg ccaggcgcgg 1260
ctagcggcga gcgcgttcga ggcgacgctg gcggccaccg tgtctccagc gatggtcgcg 1320
gccaaccgga cacggctggc gtcgctggtg gcagccaact tgctgggcca gaacgccccg 1380
gcgatcgcgg ccgcggaggc tgaatacgag cagatatggg cccaggacgt ggccgcgatg 1440
ttcggctatc actccgccgc gtcggcggtg gccacgcagc tggcgcctat tcaagagggt 1500
ttgcagcagc agctgcaaaa cgtgctggcc cagttggcta gcgggaacct gggcagcgga 1560
aatgtgggcg tcggcaacat cggcaacgac aacattggca acgcaaacat cggcttcgga 1620
aatcgaggcg acgccaacat cggcatcggg aatatcggcg acagaaacct cggcattggg 1680
aacaccggca attggaatat cggcatcggc atcaccggca acggacaaat cggcttcggc 1740
aagcctgcca accccgacgt cttggtggtg ggcaacggcg gcccgggagt aaccgcgttg 1800
gtcatgggcg gcaccgacag cctactgccg ctgcccaaca tccccttact cgagtacgct 1860
gcgcggttca tcacccccgt gcatcccgga tacaccgcta cgttcctgga aacgccatcg 1920
cagtttttcc cattcaccgg gctgaatagc ctgacctatg acgtctccgt ggcccagggc 1980
gtaacgaatc tgcacaccgc gatcatggcg caactcgcgg cgggaaacga agtcgtcgtc 2040
ttcggcacct cccaaagcgc cacgatagcc accttcgaaa tgcgctatct gcaatccctg 2100
ccagcacacc tgcgtccggg tctcgacgaa ttgtccttta cgttgaccgg caatcccaac 2160
cggcccgacg gtggcattct tacgcgtttt ggcttctcca taccgcagtt gggtttcaca 2220
ttgtccggcg cgacgcccgc cgacgcctac cccaccgtcg attacgcgtt ccagtacgac 2280
ggcgtcaacg acttccccaa atacccgctg aatgtcttcg cgaccgccaa cgcgatcgcg 2340
ggcatccttt tcctgcactc cgggttgatt gcgttgccgc ccgatcttgc ctcgggcgtg 2400
gttcaaccgg tgtcctcacc ggacgtcctg accacctaca tcctgctgcc cagccaagat 2460
ctgccgctgc tggtcccgct gcgtgctatc cccctgctgg gaaacccgct tgccgacctc 2520
atccagccgg acttgcgggt gctcgtcgag ttgggttatg accgcaccgc ccaccaggac 2580
gtgcccagcc cgttcggact gtttccggac gtcgattggg ccgaggtggc cgcggacctg 2640
cagcaaggcg ccgtgcaagg cgtcaacgac gccctgtccg gactggggct gccgccgccg 2700
tggcagccgg cgctaccccg acttttcagt actttctccc ggccggggct gccggtcgag 2760
tacctgcagg tgccgtcgcc gtcgatgggc cgcgacatca aggttcagtt ccagagcggt 2820
gggaacaact cacctgcggt ttatctgctc gacggcctgc gcgcccaaga cgactacaac 2880
ggctgggata tcaacacccc ggcgttcgag tggtactacc agtcgggact gtcgatagtc 2940
atgccggtcg gcgggcagtc cagcttctac agcgactggt acagcccggc ctgcggtaag 3000
gctggctgcc agacttacaa gtgggaaacc ttcctgacca gcgagctgcc gcaatggttg 3060
tccgccaaca gggccgtgaa gcccaccggc agcgctgcaa tcggcttgtc gatggccggc 3120
tcgtcggcaa tgatcttggc cgcctaccac ccccagcagt tcatctacgc cggctcgctg 3180
tcggccctgc tggacccctc tcaggggatg ggcctagcc tgatcggcct cgcgatgggt 3240
gacgccggcg gttacaaggc cgcagacatg tggggtccct cgagtgaccc ggcatgggag 3300
cgcaacgacc ctacgcagca gatccccaag ctggtcgcaa acaacacccg gctatgggtt 3360
tattgcggga acggcacccc gaacgagttg ggcggtgcca acatacccgc cgagttcttg 3420
gagaacttcg ttcgtagcag caacctgaag ttccaggatg cgtacaacgc cgcgggcggg 3480
cacaacgccg tgttcaactt cccgcccaac ggcacgcaca gctgggagta ctggggcgct 3540
cagctcaacg ccatgaaggg tgacctgcag agttcgttag gcgccggctg aaagctt 3597

<210> SEQ ID NO 253
<211> LENGTH: 33
<212> TYPE: DNA
<213> ORGANISM: Artificial Sequence
<220> FEATURE:
<223> OTHER INFORMATION: Primer

<400> SEQUENCE: 253
caattagtcg acatgaattt cgccgttttg ccg 33

<210> SEQ ID NO 254
<211> LENGTH: 42
<212> TYPE: DNA
<213> ORGANISM: Artificial Sequence
<220> FEATURE:
<223> OTHER INFORMATION: Primer

<400> SEQUENCE: 254
caattaaagc ttttaagtac tgaaaagtcg ggtagcgcc gg 42

<210> SEQ ID NO 255
<211> LENGTH: 47
<212> TYPE: DNA
<213> ORGANISM: Artificial Sequence
<220> FEATURE:
<223> OTHER INFORMATION: Primer

<400> SEQUENCE: 255
cggcgctacc ccgacttttc agtactttct cccggccggg gctgccg 47

<210> SEQ ID NO 256
<211> LENGTH: 32
<212> TYPE: DNA
<213> ORGANISM: Artificial Sequence
<220> FEATURE:
<223> OTHER INFORMATION: Primer

<400> SEQUENCE: 256
gatatcaagc tttcagccgg cgcctaacga ac 32

<210> SEQ ID NO 257
<211> LENGTH: 1196
<212> TYPE: PRT
<213> ORGANISM: Mycobacterium tuberculosis

<400> SEQUENCE: 257

Met Gly Ser Ser His His His His His His Ser Ser Gly Leu Val Pro
1 5 10 15

Arg Gly Ser His Met Thr Ile Asn Tyr Gln Phe Gly Asp Val Asp Ala
20 25 30

His Gly Ala Met Ile Arg Ala Gln Ala Gly Ser Leu Glu Ala Glu His
35 40 45

Gln Ala Ile Ile Ser Asp Val Leu Thr Ala Ser Asp Phe Trp Gly Gly
50 55 60

Ala Gly Ser Ala Ala Cys Gln Gly Phe Ile Thr Gln Leu Gly Arg Asn
65 70 75 80

-continued

```
Phe Gln Val Ile Tyr Glu Gln Ala Asn Ala His Gly Gln Lys Val Gln
                85                  90                  95

Ala Ala Gly Asn Asn Met Ala Gln Thr Asp Ser Ala Val Gly Ser Ser
            100                 105                 110

Trp Ala Gly Thr His Leu Ala Asn Gly Ser Met Ser Glu Val Met Met
        115                 120                 125

Ser Glu Ile Ala Gly Leu Pro Ile Pro Pro Ile Ile His Tyr Gly Ala
    130                 135                 140

Ile Ala Tyr Ala Pro Ser Gly Ala Ser Gly Lys Ala Trp His Gln Arg
145                 150                 155                 160

Thr Pro Ala Arg Ala Glu Gln Val Ala Leu Glu Lys Cys Gly Asp Lys
                165                 170                 175

Thr Cys Lys Val Val Ser Arg Phe Thr Arg Cys Gly Ala Val Ala Tyr
            180                 185                 190

Asn Gly Ser Lys Tyr Gln Gly Gly Thr Gly Leu Thr Arg Arg Ala Ala
        195                 200                 205

Glu Asp Asp Ala Val Asn Arg Leu Glu Gly Gly Arg Ile Val Asn Trp
    210                 215                 220

Ala Cys Asn Glu Leu Met Thr Ser Arg Phe Met Thr Asp Pro His Ala
225                 230                 235                 240

Met Arg Asp Met Ala Gly Arg Phe Glu Val His Ala Gln Thr Val Glu
                245                 250                 255

Asp Glu Ala Arg Arg Met Trp Ala Ser Ala Gln Asn Ile Ser Gly Ala
            260                 265                 270

Gly Trp Ser Gly Met Ala Glu Ala Thr Ser Leu Asp Thr Met Thr Gln
        275                 280                 285

Met Asn Gln Ala Phe Arg Asn Ile Val Asn Met Leu His Gly Val Arg
    290                 295                 300

Asp Gly Leu Val Arg Asp Ala Asn Asn Tyr Glu Gln Gln Glu Gln Ala
305                 310                 315                 320

Ser Gln Gln Ile Leu Ser Ser Val Asp Ile Asn Phe Ala Val Leu Pro
                325                 330                 335

Pro Glu Val Asn Ser Ala Arg Ile Phe Ala Gly Ala Gly Leu Gly Pro
            340                 345                 350

Met Leu Ala Ala Ala Ser Ala Trp Asp Gly Leu Ala Glu Glu Leu His
        355                 360                 365

Ala Ala Ala Gly Ser Phe Ala Ser Val Thr Thr Gly Leu Ala Gly Asp
    370                 375                 380

Ala Trp His Gly Pro Ala Ser Leu Ala Met Thr Arg Ala Ala Ser Pro
385                 390                 395                 400

Tyr Val Gly Trp Leu Asn Thr Ala Ala Gly Gln Ala Ala Gln Ala Ala
                405                 410                 415

Gly Gln Ala Arg Leu Ala Ala Ser Ala Phe Glu Ala Thr Leu Ala Ala
            420                 425                 430

Thr Val Ser Pro Ala Met Val Ala Ala Asn Arg Thr Arg Leu Ala Ser
        435                 440                 445

Leu Val Ala Ala Asn Leu Leu Gly Gln Asn Ala Pro Ala Ile Ala Ala
    450                 455                 460

Ala Glu Ala Glu Tyr Glu Gln Ile Trp Ala Gln Asp Val Ala Ala Met
465                 470                 475                 480

Phe Gly Tyr His Ser Ala Ala Ser Ala Val Ala Thr Gln Leu Ala Pro
                485                 490                 495

Ile Gln Glu Gly Leu Gln Gln Gln Leu Gln Asn Val Leu Ala Gln Leu
```

-continued

```
            500                 505                 510

Ala Ser Gly Asn Leu Gly Ser Gly Asn Val Gly Val Gly Asn Ile Gly
        515                 520                 525

Asn Asp Asn Ile Gly Asn Ala Asn Ile Gly Phe Gly Asn Arg Gly Asp
    530                 535                 540

Ala Asn Ile Gly Ile Gly Asn Ile Gly Asp Arg Asn Leu Gly Ile Gly
545                 550                 555                 560

Asn Thr Gly Asn Trp Asn Ile Gly Ile Gly Ile Thr Gly Asn Gly Gln
                565                 570                 575

Ile Gly Phe Gly Lys Pro Ala Asn Pro Asp Val Leu Val Val Gly Asn
            580                 585                 590

Gly Gly Pro Gly Val Thr Ala Leu Val Met Gly Gly Thr Asp Ser Leu
        595                 600                 605

Leu Pro Leu Pro Asn Ile Pro Leu Leu Glu Tyr Ala Ala Arg Phe Ile
    610                 615                 620

Thr Pro Val His Pro Gly Tyr Thr Ala Thr Phe Leu Glu Thr Pro Ser
625                 630                 635                 640

Gln Phe Phe Pro Phe Thr Gly Leu Asn Ser Leu Thr Tyr Asp Val Ser
                645                 650                 655

Val Ala Gln Gly Val Thr Asn Leu His Thr Ala Ile Met Ala Gln Leu
            660                 665                 670

Ala Ala Gly Asn Glu Val Val Val Phe Gly Thr Ser Gln Ser Ala Thr
        675                 680                 685

Ile Ala Thr Phe Glu Met Arg Tyr Leu Gln Ser Leu Pro Ala His Leu
    690                 695                 700

Arg Pro Gly Leu Asp Glu Leu Ser Phe Thr Leu Thr Gly Asn Pro Asn
705                 710                 715                 720

Arg Pro Asp Gly Gly Ile Leu Thr Arg Phe Gly Phe Ser Ile Pro Gln
                725                 730                 735

Leu Gly Phe Thr Leu Ser Gly Ala Thr Pro Ala Asp Ala Tyr Pro Thr
            740                 745                 750

Val Asp Tyr Ala Phe Gln Tyr Asp Gly Val Asn Asp Phe Pro Lys Tyr
        755                 760                 765

Pro Leu Asn Val Phe Ala Thr Ala Asn Ala Ile Ala Gly Ile Leu Phe
    770                 775                 780

Leu His Ser Gly Leu Ile Ala Leu Pro Pro Asp Leu Ala Ser Gly Val
785                 790                 795                 800

Val Gln Pro Val Ser Ser Pro Asp Val Leu Thr Thr Tyr Ile Leu Leu
                805                 810                 815

Pro Ser Gln Asp Leu Pro Leu Leu Val Pro Leu Arg Ala Ile Pro Leu
            820                 825                 830

Leu Gly Asn Pro Leu Ala Asp Leu Ile Gln Pro Asp Leu Arg Val Leu
        835                 840                 845

Val Glu Leu Gly Tyr Asp Arg Thr Ala His Gln Asp Val Pro Ser Pro
    850                 855                 860

Phe Gly Leu Phe Pro Asp Val Asp Trp Ala Glu Val Ala Ala Asp Leu
865                 870                 875                 880

Gln Gln Gly Ala Val Gln Gly Val Asn Asp Ala Leu Ser Gly Leu Gly
                885                 890                 895

Leu Pro Pro Pro Trp Gln Pro Ala Leu Pro Arg Leu Phe Ser Thr Phe
            900                 905                 910

Ser Arg Pro Gly Leu Pro Val Glu Tyr Leu Gln Val Pro Ser Pro Ser
        915                 920                 925
```

Met Gly Arg Asp Ile Lys Val Gln Phe Gln Ser Gly Gly Asn Asn Ser
    930                 935                 940

Pro Ala Val Tyr Leu Leu Asp Gly Leu Arg Ala Gln Asp Asp Tyr Asn
945                 950                 955                 960

Gly Trp Asp Ile Asn Thr Pro Ala Phe Glu Trp Tyr Tyr Gln Ser Gly
                965                 970                 975

Leu Ser Ile Val Met Pro Val Gly Gly Gln Ser Ser Phe Tyr Ser Asp
            980                 985                 990

Trp Tyr Ser Pro Ala Cys Gly Lys Ala Gly Cys Gln Thr Tyr Lys Trp
        995                 1000                1005

Glu Thr Phe Leu Thr Ser Glu Leu Pro Gln Trp Leu Ser Ala Asn Arg
    1010                1015                1020

Ala Val Lys Pro Thr Gly Ser Ala Ala Ile Gly Leu Ser Met Ala Gly
1025                1030                1035                1040

Ser Ser Ala Met Ile Leu Ala Ala Tyr His Pro Gln Gln Phe Ile Tyr
                1045                1050                1055

Ala Gly Ser Leu Ser Ala Leu Leu Asp Pro Ser Gln Gly Met Gly Pro
            1060                1065                1070

Ser Leu Ile Gly Leu Ala Met Gly Asp Ala Gly Gly Tyr Lys Ala Ala
        1075                1080                1085

Asp Met Trp Gly Pro Ser Ser Asp Pro Ala Trp Glu Arg Asn Asp Pro
    1090                1095                1100

Thr Gln Gln Ile Pro Lys Leu Val Ala Asn Asn Thr Arg Leu Trp Val
1105                1110                1115                1120

Tyr Cys Gly Asn Gly Thr Pro Asn Glu Leu Gly Gly Ala Asn Ile Pro
                1125                1130                1135

Ala Glu Phe Leu Glu Asn Phe Val Arg Ser Ser Asn Leu Lys Phe Gln
            1140                1145                1150

Asp Ala Tyr Asn Ala Ala Gly Gly His Asn Ala Val Phe Asn Phe Pro
        1155                1160                1165

Pro Asn Gly Thr His Ser Trp Glu Tyr Trp Gly Ala Gln Leu Asn Ala
    1170                1175                1180

Met Lys Gly Asp Leu Gln Ser Ser Leu Gly Ala Gly
1185                1190                1195

<210> SEQ ID NO 258
<211> LENGTH: 2379
<212> TYPE: DNA
<213> ORGANISM: Mycobacterium tuberculosis

<400> SEQUENCE: 258
catatgcatc accatcacca tcacatgccg gacaccatgg tgaccaccga tgtcatcaag 60
agcgcggtgc agttggcctg ccgcgcaccg tcgctccaca acagccagcc ctggcgctgg 120
atagccgagg accacacggt tgcgctgttc ctcgacaagg atcgggtgct ttacgcgacc 180
gaccactccg gccgggaagc gctgctgggg tgcggcgccg tactcgacca ctttcgggtg 240
gcgatggcgg ccgcgggtac caccgccaat gtggaacggt ttcccaaccc caacgatcct 300
ttgcatctgg cgtcaattga cttcagcccg gccgatttcg tcaccgaggg ccaccgtcta 360
agggcggatg cgatcctact gcgccgtacc gaccggctgc ctttcgccga gccgccggat 420
tgggacttgg tggagtcgca gttgcgcacg accgtcaccg ccgacacggt gcgcatcgac 480
gtcatcgccg acgatatgcg tcccgaactg gcggcggcgt ccaaactcac cgaatcgctg 540
cggctctacg attcgtcgta tcatgccgaa ctcttttggt ggacaggggc ttttgagact 600

```
tctgagggca taccgcacag ttcattggta tcggcggccg aaagtgaccg ggtcaccttc    660

ggacgcgact tcccggtcgt cgccaacacc gataggcgcc cggagtttgg ccacgaccgc    720

tctaaggtcc tggtgctctc cacctacgac aacgaacgcg ccagcctact gcgctgcggc    780

gagatgcttt ccgccgtatt gcttgacgcc accatggctg ggcttgccac ctgcacgctg    840

acccacatca ccgaactgca cgccagccga gacctggtcg cagcgctgat tgggcagccc    900

gcaactccgc aagccttggt tcgcgtcggt ctggccccgg agatggaaga gccgccaccg    960

gcaacgcctc ggcgaccaat cgatgaagtg tttcacgttc gggctaagga tcaccggggt   1020

ggttctggcg gtagcggatt catgggcgat ctggtgggcc cgggctgcgc ggaatacgcg   1080

gcagccaatc ccactgggcc ggcctcggtg cagggaatgt cgcaggaccc ggtcgcggtg   1140

gcggcctcga acaatccgga gttgacaacg ctgacggctg cactgtcggg ccagctcaat   1200

ccgcaagtaa acctggtgga caccctcaac agcggtcagt acacggtgtt cgcaccgacc   1260

aacgcggcat ttagcaagct gccggcatcc acgatcgacg agctcaagac caattcgtca   1320

ctgctgacca gcatcctgac ctaccacgta gtggccggcc aaaccagccc ggccaacgtc   1380

gtcggcaccc gtcagaccct ccagggcgcc agcgtgacgg tgaccggtca gggtaacagc   1440

ctcaaggtcg gtaacgccga cgtcgtctgt ggtggggtgt ctaccgccaa cgcgacggtg   1500

tacatgattg acagcgtgct aatgcctccg gcgggcggaa gcggcggttc tgaattcatg   1560

ctccccgaga caaatcagga tgaggtccag cccaacgcac ccgttgccct ggtgacggtg   1620

gaaatccgtc acccgacaac ggattcgctc accgaatcag cgaaccggga gctcaaacac   1680

ctgcttatca atgatctacc gatcgaacgc caggcgcagg acgtcagctg gggatgacg    1740

gcgcccggtg gagcccccac cccggtcgcg gatcgtttcg ttcgttatgt caatcgcgat   1800

aacaccaccg ccgcttcact gaagaaccag gcgatagtcg tggagaccac cgcctaccgc   1860

agctttgagg cctttaccga cgttgtgatg cgggtcgtgg atgctcgcgc gcaggtctcg   1920

tcaatcgttg ggttggagcg tatcggtctt cgctttgttc tggagatccg cgtccccgcg   1980

ggtgtcgacg gccggatcac gtggagcaac tggatcgacg agcagctgct cgggccgcag   2040

cgtttcactc ccggcggcct ggtcctgacc gagtggcagg gtgccgcagt ctaccgtgag   2100

ctacaaccag gcaaatcgct catcgtgcgc tacggcccgg gtatgggcca agcgcttgat   2160

cccaattacc atctgcgccg aataacaccc gcccaaaccg gaccattctt cctgctggac   2220

atcgatagct tttggactcc cagtggcggc tccattcccg agtacaacag ggacgcctta   2280

gtgtcgacat tccaggacct gtacggtccg gcccaggtcg tgtttcagga gatgatcacc   2340

agtcgcctga aagatgagct gcttcgccag taaaagctt                          2379
```

<210> SEQ ID NO 259
<211> LENGTH: 50
<212> TYPE: DNA
<213> ORGANISM: Artificial Sequence
<220> FEATURE:
<223> OTHER INFORMATION: Primer

<400> SEQUENCE: 259

```
gatacacata tgcaccatca ccatcaccac atgccggaca ccatggtgac                 50
```

<210> SEQ ID NO 260
<211> LENGTH: 48
<212> TYPE: DNA
<213> ORGANISM: Artificial Sequence
<220> FEATURE:

<223> OTHER INFORMATION: Primer

<400> SEQUENCE: 260
catggatccg ctaccgccag aaccaccccg gtgatcctta gcccgaac 48

<210> SEQ ID NO 261
<211> LENGTH: 45
<212> TYPE: DNA
<213> ORGANISM: Artificial Sequence
<220> FEATURE:
<223> OTHER INFORMATION: Primer

<400> SEQUENCE: 261
ggtggttctg gcggtagcgg attcatgggc gatctggtga gcccg 45

<210> SEQ ID NO 262
<211> LENGTH: 47
<212> TYPE: DNA
<213> ORGANISM: Artificial Sequence
<220> FEATURE:
<223> OTHER INFORMATION: Primer

<400> SEQUENCE: 262
catgaattca gaaccgccgc ttccgcccgc cggaggcatt agcacgc 47

<210> SEQ ID NO 263
<211> LENGTH: 45
<212> TYPE: DNA
<213> ORGANISM: Artificial Sequence
<220> FEATURE:
<223> OTHER INFORMATION: Primer

<400> SEQUENCE: 263
ggcggaagcg gcggttctga attcatgctc cccgagacaa atcag 45

<210> SEQ ID NO 264
<211> LENGTH: 35
<212> TYPE: DNA
<213> ORGANISM: Artificial Sequence
<220> FEATURE:
<223> OTHER INFORMATION: Primer

<400> SEQUENCE: 264
tagaattcaa gcttttactg gcgaagcagc tcatc 35

<210> SEQ ID NO 265
<211> LENGTH: 790
<212> TYPE: PRT
<213> ORGANISM: Mycobacterium tuberculosis

<400> SEQUENCE: 265

His Met His His His His His His Met Pro Asp Thr Met Val Thr Thr
1 5 10 15

Asp Val Ile Lys Ser Ala Val Gln Leu Ala Cys Arg Ala Pro Ser Leu
20 25 30

His Asn Ser Gln Pro Trp Arg Trp Ile Ala Glu Asp His Thr Val Ala
35 40 45

Leu Phe Leu Asp Lys Asp Arg Val Leu Tyr Ala Thr Asp His Ser Gly
50 55 60

Arg Glu Ala Leu Leu Gly Cys Gly Ala Val Leu Asp His Phe Arg Val
65 70 75 80

Ala Met Ala Ala Ala Gly Thr Thr Ala Asn Val Glu Arg Phe Pro Asn
85 90 95

```
Pro Asn Asp Pro Leu His Leu Ala Ser Ile Asp Phe Ser Pro Ala Asp
            100                 105                 110

Phe Val Thr Glu Gly His Arg Leu Arg Ala Asp Ala Ile Leu Leu Arg
        115                 120                 125

Arg Thr Asp Arg Leu Pro Phe Ala Glu Pro Pro Asp Trp Asp Leu Val
    130                 135                 140

Glu Ser Gln Leu Arg Thr Thr Val Thr Ala Asp Thr Val Arg Ile Asp
145                 150                 155                 160

Val Ile Ala Asp Asp Met Arg Pro Glu Leu Ala Ala Ala Ser Lys Leu
                165                 170                 175

Thr Glu Ser Leu Arg Leu Tyr Asp Ser Ser Tyr His Ala Glu Leu Phe
            180                 185                 190

Trp Trp Thr Gly Ala Phe Glu Thr Ser Glu Gly Ile Pro His Ser Ser
        195                 200                 205

Leu Val Ser Ala Ala Glu Ser Asp Arg Val Thr Phe Gly Arg Asp Phe
    210                 215                 220

Pro Val Val Ala Asn Thr Asp Arg Arg Pro Glu Phe Gly His Asp Arg
225                 230                 235                 240

Ser Lys Val Leu Val Leu Ser Thr Tyr Asp Asn Glu Arg Ala Ser Leu
                245                 250                 255

Leu Arg Cys Gly Glu Met Leu Ser Ala Val Leu Leu Asp Ala Thr Met
            260                 265                 270

Ala Gly Leu Ala Thr Cys Thr Leu Thr His Ile Thr Glu Leu His Ala
        275                 280                 285

Ser Arg Asp Leu Val Ala Ala Leu Ile Gly Gln Pro Ala Thr Pro Gln
    290                 295                 300

Ala Leu Val Arg Val Gly Leu Ala Pro Glu Met Glu Glu Pro Pro Pro
305                 310                 315                 320

Ala Thr Pro Arg Arg Pro Ile Asp Glu Val Phe His Val Arg Ala Lys
                325                 330                 335

Asp His Arg Gly Gly Ser Gly Gly Ser Gly Phe Met Gly Asp Leu Val
            340                 345                 350

Gly Pro Gly Cys Ala Glu Tyr Ala Ala Ala Asn Pro Thr Gly Pro Ala
        355                 360                 365

Ser Val Gln Gly Met Ser Gln Asp Pro Val Ala Val Ala Ala Ser Asn
    370                 375                 380

Asn Pro Glu Leu Thr Thr Leu Thr Ala Ala Leu Ser Gly Gln Leu Asn
385                 390                 395                 400

Pro Gln Val Asn Leu Val Asp Thr Leu Asn Ser Gly Gln Tyr Thr Val
                405                 410                 415

Phe Ala Pro Thr Asn Ala Ala Phe Ser Lys Leu Pro Ala Ser Thr Ile
            420                 425                 430

Asp Glu Leu Lys Thr Asn Ser Ser Leu Leu Thr Ser Ile Leu Thr Tyr
        435                 440                 445

His Val Val Ala Gly Gln Thr Ser Pro Ala Asn Val Val Gly Thr Arg
    450                 455                 460

Gln Thr Leu Gln Gly Ala Ser Val Thr Val Thr Gly Gln Gly Asn Ser
465                 470                 475                 480

Leu Lys Val Gly Asn Ala Asp Val Val Cys Gly Gly Val Ser Thr Ala
                485                 490                 495

Asn Ala Thr Val Tyr Met Ile Asp Ser Val Leu Met Pro Pro Ala Gly
            500                 505                 510
```

```
Gly Ser Gly Gly Ser Glu Phe Met Leu Pro Glu Thr Asn Gln Asp Glu
        515                 520                 525

Val Gln Pro Asn Ala Pro Val Ala Leu Val Thr Val Glu Ile Arg His
    530                 535                 540

Pro Thr Thr Asp Ser Leu Thr Glu Ser Ala Asn Arg Glu Leu Lys His
545                 550                 555                 560

Leu Leu Ile Asn Asp Leu Pro Ile Glu Arg Gln Ala Gln Asp Val Ser
                565                 570                 575

Trp Gly Met Thr Ala Pro Gly Gly Ala Pro Thr Pro Val Ala Asp Arg
            580                 585                 590

Phe Val Arg Tyr Val Asn Arg Asp Asn Thr Thr Ala Ala Ser Leu Lys
        595                 600                 605

Asn Gln Ala Ile Val Val Glu Thr Thr Ala Tyr Arg Ser Phe Glu Ala
    610                 615                 620

Phe Thr Asp Val Val Met Arg Val Val Asp Ala Arg Ala Gln Val Ser
625                 630                 635                 640

Ser Ile Val Gly Leu Glu Arg Ile Gly Leu Arg Phe Val Leu Glu Ile
                645                 650                 655

Arg Val Pro Ala Gly Val Asp Gly Arg Ile Thr Trp Ser Asn Trp Ile
            660                 665                 670

Asp Glu Gln Leu Leu Gly Pro Gln Arg Phe Thr Pro Gly Gly Leu Val
        675                 680                 685

Leu Thr Glu Trp Gln Gly Ala Ala Val Tyr Arg Glu Leu Gln Pro Gly
    690                 695                 700

Lys Ser Leu Ile Val Arg Tyr Gly Pro Gly Met Gly Gln Ala Leu Asp
705                 710                 715                 720

Pro Asn Tyr His Leu Arg Arg Ile Thr Pro Ala Gln Thr Gly Pro Phe
                725                 730                 735

Phe Leu Leu Asp Ile Asp Ser Phe Trp Thr Pro Ser Gly Gly Ser Ile
            740                 745                 750

Pro Glu Tyr Asn Arg Asp Ala Leu Val Ser Thr Phe Gln Asp Leu Tyr
        755                 760                 765

Gly Pro Ala Gln Val Val Phe Gln Glu Met Ile Thr Ser Arg Leu Lys
    770                 775                 780

Asp Glu Leu Leu Arg Gln
785                 790
```

<210> SEQ ID NO 266
<211> LENGTH: 2622
<212> TYPE: DNA
<213> ORGANISM: Mycobacterium tuberculosis

<400> SEQUENCE: 266

```
atgggcagca gccatcatca tcatcatcac agcagcggcc tggtgccgcg cggcagccat      60

atgcataagg cgtcacaatc gatgatcacg cccaccaccc agatcgccgg cgccggggtg     120

ctgggaaacg acagaaagcc ggatgagtcg tgcgcgcgtg cggcggccgc ggccgatccg     180

gggccaccga cccgaccagc gcacaatgcg gcgggagtca gcccggagat ggtgcaggtg     240

ccggcggagg cgcagcgcat cgtggtgctc tccggtgacc agctcgacgc gctgtgcgcg     300

ctgggcctgc aatcgcggat cgtcgccgcc gcgttgccga acagctcctc aagtcaacct     360

tcctatctgg gcacgaccgt gcatgatctg cccggtgtcg gtactcgcag cgccccccgac     420

ctgcgcgcca ttgcggcggc tcacccggat ctgatcctgg gttcgcaggg tttgacgccg     480

cagttgtatc cgcagctggc ggcgatcgcc ccgacggtgt ttaccgcggc accgggcgcg     540
```

```
gactgggaaa ataacctgcg tggtgtcggt gccgccacgg cccgtatcgc cgcggtggac    600
gcgctgatca ccgggttcgc cgaacacgcc acccaggtcg ggaccaagca tgacgcgacc    660
cacttccaag cgtcgatcgt gcagctgacc gccaacacca tgcgggtata cggcgccaac    720
aacttcccgg ccagcgtgct gagcgcggtc ggcgtcgacc gaccgccgtc tcaacggttc    780
accgacaagg cctacatcga gatcggcacc acggccgccg acctggcgaa atcaccggac    840
ttctcggcgg ccgacgccga tatcgtctac ctgtcgtgcg cgtcggaagc agccgcggaa    900
cgcgcggccg tcatcctgga tagcgaccca tggcgcaagc tgtccgccaa ccgtgacaac    960
cgggtcttcg tcgtcaacga ccaggtatgg cagaccggcg agggtatggt cgctgcccgc   1020
ggcattgtcg atgatctgcg ctgggtcgac gcgccgatca acgagctcgg aggttctggt   1080
ggaagcgcat gcaaaacggt gacgttgacc gtcgacggaa ccgcgatgcg ggtgaccacg   1140
atgaaatcgc gggtgatcga catcgtcgaa gagaacgggt tctcagtcga cgaccgcgac   1200
gacctgtatc ccgcggccgg cgtgcaggtc catgacgccg acaccatcgt gctgcggcgt   1260
agccgtccgc tgcagatctc gctggatggt cacgacgcta agcaggtgtg gacgaccgcg   1320
tcgacggtgg acgaggcgct ggcccaactc gcgatgaccg acacggcgcc ggccgcggct   1380
tctcgcgcca gccgcgtccc gctgtccggg atggcgctac cggtcgtcag cgccaagacg   1440
gtgcagctca acgacggcgg gttggtgcgc acggtgcact tgccggcccc caatgtcgcg   1500
gggctgctga gtgcggccgg cgtgccgctg ttgcaaagcg accacgtggt gcccgccgcg   1560
acggccccga tcgtcgaagg catgcagatc caggtgaccc gcaatcggat caagaaggtc   1620
accgagcggc tgccgctgcc gccgaacgcg cgtcgtgtcg aggacccgga gatgaacatg   1680
agccgggagg tcgtcgaaga cccgggggtt ccggggaccc aggatgtgac gttcgcggta   1740
gctgaggtca acggcgtcga gaccggccgt ttgcccgtcg ccaacgtcgt ggtgaccccg   1800
gcccacgaag ccgtggtgcg ggtgggcacc aagcccggta ccgaggtgcc cccggtgatc   1860
gacggaagca tctgggacgc gatcgccggc tgtgaggccg gtggcaactg ggcgatcaac   1920
accggcaacg ggtattacgg tggtgtgcag tttgaccagg gcacctggga ggccaacggc   1980
gggctgcggt atgcaccccg cgctgacctc gccacccgcg aagagcagat cgccgttgcc   2040
gaggtgaccc gactgcgtca aggttggggc gcctggccgg tatgtgctgc acgagcgggt   2100
gcgcgcgaat tcggtggaag cggaggttct atgacggcaa tctcgtgctc accgcgaccc   2160
aggtatgctt cccgaatgcc agttttgagc aagaccgtcg aggtcaccgc cgacgccgca   2220
tcgatcatgg ccatcgttgc cgatatcgag cgctacccag agtggaatga aggggtcaag   2280
ggcgcatggg tgctcgctcg ctacgatgac gggcgtccca gccaggtgcg gctcgacacc   2340
gctgttcaag gcatcgaggg cacctatatc cacgccgtgt actacccagg cgaaaaccag   2400
attcaaaccg tcatgcagca gggtgaactg tttgccaagc aggagcagct gttcagtgtg   2460
gtggcaaccg gcgccgcgag cttgctcacg gtggacatgg acgtccaggt caccatgccg   2520
gtgcccgagc cgatggtgaa gatgctgctc aacaacgtcc tggagcatct cgccgaaaat   2580
ctcaagcagc gcgccgagca gctggcggcc agctaaaagc tt                      2622
```

<210> SEQ ID NO 267
<211> LENGTH: 52
<212> TYPE: DNA
<213> ORGANISM: Artificial Sequence
<220> FEATURE:
<223> OTHER INFORMATION: Primer

<400> SEQUENCE: 267
gatacacata tgcaccatca ccatcaccac atgggcagca gccatcatca tc 52

<210> SEQ ID NO 268
<211> LENGTH: 32
<212> TYPE: DNA
<213> ORGANISM: Artificial Sequence
<220> FEATURE:
<223> OTHER INFORMATION: Primer

<400> SEQUENCE: 268
catatcgagc tcgttgatcg gcgcgtcgac cc 32

<210> SEQ ID NO 269
<211> LENGTH: 53
<212> TYPE: DNA
<213> ORGANISM: Artificial Sequence
<220> FEATURE:
<223> OTHER INFORMATION: Primer

<400> SEQUENCE: 269
atcaacgagc tcggaggttc tggtggaagc gcatgcaaaa cggtgacgtt gac 53

<210> SEQ ID NO 270
<211> LENGTH: 33
<212> TYPE: DNA
<213> ORGANISM: Artificial Sequence
<220> FEATURE:
<223> OTHER INFORMATION: Primer

<400> SEQUENCE: 270
catatcgaat tcgcgcgcac ccgctcgtgc agc 33

<210> SEQ ID NO 271
<211> LENGTH: 52
<212> TYPE: DNA
<213> ORGANISM: Artificial Sequence
<220> FEATURE:
<223> OTHER INFORMATION: Primer

<400> SEQUENCE: 271
catgtcgaat tcggtggaag cggaggttct atgacggcaa tctcgtgctc ac 52

<210> SEQ ID NO 272
<211> LENGTH: 33
<212> TYPE: DNA
<213> ORGANISM: Artificial Sequence
<220> FEATURE:
<223> OTHER INFORMATION: Primer

<400> SEQUENCE: 272
catatcaagc ttttagctgg ccgccagctg ctc 33

<210> SEQ ID NO 273
<211> LENGTH: 871
<212> TYPE: PRT
<213> ORGANISM: Mycobacterium tuberculosis

<400> SEQUENCE: 273

Met Gly Ser Ser His His His His His His Ser Ser Gly Leu Val Pro
1               5                   10                  15

Arg Gly Ser His Met His Lys Ala Ser Gln Ser Met Ile Thr Pro Thr
            20                  25                  30

Thr Gln Ile Ala Gly Ala Gly Val Leu Gly Asn Asp Arg Lys Pro Asp

```
        35                  40                  45

Glu Ser Cys Ala Arg Ala Ala Ala Ala Ala Asp Pro Gly Pro Pro Thr
    50                  55                  60

Arg Pro Ala His Asn Ala Ala Gly Val Ser Pro Glu Met Val Gln Val
65                  70                  75                  80

Pro Ala Glu Ala Gln Arg Ile Val Val Leu Ser Gly Asp Gln Leu Asp
                85                  90                  95

Ala Leu Cys Ala Leu Gly Leu Gln Ser Arg Ile Val Ala Ala Ala Leu
            100                 105                 110

Pro Asn Ser Ser Ser Ser Gln Pro Ser Tyr Leu Gly Thr Thr Val His
        115                 120                 125

Asp Leu Pro Gly Val Gly Thr Arg Ser Ala Pro Asp Leu Arg Ala Ile
    130                 135                 140

Ala Ala Ala His Pro Asp Leu Ile Leu Gly Ser Gln Gly Leu Thr Pro
145                 150                 155                 160

Gln Leu Tyr Pro Gln Leu Ala Ala Ile Ala Pro Thr Val Phe Thr Ala
                165                 170                 175

Ala Pro Gly Ala Asp Trp Glu Asn Asn Leu Arg Gly Val Gly Ala Ala
            180                 185                 190

Thr Ala Arg Ile Ala Ala Val Asp Ala Leu Ile Thr Gly Phe Ala Glu
        195                 200                 205

His Ala Thr Gln Val Gly Thr Lys His Asp Ala Thr His Phe Gln Ala
    210                 215                 220

Ser Ile Val Gln Leu Thr Ala Asn Thr Met Arg Val Tyr Gly Ala Asn
225                 230                 235                 240

Asn Phe Pro Ala Ser Val Leu Ser Ala Val Gly Val Asp Arg Pro Pro
                245                 250                 255

Ser Gln Arg Phe Thr Asp Lys Ala Tyr Ile Glu Ile Gly Thr Thr Ala
            260                 265                 270

Ala Asp Leu Ala Lys Ser Pro Asp Phe Ser Ala Ala Asp Ala Asp Ile
        275                 280                 285

Val Tyr Leu Ser Cys Ala Ser Glu Ala Ala Ala Glu Arg Ala Ala Val
    290                 295                 300

Ile Leu Asp Ser Asp Pro Trp Arg Lys Leu Ser Ala Asn Arg Asp Asn
305                 310                 315                 320

Arg Val Phe Val Val Asn Asp Gln Val Trp Gln Thr Gly Glu Gly Met
                325                 330                 335

Val Ala Ala Arg Gly Ile Val Asp Asp Leu Arg Trp Val Asp Ala Pro
            340                 345                 350

Ile Asn Glu Leu Gly Gly Ser Gly Gly Ser Ala Cys Lys Thr Val Thr
        355                 360                 365

Leu Thr Val Asp Gly Thr Ala Met Arg Val Thr Thr Met Lys Ser Arg
    370                 375                 380

Val Ile Asp Ile Val Glu Glu Asn Gly Phe Ser Val Asp Asp Arg Asp
385                 390                 395                 400

Asp Leu Tyr Pro Ala Ala Gly Val Gln Val His Asp Ala Asp Thr Ile
                405                 410                 415

Val Leu Arg Arg Ser Arg Pro Leu Gln Ile Ser Leu Asp Gly His Asp
            420                 425                 430

Ala Lys Gln Val Trp Thr Thr Ala Ser Thr Val Asp Glu Ala Leu Ala
        435                 440                 445

Gln Leu Ala Met Thr Asp Thr Ala Pro Ala Ala Ala Ser Arg Ala Ser
    450                 455                 460
```

```
Arg Val Pro Leu Ser Gly Met Ala Leu Pro Val Val Ser Ala Lys Thr
465                 470                 475                 480

Val Gln Leu Asn Asp Gly Gly Leu Val Arg Thr Val His Leu Pro Ala
                485                 490                 495

Pro Asn Val Ala Gly Leu Leu Ser Ala Ala Gly Val Pro Leu Leu Gln
            500                 505                 510

Ser Asp His Val Val Pro Ala Ala Thr Ala Pro Ile Val Glu Gly Met
        515                 520                 525

Gln Ile Gln Val Thr Arg Asn Arg Ile Lys Lys Val Thr Glu Arg Leu
    530                 535                 540

Pro Leu Pro Pro Asn Ala Arg Arg Val Glu Asp Pro Glu Met Asn Met
545                 550                 555                 560

Ser Arg Glu Val Val Glu Asp Pro Gly Val Pro Gly Thr Gln Asp Val
                565                 570                 575

Thr Phe Ala Val Ala Glu Val Asn Gly Val Glu Thr Gly Arg Leu Pro
            580                 585                 590

Val Ala Asn Val Val Val Thr Pro Ala His Glu Ala Val Val Arg Val
        595                 600                 605

Gly Thr Lys Pro Gly Thr Glu Val Pro Pro Val Ile Asp Gly Ser Ile
    610                 615                 620

Trp Asp Ala Ile Ala Gly Cys Glu Ala Gly Gly Asn Trp Ala Ile Asn
625                 630                 635                 640

Thr Gly Asn Gly Tyr Tyr Gly Gly Val Gln Phe Asp Gln Gly Thr Trp
                645                 650                 655

Glu Ala Asn Gly Gly Leu Arg Tyr Ala Pro Arg Ala Asp Leu Ala Thr
            660                 665                 670

Arg Glu Glu Gln Ile Ala Val Ala Glu Val Thr Arg Leu Arg Gln Gly
        675                 680                 685

Trp Gly Ala Trp Pro Val Cys Ala Ala Arg Ala Gly Ala Arg Glu Phe
    690                 695                 700

Gly Gly Ser Gly Gly Ser Met Thr Ala Ile Ser Cys Ser Pro Arg Pro
705                 710                 715                 720

Arg Tyr Ala Ser Arg Met Pro Val Leu Ser Lys Thr Val Glu Val Thr
                725                 730                 735

Ala Asp Ala Ala Ser Ile Met Ala Ile Val Ala Asp Ile Glu Arg Tyr
            740                 745                 750

Pro Glu Trp Asn Glu Gly Val Lys Gly Ala Trp Val Leu Ala Arg Tyr
        755                 760                 765

Asp Asp Gly Arg Pro Ser Gln Val Arg Leu Asp Thr Ala Val Gln Gly
    770                 775                 780

Ile Glu Gly Thr Tyr Ile His Ala Val Tyr Tyr Pro Gly Glu Asn Gln
785                 790                 795                 800

Ile Gln Thr Val Met Gln Gln Gly Glu Leu Phe Ala Lys Gln Glu Gln
                805                 810                 815

Leu Phe Ser Val Val Ala Thr Gly Ala Ala Ser Leu Leu Thr Val Asp
            820                 825                 830

Met Asp Val Gln Val Thr Met Pro Val Pro Glu Pro Met Val Lys Met
        835                 840                 845

Leu Leu Asn Asn Val Leu Glu His Leu Ala Glu Asn Leu Lys Gln Arg
    850                 855                 860

Ala Glu Gln Leu Ala Ala Ser
865                 870
```

<210> SEQ ID NO 274
<211> LENGTH: 3171
<212> TYPE: DNA
<213> ORGANISM: Mycobacterium tuberculosis

<400> SEQUENCE: 274
catatgcacc atcaccatca ccacatggaa aaaatgtcac atgatccgat cgctgccgac 60
attggcacgc aagtgagcga caacgctctg cacggcgtga cggccggctc gacggcgctg 120
acgtcggtga ccgggctggt tcccgcgggg gccgatgagg tctccgccca agcggcgacg 180
gcgttcacat cggagggcat ccaattgctg gcttccaatg catcggccca agaccagctc 240
caccgtgcgg gcgaagcggt ccaggacgtc gcccgcacct attcgcaaat cgacgacggc 300
gccgccggcg tcttcgccga agagctcgga ggttccggtg gaagcatgct gtggcacgca 360
atgccaccgg agctaaatac cgcacggctg atggccggcg cgggtccggc tccaatgctt 420
gcggcggccg cgggatggca gacgctttcg gcggctctgg acgctcaggc cgtcgagttg 480
accgcgcgcc tgaactctct gggagaagcc tggactggag gtggcagcga caaggcgctt 540
gcggctgcaa cgccgatggt ggtctggcta caaaccgcgt caacacaggc caagacccgt 600
gcgatgcagg cgacggcgca agccgcggca tacacccagg ccatggccac gacgccgtcg 660
ctgccggaga tcgccgccaa ccacatcacc caggccgtcc ttacggccac caacttcttc 720
ggtatcaaca cgatcccgat cgcgttgacc gagatggatt atttcatccg tatgtggaac 780
caggcagccc tggcaatgga ggtctaccag gccgagaccg cggttaacac gcttttcgag 840
aagctcgagc cgatggcgtc gatccttgat cccggcgcga gccagagcac gacgaacccg 900
atcttcggaa tgccctcccc tggcagctca acaccggttg gccagttgcc gccggcggct 960
acccagaccc tcggccaact gggtgagatg agcggcccga tgcagcagct gacccagccg 1020
ctgcagcagg tgacgtcgtt gttcagccag gtgggcggca ccggcggcgg caacccagcc 1080
gacgaggaag ccgcgcagat gggcctgctc ggcaccagtc cgctgtcgaa ccatccgctg 1140
gctggtggat caggccccag cgcgggcgcg ggcctgctgc gcgcggagtc gctacctggc 1200
gcaggtgggt cgttgacccg cacgccgctg atgtctcagc tgatcgaaaa gccggttgcc 1260
ccctcggtga tgccggcggc tgctgccgga tcgtcggcga cgggtggcgc cgctccggtg 1320
ggtgcgggag cgatgggcca gggtgcgcaa tccggcggct ccaccaggcc gggtctggtc 1380
gcgccggcac cgctcgcgca ggagcgtgaa gaagacgacg aggacgactg ggacgaagag 1440
gacgactggg aattcggtgg cagtggagga tctatgacag agcagcagtg gaatttcgcg 1500
ggtatcgagg ccgcggcaag cgcaatccag ggaaatgtca cgtccattca ttccctcctt 1560
gacgagggga agcagtccct gaccaagctc gcagcggcct ggggcggtag cggttcggag 1620
gcgtaccagg gtgtccagca aaaatgggac gccacggcta ccgagctgaa caacgcgctg 1680
cagaacctgg cgcggacgat cagcgaagcc ggtcaggcaa tggcttcgac cgaaggcaac 1740
gtcactggga tgttcgcagc tagcggaggt tccggtggaa gcatgacgca gtcgcagacc 1800
gtgacggtgg atcagcaaga gattttgaac agggccaacg aggtggaggc cccgatggcg 1860
gacccaccga ctgatgtccc catcacaccg tgcgaactca cggcggctaa aaacgccgcc 1920
caacagctgg tattgtccgc cgacaacatg cgggaatacc tggcggccgg tgccaaagag 1980
cggcagcgtc tggcgacctc gctgcgcaac gcggccaagg cgtatggcga ggttgatgag 2040
gaggctgcga ccgcgctgga caacgacggc gaaggaactg tgcaggcaga atcggccggg 2100
gccgtcggag gggacagttc ggccgaacta accgatacgc cgagggtggc cacggccggt 2160
gaacccaact tcatggatct caaagaagcg gcaaggaagc tcgaaacggg cgaccaaggc 2220
gcatcgctcg cgcactttgc ggatgggtgg aacactttca acctgacgct gcaaggcgac 2280
gtcaagcggt tccgggggtt tgacaactgg gaaggcgatg cggctaccgc ttgcgaggct 2340
tcgctcgatc aacaacggca atggatactc cacatggcca aattgagcgc tgcgatggcc 2400
aagcaggctc aatatgtcgc gcagctgcac gtgtgggcta ggcgggaaca tccgacttat 2460
gaagacatag tcgggctcga acggctttac gcggaaaacc cttcggcccg cgaccaaatt 2520
ctcccggtgt acgcggagta tcagcagagg tcggagaagg tgctgaccga atacaacaac 2580
aaggcagccc tggaaccggt aaacccgccg aagcctcccc ccgccatcaa gatcgacccg 2640
cccccgcctc cgcaagagca gggattgatc cctggcttcc tgatgccgcc gtctgacggc 2700
tccggtgtga ctcccggtac cgggatgcca gccgcaccga tggttccgcc taccggatcg 2760
ccgggtggtg gcctcccggc tgacacggcg gcacagctga cgtcggctgg gcgggaagcc 2820
gcagcgctgt cgggygacgt ggcggtcaaa gcggcatcgc tcggtggygg tggaggcggc 2880
ggggtgccgt cggcgccgtt gggatccgcg atcgggggcg ccgaatcggt gcggcccgct 2940
ggcgctggtg acattgccgg cttaggccag ggaagggccg gcggcggcgc cgcgctgggc 3000
ggcggtggca tgggaatgcc gatgggtgcc gcgcatcagg gacaaggggg cgccaagtcc 3060
aagggttctc agcaggaaga cgaggcgctc tacaccgagg atcgggcatg gaccgaggcc 3120
gtcattggta accgtcggcg ccaggacagt aaggagtcga agtgaaagct t 3171

<210> SEQ ID NO 275
<211> LENGTH: 52
<212> TYPE: DNA
<213> ORGANISM: Artificial Sequence
<220> FEATURE:
<223> OTHER INFORMATION: Primer

<400> SEQUENCE: 275
gatacacata tgcaccatca ccatcaccac atggaaaaaa tgtcacatga tc 52

<210> SEQ ID NO 276
<211> LENGTH: 34
<212> TYPE: DNA
<213> ORGANISM: Artificial Sequence
<220> FEATURE:
<223> OTHER INFORMATION: Primer

<400> SEQUENCE: 276
gatacatgag ctcttcggcg aagacgccgg cggc 34

<210> SEQ ID NO 277
<211> LENGTH: 50
<212> TYPE: DNA
<213> ORGANISM: Artificial Sequence
<220> FEATURE:
<223> OTHER INFORMATION: Primer

<400> SEQUENCE: 277
gatacagagc tcggaggttc cggtggaagc atgctgtggc acgcaatgcc 50

<210> SEQ ID NO 278
<211> LENGTH: 34
<212> TYPE: DNA
<213> ORGANISM: Artificial Sequence
<220> FEATURE:
<223> OTHER INFORMATION: Primer

<400> SEQUENCE: 278
gatacagaat tcccagtcgt cctcttcgtc ccag 34

<210> SEQ ID NO 279
<211> LENGTH: 49
<212> TYPE: DNA
<213> ORGANISM: Artificial Sequence
<220> FEATURE:
<223> OTHER INFORMATION: Primer

<400> SEQUENCE: 279
gacagaattc ggtggcagtg gaggatctat gacagagcag cagtggaat 49

<210> SEQ ID NO 280
<211> LENGTH: 35
<212> TYPE: DNA
<213> ORGANISM: Artificial Sequence
<220> FEATURE:
<223> OTHER INFORMATION: Primer

<400> SEQUENCE: 280
catatcagct agctgcgaac atcccagtga cgttg 35

<210> SEQ ID NO 281
<211> LENGTH: 52
<212> TYPE: DNA
<213> ORGANISM: Artificial Sequence
<220> FEATURE:
<223> OTHER INFORMATION: Primer

<400> SEQUENCE: 281
catatcagct agcggaggtt ccggtggaag catgacgcag tcgcagaccg tg 52

<210> SEQ ID NO 282
<211> LENGTH: 34
<212> TYPE: DNA
<213> ORGANISM: Artificial Sequence
<220> FEATURE:
<223> OTHER INFORMATION: Primer

<400> SEQUENCE: 282
catatcaaag ctttcacttc gactccttac tgtc 34

<210> SEQ ID NO 283
<211> LENGTH: 1054
<212> TYPE: PRT
<213> ORGANISM: Mycobacterium tuberculosis

<400> SEQUENCE: 283

His Met His His His His His His Met Glu Lys Met Ser His Asp Pro
1 5 10 15

Ile Ala Ala Asp Ile Gly Thr Gln Val Ser Asp Asn Ala Leu His Gly
20 25 30

Val Thr Ala Gly Ser Thr Ala Leu Thr Ser Val Thr Gly Leu Val Pro
35 40 45

Ala Gly Ala Asp Glu Val Ser Ala Gln Ala Ala Thr Ala Phe Thr Ser
50 55 60

Glu Gly Ile Gln Leu Leu Ala Ser Asn Ala Ser Ala Gln Asp Gln Leu
65 70 75 80

His Arg Ala Gly Glu Ala Val Gln Asp Val Ala Arg Thr Tyr Ser Gln
85 90 95

Ile Asp Asp Gly Ala Ala Gly Val Phe Ala Glu Glu Leu Gly Gly Ser

```
            100                 105                 110

Gly Gly Ser Met Leu Trp His Ala Met Pro Pro Glu Leu Asn Thr Ala
        115                 120                 125

Arg Leu Met Ala Gly Ala Gly Pro Ala Pro Met Leu Ala Ala Ala Ala
    130                 135                 140

Gly Trp Gln Thr Leu Ser Ala Ala Leu Asp Ala Gln Ala Val Glu Leu
145                 150                 155                 160

Thr Ala Arg Leu Asn Ser Leu Gly Glu Ala Trp Thr Gly Gly Gly Ser
                165                 170                 175

Asp Lys Ala Leu Ala Ala Ala Thr Pro Met Val Val Trp Leu Gln Thr
            180                 185                 190

Ala Ser Thr Gln Ala Lys Thr Arg Ala Met Gln Ala Thr Ala Gln Ala
        195                 200                 205

Ala Ala Tyr Thr Gln Ala Met Ala Thr Thr Pro Ser Leu Pro Glu Ile
    210                 215                 220

Ala Ala Asn His Ile Thr Gln Ala Val Leu Thr Ala Thr Asn Phe Phe
225                 230                 235                 240

Gly Ile Asn Thr Ile Pro Ile Ala Leu Thr Glu Met Asp Tyr Phe Ile
                245                 250                 255

Arg Met Trp Asn Gln Ala Ala Leu Ala Met Glu Val Tyr Gln Ala Glu
            260                 265                 270

Thr Ala Val Asn Thr Leu Phe Glu Lys Leu Glu Pro Met Ala Ser Ile
        275                 280                 285

Leu Asp Pro Gly Ala Ser Gln Ser Thr Thr Asn Pro Ile Phe Gly Met
    290                 295                 300

Pro Ser Pro Gly Ser Ser Thr Pro Val Gly Gln Leu Pro Pro Ala Ala
305                 310                 315                 320

Thr Gln Thr Leu Gly Gln Leu Gly Glu Met Ser Gly Pro Met Gln Gln
                325                 330                 335

Leu Thr Gln Pro Leu Gln Gln Val Thr Ser Leu Phe Ser Gln Val Gly
            340                 345                 350

Gly Thr Gly Gly Gly Asn Pro Ala Asp Glu Glu Ala Ala Gln Met Gly
        355                 360                 365

Leu Leu Gly Thr Ser Pro Leu Ser Asn His Pro Leu Ala Gly Gly Ser
    370                 375                 380

Gly Pro Ser Ala Gly Ala Gly Leu Leu Arg Ala Glu Ser Leu Pro Gly
385                 390                 395                 400

Ala Gly Gly Ser Leu Thr Arg Thr Pro Leu Met Ser Gln Leu Ile Glu
                405                 410                 415

Lys Pro Val Ala Pro Ser Val Met Pro Ala Ala Ala Ala Gly Ser Ser
            420                 425                 430

Ala Thr Gly Gly Ala Ala Pro Val Gly Ala Gly Ala Met Gly Gln Gly
        435                 440                 445

Ala Gln Ser Gly Gly Ser Thr Arg Pro Gly Leu Val Ala Pro Ala Pro
    450                 455                 460

Leu Ala Gln Glu Arg Glu Glu Asp Asp Glu Asp Asp Trp Asp Glu Glu
465                 470                 475                 480

Asp Asp Trp Glu Phe Gly Gly Ser Gly Gly Ser Met Thr Glu Gln Gln
                485                 490                 495

Trp Asn Phe Ala Gly Ile Glu Ala Ala Ala Ser Ala Ile Gln Gly Asn
            500                 505                 510

Val Thr Ser Ile His Ser Leu Leu Asp Glu Gly Lys Gln Ser Leu Thr
        515                 520                 525
```

-continued

```
Lys Leu Ala Ala Ala Trp Gly Gly Ser Gly Ser Glu Ala Tyr Gln Gly
    530                 535                 540

Val Gln Gln Lys Trp Asp Ala Thr Ala Thr Glu Leu Asn Asn Ala Leu
545                 550                 555                 560

Gln Asn Leu Ala Arg Thr Ile Ser Glu Ala Gly Gln Ala Met Ala Ser
                565                 570                 575

Thr Glu Gly Asn Val Thr Gly Met Phe Ala Ala Ser Gly Gly Ser Gly
            580                 585                 590

Gly Ser Met Thr Gln Ser Gln Thr Val Thr Val Asp Gln Gln Glu Ile
        595                 600                 605

Leu Asn Arg Ala Asn Glu Val Glu Ala Pro Met Ala Asp Pro Pro Thr
    610                 615                 620

Asp Val Pro Ile Thr Pro Cys Glu Leu Thr Ala Ala Lys Asn Ala Ala
625                 630                 635                 640

Gln Gln Leu Val Leu Ser Ala Asp Asn Met Arg Glu Tyr Leu Ala Ala
                645                 650                 655

Gly Ala Lys Glu Arg Gln Arg Leu Ala Thr Ser Leu Arg Asn Ala Ala
            660                 665                 670

Lys Ala Tyr Gly Glu Val Asp Glu Glu Ala Ala Thr Ala Leu Asp Asn
        675                 680                 685

Asp Gly Glu Gly Thr Val Gln Ala Glu Ser Ala Gly Ala Val Gly Gly
    690                 695                 700

Asp Ser Ser Ala Glu Leu Thr Asp Thr Pro Arg Val Ala Thr Ala Gly
705                 710                 715                 720

Glu Pro Asn Phe Met Asp Leu Lys Glu Ala Ala Arg Lys Leu Glu Thr
                725                 730                 735

Gly Asp Gln Gly Ala Ser Leu Ala His Phe Ala Asp Gly Trp Asn Thr
            740                 745                 750

Phe Asn Leu Thr Leu Gln Gly Asp Val Lys Arg Phe Arg Gly Phe Asp
        755                 760                 765

Asn Trp Glu Gly Asp Ala Ala Thr Ala Cys Glu Ala Ser Leu Asp Gln
    770                 775                 780

Gln Arg Gln Trp Ile Leu His Met Ala Lys Leu Ser Ala Ala Met Ala
785                 790                 795                 800

Lys Gln Ala Gln Tyr Val Ala Gln Leu His Val Trp Ala Arg Arg Glu
                805                 810                 815

His Pro Thr Tyr Glu Asp Ile Val Gly Leu Glu Arg Leu Tyr Ala Glu
            820                 825                 830

Asn Pro Ser Ala Arg Asp Gln Ile Leu Pro Val Tyr Ala Glu Tyr Gln
        835                 840                 845

Gln Arg Ser Glu Lys Val Leu Thr Glu Tyr Asn Asn Lys Ala Ala Leu
    850                 855                 860

Glu Pro Val Asn Pro Pro Lys Pro Pro Pro Ala Ile Lys Ile Asp Pro
865                 870                 875                 880

Pro Pro Pro Pro Gln Glu Gln Gly Leu Ile Pro Gly Phe Leu Met Pro
                885                 890                 895

Pro Ser Asp Gly Ser Gly Val Thr Pro Gly Thr Gly Met Pro Ala Ala
            900                 905                 910

Pro Met Val Pro Pro Thr Gly Ser Pro Gly Gly Gly Leu Pro Ala Asp
        915                 920                 925

Thr Ala Ala Gln Leu Thr Ser Ala Gly Arg Glu Ala Ala Ala Leu Ser
    930                 935                 940
```

```
Gly Asp Val Ala Val Lys Ala Ala Ser Leu Gly Gly Gly Gly Gly Gly
945                 950                 955                 960

Gly Val Pro Ser Ala Pro Leu Gly Ser Ala Ile Gly Gly Ala Glu Ser
                965                 970                 975

Val Arg Pro Ala Gly Ala Gly Asp Ile Ala Gly Leu Gly Gln Gly Arg
            980                 985                 990

Ala Gly Gly Gly Ala Ala Leu Gly Gly Gly Gly Met Gly Met Pro Met
        995                 1000                1005

Gly Ala Ala His Gln Gly Gln Gly Gly Ala Lys Ser Lys Gly Ser Gln
    1010                1015                1020

Gln Glu Asp Glu Ala Leu Tyr Thr Glu Asp Arg Ala Trp Thr Glu Ala
1025                1030                1035                1040

Val Ile Gly Asn Arg Arg Arg Gln Asp Ser Lys Glu Ser Lys
                1045                1050
```

```
<210> SEQ ID NO 284
<211> LENGTH: 2613
<212> TYPE: DNA
<213> ORGANISM: Mycobacterium tuberculosis

<400> SEQUENCE: 284

catatggagc tggtccgggt gaccgaggcc ggagccatgg ccgcgggccg ctgggtaggc      60

cgcggcgaca aggagggcgg cgacggcgcg gcggtcgacg cgatgcgcga actggtcaac     120

tcggtttcca tgcgcggggt ggtggtcatc ggcgaaggcg aaaaggacca cgcaccaatg     180

ctctacaacg gcgaagaagt gggcaacggc gacggaccgg aatgcgactt tgccgtcgac     240

cccattgacg gcaccacgct gatgagcaag ggcatgacca acgccatctc ggtgctggcg     300

gtagccgatc gcggcaccat gttcgacccg tcggcggtgt tctacatgaa caaaatcgcc     360

gtcggccccg atgccgcaca cgtgctggat atcaccgcgc cgatctcgga aaacatccga     420

gcggtcgcca aggtcaagga cctgtcggtg cgagacatga cggtgtgcat cctggacagg     480

ccgcggcacg cgcaactcat ccacgacgtc cgcgccaccg gggcccggat ccggctgatc     540

accgatggcg acgtcgccgg cgcgatctcg gcgtgccgac cgcactccgg caccgacctg     600

ctagctggga tcggcggcac cccggaggga atcatcgccg ccgcggcgat ccgctgcatg     660

ggcggggcga tccaggcgca gctcgccccg cgcgacgacg cggaacgccg caaggcccta     720

gaagccggtt acgacctgaa ccaggtcttg accaccgaag atctggtgtc cggggaaaac     780

gtcttcttct gcgccactgg ggtcaccgac ggcgacctgc tcaagggagt gcgttactac     840

cccggcggct gcaccaccca ttcgatcgtg atgcgctcga agtccggcac cgtccggatg     900

atcgaggcct accaccggct ttcaaagctc aacgaatact ccgcgatcga cttcaccggc     960

gacagcagcg ccgtgtaccc attgcccgga ggttctggtg gaagcgaatt cgtgcgatac    1020

agtgactcat accacacaac gggccggtgg cagccacgag cgtcgacaga agggtttccc    1080

atgggcgtca gcatcgaggt caacggacta acgaagtcct tcgggtcctc gaggatctgg    1140

gaagatgtca cgctaacgat ccccgccggg gaggtcagcg tgctgctggg cccatcgggt    1200

accggcaaat cggtgtttct gaaatctctg atcggcctcc tgcggccgga gcgcggctcg    1260

atcatcatcg acggcaccga catcatcgaa tgctcggcca aggagcttta cgagatccgc    1320

acattgttcg gcgtgctgtt tcaggacggt gccctgttcg ggtcgatgaa cctctacgac    1380

aacaccgcgt tccccctgcg tgagcacacc aagaaaaagg aaagcgagat ccgtgacatc    1440

gtcatggaga agctggccct agtcggcctg ggtggggacg agaagaagtt ccccggcgag    1500
```

atctccggcg ggatgcgtaa gcgtgccggc ctagcgcgtg ccctggtcct tgacccgcag 1560
atcattctct gcgacgagcc cgactcgggt ctggacccgg ttcgtaccgc ctacctgagc 1620
cagctgatca tggacatcaa cgcccagatc gacgccacca tcctgatcgt gacgcacaac 1680
atcaacatcg cccgcaccgt gccggacaac atgggcatgt tgttccgcaa gcatttggtg 1740
atgttcgggc cgcgggaggt gctactcacc agcgacgagc cggtggtgcg gcagttcctc 1800
aacggccggc gcatcggccc gatcggcatg tccgaggaga aggacgaggc caccatggcc 1860
gaagagcagg ccctgctcga tgccggccac cacgcgggcg gtgtcgagga aatcgagggc 1920
gtgccgccgc agatcagcgc gacaccgggc atgccggagc gcaaagcggt cgcccggcgt 1980
caggctcggg ttcgcgagat gttgcacacg ctgcccaaaa aggcccaggc ggcgatcctc 2040
gacgatctcg agggcacgca caagtacgcg gtgcacgaaa tcggccaggg tggaagcggc 2100
ggttctgagc tcgtggctgg tgacaccacc atcaccatcg tcggaaatct gaccgctgac 2160
cccgagctgc ggttcacccc gtccggtgcg gccgtggcga atttcaccgt ggcgtcaacg 2220
ccccggatct atgaccgtca gaccggcgaa tggaaagacg gcgaagcgct gttcctccgg 2280
tgcaatatct ggcgggaggc ggccgagaac gtggccgaga gcctcacccg gggggcacga 2340
gtcatcgtta gcgggcggct taagcagcgg tcgtttgaaa cccgtgaggg cgagaagcgc 2400
accgtcatcg aggtcgaggt cgatgagatt gggccttcgc ttcggtacgc caccgccaag 2460
gtcaacaagg ccagccgcag cggcgggttt ggcagcggat cccgtccggc gccggcgcag 2520
accagcagcg cctcgggaga tgacccgtgg ggcagcgcac cggcgtcggg ttcgttcggc 2580
ggcggcgatg acgaaccgcc attctgaaag ctt 2613

<210> SEQ ID NO 285
<211> LENGTH: 32
<212> TYPE: DNA
<213> ORGANISM: Artificial Sequence
<220> FEATURE:
<223> OTHER INFORMATION: Primer

<400> SEQUENCE: 285
taggatccca tatggagctg gtccgggtga cc 32

<210> SEQ ID NO 286
<211> LENGTH: 47
<212> TYPE: DNA
<213> ORGANISM: Artificial Sequence
<220> FEATURE:
<223> OTHER INFORMATION: Primer

<400> SEQUENCE: 286
cacgaattcg cttccaccag aacctccggg caatgggtac acggcgc 47

<210> SEQ ID NO 287
<211> LENGTH: 45
<212> TYPE: DNA
<213> ORGANISM: Artificial Sequence
<220> FEATURE:
<223> OTHER INFORMATION: Primer

<400> SEQUENCE: 287
ggaggttctg gtggaagcga attcgtgcga tacagtgact catac 45

<210> SEQ ID NO 288
<211> LENGTH: 50
<212> TYPE: DNA
<213> ORGANISM: Artificial Sequence
<220> FEATURE:
<223> OTHER INFORMATION: Primer

<400> SEQUENCE: 288
gccacgagct cagaaccgcc gcttccaccc tggccgattt cgtgcaccgc 50

<210> SEQ ID NO 289
<211> LENGTH: 50
<212> TYPE: DNA
<213> ORGANISM: Artificial Sequence
<220> FEATURE:
<223> OTHER INFORMATION: Primer

<400> SEQUENCE: 289
gccagggtgg aagcggcggt tctgagctcg tggctggtga caccaccatc 50

<210> SEQ ID NO 290
<211> LENGTH: 36
<212> TYPE: DNA
<213> ORGANISM: Artificial Sequence
<220> FEATURE:
<223> OTHER INFORMATION: Primer

<400> SEQUENCE: 290
caattaaagc tttcagaatg gcggttcgtc atcgcc 36

<210> SEQ ID NO 291
<211> LENGTH: 887
<212> TYPE: PRT
<213> ORGANISM: Mycobacterium tuberculosis

<400> SEQUENCE: 291

Met Gly Ser Ser His His His His His His Ser Ser Gly Leu Val Pro
1 5 10 15

Arg Gly Ser His Met Glu Leu Val Arg Val Thr Glu Ala Gly Ala Met
20 25 30

Ala Ala Gly Arg Trp Val Gly Arg Gly Asp Lys Glu Gly Gly Asp Gly
35 40 45

Ala Ala Val Asp Ala Met Arg Glu Leu Val Asn Ser Val Ser Met Arg
50 55 60

Gly Val Val Val Ile Gly Glu Gly Glu Lys Asp His Ala Pro Met Leu
65 70 75 80

Tyr Asn Gly Glu Glu Val Gly Asn Gly Asp Gly Pro Glu Cys Asp Phe
85 90 95

Ala Val Asp Pro Ile Asp Gly Thr Thr Leu Met Ser Lys Gly Met Thr
100 105 110

Asn Ala Ile Ser Val Leu Ala Val Ala Asp Arg Gly Thr Met Phe Asp
115 120 125

Pro Ser Ala Val Phe Tyr Met Asn Lys Ile Ala Val Gly Pro Asp Ala
130 135 140

Ala His Val Leu Asp Ile Thr Ala Pro Ile Ser Glu Asn Ile Arg Ala
145 150 155 160

Val Ala Lys Val Lys Asp Leu Ser Val Arg Asp Met Thr Val Cys Ile
165 170 175

Leu Asp Arg Pro Arg His Ala Gln Leu Ile His Asp Val Arg Ala Thr
180 185 190

Gly Ala Arg Ile Arg Leu Ile Thr Asp Gly Asp Val Ala Gly Ala Ile
195 200 205

Ser Ala Cys Arg Pro His Ser Gly Thr Asp Leu Leu Ala Gly Ile Gly

-continued

```
    210                 215                 220

Gly Thr Pro Glu Gly Ile Ile Ala Ala Ala Ala Ile Arg Cys Met Gly
225                 230                 235                 240

Gly Ala Ile Gln Ala Gln Leu Ala Pro Arg Asp Asp Ala Glu Arg Arg
                245                 250                 255

Lys Ala Leu Glu Ala Gly Tyr Asp Leu Asn Gln Val Leu Thr Thr Glu
            260                 265                 270

Asp Leu Val Ser Gly Glu Asn Val Phe Phe Cys Ala Thr Gly Val Thr
        275                 280                 285

Asp Gly Asp Leu Leu Lys Gly Val Arg Tyr Tyr Pro Gly Gly Cys Thr
    290                 295                 300

Thr His Ser Ile Val Met Arg Ser Lys Ser Gly Thr Val Arg Met Ile
305                 310                 315                 320

Glu Ala Tyr His Arg Leu Ser Lys Leu Asn Glu Tyr Ser Ala Ile Asp
                325                 330                 335

Phe Thr Gly Asp Ser Ser Ala Val Tyr Pro Leu Pro Gly Gly Ser Gly
            340                 345                 350

Gly Ser Glu Phe Val Arg Tyr Ser Asp Ser Tyr His Thr Thr Gly Arg
        355                 360                 365

Trp Gln Pro Arg Ala Ser Thr Glu Gly Phe Pro Met Gly Val Ser Ile
    370                 375                 380

Glu Val Asn Gly Leu Thr Lys Ser Phe Gly Ser Ser Arg Ile Trp Glu
385                 390                 395                 400

Asp Val Thr Leu Thr Ile Pro Ala Gly Glu Val Ser Val Leu Leu Gly
                405                 410                 415

Pro Ser Gly Thr Gly Lys Ser Val Phe Leu Lys Ser Leu Ile Gly Leu
            420                 425                 430

Leu Arg Pro Glu Arg Gly Ser Ile Ile Ile Asp Gly Thr Asp Ile Ile
        435                 440                 445

Glu Cys Ser Ala Lys Glu Leu Tyr Glu Ile Arg Thr Leu Phe Gly Val
    450                 455                 460

Leu Phe Gln Asp Gly Ala Leu Phe Gly Ser Met Asn Leu Tyr Asp Asn
465                 470                 475                 480

Thr Ala Phe Pro Leu Arg Glu His Thr Lys Lys Lys Glu Ser Glu Ile
                485                 490                 495

Arg Asp Ile Val Met Glu Lys Leu Ala Leu Val Gly Leu Gly Gly Asp
            500                 505                 510

Glu Lys Lys Phe Pro Gly Glu Ile Ser Gly Gly Met Arg Lys Arg Ala
        515                 520                 525

Gly Leu Ala Arg Ala Leu Val Leu Asp Pro Gln Ile Ile Leu Cys Asp
    530                 535                 540

Glu Pro Asp Ser Gly Leu Asp Pro Val Arg Thr Ala Tyr Leu Ser Gln
545                 550                 555                 560

Leu Ile Met Asp Ile Asn Ala Gln Ile Asp Ala Thr Ile Leu Ile Val
                565                 570                 575

Thr His Asn Ile Asn Ile Ala Arg Thr Val Pro Asp Asn Met Gly Met
            580                 585                 590

Leu Phe Arg Lys His Leu Val Met Phe Gly Pro Arg Glu Val Leu Leu
        595                 600                 605

Thr Ser Asp Glu Pro Val Val Arg Gln Phe Leu Asn Gly Arg Arg Ile
    610                 615                 620

Gly Pro Ile Gly Met Ser Glu Glu Lys Asp Glu Ala Thr Met Ala Glu
625                 630                 635                 640
```

```
Glu Gln Ala Leu Leu Asp Ala Gly His His Ala Gly Gly Val Glu Glu
                645                 650                 655

Ile Glu Gly Val Pro Pro Gln Ile Ser Ala Thr Pro Gly Met Pro Glu
            660                 665                 670

Arg Lys Ala Val Ala Arg Arg Gln Ala Arg Val Arg Glu Met Leu His
        675                 680                 685

Thr Leu Pro Lys Lys Ala Gln Ala Ala Ile Leu Asp Asp Leu Glu Gly
    690                 695                 700

Thr His Lys Tyr Ala Val His Glu Ile Gly Gln Gly Gly Ser Gly Gly
705                 710                 715                 720

Ser Glu Leu Val Ala Gly Asp Thr Thr Ile Thr Ile Val Gly Asn Leu
                725                 730                 735

Thr Ala Asp Pro Glu Leu Arg Phe Thr Pro Ser Gly Ala Ala Val Ala
            740                 745                 750

Asn Phe Thr Val Ala Ser Thr Pro Arg Ile Tyr Asp Arg Gln Thr Gly
        755                 760                 765

Glu Trp Lys Asp Gly Glu Ala Leu Phe Leu Arg Cys Asn Ile Trp Arg
    770                 775                 780

Glu Ala Ala Glu Asn Val Ala Glu Ser Leu Thr Arg Gly Ala Arg Val
785                 790                 795                 800

Ile Val Ser Gly Arg Leu Lys Gln Arg Ser Phe Glu Thr Arg Glu Gly
                805                 810                 815

Glu Lys Arg Thr Val Ile Glu Val Glu Val Asp Glu Ile Gly Pro Ser
            820                 825                 830

Leu Arg Tyr Ala Thr Ala Lys Val Asn Lys Ala Ser Arg Ser Gly Gly
        835                 840                 845

Phe Gly Ser Gly Ser Arg Pro Ala Pro Ala Gln Thr Ser Ser Ala Ser
    850                 855                 860

Gly Asp Asp Pro Trp Gly Ser Ala Pro Ala Ser Gly Ser Phe Gly Gly
865                 870                 875                 880

Gly Asp Asp Glu Pro Pro Phe
                885
```

<210> SEQ ID NO 292
<211> LENGTH: 95
<212> TYPE: PRT
<213> ORGANISM: Mycobacterium tuberculosis

<400> SEQUENCE: 292

```
Met Thr Glu Gln Gln Trp Asn Phe Ala Gly Ile Glu Ala Ala Ala Ser
1               5                   10                  15

Ala Ile Gln Gly Asn Val Thr Ser Ile His Ser Leu Leu Asp Glu Gly
            20                  25                  30

Lys Gln Ser Leu Thr Lys Leu Ala Ala Ala Trp Gly Gly Ser Gly Ser
        35                  40                  45

Glu Ala Tyr Gln Gly Val Gln Gln Lys Trp Asp Ala Thr Ala Thr Glu
    50                  55                  60

Leu Asn Asn Ala Leu Gln Asn Leu Ala Arg Thr Ile Ser Glu Ala Gly
65                  70                  75                  80

Gln Ala Met Ala Ser Thr Glu Gly Asn Val Thr Gly Met Phe Ala
                85                  90                  95
```

<210> SEQ ID NO 293
<211> LENGTH: 318
<212> TYPE: DNA

<213> ORGANISM: Mycobacterium tuberculosis

<400> SEQUENCE: 293
catatgcatc accatcacca tcacatgaca gagcagcagt ggaatttcgc gggtatcgag 60
gccgcggcaa gcgcaatcca gggaaatgtc acgtccattc attccctcct tgacgagggg 120
aagcagtccc tgaccaagct cgcagcggcc tggggcggta gcggttcgga ggcgtaccag 180
ggtgtccagc aaaaatggga cgccacggct accgagctga acaacgcgct gcagaacctg 240
gcgcggacga tcagcgaagc cggtcaggca atggcttcga ccgaaggcaa cgtcactggg 300
atgttcgcat aggaattc 318

<210> SEQ ID NO 294
<211> LENGTH: 102
<212> TYPE: PRT
<213> ORGANISM: Mycobacterium tuberculosis

<400> SEQUENCE: 294

Met His His His His His His Met Thr Glu Gln Gln Trp Asn Phe Ala
1 5 10 15

Gly Ile Glu Ala Ala Ala Ser Ala Ile Gln Gly Asn Val Thr Ser Ile
20 25 30

His Ser Leu Leu Asp Glu Gly Lys Gln Ser Leu Thr Lys Leu Ala Ala
35 40 45

Ala Trp Gly Gly Ser Gly Ser Glu Ala Tyr Gln Gly Val Gln Gln Lys
50 55 60

Trp Asp Ala Thr Ala Thr Glu Leu Asn Asn Ala Leu Gln Asn Leu Ala
65 70 75 80

Arg Thr Ile Ser Glu Ala Gly Gln Ala Met Ala Ser Thr Glu Gly Asn
85 90 95

Val Thr Gly Met Phe Ala
100

<210> SEQ ID NO 295
<211> LENGTH: 33
<212> TYPE: DNA
<213> ORGANISM: Artificial Sequence
<220> FEATURE:
<223> OTHER INFORMATION: Primer

<400> SEQUENCE: 295
caattacata tgagagtttt gttgctggga ccg 33

<210> SEQ ID NO 296
<211> LENGTH: 35
<212> TYPE: DNA
<213> ORGANISM: Artificial Sequence
<220> FEATURE:
<223> OTHER INFORMATION: Primer

<400> SEQUENCE: 296
caattaaagc ttctactttc cagagcccgc aacgc 35

<210> SEQ ID NO 297
<211> LENGTH: 32
<212> TYPE: DNA
<213> ORGANISM: Artificial Sequence
<220> FEATURE:
<223> OTHER INFORMATION: Primer

<400> SEQUENCE: 297
caattacata tgaccggccc caccaccgcg cc 32

<210> SEQ ID NO 298
<211> LENGTH: 36
<212> TYPE: DNA
<213> ORGANISM: Artificial Sequence
<220> FEATURE:
<223> OTHER INFORMATION: Primer

<400> SEQUENCE: 298
caattaaagc tttcaggtgt ctttgggtgt tccgag 36

<210> SEQ ID NO 299
<211> LENGTH: 33
<212> TYPE: DNA
<213> ORGANISM: Artificial Sequence
<220> FEATURE:
<223> OTHER INFORMATION: Primer

<400> SEQUENCE: 299
caattacata tgagagtttt gttgctggga ccg 33

<210> SEQ ID NO 300
<211> LENGTH: 35
<212> TYPE: DNA
<213> ORGANISM: Artificial Sequence
<220> FEATURE:
<223> OTHER INFORMATION: Primer

<400> SEQUENCE: 300
caattaaagc ttctactttc cagagcccgc aacgc 35

<210> SEQ ID NO 301
<211> LENGTH: 54
<212> TYPE: DNA
<213> ORGANISM: Artificial Sequence
<220> FEATURE:
<223> OTHER INFORMATION: Primer

<400> SEQUENCE: 301
caattacata tgcatcacca tcaccatcac gtggtggacc gcgatcccaa tacc 54

<210> SEQ ID NO 302
<211> LENGTH: 33
<212> TYPE: DNA
<213> ORGANISM: Artificial Sequence
<220> FEATURE:
<223> OTHER INFORMATION: Primer

<400> SEQUENCE: 302
caattagaat tctcagcgat tcctgatctt gtg 33

<210> SEQ ID NO 303
<211> LENGTH: 33
<212> TYPE: DNA
<213> ORGANISM: Artificial Sequence
<220> FEATURE:
<223> OTHER INFORMATION: Primer

<400> SEQUENCE: 303
ctggatccca tatggccttc ccggaatatt cgc 33

<210> SEQ ID NO 304
<211> LENGTH: 33
<212> TYPE: DNA
<213> ORGANISM: Artificial Sequence
<220> FEATURE:
<223> OTHER INFORMATION: Primer

<400> SEQUENCE: 304
ctagctgaat tctcatccga cgtgtttccg ccg 33

<210> SEQ ID NO 305
<211> LENGTH: 33
<212> TYPE: DNA
<213> ORGANISM: Artificial Sequence
<220> FEATURE:
<223> OTHER INFORMATION: Primer

<400> SEQUENCE: 305
caattacata tggcgcccaa gacctactgc gag 33

<210> SEQ ID NO 306
<211> LENGTH: 36
<212> TYPE: DNA
<213> ORGANISM: Artificial Sequence
<220> FEATURE:
<223> OTHER INFORMATION: Primer

<400> SEQUENCE: 306
caattaaagc ttctaggcca gcatcgagtc gatcgc 36

<210> SEQ ID NO 307
<211> LENGTH: 51
<212> TYPE: DNA
<213> ORGANISM: Artificial Sequence
<220> FEATURE:
<223> OTHER INFORMATION: Primer

<400> SEQUENCE: 307
caattacata tgcatcacca tcaccatcac atgcaattcg acgtgaccat c 51

<210> SEQ ID NO 308
<211> LENGTH: 36
<212> TYPE: DNA
<213> ORGANISM: Artificial Sequence
<220> FEATURE:
<223> OTHER INFORMATION: Primer

<400> SEQUENCE: 308
caattagaat tctcagtgtg taccggcctt gaagcg 36

<210> SEQ ID NO 309
<211> LENGTH: 51
<212> TYPE: DNA
<213> ORGANISM: Artificial Sequence
<220> FEATURE:
<223> OTHER INFORMATION: Primer

<400> SEQUENCE: 309
caattacata tgcatcacca tcaccatcac acttccggcg atatgtcgag c 51

<210> SEQ ID NO 310
<211> LENGTH: 33
<212> TYPE: DNA
<213> ORGANISM: Artificial Sequence
<220> FEATURE:
<223> OTHER INFORMATION: Primer

<400> SEQUENCE: 310
caattagaat tctcagcgcg gaatacttgc ctg 33

<210> SEQ ID NO 311
<211> LENGTH: 33
<212> TYPE: DNA
<213> ORGANISM: Artificial Sequence
<220> FEATURE:
<223> OTHER INFORMATION: Primer

<400> SEQUENCE: 311
gtgctagcca tatggaaaaa atgtcacatg atc 33

<210> SEQ ID NO 312
<211> LENGTH: 35
<212> TYPE: DNA
<213> ORGANISM: Artificial Sequence
<220> FEATURE:
<223> OTHER INFORMATION: Primer

<400> SEQUENCE: 312
ctggatccaa gcttctattc ggcgaagacg ccggc 35

<210> SEQ ID NO 313
<211> LENGTH: 33
<212> TYPE: DNA
<213> ORGANISM: Artificial Sequence
<220> FEATURE:
<223> OTHER INFORMATION: Primer

<400> SEQUENCE: 313
gtgctagcca tatgctgtgg cacgcaatgc cac 33

<210> SEQ ID NO 314
<211> LENGTH: 35
<212> TYPE: DNA
<213> ORGANISM: Artificial Sequence
<220> FEATURE:
<223> OTHER INFORMATION: Primer

<400> SEQUENCE: 314
ctggatccaa gctttcacca gtcgtcctct tcgtc 35

<210> SEQ ID NO 315
<211> LENGTH: 51
<212> TYPE: DNA
<213> ORGANISM: Artificial Sequence
<220> FEATURE:
<223> OTHER INFORMATION: Primer

<400> SEQUENCE: 315
caattacata tgcatcacca tcaccatcac gtgaagcgag cgctcatcac c 51

<210> SEQ ID NO 316
<211> LENGTH: 35
<212> TYPE: DNA
<213> ORGANISM: Artificial Sequence
<220> FEATURE:
<223> OTHER INFORMATION: Primer

<400> SEQUENCE: 316
caattagaat tctcatgtcc ggccggcgat catcg 35

<210> SEQ ID NO 317
<211> LENGTH: 50
<212> TYPE: DNA
<213> ORGANISM: Artificial Sequence
<220> FEATURE:
<223> OTHER INFORMATION: Primer -continued

<400> SEQUENCE: 317
ccattacata tgcatcacca tcaccatcac atgacagagc agcagtggaa 50

<210> SEQ ID NO 318
<211> LENGTH: 33
<212> TYPE: DNA
<213> ORGANISM: Artificial Sequence
<220> FEATURE:
<223> OTHER INFORMATION: Primer

<400> SEQUENCE: 318
ccattagaat tcctatgcga acatcccagt gac 33

IMMUNOGENIC COMPOSITIONS COMPRISING *MYCOBACTERIUM TUBERCULOSIS* POLYPEPTIDES AND FUSIONS THEREOF

CROSS-REFERENCE TO RELATED APPLICATION(S)

This non-provisional application is a division of U.S. application Ser. No. 15/815,512, filed on Nov. 16, 2017, which is a divisional of Ser. No. 13/791,511, filed Mar. 8, 2013, now U.S. Pat. No. 9,822,152, which is a continuation of Ser. No. 12/594,806, filed Jan. 6, 2010, now U.S. Pat. No. 8,486,414, which is a 371 of international number PCT/US2008/059500, filed Apr. 4, 2008 which claims the benefit and priority of U.S. provisional application Ser. No. 60/910,169, filed Apr. 4, 2007, all of which are hereby incorporated by reference herein in their entirety, including all references and appendices cited therein, for all purposes, as if fully set forth herein.

STATEMENT OF GOVERNMENT INTEREST

This invention was made in part with government support under Grant Nos. AI-025038 and AI-067251 awarded by the National Institutes of Health. The government has certain rights in this invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 05-US-03_Sequence_Listing.txt. The text file is 515 KB, was created on Jul. 5, 2021, and is being submitted electronically via EFS-Web, concurrent with the filing of the specification.

BACKGROUND

Technical Field

The present invention relates generally to compositions comprising antigenic and/or immunogenic combinations of *Mycobacterium* tuberculosis antigens and their use in the diagnosis, treatment, and prevention of tuberculosis.

Description of the Related Art

Tuberculosis is a chronic infectious disease caused by infection with *Mycobacterium tuberculosis* and other *Mycobacterium* species. It is a major disease in developing countries, as well as an increasing problem in developed areas of the world, with several million new cases each year.

Although infection may be asymptomatic for a considerable period of time, the disease is most commonly manifested as an acute inflammation of the lungs, resulting in fever and a nonproductive cough. If untreated, serious complications and death typically result.

Although tuberculosis can generally be controlled using extended antibiotic therapy, such treatment is not sufficient to prevent the spread of the disease. Infected individuals may be asymptomatic, but contagious, for some time. In addition, although compliance with the treatment regimen is critical, patient behavior is difficult to monitor. Some patients do not complete the course of treatment, which can lead to ineffective treatment and the development of drug resistance.

In order to control the spread of tuberculosis, effective vaccination and accurate early diagnosis of the disease are critical. Currently, vaccination with live bacteria is the most widely used method for inducing protective immunity. The most common *Mycobacterium* employed for this purpose is Bacillus Calmette-Guérin (BCG), an avirulent strain of *Mycobacterium bovis*. However, the safety and efficacy of BCG is a source of controversy and some countries, such as the United States, do not vaccinate the general public with this agent.

Diagnosis of tuberculosis is commonly achieved using a skin test, which involves intradermal exposure to tuberculin PPD (protein-purified derivative). Antigen-specific T cell responses result in measurable induration at the injection site by 48-72 hours after injection, which indicates exposure to mycobacterial antigens. Sensitivity and specificity have, however, been problematic, and individuals vaccinated with BCG cannot be distinguished from infected individuals.

Accordingly, there is a need for improved reagents and methods for diagnosing, preventing and treating tuberculosis. The present invention fulfills these needs and offers other related advantages.

BRIEF SUMMARY

The present invention relates generally to compositions comprising at least two heterologous antigens, fusion polypeptides comprising the antigens and polynucleotides encoding the antigens, where the antigens are from a *Mycobacterium* species, particularly *Mycobacterium tuberculosis*. The present invention also relates methods of using the polypeptides and polynucleotides of the invention in the diagnosis, treatment and prevention of *Mycobacterium* infection. The antigens of the invention, when employed in combination and/or as fusion polypeptides or polynucleotides as described herein, offer improved and unexpected levels of immunogenicity, resulting in decrease in lung bacterial burden, and thus are particularly useful in the context of vaccine development.

For example, in one aspect of the invention, there are provided compositions comprising an immunostimulant and a combination of two or more *Mycobacterium tuberculosis* antigens, or immunogenic fragments thereof, wherein the antigens are selected from the group consisting of Rv0164 (SEQ ID NO: 1), Rv0496 (SEQ ID NO: 6), Rv2608 (SEQ ID NO: 26), Rv3020 (SEQ ID NO: 36), Rv3478 (SEQ ID NO: 41), Rv3619 (SEQ ID NO: 46), Rv3620 (SEQ ID NO: 51), RV1738 (SEQ ID NO: 11), Rv1813 (SEQ ID NO: 16), Rv3810 (SEQ ID NO: 56), Rv2389 (SEQ ID NO: 21). Rv2866 (SEQ ID NO: 31), Rv3876 (SEQ ID NO: 61), Rv0054 (SEQ ID NO: 100), Rv0410 (SEQ ID NO: 106), Rv0655 (SEQ ID NO: 112), Rv0831 (SEQ ID NO: 115), Rv1009 (SEQ ID NO: 118), Rv1099 (SEQ ID NO: 121), Rv1240 (SEQ ID NO: 124), Rv1288 (SEQ ID NO: 127), Rv1410 (SEQ ID NO: 130), Rv1569 (SEQ ID NO: 133), Rv1789 (SEQ ID NO: 136), Rv1818 (SEQ ID NO: 139), Rv1860 (SEQ ID NO: 142), Rv1886 (SEQ ID NO: 145), Rv1908 (SEQ ID NO: 148), Rv2220 (SEQ ID NO: 154), Rv2032 (SEQ ID NO: 151), Rv2623 (SEQ ID NO: 160), Rv2875 (SEQ ID NO: 163), Rv3044 (SEQ ID NO: 166), Rv3310 (SEQ ID NO: 169). Rv3881 (SEQ ID NO: 178), Rv0577 (SEQ ID NO: 184), Rv1626 (SEQ ID NO: 187), Rv0733 (SEQ ID NO: 190), Rv2520 (SEQ ID NO: 193). Rv1253 (SEQ ID NO: 196), Rv1980 (SEQ ID NO: 199), Rv3628 (SEQ ID NO: 202) Rv1884 (SEQ ID NO: 205), Rv3872 (SEQ ID NO: 208), Rv3873 (SEQ ID NO: 211), Rv1511 (SEQ ID NO: 214) and Rv3875 (SEQ ID NO: 292) and antigens having at least 80%, 90% or 95% identity to any of the foregoing sequences.

In certain embodiments, the combination of two or more antigens is selected from the group consisting of:

(a) a combination comprising Rv1813 (SEQ ID NO: 16); Rv3620 (SEQ ID NO: 51) and Rv2608 (SEQ ID NO: 26);

(b) a combination comprising Rv2608 (SEQ ID NO: 26) and Rv3619 (SEQ ID NO: 46); and (c) a combination comprising Rv3478 (SEQ ID NO: 41) and Rv3619 (SEQ ID NO: 46).

In a particular embodiment, the composition of (a) above, comprising Rv2608 (SEQ ID NO: 26), Rv1813 (SEQ ID NO: 16) and Rv3620 (SEQ ID NO: 51), further comprises one or more antigens selected from the group consisting of: Rv1886 (SEQ ID NO: 145), Rv2389 (SEQ ID NO: 21), Rv3478 (SEQ ID NO: 41), Rv2875 (SEQ ID NO: 163), Rv2220 (SEQ ID NO: 154), Rv0733 (SEQ ID NO: 190), Rv0577 (SEQ ID NO: 184), Rv3044 (SEQ ID NO: 166), Rv1626 (SEQ ID NO: 187), Rv3619 (SEQ ID NO: 46) and Rv3020 (SEQ ID NO: 36).

In a more particular embodiment, the composition comprises Rv1813 (SEQ ID NO: 16); Rv3620 (SEQ ID NO: 51), Rv2608 (SEQ ID NO: 26) and Rv2389 (SEQ ID NO: 21).

In related particular embodiment, the composition comprises Rv2608 (SEQ ID NO: 26); Rv1813 (SEQ ID NO: 16), Rv3620 (SEQ ID NO: 51) and Rv3619 (SEQ ID NO: 46).

In certain other embodiments of the invention, the composition of (b) above, comprising Rv2608 (SEQ ID NO: 26) and Rv3619 (SEQ ID NO: 46), further comprises one or more antigens selected from the group consisting of: Rv1886 (SEQ ID NO: 145), Rv2389 (SEQ ID NO: 21), Rv1813 (SEQ ID NO: 16), Rv2875 (SEQ ID NO: 163), Rv2220 (SEQ ID NO: 154), Rv0733 (SEQ ID NO: 190), Rv0577 (SEQ ID NO: 184), Rv3044 (SEQ ID NO: 166), Rv1626 (SEQ ID NO: 187), Rv3620 (SEQ ID NO: 51), Rv3478 (SEQ ID NO: 41), and Rv3020 (SEQ ID NO: 36).

In a particular embodiment, the composition comprises Rv2608 (SEQ ID NO: 26), Rv3619 (SEQ ID NO: 46), and Rv1886 (SEQ ID NO: 145).

In another particular embodiment, the composition further comprises one or more antigens selected from the group consisting of: Rv2389 (SEQ ID NO: 21), Rv1813 (SEQ ID NO: 16), Rv2875 (SEQ ID NO: 163), Rv2220 (SEQ ID NO: 154), Rv0733 (SEQ ID NO: 190), Rv0577 (SEQ ID NO: 184), Rv3044 (SEQ ID NO: 166), Rv1626 (SEQ ID NO: 187), Rv3620 (SEQ ID NO: 51) and Rv3020 (SEQ ID NO: 36).

In a more particular embodiment, the composition comprises Rv2608 (SEQ ID NO: 26), Rv3619 (SEQ ID NO: 46), Rv1813 (SEQ ID NO: 16) and Rv3620 (SEQ ID NO: 51).

In certain other embodiments of the invention, the composition of (c) above, comprising Rv3478 (SEQ ID NO: 41) and Rv3619 (SEQ ID NO: 46), further comprises one or more antigens selected from the group consisting of: Rv1886 (SEQ ID NO: 145), Rv2389 (SEQ ID NO: 21), Rv1813 (SEQ ID NO: 16), Rv2875 (SEQ ID NO: 163), Rv2220 (SEQ ID NO: 154), Rv0733 (SEQ ID NO: 190), Rv0577 (SEQ ID NO: 184), Rv3044 (SEQ ID NO: 166), Rv1626 (SEQ ID NO: 187), Rv3620 (SEQ ID NO: 51), Rv2608 (SEQ ID NO: 26), and Rv3020 (SEQ ID NO: 36).

In a particular embodiment, the composition comprises Rv3478 (SEQ ID NO: 41), Rv3619 (SEQ ID NO: 46) and Rv1886 (SEQ ID NO: 145).

In another embodiment, the combination further comprises one or more antigens selected from the group consisting of: Rv2389 (SEQ ID NO: 21), Rv1813 (SEQ ID NO: 16), Rv2875 (SEQ ID NO: 163), Rv2220 (SEQ ID NO: 154), Rv0733 (SEQ ID NO: 190), Rv0577 (SEQ ID NO: 184), Rv3044 (SEQ ID NO: 166), Rv1626 (SEQ ID NO: 187) and Rv3020 (SEQ ID NO: 36).

The combination of two or more antigens described herein can include a combination of two or more separate recombinant antigens, or antigenic/immunogenic fragments thereof. Alternatively, the two or more antigens, or antigenic/immunogenic fragments thereof, may be covalently linked in the form of a fusion polypeptide.

According to another aspect of the invention, there are provided isolated fusion polypeptides comprising a combination of two or more covalently linked *Mycobacterium tuberculosis* antigens, or immunogenic fragments thereof, wherein the antigens are selected from the group consisting of Rv0164 (SEQ ID NO: 1), Rv0496 (SEQ ID NO: 6), Rv2608 (SEQ ID NO: 26), Rv3020 (SEQ ID NO: 36), Rv3478 (SEQ ID NO: 41), Rv3619 (SEQ ID NO: 46), Rv3620 (SEQ ID NO: 51), RV1738 (SEQ ID NO: 11), Rv1813 (SEQ ID NO: 16), Rv3810 (SEQ ID NO: 56), Rv2389 (SEQ ID NO: 21), Rv2866 (SEQ ID NO: 31), Rv3876 (SEQ ID NO: 61), Rv0054 (SEQ ID NO: 100), Rv0410 (SEQ ID NO: 106), Rv0655 (SEQ ID NO: 112), Rv0831 (SEQ ID NO: 115), Rv1009 (SEQ ID NO: 118), Rv1099 (SEQ ID NO: 121). Rv1240 (SEQ ID NO: 124), Rv1288 (SEQ ID NO: 127), Rv1410 (SEQ ID NO: 130), Rv1569 (SEQ ID NO: 133), Rv1789 (SEQ ID NO: 136), Rv1818 (SEQ ID NO: 139), Rv1860 (SEQ ID NO: 142), Rv1886 (SEQ ID NO: 145), Rv1908 (SEQ ID NO: 148), Rv2220 (SEQ ID NO: 154), Rv2032 (SEQ ID NO: 151), Rv2623 (SEQ ID NO: 160), Rv2875 (SEQ ID NO: 163), Rv3044 (SEQ ID NO: 166), Rv3310 (SEQ ID NO: 169), Rv3881 (SEQ ID NO: 178), Rv0577 (SEQ ID NO: 184), Rv1626 (SEQ ID NO: 187), Rv0733 (SEQ ID NO: 190), Rv2520 (SEQ ID NO: 193), Rv1253 (SEQ ID NO: 196), Rv1980 (SEQ ID NO: 199), Rv3628 (SEQ ID NO: 202) Rv1884 (SEQ ID NO: 205), Rv3872 (SEQ ID NO: 208), Rv3873 (SEQ ID NO: 211), Rv1511 (SEQ ID NO: 214), and Rv3875 (SEQ ID NO: 292) and antigens having at least 80%, 90% or 95% identity to any of the foregoing sequences.

In certain embodiments, the fusion polypeptide comprises a combination of covalently linked antigens selected from the group consisting of:

(a) a combination comprising Rv1813 (SEQ ID NO: 16); Rv3620 (SEQ ID NO: 51) and Rv2608 (SEQ ID NO: 26);

(b) a combination comprising Rv2608 (SEQ ID NO: 26) and Rv3619 (SEQ ID NO: 46); and (c) a combination comprising Rv3478 (SEQ ID NO: 41) and Rv3619 (SEQ ID NO: 46).

In a particular embodiment, the fusion polypeptide of (a) above, comprising Rv2608 (SEQ ID NO: 26), Rv1813 (SEQ ID NO: 16) and Rv3620 (SEQ ID NO: 51), further comprises one or more antigens selected from the group consisting of: Rv1886 (SEQ ID NO: 145), Rv2389 (SEQ ID NO: 21), Rv1813 (SEQ ID NO: 16), Rv2875 (SEQ ID NO: 163), Rv2220 (SEQ ID NO: 154), Rv0733 (SEQ ID NO: 190), Rv0577 (SEQ ID NO: 184), Rv3044 (SEQ ID NO: 166), Rv1626 (SEQ ID NO: 187), Rv3619 (SEQ ID NO: 46), Rv3478 (SEQ ID NO: 41) and Rv3020 (SEQ ID NO: 36).

In a more particular embodiment, the fusion polypeptide comprises Rv1813 (SEQ ID NO: 16); Rv3620 (SEQ ID NO: 51); Rv2608 (SEQ ID NO: 26) and Rv2389 (SEQ ID NO: 21).

In a related particular embodiment, the fusion polypeptide comprises Rv1813 (SEQ ID NO: 16); Rv3620 (SEQ ID NO: 51); Rv2608 (SEQ ID NO: 26) and Rv3619 (SEQ ID NO: 46).

In certain other embodiments of the invention, the fusion polypeptide of (b) above, comprising Rv2608 (SEQ ID NO: 26) and Rv3619 (SEQ ID NO: 46), further comprises one or more antigens selected from the group consisting of: Rv1886 (SEQ ID NO: 145), Rv2389 (SEQ ID NO: 21), Rv1813 (SEQ ID NO: 16), Rv2875 (SEQ ID NO: 163), Rv2220 (SEQ ID NO: 154), Rv0733 (SEQ ID NO: 190), Rv0577 (SEQ ID NO: 184), Rv3044 (SEQ ID NO: 166), Rv1626 (SEQ ID NO: 187), Rv3620 (SEQ ID NO: 51), Rv3478 (SEQ ID NO: 41), and Rv3020 (SEQ ID NO: 36).

In a particular embodiment, the fusion polypeptide comprises Rv2608 (SEQ ID NO: 26), Rv1813 (SEQ ID NO: 16), Rv3619 (SEQ ID NO: 46), and Rv1886 (SEQ ID NO: 145).

In another particular embodiment, the fusion polypeptide further comprises one or more antigens selected from the group consisting of: Rv2389 (SEQ ID NO: 21), Rv1813 (SEQ ID NO: 16), Rv2875 (SEQ ID NO: 163), Rv2220 (SEQ ID NO: 154), Rv0733 (SEQ ID NO: 190), Rv0577 (SEQ ID NO: 184), Rv3044 (SEQ ID NO: 166), Rv1626 (SEQ ID NO: 187), Rv3620 (SEQ ID NO: 51) and Rv3020 (SEQ ID NO: 36).

In a more particular embodiment, the fusion polypeptide comprises Rv2608 (SEQ ID NO: 26), Rv3619 (SEQ ID NO: 46), Rv1813 (SEQ ID NO: 16) and Rv3620 (SEQ ID NO: 51).

In certain other embodiments of the invention, the fusion polypeptide of (c) above, comprising Rv3478 (SEQ ID NO: 41) and Rv3619 (SEQ ID NO: 46), further comprises one or more antigens selected from the group consisting of: Rv1886 (SEQ ID NO: 145), Rv2389 (SEQ ID NO: 21), Rv1813 (SEQ ID NO: 16), Rv2875 (SEQ ID NO: 163), Rv2220 (SEQ ID NO: 154), Rv0733 (SEQ ID NO: 190), Rv0577 (SEQ ID NO: 184), Rv3044 (SEQ ID NO: 166), Rv1626 (SEQ ID NO: 187), Rv3620 (SEQ ID NO: 51), Rv2608 (SEQ ID NO: 26), and Rv3020 (SEQ ID NO: 36).

In a particular embodiment, the fusion polypeptide comprises Rv3478 (SEQ ID NO: 41), Rv3619 (SEQ ID NO: 46) and Rv1886 (SEQ ID NO: 145).

In another embodiment, the fusion polypeptide further comprises one or more antigens selected from the group consisting of: Rv2389 (SEQ ID NO: 21), Rv1813 (SEQ ID NO: 16), Rv2875 (SEQ ID NO: 163), Rv2220 (SEQ ID NO: 154), Rv0733 (SEQ ID NO: 190), Rv0577 (SEQ ID NO: 184), Rv3044 (SEQ ID NO: 166), Rv1626 (SEQ ID NO: 187) and Rv3020 (SEQ ID NO: 36).

In certain particular embodiments, fusion polypeptides are provided which comprise an amino acid sequence selected from the group consisting of: ID83 (SEQ ID NO: 91), 1094 (SEQ ID NO: 95), 1093 (SEQ ID NO: 226), ID91 (SEQ ID NO: 236), ID71 (SEQ ID NO: 245), 10114 (SEQ ID NO: 251), ID125 (SEQ ID NO: 257).

According to another aspect of the invention, there are provided isolated polynucleotides encoding any of the antigens and/or fusion polypeptides described herein.

It will be understood that, in many embodiments, the compositions, polypeptides and polynucleotides of the invention are preferably formulated in combination with one or more immunostimulants in order to improve the immune response elicited by the antigens described herein. Numerous immunostimulant and adjuvant systems are known and available in the art and can be used in the context of the present invention, illustrative examples of which include AS-2, ENHANZYN™, 3D-MPL™, IFA, QS21, CWS, TDM, AGPs, CpG-containing oligonucleotides, Toll-like receptor agonists (e.g., TLR9 agonists, TLR7 agonists, TLR7/8 agonists, TLR5 agonists, TLR4 agonists, TLR2 agonists, TLR3 agonists, etc.), LeIF, saponins, saponin mimetics, and biological and synthetic lipid A, imiquimod, gardiquimod, resiquimod, polyI:C, flagellin, or a combination thereof.

The fusion polynucleotides, fusion polypeptides, or compositions of the invention have been found to be highly antigenic. Therefore, according to another aspect of the invention, there are provided vaccines and related methods for stimulating a protective immune response in a subject by administering an effective amount of a composition as described herein. Isolated or purified polynucleotides may be used to produce recombinant fusion polypeptide antigens in vitro, which are then administered as a vaccine. Alternatively, the polynucleotides may be administered directly to a subject as a DNA-based vaccine to cause antigen expression in the subject, and the subsequent induction of an anti-*Mycobacterium tuberculosis* immune response.

In addition, the compositions, fusion polypeptides and polynucleotides are useful as diagnostic tools in patients that may have been infected with *Mycobacterium*. For example, the compositions, fusion polypeptides, and polynucleotides of the invention may be used in in vitro and in vivo assays for detecting humoral antibodies or cell-mediated immunity against *Mycobacterium tuberculosis* for diagnosis of infection, monitoring of disease progression and/or test-of-cure evaluation.

In one embodiment, there are provided diagnostic kits for detecting *Mycobacterium tuberculosis* infection in a biological sample, comprising (a) a polypeptide comprising at least an immunogenic portion of an antigen or fusion polypeptide described herein, (b) a detection reagent.

In another embodiment, methods are provided for detecting the presence of *Mycobacterium tuberculosis* infection in a biological sample, comprising (a) contacting a biological sample with a monoclonal antibody that binds to an antigen or fusion polypeptide described herein; and (b) detecting in the biological sample the presence of *Mycobacterium tuberculosis* proteins that bind to the monoclonal antibody.

In yet another embodiment, methods are provided for detecting *Mycobacterium tuberculosis* infection in a biological sample, comprising (a) contacting the biological sample with an antigen combination or fusion polypeptide as described herein and (b) detecting in the biological sample the presence of antibodies and/or T-cells that bind thereto.

In a particular embodiment, methods are provided for detecting *Mycobacterium tuberculosis* infection in a biological sample, comprising (a) contacting the biological sample with a combination of two or more antigens selected from the group consisting of Rv0164 (SEQ ID NO: 1), Rv0496 (SEQ ID NO: 6), Rv2608 (SEQ ID NO: 26), Rv3020 (SEQ ID NO: 36), Rv3478 (SEQ ID NO: 41), Rv3619 (SEQ ID NO: 46), Rv3620 (SEQ ID NO: 51), RV1738 (SEQ ID NO: 11), Rv1813 (SEQ ID NO: 16), Rv3810 (SEQ ID NO: 56), Rv2389 (SEQ ID NO: 21), Rv2866 (SEQ ID NO: 31), Rv3876 (SEQ ID NO: 61), Rv0054 (SEQ ID NO: 100), Rv0410 (SEQ ID NO: 106), Rv0655 (SEQ ID NO: 112), Rv0831 (SEQ ID NO: 115), Rv1009 (SEQ ID NO: 118), Rv1099 (SEQ ID NO: 121), Rv1240 (SEQ ID NO: 124), Rv1288 (SEQ ID NO: 127), Rv1410 (SEQ ID NO: 130), Rv1569 (SEQ ID NO: 133), Rv1789 (SEQ ID NO: 136), Rv1818 (SEQ ID NO: 139), Rv1860 (SEQ ID NO: 142), Rv1886 (SEQ ID NO: 145), Rv1908 (SEQ ID NO: 148), Rv2220 (SEQ ID NO: 154), Rv2032 (SEQ ID NO: 151), Rv2623 (SEQ ID NO: 160), Rv2875 (SEQ ID NO: 163), Rv3044 (SEQ ID NO: 166), Rv3310 (SEQ ID NO: 169), and Rv3881 (SEQ ID NO: 178), Rv0577 (SEQ ID NO: 184), Rv1626 (SEQ ID NO: 187), Rv0733 (SEQ ID NO: 190), Rv2520 (SEQ ID NO: 193), Rv1253 (SEQ ID NO: 196), Rv1980 (SEQ ID NO: 199), Rv3628 (SEQ ID NO: 202) Rv1884 (SEQ ID NO: 205), Rv3872 (SEQ ID NO: 208), Rv3873 (SEQ ID NO: 211), Rv1511 (SEQ ID NO: 214) and Rv3875 (SEQ ID NO: 292), or immunogenic portions thereof; and (b) detecting in the biological sample the presence of antibodies and/or T-cells that bind thereto.

In a particular embodiment, a method for detecting *Mycobacterium tuberculosis* infection in a biological sample comprises: contacting the biological sample with a fusion polypeptide selected from the group consisting of: DID85 (SEQ ID NO: 265); DID92 (SEQ ID NO: 273); DID108 (SEQ ID NO: 283) and DID93 (SEQ ID NO: 291); and detecting in the biological sample the presence of antibodies and/or T-cells that bind thereto.

In another particular embodiment, the invention provides diagnostic kits for detecting *Mycobacterium tuberculosis* infection in a biological sample, comprising: (a) a combination of two or more antigens selected from the group consisting of Rv0164 (SEQ ID NO: 1), Rv0496 (SEQ ID NO: 6), Rv2608 (SEQ ID NO: 26), Rv3020 (SEQ ID NO: 36), Rv3478 (SEQ ID NO: 41), Rv3619 (SEQ ID NO: 46), Rv3620 (SEQ ID NO: 51), RV1738 (SEQ ID NO: 11), Rv1813 (SEQ ID NO: 16), Rv3810 (SEQ ID NO: 56), Rv2389 (SEQ ID NO: 21), Rv2866 (SEQ ID NO: 31), Rv3876 (SEQ ID NO: 61), Rv0054 (SEQ ID NO: 100), Rv0410 (SEQ. ID NO: 106), Rv0655 (SEQ ID NO: 112), Rv0831 (SEQ ID NO: 115), Rv1009 (SEQ ID NO: 118), Rv1099 (SEQ ID NO: 121), Rv1240 (SEQ ID NO: 124), Rv1288 (SEQ ID NO: 127), Rv1410 (SEQ ID NO: 130), Rv1569 (SEQ ID NO: 133), Rv1789 (SEQ ID NO: 136), Rv1818 (SEQ ID NO: 139), Rv1860 (SEQ ID NO: 142), Rv1886 (SEQ ID NO: 145), Rv1908 (SEQ ID NO: 148), Rv2220 (SEQ ID NO: 154), Rv2032 (SEQ ID NO: 151), Rv2623 (SEQ ID NO: 160), Rv2875 (SEQ ID NO: 163), Rv3044 (SEQ ID NO: 166), Rv3310 (SEQ ID NO: 169), and Rv3881 (SEQ ID NO: 178), Rv0577 (SEQ ID NO: 184), Rv1626 (SEQ ID NO: 187), Rv0733 (SEQ ID NO: 190), Rv2520 (SEQ ID NO: 193), Rv1253 (SEQ ID NO: 196), Rv1980 (SEQ ID NO: 199), Rv3628 (SEQ ID NO: 202) Rv1884 (SEQ ID NO: 205), Rv3872 (SEQ ID NO: 208), Rv3873 (SEQ ID NO: 211), Rv1511 (SEQ ID NO: 214) and Rv3875 (SEQ ID NO: 292), or immunogenic portions thereof; and (b) a detection reagent.

In a particular embodiment, a kit of the present invention for detecting *Mycobacterium tuberculosis* infection in a biological sample comprises: a fusion polypeptide selected from the group consisting of: DID85 (SEQ ID NO: 265), DID92 (SEQ ID NO: 273), DID108 (SEQ ID NO: 283) and DID93 (SEQ ID NO: 291), and a detection reagent.

BRIEF DESCRIPTION OF THE SEVERAL VIEWS OF THE DRAWINGS

FIG. 3A shows Log 10 CFU in the lung of immunized mice after an aerosol challenge with *M. tuberculosis*. Lungs from mice (n=7) immunized with CpG, 3 various Mtb Rv antigens, or a combination thereof were collected 4 wks after an aerosol challenge with 50-100 Mtb bacilli. CFU were counted after 2 wks of in vitro growth on agar plate. The data shown is the mean ±SEM of a representative experiment. FIG. 3B shows serum IgG2c antibody endpoint titers. Sera from mice (n=3-6) immunized with CpG, 3 various Mtb Rv antigens, or a combination thereof were collected 1 week after the $3^{rd}$ immunization and tested for antigen specific IgG2c antibodies by ELISA. The sera from CpG groups were tested against all Rv antigens, while the other sera were tested against the Rv antigen used for immunization. The data shown is the mean±SD of a representative experiment. FIG. 3C shows IFN-γ released by antigen stimulated splenocytes. Splenocytes from mice immunized with CpG, 3 various Mtb Rv antigens, or a combination thereof were collected 3 weeks after the 3' immunization and tested for antigen specific IFN-γ cytokine responses by ELISA. The splenocytes were incubated for 72 h in media, or 10 μg/ml of the Rv antigens used for the immunization. The data shown is the mean±SD (n=3) in a representative experiment. FIG. 30 shows relative frequencies of TNF/splenocytes in response to antigen specific stimulation. Splenocytes from mice immunized with CpG, 3 various Mtb Rv antigens, or a combination thereof were collected 3 weeks after the $3^{rd}$ immunization and tested for antigen specific TNF cytokine responses by ELISPOT. The splenocytes were incubated for 48 h in media, or 10 μg/ml of the Rv antigens used for the immunization. The data shown is the mean±SD (n=3) in a representative experiment FIG. 4A shows antigen specific serum IgG1 and IgG2c antibody endpoint titers. Sera from mice (n=3-6) immunized with saline, 1083, or ID93 fusion protein in GLA-SE adjuvant formulations were collected 1 week after the $3^{rd}$ immunization and tested for 1083 and 1093 specific IgG1 and IgG2c antibodies by ELISA. The data shown is the mean±SD in a representative experiment. FIG. 4B shows levels of IFN-γ released by antigen stimulated splenocytes. Splenocytes from mice immunized with ID83 or ID93 in GLA-SE adjuvant formulation were collected 3 weeks after the $3^{rd}$ immunization and tested for antigen specific IFN-γ cytokine responses by ELISA. The splenocytes were incubated for 72 h in media, 3 μg/ml ConA, or 10 μg/ml of ID83 or ID93 fusion proteins. The data shown is the mean±SD (n=3) in a representative experiment.

FIG. 5A shows antigen specific serum IgG1 and IgG2c antibody endpoint titers. Sera from mice (n=3-6) immunized with saline, or ID83 fusion protein with different adjuvant formulations were collected 1 week after the $3^{rd}$ immunization and tested for 1083 specific IgG1 and IgG2c antibodies by ELISA. The data shown is the mean±SD in a representative experiment. FIG. 5B shows levels of IFN-γ released by antigen stimulated splenocytes. Splenocytes from mice immunized with saline or 1083 with different adjuvant formulation were collected 3 weeks after the 3rd immunization and tested for antigen specific IFN-γ cytokine responses by ELISA. The splenocytes were incubated for 72 h in media, 3 μg/ml ConA, or 10 μg/ml of ID83 fusion proteins. The data shown is the mean±SD (n=3) in a representative experiment.

FIG. 7A shows relative frequencies of IFN-γ+ splenocytes in response to antigen specific stimulation. Splenocytes from mice immunized with saline, or $5\times10^9$ Ad5-ID83 viral particles were collected 3 weeks after the 3rd immunization and tested for antigen specific IFN-γ cytokine responses by ELISPOT. The splenocytes were incubated for 48 h in media, or 10 μg/ml ID83 fusion protein. The data shown is the mean±SD (n=3) in a representative experiment. FIG. 7B shows Log 10 CFU in the lung of immunized mice after an aerosol challenge with *M. tuberculosis*. Lungs from mice (n=7) immunized with saline, or $5\times10^9$ Ad5-ID83 viral particles were collected 4 wks after an aerosol challenge with 50-100 Mtb bacilli. CFU were counted after 2 wks of in vitro growth on agar plate. The data shown is the mean±SEM of a representative experiment.

BRIEF DESCRIPTION OF SEQUENCE IDENTIFIERS

Figure 1:
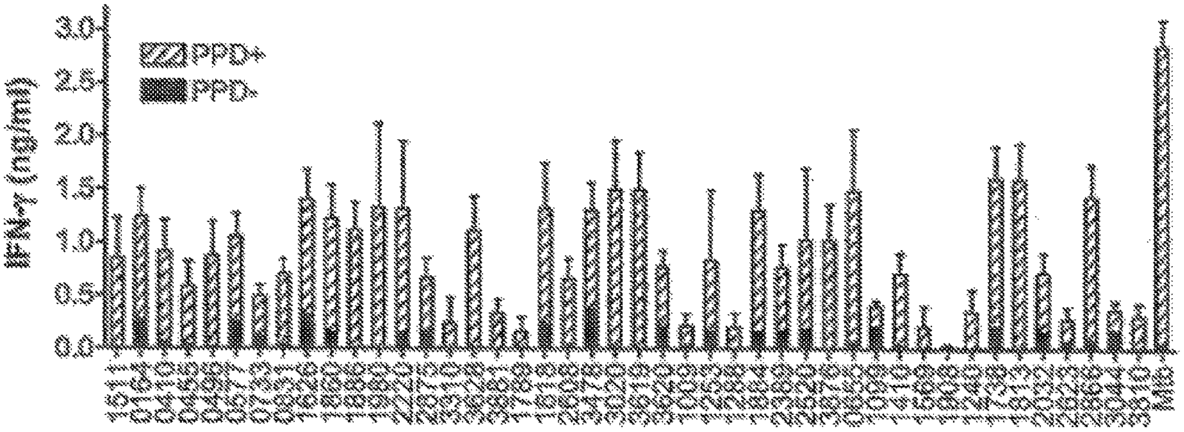
FIG. 1 shows the levels of IFN-γ released by antigen stimulated human PBMC. PPD and $PPD^-$ PBMC were incubated for 72 h in media, 10 μg/ml PHA, 10 μg/ml Mtb lysate, 50 μg/ml of the Mtb recombinant proteins, Mean ($Mean_{Ag}$−$Mean_{media}$)±SEM are shown for $PPD^+$(n=18) and $PPD^-$(n=7) PBMC.

SEQ ID NO: 1 represents the predicted amino acid sequence for Mtb Rv0164.

SEQ ID NO: 2 represents the sequence of a PCR amplified nucleic sequence encoding Mtb Rv0164.

SEQ ID NO: 3 represents the amino acid sequence of a recombinant Mtb Rv0164, including His tag.

SEQ ID NOs: 4 and 5 represent primers used to amplify Mtb Rv0164.

SEQ ID NO: 6 represents the predicted amino acid sequence for Mtb Rv0496.

SEQ ID NO: 7 represents the sequence of a PCR amplified nucleic sequence encoding Mtb Rv0496.

SEQ ID NO: 8 represents the amino acid sequence of a recombinant Mtb Rv0496, including His tag.

SEQ ID NOs: 9 and 10 represent primers used to amplify Mtb Rv0496.

SEQ ID NO: 11 represents the predicted amino acid sequence for Mtb Rv1738.

SEQ ID NO: 12 represents the sequence of a PCR amplified nucleic sequence encoding Mtb Rv1738.

SEQ ID NO: 13 represents the amino acid sequence of a recombinant Mtb Rv1738, including His tag.

SEQ ID NOs: 14 and 15 represent primers used to amplify Mtb Rv1738.

SEQ ID NO: 16 represents the predicted amino acid sequence for Mtb Rv1813.

SEQ ID NO: 17 represents the sequence of a PCR amplify nucleic sequence encoding Mtb Rv1813.

SEQ ID NO: 18 represents the amino acid sequence of a recombinant Mtb Rv1813, including His tag.

SEQ ID NOs: 19 and 20 represent primers used to amplify Mtb Rv1813.

SEQ ID NO: 21 represents the predicted amino acid sequence for Mtb Rv2389.

SEQ ID NO: 22 represents the sequence of a PCR amplified nucleic sequence encoding Mtb Rv2389.

SEQ ID NO: 23 represents the amino acid sequence of a recombinant Mtb Rv2389, including His tag.

SEQ ID NOs: 24 and 25 represent primers used to amplify Mtb Rv2389.

SEQ ID NO: 26 represents the predicted amino acid sequence for Mtb Rv2608.

SEQ ID NO: 27 represents the sequence of a PCR amplified nucleic sequence encoding Mtb Rv2608.

SEQ ID NO: 28 represents the amino acid sequence of a recombinant Mtb Rv2608, including His tag.

SEQ ID NOs: 29 and 30 represent primers used to amplify Mtb Rv2608.

SEQ ID NO: 31 represents the predicted amino acid sequence for Mtb Rv2866.

SEQ ID NO: 32 and 33 represent primers used to amplify Mtb Rv2866.

SEQ ID NO: 34 represents the sequence of a PCR amplified nucleic sequence encoding Mtb Rv2866.

SEQ ID NO: 35 represents the amino acid sequence of a recombinant Mtb Rv2866, including His tag.

SEQ ID NO: 36 represents the predicted amino acid sequence for Mtb Rv3020.

SEQ ID NO: 37 represents the sequence of a PCR amplified nucleic sequence encoding Mtb Rv3020.

SEQ ID NO: 38 represents the amino acid sequence of a recombinant Mtb Rv3020, including His tag.

SEQ ID NOs: 39 and 40 represent primers used to amplify Mtb Rv3020.

SEQ ID NO: 41 represents the predicted amino acid sequence for Mtb Rv3478.

SEQ ID NO: 42 represents the sequence of a PCR amplified nucleic sequence encoding Mtb Rv3478.

SEQ ID NO: 43 represents the amino acid sequence of a recombinant Mtb Rv3478, including His tag.

SEQ ID NOs: 44 and 45 represent primers used to amplify Mtb Rv3478.

SEQ ID NO: 46 represents the predicted amino acid sequence for Mtb Rv3619.

SEQ ID NO: 47 represents the sequence of a PCR amplified nucleic sequence encoding Mtb Rv3619.

SEQ ID NO: 48 represents the amino acid sequence of a recombinant Mtb Rv3619, including His tag.

SEQ ID NOs: 49 and 50 represent primers used to amplify Mtb Rv3619.

SEQ ID NO: 51 represents the predicted amino acid sequence for Mtb Rv3620.

SEQ ID NO: 52 represents the sequence of a PCR amplified nucleic sequence encoding Mtb Rv3620.

SEQ ID NO: 53 represents the amino acid sequence of a recombinant Mtb Rv3620, including His tag.

SEQ ID NOs: 54 and 55 represent primers used to amplify Mtb Rv3620.

SEQ ID NO: 56 represents the predicted amino acid sequence for Mtb Rv3810.

SEQ ID NO: 57 represents the sequence of a PCR amplified nucleic sequence encoding Mtb Rv3810.

SEQ ID NO: 58 represents the amino acid sequence of a recombinant Mtb Rv3810, including His tag.

SEQ ID NOs: 59 and 60 represent primers used to amplify Mtb Rv3810.

SEQ ID NO: 61 represents the predicted amino acid sequence for Mtb Rv3876.

SEQ ID NO: 62 represents the sequence of a PCR amplified nucleic sequence encoding Mtb Rv3876.

SEQ ID NO: 63 represents the amino acid sequence of a recombinant Mtb Rv3876, including His tag.

SEQ ID NOs: 64 and 65 represent primers used to amplify Mtb Rv3878.

SEQ ID NO: 66 represents a polynucleotide sequence encoding the fusion polypeptide Mtb36f.1.

SEQ ID NO: 67 represents the amino acid sequence of the recombinant Mtb fusion polypeptide Mtb36f.1, including His tag.

SEQ ID NOs: 68-71 represent primers used in the amplification and cloning of Mtb36f.1.

SEQ ID NO: 72 represents a polynucleotide sequence encoding the fusion polypeptide ID58.

SEQ ID NOs: 73-78 represent primers used in the amplification and cloning of ID58.

SEQ ID NO: 79 represents the amino acid sequence of the recombinant Mtb fusion polypeptide ID58, including His tag.

SEQ ID NO: 80 represents a polynucleotide sequence encoding the fusion polypeptide ID69.

SEQ ID NOs: 81-82 represent primers used in the amplification and cloning of ID69.

SEQ ID NO: 83 represents the amino acid sequence of the recombinant Mtb fusion polypeptide ID69, including His tag.

SEQ ID NO: 84 represents a polynucleotide sequence encoding the fusion polypeptide ID83.

SEQ ID NOs: 85-90 represent primers used in the amplification and cloning of ID83.

SEQ ID NO: 91 represents the amino acid sequence of the recombinant Mtb fusion polypeptide 1083, including His tag.

SEQ ID NO: 92 represents a polynucleotide sequence encoding the fusion polypeptide 1094.

SEQ ID NOs: 93-94 represent primers used in the amplification and cloning of ID94.

SEQ ID NO: 95 represents the amino acid sequence of the recombinant Mtb fusion polypeptide ID94, including His tag.

SEQ ID NO: 96 represents a polynucleotide sequence encoding the fusion polypeptide ID95.

SEQ ID NO: 97 represents the amino acid sequence of the recombinant Mtb fusion polypeptide ID95, including His tag.

SEQ ID NO: 98 represents a polynucleotide sequence encoding the fusion polypeptide ID120.

SEQ ID NO: 99 represents the amino acid sequence of the recombinant Mtb fusion polypeptide ID120, including His tag.

SEQ ID NO: 100 represents the predicted amino acid sequence for Rv0054.

SEQ ID NO: 101 represents the sequence of a PCR amplified nucleic sequence encoding Rv0054.

SEQ ID NO: 102 represents the amino acid sequence of a recombinant Rv0054, including His tag.

SEQ ID NO: 103 represents the predicted amino acid sequence for Rv0164.

SEQ ID NO: 104 represents the sequence of a PCR amplified nucleic sequence encoding Rv0164.

SEQ ID NO: 105 represents the amino acid sequence of a recombinant Rv0164, including His tag.

SEQ ID NO: 106 represents the predicted amino acid sequence for Rv0410.

SEQ ID NO: 107 represents the sequence of a PCR amplified nucleic sequence encoding Rv0410.

SEQ ID NO: 108 represents the amino acid sequence of a recombinant Rv0410, including His tag.

SEQ ID NO: 109 represents the predicted amino acid sequence for Rv0496.

SEQ ID NO: 110 represents the sequence of a PCR amplified nucleic sequence encoding Rv0496.

SEQ ID NO: 111 represents the amino acid sequence of a recombinant Rv0496, including His tag.

SEQ ID NO: 112 represents the predicted amino acid sequence for Rv0655.

SEQ ID NO: 113 represents the sequence of a PCR amplified nucleic sequence encoding Rv0655.

SEQ ID NO: 114 represents the amino acid sequence of a recombinant Rv0655, including His tag.

SEQ ID NO: 115 represents the predicted amino acid sequence for Rv0831.

SEQ ID NO: 116 represents tyre sequence of a PCR amplified nucleic sequence encoding Rv0831.

SEQ ID NO: 117 represents the amino acid sequence of a recombinant Rv0831, including His tag.

SEQ ID NO: 118 represents the predicted amino acid sequence for Rv1009.

SEQ ID NO: 119 represents the sequence of a PCR amplified nucleic sequence encoding Rv1009.

SEQ ID NO: 120 represents the amino acid sequence of a recombinant Rv1009, including His tag.

SEQ ID NO: 121 represents the predicted amino acid sequence for Rv1099.

SEQ ID NO: 122 represents the sequence of a PCR amplified nucleic sequence encoding Rv1099.

SEQ ID NO: 123 represents the amino acid sequence of a recombinant Rv1099, including His tag.

SEQ ID NO: 124 represents the predicted amino acid sequence for Rv1240.

SEQ ID NO: 125 represents the sequence of a PCR amplified nucleic sequence encoding Rv1240.

SEQ ID NO; 126 represents the amino acid sequence of a recombinant Rv1240, including His tag.

SEQ ID NO; 127 represents the predicted amino acid sequence for Rv1288.

SEQ ID NO: 128 represents the sequence of a PCR amplified nucleic sequence encoding Rv1288.

SEQ ID NO: 129 represents the amino acid sequence of a recombinant Rv1288, including His tag.

SEQ ID NO: 130 represents the predicted amino acid sequence for Rv1410.

SEQ ID NO: 131 represents the sequence of a PCR amplified nucleic sequence encoding Rv1410.

SEQ ID NO: 132 represents the amino acid sequence of a recombinant Rv1410, including His tag.

SEQ ID NO: 133 represents the predicted amino acid sequence for Rv1569.

SEQ ID NO: 134 represents the sequence of a PCR amplified nucleic sequence encoding Rv1569.

SEQ ID NO: 135 represents the amino acid sequence of a recombinant Rv1569, including His tag.

SEQ ID NO: 136 represents the predicted amino acid sequence for Rv1789.

SEQ ID NO: 137 represents the sequence of a PCR amplified nucleic sequence encoding Rv1789.

SEQ ID NO: 138 represents the amino acid sequence of a recombinant Rv1789, including His tag.

SEQ ID NO: 139 represents the predicted amino acid sequence for Rv1818.

SEQ ID NO: 140 represents the sequence of a PCR amplified nucleic sequence encoding Rv1818.

SEQ ID NO: 141 represents the amino acid sequence of a recombinant Rv1818, including His tag.

SEQ ID NO: 142 represents the predicted amino acid sequence for Rv1860.

SEQ ID NO: 143 represents the sequence of a PCR amplified nucleic sequence encoding Rv1860.

SEQ ID NO: 144 represents the amino acid sequence of a recombinant Rv1860, including His tag.

SEQ ID NO: 145 represents the predicted amino acid sequence for RV1886.

SEQ ID NO: 146 represents the sequence of a PCR amplified nucleic sequence encoding Rv1886.

SEQ ID NO: 147 represents the amino acid sequence f a recombinant Rv1886, including His tag.

SEQ ID NO: 148 represents the predicted amino acid sequence for Rv1908.

SEQ ID NO: 149 represents the sequence of a PCR amplified nucleic sequence encoding Rv1908.

SEQ ID NO: 150 represents the amino acid sequence of a recombinant Rv1908, including His tag.

SEQ ID NO: 151 represents the predicted amino acid sequence for Rv2032.

SEQ ID NO: 152 represents the sequence of a PCR amplified nucleic sequence encoding Rv2032.

SEQ ID NO: 153 represents the amino acid sequence of a recombinant Rv2032, including His tag.

SEQ ID NO: 154 represents the predicted amino acid sequence for Rv2220.

SEQ ID NO: 155 represents the sequence of a PCR amplified nucleic sequence encoding Rv2220.

SEQ ID NO: 156 represents the amino acid sequence of a recombinant Rv2220, including His tag.

SEQ ID NO: 157 represents the predicted amino acid sequence for Rv2608.

SEQ ID NO: 158 represents the sequence of a PCR amplified nucleic sequence encoding Rv2608.

SEQ ID NO: 159 represents the amino acid sequence of a recombinant Rv2608, including His tag.

SEQ ID NO: 160 represents the predicted amino acid sequence for Rv2623.

SEQ ID NO: 161 represents the sequence of a PCR amplified nucleic sequence encoding Rv2623.

SEQ ID NO: 162 represents the amino acid sequence of a recombinant Rv2623, including His tag.

SEQ ID NO: 163 represents the predicted amino acid sequence for Rv2875.

SEQ ID NO: 164 represents the sequence of a PCR amplified nucleic sequence encoding Rv2875.

SEQ ID NO: 165 represents the amino acid sequence of a recombinant Rv2875, including His tag.

SEQ ID NO: 166 represents the predicted amino acid sequence for Rv3044.

SEQ ID NO: 167 represents the sequence of a PCR amplified nucleic sequence encoding Rv3044.

SEQ ID NO: 168 represents the amino add sequence of a recombinant Rv3004, including His tag.

SEQ ID NO: 169 represents the predicted amino acid sequence for Rv3310.

SEQ ID NO: 170 represents the sequence of a PCR amplified nucleic sequence encoding Rv3310.

SEQ ID NO: 171 represents the amino add sequence of a recombinant Rv3310, including His tag.

SEQ ID NO: 172 represents the predicted amino acid sequence for Rv3619.

SEQ ID NO: 173 represents the sequence of a PCR amplified nucleic sequence encoding Rv3619.

SEQ ID NO: 174 represents the amino acid sequence of a recombinant Rv3619, including His tag.

SEQ ID NO: 175 represents the predicted amino acid sequence for Rv3810.

SEQ ID NO: 176 represents the sequence of a PCR amplified nucleic sequence encoding Rv3810.

SEQ ID NO: 177 represents the amino acid sequence of a recombinant Rv3810, including His tag.

SEQ ID NO: 178 represents the predicted amino acid sequence for Rv3881.

SEQ ID NO: 179 represents the sequence of a PCR amplified nucleic sequence encoding Rv3881.

SEQ ID NO: 180 represents the amino acid sequence of a recombinant Rv3881, including His tag.

SEQ ID NO: 181 represents the predicted amino acid sequence for Rv0455.

SEQ ID NO: 182 represents the sequence of a PCR amplified nucleic sequence encoding Rv0455.

SEQ ID NO: 183 represents the amino acid sequence of a recombinant Rv0455, including His tag.

SEQ ID NO: 184 represents the predicted amino acid sequence for Rv0577.

SEQ ID NO: 185 represents the sequence of a PCR amplified nucleic sequence encoding Rv0577.

SEQ ID NO: 186 represents the amino acid sequence of a recombinant Rv0577, including His tag.

SEQ ID NO: 187 represents the predicted amino acid sequence for Rv1626.

SEQ ID NO: 188 represents the sequence of PCR amplified nucleic sequence encoding Rv1626.

SEQ ID NO: 189 represents the amino acid sequence of a recombinant Rv1626, including His tag.

SEQ ID NO: 190 represents the predicted amino acid sequence for Rv0733.

SEQ ID NO: 191 represents the sequence of a PCR amplified nucleic sequence encoding Rv0733.

SEQ ID NO: 192 represents the amino acid sequence of a recombinant Rv0733, including His tag.

SEQ ID NO: 193 represents the predicted amino acid sequence for Rv2520.

SEQ ID NO: 194 represents the sequence of a PCR amplified nucleic sequence encoding Rv2520.

SEQ ID NO: 195 represents the amino acid sequence of a recombinant Rv2520, including His tag.

SEQ ID NO: 196 represents the predicted amino acid sequence for Rv1253.

SEQ ID NO: 197 represents the sequence of a PCR amplified nucleic sequence encoding Rv1253.

SEQ ID NO: 198 represents the amino acid sequence of a recombinant. Rv1253, including His tag.

SEQ ID NO: 199 represents the predicted amino acid sequence for Rv1980.

SEQ ID NO: 200 represents the sequence of a PCR amplified nucleic sequence encoding Rv1980.

SEQ ID NO: 201 represents the amino acid sequence of a recombinant Rv1980, including His tag.

SEQ ID NO: 202 represents the predicted amino acid sequence for Rv3628.

SEQ ID NO: 203 represents the sequence of a PCR amplified nucleic sequence encoding Rv3628.

SEQ ID NO: 204 represents the amino acid sequence of a recombinant Rv3628, including His tag.

SEQ ID NO: 205 represents the predicted amino acid sequence for Rv1884.

SEQ ID NO: 206 represents the sequence of a PCR amplified nucleic sequence encoding Rv1884.

SEQ ID NO: 207 represents the amino acid sequence of a recombinant Rv1884, including His tag.

SEQ ID NO: 208 represents the predicted amino acid sequence for Rv3872.

SEQ ID NO: 209 represents the sequence of a PCR amplified nucleic sequence encoding Rv3872.

SEQ ID NO: 210 represents the amino acid sequence of a recombinant Rv3872, including His tag.

SEQ ID NO: 211 represents the predicted amino acid sequence for Rv3873.

SEQ ID NO: 212 represents the sequence of a PCR amplified nucleic sequence encoding Rv3873.

SEQ ID NO: 213 represents the amino acid sequence of a recombinant Rv3873, including His tag.

SEQ ID NO: 214 represents the predicted amino acid sequence f or Rv1511.

SEQ ID NO: 215 represents the sequence of a PCR amplified nucleic sequence encoding Rv1511.

SEQ ID NO: 216 represents the amino acid sequence of a recombinant Rv1511, including His tag.

SEQ ID NO: 217 represents a polynucleotide sequence encoding the fusion polypeptide ID93.

SEQ ID NOs: 218-225 represent primers used in the amplification and cloning of 1093.

SEQ ID NO: 226 represents the amino acid sequence of the recombinant Mtb fusion polypeptide 1093, including His tag.

SEQ ID NO: 227 represents a polynucleotide sequence encoding the fusion polypeptide ID91.

SEQ ID NOs: 228-235 represent primers used in the amplification and cloning of ID91.

SEQ ID NO: 236 represents the amino add sequence of the recombinant Mtb fusion polypeptide ID91, including His tag.

SEQ ID NO: 237 represents a polynucleotide sequence encoding the fusion polypeptide ID71.

SEQ ID NOs: 238-244 represent primers used in the amplification and cloning of ID71.

SEQ ID NO: 245 represents the amino acid sequence of the recombinant Mtb fusion polypeptide ID71, including His tag.

SEQ ID NO: 246 represents a polynucleotide sequence encoding the fusion polypeptide ID114.

SEQ ID NOs: 247-250 represent primers used in the amplification and cloning of ID114.

SEQ ID NO: 251 represents the amino acid sequence of the recombinant Mtb fusion polypeptide ID114, including His tag.

SEQ ID NO: 252 represents a polynucleotide sequence encoding the fusion polypeptide ID125.

SEQ ID NOs: 253-250 represent primers used in the amplification and cloning of ID125.

SEQ ID NO: 257 represents the amino acid sequence of the recombinant. Mtb fusion polypeptide ID125, including His tag.

SEQ ID NO: 258 represents a polynucleotide sequence encoding the fusion polypeptide DID85.

SEQ ID NOs: 259-264 represent primers used in the amplification and cloning of DID85.

SEQ ID NO 265 represents the amino acid sequence of the recombinant Mtb fusion polypeptide DID85, including His tag.

SEQ ID NO: 266 represents a polynucleotide sequence encoding the fusion polypeptide DID92.

SEQ ID NOs: 267-272 represent primers used in the amplification and cloning of DID92.

SEQ ID NO: 273 represents the amino acid sequence of the recombinant Mtb fusion polypeptide DID92, including His tag.

SEQ ID NO: 274 represents a polynucleotide sequence encoding the fusion polypeptide DID108.

SEQ ID NOs: 275-282 represent primers used in the amplification and cloning of DID108.

SEQ ID NO: 283 represents the amino acid sequence of the recombinant Mtb fusion polypeptide DID108, including His tag.

SEQ ID NO: 284 represents a polynucleotide sequence encoding the fusion polypeptide DID93.

SEQ ID NOs: 285-290 represent primers used in the amplification and cloning of DID93.

SEQ ID NO: 291 represents the amino acid sequence of the recombinant Mtb fusion polypeptide DID93, including His tag.

SEQ ID NO: 292 represents the predicted amino acid sequence for Rv3875.

SEQ ID NO: 293 represents the sequence of a PCR amplified nucleic sequence encoding Rv3875.

SEQ ID NO: 294 represents the amino acid sequence of a recombinant Rv3875, including His tag.

SEQ ID NOs: 295-206 represent primers used in the amplification and cloning of Rv0577.

SEQ ID NOs: 297-298 represent primers used in the amplification and cloning of Rv1626.

SEQ ID NOs: 299-300 represent primers used in the amplification and cloning of Rv0733.

SEQ ID NOs: 301-302 represent primers used in the amplification and cloning of Rv2520.

SEQ ID NOs: 303-304 represent primers used in the amplification and cloning of Rv1253.

SEQ ID NOs: 305-306 represent primers used in the amplification and cloning of Rv1980.

SEQ ID NOs: 307-308 represent primers used in the amplification and cloning of Rv3628.

SEQ ID NOs: 309-310 represent primers used in the amplification and cloning of Rv1844.

SEQ ID NOs: 311-312 represent primers used in the amplification and cloning of Rv3872.

SEQ ID NOs: 313-314 represent primers used in the amplification and cloning of Rv3873.

SEQ ID NOs: 31-316 represent primers used in the amplification and cloning of Rv1511.

SEQ ID NOs: 317-318 represent primers used in the amplification and cloning of Rv3875.

DETAILED DESCRIPTION

The present invention relates to highly antigenic/immunogenic compositions comprising *Mycobacterium* antigens.

The compositions of the present invention generally comprise at least two heterologous polypeptides of a *Mycobacterium* species of the tuberculosis complex. A *Mycobacterium* species of the tuberculosis complex includes those species traditionally considered as causing the disease tuberculosis, as well as *Mycobacterium* environmental and opportunistic species that cause tuberculosis and lung disease in immune compromised patients, such as patients with AIDS, e.g., *Mycobacterium tuberculosis* (Mtb), *Mycobacterium bovis*, or *Mycobacterium africanum*, BCG, *Mycobacterium avium, Mycobacterium intracellulare, Mycobacterium celatum, Mycobacterium genavense, Mycobacterium haemophilum, Mycobacterium kansasii, Mycobacterium Simiae, Mycobacterium vaccae, Mycobacterium fortuitum*, and *Mycobacterium scrofulaceum* (see, e.g., Harrison's Principles of Internal Medicine, volume 1, pp. 1004-1014 and 1019-1020. In a preferred embodiment, the *Mycobacterium* species to be prevented, treated or diagnosed according to the invention is *Mycobacterium tuberculosis* (Mtb). The sequences of antigens from *Mycobacterium* species are readily available. For example, *Mycobacterium tuberculosis* sequences can be found in Cole et al., *Nature* 393:537 (1998) and can be found at websites such as those maintained by the Wellcome Trust Sanger Institute and Institut Pasteur.

A. *Mycobacterium* Antigens and Fusions Thereof

The present invention, in one aspect, provides isolated *Mycobacterium* polypeptides, as described herein, including fusion polypeptides, and compositions containing same. Generally, a polypeptide of the invention will be an isolated polypeptide and may be a fragment (e.g., an antigenic/immunogenic portion) from an amino acid sequence disclosed herein, or may comprise an entire amino acid sequence disclosed herein. Polypeptides of the invention, antigenic/immunogenic fragments thereof, and other variants may be prepared using conventional recombinant and/or synthetic techniques.

In certain preferred embodiments, the polypeptides of the invention are antigenic/immunogenic, i.e., they react detectably within an immunoassay (such as an ELISA or T cell stimulation assay) with antisera and/or T cells from an infected subject. Screening for immunogenic activity can be performed using techniques well known to the skilled artisan. For example, such screens can be performed using methods such as those described in Harlow and Lane, *Antibodies: A Laboratory Manual*, Cold Spring Harbor Laboratory, 1988. In one illustrative example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

As would be recognized by the skilled artisan, immunogenic portions of the polypeptides disclosed herein are also encompassed by the present invention. An "immunogenic portion," as used herein, is a fragment of an immunogenic polypeptide of the invention that itself is immunologically reactive (i.e., specifically binds) with the B-cells and/or T cell surface antigen receptors that recognize the polypeptide. Immunogenic portions may generally be identified using well known techniques, such as those summarized in Paul, *Fundamental Immunology*, 3rd ed., 243-247 (Raven Press, 1993) and references cited therein. Such techniques include screening polypeptides for the ability to react with antigen-specific antibodies, antisera and/or T cell lines or clones. As used herein, antisera and antibodies are "antigen-specific" if they specifically bind to an antigen (i.e., they react with the protein in an immunoassay, and do not react detectably with unrelated proteins). Such antisera and antibodies may be prepared as described herein, and using well-known techniques.

In a particular embodiment, an antigenic/immunogenic portion of a polypeptide of the present invention is a portion that reacts with antisera and/or T cells at a level that is not substantially less than the reactivity of the full-length polypeptide (e.g., in an ELISA and/or T cell reactivity assay). Preferably, the level of immunogenic activity of the antigenic/immunogenic portion is at least about 50%, preferably at least about 70% and most preferably greater than about 90% of the immunogenicity for the full-length polypeptide. In some instances, preferred immunogenic portions will be identified that have a level of immunogenic activity greater than that of the corresponding full-length polypeptide, e.g., having greater than about 100% or 150% or more immunogenic activity.

A polypeptide composition of the invention may also comprise one or more polypeptides that are immunologically reactive with T cells and/or antibodies generated against a polypeptide of the invention, particularly a polypeptide having an amino acid sequence disclosed herein, or to an immunogenic fragment or variant thereof.

In another embodiment of the invention, polypeptides are provided that comprise one or more polypeptides that are capable of eliciting T cells and/or antibodies that are immunologically reactive with one or more polypeptides described herein, or one or more polypeptides encoded by contiguous polynucleotide sequences contained in the polynucleotide sequences disclosed herein, or immunogenic fragments or variants thereof, or to one or more polynucleotide sequences which hybridize to one or more of these sequences under conditions of moderate to high stringency.

The present invention also provides polypeptide fragments, including antigenic/immunogenic fragments, comprising at least about 5, 10, 15, 20, 25, 50, or 100 contiguous amino acids, or more, including all intermediate lengths, of a polypeptide composition set forth herein, or those encoded by a polynucleotide sequence set forth herein.

In another aspect, the present invention provides variants of the polypeptide compositions described herein. Polypeptide variants generally encompassed by the present invention will typically exhibit at least about 70%, 75%, 80%, 85%, 90%, 91%, 92%, 93%, 94%©, 95%, 96%, 97%, 98%, or 99% or more identity (determined as described below), along its length, to a polypeptide sequence set forth herein.

A polypeptide "variant," as the term is used herein, is a polypeptide that typically differs from a polypeptide specifically disclosed herein in one or more substitutions, deletions, additions and/or insertions. Such variants may be naturally occurring or may be synthetically generated, for example, by modifying one or more of the above polypeptide sequences of the invention and evaluating their immunogenic activity as described herein using any of a number of techniques well known in the art.

For example, certain illustrative variants of the polypeptides of the invention include those in which one or more portions, such as an N-terminal leader sequence or transmembrane domain, have been removed. Other illustrative variants include variants in which a small portion (e.g., about 1-30 amino acids) has been removed from the N- and/or C-terminal of a mature protein.

In many instances, a variant will contain conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. As described above, modifications may be made in the structure of the polynucleotides and polypeptides of the present invention and still obtain a functional molecule that encodes a variant or derivative polypeptide with desirable characteristics, a q, with immunogenic characteristics. When it is desired to alter the amino acid sequence of a polypeptide to create an equivalent, or even an improved, immunogenic variant or portion of a polypeptide of the invention, one skilled in the art will typically change one or more of the codons of the encoding DNA sequence according to Table 1.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the peptide sequences of the disclosed compositions, or corresponding DNA sequences which encode said peptides without appreciable loss of their biological utility or activity.

TABLE 1

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutemic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUG | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | COG | CGU |
| Serine | Ser | S | AGC | AGU | UCA | UCC | UCG | UCU |
| Threonine | Thr | T | ACA | ACC | ACC | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

In making such changes, the hydropathic index of amino acids may be considered. The importance of the hydropathic amino acid index in conferring interactive biologic function on a protein is generally understood in the art (Kyte and Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine/cystine (+2.5); methionine (1-1.9); alanine (+1.8); glycine (−0.4); threonine (−0.7); serine (−0.8): tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino adds having a similar hydropathic index or score and still result in a protein with similar biological activity, i.e. still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophillicity.

As detailed in U.S. Pat. No. 4,554,101, the following hydrophilicity values have been assigned to amino acid residues: arginine (+3_0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

In addition, any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl-methyl-, thio- and other modified forms of adenine, cytidine, guanine, thymine and uridine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine: and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gin, asn, ser, thr; (2) cys, ser, tyr, thr; (3) val, ile, leu, met, ala, phe; (4) lys, erg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

As noted above, polypeptides may comprise a signal (or leader) sequence at the N-terminal end of the protein, which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

When comparing polypeptide sequences, two sequences are said to be "identical" if the sequence of amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, WI), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington DC Vol. 5, Suppl. 3, pp. 345-358; Hein J. (1990) Unified Approach to Alignment and Phylogenes pp. 626-645 *Methods in Enzymology* vol. 183, Academic Press. Inc., San Diego, CA; Higgins, D. G. and Sharp, P. M. (1989) *CABIOS* 5:151-153; Myers, E. W. and Muller W. (1988) *CABIOS* 4:11-17; Robinson, E. D. (1971) *Comb. Theor* 11:105; Santou, N. Nes, M. (1987) *Mol. Biol. Evol.* 4:406-425; Sneath, P. H. A. and Sokal, R. R. (1973) *Numerical Taxonomy—the Principles and Practice of Numerical Taxonomy*, Freeman Press, San Francisco, CA; Wilbur, W. J. and Lipman, D. J. (1983) *Proc. Nat'l Acad., Sci. USA* 80:726-730.

Alternatively, optimal alignment of sequences for comparison may be conducted by the local identity algorithm of Smith and Waterman (1981) Add. APL. Math 2:482, by the identity alignment algorithm of Needleman and Wunsch (1970) J. Mol. Biol. 48:443, by the search for similarity methods of Pearson and Lipman (1988) Proc. Nat'l Acad. Sci. USA 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, WI), or by inspection.

One preferred example of algorithms that are suitable for determining percent sequence identity and sequence similarity are the BLAST and BLAST 2.0 algorithms, which are described in Altschul et at (1977) *Nucl. Acids Res.* 25:3389-3402 and Altschul et al. (1990) *J. Mol. Biol.* 215:403-410, respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information. For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one preferred approach, the "percentage of sequence identity" is determined by comparing two optimally aligned sequences over a window of comparison of at least 20 positions, wherein the portion of the polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the reference sequence (i.e., the window size) and multiplying the results by 100 to yield the percentage of sequence identity.

In certain preferred embodiments of the invention, there are provided *Mycobacterium tuberculosis* fusion polypeptides, and polynucleotides encoding fusion polypeptides. Fusion polypeptide and fusion proteins refer to a polypeptide having at least two heterologous *Mycobacterium* sp. polypeptides, such as *Mycobacterium tuberculosis* polypeptides, covalently linked, either directly or via an amino acid linker. The polypeptides forming the fusion protein are typically linked C-terminus to N-terminus, although they can also be linked C-terminus to C-terminus, N-terminus to N-terminus, or N-terminus to C-terminus. The polypeptides of the fusion protein can be in any order. Fusion polypeptides or fusion proteins can also include conservatively modified variants, polymorphic variants, alleles, mutants, subsequences, interspecies homologs, and immunogenic fragments of the antigens that make up the fusion protein. *Mycobacterium tuberculosis* antigens are described in Cole et at, *Nature* 393:537 (1998), which discloses the entire *Mycobacterium tuberculosis* genome. Antigens from other *Mycobacterium* species that correspond to *Mycobacterium tuberculosis* antigens can be identified, e.g., using sequence comparison algorithms, as described herein, or other methods known to those of skill in the art, e.g., hybridization assays and antibody binding assays.

The fusion polypeptides of the invention generally comprise at least two antigenic polypeptides as described herein, and may further comprise other unrelated sequences, such as a sequence that assists in providing T helper epitopes (an immunological fusion partner), preferably T helper epitopes recognized by humans, or that assists in expressing the protein (an expression enhancer) at higher yields than the native recombinant protein. Certain preferred fusion partners are both immunological and expression enhancing fusion partners. Other fusion partners may be selected so as to increase the solubility of the protein or to enable the protein to be targeted to desired intracellular compartments. Still further fusion partners include affinity tags, which facilitate purification of the protein.

Fusion proteins may generally be prepared using standard techniques. Preferably, a fusion protein is expressed as a recombinant protein. For example, DNA sequences encoding the polypeptide components of a desired fusion may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and second polypeptide components by a distance sufficient to ensure that each polypeptide folds into its secondary and tertiary structures, if desired. Such a peptide linker sequence is incorporated Into the fusion protein using standard techniques well known in the art. Certain peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39 46 (1985); Murphy et al., *Proc. Natl. Acad. Sci. USA* 83:8258 8262 (1986); U.S. Pat. Nos. 4,935,233 and 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

Within preferred embodiments, an immunological fusion partner for use in a fusion polypeptide of the invention is derived from protein D, a surface protein of the gram-negative bacterium Haemophilus influenza B (WO 91/18926). Preferably, a protein D derivative comprises approximately the first third of the protein (e.g., the first N-terminal 100 110 amino acids), and a protein derivative may be lipidated. Within certain preferred embodiments, the first 109 residues of a lipoprotein D fusion partner is included on the N-terminus to provide the polypeptide with additional exogenous T cell epitopes and to increase the expression level in *E. coli* (thus functioning as an expression enhancer). The lipid tail ensures optimal presentation of the antigen to antigen presenting cells. Other fusion partners include the non-structural protein from influenzae virus, NS1 (hemaglutinin). Typically, the N-terminal 81 amino acids are used, although different fragments that include T-helper epitopes may be used.

In another embodiment, an immunological fusion partner comprises an amino acid sequence derived from the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; Gene 43:265-292 (1986)). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see Biotechnology 10:795-798 (1992)). Within a preferred embodiment, a repeat portion of LYTA may be incorporated into a fusion protein. A repeat portion is found in the C-terminal region starting at residue 178. A particularly preferred repeat portion incorporates residues 188-305.

In general, polypeptides and fusion polypeptides (as well as their encoding polynucleotides) are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

B. Polynucleotide Compositions

The present invention also provides isolated polynucleotides, particularly those encoding the fusion polypeptides of the invention, as well as compositions comprising such polynucleotides. As used herein, the terms "DNA" and "polynucleotide" and "nucleic acid" refer to a DNA molecule that has been isolated free of total genomic DNA of a particular species. Therefore, a DNA segment encoding a polypeptide refers to a DNA segment that contains one or more coding sequences yet is substantially isolated away from, or purified free from, total genomic DNA of the species from which the DNA segment is obtained. Included within the terms "DNA segment" and "polynucleotide" are DNA segments and smaller fragments of such segments, and also recombinant vectors, including, for example, plasmids, cosmids, phagemids, phage, viruses, and the like.

As will be understood by those skilled in the art, the polynucleotide sequences of this invention can include genomic sequences, extra-genomic and plasmid-encoded sequences and smaller engineered gene segments that express, or may be adapted to express, proteins, polypeptides, peptides and the like. Such segments may be naturally isolated, or modified synthetically by the hand of roan.

As will be recognized by the skilled artisan, polynucleotides may be single-stranded (coding or antisense) or double-stranded, and may be DNA (genomic, cDNA or synthetic) or RNA molecules. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a *Mycobacterium* antigen or a portion thereof) or may comprise a variant, or a biological or antigenic functional equivalent of such a sequence. Polynucleotide variants may contain one or more substitutions, additions, deletions and/or insertions, as further described below, preferably such that the immunogenicity of the encoded polypeptide is not diminished, relative to the native protein. The effect on the immunogenicity of the encoded polypeptide may generally be assessed as described herein. The term "variants" also encompasses homologous genes of xenogenic origin.

In additional embodiments, the present invention provides isolated polynucleotides comprising various lengths of contiguous stretches of sequence identical to or complementary to one or more of the sequences disclosed herein. For example, polynucleotides are provided by this invention that comprise at least about 15, 20, 30, 40, 50, 75, 100, 150, 200, 300, 400, 500 or 1000 or more contiguous nucleotides of one or more of the sequences disclosed herein as well as all intermediate lengths there between. It will be readily understood that "intermediate lengths", in this context, means any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.: including all integers through 200 500; 500 1,000, and the like.

The polynucleotides of the present invention, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a polynucleotide fragment of almost any length may be employed, with the total length preferably being limited by the ease of preparation and use in the intended recombinant DNA protocol.

Moreover, it will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention, for example polynucleotides that are optimized for human and/or primate codon selection. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

*Mycobacterium* polynucleotides and fusions thereof may be prepared, manipulated and/or expressed using any of a variety of well established techniques known and available in the art.

For example, polynucleotide sequences or fragments thereof which encode polypeptides of the invention, or fusion proteins or functional equivalents thereof, may be used in recombinant DNA molecules to direct expression of a polypeptide in appropriate host cells. Due to the inherent degeneracy of the genetic code, other DNA sequences that encode substantially the same or a functionally equivalent amino acid sequence may be produced and these sequences may be used to clone and express a given polypeptide.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

Moreover, the polynucleotide sequences of the present invention can be engineered using methods generally known in the art in order to alter polypeptide encoding sequences for a variety of reasons, including but not limited to, alterations which modify the cloning, processing, expression and/or immunogenicity of the gene product.

In order to express a desired polypeptide, a nucleotide sequence encoding the polypeptide, or a functional equivalent, may be inserted into appropriate expression vector, i.e., a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described in Sambrook et al., Molecular Cloning, A Laboratory Manual (1989), and Ausubel et al., Current Protocols in Molecular Biology (1989).

A variety of expression vector/host systems are known and may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

In bacterial systems, a number of expression vectors may be selected depending upon the use intended for the expressed polypeptide. For example, when large quantities are needed, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding the polypeptide of interest may be ligated into the vector in frame with sequences for the amino-terminal Met and the subsequent 7 residues of □-galactosidase so that a hybrid protein is produced; pIN vectors (Van Heeke & Schuster, *J. Biol. Chem.* 264:5503 5509 (1989)); and the like. pGEX Vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al., *Methods EnZymol.* 153:516-544 (1987).

In cases where plant expression vectors are used, the expression of sequences encoding polypeptides may be driven by any of a number of promoters. For example, viral promoters such as the 35S and 191S promoters of CaMV may be used alone or in combination with the omega leader sequence from TMV (Takamatsu, *EMBO J.* 6:307-311 (1987)). Alternatively, plant promoters such as the small subunit of RUBISCO or heat shock promoters may be used (Coruzzi et al., *EMBO J.* 3:1671-1680 (1984); Broglie et al., *Science* 224:838-843 (1984); and Winter et al., *Results Probl. Cell Differ.* 17:85-105 (1991)). These constructs can be introduced into plant cells by direct DNA transformation or pathogen-mediated transfection. Such techniques are described in a number of generally available reviews (see, e.g., Hobbs in McGraw Hill, *Yearbook of Science and Technology*, pp. 191-196 (1992)).

An insect system may also be used to express a polypeptide of interest. For example, in one such system, Autographa californica nuclear polyhedrosis virus (AcNPV) is used as a vector to express foreign genes in Spodoptera frugiperda cells or in Trichoplusia larvae. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, S. frugiperda cells or Trichoplusia larvae in which the polypeptide of interest may be expressed (Engelhard et al., *Proc. Natl. Acad. Sci. U.S.A.* 91:3224-3227 (1994)).

In mammalian host cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan & Shenk, *Proc. Natl. Acad. Sci. U.S.A.* 81:3655-3659 (1984)). In addition, transcription enhancers, such as the Rous sarcoma virus (RSV) enhancer, may be used to increase expression in mammalian host cells.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, et al., *Results Probl, Cell Differ.* 20:125-162 (1994)).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MACK, HEK293, and W138, which have specific cellular machinery and characteristic mechanisms for such post-translational activities, may be chosen to ensure the correct modification and processing of the foreign protein.

For long-term, high-yield production of recombinant proteins, stable expression is generally preferred. For example, cell lines which stably express a polynucleotide of interest may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler et al., *Cell* 1:223-232 (1977)) and adenine phosphoribosyltransferase (Lowy et at, *Cell* 22:817-823 (1990)) genes which can be employed in tk- or aprt-cells, respectively. Also, antimetabolite, antibiotic or herbicide resistance can be used as the basis for selection: for example, dhfr which confers resistance to methotrexate (Wigler et al., *Proc. Natl. Acad. Sci. U.S.A.* 77:3567-70 (1980)); npt, which confers resistance to the aminoglycosides, neomycin and G-418 (Colbere-Garapin et al., *J. Mol. Biol.* 150:1-14 (1981)); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman & Mulligan, *Proc. Natl. Acad. Sci. U.S.A.* 85:8047-51 (1988)). The use of visible markers has gained popularity with such markers as anthocyanins, β-glucuronidase and its substrate GUS, and luciferase and its substrate luciferin, being widely used not only to identify transformants, but also to quantify the amount of transient or stable protein expression attributable to a specific vector system (Rhodes et at, *Methods Mol. Biol.* 55:121-131 (1995)).

A variety of protocols for detecting and measuring the expression of polynucleotide-encoded products, using either polyclonal or monoclonal antibodies specific for the product are known in the art. Examples include enzyme-linked immunosorbent assay (ELISA), radioimmunoassay (RIA), and fluorescence activated cell sorting (FACS). These and other assays are described, among other places, in Hampton et at, *Serological Methods, a Laboratory Manual* (1990) and Maddox et al., *J. Exp. Med.* 158:1211-1216 (1983).

A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used include radionuclides, enzymes, fluorescent, chemiluminescent, or chromogenic agents as well as substrates, cofactors, inhibitors, magnetic particles, and the like.

Host cells transformed with a polynucleotide sequence of interest may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides of the invention may be designed to contain signal sequences which direct secretion of the encoded polypeptide through a prokaryotic or eukaryotic cell membrane. Other recombinant constructions may be used to join sequences encoding a polypeptide of interest to nucleotide sequence encoding a polypeptide domain which will facilitate purification of soluble proteins.

In addition to recombinant production methods, polypeptides of the invention, and fragments thereof, may be produced by direct peptide synthesis using solid-phase techniques (Merrifield, *J. Am. Chem. Soc.* 85:2149-2154 (1963)). Protein synthesis may be performed using manual techniques or by automation. Automated synthesis may be achieved, for example, using Applied Biosystems 431A Peptide Synthesizer (Perkin Elmer). Alternatively, various fragments may be chemically synthesized separately and combined using chemical methods to produce the full length molecule.

C. Pharmaceutical and Vaccine Compositions

In another aspect, the present invention concerns formulations of one or more of the polynucleotide, polypeptide or other compositions disclosed herein in pharmaceutically-acceptable or physiologically-acceptable solutions for administration to a cell or an animal, either alone, or in combination with one or more other modalities of therapy. Such pharmaceutical compositions are particularly preferred for use as vaccines when formulated with a suitable immunostimulant/adjuvant system. The compositions are also suitable for use in a diagnostic context.

It will also be understood that, if desired, the compositions of the invention may be administered in combination with other agents as well, such as, e.g., other proteins or polypeptides or various pharmaceutically-active agents. There is virtually no limit to other components that may also be included, provided that the additional agents do not cause a significant adverse effect upon the objectives according to the invention.

In certain preferred embodiments the compositions of the invention are used as vaccines and are formulated in combination with one or more immunostimulants. An immunostimulant may be any substance that enhances or potentiates an immune response (antibody and/or cell-mediated) to an exogenous antigen. Examples of immunostimulants include adjuvants, biodegradable microspheres (e.g., polylactic galactide) and liposomes (into which the compound is incorporated; see, e.g., Fullerton, U.S. Pat. No. 4,235,877). Vaccine preparation is generally described in, for example, Powell & Newman, eds., Vaccine Design (the subunit and adjuvant approach) (1995).

Any of a variety of immunostimulants may be employed in the vaccines of this invention. For example, an adjuvant may be included. Many adjuvants contain a substance designed to protect the antigen from rapid catabolism, such as aluminum hydroxide or mineral oil, and a stimulator of immune responses, such as lipid A (natural or synthetic), *Bortadella pertussis* or *Mycobacterium* species or *Mycobacterium* derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 and derivatives thereof (SmithKline Beecham, Philadelphia, Pa.); CWS, TDM, Leif, aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes, biodegradable microspheres; monophosphoryl lipid A and quil A. Cytokines, such as GM-CSF or interleukin-2, -7, or -12, may also be used as adjuvants.

In certain preferred embodiments, the adjuvant used in the present invention is a glucopyranosyl lipid A (GLA) adjuvant, as described in pending U.S. patent application Ser. No. 11/862,122, the disclosure of which is incorporated herein by reference in its entirety. For example, certain GLA compounds of interest are represented by the following formula:

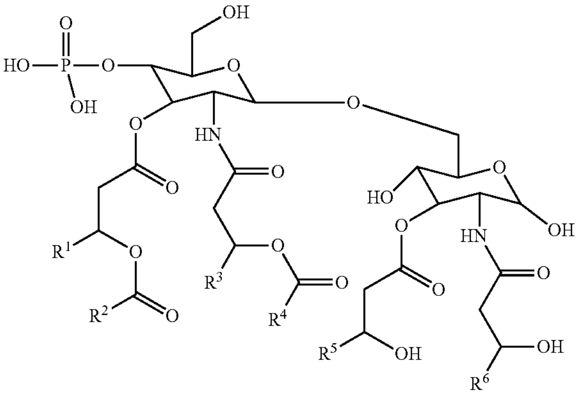

where: $R^1$, $R^3$, $R^5$ and $R^6$ are $C_{11}$-$C_{20}$ alkyl; and $R^2$ and $R^4$ are $C_{12}$-$C_{20}$ alkyl. In a more particular embodiment, $R^1$, $R^2$, $R^3$, $R^4$, $R^5$ and $R^6$ are $C_{14}$.

Other illustrative adjuvants useful in the context of the invention include Toll-like receptor agonists, such as TLR7 agonists, TLR7/8 agonists, and the like. Still other illustrative adjuvants include imiquimod (IMQ), gardiquimod (GDQ), resiquimod (RSQ), and related compounds.

Certain preferred vaccines employ adjuvant systems designed to induce an immune response predominantly of the Th1 type. High levels of Th1-type cytokines (e.g., IFN-γ, TNF, IL-2 and IL-12) tend to favor the induction of cell mediated immune responses to an administered antigen. In contrast, high levels of Th2-type cytokines (e.g., IL-4, IL-5, L-6 and IL-10) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mossman & Coffman, *Ann. Rev. Immunol.* 7:145-173 (1989).

Certain adjuvants for use in eliciting a predominantly Th1-type response include, for example, a combination of monophosphoryl lipid A, preferably 3-de-O-acylated monophosphoryl lipid A (3D-MPL™), together with an aluminum salt (U.S. Pat. Nos. 4,436,727: 4,877,611; 4,866,034; and 4,912,094). CpG-containing oligonucleotides (in which the CpG dinucleotide is unmethylated) also induce a predominantly Th1 response. Such oligonucleotides are well known and are described, for example, in WO 96/02555, WO 99/33488 and U.S. Pat. Nos. 6,008,200 and 5,856,462. Immunostimulatory DNA sequences are also described, for example, by Sato et al., *Science* 273:352 (1996). Another illustrative adjuvant comprises a saponin, such as Quil A, or derivatives thereof, including QS21 and QS7 (Aquila Biopharmaceuticals Inc., Framingham, Mass.); Escin; Digitonin; or Gypsophila or Chenopodium quinoa saponins. Other illustrative formulations include more than one saponin in the adjuvant combinations of the present invention, for example combinations of at least two of the following group comprising QS21, QS7, Quil A, escin, or digitonin.

In a particular embodiment, the adjuvant system includes the combination of a monophosphoryl lipid A and a saponin derivative, such as the combination of QS21 and 3D-MPL™ adjuvant, as described in WO 94/00153, or a less reactogenic composition where the QS21 is quenched with cholesterol, as described in WO 96/33739. Other formulations comprise an oil-in-water emulsion and tocopherol. Another adjuvant formulation employing QS21, 3D-MPL™ adjuvant and tocopherol in an oil-in-water emulsion is described in WO 95/17210.

Another enhanced adjuvant system involves the combination of a CpG-containing oligonucleotide and a saponin derivative as disclosed in WO 00/09159.

Other illustrative adjuvants include Montanide ISA 720 (Seppic, France), SAF (Novartis, Calif., United States), ISCOMS (CSL), MF-59 (Chiron), the SBAS series of adjuvants (e.g., SBAS-2, AS2', AS2, " SBAS-4, or SBAS6, available from GlaxoSmithKline, Rixensart, Belgium), Detox, RC-529 (GlaxoSmithKline, Hamilton, Mont.) and other aminoalkyl glucosaminide 4-phosphates (AGPs), such as those described in pending U.S. patent application Ser. Nos. 08/853,826 and 09/074,720, the disclosures of which are incorporated herein by reference in their entireties, and polyoxyethylene ether adjuvants such as those described in WO 99152549A1.

Compositions of the invention may also, or alternatively, comprise T cells specific for a *Mycobacterium* antigen. Such cells may generally be prepared in vitro or ex vivo, using standard procedures. For example, T cells may be isolated from bone marrow, peripheral blood, or a fraction of bone marrow or peripheral blood of a patient. Alternatively, T cells may be derived from related or unrelated humans, non-human mammals, cell lines or cultures.

T cells may be stimulated with a polypeptide of the invention, polynucleotide encoding such a polypeptide, and/or an antigen presenting cell (APC) that expresses such a polypeptide. Such stimulation is performed under conditions and for a time sufficient to permit the generation of T cells that are specific for the polypeptide. Preferably, the polypeptide or polynucleotide is present within a delivery vehicle, such as a microsphere, to facilitate the generation of specific T cells. T cells are considered to be specific for a polypeptide of the invention if the T cells specifically proliferate, secrete cytokines or kill target cells coated with the polypeptide or expressing a gene encoding the polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., *Cancer Res.* 54:1085-1070 (1994)). Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with a polypeptide of the invention (10 ng/ml-100 μg/ml, preferably 200 ng/ml-25 μg/ml) for 3-7 days should result in at least a two fold increase in proliferation of the T cells. Contact as described above for 2-3 hours should result in activation of the T cells, as measured using standard cytokine assays in which a two fold increase in the level of cytokine release (e.g., TNF or IFN-γ) is indicative of T cell activation (see Coligan et al., *Current Protocols in Immunology*, vol. 1 (1998)). T cells that have been activated in response to a polypeptide, polynucleotide or polypeptide-expressing APC may be CD4+ and/or CD8+. Protein-specific T cells may be expanded using standard techniques. Within preferred embodiments, the T cells are derived from a patient, a related donor or an unrelated donor, and are administered to the patient following stimulation and expansion.

In the pharmaceutical compositions of the invention, formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, intradermal, subcutaneous, and intramuscular administration and formulation.

In certain applications, the pharmaceutical compositions disclosed herein may be delivered via oral administration to a subject. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain circumstances it will be desirable to deliver the pharmaceutical compositions disclosed herein parenterally, intravenously, intramuscularly, or even intraperitoneally as described, for example, in U.S. Pat. Nos. 5,543,158; 5,641,515 and 5,399,363 (each specifically incorporated herein by reference in its entirety). Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion (see, e.g., *Remington: The Science and Practice of Pharmacy,* 20th Edition, Baltimore, MD Lippincott Williams & Wilkins, 2000). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologics standards.

Sterile injectable solutions are prepared by incorporating the active compounds in the required amount in the appropriate solvent with the various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like. As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

In certain embodiments, the pharmaceutical compositions may be delivered by intranasal sprays, inhalation, and/or other aerosol delivery vehicles. Methods for delivering genes, polynucleotides, and peptide compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

In certain embodiments, the delivery may occur by use of liposomes, nanocapsules, microparticles, microspheres, lipid particles, vesicles, and the like, for the introduction of the compositions of the present invention into suitable host cells. In particular, the compositions of the present invention may be formulated for delivery either encapsulated in a lipid particle, a liposome, a vesicle, a nanosphere, a nanoparticle or the like. The formulation and use of such delivery vehicles can be carried out using known and conventional techniques.

D. Diagnostic Methods and Kits

As noted above, the compositions, fusion polypeptides and polynucleotides are also useful as diagnostic reagents for detecting and/or monitoring *Mycobacterium tuberculosis* infection in a patient. For example, the compositions, fusion polypeptides, and polynucleotides of the invention may be used in in vitro and in vivo assays for detecting humoral antibodies or cell-mediated immunity against *Mycobacterium tuberculosis* for diagnosis of infection, monitoring of disease progression or test-of-cure evaluation.

Therefore, in certain embodiments, the invention provides improved diagnostic antigens for differentially diagnosing *Mycobacterium tuberculosis* infection based on serological examination, wherein the *Mycobacterium* antigens used in the diagnosis are selected from the group consisting of Rv0164 (SEQ ID NO: 1), Rv0496 (SEQ ID NO: 6), Rv2608 (SEQ ID NO: 26), Rv3020 (SEQ ID NO: 36), Rv3478 (SEQ ID NO: 41), Rv3619 (SEQ ID NO: 46), Rv3620 (SEQ ID NO: 51), RV1738 (SEQ ID NO: 11), Rv1813 (SEQ ID NO: 16), Rv3810 (SEQ ID NO: 56), Rv2389 (SEQ ID NO: 21), Rv2866 (SEQ ID NO: 31), Rv3876 (SEQ ID NO: 61), Rv0054 (SEQ ID NO: 100), Rv0410 (SEQ ID NO: 106), Rv0655 (SEQ ID NO: 112), Rv0831 (SEQ ID NO: 115), Rv1009 (SEQ ID NO: 118), Rv1099 (SEQ ID NO: 121), Rv1240 (SEQ ID NO: 124). Rv1288 (SEQ ID NO: 127), Rv1410 (SEQ ID NO: 130), Rv1569 (SEQ ID NO: 133), Rv1789 (SEQ ID NO: 136), Rv1818 (SEQ ID NO: 139), Rv1860 (SEQ ID NO: 142), Rv1886 (SEQ ID NO: 145), Rv1908 (SEQ ID NO: 148), Rv2220 (SEQ ID NO: 154), Rv2032 (SEQ ID NO: 151), Rv2623 (SEQ ID NO: 160), Rv2875 (SEQ ID NO: 163), Rv3044 (SEQ ID NO: 166), Rv3310 (SEQ ID NO: 169), and Rv3881 (SEQ ID NO: 178), Rv0577 (SEQ ID NO: 184), Rv1626 (SEQ ID NO: 187), Rv0733 (SEQ ID NO: 190), Rv2520 (SEQ ID NO: 193), Rv1253 (SEQ ID NO: 196), Rv1980 (SEQ ID NO: 199), Rv3628 (SEQ ID NO: 202) Rv1884 (SEQ ID NO: 205), Rv3872 (SEQ ID NO: 208), Rv3873 (SEQ ID NO: 211), Rv1511 (SEQ ID NO: 214) and Rv3875 (SEQ ID NO: 292), or immunogenic portions or variants thereof, in any combination thereof mixed as separate antigens, or in fusion gene constructs. As demonstrated herein, combinations of the disclosed diagnostic antigens offer Improved sensitivity in serological diagnostic testing.

The diagnostic methods and kits preferably employ a combination of two or more antigens as described herein. In certain embodiments, it will be preferred to use a multiple antigens as described herein, e.g., three or more, four or more, five or more, six or more, etc., in a diagnostic method of the invention. The antigens may be used in essentially any assay format desired, e.g., as individual antigens assayed separately, as multiple antigens assays simultaneously, as antigens immobilized on a solid support such as an array, or the like.

In a particular embodiment, the diagnostic antigens used in the methods herein are selected from the group consisting of Rv0164 (SEQ ID NO: 1). Rv0496 (SEQ ID NO: 6), Rv2608 (SEQ ID NO: 26), Rv3020 (SEQ ID NO: 36), Rv3478 (SEQ ID NO: 41), Rv3619 (SEQ ID NO: 46), Rv3620 (SEQ ID NO: 51), RV1738 (SEQ ID NO: 11), Rv1813 (SEQ ID NO: 16), Rv3810 (SEQ ID NO: 56), Rv2389 (SEQ ID NO: 21), Rv2866 (SEQ ID NO: 31), Rv3876 (SEQ ID NO: 61), Rv0054 (SEQ ID NO: 100), Rv0410 (SEQ ID NO: 106), Rv0655 (SEQ ID NO: 112), Rv0831 (SEQ ID NO: 115), Rv1009 (SEQ ID NO: 118), Rv1099 (SEQ ID NO: 121), Rv1240 (SEQ ID NO: 124), Rv1288 (SEQ ID NO: 127), Rv1410 (SEQ ID NO: 130), Rv1569 (SEQ ID NO: 133), Rv1789 (SEQ ID NO: 136), Rv1818 (SEQ ID NO: 139), Rv1860 (SEQ ID NO: 142), Rv1886 (SEQ ID NO: 145). Rv1908 (SEQ ID NO: 148). Rv2220 (SEQ ID NO: 154), Rv2032 (SEQ ID NO: 151), Rv2623 (SEQ ID NO: 160), Rv2875 (SEQ ID NO: 163), Rv3044 (SEQ ID NO: 166), Rv3310 (SEQ ID NO: 169), and Rv3881 (SEQ ID NO: 178), Rv0577 (SEQ ID NO: 184), Rv1626 (SEQ ID NO: 187), Rv0733 (SEQ ID NO: 190), Rv2520 (SEQ ID NO: 193), Rv1253 (SEQ ID NO: 196), Rv1980 (SEQ ID NO: 199), Rv3628 (SEQ ID NO: 202) Rv1884 (SEQ ID NO: 205), Rv3872 (SEQ ID NO: 208), Rv3873 (SEQ ID NO: 211), Rv1511 (SEQ ID NO: 214) and Rv3875 (SEQ ID NO: 292), or immunogenic portions or variants thereof, in any combination thereof mixed as separate antigens, or in fusion gene constructs.

In one embodiment, there are provided diagnostic kits for detecting *Mycobacterium tuberculosis* infection in a biological sample, comprising (a) a polypeptide comprising at least an immunogenic portion of an antigen or fusion polypeptide described herein, and (b) a detection reagent.

In another embodiment, there are provided diagnostic kits for detecting *Mycobacterium tuberculosis* infection in a biological sample, comprising (a) an antibody or antigen binding fragment thereof that is specific for a polypeptide comprising at least an immunogenic portion of an antigen or fusion polypeptide described herein, and (b) a detection reagent. in another embodiment, methods are provided for detecting the presence of *Mycobacterium tuberculosis* infection in a biological sample, comprising (a) contacting a biological sample with a monoclonal antibody that binds to an antigen or fusion polypeptide described herein; and (b) detecting in the biological sample the presence of *Mycobacterium tuberculosis* proteins that bind to the monoclonal antibody.

In yet another embodiment, methods are provided for detecting *Mycobacterium tuberculosis* infection in a biological sample, comprising (a) contacting the biological sample with an antigen combination or fusion polypeptide as described herein and (b) detecting in the biological sample the presence of antibodies and/or T-cells that bind thereto.

There are a variety of assay formats known to those of ordinary skill in the art for using purified antigen or fusion polypeptide to detect antibodies in a sample. See, e.g., Harlow and Lane, *Antibodies: A Laboratory Manual*, Cold Spring Harbor Laboratory, 1988. In one embodiment, the assay involves the use of polypeptide immobilized on a solid support to bind to and remove the antibody from the sample. The bound antibody may then be detected using a detection reagent that binds to the antibody/peptide complex and contains a detectable reporter group. Suitable detection reagents include antibodies that bind to the antibody/polypeptide complex and free polypeptide labeled with a reporter group (e.g., in a semi-competitive assay). Alternatively, a competitive assay may be utilized, in which an antibody that binds to the polypeptide is labeled with a reporter group and allowed to bind to the immobilized antigen after incubation of the antigen with the sample. The extent to which components of the sample inhibit the binding of the labeled antibody to the polypeptide is indicative of the reactivity of the sample with the immobilized polypeptide.

The solid support may be any solid material known to those of ordinary skill in the art to which the antigen may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681.

The polypeptide may be bound to the solid support using any of a variety of techniques known and available in the art. The term "bound" refers to both noncovalent association, such as adsorption, and covalent attachment (which may be a direct linkage between the antigen and functional groups on the support or may be a linkage by way of a cross-linking agent). Binding by adsorption to a well in a microtiter plate or to a membrane is preferred. In such cases, adsorption may be achieved by contacting the polypeptide, in a suitable buffer, with the solid support for a suitable amount of time.

In certain embodiments, the diagnostic assay employed is an enzyme linked immunosorbent assay (ELISA). This assay may be performed by first contacting a polypeptide antigen that has been immobilized on a solid support, commonly the well of a microtiter plate, with the sample, such that antibodies to the polypeptide within the sample are allowed to bind to the immobilized polypeptide. Unbound sample is then removed from the immobilized polypeptide and a detection reagent capable of binding to the immobilized antibody-polypeptide complex is added. The amount of detection reagent that remains bound to the solid support is then determined using a method appropriate for the specific detection reagent.

Once the polypeptide is immobilized on the support, the remaining protein binding sites on the support are typically blocked. Any suitable blocking agent known to those of ordinary skill in the art, such as bovine serum albumin or Tween 20™ (Sigma Chemical Co., St. Louis, MO). The immobilized polypeptide is then incubated with the sample, and antibody (if present in the sample) is allowed to bind to the antigen. The sample may be diluted with a suitable diluent, such as phosphate-buffered saline (PBS) prior to incubation. In general, an appropriate contact time (i.e., incubation time) is that period of time that is sufficient to detect the presence of antibody to *Mycobacterium tuberculosis* within an infected sample. Preferably, the contact time is sufficient to achieve a level of binding that is at least 95% of that achieved at equilibrium between bound and unbound antibody. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween™, Detection reagent may then be added to the solid support. An appropriate detection reagent is any compound that binds to the immobilized antibody-polypeptide complex and that can be detected by any of a variety of means known to those in the art. The detection reagent generally contains a binding agent (such as, for example, Protein A, Protein G, immunoglobulin, lectin or free antigen) conjugated to a reporter group. Illustrative reporter groups include enzymes (such as horseradish peroxidase), substrates, cofactors, inhibitors, dyes, radionuclides, luminescent groups, fluorescent groups and biotin. The conjugation of binding agent to reporter group may be achieved using standard methods known to those of ordinary skill in the art.

The detection reagent is then incubated with the immobilized antibody polypeptide complex for an amount of time sufficient to detect the bound antibody. An appropriate amount of time may generally be determined from the manufacturer's instructions or by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of *Mycobacterium tuberculosis* antibodies in a sample, the signal detected from the reporter group that remains bound to the solid support is generally compared to a signal that corresponds to a predetermined cut-off value. This cut-off value is preferably the average mean signal obtained when the immobilized antigen is incubated with samples from an uninfected patient. In general, a sample generating a signal that is three standard deviations above the mean is considered positive for *Mycobacterium tuberculosis* antibodies and *Mycobacterium tuberculosis* infection. In another embodiment, the cut-off value is determined using a Receiver Operator Curve, according to the method of Sackett et al., *Clinical Epidemiology: A Basic Science for Clinical Medicine*, p. 106-7 (Little Brown and Co., 1985). Briefly, in this embodiment, the cut-off value may be determined from a plot of pairs of true positive rates (i.e., sensitivity) and false positive rates (100%-specificity) that correspond to each possible cut-off value tor the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for *Mycobacterium tuberculosis* infection.

In another embodiment, a diagnostic assay may be performed in a flow-through or strip test format, wherein the antigen or fusion polypeptide is immobilized on a membrane such as nitrocellulose. In the flow-through test, antibodies within the sample bind to the immobilized polypeptide as the sample passes through the membrane. A detection reagent (e.g., protein A-colloidal gold) then binds to the antibody-polypeptide complex as the solution containing the detection reagent flows through the membrane. The detection of bound detection reagent may then be performed as described above. In the strip test foi mat, one end of the membrane to which polypeptide is bound is immersed in a solution containing the sample. The sample migrates along the membrane through a region containing detection reagent and to the area of immobilized polypeptide. Concentration of detection reagent at the polypeptide indicates the presence of *Mycobacterium tuberculosis* antibodies in the sample. Such tests can typically be performed with a very small amount (e.g., one drop) of patient serum or blood.

In yet another embodiment, methods are provided for detecting *Mycobacterium tuberculosis* in a biological sample using antibodies (which may be polyclonal or monoclonal) and/or T-cells specific for one or more antigens, fusion polypeptides and/or immunogenic portions of the invention.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments.

EXAMPLES

Example 1

Cloning and Expression of Recombinant Rv0164

Using H37Rv genomic DNA as template, Rv0164 was PCR amplified using the primers set forth in SEQ ID NOs: 4 and 5, below:

```
Primer 5'-Rv0164-5his-NdeI:
                                   (SEQ ID NO: 4)
TAGGATCCCATATGACGGCAATCTCGTGCTCAC

Primer 3'-Rv0164-3HindIII:
                                   (SEQ ID NO: 5)
TAGAATTCAAGCTTTTAGCTGGCCGCCAGCTGCTC
```

The following amplification conditions were used: 94° C. 0.5 min., 55° C. 0.5 min., 68° C. 1 min for 30 cycles to give the product set forth in SEQ ID NO: 2. The PCR product was digested with NdeI/HindIII and cloned into pET 28a. Plasmid containing the Rv0164 gene was transformed into expression host and Rosetta2 pLysS, Cultures were grown in shake flask at 37° C. in 2× YT media supplemented with 34 mg/L Chloramphenicol, 35 mg/L Kanamycin to an OD600=0.5-0.6 and induced with 1 mM IPTG for 3-4 hrs. The cell paste was pelleted at 10000×g and stored at −20° C. After lysis of a 1 L induction by sonication and clarification of the supernatant, the Rv0164 protein remained in the insoluble fraction. This fraction was then washed 2× in 1% CHAPS detergent, 20 mM Tris HCl pH 8.0, and then solubilized in 8M Urea. Purification was achieved using 2 rounds of Ni-NTA affinity chromatography (Qiagen) under denaturing conditions with and the Rv0164 protein was eluted using 300 mM Imidazole. After SDS-PAGE analysis, fractions containing the purified protein were dialyzed against 10 mM Tris pH 8.0. Protein concentration was determined by Bradford Assay and residual endotoxin levels were determined by the Llimulus Amoebcyte Assay. The amino acid sequence of the recombinant protein is set forth in SEQ ID NO: 3.

Example 2

Cloning and Expression of Recombinant Rv0496

Using H37Rv genomic DNA as template, Rv0496 was PCR amplified using the following primers:

```
5'-Rv0496-5his-NdeI
                                   (SEQ ID NO: 9)
TAGGATCCCATATGGTCGATGCCCACCGCGGC

3'-Rv0496-3HindIII
                                   (SEQ ID NO: 10)
TAGAATTCAAGCTTTCATGGTTTGCTGCCTCTCGA
```

Amplification was performed under the following conditions: 94° C. 0.5 min., 55° C. 0.5 min., 68° C. 2 min for 30 cycles, to give the product set forth in SEQ ID NO: 7. The PCR product was digested with NdeI/HindIII and cloned into pET28a. Rv0496 was transformed into expression hosts and Rosetta2 plysS. After lysis of a 1 L induction, it went into the inclusion body. Ni-NTA was performed twice under denaturing conditions, then dialyzed against 10 mM Tris pH 10. The amino acid sequence of the recombinant protein is set forth in SEQ ID NO: 8.

Example 3

Cloning and Expression of Recombinant Rv 1738

Using H37Rv genomic DNA as template, Rv1738 was PCR amplified using the following primers:

```
5'-Rv1738-5his-NdeI
                                   (SEQ ID NO: 14)
CAATTACATATGCATCACCATCACCATCACATGTGCGGCGAC

CAGTCGGAT

3'-Rv1738-3EcoRI
                                   (SEQ ID NO: 15)
CAATTAGAATTCTCAATACAACAATCGCGCCGG
```

Amplification was performed using the following conditions: 95° C. 1 min., 58° C. 1 min., 72° C. 1 min for 35 cycles, to give the product set forth as SEQ ID NO: 12. The PCR product was digested with NdeI/EcoRI and cloned into pET 17b. Rv1738 was transformed into expression hosts BL-21plysE and plysS. After lysis of a 1 L induction, protein remained in the soluble supernatant. Ni-NTA was performed under denaturing conditions, then dialyzed against 10 mM Tris pH 8.0. The amino acid sequence of the recombinant protein is set forth in SEQ ID NO: 13.

Example 4

Cloning and Expression of Recombinant Rv1813

Using H37Rv genomic DNA as template, Rv1813 was PCR amplified using the following primers:

```
5'-Rv1813-5his33-NdeI-
                                   (SEQ ID NO: 19)
CAATTACATATGCATCACCATCACCATCACCATCTCGCCAAC

GGtTTCGATG

3'-Rv1813-3EcoRI-
                                   (SEQ ID NO: 20)
CAATTAGAATTCTTAGTTGCACGCCCAGTTGAC
```

The amplification was performed using the following conditions 95° C. 1 min., 58° C. 1 min., 72° C. 1 min for 35 cycles, to give the product set forth in SEQ ID NO: 17. The PCR product was digested with NdeI/EcoRI and cloned into pET 17b. Rv1813 was transformed into expression hosts BL-21plysE and Rosetta plysS. After lysis of a 1 L induction, protein went into the inclusion body. Ni-NTA was performed under denaturing conditions, then dialyzed against 10 mM Tris pH 8.0. The amino acid sequence of the recombinant protein is set forth in SEQ ID NO: 18.

Example 5

Cloning and Expression of Recombinant Rv2389($R_{PF}$-D

Using H37Rv genomic DNA as template, Rv2389 was PCR amplified using the following primers:

```
5'-Rv2389-5his50-NdeI-
                                        (SEQ ID NO: 24)
CAATTACATATGCATCACCATCACCATCACGACGACATCGATT

GGGACGCC

3'-Rv2389-3EcoRI-
                                        (SEQ ID NO: 25)
CAATTAGAATTCTCAATCGTCCCTGCTCCCCGA
```

Amplification was performed under the following conditions: 95° C. 1 min., 58° C. 1 min., 72° C. 1 min for 35 cycles, to give the product set forth in SEQ ID NO: 22. The PCR product was digested with Ndel/EcoRI and cloned into pET 17b (pET construct begins at aa49). Rv2389 was transformed into expression hosts BL-21plysE and Rosetta plysS. After lysis of a 1 L induction, protein remained in the soluble fraction. Ni-NTA was performed under denaturing conditions, then dialyzed against 10 mM Tris pH 8.0. The amino acid sequence of the recombinant protein is set forth in SEQ ID NO: 23.

Example 6

Cloning and Expression of Recombinant Rv2608

Using H37Rv genomic DNA as template, Rv2608 was PCR amplified using the following primers:

```
5'-Rv2608-5-NdeI-
                                        (SEQ ID NO: 29)
TAGGATCCCATATGAATTTCGCCGTTTTGCCG

3'-Rv2608-3-HindIII-
                                        (SEQ ID NO: 30)
TAGAATTCAAGCTTTTAGAAAAGTCGGGGTAGCGCC
```

Amplification was performed using the following conditions 94° C. 0.5 min., 55° C. 0.5 min., 68° C. 2 min for 30 cycles, to give the product set forth in SEQ ID NO: 27. The gel purified PCR product was digested with Ndel/HindIII and cloned into the expression vector pET28a (Clonetech) (pET construct begins at amino acid 1). Rv2608 was transformed into expression hosts and Rosetta2 pLysS. Cultures were grown in shake flask at 37° C. in 2× YT media supplemented with 34 mg/L Chloramphenicol, 35 mg/L Kanamycin to an OD600=0.5-0.6 and induced with 1 mM IPTG for 3-4 hrs. The cell paste was pelleted at 10000×g and stored at −20° C. After lysis of a 1 L induction by sonication and clarification of the supernatant, the Rv2608 protein remained in the insoluble fraction. This fraction was then washed 2× in 1% CHAPS detergent, 10 mM Tris HCl pH 8.0, and then solubilized in 8M Urea, Purification was performed using Ni-NTA affinity chromatography (Qiagen) 2× under denaturing conditions with and the Rv2608 protein was eluted using 300 mM Imidazole. After SDS-PAGE analysis, fractions containing the purified protein were dialyzed against 10 mM Tris pH 8.0. Protein concentration was determined by BCA assay and residual endotoxin levels were determined by the Llimulus Amoebcyte Assay. The amino acid sequence of the recombinant protein is set forth in SEQ ID NO: 28.

Example 7

Cloning and Expression of Recombinant Rv2866

Rv2866 was amplified from genomic template by PCR, using the following primers:

```
5'-Rv2866-5NdeI-
                                        (SEQ ID NO: 32)
CAATTACATATGCCTTCCACCGTGCCCTTCACC

3'-Rv2866-3HindIII-
                                        (SEQ ID NO: 33)
CAATTAAAGCTTCTATCGGCGGTAGATGTCCGCGCG.
```

The following amplification conditions were used: 94° C. for 0.5 min., 66° C. for 0.50 min., 68° C. for 1.50 min., 35 cycles), to give the product set forth in SEQ ID NO: 34. Product was digested with NdeI/HindIII and cloned into pET28. a vector. Rv2866 was expressed by host strain BL-21plysS. The pellet and supernatant were bound with Ni resin under denaturing conditions. Dialysis was performed in 20 mM Tris pH 6. The amino acid sequence of the recombinant protein is set forth in SEQ ID NO: 35.

Example 8

Cloning and Expression of Recombinant Rv3020

Using H37 genomic DNA as template, Rv3020 was PCR amplified using the following primers:

```
5'-Rv3020-5his-NdeI-
                                        (SEQ ID NO: 39)
TAGGATCCCATATGAGTTTGTTGGATGCCCATAT

3'-Rv3020-3HindIII-
                                        (SEQ ID NO: 40)
TAGAATTCAAGCTTTTAAAACCCGGTGTAGCTGGAC
```

The following amplification conditions were employed: 94° C. 0.5 min., 55° C. 0.5 min., 68° C. 1 min. for 30 cycles, yielding the product set forth in SEQ ID NO: 37. The PCR product was digested with Ndel/HindIII and cloned into pET 28a. Plasmid containing the Rv3020 gene was transformed into expression host and Rosetta2 pLysS. Cultures were grown in shake flask at 37° C. in 2× YT media supplemented with 34 mg/L Chloramphenicol, 35 mg/L Kanamycin to an OD600=0.5-0.6 and induced with 1 mM IPTG for 3-4 hrs. The cell paste was pelleted at 10000×g and stored at −20° C. After lysis of a 1 L induction by sonication and clarification of the supernatant, the Rv3020 protein remained in the insoluble fraction. This fraction was then washed 2× in 1% CHAPS detergent, 20 mM Tris HCl pH 8.0, and then solubilized in 8M Urea. Purification was performed using Ni-NTA affinity chromatography (Qiagen) under denaturing conditions with and the Rv3020 protein was eluted using 250 mM Imidazole. After SDS-PAGE analysis, fractions containing the purified protein were dialyzed against 10 mM Tris pH 8.0. Protein concentration was determined by Bradford Assay and residual endotoxin levels were determined by the Llimulus Amoebcyte Assay. The amino acid sequence of the recombinant protein is set forth in SEQ ID NO: 38.

Example 9

Cloning and Expression of Recombinant Rv3478

Using H37Rv genomic DNA as template, Rv3478 was amplified using the following primers:

```
5'-Rv3478-5his-NdeI-
                                   (SEQ ID NO: 44)
TAGGATCCCATATGGTGGATTTCGGGGCGTTAC

3'-Rv3478-3HindIII-
                                   (SEQ ID NO: 45)
TAGAATTCAAGCTTCTATCCGGCGGCCGGTGTGCG
```

Rv3478 was amplified using polymerase chain reaction (PCR) with the following conditions 94° C. 0.5 min., 55° C. 0.5 min., 68° C. 2 min. for 30 cycles. The gel purified PCR product (SEQ ID NO: 42) was digested with Ndel/HindIII and cloned into the expression vector pET28a (Clonetech). Rv3478 was transformed into expression hosts and Rosetta2 pLysS. Cultures were grown in shake flask at 37° C. in 2× YT media supplemented with 34 mg/L. Chloramphenicol, 35 mg/L Kanamycin to an OD600=0.5-0.6 and induced with 1 mM IPTG for 3-4 hrs. The cell paste was pelleted at 10000×g and stored at −20° C. After lysis of a 1 L induction by sonication and clarification of the supernatant, the Rv3478 protein remained in the insoluble fraction. This fraction was then washed 2× in 1% CHAPS detergent, 10 mM Tris HCl pH 8.0, and then solubilized in 8M Urea. Purification was done using Ni-NTA affinity chromatography (Qiagen) 2× under denaturing conditions with and the Rv3478 protein was eluted using 300 mM Imidazole. After SDS-PAGE analysis, fractions containing the purified protein were dialyzed against 10 mM Tris pH 8.0. Protein concentration was determined by BCA assay and residual endotoxin levels were determined by the Llimulus Amoebcyte Assay. The amino acid sequence of the recombinant protein is set forth in SEQ ID NO: 43.

Example 10

Cloning and Expression of Recombinant Rv3619

Using H37Rv genomic DNA as template, Rv3619 was amplified using the following primers.

```
5'-Rv3619-5his-NdeI-
                         (SEQ ID NO: 49)
TAGGATCCCATATGACCAT

CAACTATCAATTCG

3'-Rv3619-3HindIII-
                         (SEQ ID NO: 50)
TAGAATTCAAGCTTTTAGG

CCCAGCTGGAGCCGAC
```

Rv3619 was amplified using polymerase chain reaction (PCR) with the following conditions 94° C. 0.5 min., 55° C. 0.5 min., 68° C. 1 min. for 30 cycles. The gel purified PCR product (SEQ ID NO: 47) was digested with Ndel/HindIII and cloned into the expression vector pET28a (Clonetech).

Rv3619 was transformed into expression hosts and Rosetta2 pLysS. Cultures were grown in shake flask at 37° C. in 2× YT media supplemented with 34 mg/L Chloramphenicol, 35 mg/L Kanamycin to an OD600=0.5-0.6 and induced with 1 M IPTG for 3-4 hrs. The cell paste was pelleted at 10000×g and stored at −20° C. After lysis of a 1 L induction by sonication and clarification of the supernatant, the Rv3619 protein remained in the insoluble fraction. This fraction was then washed 2× in 1% CHAPS detergent, 10 mM Tris HCl pH 8.0, and then solubilized in 8M Urea. Purification was performed using Ni-NTA affinity chromatography (Qiagen) under denaturing conditions with and the Rv3619 protein was eluted using 300 mM Imidazole. After SDS-PAGE analysis, fractions containing the purified protein were dialyzed against 10 mM Tris pH 8.0. Protein concentration was determined by Bradford Assay and residual endotoxin levels were determined by the Llimulus Amoebcyte Assay. The amino acid sequence of the recombinant protein is set forth in SEQ ID NO: 48.

Example 11

Cloning and Expression of Recombinant Rv3620

Using H37Rv genomic DNA as template, Rv3620 was PCR amplified using the following primers:

```
5'-Rv3620-5his-NdeI-
                         (SEQ ID NO: 54)
TAGGATCCCATATGACCT

CGCGTTTTATGACG

3'-Rv3620-3HindIII-
                         (SEQ ID NO: 55)
TAGAATTCAAGCTTTCAGC

TGCTGAGGATCTGCTG
```

Rv3620 was PCR amplified with conditions 94° C. 0.5 min., 55° C. 0.5 min., 68° C. 1 min. for 30 cycles. The PCR product (SEQ ID NO: 52) was digested with Ndel/HindIII and cloned into pET28a. Rv3620 was transformed into expression host Rosetta2 plysS. After lysis of a 1 L induction, protein went into the inclusion body. Ni-NTA was performed under denaturing conditions, then purified antigen dialyzed against 20 mM Tris pH 8.0, 50 mM NaCl. The amino acid sequence of the recombinant protein is set forth in SEQ ID NO: 53.

Example 12

Cloning and Expression of Recombinant Rv3810

Using H37Rv genomic DNA as template, Rv3810 was PCR amplified using the following primers:

```
5'-Rv3810-5his23-NdeI-
                         (SEQ ID NO: 59)
CAATTACATATGCATCACCATCA

CCATCACAGTCCTTGTGCATATT

TTCTTGTC

3'-Rv3810-3XhoI-
                         (SEQ ID NO: 60)
CAATTACTCGAGTT

AGGCGACCGGCACGGTGATTGG
```

Rv3810 was PCR amplified with conditions 95° C. 1 min., 58° C. 1 min., 72° C. 1.5 min. for 35 cycles. The PCR product (SEQ ID NO: 57) was digested with NdeI/XhoI and cloned into pET 17b (pET construct begins at amino acid 23). Rv3810 was transformed into expression hosts BL-21 plysE and Rosetta plysS. After lysis of a 1 L induction, protein went into the inclusion body. Ni-NTA was performed under denaturing conditions, then dialyzed against 10 mM Tris pH 8.0. The amino acid sequence of the recombinant protein is set forth in SEQ ID NO: 58.

Example 13

Cloning and Expression of Recombinant Rv3876

Rv3876 was PCR amplified from genomic DNA using the following amplification primers:

```
Rv3876F-Nde-5':
                                   (SEQ ID NO: 64)
GATCCCATGGGCATATGGCGGCCGACTACGAC

Rv3876R-EcorRI-3':
                                   (SEQ ID NO: 65)
GTCAGAATTCTCAACGACGTCCAGCCCT
```

Amplification was performed using the following conditions: 94° C. 30 sec., 55° C. 30 sec., 72° C. 2 min, for 30 cycles. The PCR product was ligated into the shuttle vector pGemT. Positive clones were identified on LB agar-x-gal plates by blue/white selection. The Rv3876 gene product was digested with NdeI/EcoRI and cloned into pET 28a. Rv3876c was transformed into expression host BL-21(DE3) plysS. After lysis of a 1 L induction, protein remained in the insoluble fraction. Ni-NTA was performed under denaturing conditions, then dialyzed against 20 mM Tris pH 8.0. The amino acid sequence of the recombinant protein is set forth in SEQ ID NO: 63.

Example 14

Cloning and Expression of Recombinant Fusion Protein $M_{TB}36_{F}.1$

The following primers were used in the construction of fusion construct Mtb36f.1:

```
5'-Rv2389-5NdeI50-
                              (SEQ ID NO: 68)
CAATTACATATGGACGAC

ATCGATTGGGACGCC

3'-Rv2389-3SacIgo-
                              (SEQ ID NO: 69)
CAATTAGAGCTCATCGTCC

CTGCTCCCCGAACA

5'-Rv3810-5SacI23-
                              (SEQ ID NO: 70)
CAATTAGAGCTCAGTCCT

TGTG]CATATTTTCTTG

3'-Rv3810-3HindIII-KpnI-
                              (SEQ ID NO. 71)
CAATTAAAGCTTTTAGGTACCGG

CGACCGGCACGGTGATTGG
```

Using previously cloned plasmid DNA of Rv2389 and Rv3810, the Mtb36f.1 components were PCR amplified using the following conditions: 94° C. 30 sec., 58° C. 30 sec., 68° C. 1 min. for 35 cycles. The 5' Rv2389 PCR product was digested with NdeI/SacI and cloned into pET 28a. The 3' Rv3810 PCR product was digested with SacI/HindIII and cloned into the Rv2389 containing pET 28a construct. Mtb36f.1 (SEQ ID NO: 66) was transformed into expression host BL-21(DE3)plysS. After lysis of a 1 L induction, protein remained in the soluble fraction. Ni-NTA was performed under native conditions, then dialyzed against 20 mM Tris pH 8.0. The amino acid sequence of the recombinant fusion protein is set forth in SEQ ID NO: 67.

Example 15

Cloning and Expression of Recombinant Fusion Protein ID58

The following primers were used in for cloning the fusion construct ID58, which comprises fusion partners derived from Mtb Rv1813, Rv3620 and Rv0496

```
5': Rv1813mat-5NdeI-KpnI
                              (SEQ ID NO: 73)
CAATTACATATGGGTACCCATCT

CGCCAACGGTTCGATG

3': Rv1813mat-3SacIgo
                              (SEQ ID NO: 74)
CAATTAGAGCTCGTTGCACGCC

CAGTTGACGAT

5': Rv3620-5SacI
                              (SEQ ID NO: 75)
CAATTAGAGCTCATGACCTCGC

GTTTTATGACG

3': Rv3620-3SalIgo
                              (SEQ ID NO: 76)
CAATTAGTCGACGCTGCTGAGGA

TCTGCTGGGA

5': Rv0496-5SalI
                              (SEQ ID NO: 77)
CAATTAGTCGACATGGTCGATGC

CCACCGCGGC

3': Rv0496-3ScaI-HindIII
                              (SEQ ID NO: 78)
CAATTAAAGCTTTTAAGTACTTG

GTTTGCTGCCTCTCGATCG
```

Rv1813 and Rv3620 were PCR amplified from genomic template DNA (94° C. for 0.5 min., 58° C. for 0.5 min., 58° C. for 1:5 min.; 35 cycles). Rv1813 was digested with NdeI/SacI then cloned into pET28. a vector. Rv3620 was digested with SacI/SalI then ligated into the Rv1813pET construct. Rv0496 was amplified from plasmid template by PCR (94° C. for 0:30; 60° C. for 0:30; 68° C. for 1:30; 35 cycles). Product was digested with SalI/HindIII and cloned into pET28. a-Rv1813-3620 vector. ID58-pET28. a had some point mutations so site directed mutagenesis was used to insert the correct nucleic acids. The ID58 fusion construct has a polynucleotide sequence set forth in SEQ ID NO: 72, encoding the fusion protein set forth in SEQ ID NO: 79. ID58 was expressed in host BL-21plysS (1 L, 2XYT growth media, 37° C.). Induction was with 1 mM IPTG at OD 0.471 and cells were harvested at OD 1.36. Cell pellet was suspended in lysis buffer (20 mM Tris pH8, 100 mM NaCl, 2 mM PMSF) and froze. ID58 forms an inclusion body and was processed the same as ID83. Fractions from the flow through bind were dialyzed in 20 mM Tris pH 8.5.

Example 16

Cloning and Expression of Recombinant Fusion Protein ID69

The following primers were used in for cloning the fusion construct ID69, which comprises fusion partners derived from Rv2389, Rv1813, Rv3620 and Rv0496:

```
5': Rv2389mat-5NdeI
                                   SEQ ID NO: 81)
CAATTACATATGGACGACATCGATTGGGACGC

3': Rv2389mat-3KpnI-HindIII
                                  (SEQ ID NO: 82)
CAATTAAAGCTTTTAAGTACTTGGTTTGCTGC

CTCTCGATCG
```

Rv2389 was PCR amplified from genomic template (94° C. for 0.5 min., 58° C. for 0.5 min., 68° C. for 1.5 min.; 35 cycles), digested with Ndel/HindIII, and ligated into pET28. a. ID58-pET28. a vector was digested with KpnI/HindIII to drop out the insert. ID58 was ligated into Rv2389-pET28. a vector (also digested with KpnI/HindIII). The fusion construct has a polynucleotide sequence set forth in SEQ ID NO: 80, encoding the fusion protein set forth in SEQ ID NO: 83. ID69 was expressed in host BL-21plysS (1 L, 2XYT growth media, 37 oC). Cell pellet was suspended in lysis buffer (20 mM Tris pH8, 100 mM NaCl, 2 mM PMSF) and froze. ID69 forms an inclusion body and was purified the same as ID83.

Example 17

Cloning and Expression of Recombinant Fusion Protein ID83

The following primers were used in for cloning the fusion construct ID83, which comprises fusion partners from Rv1813, Rv3620 and Rv2608:

```
5': Rv1813mat-5NdeI-KpnI
                                  (SEQ ID NO: 85)
CAATTACATATGGGTACCCATCTCGCCAACGGT

TCGATG
3': Rv1813mat-3SacIgo
                                  (SEQ ID NO: 86)
CAATTAGAGCTCGTTGCACGCCCAGTTGACGAT

5': Rv3620-5SacI
                                  (SEQ ID NO: 87)
CAATTAGAGCTCATGACCTCGCGTTTTATGACG

3': Rv3620-3SalIgo
                                  (SEQ ID NO: 88)
CAATTAGTCGACGCTGCTGAGGATCTGCTGGGA
5': Rv2608-5SalI
                                  (SEQ ID NO: 89)
CAATTAGTCGACATGAATTTCGCCGTTTTGCCG
```

-continued

```
3': Rv2608-3ScaI-HindIII
                                  (SEQ ID NO: 90)
CAATTAAAGCTTTTAAGTACTGAAAAGTCGGGG

TAGCGCCGG
```

Rv1813 and Rv3620 were PCR amplified from genomic template DNA (94° C. for 0.5 min.; 58° C. for 0.5 min., 58° C. for 1.5 min.; 35 cycles). Rv1813 was digested with Ndel/Sacl then cloned into pET28. a vector. Rv3620 was digested with Sacl/SalI then ligated into the Rv1813pET construct. Rv2608 was amplified from plasmid template by PCR (94° C. for 0.5 min., 58° C. for 0.5 min., 68° C. for 1.5 min.; 35 cycles). Product was digested with SalI/HindIII and cloned into pET28. a-Rv1813-3620 vector. The fusion construct has a polynucleotide sequence set forth in SEQ ID NO: 84, encoding the fusion protein set forth in SEQ ID NO: 91.

ID83 was expressed in host BL-21plysS (2 L, 2XYT growth media, 37° C.). Induced with 1 mM IPTG at OD 0.77 and harvested at OD 1.93. Cell pellet was suspended in lysis buffer (20 mM Tris pH8, 100 mM NaCl, 2 mM PMSF) and froze. The cell pellet was then thawed, lysed by sonication, and spun at 7,000 rcf for 20 minutes. ID83 is an inclusion body protein. The pellet was washed 2× with 1% Chaps. The pellet was solubilized in 60 mL in binding buffer (8M urea, 20 mM Tris pH 8, 100 mM NaCl) and bound to 16 mL Ni-NTA resin at RT for 1 hour. The resin was washed (50 ml 0.5% DOC for 20 minutes; 80 mL 60% IPA for 30 minutes, 50 mL 0.5% DOC rinse) and then eluted with binding buffer with 300 mM imidazol. The supernatant from the first bind was bound to an additional 8 mL resin and processed as indicated above. The aforementioned purifications removed breakdown products. Another Ni-NTA bind was performed overnight at 4° C. in 160 mL (binding buffer with 50 mM NaCl) with 32 mL resin. The resin was washed and eluted as indicated above. The fractions from this bind were dialyzed in 20 mM Tris pH8.

Example 18

Cloning and Expression of Recombinant Fusion Protein ID94

The following primers were used in for cloning the fusion construct ID94, which comprises fusion partners derived from Rv2389, Rv1813, Rv3620 and Rv2608:

```
5': Rv2389mat-5NdeI
                                  (SEQ ID NO: 93)
CAATTACATATGGACGACATCGATTGGGACGCC

3': Rv2389mat-3KpnI-HindIII
                                  (SEQ ID NO: 94)
CAATTAAAGCTTTTAAGTACTTGGTTTGCTGCCT

CTCGATCG
```

Rv2389 was PCR amplified from genomic template (94° C. for 0.5 min., 58° C. for 0.5 min., 68° C. for 1.5 min., 35 cycles), digested with Ndel/HindIII, and ligated into pET28. a. 1083-pET28. a vector was digested with KpnI/HindIII to drop out the insert. ID83 was ligated into Rv2389-pET28. a vector (also digested with KpnI/HindIII). The fusion construct has a polynucleotide sequence set forth in SEQ ID NO: 92, encoding the fusion protein set forth in SEQ ID NO: 95. ID94 was expressed in host BL-21 plysS 1 L, 2XYT growth media, 37° C.). Expression was induced with 1 mM IPTG at OD 0.50 and harvested at OD 1.41. Cell pellet was suspended in lysis buffer (20 mM Tris pH8, 100 mM NaCl, 2 mM PMSF) and froze. ID94 forms an inclusion body and was processed the same as ID83. ID94 did not bind well overnight so the volume was doubled with 8M urea and BME was added to 10 mM. The less concentrated solutions were bound the Ni-NTA resin at RT for 2 hours then overnight at 4° C. The resin was washed and eluted as previously indicated. The fractions from this purification were dialyzed in 20 mM Tris pH8.

Example 19

Cloning and Expression of Recombinant Fusion Protein ID95

ID95 is a fusion construct comprising fusion partners derived from Rv2389, Rv3810, Rv1813, Rv3620 and Rv0496. ID58-pET28. a vector was digested with KpnI/HindIII to drop out the insert. The ID58 insert was ligated into previously made 36f.1-pET28, a vector (also digested with KpnI/HindIII). The fusion construct has a polynucleotide sequence set forth in SEQ ID NO: 96, encoding the fusion protein set forth in SEQ ID NO: 97. ID95 was expressed in host BL-21plysS (1 L, 2XYT growth media, 37° C.). Cell pellet was suspended in lysis buffer (20 mM Tris pH8, 100 mM NaCl, 2 mM PMSF) and froze, ID95 forms an inclusion body and was purified the same as ID83.

Example 20

Cloning and Expression of Recombinant Fusion Protein ID120

ID120 is a fusion construct comprising fusion partners derived from Rv2389, Rv3810, Rv1813, Rv3620 and Rv2608. ID83-pET28. a vector was digested with KpnI/HindIII to drop out the insert. The ID83 insert was ligated into previously made 36f.1-pET28. a vector (also digested with KpnI/HindIII). The fusion construct has a polynucleotide sequence set forth in SEQ ID NO: 98, encoding the fusion protein set forth in SEQ ID NO: 99. ID120 was expressed in host BL-21plysS (1 L, 2XYT growth media, 37° C.). Expression was induced with 1 mM IPTG at OD 0.50 and cells were harvested at OD 1.41. Cell pellet was suspended in lysis buffer (20 mM Tris pH8, 100 mM NaCl, 2 mM PMSF) and froze. ID120 forms an inclusion body and was processed the same as ID83. ID120 did not bind well overnight so the volume was doubled with 8M urea and BME was added to 10 mM. The less concentrated solutions were bound to Ni-NTA resin at RT for 2 hours then overnight at 4° C. The resin was washed and eluted as previously indicated. The fractions from this purification were dialyzed in 20 mM Tris pH8.

Example 21

Recognition of $M_{TB}$ Antigens By PPD+ Human PBMC and Splenocytes from $M_{TB}$ Infected Mice This example demonstrates that Mtb antigen of the invention induce memory recall responses in human PBMC from PPD+ healthy donors, and splenocytes isolated from mice infected with *Mycobacterium tuberculosis.*

Material & Methods:

Human PBMC In Vitro Stimulation and Cytokine ELISA

PBMC were obtained through apheresis or purified from heparinized blood from 7 PPD−, and 15 PPD+ healthy donors. PBMC were plated in triplicate 96-well tissue culture plates at 2-2.5×$10^5$ cells/well and cultured with medium, PHA (10 μg/ml), *Mycobacterium tuberculosis* (Mtb) lysate (101 μg/ml), or each recombinant protein (50 μg/ml) for 72 h. Supernatants were harvested and analyzed for IFN-γ by a double-sandwich ELISA using specific mAb (eBioscience), and following the manufacturer's protocol.

Mouse Cytokine EL/SPOT

Spleen from *Mycobacterium tuberculosis*-Infected mice were harvested at different times post-infection- and single splenocyte suspensions were obtained by conventional procedures. An ELISPOT assay was used to determine the relative number of IFN-γ or TNF-expressing splenocytes. MultiScreen 96-well filtration plates (Millipore, Bedford, MA) were coated with 10 μg/ml rat anti-mouse IFN-γ, or TNF, capture Ab (eBioscience) and incubated overnight at 4° C. Plates were washed with PBS, blocked with RPMI 1640 and 10% FBS for at least 1 h at room temperature, and washed again. Spleen cells were plated, in duplicate, at 2×$10^5$ cells/well, and stimulated with the specific rAg at a 10 μg/ml for 48 h at 37° C. The plates were subsequently washed with PBS and 0.1% Tween and incubated overnight at 4'C with a biotin-conjugated, rat anti-mouse IFN-γ, or TNF, secondary Ab (eBioscience) at 5 μg/ml in PBS, 0.5% BSA, and 0.1% Tween. The filters were developed using the Vectastain ABC avidin peroxidase conjugate and Vectastain AEC substrate kits (Vector Laboratories, Burlingame, CA) according to the manufacturers protocol. The reaction was stopped by washing the plates with deionized water, plates were dried in the dark, and spots were counted.

Results:

Recognition of Mtb Recombinant Proteins by Human PPD+ PBMC

PBMC from PPD+ and PPD− donors were cultured for 72 h with Mtb Rv0164, Rv0455, Rv0496, Rv2608, Rv3020, Rv3478, Rv3619, Rv3620, Rv1738, Rv1813, Rv3810, Rv2389, Rv2866, Rv3876, Rv0054, Rv0410, Rv0655, Rv0831, Rv1009, Rv1099, Rv1240, Rv1288, Rv1410, Rv1569, Rv1789, Rv1818, Rv1860, Rv1886, Rv1908, Rv2220, Rv2032, Rv2623, Rv2875, Rv3044, Rv3310, Rv3881, Rv0577, Rv1626, Rv0733, Rv2520, Rv1253, Rv1980, Rv3628, Rv1884, and Rv1511 recombinant proteins. A description of the production of these recombinant antigens is described elsewhere herein. The concentration of IFN-γ was further analyzed in the cell culture supernatants.

All the recombinant proteins tested, except Rv1908, were presented to and activated T cells from PPD+donors to produce IFN-γ (FIG. 1). Only background levels of IFN-γ were detected in response to these antigens using PBMC from PPD−controls. 5- to 70-fold increases in IFN-γ concentration were measured in PBMC cultures from PPD− donors compared to PPD− controls, indicating antigen specific recognition of these recombinant proteins from donors previously exposed to *Mycobacterium tuberculosis* or *Mycobacterium bovis* (vaccinated with BCG).

Recognition of Mtb Recombinant Proteins by Splenocytes from *M. tuberculosis* Infected Mice Mice were infected by low dose aerosol exposure with *Mycobacterium tuberculosis* H37Rv strain, and spleens were harvested at different time post-infection. An ELISPOT assay was used to determine the relative number of TNF-expressing splenocytes in response to Mtb recombinant Rv0164, Rv0455, Rv0496, Rv2608, Rv3020, Rv3478, Rv3619, Rv3620, Rv1738. Rv1813, Rv3810, Rv2389, Rv2866, Rv0054, Rv0655, Rv0831, Rv1009, Rv1240, Rv1288, Rv1410, Rv1569, Rv1789, Rv1818, Rv1860, Rv1886, Rv1908, Rv2220, Rv2032, Rv2875, Rv3044, Rv3310, Rv3881, Rv0577, Rv1626, Rv0733, Rv1253, Rv1980, Rv3628, Rv1884, Rv3875, Rv1511 and ID83 proteins during a 48 h in vitro culture.

Figure 2A:
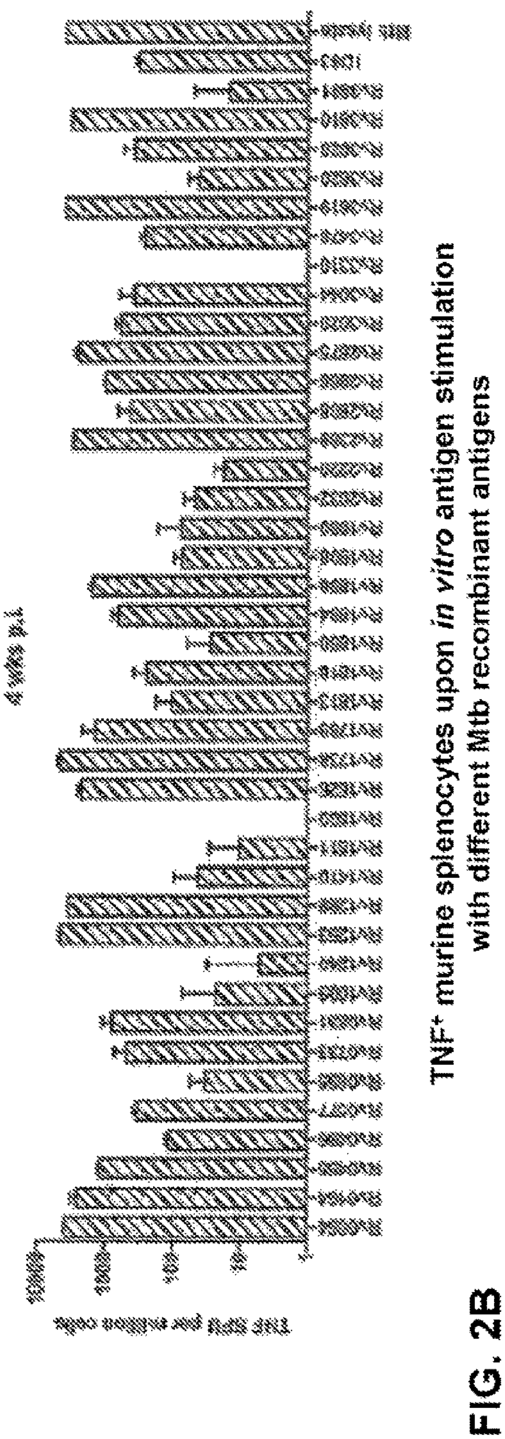
FIGS. 2A-2B show the levels of TNF' splenocytes upon in vitro antigen stimulation with different Mtb recombinant proteins. Splenocytes from mice infected with a low dose of virulent *M. tuberculosis* H37Rv were collected 4 wks and 12 wks after the infection and tested for antigen specific TNF cytokine responses by ELISPOT. The splenocytes were incubated for 48 h in media, 10 μg/ml Mtb lysate, or 10 μg/rnl of the Mtb recombinant proteins. The data shown is the mean±SD (n=2) in a representative experiment.
Figure 2B:
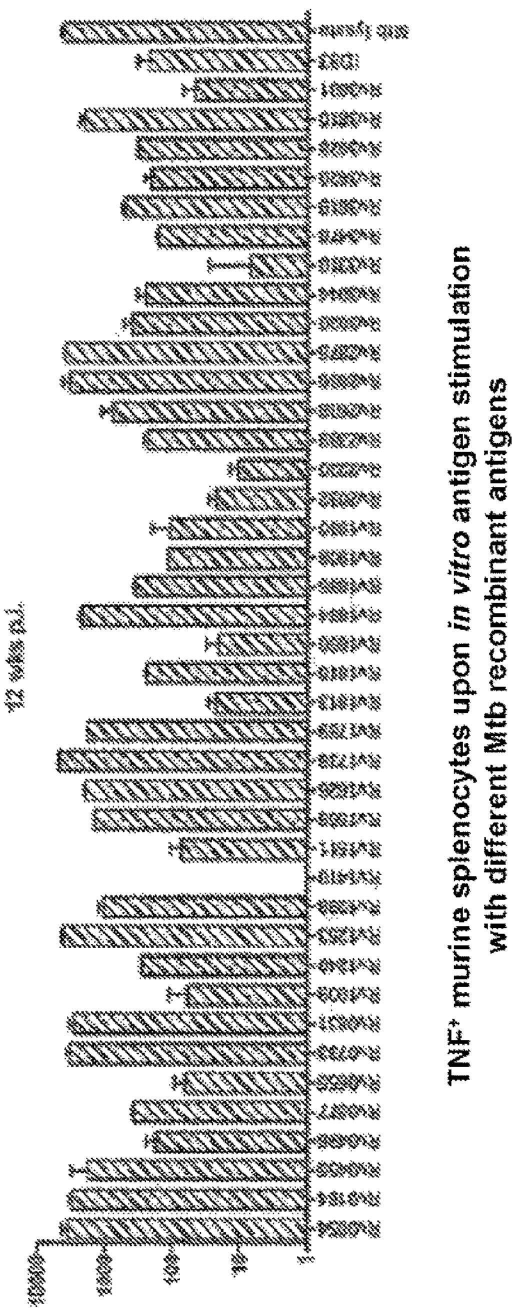

All the recombinant and fusion proteins tested induced an increase in the number of TNF+ splenocytes from *Mycobacterium tuberculosis*-infected mice 28 days (FIG. 2, upper panel), 60 days (data not shown), and 90 days post-infection (FIG. 2, lower panel).

Together these data indicate that *Mycobacterium tuberculosis* infection in mice induced immune responses to Mtb proteins, including to Rv0164, Rv0455, Rv0496, Rv2608, Rv3020, Rv3478, Rv3619, Rv3620, Rv1738, Rv1813, Rv3810, Rv2389, Rv2866, Rv0054, Rv0655, Rv0831, Rv1009, Rv1240, Rv1288, Rv1410, Rv1569, Rv1789, Rv1818, Rv1860, Rv1886, Rv1908, Rv2220, Rv2032, Rv2875, Rv3044, Rv3310, Rv3881, Rv0577, Rv1626, Rv0733, Rv1253, Rv1980, Rv3628, Rv1884, Rv1511 and ID83 proteins.

Thus, both humans naturally exposed to, and mice infected by an aerosol challenge with virulent, *Mycobacterium tuberculosis*-mounted immune responses to bacterial proteins, as evidenced by recall responses to Mtb lysate and PPD. In addition, increase in IFN-γ and TNF cytokine responses to Rv0164, Rv0455, Rv0496, Rv2608, Rv3020, Rv3478, Rv3619, Rv3620, Rv1738, Rv1813, Rv3810, Rv2389, Rv2866, Rv3876, Rv0054, Rv0410, Rv0655, Rv0831, Rv1009, Rv1099, Rv1240, Rv1288, Rv1410, Rv1569, Rv1789, Rv1818, Rv1860, Rv1886, Rv1908, Rv2220, Rv2032, Rv2623, Rv2875, Rv3044, Rv3310, Rv3881, Rv0577, Rv1626, Rv0733, Rv2520, Rv1253, Rv1980, Rv3628, Rv1884, Rv1511 and ID83 protein upon in vitro stimulation indicates that these antigens (1) are recognized by previously exposed individuals (presence of memory T cells), (2) could be used as immuno-therapeutics or (3) could be used as diagnostics.

Example 22

Immune Responses to $M_{TB}$ Antigens In C57BL/6 Mice And Protection Against Aerosol Challenge with $M_{TB}$ This example demonstrates that immunization of mice with Mtb antigens of the invention is immunogenic and can provide protection against aerosol *Mycobacterium tuberculosis* challenge.

Material & Methods:

Recombinant Antigens and Adjuvant Formulations

Recombinant proteins were produced as described above. CpG 1826 was obtained from Coley Pharmaceuticals (Wellesley, MA).

Immunization

Female C57/BL6 mice were obtained from Charles River and age-matched (5-7 week) within each experiment. Mice were immunized three times (3 week apart) with 8 μg of recombinant Rv0164 (SEQ ID NO: 1), Rv0496 (SEQ ID NO: 6), Rv2608 (SEQ ID NO: 26), Rv3020 (SEQ ID NO: 36), Rv3478 (SEQ ID NO: 41), Rv3619 (SEQ ID NO: 46), Rv3620 (SEQ ID NO: 51), Rv1738 (SEQ ID NO: 11), Rv1813 (SEQ ID NO: 16), Rv3810 (SEQ ID NO: 56), Rv2389 (SEQ ID NO: 21), Rv2866 (SEQ ID NO: 31), Rv0831 (SEQ ID NO: 115), Rv1288 (SEQ ID NO: 127). Rv1569 (SEQ ID NO: 133), Rv1789 (SEQ ID NO: 136), Rv1818 (SEQ ID NO: 139), Rv1860 (SEQ ID NO: 142), Rv1886 (SEQ ID NO: 145), Rv2220 (SEQ ID NO: 154), Rv2032 (SEQ ID NO: 151), Rv2623 (SEQ ID NO: 160), Rv2875 (SEQ ID NO: 163), Rv3044 (SEQ ID NO: 166), Rv0577 (SEQ ID NO: 184), Rv1626 (SEQ ID NO: 187), Rv0733 (SEQ ID NO: 190), Rv3628 (SEQ ID NO: 202), and Rv1884 (SEQ ID NO: 205) protein formulated with 25 μg of the adjuvant CpG. Mice in the saline, adjuvant only, and BCG control groups received three doses of PBS, three doses of adjuvant alone, or a single dose of $5\times10^4$ BCG CFU respectively. Mice were injected with a total volume of 100 μl/mouse via the s.c. route.

Cytokine ELISA

Three weeks after the last boost, spleen from animals designated for immunogenicity studies were harvested, and splenocytes were obtained by conventional procedures. For cytokine analysis, splenocytes were plated in duplicate 96-well tissue culture plates at $2.5\times10^5$ cells/well and cultured with medium, Con A 3 μg/ml, PPD 10 μg/ml, Mtb lysate 10 μg/ml, or each recombinant protein 10 μg/ml for 72 h. Supernatants were harvested and analyzed for IFN-γ by a double-sandwich ELISA using specific mAb (eBioscience), and following the manufacturer's protocol.

Cytokine ELISPOT

MultiScreen 96-well filtration plates (Millipore, Bedford, MA) were coated with 10 μg/ml rat anti-mouse IFN-γ or TNF capture Ab (eBioscience) and incubated overnight at 4° C. Plates were washed with PBS, blocked with RPMI 1640 and 10% FBS for at least 1 h at room temperature, and washed again. Splenocytes were plated in duplicate at $2\times10^5$ cells/well, and stimulated with medium, Con A 3 μg/ml, PPD 10 μg/ml, or each recombinant protein 10 μg/ml for 48 h at 37° C. The plates were subsequently washed with PBS and 0.1% Tween-20 and incubated for 2 h with a biotin-conjugated rat anti-mouse IFN-γ or TNF secondary Ab (eBioscience) at 5 μg/ml in PBS, 0.5% BSA, and 0.1% Tween-20. The filters were developed using the Vectastain ABC avidin peroxidase conjugate and Vectastain AEC substrate kits (Vector Laboratories, Burlingame, CA) according to the manufacturer's protocol. The reaction was stopped by washing the plates with deionized water, plates were dried in the dark, and spots were counted on a automated ELISPOT reader (C.T.L. Serie3A Analyzer, Cellular Technology Ltd, Cleveland, OH), and analyzed with Immunospot® (CTL Analyzer LLC).

IgG Isotype ELISA

Animals were bled 1 wk after the last immunization and serum IgG1 and IgG2c antibody titers were determined. Nunc-Immuno Polysorb plates were coated for 4 h at room temperature with 2 μg/ml of recombinant protein in 0.1 M bicarbonate buffer, blocked overnight at 4° C. with PBS Tween-20 0.05% BSA 1%, washed with PBS Tween-20 0.05%, incubated for 2 h at room temperature with sera at a 1:50 dilution and subsequent 5-fold serial dilutions, washed, and incubated for 1 h with anti-IgG1-HRP or anti-IgG2c-HRP 1:2000 in PBS Tween-20 0.05% BSA 0.1%. Plates were washed and developed using SureBlue TMB substrate (KPL Inc., Gaithersburg, MD). The enzymatic reaction was stopped with 1N $H_2SO_4$, and plates were read within 30 min at 450 nm with a reference filter set at 650 nm using a microplate ELISA reader (Molecular Devices, Sunnyvale, CA) and SoftMax Pro5. Endpoint titers were determined with GraphPad Prism 4 (GraphPad Software Inc., San Diego, CA) with a cutoff of 0.1.

Protection Experiment

Mice were immunized s.c., three times, 3 weeks apart, with 8 □g of each recombinant protein from a subset of Mtb antigens, and mixed with the adjuvant CpG. Positive control mice were immunized with BCG ($5\times10^4$ CFU) in the base of the tail (once), and negative control animals were injected with saline, or adjuvant alone. Thirty days after the last immunization, mice were challenged by low dose aerosol exposure with *Mycobacterium tuberculosis* H37Rv strain (ATCC 35718; American Type Culture Collection, Manassas, VA) using a UW-Madison aerosol exposure chamber (Madison, WI) calibrated to deliver 50-100 bacteria into the lungs. Four weeks later, mice were euthanized, and lung and spleen homogenates were prepared in PBS/Tween 80 (0.05%). Bacterial counts were determine by plating serial dilutions of individual whole organs on nutrient Middlebrook 7H11 Bacto Agar (BD Biosciences, Cockeysville, MD) and counting bacterial colony formation after 14-day incubation at 37° C. in humidified air and 5% $CO_2$. Data are expressed as Log 10 of the mean number of bacteria recovered±SD, and Log 10 Reduction in CFU=Log 10 CFU for the vaccinated group−Log 10 CFU for the Saline treated group.

Results:

Immune Responses to Recombinant Mtb Antigens Adjuvanted with CpG.

C57BL/6 mice were immunized three times, three weeks apart, with recombinant Mtb Rv0164, Rv0455, Rv0496, Rv2608, Rv3020, Rv3478, Rv3619, Rv3620, Rv1738, Rv1813, Rv3810, Rv2389, Rv2866, Rv0831, Rv1818, Rv1886, Rv2032, Rv2623, Rv2875, Rv3044, Rv0577, Rv1626, Rv3628, and Rv1884 proteins formulated with 25 μg of the adjuvant CpG. One week, and three weeks after the last immunization, the presence of antigen specific antibody, and memory T lymphocytes respectively, were assessed.

The specific serum IgG isotype Ab response was measured by conventional ELISA by coating each of the recombinant protein onto a plate and serially diluting the different sera. IgG2c:IgG1 endpoint titer ratios were determined for each vaccine group (Table 1). Saline, CpG adjuvant alone, or BCG immunization did not induce an IgG1 or IgG2c antibody response specific to any or the Mtb recombinant proteins tested (data not shown). Immunization with each of the Mtb recombinant proteins with the adjuvant CpG induced antigen specific IgG1 and IgG2c.

TABLE 1

Immune responses to Mtb antigens

| Antigen | IFN-γ[a] | TNF[a] | IrgG[b] | Antigen | IFN-γ | TNF | IgG |
|---|---|---|---|---|---|---|---|
| Rv0577 | 523(8) | 388(297) | 0.98 | Rv0496 | 68(52) | 24(5) | *1.21 |
| Rv1626 | 20(21) | 268(117) | *1.19 | Rv0831 | 24(12) | 24(8) | *1.19 |
| Rv2875 | 428(172) | 137(60) | *1.05 | Rv1886 | 590(106) | 102(37) | 1.00 |
| Rv2608 | 798(11) | 175(105) | 1.09 | Rv3020 | 48(27) | 20(16) | *1.18 |
| Rv3478 | 453(4) | 149(73) | 1.03 | Rv3619 | 604(184) | 1261(319) | *1.13 |
| Rv3044 | 331(161) | 57(1) | *1.05 | Rv1813 | 388(103) | 32(13) | *1.18 |
| Rv0164 | 163(87) | 94(58) | *1.17 | Rv2380 | 39(49) | 92(31) | 1.02 |
| Rv0455 | 24(12) | 44(24) | 1.06 | Rv2623 | 21(12) | 2(1) | *1.14 |
| Rv1738 | 24(16) | 32(16) | 1.23 | Rv2866 | 104(56) | 32(12) | *1.31 |
| Rv1818 | 155(72) | 10(2) | *0.90 | Rv3620 | 184(44) | 72(33) | *1.13 |
| Rv1684 | 1600(372) | ND[c] | 1.01 | Rv3628 | 16(8) | ND | 1.09 |
| Rv2032 | 28(16) | ND | *1.14 | Rv3810 | 44(56) | 7(10) | 1.08 |

[a]Spot-Forming-Unit per million cells (SD). Mice were immunized s.c. three times, three wks aport with Mtb antigens (RV#) + CpG. Cytokine responses to the antigens were determined by ELISPOT 3 wks after the last injection.

[b]IgG2c:IgG1 ratio,

*$P < 0.05$, Student's t Test,

[c]ND, not done.

Three weeks after the last immunization, splenocytes were prepared and assayed by ELISPOT to determine the relative number of IFN-γ or TNF-expressing splenocytes in response to medium alone, the mitogen ConA, PPD, Mtb lysate, and each of the recombinant Mtb proteins.

Injection with saline, or CpG adjuvant alone did not induce IFN-γ or TNF responses specific to any of the recombinant proteins (data not shown).

Immunization with each of the Mtb recombinant proteins with the adjuvant CpG induced antigen specific IFN-γ and/or TNF recall responses by activated splenocytes (Table 1). Lower levels of IFN-γ in response to Mtb lysate and PPD were also observed (data not shown), suggesting that these proteins are naturally found in mycobacterial lysates and partially purified derivatives.

Together, these results indicate that immunization with the different recombinant Mtb antigens in CpG induced a Th1-type memory response with predominant IgG2c, IFN-γ, and TNF.

Protection Afforded by the Different Mtb Recombinant Proteins, Adjuvanted with CpG, against an Aerosol Challenge with Mtb H37Rv.

Number of viable bacilli, expressed as mean Log 10 CFU, in the lung and spleen of mice vaccinated with Mtb recombinant protein Rv0496, Rv2608, Rv3020, Rv3478, Rv3619, Rv3620, Rv1813, Rv1569, Rv1789, Rv1860, Rv1886, Rv2220, Rv2875, Rv3044, Rv0577, FM 626, and Rv0733, adjuvanted with CpG, were determined 4 weeks post aerosol challenge with ~50 CFU of virulent *Mycobacterium tuberculosis* H37Rv. The mean Log 10 CFU in the lung of mice immunized with the different recombinant proteins was compared to the mean Log 10 CFU obtained in mice receiving placebo (saline) or BCG, the current and only vaccine against TB. The difference in mean Log 10 CFU in the saline group vs the vaccinated groups is expressed as Log 10 reduction in CFU.

Immunization of mice with three doses of Rv3478+CpG or Rv2608+CpG resulted in a decrease in viable Mtb bacilli, in lung (0.66, respectively 0.58) close to that afforded by BCG vaccination (0.78) (Table 2). Immunization with each of Rv0496, Rv3020, Rv3619, Rv3620, Rv1813, Rv1569, Rv1789, Rv1860, Rv1886, Rv2220, Rv2875, Rv3044, Rv0577, Rv1626, and Rv0733, adjuvanted with CpG, also afforded some protection against Mtb infection. CpG adjuvant alone did not reduce lung bacterial burden (−0.09).

TABLE 2

| Vaccine-induced protection against Mtb[a] CFU Reduction ($Log_{10}$)[b] | | | | | | | |
|---|---|---|---|---|---|---|---|
| Rv0496 | 0.11 | Rv0577 | 0.36 | Rv1886 | 0.20 | Rv3478 | 0.66 |
| Rv0733 | 0.23 | Rv1626 | 0.32 | Rv1569 | 0.12 | Rv3044 | 0.43 |
| Rv0831 | 0.13 | Rv2875 | 0.44 | Rv1789 | 0.15 | Rv2220 | 0.25 |
| Rv1411 | 0.11 | Rv2608 | 0.58 | Rv3020 | 0.17 | BCG | 0.78 |
| Rv1860 | 0.19 | Rv3619 | 0.24 | Rv1813 | 0.14 | CpG | −0.09 |

[a]Mice were immunized s.c. three times, three wks apart with 8 μg Mtb antigens (Rv#) + 25 μg CpG.
[b]Reduction of viable bacteria (CFU) in the lungs compared to saline immunized animals 4 wks after a low dose aerosol challenge with *M. tuberculosis* H37Rv or Erdman strains.

These results are surprising in that levels of protection against Mtb infection were achieved with 3 doses of a single recombinant protein adjuvanted with CpG.

Example 23

Immune Responses to a Mixture of $M_{TB}$ Antigens in C57BL/6 Mice and Protection Against Aerosol Challenge with $M_{TB}$ This example demonstrates that immunization of mice with a mixture of Mtb antigens of the invention is immunogenic and can provide protection against aerosol *Mycobacterium tuberculosis* challenge.

Material & Methods:

Recombinant Antigens and Adjuvant Formulations

Recombinant proteins were produced as described above. CpG 1826 was obtained from Coley Pharmaceuticals (Wellesley, MA).

Immunization

Female C57/BL6 mice were obtained from Charles River and age-matched (5-7 week) within each experiment. Mice were immunized three times (3 week apart) with 6 or 8 μg of recombinant Rv2608, Rv3620, and Rv1813 protein formulated with 25 μg of the adjuvant CpG. Mice in the adjuvant only, and BCG control groups received three doses of adjuvant alone, or a single dose of $5\times10^4$ BCG CFU respectively. Mice were injected with a total volume of 100 μl/mouse via the s.c. route.

Cytokine ELISA

Three weeks after the last boost, spleen from animals designated for immunogenicity studies were harvested, and splenocytes were obtained by conventional procedures. For cytokine analysis, splenocytes were plated in duplicate 96-well tissue culture plates at $2.5\times10^5$ cells/well and cultured with medium, Con A 3 μg/ml, PPD 10 μg/ml, Mtb lysate 10 μg/ml, or each recombinant protein 10 μg/ml for 72 h. Supernatants were harvested and analyzed for IFN-γ by a double-sandwich ELISA using specific mAb (eBioscience), and following the manufacturer's protocol.

Cytokine ELISPOT

MultiScreen 96-well filtration plates (Millipore, Bedford, MA) were coated with 10 μg/ml rat anti-mouse IFN-γ or TNF capture Ab (eBioscience) and incubated overnight at 4° C. Plates were washed with PBS, blocked with RPM 1640 and 10% FBS for at least 1 h at room temperature, and washed again, Splenocytes were plated in duplicate at $2\times10^5$ cells/well, and stimulated with medium, Con A 3 μg/ml, PPD 10 μg/ml, or each recombinant protein 10 μg/ml for 48 h at 37° C. The plates were subsequently washed with PBS and 0.1% Tween-20 and incubated for 2 h with a biotin-conjugated rat anti-mouse IFN-γ or TNF secondary Ab (eBioscience) at 5 μg/ml in PBS, 0.5% BSA, and 0.1% Tween-20. The filters were developed using the Vectastain ABC avidin peroxidase conjugate and Vectastain AEC substrate kits (Vector Laboratories, Burlingame, CA) according to the manufacturer's protocol. The reaction was stopped by washing the plates with deionized water, plates were dried in the dark, and spots were counted on a automated ELISPOT reader (C.T.L. Serie3A Analyzer, Cellular Technology Ltd, Cleveland, OH), and analyzed with Immunospot® (CTL Analyzer LLC).

IgG Isotype ELISA

Animals were bled 1 wk after the last immunization and serum IgG1 and IgG2c antibody titers were determined. Nunc-Immuno Polysorb plates were coated for 4 h at room temperature with 2 μg/ml of recombinant protein in 0.1 M bicarbonate buffer, blocked overnight at 4° C. with PBS Tween-20 0.05% BSA 1%, washed with PBS Tween-20 0.05%, incubated for 2 h at room temperature with sera at a 1:50 dilution and subsequent 5-fold serial dilutions, washed, and incubated for 1 h with anti-IgG1-HRP or anti-IgG2c-HRP 1:2000 in PBS Tween-20 0.05% BSA 0.1%. Plates were washed and developed using SureBlue TMB substrate (KPL Inc., Gaithersburg, MD). The enzymatic reaction was stopped with 1N $H_2SO_4$, and plates were read within 30 min at 450 nm with a reference filter set at 650 nm using a microplate ELISA reader (Molecular Devices, Sunnyvale, CA) and SoftMax Pro5. Endpoint titers were determined with GraphPad Prism 4 (GraphPad Software Inc., San Diego, CA) with a cutoff of 0.1.

Protection Experiment

Mice were immunized s.c., three times, 3 weeks apart, with 6 or 8 μg of each recombinant protein from a subset of Mtb antigens, and mixed with the adjuvant CpG. Positive control mice were immunized with BCG ($5\times10^4$ CFU) in the base of the tail (once), and negative control animals were injected with adjuvant alone. Thirty days after the last immunization, mice were challenged by low dose aerosol exposure with *Mycobacterium tuberculosis* H37Rv strain (ATCC 35718; American Type Culture Collection, Manassas, VA) using a UW-Madison aerosol exposure chamber (Madison, WI) calibrated to deliver 50-100 bacteria into the lungs. Four weeks later, mice were euthanized, and lung and spleen homogenates were prepared in PBS/Tween 80 (0.05%). Bacterial counts were determine by plating serial dilutions of individual whole organs on nutrient Middlebrook 7H11 Bacto Agar (BD Biosciences, Cockeysville, MD) and counting bacterial colony formation after 14-day incubation at 37° C. in humidified air and 5% $CO_2$. Data are expressed as Log 10 of the mean number of bacteria recovered±SD, and Log 10 Reduction in CFU=Log 10 CFU for the vaccinated group−Log 10 CFU for the Saline treated group.

Results:

Immune Responses to a Mixture of Recombinant Mtb Antigens Adjuvanted with CpG.

C57BL/6 mice were immunized three times, three weeks apart, with each recombinant Mtb Rv2608, Rv3620, and Rv1813 proteins, separately (8 μg) or in a mixture (6 μg each), formulated with 25 μg of the adjuvant CpG. One week, and three weeks after the last immunization, the presence of antigen specific antibody, and memory T lymphocytes respectively, were assessed.

The specific serum IgG isotype Ab response was measured by conventional ELISA by coating each of the recombinant protein onto a plate and serially diluting the different sera. IgG2c endpoint titers were determined for each vaccine group. CpG adjuvant alone or BCG immunization did not induce an IgG1 or IgG2c antibody response specific to any or the Mtb recombinant proteins tested (FIG. 38, and data not shown). Immunization with each of the Mtb recombinant proteins with the adjuvant CpG induced antigen specific IgG1 (data not shown) and IgG2c (FIG. 3B).

Three weeks after the last immunization, splenocytes were prepared and assayed by ELISA or ELISPOT to determine the relative level of IFN-γ or number of TNF-expressing splenocytes in response to medium alone, the mitogen ConA, PPD, Mtb lysate, and each of the recombinant Mtb proteins.

Figure 3A:
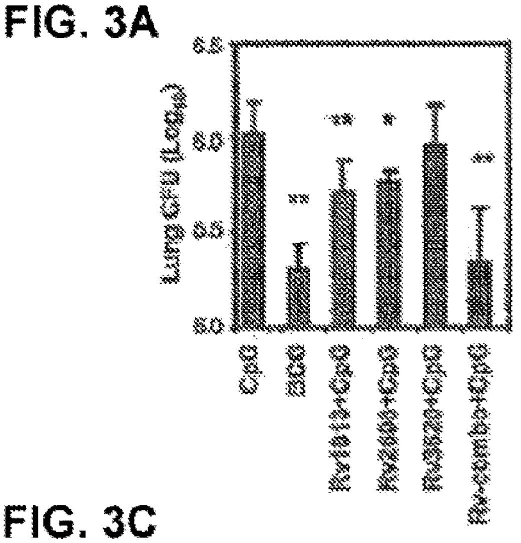
FIGS. 3A-3D shows protection against *M. tuberculosis* infection and antigen specific immune responses.
Figure 3B:
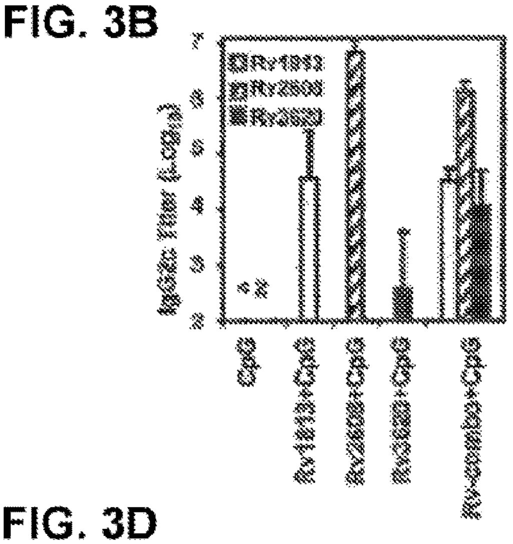
Figure 3C:
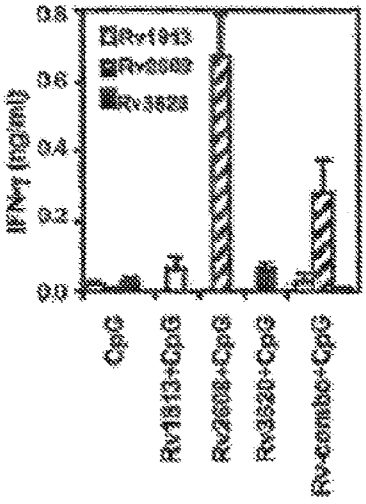
Figure 3D:
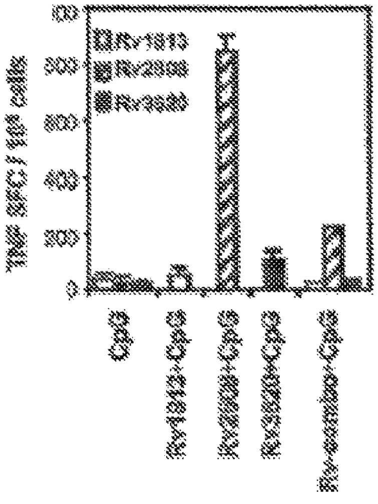

Injection with CpG adjuvant alone did not induce IFN-γ or TNF responses specific to any of the recombinant proteins (FIG. 3C-D).

Immunization with each of the Mtb recombinant proteins with the adjuvant CpG induced antigen specific IFN-γ and TNF recall responses by activated splenocytes (FIG. 3C-D). Lower levels of cytokine responses were observed when the three antigens were used as a mixture.

Together, these results indicate that immunization with the different recombinant Mtb antigens, separately or as a mixture, in CpG induced a Th1-type memory response with predominant IgG2c, IFN-γ, and TNF.

Protection Afforded by a Mixture of Different Mtb Recombinant Proteins, Adjuvanted with CpG, Against an Aerosol Challenge with Mtb H37Rv.

Number of viable bacilli, expressed as mean Log 10 CFU, in the lung of mice vaccinated with Mtb recombinant protein Rv2608, Rv3620, and Rv1813, separately (8 μg) or in a mixture (6 μg each), adjuvanted with CpG, were determined 4 weeks post aerosol challenge with ~50 CFU of virulent *Mycobacterium tuberculosis* H37Rv. The mean Log 10 CFU in the lung of mice immunized with the different recombinant proteins was compared to the mean Log 10 CFU obtained in mice receiving adjuvant alone or BCG, the current and only vaccine against TB. The difference in mean Log 10 CFU in the adjuvant group vs the vaccinated groups is expressed as Log 10 reduction in CFU.

Immunization of mice with three doses of Rv2608+Rv3620+Rv1813+CpG resulted in a decrease in viable Mtb bacilli in lung (Log 10 reduction in CFU of 0.67) close to that afforded by BCG vaccination (0.71) (FIG. 3A). Immunization with Rv2608 or Rv1813, adjuvanted with CpG, also afforded some protection against Mtb infection (0.24 and 0.30 respectively). Immunization with Rv3620+CpG or CpG adjuvant alone did not reduce lung bacterial burden. The reduction in CFU achieved by injecting a mixture of three Mtb antigens was higher than adding up individual effects.

These results are surprising in that levels of protection against Mtb infection were increased with 3 doses of a mixture or three recombinant proteins adjuvanted with CpG, compared to 3 doses of individual proteins with CpG.

Example 24

Immune Responses to ID83 and ID93 Fusion Proteins in C57BL/6 Mice and Protection Against Aerosol Challenge with $M_{TB}$ This example demonstrates that immunization of mice with fusion proteins of the invention is immunogenic and can provide protection against aerosol *Mycobacterium tuberculosis* challenge.

Material & Methods:

Fusion Proteins and Adjuvant Formulations

Fusion proteins were produced as described above. CpG 1826 was obtained from Coley Pharmaceuticals (Wellesley, MA). Glucopyranosyl lipid A (GLA) was obtained from Avanti (Alabaster, AL) and Gardiquimod (GDQ) was obtained from Invivogen (San Diego, CA). Oil-in-water sable emulsions (–SE) were prepared by standard techniques.

Immunization

Female C57/BL6 mice were obtained from Charles River and age-matched (5-7 week) within each experiment. Mice were immunized three times (3 week apart) with 8 μg of ID83 and ID93 fusion protein formulated with 20 μg of the adjuvant GLA-SE, or 8 μg ID83 fusion protein formulated with 20-25 μg of the adjuvant GLA-SE, GDQ-SE, CpG-SE, GLA/GDQ-SE, GLA/CpG-SE, CpG/GDQ-SE. Mice in the saline, adjuvant only, and BCG control groups received three doses of PBS, three doses of adjuvant alone, or a single dose of $5\times10^4$ BCG CFU respectively. Mice were injected with a total volume of 100 μl/mouse via the s.c. route.

Cytokine ELISA

Three weeks after the last boost, spleen from animals designated for immunogenicity studies were harvested, and splenocytes were obtained by conventional procedures. For cytokine analysis, splenocytes were plated in duplicate 96-well tissue culture plates at $2.5\times10^5$ cells/well and cultured with medium, Con A 3 μg/ml, PPD 10 μg/ml, Mtb lysate 10 μg/ml, or each fusion protein 10 μg/ml for 72 h. Supernatants were harvested and analyzed for IFN-γ by a double-sandwich ELISA using specific mAb (eBioscience), and following the manufacturer's protocol.

IgG Isotype ELISA

Animals were bled 1 wk after the last immunization and serum IgG1 and IgG2c antibody titers were determined. Nunc-Immuno Polysorb plates were coated for 4 h at room temperature with 2 μg/ml of recombinant protein in 0.1 M bicarbonate buffer, blocked overnight at 4° C. with PBS Tween-20 0.05% BSA 1%, washed with PBS Tween-20 0.05%, incubated for 2 h at room temperature with sera at a 1:50 dilution and subsequent 5-fold serial dilutions, washed, and incubated for 1 h with anti-IgG1-HRP or anti-IgG2c-HRP 1:2000 in PBS Tween-20 0.05% BSA 0.1%. Plates were washed and developed using SureBlue TMB substrate (KPL Inc., Gaithersburg, MD). The enzymatic reaction was stopped with 1N $H_2SO_4$, and plates were read within 30 min at 450 nm with a reference filter set at 650 nm using a microplate ELISA reader (Molecular Devices, Sunnyvale, CA) and SoftMax Pro5. Endpoint titers were determined with GraphPad Prism 4 (GraphPad Software Inc., San Diego, CA) with a cutoff of 0.1.

Protection Experiment

Mice were immunized s.c., three times, 3 weeks apart, with 8 μg of the fusion protein, formulated in the indicated adjuvant. Positive control mice were immunized with BCG ($5\times10^4$ CFU) in the base of the tail (once), and negative control animals were injected with saline, or adjuvant alone. Thirty days after the last immunization, mice were challenged by low dose aerosol exposure with *Mycobacterium tuberculosis* H37Rv strain (ATCC 35718; American Type Culture Collection, Manassas, VA) using a UW-Madison aerosol exposure chamber (Madison, WI) calibrated to deliver 50-100 bacteria into the lungs. Four weeks later, mice were euthanized, and lung and spleen homogenates were prepared in PBS/Tween 80 (0.05%). Bacterial counts were determine by plating serial dilutions of individual whole organs on nutrient Middlebrook 7H11 Bacto Agar (BD Biosciences, Cockeysville, MD) and counting bacterial colony formation after 14-day incubation at 37° C. in humidified air and 5% $CO_2$. Data are expressed as Log 10 of the mean number of bacteria recovered±SD, and Log 10

Reduction in CFU=Log 10 CFU for the vaccinated group−Logit) CFU for the Saline treated group.

Results:

Immune Responses to ID83 and ID93 adjuvanted with GLA-SE

C57BL/6 mice were immunized three times, three weeks apart, with ID83 or ID93 fusion proteins formulated with 20 µg of the adjuvant GLA-SE. One week, and three weeks after the last immunization, the presence of antigen specific antibody, and memory T lymphocytes respectively, were assessed.

Figure 4A:
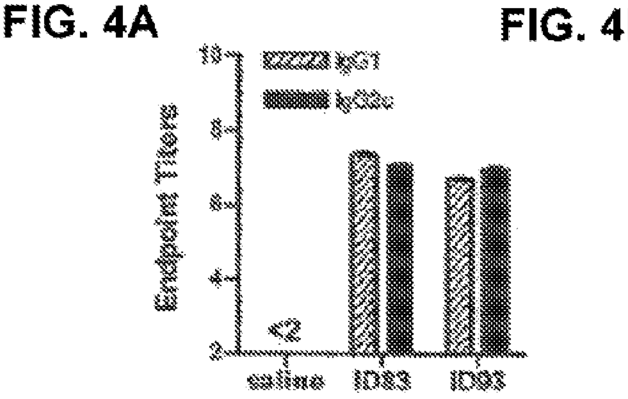
FIG. 4A-4B shows the immunogenicity of ID83 and ID93 fusion proteins with GLA-SE in C57BL/6 mice.

The specific serum IgG isotype Ab response was measured by conventional ELISA by coating each of the recombinant protein onto a plate and serially diluting the different sera. Endpoint titers were determined for each vaccine group. Saline did not induce an IgG1 or IgG2c antibody response specific to ID83 or ID93 fusion proteins (FIG. 4A) nor did GLA-SE adjuvant alone (data not shown). Immunization with ID83 or ID93 fusion protein with the adjuvant GLA-SE induced antigen specific IgG1 and IgG2c.

Three weeks after the last immunization, splenocytes were prepared and assayed by ELISA to determine the relative level of IFN-γ produced by splenocytes in response to medium alone, the mitogen ConA, and each of the fusion proteins.

Injection with saline or GLA-SE adjuvant alone did not induce IFN-γ responses specific to ID83 or ID93 fusion proteins (data not shown).

Figure 4B:
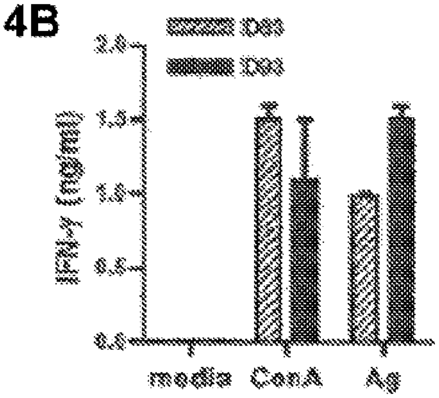

Immunization with ID83 or ID93 fusion protein with the adjuvant GLA-SE induced antigen specific IFN-γ recall responses by activated splenocytes (FIG. 4B).

relative level of IFN-γ produced by splenocytes in response to medium alone, the mitogen ConA, and ID83 fusion protein.

Figure 5A:
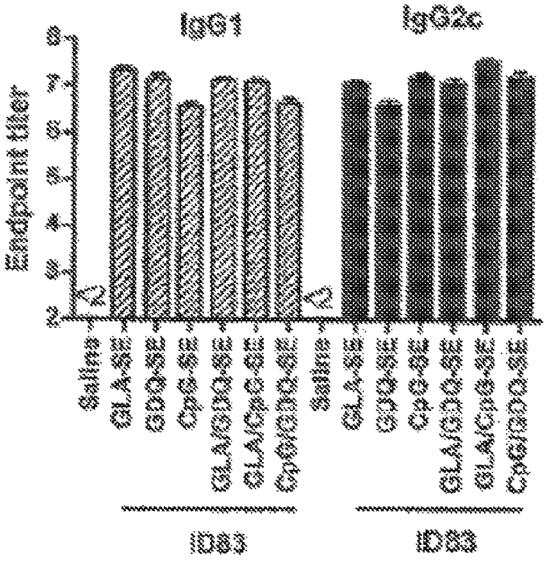
FIGS. 5A-5B shows the immunogenicity of ID83 with different adjuvant formulations in C57BL/6 mice.
Figure 5B:
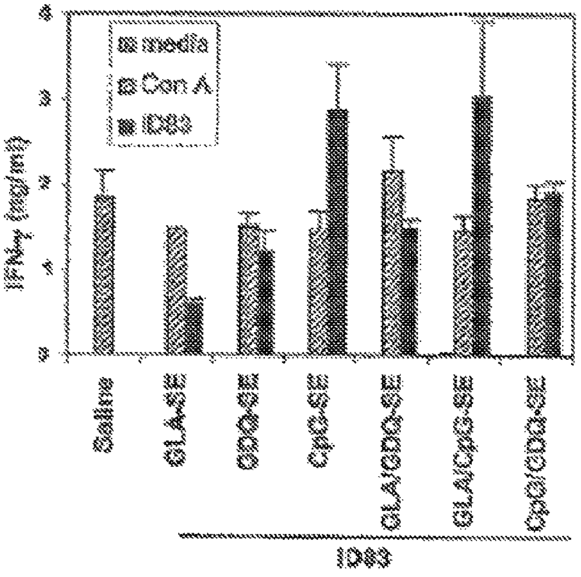

Injection with saline did not induce IFN-γ responses specific to ID83 fusion protein. Immunization with ID83 fusion protein with the different adjuvants induced antigen specific IFN-γ recall responses by activated splenocytes (FIG. 5B).

Together, these results indicate that immunization with ID83 fusion protein in a variety of adjuvants induced B and T cell immune responses.

Protection Afforded by ID83 and 11393 Fusion Proteins, Formulated with the Adjuvant GLA-SE, Against an Aerosol Challenge with Mtb H37Rv.

Number of viable bacilli, expressed as mean Log 10 CFU, in the lung of mice vaccinated with ID83 or ID93 fusion proteins adjuvanted with GLA-SE, were determined 4 weeks post aerosol challenge with ~50 CFU of virulent *M. tuberculosis* H37RV.

The mean Log 10 CFU in the lung of mice immunized with the different fusion proteins was compared to the mean Log 10 CFU obtained in mice receiving placebo (saline) or BCG. The difference in mean Log 10 CFU in the saline group vs the vaccinated groups is expressed as Log 10 reduction in CPU.

Immunization of mice with three doses of ID83+GLA-SE or ID93+GLA-SE resulted in a decrease in viable Mtb bacilli in the lung of Mtb-infected mice of 0.34, respectively 048 Log 10 (Table 3). These results demonstrate that protection against Mtb infection was achieved with 3 doses of two different fusion proteins adjuvanted with GLA-SE.

TABLE 3

Number of viable bacilli in the lung of vaccinated mice.

| Groups | CFU[a] | SD | Diff[b] | Groups | CFU | SD | Diff. |
|---|---|---|---|---|---|---|---|
| Saline | 5.79 | 0.09 | N/A[c] | Saline | 5.94 | 0.15 | N/A |
| BCG | 5.06 | 0.18 | 0.73 | BCG | 5.07 | 0.20 | 0.57 |
| ID83 + GLA − SE | 5.45 | 0.23 | 0.34 | ID93 + GLA − SE | 5.46 | 0.21 | 0.48 |

[a]CFU = colony-forming-units. Values represent the number of viable bacilli in the lungs of infected mice and are expressed as $Log_{10}$.

[b]Difference = $Log_{10}$ CFU for the Saline group-$Log_{10}$ CFU for the vaccinated treated group.

[c]N/A = not applicable.

Together, these results indicate that immunization with the different fusion proteins in GLA-SE induced B and T cell immune responses.

Immunogenicity of ID83 Formulated with Different Adjuvants

C57BL/6 mice were immunized three times, three weeks apart, with ID83 fusion protein formulated with 20-25 µg of the adjuvant GLA-SE, GDQ-SE, CpG-SE, GLA/GDQ-SE, GLA/CpG-SE, CpG/GDQ-SE. One week, and three weeks after the last immunization, the presence of antigen specific antibody, and memory T lymphocytes respectively, were assessed.

The specific serum IgG isotype Ab response was measured by conventional ELISA by coating each of the recombinant protein onto a plate and serially diluting the different sera. Endpoint titers were determined for each vaccine group. Saline did not induce an IgG1 or IgG2c antibody response specific to ID83 fusion proteins. Immunization with ID83 with the different adjuvants induced antigen specific IgG1 and IgG2c (FIG. 5A).

Three weeks after the last immunization, splenocytes were prepared and assayed by ELISA to determine the Protection Afforded by ID83 Formulated with Different Adjuvants, in C57BL/6 Mice, Against an Aerosol Challenge with Mtb H37Rv.

Number of viable bacilli, expressed as mean Log 10 CFU, in the lung of mice vaccinated with ID83 fusion protein formulated with 20-25 µg of the adjuvant GLA-SE, CpG-SE, or GLA/CpG-SE were determined 4 weeks post aerosol challenge with ~50 CFU of virulent *M. tuberculosis* H37Rv.

The mean Log 10 CFU in the lung of mice immunized with ID83 in the different adjuvants was compared to the mean Log 10 CFU obtained in mice receiving placebo (saline) or BCG. The difference in mean Log 10 CFU in the saline group vs the vaccinated groups is expressed as Log 10 reduction in CFU.

Immunization of mice with three doses of ID83 with different adjuvants resulted in a decrease in viable Mtb bacilli in the lung of Mtb-infected mice (Table 4). These results are promising in that protection against Mtb infection was achieved with 3 doses of two different fusion proteins adjuvanted with GLA-SE

TABLE 4

| Number of viable bacilli in the lung of vaccinated mice. | | | | |
|---|---|---|---|---|
| Groups | CFU[a] | SD[b] | CFU Reduction[c] | P value[d] |
| Saline | 6.28 | 0.22 | | |
| BCG | 5.01 | 0.15 | 1.27 | <0.01 |
| ID83 + GLA-SE | 5.75 | 0.22 | 0.53 | <0.01 |
| ID83 + CpG-SE | 5.79 | 0.12 | 0.49 | <0.01 |
| ID83 + GLA/CpG-SE | 5.62 | 0.22 | 0.66 | <0.01 |

[a]CFU = colony-forming-units. Values represents the number of viable bacilli in the lungs of infected mice and are expressed as $Log_{10}$.
[b]SD, standard deviation
[c]CFU Reduction = $Log_{10}$ CFU for the Saline group - $Log_{10}$ CFU for the vaccinated treated group.
[d]P value is calculated with one-way ANOVA followed by Dunnett's multiple comparison Test. P values <0.05 are considered statistically significant Together, these results indicate that vaccination with ID83 fusion protein adjuvanted with CpG-SE, GLA-SE, or CpG/GLA-SE reduced the bacterial burden and partially protected mice from *M. tuberculosis* infection. ID83+CpG/GLA-SE was the most effective formulation in reducing the number of viable bacteria in the lungs of Mtb-infected mice.

Protection Afforded by ID83 Formulated with GLA/CpG-SE, in Guinea Pigs, Against an Aerosol Challenge with Mtb H37Rv.

Survival of guinea pigs vaccinated with ID83 fusion protein formulated with 20/25 μg of the adjuvant GLA/CpG-SE were followed for 200 days post aerosol challenge with ~50 CFU of virulent *M. tuberculosis* H37Rv.

The survival of guinea pigs immunized with ID83 in GLA/CpG-SE adjuvant was compared to the survival of guinea pigs receiving placebo (saline) or BCG.

Figure 6:
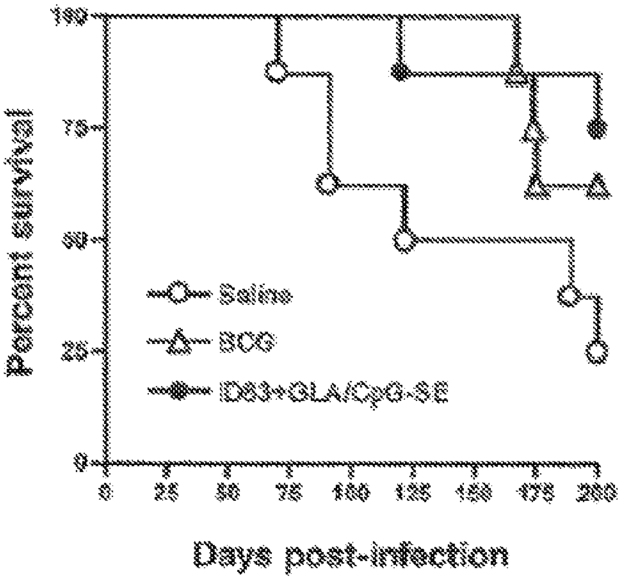
FIG. 6 shows the survival after infection with Mtb of guinea pigs immunized with ID83 fusion protein with GLA/CpG-SE. Guinea pigs were immunized with 1 dose of BCG, or 3 doses of ID83 with GLA/CpG-SE adjuvant, and challenged with a low dose aerosol of *M. tuberculosis* H37Rv 4 wks after the last boost. Survival was monitored for 200 days until ¾ of the animal in the placebo group (saline) died.

Immunization of guinea pigs with three doses of ID83 with different adjuvants resulted in increased survival of Mtb-infected guinea pig (FIG. 6). At day 200 post-infection, 75% of the animals vaccinated with ID83+GLA/CpG-SE were still alive, compared with 25% of the guinea pigs in the placebo group. 62% of guinea pigs immunized with BCG were alive at day 200 post-infection with Mtb.

These results demonstrate that protection against Mtb infection was achieved with 3 doses of ID83 fusion protein formulated with GLA/CpG-SE. In addition, vaccination with ID83+GLA/CpG-SE protected Mtb-infected guinea pigs longer than BCG.

Together, these results indicate that vaccination with ID83 fusion protein adjuvanted with CpG-SE, GLA-SE, or CpG/GLA-SE reduced the bacterial burden in the lungs of Mtb-infected mice, and partially protected guinea pigs from *M. tuberculosis* infection. ID83+CpG/GLA-SE was the most effective formulation in reducing the number of viable bacteria in the lungs of Mtb-infected mice and prolonging the survival of Mtb-infected guinea pigs.

Vaccination of mice with three doses of ID83 or ID93 fusion protein, adjuvanted with GLA-SE, induced antibody and Th1 T cell memory responses along with reduction in viable bacilli counts in the lung of mice infected with *M. tuberculosis*. Furthermore, a combination of CpG and GLA-SE was observed to be most immunogenic and conferred increased protection to *M. tuberculosis* challenge.

Example 25

Immune Responses to $A_D5$-ID83 In C57BL/6 Mice and Protection Against an Aerosol M. Tuberculosis Challenge This example demonstrates that immunization of mice with an adenovirus vector engineered to express ID83 fusion proteins of the invention is immunogenic in C57BL/6 mice.

Material & Methods:

Virus Construction and Purification

Ad5-ID83 was constructed using the AdEasy™ XL Adenoviral Vector System (Stratagene #240010). Briefly, ID83 was amplified from plasmid DNA using PCR, digested with HinDIII and EcoRV, and ligated into pShuttle-CMV to make ID83-pShuttleCMV. ID83-pShuttleCMV was linearized by digesting with Pmel and electroporated (2.4 kV, 1861 Ω, 0.2 cm gap cuvette) into *Escherichia coli* BJ5183-AD-1 electro-competent cells (Stratagene #200157). Recombinant Ad1-ID83 plasmids were identified by digesting with Pacl. Pacl digested Ad5-ID83 plasmid (4 μg) was transfected into AD-239 cells in 60 mm plates using Polyfect reagent (Invitrogen #301107). After 4 days cells were harvested in 3 mL media and lysed by three cycles of freeze/thaw. Lysate supernatant was used to amplify virus for purification by CsCl gradient centrifugation Immunization Female C57/BL6 mice were obtained from Charles River and age-matched (5-7 week) within each experiment. Mice were immunized two times (3 week apart) with $5\times10^8$ Ad5-ID83 viral particles. Mice in the saline, and BCG control groups received PBS or a single dose of $5\times10^4$ BCG CFU respectively. Mice were injected with a total volume of 100 μl/mouse via the i.m. route.

Cytokine ELISPOT

MultiScreen 96-well filtration plates (Millipore, Bedford, MA) were coated with 10 μg/ml rat anti-mouse IFN-γ or TNF capture Ab (eBioscience) and incubated overnight at 4° C. Plates were washed with PBS, blocked with RPMI 1640 and 10% FBS for at least 1 h at room temperature, and washed again. Splenocytes were plated in duplicate at $2\times10^6$ cells/well, and stimulated with medium, Con A 3 μg/ml, PPD 10 μg/ml, or each recombinant protein 10 μg/ml for 48 h at 37° C. The plates were subsequently washed with PBS and 0.1% Tween-20 and incubated for 2 h with a biotin-conjugated rat anti-mouse IFN-γ or TNF secondary Ab (eBioscience) at 5 μg/ml in PBS, 0.5% BSA, and 0.1% Tween-20. The filters were developed using the Vectastain ABC avidin peroxidase conjugate and Vectastain AEC substrate kits (Vector Laboratories, Burlingame, CA) according to the manufacturer's protocol. The reaction was stopped by washing the plates with deionized water, plates were dried in the dark, and spots were counted on a automated ELISPOT reader (C.T.L. Serie3A Analyzer, Cellular Technology Ltd, Cleveland, OH), and analyzed with Immunospot® (CTL Analyzer LLC).

Protection Experiment

Mice were immunized s.c., three times, 3 weeks apart, with 8 μg of the fusion protein, formulated in the indicated adjuvant. Positive control mice were immunized with BCG ($5\times10^4$ CFU) in the base of the tail (once), and negative control animals were injected with saline, or adjuvant alone. Thirty days after the last immunization, mice were challenged by low dose aerosol exposure with *Mycobacterium tuberculosis* H37Rv strain (ATCC 35718; American Type Culture Collection, Manassas, VA) using a UW-Madison aerosol exposure chamber (Madison, WI) calibrated to deliver 50-100 bacteria into the lungs. Four weeks later, mice were euthanized, and lung and spleen homogenates were prepared in PBS/Tween 80 (0.05%). Bacterial counts were determine by plating serial dilutions of individual whole organs on nutrient Middlebrook 7H11 Bacto Agar (BD Biosciences, Cockeysville, MD) and counting bacterial colony formation after 14-day incubation at 37° C. in humidified air and 5% $CO_2$. Data are expressed as Log 10 of the mean number of bacteria recovered±SD, and Log 10

Reduction in CFU=Log 10 CFU for the vaccinated group—Log 10 CFU for the Saline treated group.

Results:

Immune Responses to Ad5-ID83

C57BL/6 mice were immunized two times, three weeks apart, with Ad5-ID83.

Three weeks after the last immunization, splenocytes were prepared and assayed by ELISPOT to determine the relative number of IFN-γ-expressing splenocytes in response to medium alone, the mitogen ConA, and each of the fusion proteins.

Figure 7A:
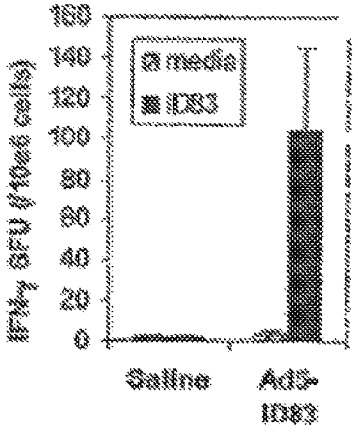
FIGS. 7A-7B shows Ad5-ID83-specific immune responses and protection against an *M. tuberculosis* challenge.

Immunization with Ad5-ID83 induced antigen specific IFN-γ recall responses by activated splenocytes (FIG. 7A), Injection with saline did not induce IFN-γ responses specific to ID83.

Protection Afforded by Ad5-ID83 Against an Aerosol Challenge with Mtb H37Rv.

Number of viable bacilli, expressed as mean Log 10 CFU, in the lung of mice vaccinated with $5\times10^8$ Ad5-ID83 viral particles, were determined 4 weeks post aerosol challenge with ~50 CFU of virulent *M. tuberculosis* H37RV.

The mean Log 10 CFU in the lung of mice immunized with Ad5-ID83 was compared to the mean Log 10 CFU obtained in mice receiving placebo (saline). The difference in mean Log 10 CFU in the saline group vs the vaccinated groups is expressed as Log 10 reduction in CFU.

Figure 7B:
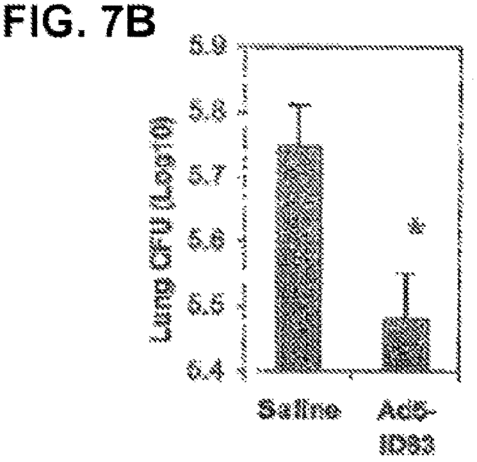

Immunization of mice with two doses of Ad5-ID83 resulted in a decrease in viable Mtb bacilli in the lung of Mtb-infected mice of 0.27 (FIG. 7B). These results are promising in that protection against Mtb infection was achieved with only 2 doses of Ad5-ID83.

Together, these results indicate that immunization with Ad5-ID83 induced T cell immune responses and partially protected mice from an aerosol *M. tuberculosis* challenge.

Example 26

Immunotherapy with MTB Rv1813, Rv2608, and Rv3620 Recombinant Proteins with the Adjuvant GLA-SE This example demonstrates that immunization of mice with a mixture of recombinant proteins of the invention along with standard antibiotic therapy can prolong the life of *M. tuberculosis*-infected mice.

Material & Methods:

Recombinant Proteins and Adjuvant Formulations

Recombinant proteins were produced as described above. Glucopyranosyl lipid A (GLA) was obtained from Avanti (Alabaster, AL). Stable oil-in-water emulsions (–SE) were prepared.

Aerosol Challenge with *M. tuberculosis*

Female SWR/J mice were obtained from Jackson Laboratories and age-matched (5-7 week) within each experiment. Mice were challenged by low dose aerosol exposure with *M. tuberculosis* H37Rv strain (ATCC 35718; American Type Culture Collection, Manassas, VA) using a UW-Madison aerosol exposure chamber (Madison, WI) calibrated to deliver 50-100 bacteria into the lungs. Survival of mice was monitored for 225 days post-infection Therapy Two weeks after an aerosol challenge with *M. tuberculosis*, standard antibiotic treatment was started. Mice were given 50 mg/l of rifampin and 85 mg/l isoniazide in their drinking water for 60 days. Some mice received additional immunotherapy and were immunized on day76, day97, and day118 post-infection with 6 μg of each Rv1813, Rv2608, and Rv3620 recombinant protein formulated with 20 μg of the adjuvant GLA-SE. Mice were injected with a total volume of 100 μl/mouse via the s.c. route. Mouse survival was monitored for 225 days.

Results:

Protection Afforded by a Combination of Antibiotics+Rv1813, Rv2608, and Rv3620 with GLA-SE immunotherapy, in *M. tuberculosis*-Infected Mice.

Survival of Mtb-infected mice treated with a standard regimen of rifampin+isolazide antibiotics (Rx) or with a combination of Rx+immunization with Rv1813, Rv2608, and Rv3620 recombinant proteins formulated with 20 μg of the adjuvant GLA-SE (immunotherapy) was followed for 225 days post aerosol challenge with ~50 CFU of virulent *M. tuberculosis* H37Rv.

The survival of mice treated with Rx+immunotherapy was compared to the survival of mice receiving Rx alone or placebo (saline).

Figure 8:
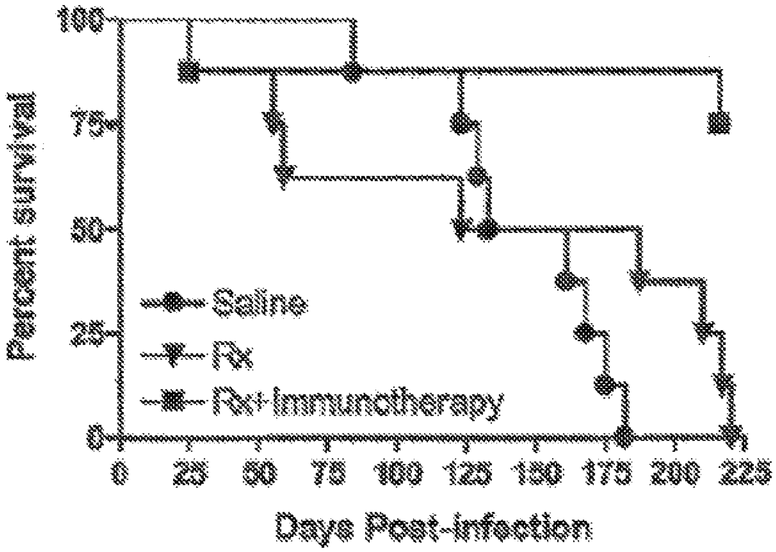
FIG. 8 shows the survival of *M. tuberculosis* infected SWR mice (n=8) treated with a combination of antibiotics (Rx; rifampin+ioniazide for 60 days)+immunotherapy (three injections of a mixture containing Rv2608, Rv1813, and Rv3620 with GLA-SE), antibiotics alone (Rx; rifampin+ioniazide for 60 days), or left untreated (saline). The results demonstrate that the combination of drugs+immunotherapy extends the survival of mice infected with *M. tuberculosis*.

Treatment of mice with three doses of Rv1813, Rv2608, and Rv3620 recombinant proteins with GLA-SE, in addition to Rx, resulted in increased survival of Mtb-infected mice (FIG. 8). At day 225 post-infection, 75% of the animal vaccinated with Rv1813, Rv2608, and Rv3620 with GLA-SE were still alive, compared with 0% of the mice in the antibiotic (Rx) treatment alone group, and 0% in the placebo group.

These results demonstrate that protection against Mtb infection was achieved with antibiotics+3 doses of Rv1813, Rv2608, and Rv3620 with GLA-SE. In addition, treatment with antibiotics+Rv1813, Rv2608, and Rv3620 with GLA-SE protected Mtb-infected mice longer than antibiotics alone.

Together, these results indicate that immunotherapy with Rv1813, Rv2608, and Rv3620 with GLA-SE along with antibiotics induced immune responses that helped mice control an established *M. tuberculosis* infection.

Example 27

Serological Diagnosis of Tuberculosis

This example identifies *M. tuberculosis* antigens and antigen fusions having increased sensitivity and specificity for serological diagnosis of tuberculosis infection.

Polysorp 96 well plates (Nunc, Rochester, NY) were coated with 2 μg/ml recombinant antigen in bicarbonate buffer overnight at 4° C. and blocked for 2 hours at room temperature with PBST with 1% (w/v) BSA on a plate shaker. Serum were diluted appropriately to 1/200 in PBST with 0.1% BSA, added to each well and plates were incubated at room temperature for 2 hours with shaking. Plates were washed with PBST with 0.1% BSA and then HRP conjugated IgG immunoglobulin (Sigma, St. Louis, MO), diluted 1:10000 in PBST and 0.1% BSA, was added to each well and incubated at room temperature for 60 minutes with shaking. After washing, plates were developed with peroxidase color substrate (KPL, Baltimore MD) with reaction quenched by addition of 1N $H_2SO_4$ after 10 minutes. The corrected optical density of each well at 450-570 nm was read using a VERSAmax® microplate reader (Molecular Devices, Sunnyvale, CA).

Figure 9:
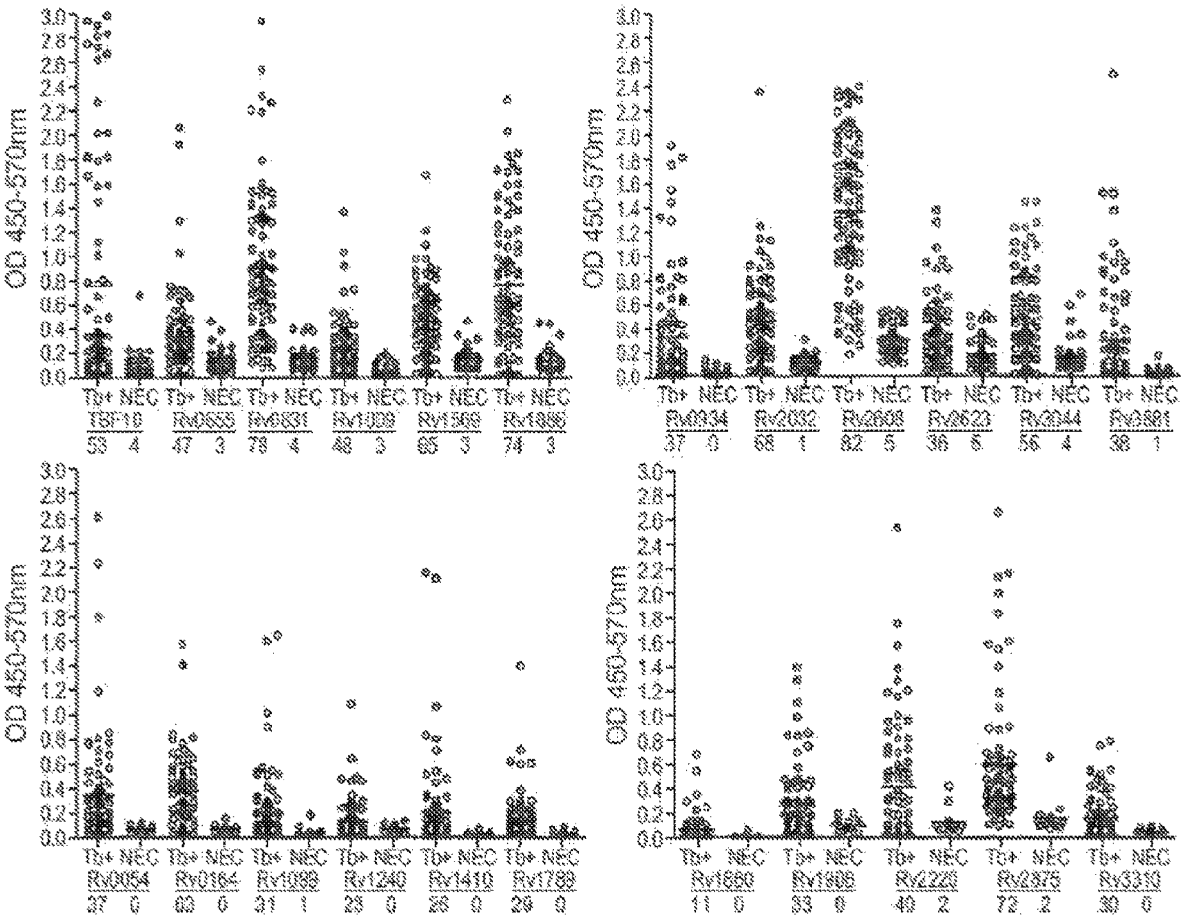
FIG. 9 shows the results of ELISA experiments in which a panel of sputum positive, Tb confirmed serum samples (n=80-92) and a panel of Tb negative, healthy control serum (n=40-46) were analyzed for reactivity with selected Tb antigens. The results demonstrate that 100% positive responses can be obtained by employing different antigen combinations.

The results of these experiments are summarized in FIG. 9. A panel of sputum positive, tuberculosis confirmed serum samples (TB, N=80−92) and a panel of tuberculosis negative, healthy control serum (NEC, N=40−46) were analyzed for reactivity with selected tuberculosis antigens. A previously characterized antigen, TBF10, was used as a positive control and found to give seropositive responses to 53 of the 92 tuberculosis positive serum samples. The reactivity of individual antigens are shown in FIGS. 9, with all the antigens listed displaying reactivity to 11-82 of the tuberculosis serum samples, with low or no reactivity to the healthy controls. The reactivity of a given antigen varied to the serum panel such that 100% positive responses could be obtained through selection of proper antigen combinations.

Example 28

Cloning and Expression of Recombinant Rv0577

Using H37Rv genomic DNA as template, Rv0577 was PCR amplified using the following primers:

5'-Rv0577-NdeI
(SEQ ID NO: 295)
CAATTA*CATATG*AGAGTTTTGTTGCTGGGACCG

3': Rv0577-HindIII-
(SEQ ID NO: 296)
CAATT*AAAGCTT*CTACTTTCCAGAGCCCGCAACGC

Amplification was performed under the following conditions: 94° C. 0.5 min., 55° C. 0.5 min., 68° C. 2 min for 30 cycles, to give the product set forth in SEQ ID NO: 185. The PCR product was digested with Ndel/HindIII and cloned into pET28. a vector. Rv0733 was expressed by host strain BL-21plysS. The supernatant was bound with Ni resin under denaturing conditions. The Ni-NTA purification was followed by an anion exchange purification. Dialyzed in 20 mM Tris pH 8. The amino acid sequence of the recombinant protein is set forth in SEQ ID NO: 186.

Example 29

Cloning and Expression of Recombinant Rv1626

Using H37Rv genomic DNA as template, Rv1626 was PCR amplified using the following primers:

5'-Rv1626-NdeI
(SEQ ID NO: 297)
CAATTA*CATATG*ACCGGCCCCACCACCGCGCC

3'-Rv1628-HIndIII
(SEQ ID NO: 298)
CAATT*AAAGCTT*TCAGGTGTCTTTGGGTGTTCCGAG

Amplification was performed under the following conditions: 94° C. 0.5 min., 55° C. 0.5 min., 68° C. 2 min for 30 cycles, to give the product set forth in SEQ ID NO: 188. The PCR product was digested with Ndel/HindIII and cloned into pET28. a vector, Rv1626 was expressed by host strain BL-21plysS. The supernatant was bound with Ni resin under denaturing conditions. The Ni-NTA purification was followed by an anion exchange purification. Dialyzed in 20 mM Tris pH 8. The amino acid sequence of the recombinant protein is set forth in SEQ ID NO: 189.

Example 30

Cloning and Expression of Recombinant Rv0733

Using H37Rv genomic DNA as template, Rv0733 was PCR amplified using the following primers:

5'-Rv0733-5NdeI
(SEQ ID NO: 299)
CAATTA*CATATG*AGAGTTTTGTTGCTGGGACCG

3'-Rv0733-HindIII
(SEQ ID NO: 300)
CAATT*AAAGCTT*CTACTTTCCAGAGCCCGCAACGC

Amplification was performed under the following conditions: 94° C. 0.5 min., 55° C. 0.5 min., 68° C. 2 min for 30 cycles, to give the product set forth in SEQ ID NO: 191. The PCR product was digested with Ndel/HindIII and cloned into pET28. a vector. Rv0733 was expressed by host strain BL-21plysS. The supernatant was bound with Ni resin under denaturing conditions. The Ni-NTA purification was followed by an anion exchange purification. Dialyzed in 20 mM Tris pH 8. The amino acid sequence of the recombinant protein is set forth in SEQ ID NO: 192.

Example 31

Cloning and Expression of Recombinant Rv2520

Using H37Rv genomic DNA as template, Rv2520 was PCR amplified using the following primers:

5'-Rv2520-NdeI-6his
(SEQ ID NO: 301)
CAATTA*CATATG*CATCACCATCACCATCACGTG
GTGGACCGCGATCCCAATACC 3'-Rv2520-EcoRI
(SEQ ID NO: 302)
CAATTA*GAATTC*TCAGCGATTCCTGATCTTGTG Amplification was performed under the following conditions. 94° C. 0.5 min., 55° C. 0.5 min., 68° C. 2 min for 30 cycles, to give the product set forth in SEQ ID NO: 194. The PCR product was digested with Ndel/EcoRI and cloned into a modified pET 28a missing the upstream 6 histidine and the 5'linker sequence. Rv2520 was transformed into expression hosts BL-21 pLysS and Rosetta pLysS. Both expressed equally, but proceeded with the BL-21pLysS cell strain. Following cell lysis, the supernatant fraction was bound with Ni-NTA resin under denaturing conditions. The Ni-NTA purification was followed by an anion exchange purification. Purified fractions were dialyzed into 20 mM Tris pH 8. The amino acid sequence of the recombinant protein is set forth in SEQ ID NO: 195.

Example 32

Cloning and Expression of Recombinant Rv1253

Using H37Rv genomic DNA as template, Rv1253 was PCR amplified using the following primers:

5'-Rv1253-NdeI
(SEQ ID NO: 303)
CTGGATCCC*ATATG*GCCTTCCCGGAATATTCGC

3'-Rv1253-EcoRI
(SEQ ID NO: 304)
CTAGCTG*AATTC*TCATCCGACGTGTTTCCGCCG

Amplification was performed under the following conditions: 94° C. 0.5 min., 55° C. 0.5 min., 68° C. 2 min for 30 cycles, to give the product set forth in SEQ ID NO:197. The PCR product was digested with NdeI/EcoRII and cloned into the pET28. a vector. Rv1511 was transformed into expression host Rosetta plysS. After lysis of a 1 L induction, the recombinant protein was expressed in the inclusion body pellet. Ni-NTA affinity purification was done under denaturing conditions, then dialyzed against 20 mM Tris pH 8.0. The amino acid sequence of the recombinant protein is set forth in SEQ ID NO: 198.

Example 33

Cloning and Expression of Recombinant Rv1980

Using H37Rv genomic DNA as template, Rv1980 was PCR amplified using the following primers:

```
5'-Rv1980-NdeI-24
                                        (SEQ ID NO: 305)
CAATTACATATGGCGCCCAAGACCTACTGCGAG

3'-Rv1980-HindII
                                        (SEQ ID NO: 306)
CAATTAAAGCTTCTAGGCCAGCATCGAGTCGATCGC
```

Amplification was performed under the following conditions: 94° C. 0.5 min., 55° C. 0.5 min., 68° C., 2 min for 30 cycles, to give the product set forth in SEQ ID NO: 200. The PCR product was digested with NdeI/HindIII and cloned into pET28. a vector. Rv1980 was transformed into expression host Rosetta plysS. After lysis of a 1 L induction, the recombinant protein was expressed in the inclusion body pellet. Ni-NTA affinity purification was done under denaturing conditions, then dialyzed against 20 mM Tris pH 8.0. The amino acid sequence of the recombinant protein is set forth in SEQ. ID NO: 201.

Example 34

Cloning and Expression of Recombinant Rv3628

Using H37Rv genomic DNA as template, Rv3628 was PCR amplified using the following primers:

```
5'-Rv3628-Nde-6hisI
                                        (SEQ ID NO: 307)
CAATTACATATGCATCACCATCACCATCACATGCAATTCGACG

TGACCATC

3'-Rv3628-EcoRI
                                        (SEQ ID NO: 308)
CAATTAGAATTCTCAGTGTGTACCGGCCTTGAAGCG
```

Amplification was performed under the following conditions: 94° C. 0.5 min., 55° C. 0.5 min., 68° C. 2 min for 30 cycles, to give the product set forth in SEQ ID NO: 203. Using H37Rv genomic DNA as template, Rv3628 was PCR'd with conditions 95° C. 1 min., 58° C. 1 min., 72° C. 1.5 min for 35 cycles. The PCR product was digested with NdeI/EcoRI and cloned into pET 17b. Rv3628 was transformed into expression hosts BL-21plysE and Rosetta plysS. Both expressed equally, but proceeded with the plysE construct. After lysis of a 1 L induction, it went into the inclusion body. Ni-NTA was done under denaturing conditions, then dialyzed against 10 mM Tris pH 8.0. The amino acid sequence of the recombinant protein is set forth in SEQ ID NO: 204.

Example 35

Cloning and Expression of Recombinant Rv1844

Using H37Rv genomic DNA as template, Rv1844 was PCR amplified using the following primers:

```
5'-Rv1884-NdeI-6his30
                                        (SEQ ID NO: 309)
CAATTACATATGCATCACCATCACCATCACACTTCCGGCGAT

ATGTCGAGC

3'-Rv1884-EcoRI
                                        (SEQ ID NO: 310)
CAATTAGAATTCTCAGCGCGGAATACTTGCCTG
```

Amplification was performed under the following conditions: 94° C. 0.5 min., 55° C. 0.5 min., 68° C. 2 min for 30 cycles, to give the product set forth in SEQ ID NO: 206. The PGR product was digested with NdeI/EcoRI and cloned into pET 17b. Plasmid containing the Rv1884 gene was transformed into expression hosts BL-21plysE and plysS. Both expressed equally, but proceeded with the plysE. After lysis of a 1 L induction, it remained in the insoluble inclusion body fraction. Ni-NTA was done under denaturing conditions, then dialyzed against 10 mM Tris pH 8.0. The amino acid sequence of the recombinant protein is set forth in SEQ ID NO: 207.

Example 36

Cloning and Expression of Recombinant Rv3872

Using H37Rv genomic DNA as template. Rv3872 was PCR amplified using the following primers:

```
5'-Rv3872-NdeI
                                        (SEQ ID NO: 311)
GTGCTAGCCATATGGAAAAAATGTCACATGATC

3'-Rv3872-HindIII
                                        (SEQ ID NO: 312)
CTGGATCCAAGCTTCTATTCGGCGAAGACGCCGGC
```

Amplification was performed under the following conditions: 94° C. 0.5 min., 55° C. 0.5 min., 68° C. 2 min for 30 cycles, to give the product set forth in SEQ ID NO: 209. The PCR product was digested with NdeI/HindIII and cloned into pET28. a vector. Rv3872 was transformed into expression host Rosetta plysS. After lysis of a 1 L induction, the recombinant protein was expressed in the soluble supernatant fraction. Ni-NTA affinity purification was done 2×under native conditions, then dialyzed against 20 mM Tris pH 8.0. The amino acid sequence of the recombinant protein is set forth in SEQ ID NO: 210.

Example 37

Cloning and Expression of Recombinant Rv3873

Using H37Rv genomic DNA as template, Rv3873 was PCR amplified using the following primers:

```
5'-Rv3873-NdeI
                                        (SEQ ID NO: 313)
GTGCTAGCCATATGCTGTGGCACGCAATGCCAC
```

-continued

3'-3873-HindIII
(SEQ ID NO: 314)
CTGGATCCAAGCTTTCACCAGTCGTCCTCTTCGTC

Amplification was performed under the following conditions: 94° C. 0.5 min., 55° C. 0.5 min., 68° C. 2 min for 30 cycles, to give the product set forth in SEQ ID NO: 212. The PCR product was digested with NdeI/HindIII and cloned into pET28a vector. Plasmid containing the Rv3873 gene was transformed into expression host Rosetta plysS. After lysis of a 1 L induction, the recombinant protein was expressed in the soluble supernatant fraction. Ni-NTA affinity purification was done 2× under native conditions, then dialyzed against 20 mM Tris pH 8.0. The amino acid sequence of the recombinant protein is set forth in SEQ ID NO: 213.

Example 38

Cloning and Expression of Recombinant RV1511

Using H37Rv genomic DNA as template, Rv1511 was PCR amplified using the following primers:

5'-Rv1511-NdeI
(SEQ ID NO: 315)
CAATTACATATGCATCACCATCACCATCACGTGAAGCGAGCG
CTCATCACC

3'-Rv1511-EcoRI
(SEQ ID NO: 316)
CAATTAGAATTCTCATGTCCGGCCGGCGATCATCG

Amplification was performed under the following conditions: 94° C. 0.5 min., 55° C. 0.5 min., 68° C. 2 min for 30 cycles, to give the product set forth in SEQ ID NO: 214. The PCR product was digested with NdeI/EcoRI and cloned into pET 28a, minus the 5' linker. Rv1511 was transformed into expression hosts BL-21plysS and Rosetta plysS. Both expressed equally, but proceeded with the BL-21 cells. After lysis of a 1 L induction, the recombinant protein was expressed in the inclusion body pellet. Ni-NTA affinity purification was done under denaturing conditions, then dialyzed against 10 mM Tris pH 9.5. The amino acid sequence of the recombinant protein is set forth in SEQ ID NO: 215.

Example 39

Cloning and Expression of Recombinant Fusion Protein ID93

The following primers were used in for cloning the fusion construct ID93, which comprises fusion partners derived from Rv3619, Rv1813, Rv3620 and Rv2608:

5': Rv1813mat-5NdeI-KpnI
(SEQ ID NO: 218)
CAATTACATATGGGTACCCATCTCGCCAACGGTTCGATG 3': Rv1813mat-3SacIgo
(SEQ ID NO: 219)
CAATTAGAGCTCGTTGCACGCCCAGTTGACGAT 5': Rv3620-5SacI
(SEQ ID NO: 220)
CAATTAGAGCTCATGACCTCGCGTTTTATGACG -continued 3': Rv3620-3SalIgo
(SEQ ID NO: 221)
CAATTAGTCGACGCTGCTGAGGATCTGCTGGGA 5': Rv2608-5SalI
(SEQ ID NO: 222)
CAATTAGTCGACATGAATTTCGCCGTTTTGCCG 3': Rv2608-3ScaI-HindIII
(SEQ ID NO: 223)
CAATTAAAGCTTTTAAGTACTGAAAAGTCGGGGTAGCGCCGG 5': Rv3619-5NdeI
(SEQ ID NO: 224)
CAATTACATATGACCATCAACTATCAATTC 3': Rv3619-3KpnI
(SEQ ID NO: 225)
CAATTAGGTACCGGCCCAGCTGGAGCCGACGGC Rv1813 and Rv3620 were PCR amplified from H37Rv genomic template DNA (94° C. for 0:30; 58° C. for 0:30; 58° C. for 1:30; 35 cycles). Rv1813 was digested with NdeI/SacI then cloned into pET28. a vector. Rv3620 was digested with SacI/SalI then ligated into the Rv1813pET construct. The fusion construct has a polynucleotide sequence set forth in SEQ ID NO: 217, encoding the fusion protein set forth in SEQ ID NO: 226. Rv2608 was amplified from plasmid template by PCR (94° C. for 0:30; 58° C. for 0:30; 68° C. for 1:30; 35 cycles). Product was digested with SalI/HindIII and cloned into pET28. a-Rv1813-3820 vector. Rv3619 was amplified same as above and digested with NdeI/KpnI then ligated into the ID83 vector. ID93 was expressed in host BL-21plysS (2 L, 2XYT growth media, 37° C.). Induced with 1 mM IPTG at OD 0.77 and harvested at OD 1.93. Cell pellet was suspended in lysis buffer (20 mM Tris pH8, 100 mM NaCl, 2 mM PMSF) and froze. The cell pellet was then thawed, lysed by sonication, and spun at 7,000rcf for 20 minutes ID83 is an inclusion body protein. The pellet was washed 2× with 1% Chaps. The pellet was solubilized in 60 mL in binding buffer (8M urea, 20 mM Tris pH 8, 100 mM NaCl) and bound to 16 mL Ni-NTA resin at RT for 1 hour. The resin was washed (50 mL 0.5% DOC for 20 minutes; 80 mL 60% IPA for 30 minutes, 50 mL 0.5% DOC rinse) and then eluted with binding buffer with 300 mM imidazole. The supernatant from the first bind was bound to an additional 8 mL resin and processed as indicated above. The aforementioned purifications removed breakdown products. Another Ni-NTA bind was done overnight at 4° C. in 160 mL (binding buffer with 50 mM NaCl) with 32 mL resin. The resin was washed and eluted as indicated above. The fractions from this bind were dialyzed in 20 mM Tris PH8.

Example 40

Cloning and Expression of Recombinant Fusion Protein ID91

The following primers were used in for cloning the fusion construct ID91, which comprises fusion partners derived from Rv3619, Rv2389, Rv3478 and Rv1885:

5'-Rv3619-5NdeI
(SEQ ID NO: 228)
CAATTACATATGACCATCAACTATCAATTC

-continued

3'-Rv3619-3KpnI (SEQ ID NO: 229)

CAATTA*GGTACC*GGCCCAGCTGGAGCCGACGG

5'-Rv2389-KpnI (SEQ ID NO: 230)

TGGGCC*GGTACC*GACGACATCGATTGGGACGCC

3'-Rv2389-BamHI (SEQ ID NO: 231)

AATCCACCAC*GGATCC*ATCGTCCCTGCTCCCCGAAC

5'-Rv3478-BamHI (SEQ ID NO: 232)

CAGGGACGAT*GGATCC*GTGGTGGATTTCGGGGCGTTAC

3'-Rv3478-EcoRI (SEQ ID NO: 233)

CCGGGAGAA*GAATTC*TCCGGCGGCCGGTGTGCGGG

5'-Rv1886-EcoRI (SEQ ID NO: 234)

GCCGCCGGA*GAATTC*TTCTCCCGGCCGGGGTGCC

3'-Rv1886matR HindIII (SEQ ID NO: 235)

GATATC*AAGCTT*TCAGCCGGCGCCTAACGAAC

The fusion construct has a polynucleotide sequence set forth in SEQ ID NO: 227, encoding the fusion protein set forth in SEQ ID NO: 236.

Example 41

Cloning and Expression of Recombinant Fusion Protein ID71

The following primers were used in for cloning the fusion construct ID71, which comprises fusion partners derived from Rv3619, Rv2389, Rv3478 (N180) and Rv1886:

5'-Rv3619-5NdeI (SEQ ID NO: 238)

CAATTA*CATATG*ACCATCAACTATCAATTC

3'-Rv3619-3KpnI (SEQ ID NO: 239)

CAATTA*GGTACC*GGCCCAGCTGGAGCCGACGG

5'-Rv2389-KpnI (SEQ ID NO: 240)

TGGGCC*GGTACC*GACGACATCGATTGGGACGCC

3'-Rv2389-BamHI (SEQ ID NO: 241)

AATCCACCAC*GGATCC*ATCGTCCCTGCTCCCCGAAC

5'-Rv3478-N180-EcoRI (SEQ ID NO: 242)

CGGCCGGGAGAA*GAATTC*CCCGCCGGGGTTGGTGATCAG

5'-Rv1886-EcoRI (SEQ ID NO: 243)

GCCGCCGGA*GAATTC*TTCTCCCGGCCGGGGCTGCC

3'-Rv1886matR HindIII (SEQ ID NO: 244)

GATATC*AAGCTT*TCAGCCGGCGCCTAACGAAC

The fusion construct has a polynucleotide sequence set forth in SEQ ID NO: 237, encoding the fusion protein set forth in SEQ ID NO: 245.

Example 42

Cloning and Expression of Recombinant Fusion Protein ID114

The following primers were used in for cloning the fusion construct ID114, which comprises fusion partners derived from Rv1813, Rv3620, Rv2608 and Rv1886:

5': Rv2608-5SalI (SEQ ID NO: 247)

CAATTA*GTCGAC*ATGAATTTCGCCGTTTTGCCG

3': Rv2608-3ScaI-HindIII (SEQ ID NO: 248)

CAATTA*AAGCTT*TTA*AGTACT*GAAAAGTCGGGGTAGCGCCGG

5'-Rv1886-2608-ScaI (SEQ ID NO: 249)

CGGCGCTACCCCGACTTTTC*AGTACT*TTCTCCCGGCCGGGG

CTGCCG

3'-Rv1886matR HindIII (SEQ ID NO: 250)

GATATC*AAGCTT*TCAGCCGGCGCCTAACGAAC

Rv1813 and Rv3620 were PCR amplified from H37Rv genomic template DNA (94° C. for 0:30; 58° C. for 0:30; 58° C. for 1:30; 35 cycles). The fusion construct has a polynucleotide sequence set forth in SEQ ID NO: 246, encoding the fusion protein set forth in SEQ ID NO: 251.

Example 43

Cloning and Expression of Recombinant Fusion Protein ID125

The following primers were used in for cloning the fusion construct ID125, which comprises fusion partners derived from Rv3619, Rv1813, Rv3620, Rv2608 and Rv1886:

5': Rv2608-5SalI (SEQ ID NO: 253)

CAATTA*GTCGAC*ATGAATTTCGCCGTTTTGCCG

3': Rv2608-3ScaI-HindIII (SEQ ID NO: 254)

CAATTA*AAGCTT*TTA*AGTACT*GAAAAGTCGGGGTAGCGCCGG

5'-Rv1886-2608-ScaI (SEQ ID NO: 255)

CGGCGCTACCCCGACTTTTC*AGTACT*TTCTCCCGGCCGGGG

CTGCCG

3'-Rv1886matR HindIII (SEQ ID NO: 256)

GATATC*AAGCTT*TCAGCCGGCGCCTAACGAAC

The fusion construct has a polynucleotide sequence set forth in SEQ ID NO: 252, encoding the fusion protein set forth in SEQ ID NO: 257.

Example 44

Cloning and Expression of Recombinant Fusion Protein DID85

The following primers were used in for cloning the fusion construct DID85, which comprises fusion partners derived from Rv2032, Rv2875, and Rv0831:

```
5'-Rv2032-NdeI-6his
                                    (SEQ ID NO: 259)
GATACACATATGCACCATCACCATCACCACATGCCGGACACC

ATGGTGAC

3'-Rv2032-GGSGGS-BamHI
                                    (SEQ ID NO: 260)
CATGGATCCGCTACCGCCAGAACCACCCCGGTGATCCTTAG

CCCGAAC

5'-Rv2875-BamHI
                                    (SEQ ID NO: 261)
GGTGGTTCTGGCGGTAGCGGATTCATGGGCGATCTGGTGAG

CCCG

3'-Rv2875R-EcoRI
                                    (SEQ ID NO: 262)
CATGAATTCAGAACCGCCGCTTCCGCCCGCCGGAGGCATTA

GCACGC

5'-Rv0831F-EcoRI
                                    (SEQ ID NO: 263)
GGCGGAAGCGGCGGTTCTGAATTCATGCTCCCCGAGACAAA

TCAG

3'-Rv0831R-HindIII
                                    (SEQ ID NO: 264)
TAGAATTCAAGCTTTTACTGGCGAAGCAGCTCATC
```

The genes for Rv2032, Rv2875, and Rv0831 were PCR amplified from existing Plasmid DNA (94° C. for 0:30; 58° C. for 0:30; 58° C. for 1:30; 30 cycles) using the above primer sequences. The three amplified PCR products were used in a second round of PCR to amplify the full length fusion gene product using the 5'-Rv2032-Ndel-6his and 3'-Rv0831R-HindIII primers. The resulting PCR product was digested with NdeI/HindIII and cloned into pET29a vector. DID85 was expressed by host strain BL-21plysS. The fusion construct has a polynucleotide sequence set forth in SEQ ID NO: 258, encoding the fusion protein set forth in SEQ ID NO: 265. After lysis of a 1 L induction, it went into the inclusion body. Ni-NTA was done under denaturing conditions, followed by anion exchange chromatography. Purified fractions were dialyzed against 10 mM Tris pH 8.0.

Example 45

Cloning and Expression of Recombinant Fusion Protein DID92

The following primers were used in for cloning the fusion construct DID92, which comprises fusion partners derived from Rv3044, Rv1009, and Rv0614:

```
5'-Rv3044-NdeI-6his
                                    (SEQ ID NO: 267)
GATACACATATGCACCATCACCATCACCACATGGGCAGCAGC

CATCATCATC

3'-Rv3044-NcoI
                                    (SEQ ID NO: 268)
CATATCGAGCTCGTTGATCGGCGCGTCGACCC

5'-Rv1009-NcoI-GGSGGS linker
                                    (SEQ ID NO: 269)
ATCAACGAGCTCGGAGGTTCTGGTGGAAGCGCATGCAAAAC

GGTGACGTTGAC

3'-Rv1009-EcoRI
                                    (SEQ ID NO: 270)
CATATCGAATTCGCGCGCACCCGCTCGTGCAGC

5'-Rv0164-EcoRI-GGSGGS linker
                                    (SEQ ID NO. 271)
CATGTCGAATTCGGTGGAAGCGGAGGTTCTATGACGGCAAT

CTCGTGCTCAC

3'-Rv0164-HindIII
                                    (SEQ ID NO: 272)
CATATCAAGCTTTTAGCTGGCCGCCAGCTGCTC
```

The fusion construct has a polynucleotide sequence set forth in SEQ ID NO: 266, encoding the fusion protein set forth in SEQ ID NO: 273.

Example 46

Cloning and Expression of Recombinant Fusion Protein DID108

The following primers were used in for cloning the fusion construct DID108, which comprises fusion partners derived from Rv3872, Rv3873, Rv3875 and Rv3881:

```
5'-Rv3872-NdeI-6his
                                    (SEQ ID NO: 275)
GATACACATATGCACCATCACCATCACCACATGGAAAAAATG

TCACATGATC

3'-Rv3872-SacI
                                    (SEQ ID NO: 276)
GATACATGAGCTCTTCGGCGAAGACGCCGGCGGC

5'-Rv3873-SacI-GGSGGS linker
                                    (SEQ ID NO: 277)
GATACAGAGCTCGGAGGTTCCGGTGGAAGCATGCTGTGGCA

CGCAATGCC

3'-Rv3873-EcoRI
                                    (SEQ ID NO: 278)
GATACAGAATTCCCAGTCGTCCTCTTCGTCCCAG

5'-Rv3875-EcoRI-GGSGGS linker
                                    (SEQ ID NO: 279)
GACAGAATTCGGTGGCAGTGGAGGATCTATGACAGAGCAGC

AGTGGAAT

3'-Rv3875-NheI
                                    (SEQ ID NO: 280)
CATATCAGCTAGC TGCGAACATCCCAGTGACGTTG

5'-Rv3881-NheI-GGSGGS linker
                                    (SEQ ID NO: 281)
CATATCAGCTAGCGGAGGTTCCGGTGGAAGCATGACGCAGT

CGCAGACCGTG

3'-Rv3881-HindIII
                                    (SEQ ID NO: 282)
CATATCAAAGCTT TCACTTCGACTCCTTACTGTC
```

The fusion construct has a polynucleotide sequence set forth in SEQ ID NO: 274, encoding the fusion protein sot forth in SEQ ID NO: 283.

Example 47

Cloning and Expression of Recombinant Fusion Protein DID93

The following primers were used in for cloning the fusion construct DID93, which comprises fusion partners derived from Rv1099, Rv0655, and Rv005-4:

5'-Rv1099-NdeI
(SEQ ID NO: 285)
TAGGATCC*CATATG*GAGCTGGTCCGGGTGACC

3'-Rv1099-EcoRI-GGSGGS linker
(SEQ ID NO: 286)
CAC*GAATTC*GCTTCCACCAGAACCTCCGGGCAATGGGTACA
CGGCGC 5'-Rv0655-EcoRI-GGSGGS Linker
(SEQ ID NO: 287)
GGAGGTTCTGGTGGAAGC*GAATTC*GTGCGATACAGTGACTC
ATAC 3'-Rv0655-SacI
(SEQ ID NO: 288)
GCCAC*GAGCTC*AGAACCGCCGCTTCCACCCTGGCCGATTTC
GTGCACCGC 5'-Rv0054-SacI-GGSGGS linker
(SEQ ID NO: 289)
GCCAGGGTGGAAGCGGCGGTTCT*GAGCTC*GTGGCTGGTGA
CACCACCATC -continued 3'Rv0054-HindIII
(SEQ ID NO: 290)
CAATTA*AAGCTT*TCAGAATGGCGGTTCGTCATCGCC The fusion construct has a polynucleotide sequence set forth in SEQ ID NO:284, encoding the fusion protein set forth in SEQ ID NO: 291

Example 48

Cloning and Expression of Recombinant Fusion Protein Rv3875

Using H37Rv genomic DNA as template, Rv3875 was PCR amplified using the following primers:

5'-Rv3875-6His-NdeI
(SEQ ID NO: 317)
CCATTA*CATATG*CATCACCATCACCATCACATGACAGAGCAG
CAGTGGAA

3'-Rv3875-EcoRI
(SEQ ID NO: 318)
CCATTA*GAATTC*CTATGCGAACATCCCAGTGAC

The amino acid sequence of the recombinant protein is set forth in SEQ ID NO: 294.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method for stimulating an immune response comprising administering to a subject an effective amount of a composition comprising two or more *Mycobacterium tuberculosis* antigens, wherein the two or more antigens comprise the antigen Rv3478 comprising the amino acid sequence set forth in SEQ ID NO: 41, the antigen Rv3619 comprising the amino acid sequence set forth in SEQ ID NO:46, the antigen Rv2389 comprising the amino acid sequence set forth in SEQ ID NO: 21, and the antigen Rv1886 comprising the amino acid sequence set forth in SEQ ID NO: 145 or an antigen comprising an amino acid sequence having at least 90% sequence identity to the amino acid sequence set forth in SEQ ID NO: 41, an antigen comprising an amino acid sequence having at least 90% sequence identity to the amino acid sequence set forth in SEQ ID NO: 46, an antigen comprising an amino acid sequence having at least 90% sequence identity to the amino acid sequence set forth in SEQ ID NO: 21, and an antigen comprising an amino acid sequence having at least 90% sequence identity to the amino acid sequence set forth in SEQ ID NO: 145; and wherein the two or more antigens are covalently linked in the form of a fusion polypeptide.

2. The method of claim 1, wherein the two or more antigens comprise an antigen comprising an amino acid sequence having at least 99% sequence identity to the amino acid sequence set forth in SEQ ID NO: 41 and an antigen comprising an amino acid sequence having at least 99% sequence identity to the amino acid sequence set forth in SEQ ID NO: 46.

3. The method of claim 1, wherein the two or more antigens are directly linked.

4. The method of claim 1, wherein the two or more antigens are linked via an amino acid linker.

5. The method of claim 1, wherein the composition further comprises an immunostimulant.

6. The method of claim 5, wherein the immunostimulant is selected from the group consisting of glucopyranosyl lipid adjuvant (GLA), adjuvant system-2 (AS-2), monophosphoryl lipid A, 3-de-O-acylated monophosphoryl lipid A, incomplete Freund's adjuvant (IFA), Quillaja *saponaria* 21 (QS21), cell wall skeleton (CWS), trehalose dicorynomycolate (TDM), aminoalkyl glucosaminide phosphates (AGPs), CpG-containing oligonucleotides, Toll-like receptor agonists, LeIF, saponins, saponin mimetics, biological and synthetic lipid A, imiquimod, gardiquimod, resiquimod, polyI:C, and flagellin, or a combination thereof.

7. The method of claim 6, wherein the immunostimulant is GLA.

8. The method of claim 1, wherein the two or more antigens further comprise an antigen comprising an amino acid sequence having at least 99% sequence identity to the amino acid sequence set forth in SEQ ID NO: 21.

9. The method of claim 1, wherein the two or more antigens further comprise an antigen comprising an amino acid sequence having at least 99% sequence identity to the amino acid sequence set forth in SEQ ID NO: 145.

10. The method of claim 1, wherein the two or more antigens further comprise an antigen comprising an amino acid sequence having at least 99% sequence identity to the amino acid sequence set forth in SEQ ID NO: 21 and an amino acid sequence having at least 99% sequence identity to the amino acid sequence set forth in SEQ ID NO: 145.

11. The method of claim 1, wherein the fusion polypeptide is ID91 comprising the amino acid sequence set forth in SEQ ID NO: 236 or an amino acid sequence having at least 90% sequence identity to the amino acid sequence set forth in SEQ ID NO: 236.

12. The method of claim 11, wherein the fusion polypeptide comprises an amino acid sequence having at least 99% sequence identity to the amino acid sequence set forth in SEQ ID NO: 236.

* * * * *